US011021694B2

(12) United States Patent
Lo et al.

(10) Patent No.: US 11,021,694 B2
(45) Date of Patent: Jun. 1, 2021

(54) SIRP-α IMMUNOGLOBULIN FUSION PROTEINS

(71) Applicant: Merck Patent GmbH, Darmstadt (DE)

(72) Inventors: Kin-Ming Lo, Lexington, MA (US); Nora Zizlsperger, Newton, MA (US); Aroop Sircar, Billerica, MA (US)

(73) Assignee: Merck Patent GmbH, Darmstadt (DE)

( * ) Notice: Subject to any disclaimer, the term of this patent is extended or adjusted under 35 U.S.C. 154(b) by 229 days.

(21) Appl. No.: 14/827,003

(22) Filed: Aug. 14, 2015

(65) Prior Publication Data

US 2016/0177276 A1 Jun. 23, 2016

Related U.S. Application Data

(60) Provisional application No. 62/038,196, filed on Aug. 15, 2014.

(51) Int. Cl.
| C07K 14/00 | (2006.01) |
| C12N 9/16 | (2006.01) |
| C07K 16/28 | (2006.01) |
| C07K 16/30 | (2006.01) |
| C07K 16/32 | (2006.01) |
| C07K 14/705 | (2006.01) |
| A61K 38/00 | (2006.01) |

(52) U.S. Cl.
CPC .......... *C12N 9/16* (2013.01); *C07K 14/70596* (2013.01); *C07K 16/2803* (2013.01); *C07K 16/2827* (2013.01); *C07K 16/2863* (2013.01); *C07K 16/2887* (2013.01); *C07K 16/30* (2013.01); *C07K 16/32* (2013.01); *A61K 38/00* (2013.01); *C07K 2317/31* (2013.01); *C07K 2317/622* (2013.01); *C07K 2319/33* (2013.01); *C07K 2319/74* (2013.01); *C12Y 301/03048* (2013.01)

(58) Field of Classification Search
None
See application file for complete search history.

(56) References Cited

U.S. PATENT DOCUMENTS

| 7,820,165 B2 | 10/2010 | McKenna et al. |
| 2003/0026803 A1 | 2/2003 | Barclay |
| 2014/0161805 A1 | 6/2014 | Jamieson et al. |
| 2015/0266942 A1* | 9/2015 | Tian .................... C07K 14/705 424/134.1 |

FOREIGN PATENT DOCUMENTS

| WO | WO-2008/003103 A2 | 1/2008 |
| WO | WO-2009/046541 A1 | 4/2009 |
| WO | WO-2009/131453 A1 | 10/2009 |
| WO | WO-2010/070047 A1 | 6/2010 |
| WO | WO-2010/130053 A1 | 11/2010 |
| WO | WO-2011/034969 A1 | 3/2011 |
| WO | WO-2011/143624 A2 | 11/2011 |
| WO | WO-2012/007167 A1 | 1/2012 |
| WO | WO-2013/079174 A1 | 6/2013 |
| WO | WO-2013/109752 A1 | 7/2013 |
| WO | WO-2014/094122 A1 | 6/2014 |
| WO | WO2014/121093 | * 8/2014 |
| WO | WO-2014/121093 A1 | 8/2014 |
| WO | WO-2014/144357 A1 | 9/2014 |
| WO | WO-2015/148416 A1 | 10/2015 |
| WO | WO-2016/022971 A1 | 2/2016 |

OTHER PUBLICATIONS

Weiskopf et al. (Science, vol. 341, No. 6141, pp. 88-91 May 30, 2013).*
Kershaw and Smyth (Science, vol. 341, Jul. 5, 2013) (Year: 2013).*
Herve et al. (The American J. of Pathology, vol. 172, No. 1, Jan. 2008) (Year: 2008).*
Ran M. et al, "Increased expression of Fc gamma receptor in cancer patients and tumor bearing mice," *Mol Immunol*, Nov. 30, 1988, vol. 25, No. 11, pp. 1159-1167.
Chen et al., (2013), "Fusion protein linkers: property, design and functionality," *Advanced Drug Delivery Reviews*, 65(10):1357-1369.
Gasser et al., (2007), Antibody production with yeasts and filamentous fungi: on the road to large scale?, *Biotechnology Letters*, 29(2):201-212.
Maeda et al., (1997), "Engineering of functional chimeric protein GVargulaLuciferase," *Analytical Biochemistry*, 1997, 249( 2):147-152.
Markovic-Mueller et al., (2017), "Structure of the Full-length VEGFR-1 Extracellular Domain in Complex with VEGF-A," *Structure*, 25:341-352.
Pakula et al., (1989), "Genetic analysis of protein stability and function," *Annual Review of Genetics*, 23(1):289-310.
Kosobokova et al., (2013), "Antibody-Cytokine Fusion Proteins: Production, Functionality and Application Prospects in Oncology," *Sovremennye tekhnologii v medicine*, 5(4):102-110 (English translation from Russian).
Hatherley et al., (2009), "Structure of signal-regulatory protein alpha: a link to antigen receptor evolution," *J. Biol. Chem.*, 284(39):26613-9.
Carter P et al., (1992) 'Humanization of an Anti-p185HER2 Antibody for Human Cancer Therapy,' Proc Natl Acad Sci USA, 89(10):4285-9.
Chao MP et al., (2010) 'Anti-CD47 Antibody Synergizes with Rituximab to Promote Phagocytosis and Eradicate Non-Hodgkin Lymphoma,' Cell,142(5):699-713.

(Continued)

Primary Examiner — Meera Natarajan
(74) Attorney, Agent, or Firm — Goodwin Procter LLP

(57) ABSTRACT

The invention discloses immunoglobulin fusion proteins designed to bind both CD47 and a tumor cell antigen. The immunoglobulin fusion proteins include a SIRPα moiety that binds CD47 and an antigen binding site for a tumor cell antigen.

20 Claims, 36 Drawing Sheets

Specification includes a Sequence Listing.

(56) References Cited

OTHER PUBLICATIONS

Chao MP et al., (2010) 'Calreticulin is the Dominant Pro-Phagocytic Signal on Multiple Human Cancers and is Counterbalanced by CD47,' Sci Transl Med,2(63):63ra94.

Chao MP et al., (2012) 'The CD47-SIRPalpha Pathway in Cancer Immune Evasion and Potential Therapeutic Implications,' Curr Opin Immunol, 24(2):225-32.

Coloma MJ and Morrison SL, (1997) 'Design and Production of Novel Tetravalent Bispecific Antibodies,' Nat Biotechnol, 15(2):159-63.

Davis JH et al., (2010) 'SEEDbodies: Fusion Proteins Based on Strand-Exchange Engineered Domain (SEED) CH3 Heterodimers in an Fc Analogue Platform for Asymmetric Binders or Immunofusions and Bispecific Antibodies,' Protein Eng Des Sel, 23(4):195-202.

Demarest SJ and Glaser SM, (2008) 'Antibody Therapeutics, Antibody Engineering, and the Merits of Protein Stability,' Curr Opin Drug Discov Devel, 11(5):675-87.

Edris B et al., (2012) 'Antibody Therapy Targeting the CD47 Protein is Effective in a Model of Aggressive Metastatic Leiomyosarcoma,' Proc Natl Acad Sci USA, 109(17):6656-61.

Gardai SJ et al., (2005) 'Call-Surface Calreticulin Initiates Clearance of Viable or Apoptotic Cells Through Trans-Activation of LRP on the Phagocyte,' Cell,123(2):321-34.

Hank JA et al., (2009) 'Immunogenicity of the hu14.18-IL2 Immunocytokine Molecule in Adults with Melanoma and Children with Neuroblastoma,' Clin Cancer Res, 15(18):5923-30.

Harms BD et al., (2014) 'Understanding the Role of Cross-Arm Binding Efficiency in the Activity of Monoclonal and Multispecific Therapeutic Antibodies,' Methods, 65(1):95-104.

International Search Report (Form PCT/ISA/210) for International Patent Application No. PCT/EP2015/068798 dated Nov. 19, 2015 (6 pages).

Jaiswal S et al., (2009) 'CD47 is Upregulated on Circulating Hematopoietic Stem Cells and Leukemia Cells to Avoid Phagocytosis,' Cell, 138(2):271-85.

Jiang P et al., (1999) 'Integrin-Associated Protein is a Ligand for the P84 Neural Adhesion Molecule,' J Biol Chem, 274(2):559-62.

Kawamoto T et al., (1983) 'Growth Stimulation of A431 by Epidermal Growth Factor: Identification of High-Affinity Receptors for Epidermal Growth Factor by an Anti-Receptor Monoclonal Antibody,' Proc Natl Acad Sci USA, 80(5):1337-41.

Kershaw MH and Smyth MJ, (2013) 'Immunology. Making Macrophages Eat Cancer,' Science, 341(6141):41-2.

Lindberg FP et al., (1994) 'Rh-Related Antigen CD47 is the Signal-Transducer Integrin-Associated Protein,' J Biol Chem, 269(3):1567-70.

Liu Y et al., (2006) 'Functional Elements on SIRPalpha IgV Domain Mediate Cell Surface Binding to CD47,' J Mol Biol, 365(3):680-93.

Lu D et al., (2005) 'A Fully Human Recombinant IgG-Like Bispecific Antibody to Both the Epidermal Growth Factor Receptor and the Insulin-Like Growth Factor Receptor for Enhanced Antitumor Activity,' J Biol Chem, 280(20):19665-72.

Majeti R et al., (2009) 'CD47 is an Adverse Prognostic Factor and Therapeutic Antibody Target on Human Acute Myeloid Leukemia Stem Cells,' Cell, 138(2):286-99.

Merchant AM et al., (1998) 'An Efficient Route to Human Bispecific IgG,' Nat Biotechnol, 16(7):677-81.

Michaelson JS et al., (2009) 'Anti-Tumor Activity of Stability-Engineered IgG-Like Bispecific Antibodies Targeting TRAIL-R2 and LTβR,' MAbs, 1(2):128-41.

Nicholson IC et al., (1997) 'Construction and Characterization of a Functional CD19 Specific Single Chain Fv Fragment for Immunotherapy of B Lineage Leukemia and Lymphoma,' Mol Immunol, 34(16-17):1157-65.

Nielsen UB et al., (2000) 'Targeting of Bivalent Anti-Erbβ2 Diabody Fragments to Tumor Cells is Independent of the Intrinsic Antibody Affinity,' Cancer Res, 60(22):6434-40.

Ogura T et al., (2004) 'Resistance of B16 Melanoma Cells to CD47-Induced Negative Regulation of Motility as a Result of Aberrant N-Glycosylation of SHPS-1,' J Biol Chem, 279(14):13711-20.

Oldenborg PA et al., (2000) 'Role of CD47 as a Marker of Self on Red Blood Cells,' Science, 288(5473):2051-4.

Orcutt KD et al., (2009) 'A Modular IgG-scFv Bispecific Antibody Topology,' Protein Eng Des Sel, 23(4):221-8.

Polanski M and Anderson NL, (2007) 'A List of Candidate Cancer Biomarkers for Targeted Proteomics,' Biomark Insights, 1:1-48.

Plückthun A and Pack P, (1997) 'New Protein Engineering to Multivalent and Bispecific Antibody Fragments,' Immunotechnology, 3(2):83-105.

Reff ME et al., (1994) 'Depletion of B Cells in vivo by a Chimeric Mouse Human Monoclonal Antibody to CD20,' Blood, 83(2):435-45.

Ridgway JB et al., (1996) '"Knobs-Into-Holes" Engineering of Antibody CH3 Domains for Heavy Chain Heterodimerization,' Protein Eng, 9(7):617-21.

Robinson MK et al., (2008) 'Targeting Erbβ2 and Erbβ3 with Bispecific Single-Chain Fv Enhances Targeting Selectivity and Induces a Therapeutic Effect in vitro,' Br J Cancer, 99(9):1415-25.

Schaefer W et al., (2011) 'Immunoglobulin Domain Crossover as a Generic Approach for the Production of Bispecific IgG Antibodies,' Proc Natl Acad Sci USA, 108(27):11187-92.

Takenaka K et al., (2007) 'Polymorphism in SiRPalpha Modulates Engraftment of Human Hematopoietic Stem Cells,' Nat Immunol, 8(12):1313-23.

Theocharides AP et al., (2012) 'Disruption of SIRPalpha Signaling in Macrophages Eliminates Human Acute Myeloid Leukemia Stem Cells in Xenografts,' J Exp Med, 209(10):1883-99.

Uger RA et al., (2014) 'Cancer Immunotherapy Targeting CD47" Wild Type SIRPalphaFc is the Ideal CD47-Blocking Agent to Minimize Unwanted Erythrocyte Binding,' AACR Annual Meeting Poster Session, San Diego, CA, American Association for Cancer Research, Philadelphia PA (Publ), Abstract No. 5011 (Abstract).

Vauquelin G and Charlton SJ, (2013) 'Exploring Avidity: Understanding the Potential Gains in Functional Affinity and Target Residence Time of Bivalent and Heterobivalent Ligands,' Br J Pharmacol, 168(8):1771-85.

Wang L et al., (2013) 'Retargeting T Cells for HER2-Positive Tumor Killing by a Bispecific Fv-Fc Antibody,' PLOS One, 8(9):e75589 (11 pages).

Weiskopf K et al., (2013) 'Engineered SIRPalpha Variants as Immunotherapeutic Adjuvants to Anticancer Antibodies,' Science, 341(6141):88-91.

Weiskopf K et al., (2013) 'Improving Macrophage Responses to Therapeutic Antibodies by Molecular Engineering of SIRPalpha Variants,' Oncoimmunology, 2(9):e25773.

Williams SCP, (2012) 'One Drug to Shrink All Tumors,' Science News, Society for Science & The Public, Washington, DC (Publ), (3 pages) http://news.science.org/health/2012/03/one-drug-shrink-all-tumors.

Willingham SB et al., (2012) 'The CD47-Signal Regulatory Protein Alpha (SIRPalpha) Interaction is a Therapeutic Target for Human Solid Tumors,' Proc Natl Acad Sci USA,109(17):6662-7.

Wozniak-Knopp G et al., (2010) 'Introducing Antigen-Binding Sites in Structural Loops of Immunoglobulin Constant Domains: Fc Fragments with Engineered HER2/neu-Binding Sites and Antibody Properties,' Protein Eng Des Sel, 23(4):289-97.

Written Opinion of the International Searching Authority (Form PCT/ISA/237) for International Patent Application No. PCT/EP2015/068798, dated Nov. 19, 2015 (7 pages).

Xu L et al., (2012) 'Heterobivalent Ligands Target Cell-Surface Receptor Combinations in vivo,' Proc Natl Acad Sci USA, 109(52):21295-300.

Zhao XW et al., (2011) 'CD47-Signal Regulatory Protein-alpha (SIRPalpha) Interactions Form a Barrier for Antibody-Mediated Tumor Cell Destruction,' Proc Natl Acad Sci USA, 108(45):18342-7.

Communication Pursuant to Rule 114(2) EPC ("Third Party Observations") filed in European Patent Application No. 15750744.3 dated Sep. 9, 2019, (22 pages) including: Exhibit TP01—"GenBank

(56) References Cited

OTHER PUBLICATIONS

Entry for SIRPA protein [Homo sapiens] GenBank ID No. AAH33092.1 accessed from <https://www.ncbi.nlm.nih.gov./protein/AAH33092.1>" and Exhibit TP02—Greco et al., "Phase 2 study of mapatumumab, a fully human agonistic monoclonal antibody which targets and activates the TRAIL receptor-1, in patients with advanced non-small cell lung cancer," *Lung Cancer* 61:82-90, 2008.

Maynard and Georgiou, (2000), "Antibody Engineering,"Annu. Rev. Biomed. Eng., 2:339-76.

Notice of Opposition by Script IP Limited in European Patent No. 3180363 (European Patent Application No. 15750744.3) filed with the European Patent Office dated Jun. 24, 2020 (27 pages).

Response by Merck Patent GmbH to Notice of Opposition in European patent No. 3180363 (European Patent Application No. 15750744.3) filed with the European Patent Office dated Nov. 20, 2020 (59 pages).

Uger RA et al., (2014) Poster Presentation by Trillium Therapeutics, Inc & StemCell Therapeutics, Inc.: "Cancer Immunotherapy Targeting CD47" Wild Type SIRPαFc is the Ideal CD47-Blocking Agent to Minimize Unwanted Erythrocyte Binding," AACR Annual Meeting Poster Session, San Diego, CA, American Association for Cancer Research, Philadelphia PA.

"Summons to Attend Oral Proceedings Pursuant to Rule 115(1)EPC," including Preliminary Nonbinding Opinion of the Opposition Division in Opposition of EP Patent No. 3180363 mailed from the European Patent Office dated Mar. 9, 2021 (7 pages).

\* cited by examiner

FIG. 26

```
            1          11         21         31         41         51
IgV(V1)   EEELQVIQPDKSVLVAAGETATLRCTATSLIPVGPIQWFRGAGPGRELIYNQKEGHFPRV
IgV(V2)   EEELQVIQPDKSVSVAAGESAILHCTVTSLIPVGPIQWFRGAGPARELIYNQKEGHFPRV
IgV(V3)   EEELQVIQPDKSVSVAAGESAILLCTVTSLIPVGPIQWFRGAGPARELIYNQKEGHFPRV
IgV(V4)   EEGLQVIQPDKSVSVAAGESAILHCTATSLIPVGPIQWFRGAGPGRELIYNQKEGHFPRV
IgV(V5)   EEELQVIQPDKFVLVAAGETATLRCTATSLIPVGPIQWFRGAGPGRELIYNQKEGHFPRV
IgV(V6)   EEELQVIQPDKSVLVAAGETATLRCTATSLIPVGPIQWFRGAGPGRELIYNQKEGHFPRV
IgV(V7)   EEELQVIQPDKSVSVAAGESAILHCTVTSLIPVGPIQWFRGAGPARELIYNQKEGHFPRV
IgV(V8)   EEELQVIQPDKSVLVAAGETATLRCTATSLIPVGPIQWFRGAGPARELIYNQKEGHFPRV
IgV(V9)   EEELQVIQPDKSVLVAAGETATLRCTATSLIPVGPIQWFRGAGPGRELIYNQKEGHFPRV
IgV(V10)  EEELQVIQPDKSVSVAAGESAILHCTVTSLIPVGPIQWFRGAGPARELIYNQKEGHFPRV 61         71         81         91        101        111
IgV(V1)   TTVSDLTKRNNMDFSIRIGNITPADAGTYYCVKFRKGSPDDVEFKSGAGTELSVR
IgV(V2)   TTVSESTKRENMDFSISISNITPADAGTYYCVKFRKGSPD-TEFKSGAGTELSVR
IgV(V3)   TTVSESTKRENMDFSISISNITPADAGTYYCVKFRKGSPD-TEFKSGAGTELSVR
IgV(V4)   TTVSDLTKRNNMDFSIRIGNITPADAGTYYCVKFRKGSPDDVEFKSGAGTELSVR
IgV(V5)   TTVSDLTKRNNMDFSIRIGNITPADAGTYYCVKFRKGSPDDVEFKSGAGTELSVR
IgV(V6)   TTVSDLTKRNNMDFPIRIGNITPADAGTYYCVKFRKGSPDDVEFKSGAGTELSVR
IgV(V7)   TTVSESTKRENMDFSISISNITPADAGTYYCVKFRKGSPD-TEFKSGAGTELSVR
IgV(V8)   TTVSESTKRENMDFSISISNITPADAGTYYCVKFRKGSPD-TEFKSGAGTELSVR
IgV(V9)   TTVSDLTKRNNMDFSIRISNITPADAGTYYCVKFRKGSPDDVEFKSGAGTELSVR
IgV(V10)  TTVSESTKRENMDFSISISNITPADAGTYYCVKFRKGSPD-TEFKSGAGTELSVR
```

SIRP-α IMMUNOGLOBULIN FUSION PROTEINS

CROSS-REFERENCE TO RELATED APPLICATIONS

This application claims priority to and the benefit of U.S. Provisional Patent Application No. 62/038,196, filed Aug. 15, 2014, the contents of which are incorporated by reference herein.

SEQUENCE LISTING

The instant application contains a Sequence Listing which has been submitted electronically in ASCII format and is hereby incorporated by reference in its entirety. Said ASCII copy, created on Sep. 24, 2015, is named EMD-003 SL.txt and is 603,918 bytes in size.

FIELD OF THE INVENTION

This invention relates generally to fusion proteins that have the ability to bind CD47 and a surface antigen on a disease promoting cell, such as a tumor cell.

BACKGROUND OF THE INVENTION

Macrophages are the principal phagocytes that clear diseased cells, such as cancer cells, by phagocytosis. Whether a macrophage phagocytoses a target cell or not depends on the relative strengths of the pro-phagocytic and anti-phagocytic signals.

Normal, healthy cells are spared from phagocytosis because the ubiquitously expressed CD47 on normal cells interacts with the signal regulatory protein alpha (SIRPα) on the macrophage triggering a self "don't eat me" signal.

However, as cancer cells adapt to enhance their survival, they subvert normal immune control mechanisms to escape immune surveillance by over-expressing CD47, rendering them resistant to macrophages. For example, CD47 has been shown to be upregulated on human leukemia cells in order to avoid phagocytosis (Jaiswal et al., Cell, 138:271-285, 2009). Furthermore, CD47 is highly expressed on human acute myeloid leukemia (AML) stem cells and is an adverse prognostic factor (Majeti et al., Cell, 138:266-299, 2009). CD47 overexpression as a survival mechanism partly explains why many therapeutic antibodies have limited anti-tumor efficacy despite the fact that antibody-opsonized tumor cells are expected to engage the activating Fc receptors (FcR) on immune cells to elicit antibody-dependent cellular phagocytosis (ADCP) and antibody-dependent cellular cytotoxicity (ADCC).

Accordingly, there is a need in the art for therapies that interfere with tumor cells' ability to avoid phagocytosis through expression of CD47.

SUMMARY OF THE INVENTION

Described herein are methods and compositions for targeting tumor cells with an immunoglobulin fusion protein specific for both a tumor cell antigen and CD47. Specifically, the immunoglobulin fusion protein includes an immunoglobulin moiety that is specific for a tumor cell antigen and has a second moiety that is specific for CD47.

In one aspect, the invention is directed to SIRPα immunoglobulin fusion proteins. The fusion protein includes an IgV extracellular domain of SIRPα or a SIRPα variant having an amino acid sequence at least 80% identical to residues 3-115 of SEQ ID NO:6 or to 3-114 of SEQ ID NO:8. The fusion protein also includes an immunoglobulin molecule or portion thereof that binds to a surface antigen on a disease promoting cell. In one embodiment, the disease promoting cell is a tumor cell and the surface antigen is a tumor antigen.

In certain embodiments, the immunoglobulin fusion protein includes a SIRPα variant with an amino acid sequence at least 85%, at least 90%, or at least 95% identical to residues 3-115 of SEQ ID NO:6 or to 3-114 of SEQ ID NO:8.

In certain embodiments, the immunoglobulin fusion protein includes a SIRPα variant with an amino acid sequence at least 80%, at least 85%, at least 90%, or at least 95% identical to residues 1-115 of SEQ ID NO:6 or to 1-114 of SEQ ID NO:8.

In some embodiments, the IgV extracellular domain is residues 1-115 of SEQ ID NO: 6, while in other embodiments, the IgV extracellular domain is residues 1-114 of SEQ ID NO:8. In some embodiments, the IgV extracellular domain is residues 3-115 of SEQ ID NO: 6 while in other embodiments, the IgV extracellular domain is residues 3-114 of SEQ ID NO:8. In yet other embodiments, the IgV extracellular domain is residues 1-114 of SEQ ID NO:193 or residues 1-115 of SEQ ID NO:194 or residues 1-115 of SEQ ID NO:195 or residues 1-115 of SEQ ID NO:196 or residues 1-114 of SEQ ID NO:197 or residues 1-114 of SEQ ID NO:198 or residues 1-115 of SEQ ID NO:199 or residues 1-114 of SEQ ID NO:200 or residues 1-115 of SEQ ID NO: 190.

In other embodiments, the SIRPα variant has an amino acid sequence at least 80%, at least 85%, at least 90%, or at least 95% identical to residues 1-343 of SEQ ID NO:6. In other embodiments, the IgV extracellular domain of SIRPα is a wild-type human SIRPα IgV extracellular domain.

In other embodiments, the SIRPα variant has an amino acid sequence at least 80%, at least 85%, at least 90%, or at least 95% identical to residues 1-114 of SEQ ID NO:193 or residues 1-115 of SEQ ID NO:194 or residues 1-115 of SEQ ID NO:195 or residues 1-115 of SEQ ID NO:196 or residues 1-114 of SEQ ID NO:197 or residues 1-114 of SEQ ID NO:198 or residues 1-115 of SEQ ID NO:199 or residues 1-114 of SEQ ID NO:200 or residues 1-115 of SEQ ID NO: 190.

In certain embodiments, the SIRPα variant of the immunoglobulin fusion protein has a modification to an amino acid at one or more of positions 6, 27, 31, 37, 54, 56, 66, or 72 corresponding to SEQ ID NO:6 or to SEQ ID NO:8. The modification may be a substitution, deletion, or insertion of an amino acid. In a preferred embodiment, the modification is a substitution.

In certain embodiments, the SIRPα variant of the immunoglobulin fusion protein includes one or more substitutions at positions corresponding to positions 6, 27, 31, 37, 54, 56, 66, or 72 of SEQ ID NO:6 or of SEQ ID NO:8 selected from the group consisting of: V6I, V27I, A27I, I31R, I31T, Q37W, Q37H, E54P, H56P, S66Q, L66A, and M72R. In one embodiment, the substitution corresponds to V6I. In another embodiment, the substitution corresponds to V27I or A27I. In another embodiment, the substitution corresponds to I31R. In another embodiment, the substitution corresponds to I31T. In another embodiment, the substitution corresponds to Q37W. In another embodiment the substitution corresponds to Q37H. In another embodiment, the substitution corresponds to E54P. In another embodiment, the substitution corresponds to H56P. In another embodiment, the substitution corresponds to S66Q or L66Q. In another embodiment, the substitution corresponds to M72R.

In certain embodiments, the SIRPα variant of the immunoglobulin fusion protein has a modification to an amino acid at one or more of positions corresponding to positions 4, 6, 27, 31, 35, 37, 47, 52, 53, 54, 56, 66, 67, 68, 72, 92 or 94 of SEQ ID NO:6 or of SEQ ID NO:8. The modification may be a substitution, deletion, or insertion of an amino acid. In a preferred embodiment, the modification is a substitution.

In certain embodiments, the SIRPα variant of the immunoglobulin fusion protein includes one or more of the following substitutions:

a. a substitution at a position corresponding to position 4 wherein the substitution is L4V;
b. a substitution at a position corresponding to position 6 selected from V6A, V6C, V6D, V6E, V6G, V6I, V6L, V6M, V6N, V6Q, V6S, or V6T;
c. a substitution at a position corresponding to position 27 selected from A27C, A27D, A27G, A27H, A27I, A27K, A27L, A27N, A27Q, A27R, A27S, A27T, or A27V; or V27A, V27C, V27D, V27G, V27H, V27I, V27K, V27L, V27N, V27Q, V27R, V27S, or V27T;
d. a substitution at a position corresponding to position 31 selected from I31A, I31C, I31E, I31K, I31Q, I31R, I31T, or I31V;
e. a substitution at a position corresponding to position 35 selected from P35A, P35C, P35E, P35G, P35N, P35Q, or P35S;
f. a substitution at a position corresponding to position 37 selected from Q37A, Q37C, Q37E, Q37G, Q37H, Q37K, Q37L, Q37M, Q37N, Q37R, Q37S, Q37T, or Q37W;
g. a substitution at a position corresponding to position 47 selected from E47A, E47C, E47D, E47F, E47G, E47H, E47I, E47K, E47L, E47M, E47N, E47Q, E47R, E47S, E47T, E47V, E47W, or E47Y;
h. a substitution at a position corresponding to position 52 selected from Q52A, Q52C, Q52E, Q52H or Q52M;
i. a substitution at a position corresponding to position 53 wherein the substitution is K53R;
j. a substitution at a position corresponding to position 54 selected from E54D or E54P;
k. a substitution at a position corresponding to position 56 selected from H56A, H56C, H56D, H56E, H56F, H56G, H56I, H56K, H56L, H56M, H56N, H56P, H56Q, H56R, H56S, H56T, H56V, H56W, or H56Y;
l. a substitution at a position corresponding to position 66 selected from L66A, L66C, L66D, L66E, L66F, L66G, L66H, L66I, L66K, L66M, L66N, L66P, L66Q, L66S, L66T, L66V, L66W, or L66Y; or S66A, S66C, S66D, S66E, S66F, S66G, S66H, S66I, S66K, S66L, S66M, S66N, S66P, S66Q, S66T, S66V, S66W, or S66Y;
m. a substitution at a position corresponding to position 67 selected from T67A, T67C, T67D, T67E, T67F, T67G, T67H, T67I, T67L, T67M, T67N, T67Q, T67R, T67S, T67V, T67W, or T67Y;
n. a substitution at a position corresponding to position 68 wherein the substitution is K68R
o. a substitution at a position corresponding to position 72 selected from M72A, M72C, M72D, M72E, M72F, M72G, M72H, M72I, M72K, M72L, M72N, M72Q, M72R, M72S, M72T, M72V, M72W, or M72Y;
p. a substitution at a position corresponding to position 92 selected from V92A, V92C, V92D, V92E, V92G, V92I, V92M, V92N, V92Q, V92R, V92S, or V92T; and/or
q. a substitution at a position corresponding to position 94 wherein the substitution is F94L.

In some embodiments, the SIRPα variant has a modification, preferably a substitution, that decreases the binding affinity of the SIRPα variant for CD47 as compared to wild-type SIRPα. In yet other embodiments, the SIRPα variant has a modification, preferably a substitution, that increases the binding affinity of the SIRPα variant for CD47 as compared to wild-type SIRPα.

In certain embodiments, the immunoglobulin molecule is an intact antibody, while in other embodiments, the immunoglobulin molecule is an antigen binding portion of an antibody. In yet another embodiment, the immunoglobulin molecule is a portion of an antibody that is an antibody variable domain. In some embodiments, the antibody variable domain is an antigen-binding fragment such as an Fab, Fab', F(ab')$_2$, Fv, scFv, single chain antibody, minibody, diabody, or single-domain antibody (nanobody). In one embodiment, the intact antibody is an anti-EGFR antibody, such as cetuximab.

In other embodiments, immunoglobulin molecule is an antigen binding portion of an antibody that is an Fc region, wherein the Fc region is engineered to contain an antigen binding site, for example, an Fcab moiety. In some embodiments, when the immunoglobulin molecule is an Fcab, the SIRPα or SIRPα variant is connected by its N-terminus to the immunoglobulin molecule, whereas in other embodiments the SIRPα or SIRPα variant is connected to the immunoglobulin molecule via its C-terminus.

In some embodiments, the SIRPα or SIRPα variant is connected by its N-terminus to the immunoglobulin molecule, whereas in other embodiments the SIRPα or SIRPα variant is connected via its C-terminus to the immunoglobulin molecule. In other embodiments, when the immunoglobulin molecule is an intact antibody, the SIRPα or SIRPα variant is connected to the C-terminus of the heavy chain, or the C-terminus of the light chain, and optionally, via a linker. In other embodiments, when the immunoglobulin molecule is an intact antibody, the SIRPα or SIRPα variant is connected to the N-terminus of the heavy chain, or the N-terminus of the light chain, and optionally, via a linker.

In yet other embodiments, the immunoglobulin molecule or portion thereof is connected to the SIRPα or SIRPα variant via a linker moiety. The linker moiety may be fused to the SIRPα or SIRPα variant at either the N-terminus or C-terminus of the SIRPα moiety.

In yet other embodiments, the immunoglobulin molecule or portion thereof is connected via its N-terminus to the SIRPα or SIRPα variant, optionally via a linker moiety, while in other embodiments, the immunoglobulin molecule or portion thereof is connected via its C-terminus to the SIRPα or SIRPα variant, optionally via a linker moiety. In other embodiments, the SIRPα or SIRPα variant is connected to the N-terminus of an antibody light chain or a portion thereof, while in another embodiment, the SIRPα or SIRPα variant is connected to the C-terminus of an antibody light chain or a portion thereof. In other embodiments, the SIRPα or SIRPα variant is connected to the N-terminus of an antibody heavy chain or a portion thereof, while in another embodiment, the SIRPα or SIRPα variant is connected to the C-terminus of an antibody heavy chain or a portion thereof. A linker between SIRPα or a SIRPα variant and an immunoglobulin molecule or portion thereof is contemplated in some embodiments.

In certain embodiments, the tumor antigen to which the immunoglobulin molecule or portion thereof binds is selected from HER2, HER3, EGFR, CD20, GD2, PD-L1, and CD19.

In another embodiment, the invention is directed to a SIRPα immunoglobulin fusion protein that includes an IgV extracellular domain of SIRPα or of a SIRPα variant having an amino acid sequence at least 80% identical to residues 1-115 of SEQ ID NO:190; and an immunoglobulin molecule or portion thereof that binds to a surface antigen on a disease promoting cell. The disease promoting cell may be a tumor cell and the surface antigen may be a tumor antigen.

In one embodiment, the SIRPα variant has an amino acid sequence at least 85%, at least 90%, or at least 95% identical to residues 1-115 of SEQ ID NO:190.

In another embodiment, the SIRPα variant has a modification to an amino acid at one or more positions corresponding to positions 6, 27, 31, 37, 54, 56, 66, or 72 of SEQ ID NO:190. In a further embodiment, the modification is selected from the group consisting of: V6I; V27I; A27I; I31R; I31T; Q37W; Q37H; E54P; H56P; S66Q; L66Q; and M72R.

In another embodiment, the invention is directed to a SIRPα immunoglobulin fusion protein that includes an anti-EGFR antibody or an antigen binding portion thereof and an IgV extracellular domain of SIRPα or of a SIRPα variant having an amino acid sequence at least 80% identical to residues 3-115 of SEQ ID NO:6 or to 3-114 of SEQ ID NO:8.

In a further embodiment, the SIRPα or of a SIRPα variant has an amino acid sequence at least 85% identical, at least 90% identical, or at least 95% identical to residues 3-115 of SEQ ID NO:6 or to 3-114 of SEQ ID NO:8.

In yet another embodiment, the SIRPα or of a SIRPα variant has an amino acid sequence at least 80% identical, at least 85% identical, at least 90% identical, or at least 95% identical to residues 1-115 of SEQ ID NO:6 or to 1-114 of SEQ ID NO:8.

In a further embodiment, the anti-EGFR antibody or antigen binding portion thereof contains the heavy chain variable region and light chain variable region from an antibody selected from cetuximab, panitumumab, nimotuzumumab, matuzumab, futuximab, imgatuzumab, or necitumumab. In yet another embodiment, the anti-EGFR antibody or antigen binding portion thereof contains the complementarity determining regions from an antibody selected from cetuximab, panitumumab, nimotuzumumab, matuzumab, futuximab, imgatuzumab, or necitumumab. In yet another embodiment, the anti-EGFR antibody or antigen binding portion thereof contains the heavy chain variable region and the light chain variable region from an antibody selected from cetuximab, panitumumab, nimotuzumumab, matuzumab, futuximab, imgatuzumab, or necitumumab. In yet a further embodiment, the anti-EGFR antibody is selected from cetuximab, panitumumab, nimotuzumumab, matuzumab, futuximab, imgatuzumab, or necitumumab. In another embodiment, the anti-EGFR antibody is cetuximab.

In another embodiment, the SIRPα or SIRPα variant is connected to the N-terminus of the heavy or light chain of the anti-EGFR antibody or antigen binding portion thereof, optionally via a linker. In another embodiment, the SIRPα or SIRPα variant is connected to the C-terminus of the heavy or light chain of the anti-EGFR antibody or antigen binding portion thereof, optionally via a linker.

In a further embodiment, the SIRPα-anti-EGFR immunoglobulin fusion protein includes an IgV extracellular domain of SIRPα or of a SIRPα variant having a modification at one or more of positions corresponding to positions 6, 27, 31,37, 54,56, 66 or 72 of SEQ ID NO:6 or SEQ ID NO:8. In one embodiment, the modification is a substitution corresponding to Q37W. In another embodiment, the modification is one or more substitutions corresponding to substitutions selected from V6I, C27I, A27I, I31R, Q37W, Q37H, E54P, H56P, S66Q, L66Q, and M72R.

In a further embodiment, the invention is directed to an immunoglobulin fusion protein having an immunoglobulin molecule or portion thereof that binds a tumor cell antigen and a CD47 binding moiety comprising an IgV extracellular domain of SIRPα or a SIRPα variant having an amino acid sequence at least 80% identical to residues 3-115 of SEQ ID NO:6 or 3-114 of SEQ ID NO:8. The fusion protein has a % red blood cell (RBC) binding mean fluorescence intensity (MFI) of 35% or less when % RBC binding MFI to an anti-CD47 antibody is calibrated at 100%. The anti-CD47 antibody is B6H12/huIgG1. The fusion protein also binds to CD47 on a non-red blood cell. The non-red blood cell, in one embodiment, is a tumor cell.

In some embodiments, the immunoglobulin fusion protein has an IgV extracellular domain of SIRPα or a SIRPα variant having an amino acid sequence at least 85%, at least 90%, at least 95% identical to residues 3-115 of SEQ ID NO:6 or 3-114 of SEQ ID NO:8.

In some embodiments, the immunoglobulin fusion protein has an IgV extracellular domain of SIRPα or a SIRPα variant having an amino acid sequence at least 80%, at least 85%, at least 90%, at least 95% identical to residues 1-115 of SEQ ID NO:6 or 1-114 of SEQ ID NO:8.

In some embodiments, the tumor cell antigen is EGFR. In some embodiments, the immunoglobulin molecule is an intact antibody. For example, the intact antibody is an anti-EGFR antibody in some embodiments, while in certain embodiments the anti-EGFR-antibody is cetuximab.

In one embodiment, the fusion protein has a % RBC binding MFI of less than 30%, less than 25%, less than 20%, less than 15%, less than 10%, less than 5%, less than 4%, less than 3%, less than 2%, or less than 1%. In one embodiment, the % RBC binding MFI is less than 10%.

In yet another embodiment, the fusion protein has a % RBC binding MFI of between 0-1%, 0-2%, 0-3%, 0-4%, 1-2%, 1-3%, 1-4%, 2-3%, 2-4%, 3-4%, 3-7%, 3-10% or 5-10%.

In yet another embodiment, the fusion protein has a % RBC binding MFI of 5% or less, 4% or less, 3% or less, 2% or less, or 1% or less.

In a further embodiment, the antibody moiety is an anti-EGFR antibody. For example, the anti-EGFR antibody is cetuximab, whereas in another embodiment, the anti-EGFR antibody is panitumumab, nimotuzumumab, matuzumab, futuximab, imgatuzumab, or necitumumab.

In another aspect, the invention includes nucleic acids encoding the SIRPα immunoglobulin fusion proteins described herein. Because immunoglobulin fusion proteins described herein may require assembly of two or more peptide chains, the invention contemplates the nucleic acids required to encode the individual peptide chains that upon expression assemble to form the fusion protein. In another aspect, the invention includes a cell comprising a nucleic acid or the nucleic acids encoding an immunoglobulin fusion protein as described herein. In yet another aspect, the invention includes a method of producing an immunoglobulin fusion protein by maintaining such a cell under conditions that permit expression of the nucleic acid or nucleic acids encoding an immunoglobulin fusion protein of the invention.

In a further aspect, the invention is directed to pharmaceutical compositions that include pharmaceutically effective amounts of an immunoglobulin fusion protein described herein including a pharmaceutically acceptable carrier.

In yet a further aspect, the invention is directed to methods of treating cancer by administering an effective amount of an immunoglobulin fusion protein described herein. The cancers that can be treated include breast, colorectal, lung, pancreatic, endometrial, ovarian, gastric, prostate, renal, cervical, myeloma, lymphoma, leukemia, thyroid, uterine, bladder, neuroendocrine, head and neck, liver, nasopharyngeal, testicular, small cell lung cancer, non-small cell lung cancer, melanoma, basal cell skin cancer, squamous cell skin cancer, dermatofibrosarcoma protuberans, Merkel cell carcinoma, glioblastoma, glioma, sarcoma, mesothelioma, or myelodisplastic syndromes.

BRIEF DESCRIPTION OF THE DRAWINGS

FIG. 1A shows two schematic diagrams of DNA constructs for the expression of an antibody-SIRPα fusion protein. DNA construct 1 (top) encodes the heavy chain variable domain of the antibody (VH) followed by heavy chain constant domains (CH1, hinge (H)-CH2-CH3) genetically fused via an optional linker (L) to SIRPα. DNA construct 2 (bottom) encodes the light chain variable domain of the antibody (VL) followed by light chain constant domain (CL).

FIG. 1O is a schematic drawing of a SIRPα-Fcab showing the dimeric structure comprising the polypeptide component encoded by the DNA construct shown in FIG. 1N. Interchain disulfide bonds are depicted as short bars between two polypeptide chains. The linker is optional.

FIG. 6B discloses "(G4S)$_3$," as SEQ ID NO: 203, "(G4S)$_4$," as SEQ ID NO: 201 and "(G4S)$_5$ as SEQ ID NO: 204.

FIG. 7A discloses "(G4S)$_3$," as SEQ ID NO: 203, "(G4S)$_4$," as SEQ ID NO: 201 and "(G4S)$_5$ as SEQ ID NO: 204.

FIG. 8 discloses "(G4S)$_4$," as SEQ ID NO: 201.

FIG. 15 discloses "(G4S)$_4$," as SEQ ID NO: 201.

FIGS. 17A and 17B disclose "(G4S)$_4$," as SEQ ID NO: 201.

FIG. 26 shows an alignment of the IgV domain of known human SIRPα alleles: IgV (V1) (residues 1-115 of SEQ ID NO:6), IgV (V2) (SEQ ID NO:8), IgV (V3) (SEQ ID NO:193), IgV (V4) (SEQ ID NO:194), IgV (V5) (SEQ ID NO:195), IgV (V6) (SEQ ID NO:196), IgV (V7) (SEQ ID NO:197), IgV (V8) (SEQ ID NO:198), IgV (V9) (SEQ ID NO:199), and IgV (V10) (SEQ ID NO:200).

DETAILED DESCRIPTION OF THE INVENTION

Figure 1A:
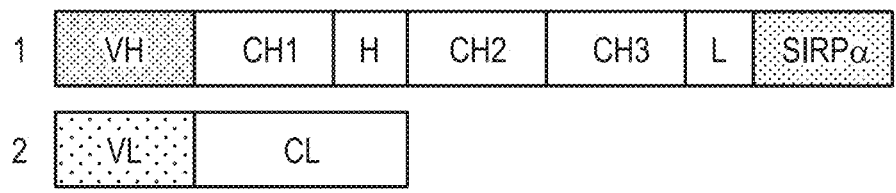
FIGS. 1A-O schematically illustrate the different DNA and protein constructs of the fusion proteins of the invention.

The present invention is directed to immunoglobulin fusion proteins with enhanced tumor targeting and effector functions. Generally, immunoglobulin fusion proteins of the invention include a CD47 binding agent moiety and an immunoglobulin moiety. The immunoglobulin moiety binds to a surface antigen on a disease promoting cell, while the CD47 binding agent moiety binds to CD47 on the same cell. In one embodiment, the invention involves genetically joining a tumor-specific immunoglobulin moiety to a moiety that binds CD47. The preferred CD47 binding agent is SIRPα or a variant of SIRPα. Accordingly, certain embodiments of the invention are directed to immunoglobulin fusion proteins that bind to tumor cells expressing CD47.

CD47 is ubiquitously expressed on all human cells. Although tumor cells, especially cancer stem cells, express higher levels of CD47, hematopoietic stem cells also overexpress CD47. Therefore, SIRPα, a SIRPα variant, or another CD47 binding agent with sufficient binding affinity for CD47 is unlikely to discriminate between cancer cells and normal cells, including red blood cells, which are present in circulation at 5 billion cells/mL and occupy about half of the blood volume. Accordingly, the immunoglobulin fusion proteins of the present invention are designed to have high affinity binding to a tumor antigen on tumor cells and low binding affinity for CD47. This results in weak binding of the immunoglobulin fusion protein to CD47 on normal cells. This way, the immunoglobulin fusion proteins are designed to not target normal cells, thereby circumventing the toxicity to normal cells resulting from ubiquitous expression of CD47 and also preventing the ubiquitously expressed CD47 on normal cells from becoming a drug sink for anti-CD47 therapy which would otherwise result in unfavorable pharmacokinetics that would be incompatible with the once weekly or once biweekly regiment typical for antibody therapy. For this reason, it is preferred that the fusion moiety bind CD47 with low affinity while still blocking CD47's ability to interact with SIRPα.

The immunoglobulin fusion proteins of the invention (1) have high binding affinity for a tumor-specific antigen on a tumor cell; (2) achieve enhanced tumor targeting through additional avidity provided by low affinity binding of the fusion moiety to CD47 on the same tumor cell; (3) elicit potent ADCP and ADCC through a combination of blockade of the CD47 "don't eat me" signal and Fc-dependent activation of immune effector cells; and (4) avoid toxicity by low affinity binding to CD47 on normal cells, including red blood cells. Importantly, the ADCC/ADCP induced toxicity to normal cells is further lowered when the CD47 binder, e.g., SIRPα or a SIRPα variant, is joined to the Fc region of the antibody moiety in a configuration that is not optimal for FcR engagement, e.g., the X-Fc configuration, which has an amino-to-carboxyl orientation similar to that of a native antibody, elicits higher ADCC activity than the Fc-X configuration.

According to the present invention, the targeting specificity of the immunoglobulin fusion protein is driven primarily by the binding of an antibody moiety to its cognate tumor-specific antigen rather than CD47, a ubiquitously expressed antigen. Moreover, the targeting specificity is further enhanced by an avidity effect provided by binding in cis of the fusion partner to CD47 overexpressed on the tumor cell. Successful bispecific targeting in cis depends critically on the relative receptor density and the physical location of the two targets on the cell surface. Such enhanced tumor targeting should offer a better therapeutic index in terms of both superior efficacy and safety, when compared to anti-CD47 antibodies and other CD47 blockade agents.

CD47 Binding Agents

Immunoglobulin fusion proteins of the invention include a moiety that is capable of binding CD47. In one embodiment, CD47 binding agents include antibodies to CD47. In other embodiments, CD47 binding agents are non-antibody proteins or molecules that have binding affinity for CD47, for example, ligands that bind the CD47 receptor. For example, in one embodiment, the CD47 binding agent portion of the fusion protein is an anti-CD47 antibody. In a preferred embodiment, the CD47 binding agent is SIRPα, SIRPα variant, or an affinity optimized variant of SIRPα.

"SIRPα" refers to wild-type signal-regulatory protein alpha or an amino acid sequence of a recombinant or non-recombinant polypeptide having the amino acid sequence of wild-type signal-regulatory protein alpha or a native or naturally occurring allelic variant of signal-regulatory protein alpha. In one embodiment, SIRPα is a wild-type mammalian SIRPα, whereas in a preferred embodiment, SIRPα is a wild-type human SIRPα. The amino acid sequence for the mature form of the predominant wild type human SIRPα (SIRPαV1) is provided in Table 4 as SEQ ID NO:6. In one embodiment, SIRPα includes a signal sequence, whereas in another embodiment, SIRPα refers to the mature form of the protein.

According to one embodiment, a SIRPα is a SIRPα extracellular domain, i.e., a SIRPα protein engineered to exclude the transmembrane and cellular domain. In another embodiment, a SIRPα includes at least the extracellular domain. In one embodiment, the SIRPα protein is a human SIRPα extracellular domain. The sequence of the wild-type SIRPαV1's extracellular domain is residues 1-343 of SEQ ID NO:6.

In yet another embodiment, a SIRPα is a SIRPα IgV domain of the extracellular domain. In one embodiment, a SIRPα IgV domain is a human SIRPα IgV domain. For example, in one embodiment, a SIRPα IgV domain is residues 1-115 of SEQ ID NO:6, while in another embodiment, a SIRPα IgV is residues 1-114 of SEQ ID NO:8, while in yet another embodiment, a SIRPα IgV is residues 3-115 or SEQ ID NO:6, while in yet another embodiment a SIRPα IgV is residues 3-114 of SEQ ID NO:8. In another embodiment, a SIRPα IgV domain is residues 1-114 of SEQ ID NO:193. In another embodiment, a SIRPα IgV domain is residues 1-115 of SEQ ID NO:194. In another embodiment, a SIRPα IgV domain is residues 1-115 of SEQ ID NO:195. In another embodiment, a SIRPα IgV domain is residues 1-115 of SEQ ID NO:196. In another embodiment, a SIRPα IgV domain is residues 1-114 of SEQ ID NO:197. In another embodiment, a SIRPα IgV domain is residues 1-114 of SEQ ID NO:198. In another embodiment, a SIRPα IgV domain is residues 1-115 of SEQ ID NO:199. In another embodiment, a SIRPα IgV domain is residues 1-114 of SEQ ID NO:200. In yet another embodiment, a SIRPα includes at least the SIRPα IgV domain of the extracellular domain.

The invention also includes "variants" of SIRPα. A "variant" of SIRPα is defined as a SIRPα amino acid sequence that is altered by one or more amino acids as compared to wild-type SIRPα. The variant may have "conservative" changes, wherein a substituted amino acid has similar structural or chemical properties, e.g., replacement of leucine with isoleucine. More rarely, a variant can have "nonconservative" changes, e.g., replacement of a glycine with a tryptophan. Similar minor variations can also include amino acid deletions or insertions, or both.

In one embodiment, SIRPα variants include polypeptides that have at least about 70%, 75%, 80%, 81%, 82%, 83%, 84%, 85%, 86%, 87%, 88%, 89%, 90%, 91%, 92%, 93%, 94%, 95%, 96%, 97%, 98%, 99%, or more sequence identity with wild-type SIRPα.

In another embodiment, SIRPα variants include polypeptides that have at least about 70%, 75%, 80%, 81%, 82%, 83%, 84%, 85%, 86%, 87%, 88%, 89%, 90%, 91%, 92%, 93%, 94%, 95%, 96%, 97%, 98%, 99%, or more sequence identity with a wild-type SIRPα extracellular domain. In one embodiment, SIRPα variants include polypeptides that have at least about 70%, 75%, 80%, 81%, 82%, 83%, 84%, 85%, 86%, 87%, 88%, 89%, 90%, 91%, 92%, 93%, 94%, 95%, 96%, 97%, 98%, 99%, or more sequence identity with residues 1-343 of SEQ ID NO:6.

In yet another embodiment, SIRPα variants include polypeptides that have at least about 70%, 75%, 80%, 81%, 82%, 83%, 84%, 85%, 86%, 87%, 88%, 89%, 90%, 91%, 92%, 93%, 94%, 95%, 96%, 97%, 98%, 99%, or more sequence identity with the IgV domain of a wild-type SIRPα extracellular domain, for example, residues 1-115 of SEQ ID NO:6 in one embodiment, residues 1-114 of SEQ ID NO:8 in another embodiment, residues 1-114 of SEQ ID NO: 193 in yet another embodiment, 1-115 of SEQ ID NO: 194 in yet another embodiment, 1-115 of SEQ ID NO: 195 in yet another embodiment, 1-115 of SEQ ID NO: 196 in yet another embodiment, 1-114 of SEQ ID NO: 197 in yet another embodiment, 1-114 of SEQ ID NO: 198 in yet another embodiment, 1-115 of SEQ ID NO: 199 in yet another embodiment, or 1-114 of SEQ ID NO:200 in yet another embodiment. In one particular embodiment, SIRPα variants include polypeptides that have at least about 70%, 75%, 80%, 81%, 82%, 83%, 84%, 85%, 86%, 87%, 88%, 89%, 90%, 91%, 92%, 93%, 94%, 95%, 96%, 97%, 98%, 99%, or more sequence identity with the IgV domain of a residues 1-115 of SEQ ID NO:6. In another embodiment, SIRPα variants include polypeptides that have at least about 70%, 75%, 80%, 81%, 82%, 83%, 84%, 85%, 86%, 87%, 88%, 89%, 90%, 91%, 92%, 93%, 94%, 95%, 96%, 97%, 98%, 99%, or more sequence identity with the IgV domain of a residues 1-114 of SEQ ID NO:8. In another embodiment, SIRPα variants include polypeptides that have at least about 70%, 75%, 80%, 81%, 82%, 83%, 84%, 85%, 86%, 87%, 88%, 89%, 90%, 91%, 92%, 93%, 94%, 95%, 96%, 97%, 98%, 99%, or more sequence identity with the IgV domain of a residues 1-114 of SEQ ID NO:193. In another embodiment, SIRPα variants include polypeptides that have at least about 70%, 75%, 80%, 81%, 82%, 83%, 84%, 85%, 86%, 87%, 88%, 89%, 90%, 91%, 92%, 93%, 94%, 95%, 96%, 97%, 98%, 99%, or more sequence identity with the IgV domain of a residues 1-115 of SEQ ID NO:194. In another embodiment, SIRPα variants include polypeptides that have at least about 70%, 75%, 80%, 81%, 82%, 83%, 84%, 85%, 86%, 87%, 88%, 89%, 90%, 91%, 92%, 93%, 94%, 95%, 96%, 97%, 98%, 99%, or more sequence identity with the IgV domain of a residues 1-115 of SEQ ID NO:195. In another embodiment, SIRPα variants include polypeptides that have at least about 70%, 75%, 80%, 81%, 82%, 83%, 84%, 85%, 86%, 87%, 88%, 89%, 90%, 91%, 92%, 93%, 94%, 95%, 96%, 97%, 98%, 99%, or more sequence identity with the IgV domain of a residues 1-115 of SEQ ID NO:196. In another embodiment, SIRPα variants include polypeptides that have at least about 70%, 75%, 80%, 81%, 82%, 83%, 84%, 85%, 86%, 87%, 88%, 89%, 90%, 91%, 92%, 93%, 94%, 95%, 96%, 97%, 98%, 99%, or more sequence identity with the IgV domain of a residues 1-114 of SEQ ID NO:197. In another embodiment, SIRPα variants include polypeptides that have at least about 70%, 75%, 80%, 81%, 82%, 83%, 84%, 85%, 86%, 87%, 88%, 89%, 90%, 91%, 92%, 93%, 94%, 95%, 96%, 97%, 98%, 99%, or more sequence identity with the IgV domain of a residues 1-114 of SEQ ID NO:198. In another embodiment, SIRPα variants include polypeptides that have at least about 70%, 75%, 80%, 81%, 82%, 83%, 84%, 85%, 86%, 87%, 88%, 89%, 90%, 91%, 92%, 93%, 94%, 95%, 96%, 97%, 98%, 99%, or more sequence identity with the IgV domain of a residues 1-115 of SEQ ID NO:199. In another embodiment, SIRPα variants include polypeptides that have at least about 70%, 75%, 80%, 81%, 82%, 83%, 84%, 85%, 86%, 87%, 88%, 89%, 90%, 91%, 92%, 93%, 94%, 95%, 96%, 97%, 98%, 99%, or more sequence identity with the IgV domain of a residues 1-114 of SEQ ID NO:200. In another embodiment, SIRPα variants include polypeptides that have at least about 70%, 75%, 80%, 81%, 82%, 83%, 84%, 85%, 86%, 87%, 88%, 89%, 90%, 91%, 92%, 93%, 94%, 95%, 96%, 97%, 98%, 99%, or more sequence identity with the IgV domain of a residues 1-114 of SEQ ID NO:190. SEQ ID NO:190 is a consensus sequence of ten known human SIRPα IgV domains.

To determine the percent identity of two amino acid sequences or of two nucleic acids, the sequences are aligned for optimal comparison purposes (e.g., gaps can be introduced in the sequence of a first amino acid or nucleic acid sequence for optimal alignment with a second amino acid or nucleic acid sequence). The percent identity between the two sequences is a function of the number of identical positions shared by the sequences (i.e., % homology=(# of identical positions/total # of positions)times 100). The determination of percent homology between two sequences can be accomplished using a mathematical algorithm. A non-limiting example of a mathematical algorithm utilized for the comparison of two sequences is the algorithm of Karlin and Altschul, (1990) Proc. Natl. Acad. Sci. USA, 87:2264-68, modified as in Karlin and Altschul, (1993) Proc. Natl. Acad. Sci. USA, 90:5873-77. Such an algorithm is incorporated into the NBLAST and XBLAST programs of Altschul et al., (1990) J. Mol. Biol., 215:403-10. BLAST nucleotide searches can be performed with the NBLAST program, score=100, wordlength=12. BLAST protein searches can be performed with the XBLAST program, score=50, wordlength=3. To obtain gapped alignments for comparison purposes, Gapped BLAST can be utilized as described in Altschul et al., (1997) Nucleic Acids Research, 25(17):3389-3402. When utilizing BLAST and Gapped BLAST programs, the default parameters of the respective programs (e.g., XBLAST and NBLAST) can be used.

In some embodiments, a SIRPα variant includes one or more mutations in the variable domain of the extracellular domain as compared to wild-type SIRPα. Mutations contemplated by the invention are described below and are also provided in Tables 1 and 2 found in Example 16 below, as well as in Table 3 found in Example 17 below.

In one embodiment, a SIRPα variant of the invention has a modification to an amino acid a position corresponding to one or more of positions 6, 27, 31, 37, 54, 56, 66, or 72 corresponding to SEQ ID NO:6 or to SEQ ID NO:8 or to SEQ ID NO:190. The modification may be a deletion, substitution, or insertion. In a preferred embodiment, the modification is a substitution. In other embodiments, the SIRPα variant has a modification to an amino acid at two or more, at three or more, at four or more, at five or more, at six or more, at seven or more, or at eight positions corresponding to positions 6, 27, 31, 37, 54, 56, 66, or 72 corresponding to SEQ ID NO:6 or to SEQ ID NO:8 or to SEQ ID NO:190.

In a further embodiment, a SIRPα variant of the invention has one or more substitutions as follows: V6I, V27I, A27I, I31R, I31T, Q37W, Q37H, E54P, H56P, S66Q, L66A, and M72R. In one embodiment, the substitution corresponds to V6I. In another embodiment, the substitution corresponds to V27I or A27I. In another embodiment, the substitution corresponds to I31R. In another embodiment, the substitution corresponds to I31T. In another embodiment, the substitution corresponds to Q37W. In another embodiment the substitution corresponds to Q37H. In another embodiment, the substitution corresponds to E54P. In another embodiment, the substitution corresponds to H56P. In another embodiment, the substitution corresponds to S66Q or L66Q. In another embodiment, the substitution corresponds to M72R.

In one embodiment, a SIRPα variant of the invention has a modification to an amino acid at one or more positions corresponding to positions 4, 6, 27, 31, 35, 37, 47, 52, 53, 54, 56, 66, 67, 68, 72, 92 or 94 of SEQ ID NO:6 or of SEQ ID NO:8 or of SEQ ID NO:190. The modification may be a deletion, substitution, or insertion. In a preferred embodiment, the modification is a substitution. In other embodiments, the SIRPα variant has a modification to an amino acid at two or more, at three or more, at four or more, at five or more, at six or more, at seven or more, at eight or more, at nine or more, at ten or more, at eleven or more, at twelve or more, at thirteen or more, at fourteen or more, at fifteen or more, at sixteen or more, or at seventeen positions corresponding to positions 4, 6, 27, 31, 35, 37, 47, 52, 53, 54, 56, 66, 67, 68, 72, 92 or 94 of SEQ ID NO:6 or of SEQ ID NO:8 or of SEQ ID NO:190.

In a further embodiment, a SIRPα variant of the invention has one or more substitutions as follows:
a. a substitution at a position corresponding to position 4 wherein the substitution is L4V;
b. a substitution at a position corresponding to position 6 selected from V6A, V6C, V6D, V6E, V6G, V6I, V6L, V6M, V6N, V6Q, V6S, or V6T;
c. a substitution at a position corresponding to position 27 selected from A27C, A27D, A27G, A27H, A27I, A27K, A27L, A27N, A27Q, A27R, A27S, A27T, or A27V; or V27A, V27C, V27D, V27G, V27H, V27I, V27K, V27L, V27N, V27Q, V27R, V27S, or V27T;
d. a substitution at a position corresponding to position 31 selected from I31A, I31C, I31E, I31K, I31Q, I31R, I31T, or I31V;
e. a substitution at a position corresponding to position 35 selected from P35A, P35C, P35E, P35G, P35N, P35Q, or P35S;
f. a substitution at a position corresponding to position 37 selected from Q37A, Q37C, Q37E, Q37G, Q37H, Q37K, Q37L, Q37M, Q37N, Q37R, Q37S, Q37T, or Q37W;
g. a substitution at a position corresponding to position 47 selected from E47A, E47C, E47D, E47F, E47G, E47H, E47I, E47K, E47L, E47M, E47N, E47Q, E47R, E47S, E47T, E47V, E47W, or E47Y;
h. a substitution at a position corresponding to position 52 selected from Q52A, Q52C, Q52E, Q52H or Q52M;
i. a substitution at a position corresponding to position 53 wherein the substitution is K53R;
j. a substitution at a position corresponding to position 54 selected from E54D or E54P;
k. a substitution at a position corresponding to position 56 selected from H56A, H56C, H56D, H56E, H56F, H56G, H56I, H56K, H56L, H56M, H56N, H56P, H56Q, H56R, H56S, H56T, H56V, H56W, or H56Y;
l. a substitution at a position corresponding to position 66 selected from L66A, L66C, L66D, L66E, L66F, L66G, L66H, L66I, L66K, L66M, L66N, L66P, L66Q, L66S, L66T, L66V, L66W, or L66Y; or S66A, S66C, S66D, S66E, S66F, S66G, S66H, S66I, S66K, S66L, S66M, S66N, S66P, S66Q, S66T, S66V, S66W, or S66Y;
m. a substitution at a position corresponding to position 67 selected from T67A, T67C, T67D, T67E, T67F, T67G, T67H, T67I, T67L, T67M, T67N, T67Q, T67R, T67S, T67V, T67W, or T67Y;
n. a substitution at a position corresponding to position 68 wherein the substitution is K68R
o. a substitution at a position corresponding to position 72 selected from M72A, M72C, M72D, M72E, M72F, M72G, M72H, M72I, M72K, M72L, M72N, M72Q, M72R, M72S, M72T, M72V, M72W, or M72Y;
p. a substitution at a position corresponding to position 92 selected from V92A, V92C, V92D, V92E, V92G, V92I, V92M, V92N, V92Q, V92R, V92S, or V92T; and/or
q. a substitution at a position corresponding to position 94 wherein the substitution is F94L.

To determine the affinity of a SIRPα variant for binding CD47, surface plasmon resonance (SPR) may be used. In an exemplary protocol, purified goat anti-human IgG Fc (Jackson Immuno Research Laboratories) is immobilized onto the CM5 chip using amine coupling chemistry using a Biacore 4000 instrument (GE Healthcare). Biacore CM-5 chips, ethanolamine, NHS/EDC coupling reagents and buffers are obtained from Biacore (GE Healthcare). The immobilization steps are carried out at a flow rate of 30 µl/min in HEPES buffer (20 mM HEPES, 150 mM NaCl, 3.4 mM EDTA and 0.005% P20 surfactant). The sensor surfaces are activated for 7 min with a mixture of NHS (0.05 M) and EDC (0.2 M). The goat anti-human IgG Fc is injected at a concentration of ~30 µg/ml in 10 mM sodium acetate, pH 5.0, for 7 min. Ethanolamine (1 M, pH 8.5) is injected for 7 min to block any remaining activated groups. An average of 12,000 response units (RU) of capture antibody is immobilized on each flow cell. Kinetic binding experiments are performed using the same HEPES buffer (20 mM HEPES, 150 mM NaCl, 3.4 mM EDTA and 0.005% P20 surfactant) and are equilibrated at 25° C. Kinetic data are collected by injecting SIRPα variants at 0.5 and 1 µg/ml for two minutes at a flow rate of 30 µl/min, followed by a buffer wash for 30 s at the same flow rate. Human CD47-His is bound at different concentrations for 3 min followed by a dissociation step for 10 min at the 30 µl/min flow rate. The data are fit using a 1:1 Langmuir binding model with the BIA evaluation software. Kinetic rate constants are determined from the fits of the association and dissociation phases, and the $K_D$ is derived from the ratio of these constants.

In an alternative method to determine the avidity of a SIRPα variant for binding CD47, a cell binding assay may be used. In an exemplary protocol, $2 \times 10^5$ Chinese hamster ovary (CHO) cells transfected with CD47 per well are incubated with varying concentrations of antibodies diluted in PBS+1% FBS in a 96 well plate for 60 min on ice. After washing with PBS+1% FBS, cells are incubated with FITC F(ab')2 goat Anti-Human IgG, Fcγ (Jackson ImmunoResearch, West Grove, Pa.) diluted 1:200 in PBS+1% FBS for 60 min on ice. After washing again, cells are fixed with 1% formaldehyde in PBS. Cells are analyzed by flow cytometry (MACSQuant, Miltenyi Biotec, Cologne, Germany). An EC50 is calculated by fitting data to a sigmoidal curve (log(agonist) vs. response—Variable slope (four parameters)) with Graph Pad Prism.

When these mutations are introduced into SIRPα or a fusion protein comprising SIRPα, the resulting variant generally has enough SIRPα biological activity to be useful as a therapeutic protein. In some embodiments, the biological activity of the SIRPα variant is at least 0.01 fold, 0.03 fold, 0.06 fold, 0.1 fold, 0.3 fold, 0.6 fold, 1 fold, 3 fold, 5, fold, 6 fold, 10 fold, 20 fold, 30 fold, 40 fold, 50 fold, 60 fold or 100 fold of the biological activity of wild type SIRPα or a fusion protein containing wild-type SIRPα. Biological activity of the SIRPα variants of the invention can be tested in an in-vitro or in-vivo assay. In-vitro assays to determine the biological activity of SIRPα on a cell expressing CD47 are well established in the art. For example, the biological activity may be determined in a leukocyte transmigration assay, as described by Liu et. al. (J. Mol. Bio., 365:680, 2007).

Immunoglobulin Moieties

As used herein, the term "antibody" means an intact antibody (e.g., an intact monoclonal antibody). In some embodiments, an "antibody" includes an antigen-binding fragment of an antibody. Antigen-binding fragments include Fab, Fab', F(ab')2, Fv, single chain antibodies (e.g., scFv), minibodies, diabodies, and single-domain antibodies ("sdAb" or "nanobodies" or "camelids"). In yet other embodiments, an antibody includes an intact antibody or antigen-binding fragment of an antibody (e.g., a phage display antibody including a fully human antibody, a semisynthetic antibody or a fully synthetic antibody) that has been optimized, engineered or chemically conjugated. Examples of antibodies that have been optimized are affinity-matured antibodies. Examples of antibodies that have been engineered are Fc optimized antibodies, and multispecific antibodies (e.g., bispecific antibodies). An antibody conjugated to a toxin moiety is an example of a chemically conjugated antibody. In some embodiments, antibodies may be IgG1, IgG2, IgG3, IgG4, IgM, IgE, IgD, or IgA.

As used herein, the term "immunoglobulin" or "immunoglobulin molecule" means an antibody or antigen binding fragment of an antibody as defined herein, but also includes portions of an antibody, such as a heavy chain or light chain variable or constant region. Examples of portions of an immunoglobulin include CH1, CH2, CH3, hinge, VH1, CL and VL domains as well as an Fc region. Further, "immunoglobulin" includes an Fc fragment or region that has been engineered to include an antigen binding site ("Fcab"). For example, in one embodiment, the immunoglobulin fusion protein of the invention includes an "Fcab" moiety with binding specificity for a tumor antigen. "Fcabs" are discussed in the art, for example, in WO2008/003103 and WO2012/007167. Further, Example 15 provides an example of an immunoglobulin fusion protein of the invention where the immunoglobulin moiety is an Fcab to HER2. In some embodiments, "immunoglobulin" includes engineered antibodies where further variable or constant heavy or light chain regions are added to an otherwise intact antibody, or where variable or constant regions are relocated or rearranged from an original position to a new position within an antibody. For example, FIG. 1E shows an immunoglobulin that is a tetravalent bispecific antibody, i.e., an antibody engineered to include a second variable region. One example of relocation or rearrangement is shown in FIG. 1I where the immunoglobulin portion is an Fc region fused to the heavy chain variable domain of antibody (VH) followed by heavy chain constant domain 1 (CH1), and an upper hinge region (H).

According to the present invention, the fusion moiety, for example, SIRPα, can be genetically joined to the immunoglobulin in a way that does not adversely affect the binding of the antibody to the tumor antigen. Preferably, the fusion moiety is joined to the Fc in a configuration that is not optimal for FcR engagement, resulting in diminished ADCC/ADCP activities on normal cells. In some embodiments, the Fc region retains or has modified FcR binding capability. Human antibody fragments (e.g., parental and optimized variants) can be engineered to contain certain constant (i.e., Fc) regions with a specified effector function (e.g., antibody-dependent cellular cytotoxicity (ADCC)). Human constant regions are known in the art.

Fragments of antibodies that have the same or comparable binding characteristics to those of the whole antibody may also be present. Such fragments may contain one or both Fab fragments or the F(ab')$_2$ fragment. The antibody fragments may contain all six CDRs of the whole antibody, although fragments containing fewer than all of such regions, such as three, four or five CDRs, are also functional.

According to the present invention, the immunoglobulin moiety of the immunoglobulin fusion protein in one embodiment is an intact antibody. In yet another embodiment, the immunoglobulin moiety is a tetravalent bispecific antibody. This embodiment is exemplified, for example, in FIG. 1E. In certain embodiments, the SIRPα moiety is fused to the C-terminus of the heavy chain, for example, in FIG. 1B or FIG. 1M, while in other embodiments, the SIRPα moiety is fused to the C-terminus of the light chain, for example, in FIG. 1G. The SIRPα moiety may be fused to the immunoglobulin moiety by an optional linker.

In still a further embodiment, the immunoglobulin moiety is an Fc engineered to include at its C-terminus VH and CH1 domains, with the light chain binding to the heavy chain variable region, for example, in FIG. 1I. In some embodiments, the SIRPα moiety is fused to the N-terminus of the Fc portion, optionally via a linker. In other embodiments, the SIRPα moiety is fused to the C-terminus of the light chain or the C-terminus of heavy chain, optionally via a linker.

In yet another embodiment, the immunoglobulin moiety is an Fc joined at its C-terminus to an scFv. This embodiment is exemplified, for example, in FIG. 1K. In such an embodiment, the SIRPα moiety may be fused to the N-terminus of the Fc region, optionally via a linker. In yet another embodiment, the immunoglobulin moiety is an scFv joined at its C-terminus to an Fc region. This embodiment is exemplified, for example, in FIG. 1M. In such an embodiment, the SIRPα moiety may be fused the C-terminus of the Fc region, optionally via a linker.

In a further embodiment, the immunoglobulin moiety is an Fc region engineered to include an antigen binding domain. For example, in some embodiments, the Fc region is an Fcab region which is an Fc region engineered, for example, to include an antigen binding domain in the CH3 domain. This embodiment, is exemplified, for example in FIG. 1O. In some embodiments, the SIRPα moiety may be fused to the N-terminus of the Fc or Fcab region, optionally via a linker, while in other embodiments, the SIRPα moiety may be fused to the C-terminus, optionally via a linker.

In yet another embodiment, the immunoglobulin moiety is a Fab. In yet another embodiment, the immunoglobulin moiety is a Fab'. In yet another embodiment, the immunoglobulin moiety is a F(ab')2. In yet another embodiment, the immunoglobulin moiety is an Fv. In yet another embodiment, the immunoglobulin moiety is an scFv. In yet another embodiment, the immunoglobulin moiety is a minibody. In yet another embodiment, the immunoglobulin moiety is a diabody. In yet a further embodiment, the immunoglobulin moiety is a single-domain antibody (nanobody).

Any of the immunoglobulin moieties disclosed herein may be linked to the CD47 binding agent at the N-terminus of the immunoglobulin moiety or at the C-terminus of the immunoglobulin moiety. In embodiments where the immunoglobulin moiety is an intact antibody or includes both a heavy chain (or a portion of a heavy chain) and a light chain (or a portion of a light chain) the CD47 binding agent is preferably attached to the C-terminus of the heavy chain; however, it is also contemplated that the CD47 binding agent may be attached to the C-terminus of the light chain, or to the N-terminus of the heavy chain, or to the N-terminus of the light chain. In embodiments where the immunoglobulin moiety is an Fc or an Fcab, the CD47 binding agent is preferably attached at the N-terminus of the Fc portion, although in some embodiments, the CD47 binding agent is attached at the C-terminus of the Fc portion. In one embodiment, the CD47 binding agent is fused to the N terminus of the immunoglobulin moiety. In another embodiment, the CD47 binding agent is fused to the C terminus of the immunoglobulin moiety.

Antibodies known in the art that could be useful in creating the immunoglobulin fusion proteins of the invention include anti-EGFR antibodies such as Cetuximab, Panitumumab, Nimotuzumab, Matuzumab, Futuximab, Modotuximab, Imgatuzumab, Necitumumab; anti-CD20 antibodies such as Rituximab, Ofatumumab, Obinutuzumab, Ibritumomab tiuxetan, Ocaratuzumab, Ocrelizumab, Tositumomab I-131, Ublituximab, Veltuzumab; and anti-HER2 antibodies such as Trastuzumab, Pertuzumab, Margetuximab; and anti-PD-L1 antibodies such as Atezolizumab, Avelumab, and Durvalumab. In another embodiment, the invention contemplates modifications to the known heavy and/or light chain sequences of the aforementioned antibodies so long as those modified antibodies retain the unique heavy and light chain complementarity determining regions or enough of the complementarity determining regions to retain binding specificity for the antigen of the non-modified antibody.

Linker Sequences

The immunoglobulin fusion proteins of the invention may include a linker sequence that joins the CD47 binding agent portion of the fusion protein with the antibody or immunoglobulin portion of the fusion protein. A preferred linker is a Gly$_4$Ser flexible linker of variable length. For example, the linker sequence is (Gly$_4$Ser)$_n$ where according to various embodiments, n=1, 2, 3, 4, 5, 6, 7, 8, 9, or 10. In one embodiment, n=4. A Gly$_4$Ser flexible linker of variable length may be introduced to optimize the targeting and effector functions.

In one embodiment, the CD47 binding agent, which in one embodiment may be a SIRPα or a SIRPα variant, is joined to the antibody or immunoglobulin portion via a polypeptide linker sequence that connects the N-terminus of the CD47 binding agent with the C-terminus of the antibody of immunoglobulin portion of the fusion protein.

In another embodiment, the CD47 binding agent, which in one embodiment may be a SIRPα or a SIRPα variant, is joined to the antibody or immunoglobulin portion via a polypeptide linker sequence that connects the C-terminus of the CD47 binding agent with the N-terminus of the antibody or immunoglobulin portion of the fusion protein.

The invention also contemplates that the CD47 binding agent portion of the fusion protein and the antibody or immunoglobulin portion of the fusion protein is a chemical linker.

Tumor Cell Antigens

The immunoglobulin fusion proteins of the invention are designed to be specific for a tumor cell antigen in addition to being specific for CD47. As described above, the immunoglobulin fusion proteins of the invention may achieve the desired outcome of avoiding binding CD47 on healthy cells by being bispecific for both CD47 and a tumor cell antigen. Accordingly, the immunoglobulin fusion proteins of the invention can be specific for any tumor antigen. Exemplary tumor cell antigens include but are not limited to: 4-1BB, 4F2, a-LEWISy, A2aR, AATK, ACKR, ACVR, ADCYAP1R1, ADIPOR1, ADIPOR2, ADORA1, ADORA2, ADORA3, ADR, AGTR, AHR, ALK, AMHR2, ANGPT1, ANGPT2, ANGPT4, APLNR, APRILR, AR, AVPR1A, AVPR1B, AVPR2, AXL, B7.1, B7.2, B7-DC, B7-H1, B7-H2, B7-H3, B7-H4, B7RP1, BAFF, BAFFR, BAI1, BAI2, BDKRB1, BDKRB2, BMPR1A, BMPR1B, BMPR2, BRD8, BRS3, BTLA, C3AR1, C5AR1, C5AR2, CALCR, CASR, CCKAR, CCKBR, CCR1, CCR10, CCR2, CCR3, CCR4, CCR5, CCR6, CCR7, CCR8, CCR9, CCRL1, CCRL2, CD2, CD3, CD4, CD5, CD6, CD7, CD11, CD15, CD18, CD19, CD20, CD22, CD24, CD25, CD27, CD28, CD30, CD33, CD37, CD38, CD3E, CD40, CD40L, CD43, CD44, CD47, CD52, CD54, CD55, CD56, CD66, CD70, CD73, CD74, CD80, CD86, CD97, CD112, CD123, CD133, CD137, CD137L, CD152, CD154, CD155, CD161, CD163, CD166, CD172, CD200, CD200R, CD206, CD244, CD300, CEA, CEACAM3, CELSR, CHRM1, CHRM2, CHRM3, CHRM4, CHRM5, CIITA, CMKLR1, CNR1, CNR2, CNTFR, CRHR1, CRHR2, CRIM1, CRLF1, CRLF2, CRLF3, CSPG4, CSF1R, CSF2R, CSF3R, CTLA4, CX3CR1, CXCR1, CXCR2, CXCR3, CXCR4, CXCR5, CXCR6, CXCR7, CYSLTR1, CYSLTR2, Cripto, DARC, DDR1, DDR2, Digoxin, DII4, DRD1, DRD2, DRD3, DRD4, DRD5, DTR4, EDA2R, EDAR, ED-B, EDNRA, EDNRB, EGFR, EGFRvIII, ELTD1, EMR1, EMR2, EMR3, EMR4P, ENG, EPCAM, EPHR, Episialin, EPOR, ERBB2, ERBB3, ERBB4, ESR1, ESR2, ESRR, F2R, F4/80, FAS, FCER2, FCGR1, FDF, FFAR, FGFR1, FGFR2, FGFR3, FGFR4, FGFRL1, Fibrin, FKBP, FLT1, FLT3, FLT4, FN14, FOLR1, FPR1, FSHR, FZD1, FZD10, FZD2, FZD3, FZD4, FZD5, FZD6, FZD7, FZD8, FZD9, G-28, GABBR, GAL9, GALR, GCGR, GD2, GD3, GDNFR, GHR, GHRHR, GHSR, GIPR, GITR, GLP1R, GLP2R, GM3, GM-CSFR, GNRHR, GPBAR1, GPER, Gr-1, Hapten, HCAR, HCRTR, HER1, HER2, HER3, HER4, HLA-DR10, HLA-DRB, HLA-G, HPV16, HPVE6, HPVE7, HMGB1, HMW-MAA, HRH, HTR1, HTR2, HTR3, HTR4, HTR5, HTR6, HTR7, HIVE, ICOS, IDO, IFNAR, IFNGR, IFNLR, IGF1R, IGF2R, IL10R, IL11R, IL12R, IL13R, IL15R, IL17R, IL18R1, IL18RAP, IL1R, IL1RL, IL20R, IL21R, IL22R, IL23R, IL27RA, IL28RA, IL2R, IL31RA, IL35R, IL3RA, IL4R, IL5RA, IL6R, IL7R, IL9R, ILT2, ILT3, ILT4, ILT5, INSR, INSRR, IRAK, IRP-2, ITGA1, ITGA10, ITGA11, ITGA2, ITGA2B, ITGA3, ITGA4, ITGA5, ITGA6, ITGA7, ITGA8, ITGA9, ITGAD, ITGAE, ITGAL, ITGAM, ITGAV, ITGAX, ITGB1, ITGB2, ITGB3, ITGB4, ITGB5, ITGB6, ITGB7, ITGB8, KAR, KIR, KISS1R, KIT, L6-antigen, LAG3, LAIR1, LEPR, Lewis Y, LGR4, LGR5, LGR6, LHCGR, LIFR, LIR, LMTK2, LMTK3, LPAR, LPHN, LTB4R, LTBR, LTK, Lysozyme, MAGE-1, MAGE-3, MAS1, MAS1L, MC1R, MC2R, MC3R, MC4R, MC5R, MCHR, MERTK, mesothelin, MET, MFG-E8, MIR, MIG, MLNR, MPL, MRGPRD, MRGPRE, MRGPRF, MRGPRG, MRGPRX1, MRGPRX2, MRGPRX3, MRGPRX4, MST1R, MTNR1, MUC1, MUC16, MUSK, NAIP, NCAM1, NGFR, NIP-cap, NKG2A, NKp46, NLRC, NLRP, NLRX1, NMBR, NMUR1, NMUR2, NOD1, NOD2, NPBWR1, NPBWR2, NPFFR, NPR1, NPR2, NPR3, NPSR1, NPY1R, NPY2R, NPY4R, NPY5R, NPY6R, NR0B1, NR0B2, NR1D1, NR1D2, NR1H2, NR1H3, NR1H4, NR1H5P, NR1I2, NR1I3, NR2C1, NR2C2, NR2E1, NR2E3, NR2F1, NR2F2, NR2F6, NR3C1, NR3C2, NR4A1, NR4A2, NR4A3, NR5A1, NR5A2, NR6A1, NRP1, NRP2, NTRK, NTSR2, OGFR, OPR, OSMR, OX40, OX40L, OXER1, OXGR1, OXTR, P2RY, PD-1, PDGFR, PD-L1, PGR, PGRMC2, Phosphatidylserine, PLAP, PLAUR, PLXN, PPAR, PRLHR, PRLR, PODXL, PROKR, PSCA, PSMA, PTAFR, PTGDR, PTGDS, PTGER, PTGFR, PTGIR, PTH1R, PTH2R, PTPR, QRFPR, RANK, RAR, RELT, RET, ROBO, ROR, ROS1, RXFP, RXR, RYK, S100A8, S100A9, S1PR, SCTR, SERPINB1, Siglec-F, SDC, SLAM7, SMO, SORT1, SPOCK2, SSEA-1, SSTR, ST2, STYK1, SUCNR1, TAAR, TACR, TAG72, TBXA2R, TEK, TGFBR, THR, TIE1, TIGIT, TIM1, TIM2, TIM3, TIM4, TLR1, TLR10, TLR2, TLR3, TLR4, TLR5, TLR6, TLR7, TLR8, TLR9, TNC, TNFRSF11A, TNFRSF11B, TNFRSF 13B, TNFRSF14, TNFRSF17, TNFRSF19, TNFRSF1A, TNFRSF1B, TNFRSF21, TNFRSF25, TNFRSF6B, TPRA1, TRAIL-R1, TRAIL-R2, TRAIL-R3, TRAIL-R4, TRHR, TSHR, TUBB3, TWEAKR, TYRO3, UTS2R, VCAM1, VDR, VEGFR, VEGFR2, VIPR1, VIPR2, VISTA, and XCR1.

Methods of preparing antibodies to a tumor cell antigen are known in the art and include hybridoma based methods, phage display based methods, and yeast display.

Further, it is possible to create new antibodies to any tumor cell antigen according to known methods and use the antibodies generated thereby to create immunoglobulin fusion proteins of the invention.

Properties of Immunoglobulin Fusion Proteins

As described herein, it is desirable that the immunoglobulin fusion proteins of the invention, while having the ability to bind to CD47 on disease producing cells, such as tumor cells, do not bind, or at least bind at acceptably low levels to CD47 on normal cells and, in particular, red blood cells (erythrocytes), such that any levels of CD47 binding by the immunoglobulin fusion protein remain at acceptable levels for therapeutic use of the fusion protein.

Accordingly, the invention contemplates that immunoglobulin fusion proteins of the invention may be characterized by their relative binding to red blood cells (erythrocytes) as compared to binding of a control to red blood cells. An example of testing the relative binding of immunoglobulin fusion proteins of the invention to erythrocytes is provided in Example 17 below.

For example, using a technique such as flow cytometry to identify the mean fluorescence intensity (MFI) of % red blood cell binding to a CD47 antibody as a control and setting that value at 100%, the relative % red blood cell binding MFI of the fusion protein can be measured. In one embodiment, the immunoglobulin fusion protein of the invention has less than 35%, less than 30%, less than 25% less than 20%, less than 15%, less than 10%, less than 9%, less than 8%, less 7%, less than 6%, less than 5%, less than 4%, less than 3%, less than 2%, or less than 1% red blood cell binding MFI compared to the control antibody which has its RBC MFI calibrated at 100%. In other embodiments, the % RBC MFI of the immunoglobulin fusion protein of the invention is between 0-1%, 0-2%, 0-3%, 0-4%, 0-5%, 0-6%, 0-7%, 0-8%, 0-9%, 0-10%, 0-15%, 0-20%, 0-25%, 0-30%, 0-35%, 1-2%, 1-3%, 1-4%, 1-5%, 1-6%, 1-7%, 1-8%, 1-9%, 1-10%, 1-15%, 1-20%, 1-25%, 1-30%, 1-35%, 2-3%, 2-4%, 2-5%, 2-6%, 2-7%, 2-8%, 2-9%, 2-10%, 3-4%, 3-5%, 3-6%, 3-7%, 3-8%, 3-9%, 3-10%, 4-5%, 4-6%, 4-7%, 4-8%, 4-9%, 4-10%, 5-6%, 5-7%, 5-8%, 5-9%, 5-10%, 5-15%, 5-20%, 5-25%, 5-30%, 5-35%, 6-7%, 6-8%, 6-9%, 6-10%, 7-8%, 7-9%, 7-10%, 8-9%, 8-10%, 9-10%, 10-15%, 10-20%, 10-25%, 10-30%, or 10-35%, when the % RBC MFI of the anti-CD47 antibody is calibrated at 100%. In yet another embodiment, the % RBC MFI of the immunoglobulin fusion protein of the invention is 35% or less, 30% or less, 25% or less, 20% or less, 15% or less, 10% or less, 9% or less, 8% or less, 7% or less, 6% or less, 5% or less, 4% or less, 3% or less, 2% or less, or 1% or less, when the % RBC MFI of the anti-CD47 antibody is calibrated at 100%. In one embodiment, the anti-CD47 antibody used as the control is B6H12/huIgG1 whose light and heavy chain amino acid sequences are found in Table 4 as SEQ ID NO: 146 (light chain) and SEQ ID NO:148 (heavy chain). The fusion protein also binds to CD47 on a non-red blood cell. The non-red blood cell, in one embodiment, is a tumor cell.

The invention also contemplates methods of identifying fusion proteins of the invention based on their hemagglutination profiles. An example of testing for hemagglutination of immunoglobulin fusion proteins of the invention to erythrocytes is provided in Example 18 below.

Use of Fusion Proteins

The fusion proteins disclosed herein can be used to treat various forms of cancer. A non-limiting list of cancers for which the immunoglobulin fusion proteins of the invention may be used to treat include Adrenal Cancer, Anal Cancer, Bile Duct Cancer, Bladder Cancer, Bone Cancer, Brain/CNS, Basal Cell Skin Cancer, Breast Cancer, Cancer of Unknown Primary, Castleman Disease, Cervical Cancer, Colorectal Cancer, Endometrial Cancer, Esophagus Cancer, Dermatofibrosarcoma Protuberans, Ewing Family Of Tumors, Eye Cancer, Gallbladder Cancer, Gastrointestinal Carcinoid Tumors, Gastrointestinal Stromal Tumor (GIST), Gastric Cancer, Gestational Trophoblastic Disease, Glioma, Glioblastoma, Head and Neck Cancer, Hodgkin Disease, Kaposi Sarcoma, Kidney Cancer, Laryngeal and Hypopharyngeal Cancer, Leukemia, Acute Lymphocytic Leukemia (ALL), Acute Myeloid Leukemia (AML), Chronic Lymphocytic Leukemia (CLL), Chronic Myeloid Leukemia, Chronic Myelomonocytic Leukemia (CMML), Liver Cancer, Lung Cancer, Non-Small Cell Lung Cancer, Small Cell Lung Cancer, Lung Carcinoid Tumor, Liver Cancer, Lymphoma, Lymphoma of the Skin, Malignant Mesothelioma, Merkel Cell Carcinoma, Melanoma, Multiple Myeloma, Myeloma, Myelodysplastic Syndrome, Nasal Cavity and Paranasal Sinus Cancer, Nasopharyngeal Cancer, Neuroendocrine Cancer, Neuroblastoma, Non-Hodgkin Lymphoma, Oral Cavity and Oropharyngeal Cancer, Osteosarcoma, Ovarian Cancer, Pancreatic Cancer, Penile Cancer, Pituitary Tumors, Prostate Cancer, Renal Cancer, Retinoblastoma, Rhabdomyosarcoma, Salivary Gland Cancer, Sarcoma, Sarcoma—Adult Soft Tissue Cancer, Squamous Cell Skin Cancer, Small Intestine Cancer, Stomach Cancer, Testicular Cancer, Thymus Cancer, Thyroid Cancer, Uterine Cancer, Uterine Sarcoma, Vaginal Cancer, Vulvar Cancer, Waldenstrom Macroglobulinemia, and Wilms Tumor.

The cancer cells are exposed to a therapeutically effective amount of the fusion protein so as to inhibit proliferation of the cancer cell. In some embodiments, the fusion proteins inhibit cancer cell proliferation by at least 40%, 50%, 60%, 70%, 80%, 90%, 95%, 98%, 99%, or 100%.

In some embodiments, the fusion protein is used in therapy. For example, the fusion protein can be used to inhibit tumor growth in a mammal (e.g., a human patient). In some embodiments, use of the fusion protein to inhibit tumor growth in a mammal includes administering to the mammal a therapeutically effective amount of the fusion protein. In other embodiments, the fusion protein can be used for inhibiting proliferation of a tumor cell.

As used herein, "treat," "treating," and "treatment" mean the treatment of a disease in a mammal, e.g., in a human. This includes: (a) inhibiting the disease, i.e., arresting its development; and (b) relieving the disease, i.e., causing regression of the disease state.

Generally, a therapeutically effective amount of active component is in the range of 0.1 mg/kg to 100 mg/kg, e.g., 1 mg/kg to 100 mg/kg, e.g., 1 mg/kg to 10 mg/kg. The amount administered will depend on variables such as the type and extent of disease or indication to be treated, the overall health of the patient, the in vivo potency of the antibody, the pharmaceutical formulation, and the route of administration. The initial dosage can be increased beyond the upper level in order to rapidly achieve the desired blood-level or tissue level. Alternatively, the initial dosage can be smaller than the optimum, and the dosage may be progressively increased during the course of treatment. The optimal dose can be determined by routine experimentation. For parenteral administration a dose between 0.1 mg/kg and 100 mg/kg, alternatively between 0.5 mg/kg and 50 mg/kg, alternatively, between 1 mg/kg and 25 mg/kg, alternatively between 2 mg/kg and 10 mg/kg, alternatively between 5 mg/kg and 10 mg/kg is administered and may be given, for example, once weekly, once every other week, once every third week, or once monthly per treatment cycle.

For therapeutic use, a fusion protein of the invention is preferably combined with a pharmaceutically acceptable carrier. As used herein, "pharmaceutically acceptable carrier" means buffers, carriers, and excipients suitable for use in contact with the tissues of human beings and animals without excessive toxicity, irritation, allergic response, or other problem or complication, commensurate with a reasonable benefit/risk ratio. The carrier(s) should be "acceptable" in the sense of being compatible with the other ingredients of the formulations and not deleterious to the recipient. Pharmaceutically acceptable carriers include buffers, solvents, dispersion media, coatings, isotonic and absorption delaying agents, and the like, that are compatible with pharmaceutical administration. The use of such media and agents for pharmaceutically active substances is known in the art.

Pharmaceutical compositions containing fusion proteins, such as those disclosed herein, can be presented in a dosage unit form and can be prepared by any suitable method. A pharmaceutical composition should be formulated to be compatible with its intended route of administration. Examples of routes of administration are intravenous (IV), intradermal, inhalation, transdermal, topical, transmucosal, and rectal administration. The pharmaceutical compositions are intended for parenteral, intranasal, topical, oral, or local administration, such as by a transdermal means, for therapeutic treatment. The pharmaceutical compositions can be administered parenterally (e.g., by intravenous, intramuscular, or subcutaneous injection), or by oral ingestion, or by topical application or intraarticular injection at areas affected by the vascular or cancer condition. Additional routes of administration include intravascular, intra-arterial, intratumor, intraperitoneal, intraventricular, intraepidural, as well as nasal, ophthalmic, intrascleral, intraorbital, rectal, topical, or aerosol inhalation administration.

The invention provides compositions for parenteral administration that comprise the above mention agents dissolved or suspended in an acceptable carrier, preferably an aqueous carrier, e.g., water, buffered water, saline, PBS, and the like. The compositions may contain pharmaceutically acceptable auxiliary substances as required to approximate physiological conditions, such as pH adjusting and buffering agents, tonicity adjusting agents, wetting agents, detergents and the like. The invention also provides compositions for oral delivery, which may contain inert ingredients such as binders or fillers for the formulation of a tablet, a capsule, and the like. Furthermore, this invention provides compositions for local administration, which may contain inert ingredients such as solvents or emulsifiers for the formulation of a cream, an ointment, and the like.

A preferred route of administration for fusion proteins is IV infusion. Useful formulations can be prepared by methods well known in the pharmaceutical art. For example, see Remington's Pharmaceutical Sciences, 18th ed. (Mack Publishing Company, 1990). Formulation components suitable for parenteral administration include a sterile diluent such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as EDTA; buffers such as acetates, citrates or phosphates; and agents for the adjustment of tonicity such as sodium chloride or dextrose.

For intravenous administration, suitable carriers include physiological saline, bacteriostatic water, Cremophor ELTM (BASF, Parsippany, N.J.) or phosphate buffered saline (PBS). The carrier should be stable under the conditions of manufacture and storage, and should be preserved against microorganisms. The carrier can be a solvent or dispersion medium containing, for example, water, ethanol, polyol (for example, glycerol, propylene glycol, and liquid polyethylene glycol), and suitable mixtures thereof.

Pharmaceutical formulations preferably are sterile. Sterilization can be accomplished, for example, by filtration through sterile filtration membranes. Where the composition is lyophilized, filter sterilization can be conducted prior to or following lyophilization and reconstitution. Aqueous solutions may be packaged for use as-is, or lyophilized, the lyophilized preparation being combined with a sterile aqueous carrier prior to administration. The pH of the preparations typically will be between 3 and 11, more preferably between 5 and 9 or between 6 and 8, and most preferably between 7 and 8, such as 7 to 7.5. The resulting compositions in solid form may be packaged in multiple single dose units, each containing a fixed amount of the above-mentioned agent or agents, such as in a sealed package of tablets or capsules.

Fusion Protein Production

The immunoglobulin fusion proteins of the invention are generally produced recombinantly, using mammalian cells containing a nucleic acid or nucleic acids engineered to express the fusion protein. If an immunoglobulin fusion protein of the invention requires two or more polypeptide chains to be expressed in order for assembly of the fusion protein, then the invention contemplates that nucleic acids encoding each of the polypeptide chains be contained within a cell or cells in order to facilitate recombinant production of the immunoglobulin fusion protein. For example, in one embodiment, a nucleic acid encodes a heavy chain or portion thereof of an immunoglobulin fusion protein of the invention while another nucleic acid encodes a light chain or portion thereof of an immunoglobulin fusion protein of the invention. Either the nucleic acid encoding the heavy chain or portion thereof or the nucleic acid encoding the light chain or portion thereof also includes a nucleic acid sequence encoding the CD47 binding moiety, for example, a SIRPα moiety, as described herein In a further embodiment, a cell contains a nucleic acid encoding a heavy chain or portion thereof of an immunoglobulin fusion protein of the invention and contains a nucleic acid encoding a light chain or portion thereof of an immunoglobulin fusion protein of the invention. Either the nucleic acid encoding the heavy chain or portion thereof or the nucleic acid encoding the light chain or portion thereof of an immunoglobulin fusion protein of the invention also contains a nucleic acid encoding a CD47 binding moiety, such as a SIRPα moiety as described herein.

Although exemplary methods of fusion protein expression and production are described in, for example, Examples 2 and 4 below, a wide variety of suitable vectors, cell lines and protein production methods have been used to produce biopharmaceuticals and could be used in the synthesis of the fusion proteins of the invention. Such methods are within the knowledge of the skilled artisan.

EXAMPLES

Example 1: Effect of Anti-CD47 B6H12 on Red Blood Cells in Cynomolgus Monkeys

Figure 2A:
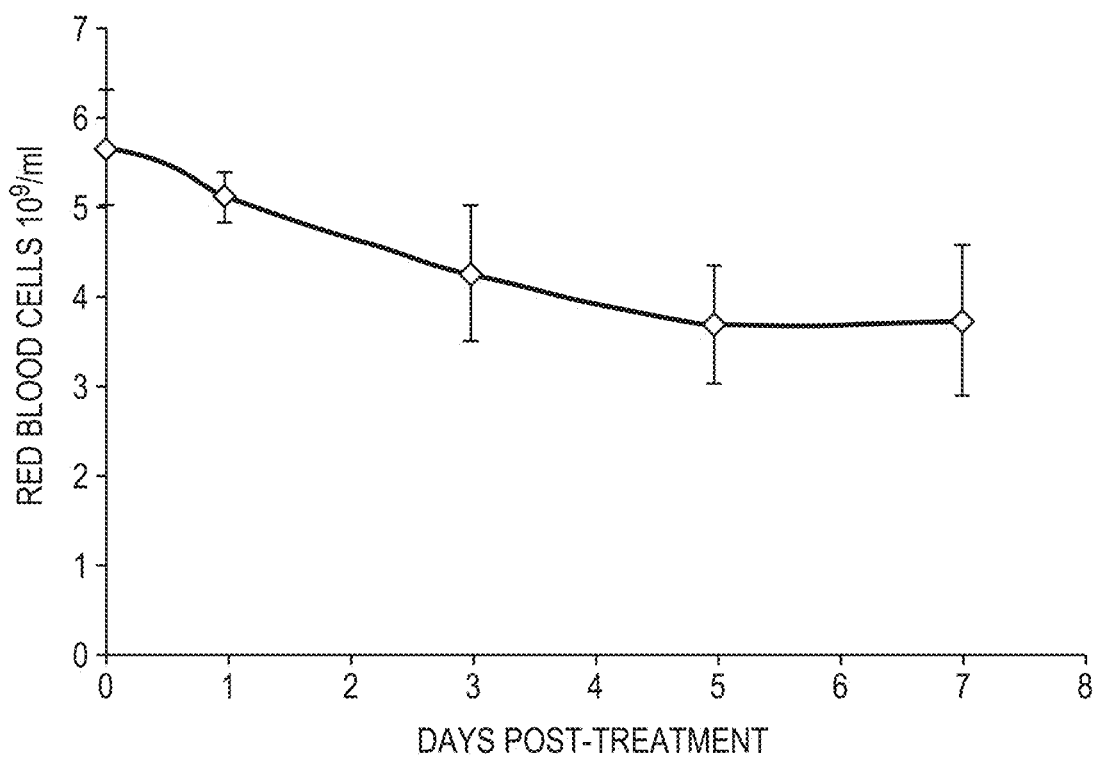
FIGS. 2A-B are line graphs showing the effect of anti-CD47 B6H12 on red blood cell counts (FIG. 2A) and hematocrit levels (FIG. 2B) in cynomolgus monkeys.
Figure 2B:
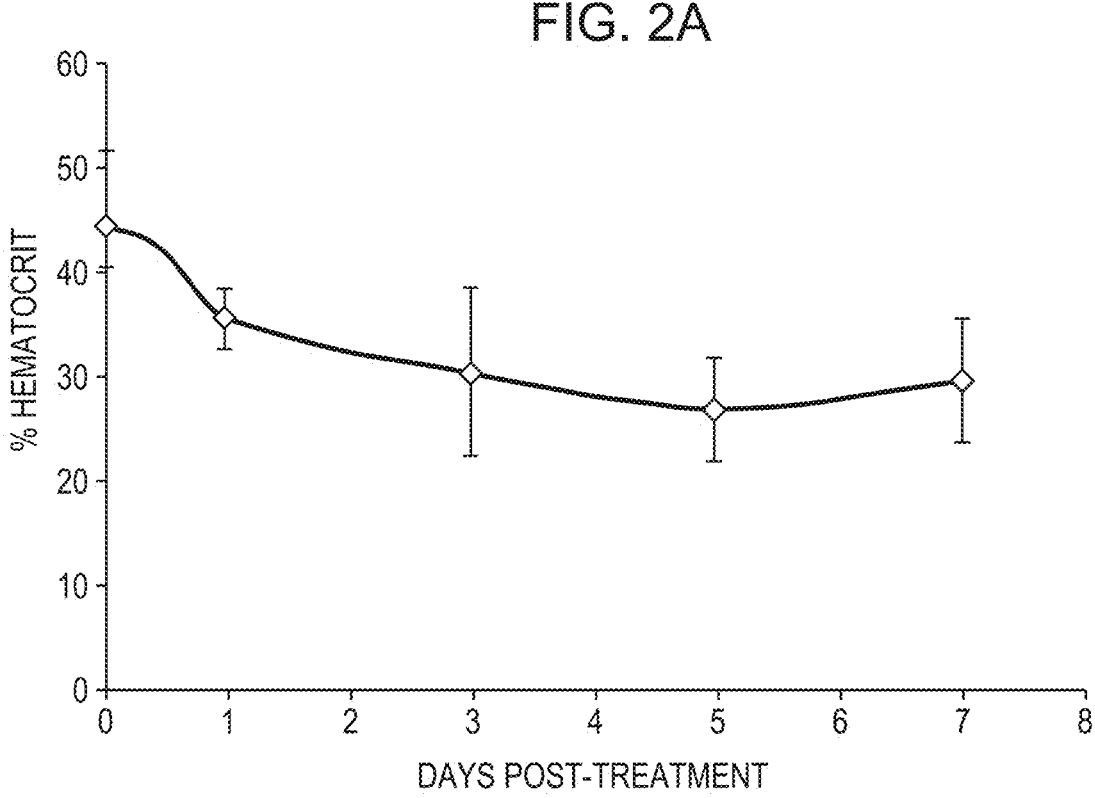

The in vivo effect of anti-CD47 B6H12 monoclonal antibody (chimeric B6H12-human IgG4 (Lindberg et al, JBC 269: 1567, 1994)) on red blood cells (RBC) was evaluated in cynomolgus monkeys. A group of 3 monkeys received a single intravenous dose of B6H12 each at 12 mg/kg on Day 0. Blood samples were withdrawn on −10 (ten days before injection to obtain baseline level), 0, 1, 3, 5 and 7 days after the single intravenous dose for RBC count and hematocrit (HCT) determination. FIGS. 2A-B shows that there was a strong reduction of red blood cells from $5.8 \times 10^9$ to $3.7 \times 10^9$ RBC/mL, i.e., a 40% decrease, by Day 5 (FIG. 2A), together with a corresponding reduction in the hematocrit level (FIG. 2B). Therefore, treatment with anti-CD47 antibodies can lead to severe anemia.

Example 2: Anti-CD20-huIgG1-SIRPα Immunoglobulin Fusion Protein

2(A) Construction and Expression of anti-CD20-huIgG1-SIRPα

The generation of an exemplary anti-CD20-huIgG1-SIRPα is based on the anti-CD20 2B8 (rituximab) monoclonal antibody (Reff et al, Blood 83:435, 1994) and the SIRPα protein (Jiang et al, JBC 274: 559, 1999). The DNA and protein sequence of the Fab light chain for 2B8 are provided in SEQ ID NO: I and SEQ ID NO:2, respectively. The DNA and protein sequence of the Fab heavy chain for 2B8 are provided in SEQ ID NO:3 and SEQ ID NO:4, respectively. The DNA and protein sequence of SIRPα allele VI are provided in SEQ ID NO: 5 and SEQ ID NO:6, respectively. The DNA and protein sequence of the IgV domain of SIR % allele V2 are provided in SEQ ID NO: 7 and SEQ ID NO:8, respectively. Anti-CD20-huIgG1-SIRPαV2 was generated by linking the C-terminus of the anti-CD20 heavy chain polypeptide to the IgV domain of SIRPαV2 via a (G4S)$_4$ linker (SEQ ID NO: 201).

Figure 1B:
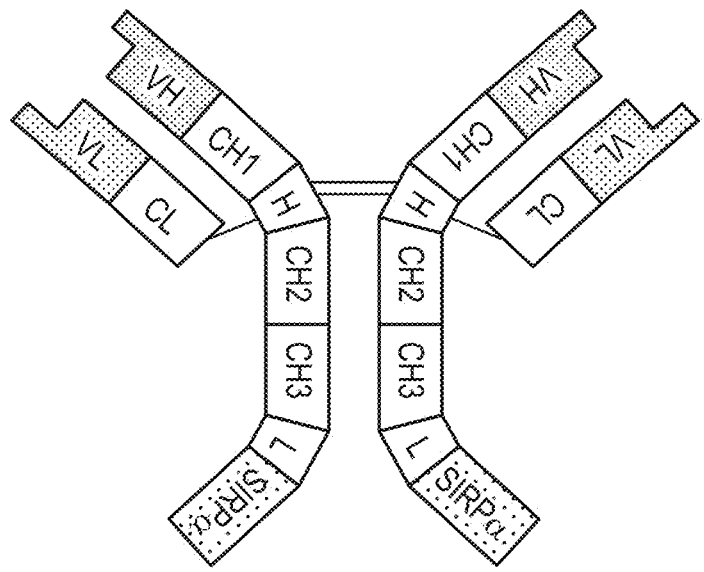
FIG. 1B is a schematic drawing of an antibody-SIRPα fusion protein having a tetrameric structure where the two polypeptide components (i.e., light chain and heavy chain) are each encoded by a DNA construct shown in FIG. 1A.

For expression of anti-CD20-huIgG1-SIRPαV2, the following two gene constructs were assembled by standard recombinant DNA techniques and cloned into the mammalian expression vector pTT5 (containing the mouse light chain signal peptide sequence for secretion) as in FIG. 1A: (1) Construct VH(anti-CD20)-CH1-H-CH2-CH3-(G4S)$_4$—SIRPαV2 (SEQ ID NO:11) ("(G4S)$_4$" disclosed as SEQ ID NO: 201) encoding the following elements: anti-CD20 heavy chain variable domain followed by human heavy chain constant domains 1-3 isotype IgG1 followed by a (G4S)$_4$ linker (SEQ ID NO: 201) and SIRPαV2 and (2) Construct VL(anti-CD20)-CL (SEQ ID NO:1) encoding the anti-CD20 light chain variable domain followed by human kappa light chain constant domain. The corresponding amino acid sequences for these two exemplary constructs are shown in SEQ ID NO:12 and SEQ ID NO:2, respectively.

Figure 3A:
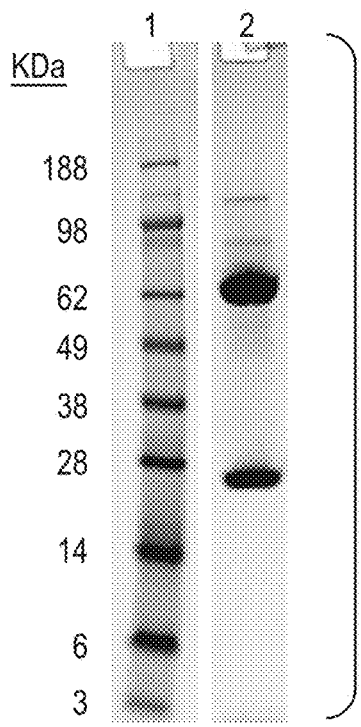
FIGS. 3A-B show the analysis of the expression of the two polypeptides of anti-CD20-huIgG1-SIRPαV2 by SDS-PAGE (FIG. 3A) and assembly of the full tetrameric molecule by size exclusion chromatography (SEC) (FIG. 3B) as described in Example 2.
Figure 3B:
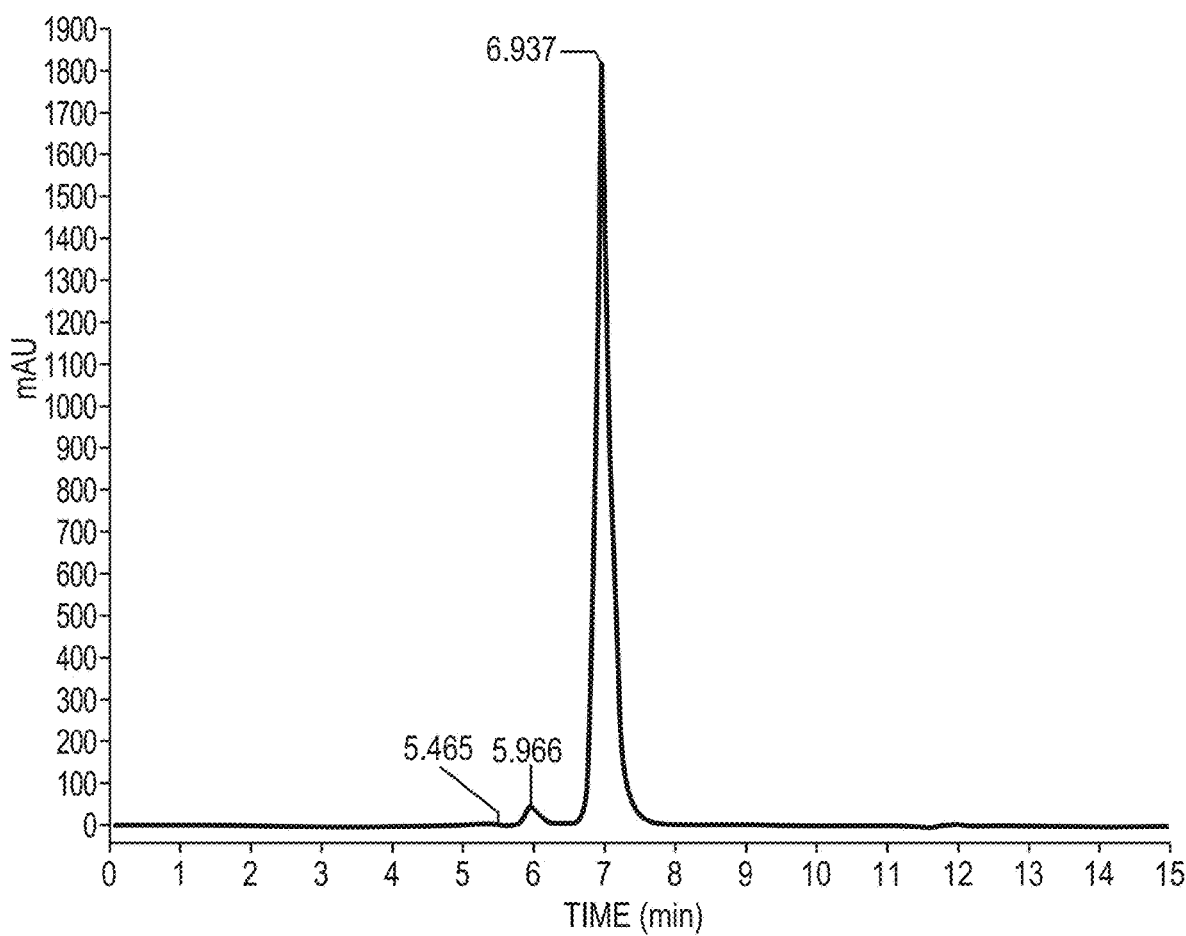

The set of two vectors for anti-CD20-huIgG1-SIRPαV2 expression was co-transfected transiently into Expi293 cells using Expi293fectin (Life Technologies, Grand Island, N.Y.). The protein was purified in a single step by protein A affinity chromatography. Expression of the two polypeptides and assembly of the full tetrameric molecule were confirmed on SDS-PAGE and SEC. For SDS-PAGE, the purified protein samples were reduced with DTT and run on NuPAGE MES 4-12% Gel, 200V for 35 min, followed by Coomassie staining. The two major bands on the gel had the expected MW and the correct stoichiometirc ratio with >95% purity (FIG. 3A). In FIG. 3A, lane 1 shows the molecular weight (MW) marker and lane 2 shows the expected MW (63, 23 kDa) and the correct stoichiometric ratio (1:1) of the two polypeptides of anti-CD20-huIgG1-SIRPαV2. For SEC, the purified protein samples were analyzed on a TSK-GEL Super SW3000 SEC column 4.6× 300 mm (Tosoh Biosciences, Tokyo, Japan) that was equilibrated with 50 mM sodium phosphate, 400 mM sodium perchlorate, pH 6.3+0.1 and 38+2.0 mS/cm$^2$. Size exclusion chromatography showed a peak at the expected MW of about 172 kDa for the monomeric anti-CD20-huIgG1-SIRPαV2 (FIG. 3B).

Figure 1C:
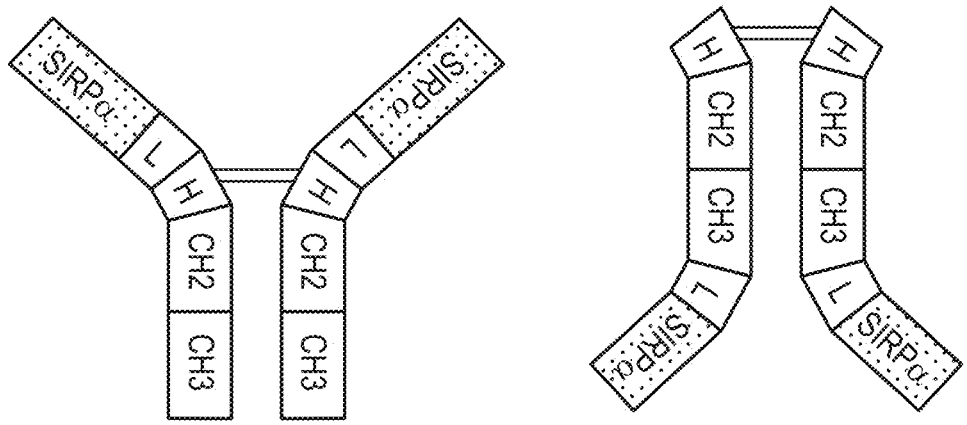
FIG. 1C shows two schematic drawings of Fc fusion proteins. They are from left to right (1) SIRPα-Fc and (2) Fc-SIRPα.

In addition, anti-CD20 and anti-CD47 in a standard monoclonal antibody format (anti-CD20 huIgG1 and anti-CD47 huIgG1) and SIRPα in a Fc-fusion protein format (SIRPαV2-Fc and Fc-SIRPαV2) (FIG. 1C) were generated as controls to compare with the anti-CD20-huIgG1-SIRPα format.

2(B)(i) Binding of anti-CD20-huIgG1-SIRPα to CD47 Expressed on Cells

The ability of anti-CD20-huIgG1SIRPαV2 to bind to CD47 overexpressed on the cell surface was measured, and compared to the control molecules. $2 \times 10^5$ Chinese hamster ovary (CHO) cells transfected with CD47 per well were incubated with varying concentrations of proteins diluted in PBS+1% FBS in a 96 well plate for 60 min on ice. After washing with PBS+1% FBS, cells were incubated with FITC F(ab')2 goat Anti-Human IgG, Fcγ (Jackson ImmunoResearch, West Grove, Pa.) diluted 1:200 in PBS+1% FBS for 60 min on ice. After washing again, cells were fixed with 1% formaldehyde in PBS. Cells were analyzed by flow cytometry (MACSQuant, Miltenyi Biotec, Cologne, Germany).

Figure 4A:
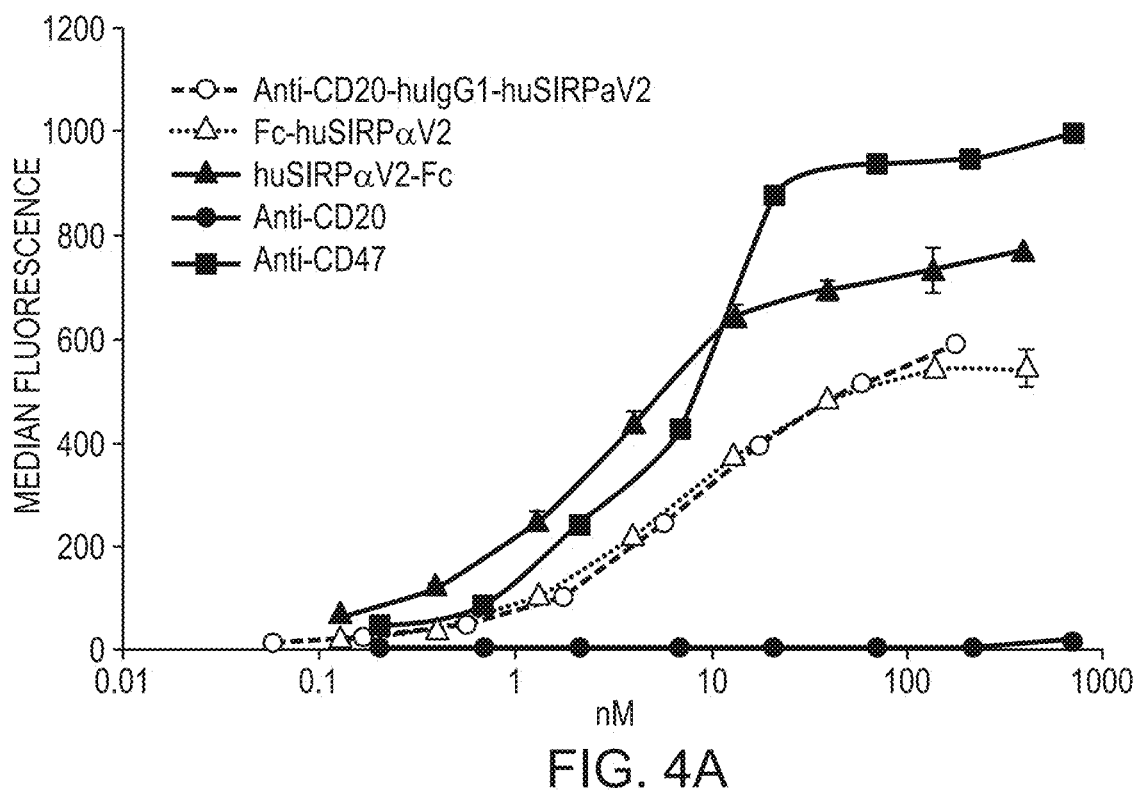
FIGS. 4A-D show binding of anti-CD20-huIgG1-SIRPαV2 to cells expressing CD47 (CD47-transfected CHO cells, FIG. 4A; leukocyte-enriched whole blood, FIG. 4B) or expressing both CD20 and CD47 (Raji cells, FIG. 4C; Namalwa cells, FIG. 4D).

The results show that anti-CD20-huIgG1-SIRPαV2, anti-CD47, SIRPαV2-Fc and Fc-SIRPαV2 bound to CD47 expressed on CD47-tranfected CHO cells, but anti-CD20 did not bind because CD20 is not expressed (FIG. 4A). Fc-SIRPαV2 and anti-CD47 bound with similar EC50's (7-8 nM), but SIRPαV2-Fc bound better (EC50=3 nM). However, the median fluorescence was highest for anti-CD47, followed by SIRPαV2-Fc, and lowest for Fc-SIRPαV2 and anti-CD20-huIgG1-SIRPαV2.

The ability of anti-CD20-huIgG1-SIRPαV2 to bind to CD47 expressed on the cell surface of blood cells was measured, and compared to the control molecules. Fresh whole blood from healthy human donors was enriched for leukocytes with dextran precipitation and was washed with PBS+1% FBS. $2 \times 10^5$ leukocyte-enriched human whole blood cells per well were incubated with 50 µg/ml proteins diluted in PBS+1% FBS in a 96 well plate for 60 min on ice. After washing with PBS+1% FBS, cells were incubated with a 1:200 dilution of FITC F(ab')2 goat Anti-Human IgG, Fcγ (Jackson ImmunoResearch, West Grove, Pa.), a 1:100 dilution of PE mouse anti-human CD235a (BD Biosciences, San Jose, Calif.), and a 1:100 dilution of eFluor 450 mouse anti-human CD45 (eBioscience, San Diego, Calif.) in PBS+1% FBS for 60 min on ice for protein detection and cell sorting by flow cytometry. After washing again, cells were fixed with 1% formaldehyde in PBS. Cells were analyzed by flow cytometry (MACSQuant, Miltenyi Biotec, Cologne, Germany).

Figure 4B:
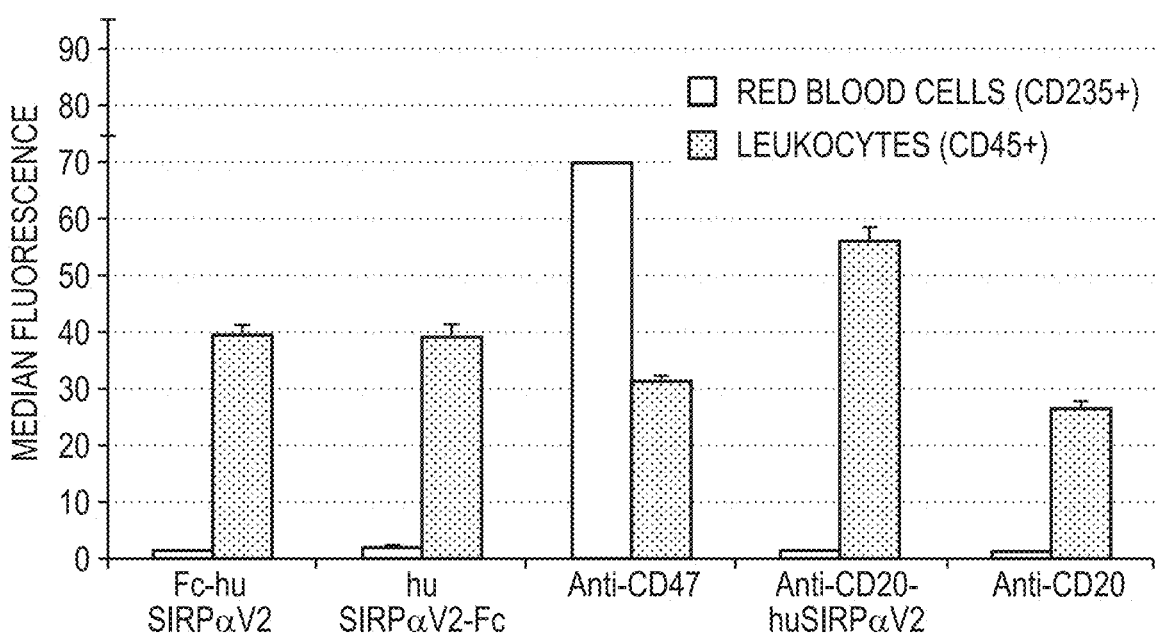

The results show that anti-CD47 bound to CD47 expressed on erythrocytes and leukocytes, but anti-CD20-huIgG1-SIRPαV2-Fc and Fc-SIRPαV2 only bound to CD47 expressed on leukocytes and not to CD47 expressed on erythrocytes (FIG. 4B).

2(B)(ii) Demonstration of Avidity of anti-CD20-huIgG1-SIRPα by Binding Both Antigens Expressed on Cells Binding of anti-CD20-huIgG1-SIRPαV2 to CD20 and CD47 on the cell surface was measured on human Ramos B cell lymphoma cells that overexpress CD20 and express CD47, and human Namalwa B cell lymphoma cells that overexpress CD47 and express CD20. $2 \times 10^5$ Raji or Namalwa cells per well were incubated with varying concentrations of proteins diluted in PBS+1% FBS in a 96 well plate for 60 min on ice. After washing with PBS+1% FBS, cells were incubated with FITC F(ab')2 goat Anti-Human IgG, Fcγ (Jackson ImmunoResearch, West Grove, Pa.) diluted 1:200 in PBS+1% FBS for 60 min on ice. After washing again, cells were analyzed by flow cytometry (MACSQuant, Miltenyi Biotec, Cologne, Germany).

Figure 4C:
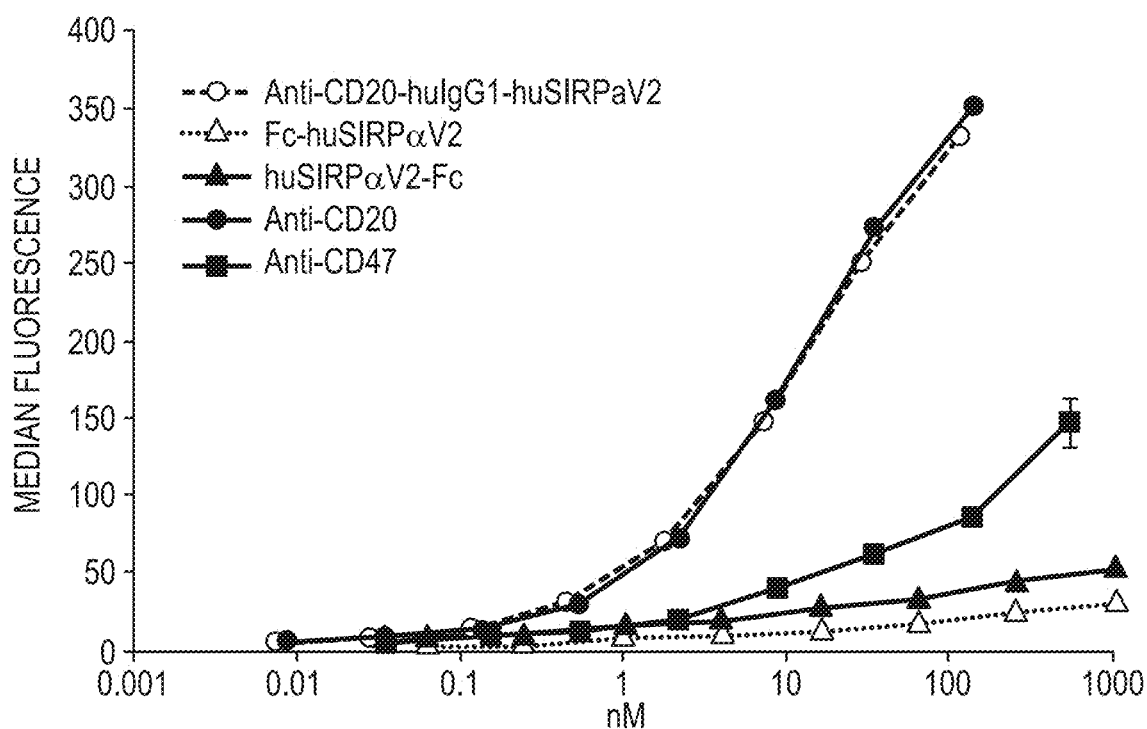
Figure 4D:
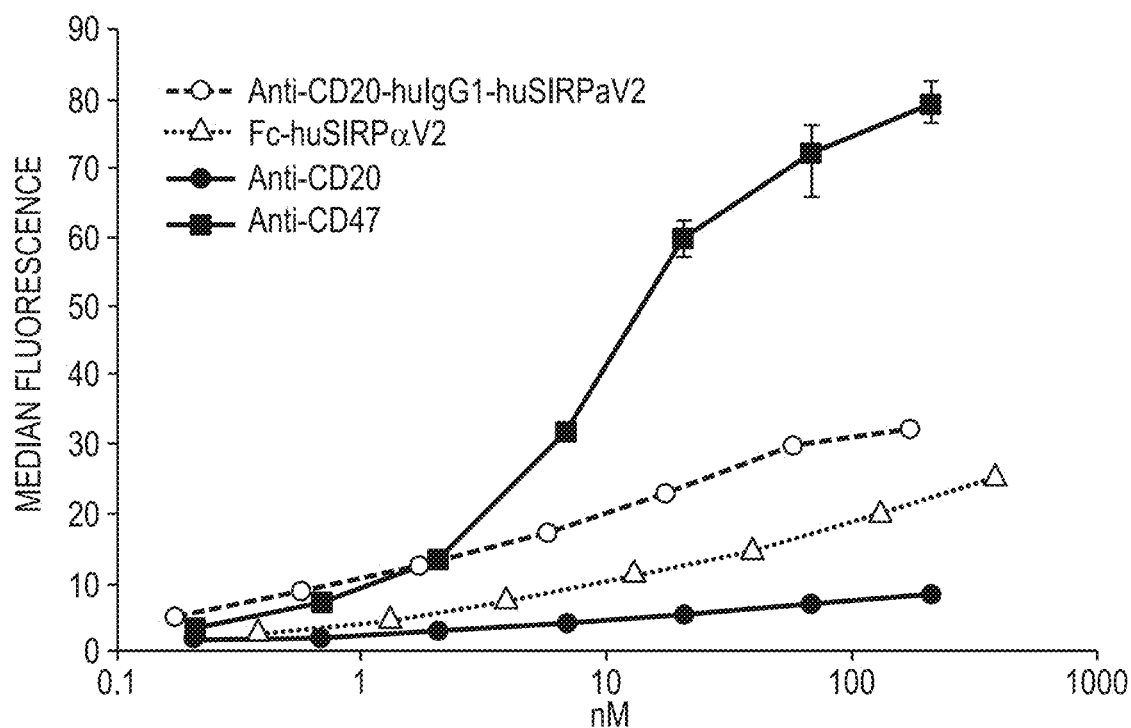

The results show that anti-CD20-huIgG1-SIRPαV2 binding to both Raji and Namalwa cells was somewhat enhanced compared to control molecules (FIGS. 4C-D), suggesting an avidity effect. Because fluorophore labeling abolished binding of SIRPα to CD47, binding was assayed by anti-Fc detection. However, it has previously been found that anti-Fc binding to an Fc region that has an additional protein moiety attached to its C-terminus is diminished compared to the same Fc region without an additional moiety in a cell binding assay (data not shown), suggesting, without wishing to be bound by theory, that anti-Fc binding to the Fc fusion protein may be sterically hindered in that context. Thus, the observation of similar binding of anti-CD20-huIgG1-SIRPαV2 and anti-CD20 by anti-Fc likely underestimates the amount of anti-CD20-huIgG1-SIRPαV2 cell binding and indeed suggests an avidity effect for anti-CD20-huIgG1-SIRPαV2 binding to the cells. The ability of anti-CD20-huIgG1-SIRPαV2 to harness the avidity of binding to the tumor cells by binding to two tumor targets on the same cell may result in more specific targeting and less side effects in vivo.

Example 3: Anti-CD20/anti-CD47 Bispecific Antibody

3(A) Description of anti-CD20/anti-CD47

Figure 1D:
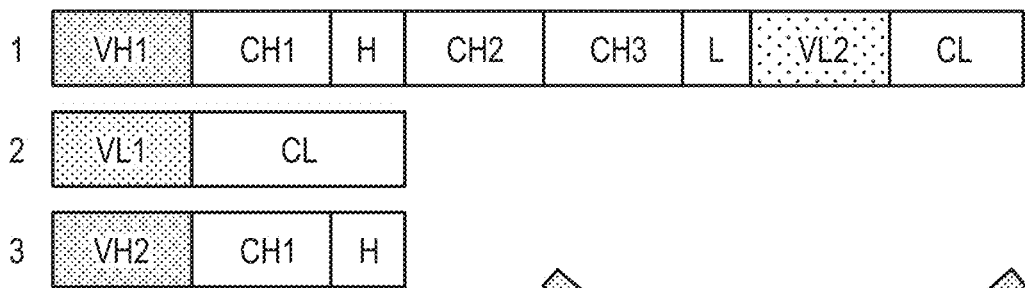
FIG. 1D shows three DNA constructs for the expression of tetravalent bispecific antibodies. DNA construct 1 (top) encodes the heavy chain variable domain of a first antibody (VH(1)) followed by the heavy chain constant domains (CH1, hinge (H)-CH2-CH3) genetically fused via an optional linker (L) to the light chain variable domain of second antibody (VL(2)) followed by the light chain constant domain (CL). DNA construct 2 (middle) encodes the light chain variable domain of the first antibody (VL(1)) followed by light chain constant domain (CL). DNA construct 3 (bottom) encodes the heavy chain variable domain of the second antibody (VH(2)) followed by heavy chain constant domain 1 (CH1), and an upper hinge region (H*).
Figure 1E:
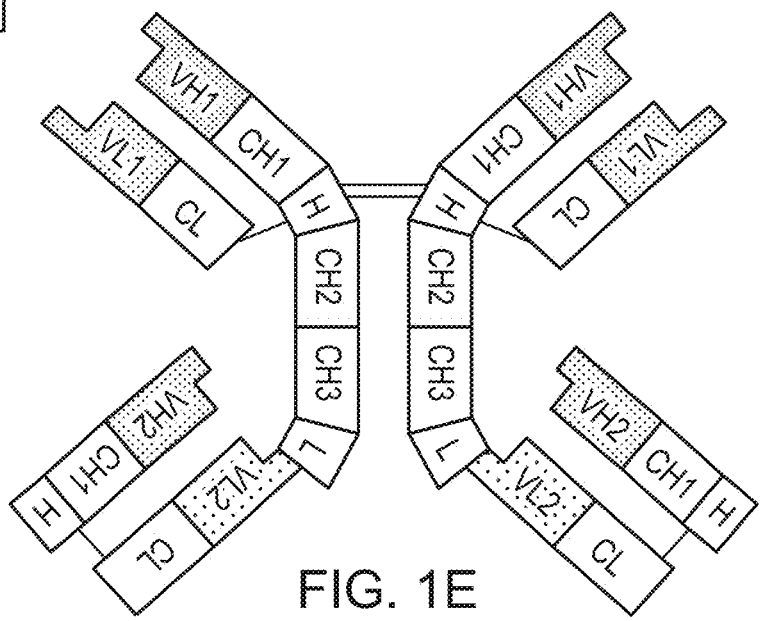
FIG. 1E is a schematic drawing of a tetravalent bispecific antibody (TetBiAb) having a hexameric structure where the three polypeptide components are encoded by the DNA constructs shown in FIG. 1D.

The generation of an exemplary tetravalent bispecific antibody (TetBiAb) against CD20 and CD47 is based on the anti-CD20 2B8 (rituximab) monoclonal antibody (Reff et al, Blood 83:435, 1994) and the anti-CD47 B6H12 monoclonal antibody (Lindberg et al, JBC 269: 1567, 1994), In the anti-CD20/anti-CD47 TetBiAb against CD20 and CD47, the C-terminus of the anti-CD20 heavy chain polypeptide is linked to the N-terminus of the anti-CD47 Fab light chain via a G4S linker (SEQ ID NO: 202) (FIG. 1D+E). The construction, expression, and binding properties of anti-CD20/anti-CD47 are described in International Patent Application Publication No. WO2014/144357.

3(B) In Vivo Biological Activities of anti-CD20/anti-CD47

Figure 5A:
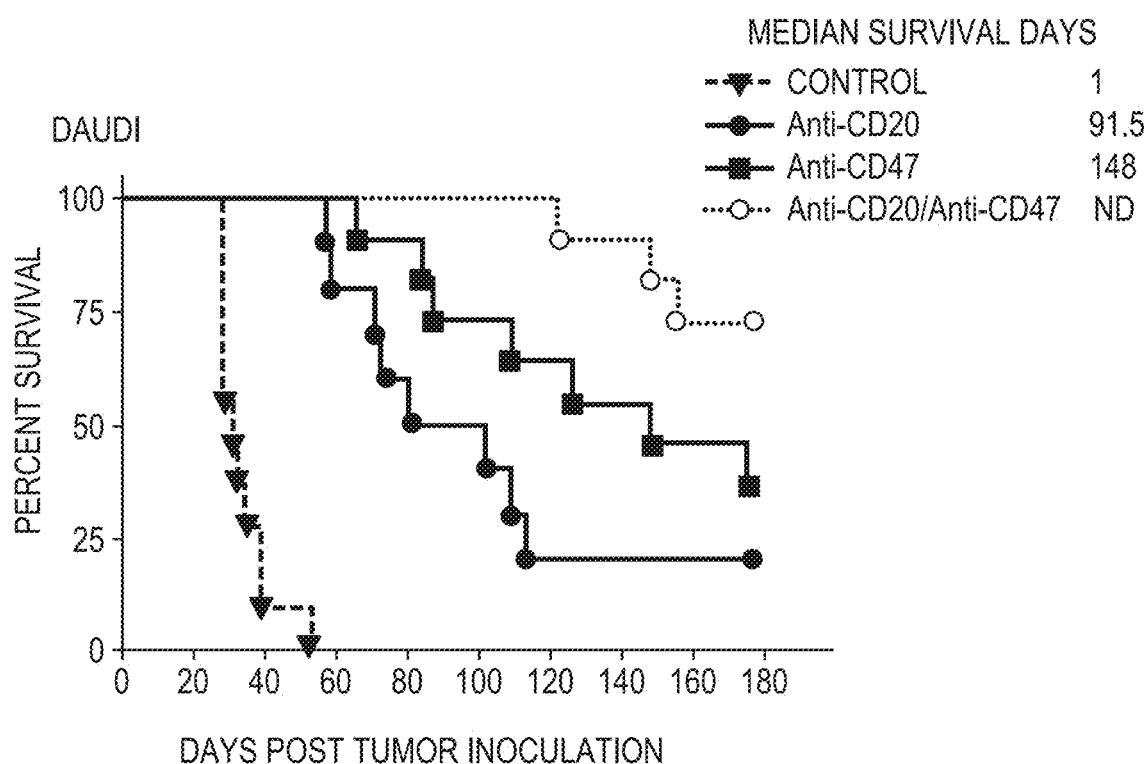
FIGS. 5A-B show the survival of mice after injection with Daudi cells (FIG. 5A) or with Raji cells (FIG. 5B) and treatment with the tetravalent bispecific anti-CD20/anti-CD47.
Figure 5B:
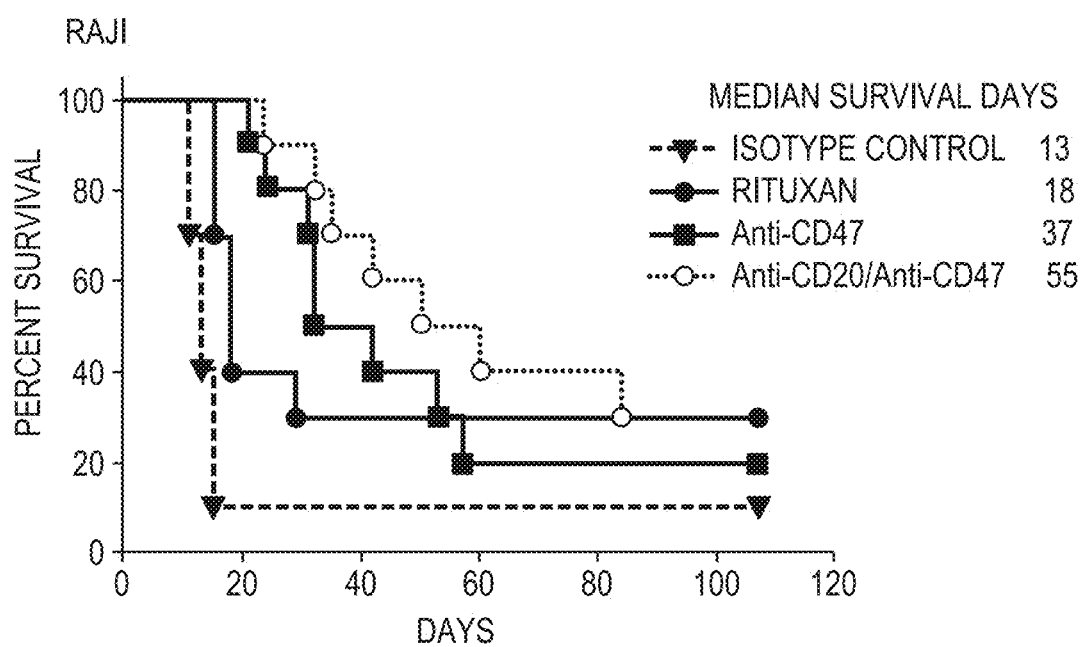

The utility of anti-CD20/anti-CD47, as a proxy for anti-CD20-huIgG1-SIRPα, was shown by the following in vivo experiments. In disseminated lymphoma models, SCID mice were injected i.v. either with 5×10$^6$ CD20+human Daudi lymphoma cells or with 1×10$^6$ CD20+human Raji lymphoma cells, followed by i.p. injection of 25 µg/mouse of an antibody isotype control, 25 µg/mouse of anti-CD20, 25 µg/mouse of anti-CD47, or 42 µg/mouse of anti-CD20/anti-CD47, which is the equimolar amount of tetravalent bispecific antibody. All the groups (n=10-11) received treatment twice per week for 3 weeks, and results were reported as general health, e.g., paralysis, which precedes death by 10-14 days, and survival of mice. Treatment with anti-CD20/anti-CD47 tetravalent bispecific antibody was found to be superior to the two monotherapies in both Daudi (FIG. 5A) and Raji (FIG. 5B) tumor models. Similar results are expected for an anti-CD20-huIgG1-SIRPα.

Example 4: Anti-EGFR-huIgG1-SIRPα Immunoglobulin Fusion Protein

4(A) Construction and Expression of anti-EGFR-huIgG1-SIRPα

The generation of an exemplary anti-EGFR-huIgG1-SIRPα is based on the anti-EGFR C225 (cetuximab) monoclonal antibody (Kawamoto, PNAS 80:1337, 1983) and the SIRPα protein (Jiang et al, JBC 274: 559, 1999). The DNA and protein sequence of the Fab light chain for C225 are provided in SEQ ID NO:13 and SEQ ID NO:14, respectively. The DNA and protein sequence of the Fab heavy chain for C225 are provided in SEQ ID NO:15 and SEQ ID NO:16, respectively. The DNA and protein sequence of SIRPα allele V1 are provided in SEQ ID NO: 5 and SEQ ID NO:6, respectively. The DNA and protein sequence of the IgV domain of SIRPα allele V2 are provided in SEQ ID NO: 7 and SEQ ID NO:8, respectively. An exemplary anti-EGFR-huIgG1-SIRPαV1 was generated by linking the C-terminus of the anti-EGFR heavy chain polypeptide to the IgV domain of SIRPαV1 via a (G4S)$_4$ linker (SEQ ID NO: 201). An exemplary anti-EGFR-huIgG1-SIRPαV2 was generated by linking the C-terminus of the anti-EGFR heavy chain polypeptide to the IgV domain of SIRPαV2 via a (G4S)$_3$ (SEQ ID NO: 203), (G4S)$_4$ (SEQ ID NO: 201), or (G4S)$_5$ linker (SEQ ID NO: 204).

For expression of the anti-EGFR-huIgG1-SIRPαV1, the following two gene constructs were assembled by standard recombinant DNA techniques and are cloned into the mammalian expression vector pTT5 (containing the mouse light chain signal peptide sequence for secretion) as in FIG. 1A: (1) Construct VH(anti-EGFR)-CH1-H-CH2-CH3-(G4S)$_4$—SIRPαV1 (SEQ ID NO:17) ("(G4S)$_4$" disclosed as SEQ ID NO: 201) encoding the following elements: anti-EGFR heavy chain variable domain followed by human heavy chain constant domains 1-3 isotype IgG1 followed by a (G4S)$_4$ linker (SEQ ID NO: 201) and the IgV domain of SIRPαV1 and (2) Construct VL(anti-EGFR)-CL (SEQ ID NO:13) encoding the anti-EGFR light chain variable domain followed by human kappa light chain constant domain. The corresponding amino acid sequences for these two constructs are shown in SEQ ID NO:18 and SEQ ID NO:14 respectively.

For expression of the anti-EGFR-huIgG1-SIRPαV2 with varying linker lengths, the following four gene constructs were assembled by standard recombinant DNA techniques and cloned into the mammalian expression vector pTT5 (containing the mouse light chain signal peptide sequence for secretion) as in FIG. 1A: (1) Construct VH(anti-EGFR)-CH1-H-CH2-CH3-(G4S)3-SIRPαV2 (SEQ ID NO:69) ("(G4S)$_3$" disclosed as SEQ ID NO: 203), encoding the following elements: anti-EGFR heavy chain variable domain followed by human heavy chain constant domains 1-3 isotype IgG1 followed by a (G4S)3 linker (SEQ ID NO: 203) and the IgV domain of SIRPαV2, (2) Construct VH(anti-EGFR)-CH1-H-CH2-CH3-(G4S)4-SIRPαV2 (SEQ ID NO:19) ("(G4S)$_4$" disclosed as SEQ ID NO: 201), encoding the following elements: anti-EGFR heavy chain variable domain followed by human heavy chain constant domains 1-3 isotype IgG1 followed by a (G4S)4 linker (SEQ ID NO: 201) and the IgV domain of SIRPαV2, (3) Construct VH(anti-EGFR)-CH1-H-CH2-CH3-(G4S)5-SIRPαV2 (SEQ ID NO:71) ("(G4S)$_5$" disclosed as SEQ ID NO: 204), encoding the following elements: anti-EGFR heavy chain variable domain followed by human heavy chain constant domains 1-3 isotype IgG1 followed by a (G4S)5 linker (SEQ ID NO: 204) and the IgV domain of SIRPαV2, and (4)

Construct VL(anti-EGFR)-CL (SEQ ID NO:13), encoding the following elements: anti-EGFR light chain variable domain followed by human kappa light chain constant domain. The corresponding amino acid sequences for these four constructs are shown in SEQ ID NO:70, 20, 72 and SEQ ID NO:14 respectively.

Figure 6A:
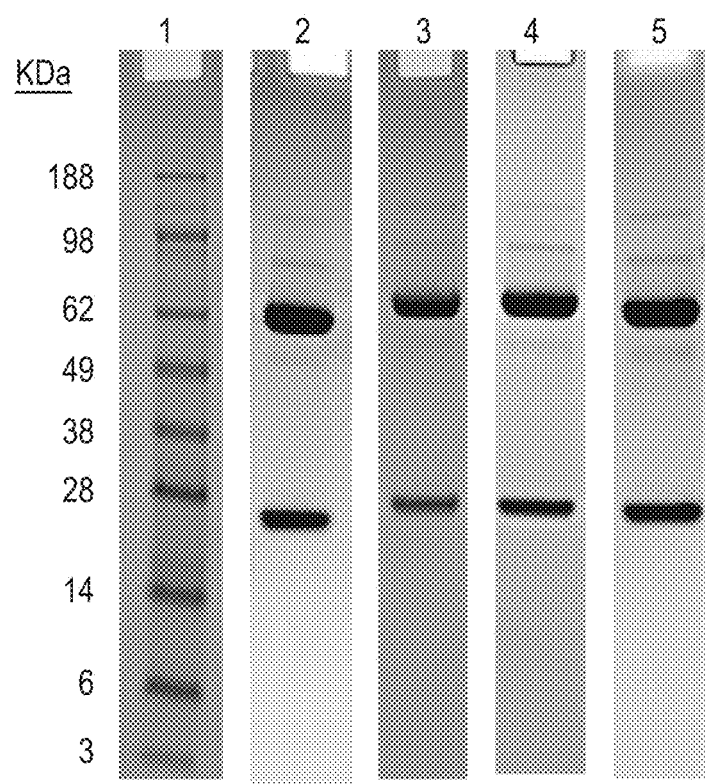
FIGS. 6A-B show the analysis of the expression of the two polypeptides of anti-EGFR-huIgG1-SIRPα by SDS-PAGE (FIG. 6A) and assembly of the full tetrameric molecule by size exclusion chromatography (SEC) (FIG. 6B) as described in Example 4.
Figure 6B:
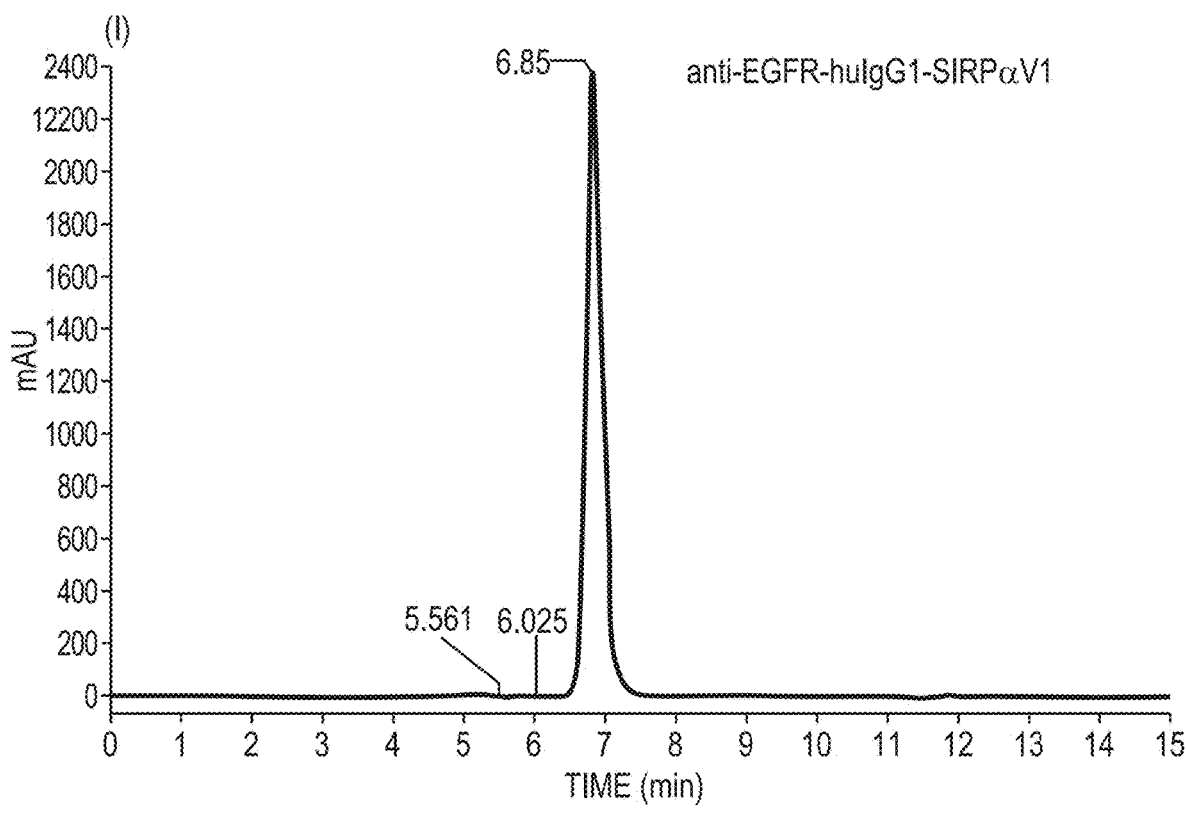
Figure 6B:
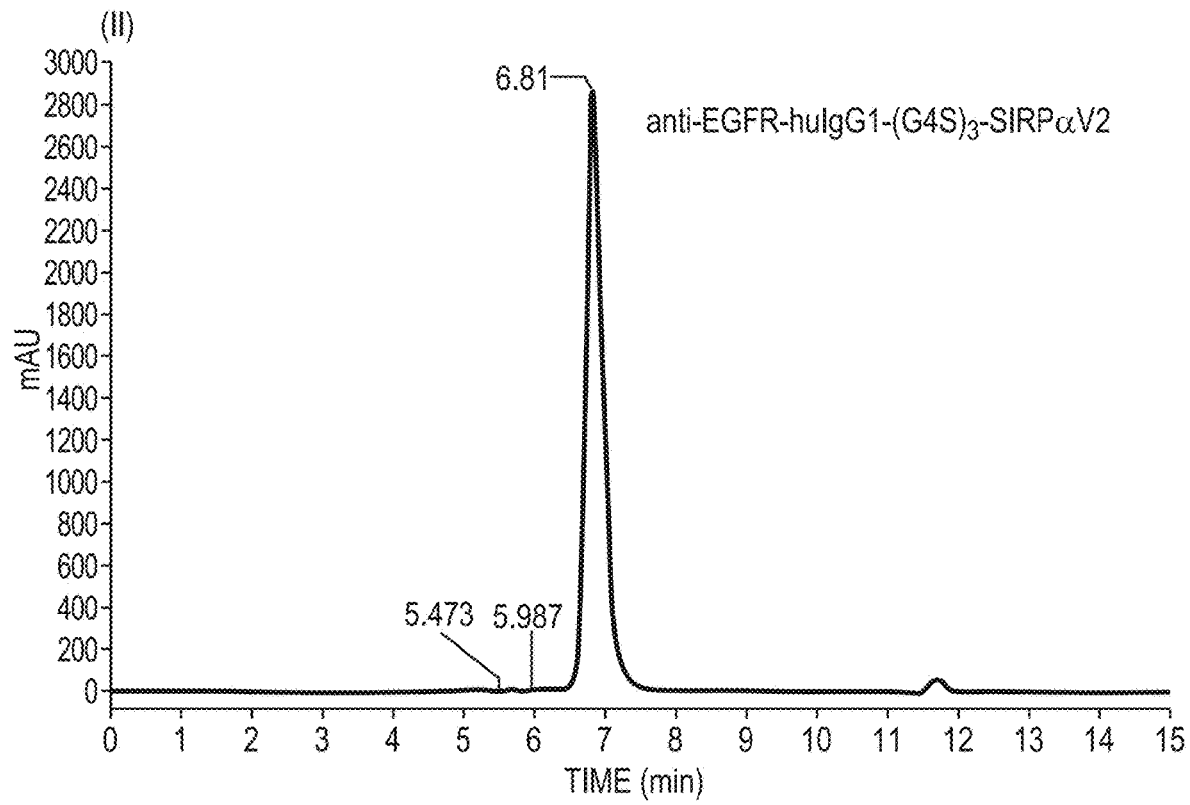
Figure 6B:
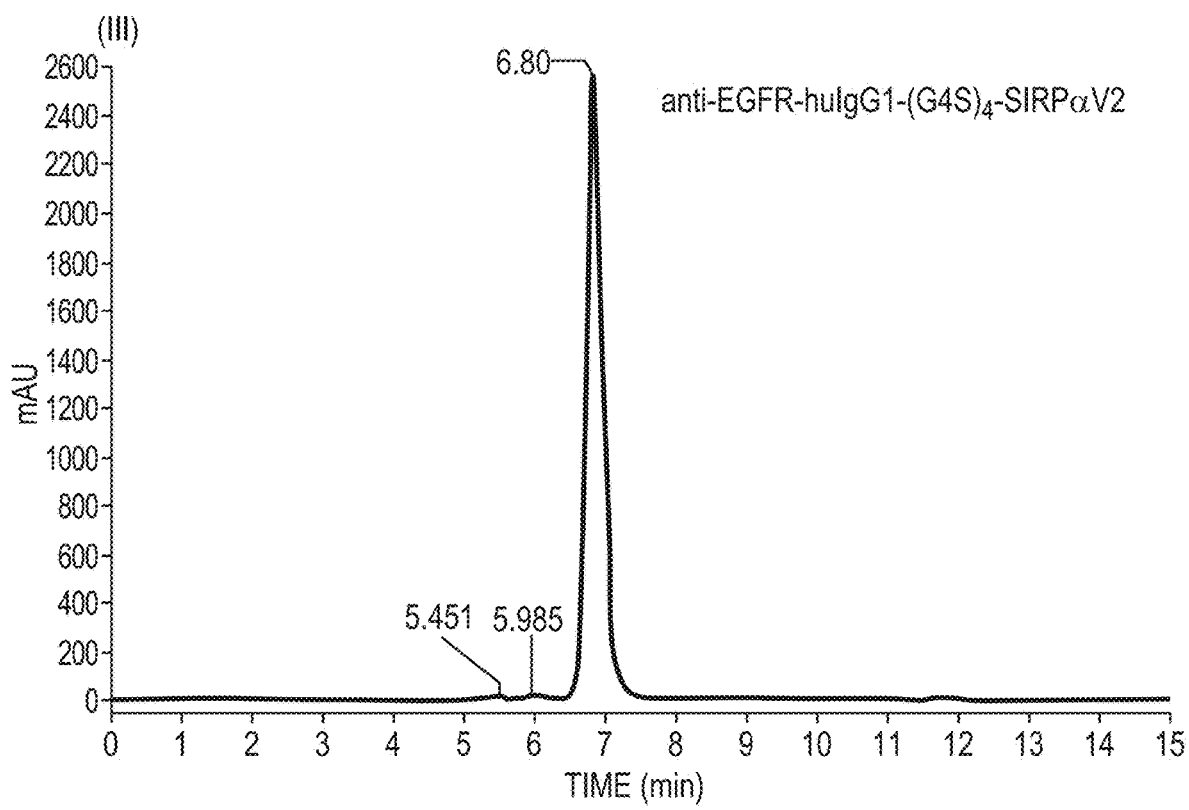
Figure 6B:
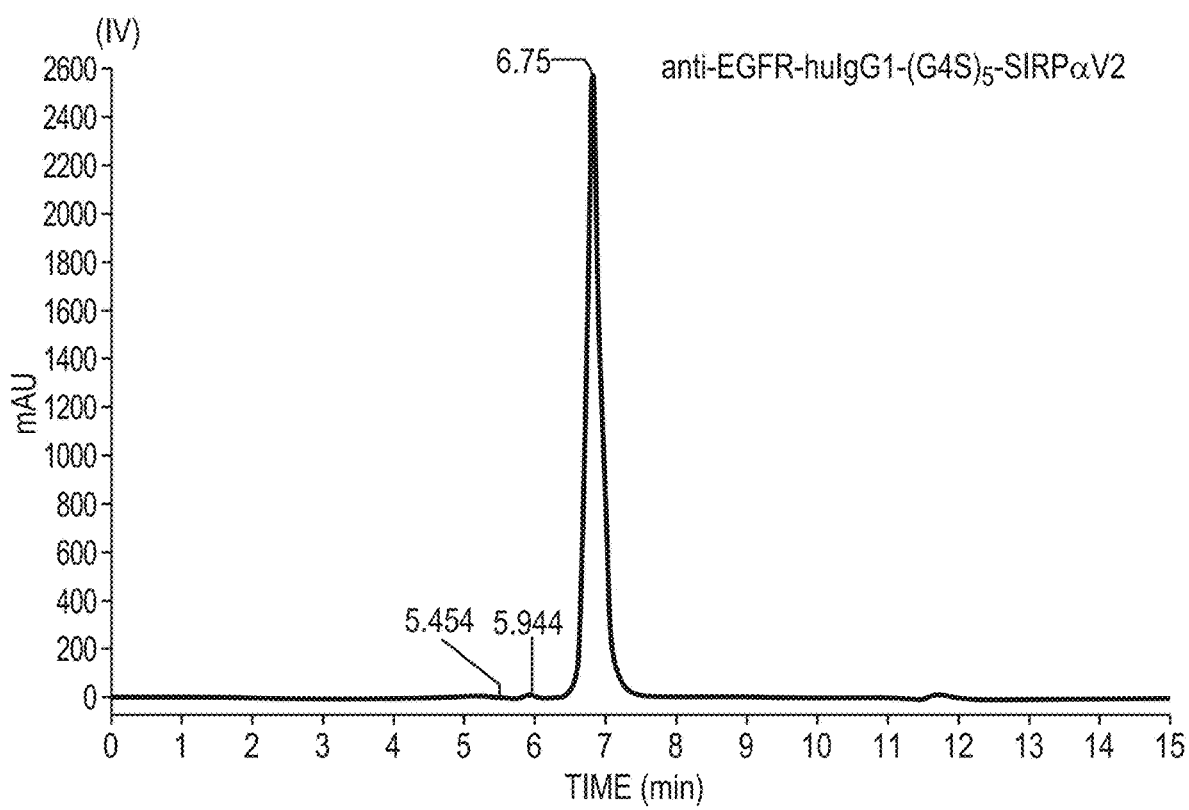

Each set of two vectors for anti-EGFR-huIgG1-SIRPαV2 expression was co-transfected transiently into Expi293 cells using Expi293fectin (Life Technologies, Grand Island, N.Y.). The proteins were purified in a single step by protein A affinity chromatography. Expression of the two polypeptides and assembly of the full tetrameric molecules were confirmed on sodium dodecyl sulfate-polyacrylamide gel electrophoresis (SDS-PAGE) and size exclusion chromatography (SEC). For SDS-PAGE, the purified protein samples were reduced with DTT and run on NuPAGE MES 4-12% Gel, 200V for 35 min, followed by Coomassie staining. The two major bands on the gel had the expected molecular weights (MW) and the correct stoichiometric ratio with >95% purity (FIG. 6A). In FIG. 6A, lane 1 shows the molecular weight (MW) marker, lane 2 shows the expected MW (64, 23 kDa) and the correct stoichiometric ratio (1:1) of the two polypeptides of anti-EGFR-huIgG1-SIRPαV1, lane 3 shows the expected MW (64, 23 kDa) and the correct stoichiometric ratio (1:1) of the two polypeptides of anti-EGFR-huIgG1-(G4S)$_3$—SIRPαV2 ("(G4S)$_3$" disclosed as SEQ ID NO: 203), lane 4 shows the expected MW (64, 23 kDa) and the correct stoichiometric ratio (1:1) of the two polypeptides of anti-EGFR-huIgG1-(G4S)$_4$-SIRPαV2 ("(G4S)$_4$" disclosed as SEQ ID NO: 201), and lane 5 shows the expected MW (64, 23 kDa) and the correct stoichiometric ratio (1:1) of the two polypeptides of anti-EGFR-huIgG1-(G4S)$_5$-SIRPαV2 ("(G4S)5" disclosed as SEQ ID NO: 204). For SEC, the purified protein samples were analyzed on a TSK-GEL Super SW3000 SEC column 4.6 300 mm (Tosoh Biosciences, Tokyo, Japan) that was equilibrated with 50 mM sodium phosphate, 400 mM sodium perchlorate, pH 6.3+0.1 and 38+2.0 mS/cm2. Size exclusion chromatography showed a peak at the expected MW of about 173 kDa for each of the monomeric anti-EGFR-huIgG1-SIRPα proteins (FIG. 6B(i)-(iv)).

In addition, anti-EGFR and anti-CD47 in a standard monoclonal antibody format (anti-EGFR huIgG1 and anti-CD47 huIgG1) and SIRPα in an Fc-fusion protein format (SIRPαV2-Fc, Fc-SIRPαV2, and Fc-SIRPαV2CC) (FIG. 1C) were generated as controls to compare with the anti-EGFR-huIgG1-SIRPα format. Fc-SIRPαV2CC is an Fc-fusion protein in which the SIRPα ECD moiety has the IgV domain of allele V2 connected to the IgC domains of allele V1 (SEQ ID NO: 192).

4(B)(i) Binding of anti-EGFR-huIgG1-SIRPα to CD47 Expressed on Cells

The ability of the exemplary anti-EGFR-huIgG1-SIRPα to bind to CD47 overexpressed on the cell surface was measured, and compared to the control molecules. 2×10$^5$ CHO cells transfected with CD47 per well were incubated with varying concentrations of antibodies diluted in PBS+1% FBS in a 96 well plate for 60 min on ice. After washing with PBS+1% FBS, cells were incubated with FITC F(ab')2 goat Anti-Human IgG, Fcγ (Jackson ImmunoResearch, West Grove, Pa.) diluted 1:200 in PBS+1% FBS for 60 min on ice. After washing again, cells were fixed with 1% formaldehyde in PBS. Cells were analyzed by flow cytometry (MACSQuant, Miltenyi Biotec, Cologne, Germany).

Figure 7A:
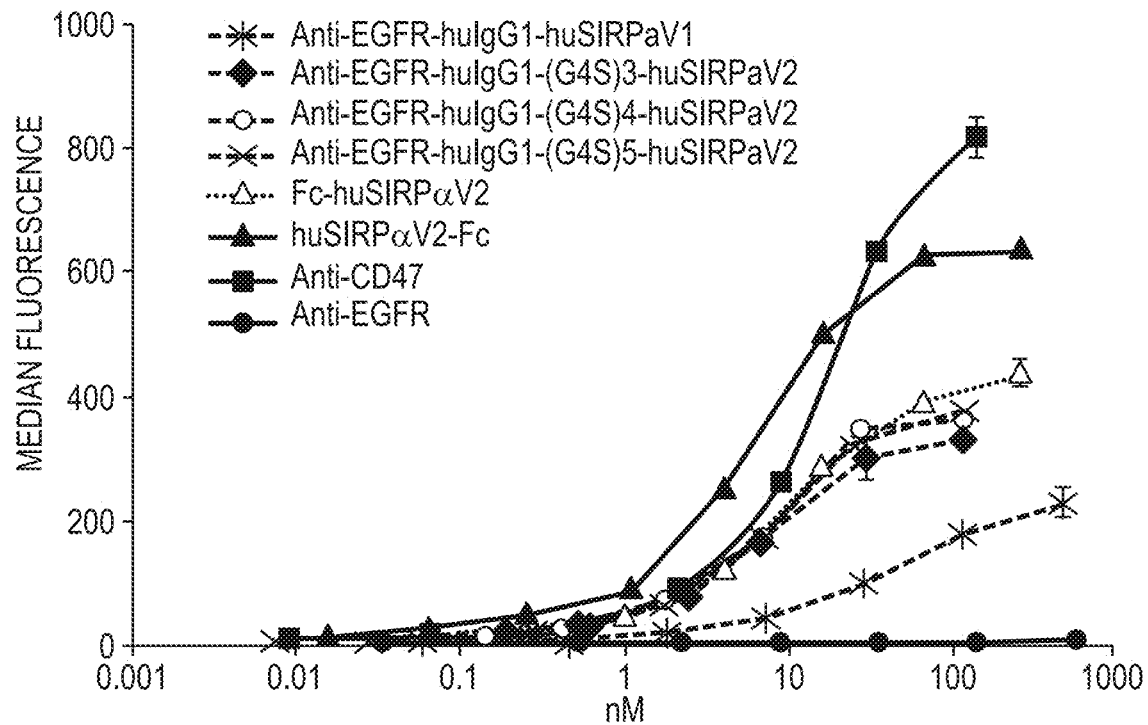
FIGS. 7A-C show binding of anti-EGFR-huIgG1-SIRPα proteins to cells expressing CD47 (CD47-transfected CHO cells, FIG. 7A; leukocyte-enriched whole blood, FIG. 7B) or expressing both EGFR and CD47 (A549 cells, FIG. 7C).

The results show that the anti-EGFR-huIgG1-SIRPα proteins, anti-CD47, SIRPα-FcV2 and Fc-SIRPαV2 bound to CD47 expressed on CD47-transfected CHO cells, but anti-EGFR did not bind because EGFR is not expressed (FIG. 7A). Anti-EGFR-huIgG1-huIgG1-huSIRPαV2 bound to CD47 expressed on CHO cells better than anti-EGFR-huIgG1-huSIRPαV1. The length of the linker in between Fc and SIRPα did not change the affinity of SIRPα for CD47 expressed on cells. It was also found that SIRPα-FcV2 bound to CD47 expressed on CD47-transfected CHO cells better than Fc-SIRPαV2, which bound better than Fc-SIRPαV2CC (data not shown).

The ability of the exemplary anti-EGFR-huIgG1-SIRPα to bind to CD47 expressed on the cell surface of blood cells was measured, and compared to the control molecules. Fresh whole blood from healthy human donors was enriched for leukocytes with dextran precipitation and was washed with PBS+1% FBS. 2×10$^5$ leukocyte-enriched human whole blood cells per well were incubated with 50 μg/ml proteins diluted in PBS+1% FBS in a 96 well plate for 60 min on ice. After washing with PBS+1% FBS, cells were incubated with a 1:200 dilution of FITC F(ab')2 goat Anti-Human IgG, Fcγ (Jackson ImmunoResearch, West Grove, Pa.), a 1:100 dilution of PE mouse anti-human CD235a (BD Biosciences, San Jose, Calif.), and a 1:100 dilution of eFluor 450 mouse anti-human CD45 (eBioscience, San Diego, Calif.) in PBS+ 1% FBS for 60 min on ice for protein detection and cell sorting by flow cytometry. After washing again, cells were fixed with 1% formaldehyde in PBS. Cells were analyzed by flow cytometry (MACSQuant, Miltenyi Biotec, Cologne, Germany).

Figure 7B:
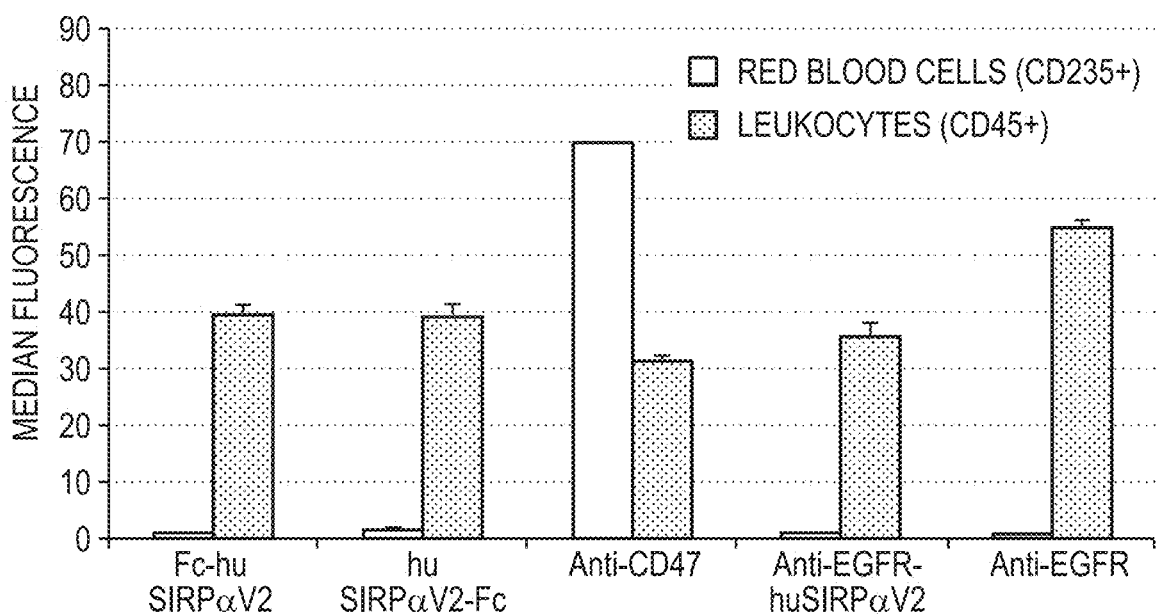

The results show that anti-CD47 bound to CD47 expressed on erythrocytes and leukocytes, but anti-EGFR-huIgG1-SIRPαV2, SIRPα-Fc and Fc-SIRPα only bound to CD47 expressed on leukocytes and not to CD47 expressed on erythrocytes (FIG. 7B).

4(B) (ii) Demonstration of Avidity of anti-EGFR-huIgG1-SIRPα by Binding Both Antigens Expressed on Cells The ability of the exemplary anti-EGFR-huIgG1-SIRPα to bind with avidity to EGFR and CD47 on the cell surface was measured on human A549 epidermoid carcinoma cells that overexpress EGFR and express CD47. 2×10$^5$ A549 cells per well were incubated with varying concentrations of antibodies diluted in PBS+1% FBS in a 96 well plate for 60 min on ice. After washing with PBS+1% FBS, cells were incubated with FITC F(ab')2 goat Anti-Human IgG, Fcγ (Jackson ImmunoResearch, West Grove, Pa.) diluted 1:200 in PBS+1% FBS for 60 min on ice. Cells were analyzed by flow cytometry (MACSQuant, Miltenyi Biotec, Cologne, Germany).

Figure 7C:
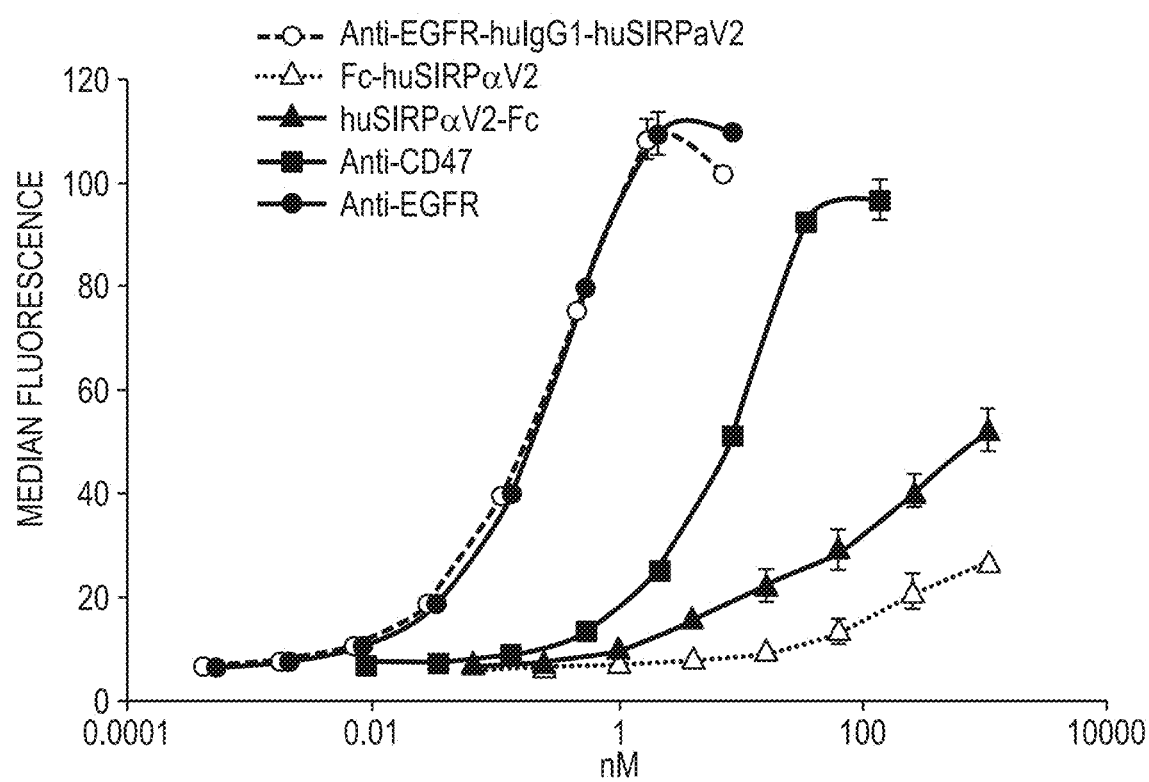

The results show that the binding of anti-EGFR-huIgG1-SIRPαV2 to A549 cells was similar to that of anti-EGFR (FIG. 7C). Because anti-Fc detection likely under-estimates the binding to cells of Fc fusion proteins having an additional C-terminal moiety (as described for Example 2B(ii)), the observation of similar binding of anti-EGFR-huIgG1-SIRPα and anti-EGFR suggests that avidity effects for anti-EGFR-huIgG1-SIRPα binding to the cells. It is noteworthy that in contrast to the binding to CD47 overexpressed on CHO cells, the binding of anti-CD47 to the endogenous CD47 on the A549 tumor cells was much better than that of SIRPα-Fc, which was in turn much better than that of Fc-SIRPα. Moreover, without wishing to be bound by theory, avidity likely contributes to the increased biological activities of anti-EGFR-huIgG1-SIRPαV2 fusion protein compared to anti-EGFR observed with respect to both the enhanced ADCC in vitro (FIG. 8) and enhanced anti-tumor activity in vivo (FIG. 9B). The ability of anti-EGFR-huIgG1-SIRPα to harness the avidity of binding to the tumor cells by binding to two tumor targets on the same cell may result in more specific targeting and less side effects in vivo.

4(C) Pharmacokinetic Analysis of anti-EGFR-huIgG1-SIRPα

Pharmacokinetic analysis of anti-EGFR-huIgG1-SIRPα was measured after injection into mice, and compared to the control molecules. 36 healthy female C57BL/6 mice (8 weeks of age) from Charles River Laboratories were allowed for acclimation for at least 3 days. Two dosing levels for each of molecule (single IV bolus) were given to the mice in a volume of 100 µL/mouse (equivalent to 20 or 200 µg per mouse, or approximately 1 or 10 mg/kg). On the dosing day, 36 mice were randomly assigned to 6 groups (N=6/group), in which each group received one dose/one molecule, intravenously via mouse tail vein, respectively. Mouse body weight was recorded. Mice received the same dose/article (N=6) were further divided into two subgroup (n=3). Four time blood withdrawals were taken from each subgroup, i.e., one subgroup at 1 h, 24 h, 72 h and 168 h, whereas another at 7 hr, 48 hr, 120 hr and 240 hr. At the indicated time points, small blood samples were taken using a heparinized micro glass capillary and collected in tubes coated with heparin to prevent clotting. After centrifugation to remove the cells, the concentration of the proteins in plasma was determined by ELISA, assayed by capture with anti-human IgG H+L (Jackson Immunoresearch, West Grove, Pa.), followed by detection with peroxidase-conjugated anti-human IgG Fc (Jackson Immunoresearch, West Grove, Pa.) to detect anti-EGFR-huIgG1-SIRPα.

Figure 9A:
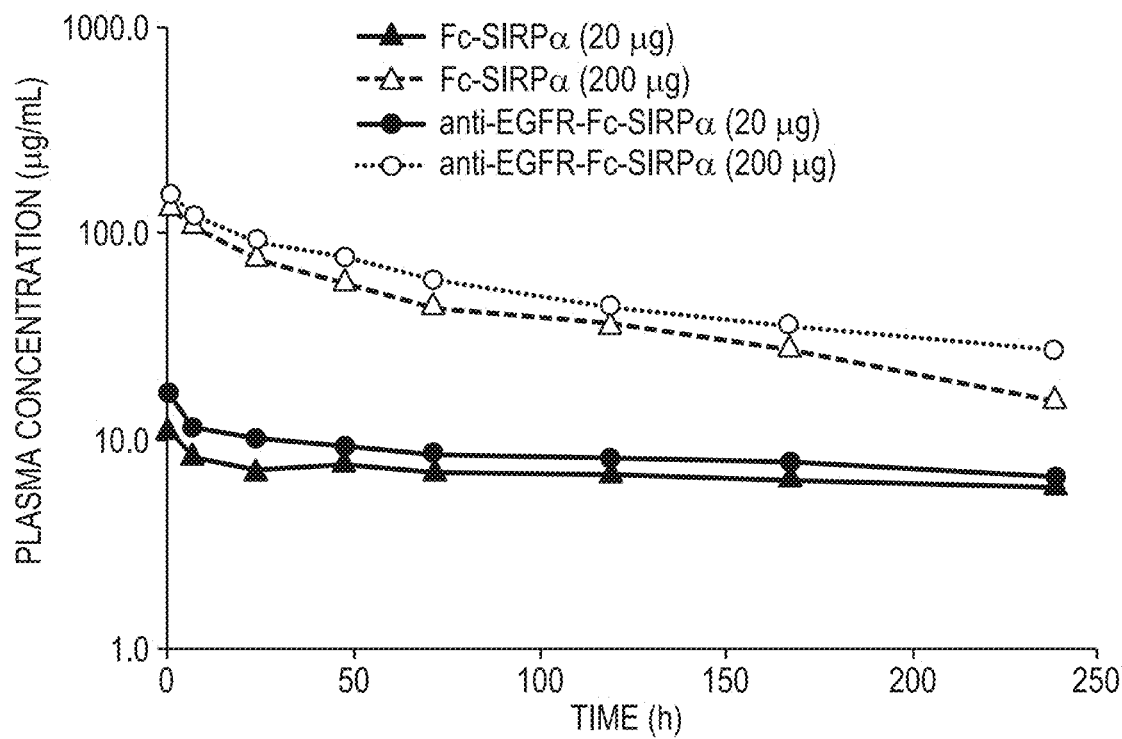
FIGS. 9A-B show the pharmacokinetic analysis of anti-EGFR-huIgG1-SIRPαV2 in mice (FIG. 9A) and the survival of mice after treatment with anti-EGFR-huIgG1-SIRPαV2 in an orthotopic A549 lung tumor model (FIG. 9B; inverted filled triangle: isotype control; filled circle: anti-EGFR; filled triangle: SIRPα-Fc; filled diamond: anti-EGFR and SIRPα-Fc; open circle: anti-EGFR-huIgG1-SIRPαV2).

The results show that anti-EGFR-huIgG1-SIRPαV2 was cleared similar to an antibody (FIG. 9A). After an initial 2-fold drop in the distribution phase at the first time-point, the plasma concentrations declined linearly according to a circulating half-life of about 8 days. Exposure was dose dependent with an AUC after 10 days of 2059 h*µg/ml for the 20 µg dose and 13164 h*µg/ml for the 200 µg dose. Clearance was dose dependent with 0.49 mL/h·kg for the 20 µg dose and 0.76 mL/h·kg for the 200 µg dose.

4(D)(i) In Vitro Biological Activities of anti-EGFR-huIgG1-SIRPα

The in vitro biological activity of anti-EGFR-huIgG1-SIRPα is shown in an antibody-dependent cell-mediated cytotoxicity (ADCC) assay. $6 \times 10^4$ human A549 epidermoid carcinoma cells were transferred to each well of a 96-well plate and incubated overnight at 37° C. The media from the cells was removed and replaced with serial dilutions of the recombinant antibodies for concentrations between 0.02-1600 ng/ml. After a 15-30 min incubation at 37° C., $1.5 \times 10^5$ effector cells (engineered Jurkat cells stably expressing the FcγRIIIa receptor, V158 (high affinity) variant, and an NFAT response element driving expression of firefly luciferase (Promega Madison, Wis.)) were added to each well of plates containing antibodies and A549 cells (effector-to-target cells ratio 2.5:1). After a 24-hour incubation, ADCC activity was measured via luciferase activity by adding Bio-Glo reagent (Promega Madison, Wis.) and measuring luminescence after a 15 min incubation.

Figure 8:
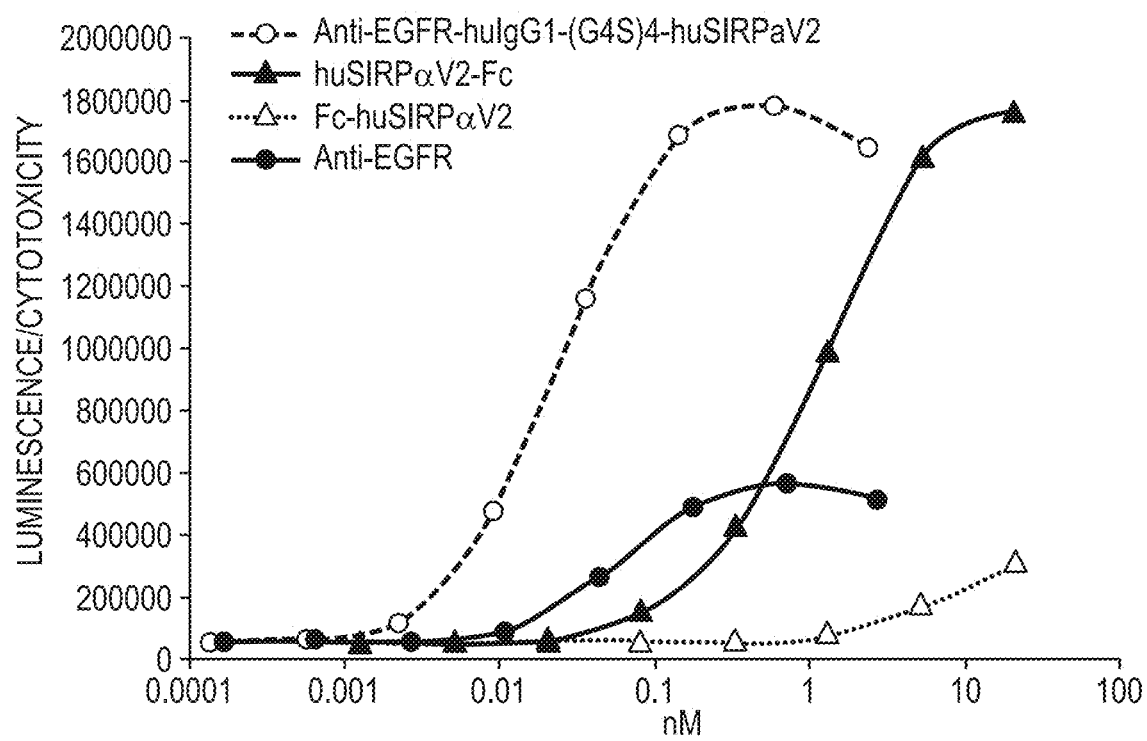
FIG. 8 shows the in vitro activity of anti-EGFR-huIgG1-SIRPαV2 in an ADCC assay using A549 target cells and engineered Jurkat effector cells.
Figure 9B:
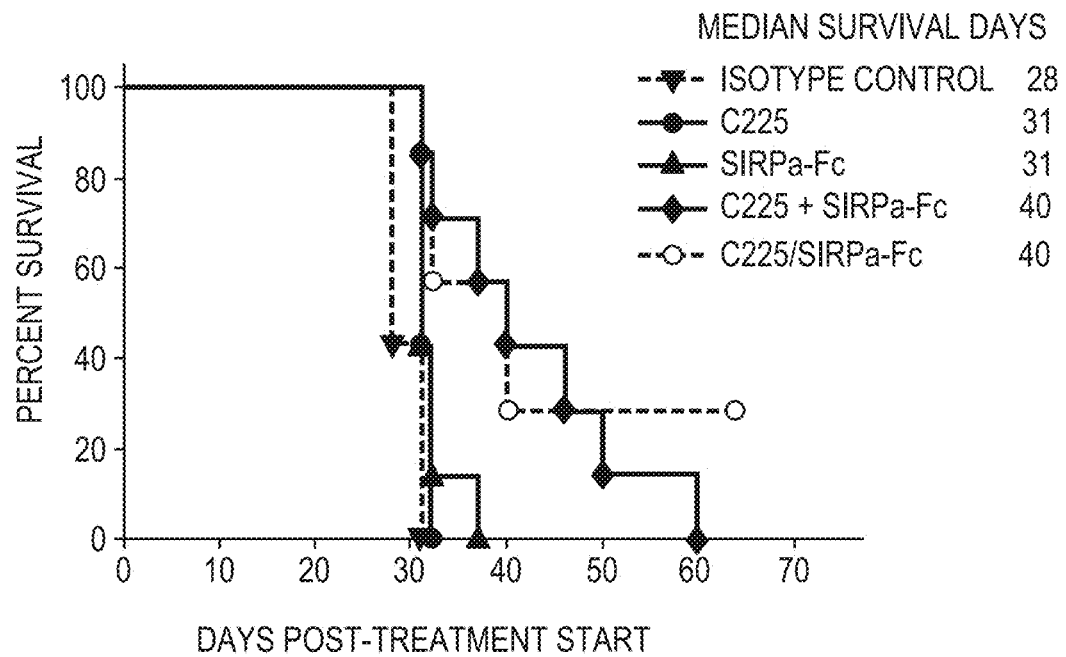

Anti-EGFR-huIgG1-SIRPαV2 was found to have significantly higher ADCC activity than anti-EGFR, SIRPαV2-Fc and Fc-SIRPαV2 (FIG. 8). Without wishing to be bound by theory, the much-enhanced in vitro activity of anti-EGFR-huIgG1-SIRPαV2 compared to anti-EGFR is most likely caused by the avidity-driven binding to CD47 once the higher-affinity interaction between EGFR and the fusion protein on the same cell has occurred, resulting in simultaneous binding of two tumor targets on the same cell.

4(D)(ii) In Vivo Biological Activities of anti-EGFR-huIgG1-SIRPα

The utility of anti-EGFR-huIgG1-SIRPα is shown by an in vivo experiment. In an orthotopic lung tumor model, NOD-SCID mice were injected i.v. with $2.5 \times 10^6$ human A549-luc epidermoid carcinoma cells, followed by i.p. injection of 250 µg/mouse of an antibody isotype control, 250 µg/mouse of anti-EGFR, 250 µg/mouse of anti-CD47, 132 µg/mouse of SIRPα-Fc, combination of 250 µg/mouse of anti-EGFR and 132 µg/mouse of SIRPα-Fc, or 292 µg/mouse of anti-EGFR-huIgG1-SIRPαV2, which is the equimolar amount of fusion protein. All the groups (n=7) received treatment twice a week for 3 weeks, and results were reported as bioluminescent signals from lungs, general health, e.g. paralysis, which preceded death by 10-14 days, and survival of mice.

Treatment with anti-EGFR-huIgG1-SIRPαV2 was found to be superior to the two monotherapies (FIG. 9B). Specifically, based on median survival days, anti-EGFR-huIgG1-SIRPαV2 was significantly more efficacious than anti-EGFR (40 days vs 31 days, p=0.0175). Moreover, based on overall survival, the fusion protein was somewhat more efficacious than the combination of the two monotherapies, despite the fact that SIRPα-Fc binds the target A549 cell better than the Fc-SIRPα. Without wishing to be bound by theory, the enhanced anti-tumor activity of anti-EGFR-huIgG1-SIRPαV2 is most likely caused by the avidity-driven binding to CD47 once the higher-affinity interaction between EGFR and the fusion protein on the same cell has occurred, resulting in enhanced ADCP and ADCC in vivo. Simultaneously blocking both the EGF/EGFR and the SIRPα/CD47 interactions, thus preventing signaling of these two pathways, may also contribute to the enhanced anti-tumor activities in vivo.

Example 5: Anti-HER2-huIgG1-SIRPα Immunoglobulin Fusion Proteins

5(A) Construction and Expression of anti-HER2-huIgG1-SIRPα

The generation of an exemplary anti-HER2-huIgG1-SIRPα is based on the anti-HER2 4D5 (trastuzumab) monoclonal antibody (Carter et al, PNAS 89: 4285, 1992) and the SIRPα protein (Jiang et al, JBC 274: 559, 1999). The DNA and protein sequence of the Fab light chain for 4D5 are provided in SEQ ID NO:21 and SEQ ID NO:22, respectively. The DNA and protein sequence of the Fab heavy chain for 4D5 are provided in SEQ ID NO:23 and SEQ ID NO:24, respectively. The DNA and protein sequence of the IgV domain of SIRPα allele V2 are provided in SEQ ID NO: 7 and SEQ ID NO:8, respectively. Anti-HER2-huIgG1-SIRPαV2 was generated by linking the C-terminus of the anti-HER2 heavy chain polypeptide to the IgV domain of SIRPαV2 via a (G4S)$_4$ linker (SEQ ID NO: 201).

For expression of anti-HER2-huIgG1-SIRPαV2, the following two gene constructs were assembled by standard recombinant DNA techniques and cloned into the mammalian expression vector pTT5 (containing the mouse light chain signal peptide sequence for secretion) as in FIG. 1A: (1) Construct VH(anti-HER2)-CH1-H-CH2-CH3-(G4S)$_4$-SIRPαV2 (SEQ ID NO:25) ("(G4S)$_4$" disclosed as SEQ ID NO: 201), encoding the following elements: anti-HER2 heavy chain variable domain followed by human heavy chain constant domains 1-3 followed by a (G4S)$_4$ linker (SEQ ID NO: 201) and IgV domain of SIRPαV2 and (2) Construct VL(anti-HER2)-CL (SEQ ID NO:21), encoding the following elements: anti-HER2 light chain variable domain followed by human kappa light chain constant domain. The corresponding amino acid for these two constructs are shown in SEQ ID NO:26 and SEQ ID NO:22 respectively.

Figure 10A:
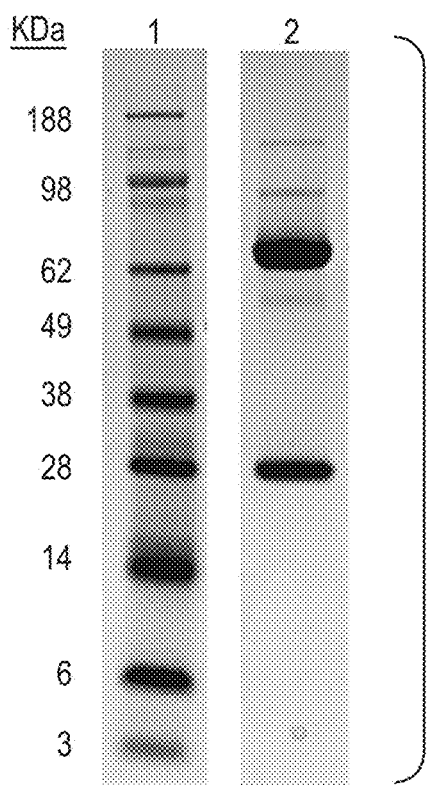
FIGS. 10A-B show the analysis of the expression of the two polypeptides of anti-HER2-huIgG1-SIRPαV2 by SDS-PAGE (FIG. 10A) and assembly of the full tetrameric molecule by size exclusion chromatography (SEC) (FIG. 10B) as described in Example 5.
Figure 10B:
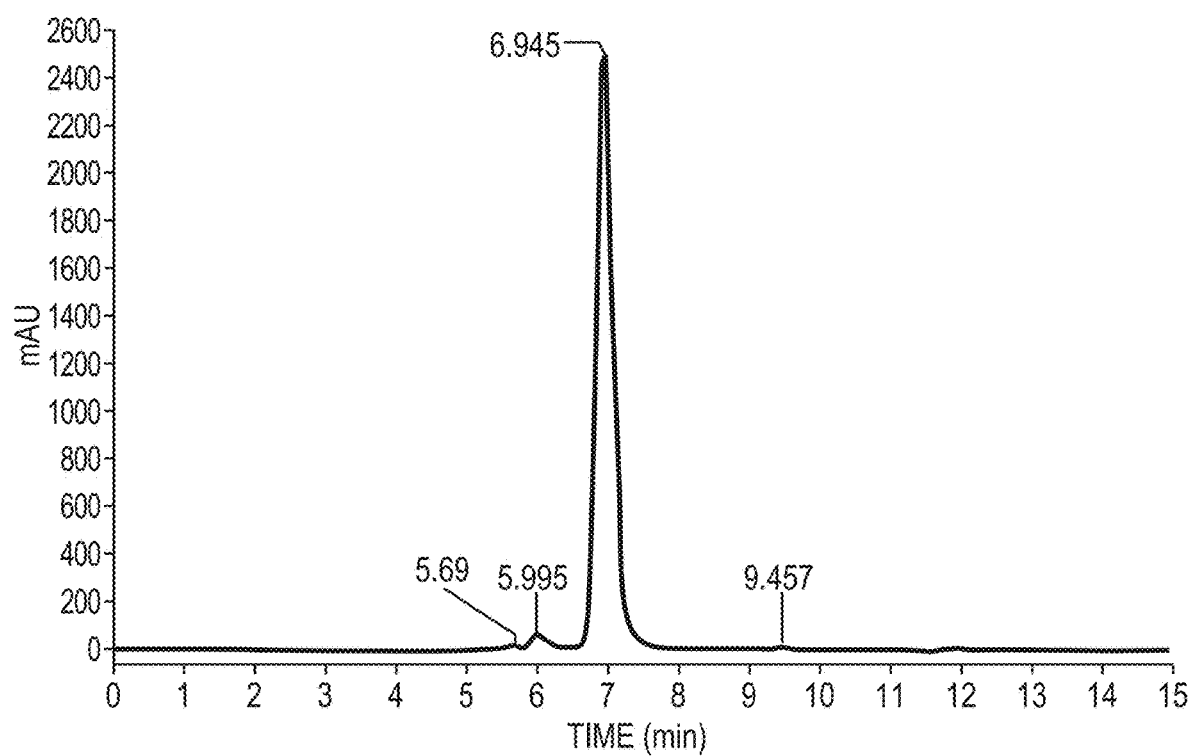

The two vectors were co-transfected transiently into Expi293 cells using Expi293fectin (Life Technologies, Grand Island, N.Y.) for expression of anti-HER2-huIgG1-SIRPα. The protein was purified in a single step by protein A affinity chromatography. Expression of the two polypeptides and assembly of the full tetrameric molecule were confirmed on sodium dodecyl sulfate-polyacrylamide gel electrophoresis (SDS-PAGE) and size exclusion chromatography (SEC). For SDS-PAGE, the purified protein samples were reduced with DTT and run on NuPAGE MES 4-12% Gel, 200V for 35 min, followed by Coomassie staining. The two major bands on the gel had the expected molecular weights (MW) and the correct stoichiometric ratio with >95% purity (FIG. 10A). In FIG. 10A, lane 1 shows the molecular weight (MW) marker and lane 2 shows the expected MW (64, 23 kDa) and the correct stoichiometric ratio (1:1) of the two polypeptides of anti-HER2-huIgG1-SIRPαV2. For SEC, the purified protein samples were analyzed on a TSK-GEL Super SW3000 SEC column 4.6× 300 mm (Tosoh Biosciences, Tokyo, Japan) that was equilibrated with 50 mM sodium phosphate, 400 mM sodium perchlorate, pH 6.3+0.1 and 38+2.0 mS/cm2. Size exclusion chromatography showed a peak at the expected MW of about 173 kDa for the monomeric anti-HER2-huIgG1-SIRPαV2 (FIG. 10B).

In addition, anti-HER2 and anti-CD47 in a standard monoclonal antibody format (anti-HER2 huIgG1 and anti-CD47 huIgG1) and SIRPα in an Fc-fusion protein format (SIRPαV2-Fc and Fc-SIRPαV2) (FIG. 1C) were generated as controls to compare with the anti-HER2-huIgG1-SIRPα format.

5(B)(i) Binding of anti-HER2-huIgG1-SIRPα to CD47 Expressed on Cells

The ability of anti-HER2-huIgG1-SIRPα to bind to CD47 expressed on the cell surface was measured, and compared to the control molecules. $2 \times 10^5$ CHO cells transfected with CD47 per well were incubated with varying concentrations of antibodies diluted in PBS+1% FBS in a 96 well plate for 60 min on ice. After washing with PBS+1% FBS, cells were incubated with FITC F(ab')2 goat Anti-Human IgG, Fcγ (Jackson ImmunoResearch, West Grove, Pa.) diluted 1:200 in PBS+1% FBS for 60 min on ice. Cells were analyzed by flow cytometry (MACSQuant, Miltenyi Biotec, Cologne, Germany).

Figure 11A:
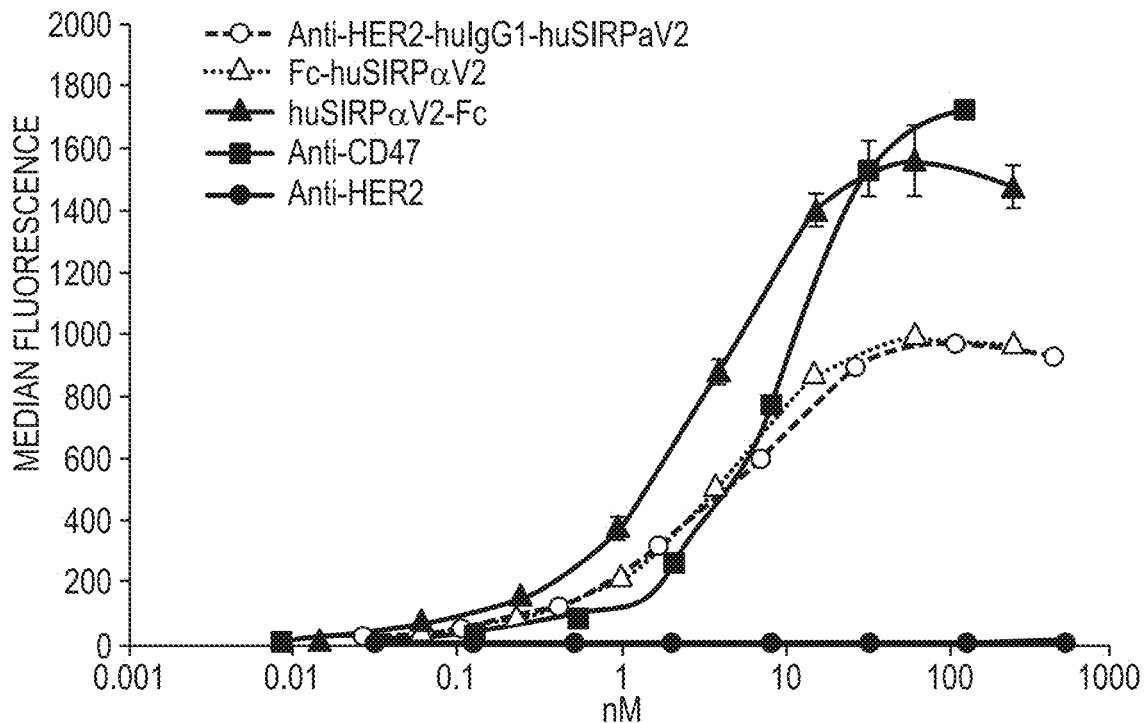
FIGS. 11A-C show binding of anti-HER2-huIgG1-SIRPαV2 to cells expressing CD47 (CD47-transfected CHO cells, FIG. 11A; leukocyte-enriched whole blood, FIG. 11B) or expressing both HER2 and CD47 (BT474 cells, FIG. 11C).

The results show that anti-HER2-huIgG1-SIRPαV2, anti-CD47, SIRPαV2-Fc and Fc-SIRPαV2 bound to CD47 overexpressed on transfected CHO cells, but anti-HER2 did not bind because HER2 is not expressed (FIG. 11A). Again, SIRPα-Fc showed a higher median fluorescence than Fc-SIRPα.

The ability of anti-HER2-huIgG1-SIRPα to bind to CD47 expressed on the cell surface of blood cells was measured, and compared to the control molecules. Fresh whole blood from healthy human donors was enriched for leukocytes with dextran precipitation and was washed with PBS+1% FBS. $2 \times 10^5$ leukocyte-enriched human whole blood cells per well were incubated with 50 μg/ml proteins diluted in PBS+1% FBS in a 96 well plate for 60 min on ice. After washing with PBS+1% FBS, cells were incubated with a 1:200 dilution of FITC F(ab')2 goat Anti-Human IgG, Fcγ (Jackson ImmunoResearch, West Grove, Pa.), a 1:100 dilution of PE mouse anti-human CD235a (BD Biosciences, San Jose, Calif.), and a 1:100 dilution of eFluor 450 mouse anti-human CD45 (eBioscience, San Diego, Calif.) in PBS+1% FBS for 60 min on ice for protein detection and cell sorting by flow cytometry. After washing again, cells were fixed with 1% formaldehyde in PBS. Cells were analyzed by flow cytometry (MACSQuant, Miltenyi Biotec, Cologne, Germany).

Figure 11B:
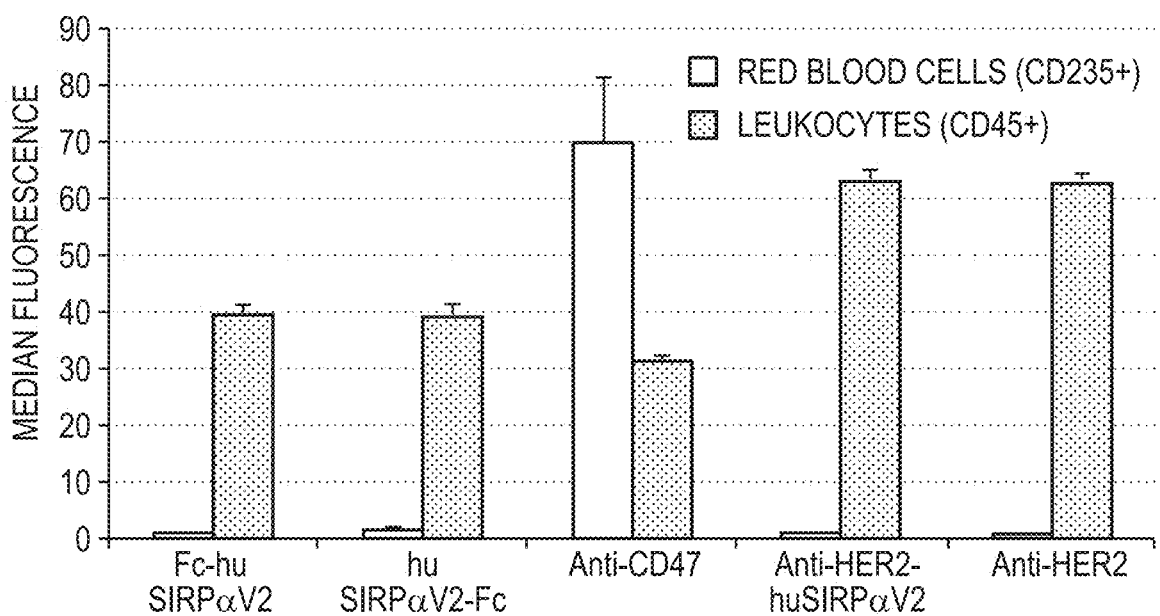

The results show that anti-CD47 bound to CD47 expressed on erythrocytes and leukocytes, but anti-HER2-huIgG1-SIRPαV2, SIRPαV2-Fc and Fc-SIRPαV2 only bound to CD47 expressed on leukocytes and not to CD47 expressed on erythrocytes (FIG. 11B).

5(B)(ii) Binding Avidity of anti-HER2-huIgG1-SIRPα on Cells Expressing Both Antigens The ability of anti-HER2-huIgG1-SIRPα to bind with avidity to HER2 and CD47 on the cell surface was measured on human BT474 mammary gland/breast adenocarcinoma cells that overexpress HER2 and express CD47. $2 \times 10^5$ BT474 cells per well were incubated with varying concentrations of anti-HER2-huIgG1-SIRPα, Fc-SIRPα, anti-HER2, and anti-CD47 diluted in PBS+1% FBS in a 96 well plate for 60 min on ice. After washing with PBS+1% FBS, cells were incubated with FITC F(ab')2 goat Anti-Human IgG, Fcγ (Jackson ImmunoResearch, West Grove, Pa.), diluted 1:200 in PBS+1% FBS for 60 min on ice. After washing again, cells were fixed with 1% formaldehyde in PBS. Cells were analyzed by flow cytometry (MACSQuant, Miltenyi Biotec, Cologne, Germany).

Figure 11C:
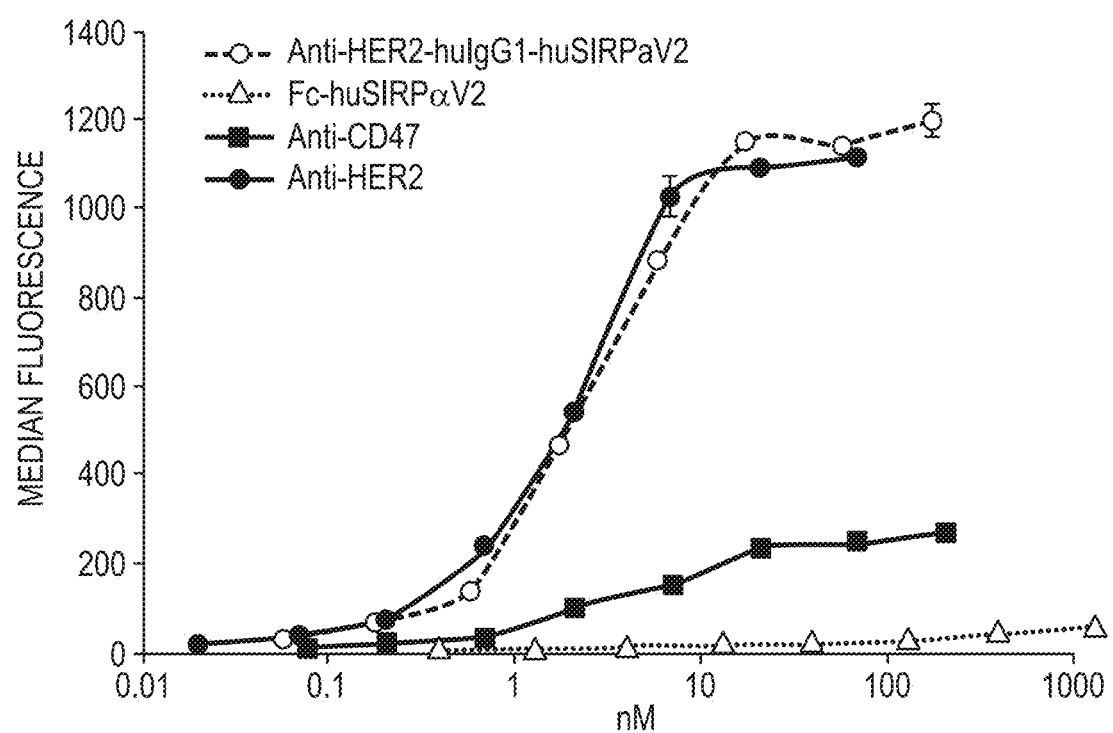

The results show that anti-HER2-huIgG1-SIRPαV2 binding to BT474 cells is enhanced compared to control molecules either individually or in combination (FIG. 11C), providing evidence for avidity. As explained in previous examples, anti-Fc based detection likely under-estimates the binding of the antibody-SIRPα fusion protein to cells. Thus, the observation of similar binding of anti-HER2-huIgG1-SIRPαV2 and anti-HER2 suggests avidity effects for anti-HER2-huIgG1-SIRPα binding to cells. The ability of anti-HER2-huIgG1-SIRPα to harness the avidity of binding to the tumor cells by binding to two tumor targets on the same cell may result in more specific targeting and less side effects in vivo.

Example 6: Anti-GD2-huIgG1-SIRPα Immunoglobulin Fusion Proteins

The generation of an exemplary anti-GD2-huIgG1-SIRPα is based on the anti-GD2 14.18 monoclonal antibody (Hank et al, Clin. Cancer Re. 15: 5923, 2009) and the SIRPα protein (Jiang et al, JBC 274: 559, 1999). The DNA and protein sequence of the Fab light chain for 14.18 are provided in SEQ ID NO:27 and SEQ ID NO:28, respectively. The DNA and protein sequence of the Fab heavy chain for 14.18 are provided in SEQ ID NO:29 and SEQ ID NO:30, respectively. The DNA and protein sequence of the IgV domain of SIRPα allele V2 are provided in SEQ ID NO: 7 and SEQ ID NO:8, respectively. Anti-GD2-huIgG1-SIRPαV2 is generated by linking the C-terminus of the anti-GD2 heavy chain polypeptide to SIRPαV2 via a (G4S)$_4$ linker (SEQ ID NO: 201).

For expression of anti-GD2-huIgG1-SIRPαV2, the following two gene constructs are assembled by standard recombinant DNA techniques and cloned into the mammalian expression vector pTT5 (containing the mouse light chain signal peptide sequence for secretion) as in FIG. 1A: (1) Construct VH(anti-GD2)-CH1-H-CH2-CH3-(G4S)$_4$— SIRPαV2 (SEQ ID NO:31) ("(G4S)$_4$" disclosed as SEQ ID NO: 201) encoding the following elements: anti-GD2 heavy chain variable domain followed by human heavy chain constant domains 1-3 followed by a (G4S)$_4$ linker (SEQ ID NO: 201) and IgV domain of SIRPαV2 and (2) Construct VL(anti-GD2)-CL (SEQ ID NO:27) encoding the following elements: anti-GD2 light chain variable domain followed by human kappa light chain constant domain. The corresponding amino acid for these two constructs are shown in SEQ ID NO:32 and SEQ ID NO:28 respectively.

In addition, anti-GD2 and anti-CD47 in a standard monoclonal antibody format (anti-GD2 huIgG1 and anti-CD47 huIgG1) and SIRPα in a Fc-fusion protein format (SIRPαV2-Fc and Fc-SIRPαV2) (FIG. 1C) are generated as controls to compare with the anti-GD2-huIgG1-SIRPα format.

Example 7: Anti-PD-L1-huIgG1-SIRPα Immunoglobulin Fusion Proteins

7(A) Construction and Expression of anti-PD-L1-huIgG1-SIRPα

The generation of an exemplary anti-PD-L1-huIgG1-SIRPα is based on the anti-PD-L1 monoclonal antibody avelumab (International Patent Application Publication No. WO2013/079174) and the SIRPα protein (Jiang et al, IBC 274: 559, 1999). The DNA and protein sequence of the Fab light chain for anti-PD-L1 are provided in SEQ ID NO:33 and SEQ ID NO:34, respectively. The DNA and protein sequence of the Fab heavy chain for anti-PD-L1 are provided in SEQ ID NO:35 and SEQ ID NO:36, respectively. The DNA and protein sequence of human IgV domain of SIRPα allele V2 are provided in SEQ ID NO:7 and SEQ ID NO:8, respectively. The DNA and protein sequence of murine SIRPα are provided in SEQ ID NO:37 and SEQ ID NO:38, respectively. Anti-PD-L1-huIgG1-muSIRPα was generated by linking the C-terminus of the anti-PD-L1 heavy chain polypeptide to the IgV domain of muSIRPα via a (G4S)$_4$ linker (SEQ ID NO: 201).

For expression of anti-PD-L1-huIgG1-muSIRPα, the following two gene constructs were assembled by standard recombinant DNA techniques and cloned into the mammalian expression vector pTT5 (containing the mouse light chain signal peptide sequence for secretion) as in FIG. 1A: (1) Construct VH(anti-PD-L1)-CH1-H-CH2-CH3-(G4S)$_4$-muSIRPα (SEQ ID NO:41) ("(G4S)$_4$" disclosed as SEQ ID NO: 201), encoding the following elements: anti-PD-L1 heavy chain variable domain followed by human heavy chain constant domains 1-3 followed by a (G4S)$_4$ linker (SEQ ID NO: 201) and IgV domain of muSIRPα and (2) Construct VL(anti-PD-L1)-CL (SEQ ID NO:33), encoding the following elements: anti-PD-L1 light chain variable domain followed by human kappa light chain constant domain. The corresponding amino acid for these two constructs are shown in SEQ ID NO:42 and SEQ ID NO:34 respectively.

Figure 12A:
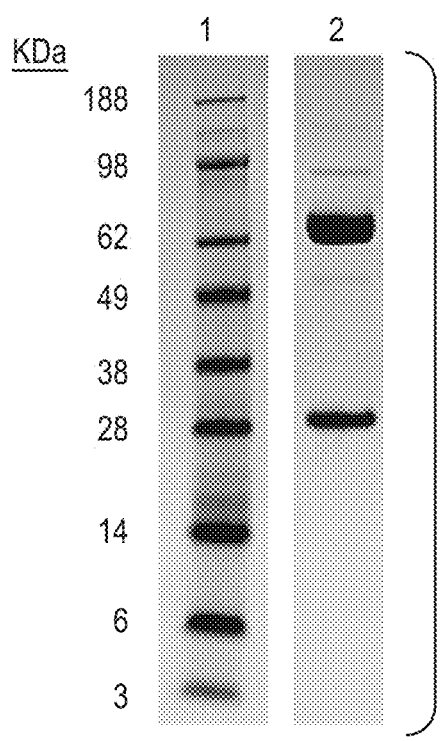
FIGS. 12A-B show the analysis of the expression of the two polypeptides of anti-PD-L1-huIgG1-muSIRPα by SDS-PAGE (FIG. 12A) and assembly of the full tetrameric molecule by size exclusion chromatography (SEC) (FIG. 12B) as described in Example 7.
Figure 12B:
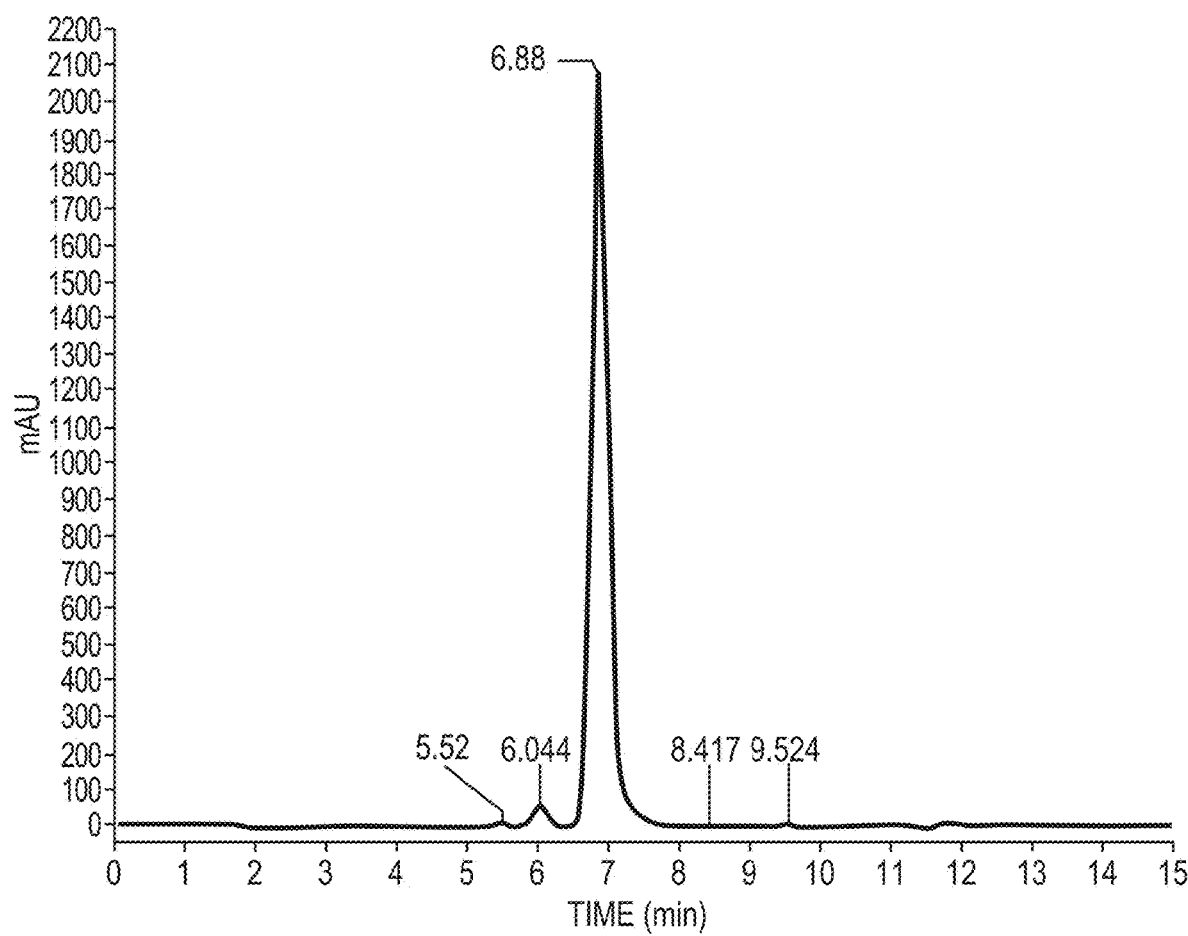

The two vectors were co-transfected transiently into Expi293 cells using Expi293fectin (Life Technologies, Grand Island, N.Y.) for expression of anti-PD-L1-huIgG1-muSIRPα. The protein was purified in a single step by protein A affinity chromatography. Expression of the two polypeptides and assembly of the full tetrameric molecule were confirmed on sodium dodecyl sulfate-polyacrylamide gel electrophoresis (SDS-PAGE) and size exclusion chromatography (SEC). For SDS-PAGE, the purified protein samples were reduced with DTT and run on NuPAGE MES 4-12% Gel, 200V for 35 min, followed by Coomassie staining. The two major bands on the gel had the expected molecular weights (MW) and the correct stoichiometric ratio with >95% purity (FIG. 12A). In FIG. 12A, lane 1 shows the molecular weight (MW) marker and lane 2 shows the expected MW (64, 23 kDa) and the correct stoichiometric ratio (1:1) of the two polypeptides of anti-PD-L1-huIgG1-muSIRPα. For SEC, the purified protein samples were analyzed on a TSK-GEL Super SW3000 SEC column 4.6× 300 mm (Tosoh Biosciences, Tokyo, Japan) that was equilibrated with 50 mM sodium phosphate, 400 mM sodium perchlorate, pH 6.3+0.1 and 38+2.0 mS/cm$^2$. Size exclusion chromatography showed a peak at the expected MW of about 173 kDa for the monomeric anti-PD-L1-huIgG1-muSIRPα (FIG. 12B).

In addition, anti-PD-L1 and anti-CD47 in a standard monoclonal antibody format (anti-PD-L1 IgG1 and anti-CD47 huIgG1) and SIRPα in a Fc-fusion protein format (SIRPαV2-Fc, Fc-huSIRPαV2, and Fc-muSIRPα) (FIG. 1C) are generated as controls to compare with the anti-PD-L1-huIgG1-SIRPα format.

7(B) Binding Avidity of anti-PD-L1-huIgG1-SIRPα on Cells Expressing Both Antigens The ability of anti-PD-L1-huIgG1-muSIRPα to bind with avidity to PD-L1 and CD47 on the cell surface was measured on mouse A20 B cell lymphoma cells that overexpress PD-L1 and express CD47. 2×10$^5$ A20 cells per well were incubated with varying concentrations of anti-PD-L1-huIgG1-muSIRPα, Fc-muSIRPα, and anti-PD-L1 diluted in PBS+1% FBS in a 96 well plate for 60 min on ice. After washing with PBS+1% FBS, cells were incubated with FITC F(ab')2 goat Anti-Human IgG, Fcγ (Jackson ImmunoResearch, West Grove, Pa.), diluted 1:200 in PBS+1% FBS for 60 min on ice. After washing again, cells were fixed with 1% formaldehyde in PBS. Cells were analyzed by flow cytometry (MACSQuant, Miltenyi Biotec, Cologne, Germany).

Figure 13:
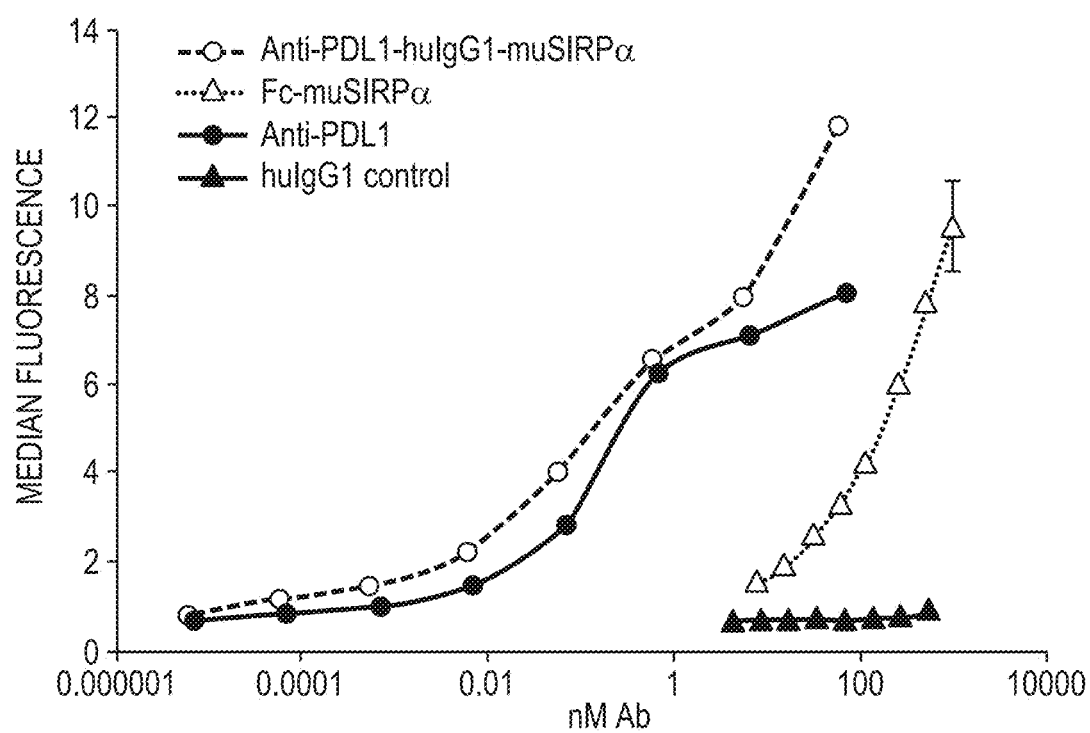
FIG. 13 shows binding of anti-PD-L1-huIgG1-muSIRPα to A20 cells expressing PD-L1 and CD47.

The results show that anti-PD-L1-huIgG1-muSIRPα binding to A20 cells was generally enhanced compared to the binding of the control molecules (FIG. 13), providing evidence for avidity. As explained in previous examples, anti-Fc based detection likely under-estimates the binding of the antibody-SIRPα fusion protein to cells. Thus, the observation of similar binding of anti-PD-L1-huIgG1-muSIRPα and anti-PD-L1 suggests avidity effects for anti-PD-L1-huIgG1-muSIRPα binding to cells. The ability of anti-PD-L1-huIgG1-muSIRPα to harness the avidity of binding to the tumor cells by binding to two tumor targets on the same cell may result in more specific targeting and less side effects in vivo.

Example 8: Anti-EGFR-huIgG1-SIRPα(aglycosylated) Immunoglobulin Fusion Proteins

8(A) Construction and Expression of anti-EGFR-huIgG1-SIRPα(aglycosylated)

The generation of an exemplary anti-EGFR-huIgG1-SIRPα(aglycosylated) is based on the anti-EGFR C225 (cetuximab) monoclonal antibody (Kawamoto, PNAS 80:1337, 1983) and the SIRPα protein with N110Q mutation (Jiang et al, JBC 274: 559, 1999). Aglycosylated SIRPα, via N110Q, was shown to bind worse to CD47 than glycosylated SIRPα (Ogura et al, JBC 279: 13711, 2004). The DNA and protein sequence of the Fab light chain for C225 are provided in SEQ ID NO:13 and SEQ ID NO:14, respectively. The DNA and protein sequence of the Fab heavy chain for C225 are provided in SEQ ID NO:15 and SEQ ID NO:16, respectively. The DNA and protein sequence of SIRPα allele V1 are provided in SEQ ID NO: 5 and SEQ ID NO:6, respectively. Anti-EGFR-huIgG1-SIRPαV1(N110Q) is generated by linking the C-terminus of the anti-EGFR heavy chain polypeptide to the IgV domain of SIRPαV1 (N110Q) via a (G4S)₄ linker (SEQ ID NO: 201).

For expression of the anti-EGFR-huIgG1-SIRPαV1 (N110Q), the following two gene constructs were assembled by standard recombinant DNA techniques and are cloned into the mammalian expression vector pTT5 (containing the mouse light chain signal peptide sequence for secretion) as in FIG. 1A: (1) Construct VH(anti-EGFR)-CH1-H-CH2-CH3-(G4S)₄-SIRPαV1(N110Q) (SEQ ID NO:43) ("(G4S)₄" disclosed as SEQ ID NO: 201), encoding the following elements: anti-EGFR heavy chain variable domain followed by human heavy chain constant domains 1-3 isotype IgG1 followed by a (G4S)₄ linker (SEQ ID NO: 201) and IgV domain of SIRPαV1(N110Q). 2) Construct VL(anti-EGFR)-CL (SEQ ID NO:13), encoding the following elements: anti-EGFR light chain variable domain followed by human kappa light chain constant domain. The corresponding amino acid sequences for these two constructs are shown in SEQ ID NO:44 and SEQ ID NO:14 respectively.

Figure 14A:
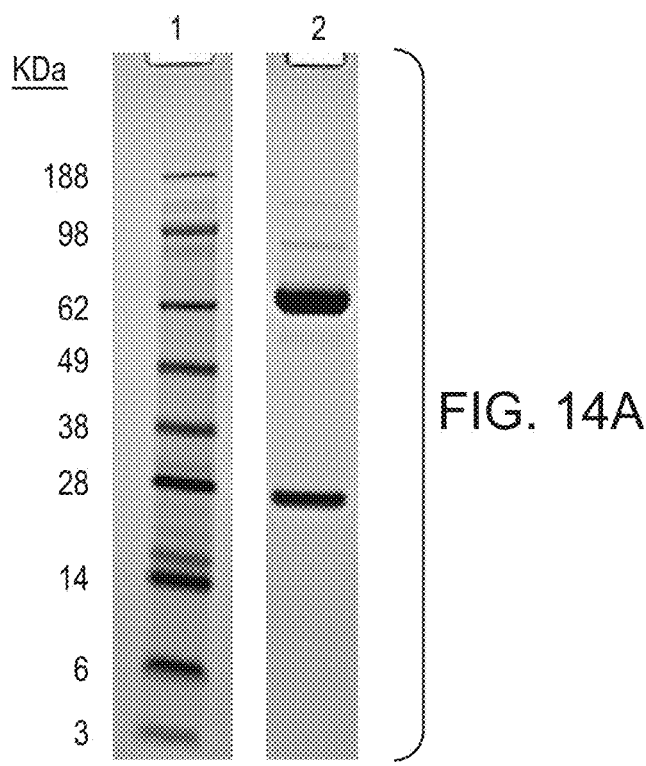
FIGS. 14A-B show the analysis of the expression of the two polypeptides of anti-EGFR-huIgG1-SIRPα(N110Q) by SDS-PAGE (FIG. 14A) and assembly of the full tetrameric molecule by size exclusion chromatography (SEC) (FIG. 14B) as described in Example 8.
Figure 14B:
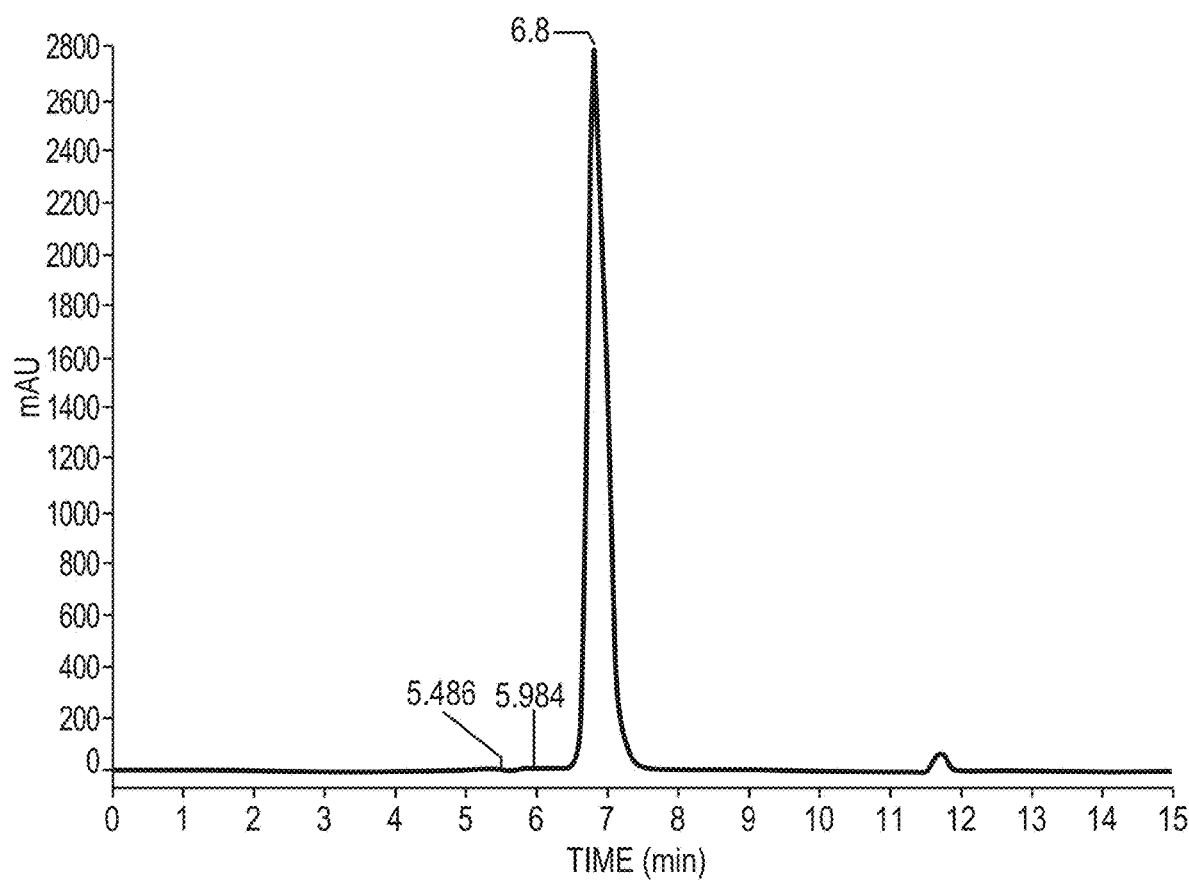

The two vectors were co-transfected transiently into Expi293 cells using Expi293fectin (Life Technologies, Grand Island, N.Y.) for expression of anti-EGFR-huIgG1-SIRPαV1(N110Q). The protein was purified in a single step by protein A affinity chromatography. Expression of the two polypeptides and assembly of the full tetrameric molecule were confirmed on sodium dodecyl sulfate-polyacrylamide gel electrophoresis (SDS-PAGE) and size exclusion chromatography (SEC). For SDS-PAGE, the purified protein samples were reduced with DTT and run on NuPAGE MES 4-12% Gel, 200V for 35 min, followed by Coomassie staining. The two major bands on the gel had the expected molecular weights (MW) and the correct stoichiometric ratio with >95% purity (FIG. 14A). In FIG. 14A, lane 1 shows the molecular weight (MW) marker and lane 2 shows the expected MW (64, 23 kDa) and the correct stoichiometric ratio (1:1) of the two polypeptides of anti-EGFR-huIgG1-SIRPαV1(N110Q). For SEC, the purified protein samples were analyzed on a TSK-GEL Super SW3000 SEC column 4.6×300 mm (Tosoh Biosciences, Tokyo, Japan) that was equilibrated with 50 mM sodium phosphate, 400 mM sodium perchlorate, pH 6.3+0.1 and 38+2.0 mS/cm². Size exclusion chromatography showed a peak at the expected MW of about 173 kDa for the monomeric anti-EGFR-huIgG1-SIRPαV1(N110Q) (FIG. 14B).

In addition, anti-EGFR and anti-CD47 in a standard monoclonal antibody format (anti-EGFR huIgG1 and anti-CD47 huIgG1) and SIRPα in a Fc-fusion protein format (SIRPαV2-Fc and Fc-SIRPαV2) (FIG. 1C) are generated as controls to compare with the anti-EGFR-huIgG1-SIRPα format.

8(B) Binding of anti-EGFR-huIgG1-SIRPα(aglycosylated) to CD47 Expressed on Cells The ability of anti-EGFR-huIgG1-SIRPαV1(N110Q) to bind to CD47 overexpressed on the cell surface was measured, and compared to the control molecules. 2×10⁵ CHO cells transfected with CD47 per well were incubated with varying concentrations of antibodies diluted in PBS+1% FBS in a 96 well plate for 60 min on ice. After washing with PBS+1% FBS, cells were incubated with FITC F(ab')2 goat Anti-Human IgG, Fcγ (Jackson ImmunoResearch, West Grove, Pa.) diluted 1:200 in PBS+1% FBS for 60 min on ice. After washing again, cells were fixed with 1% formaldehyde in PBS. Cells were analyzed by flow cytometry (MACSQuant, Miltenyi Biotec, Cologne, Germany).

Figure 15:
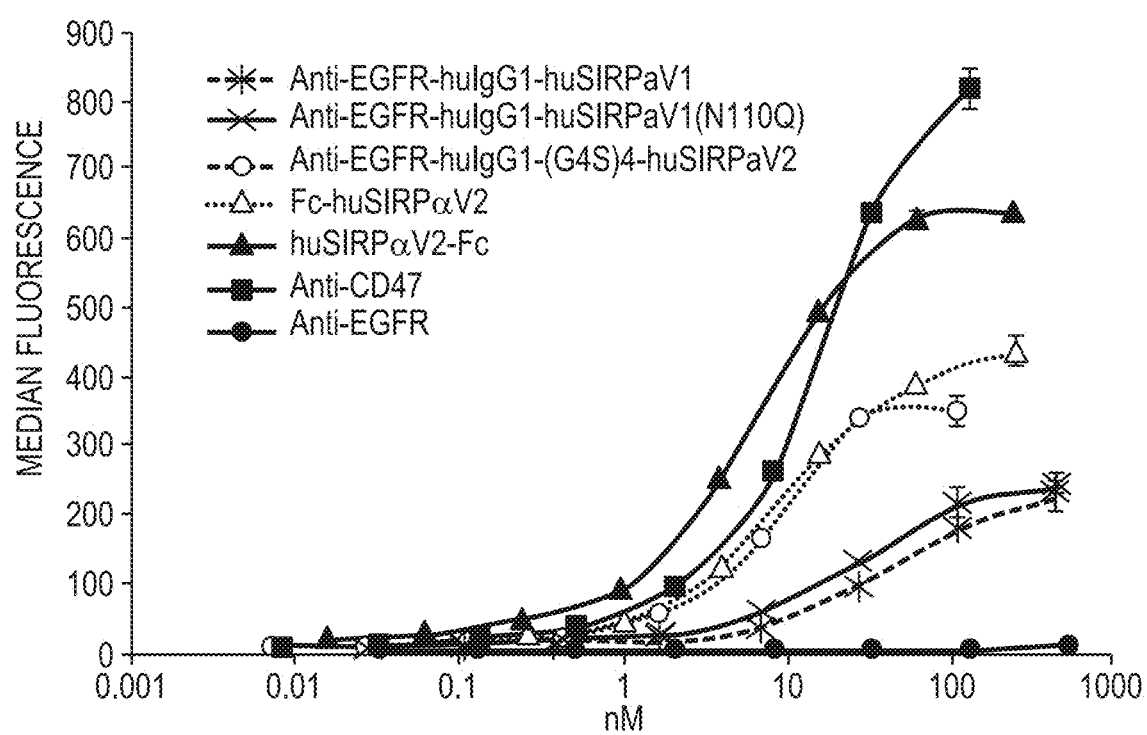
FIG. 15 shows binding of anti-EGFR-huIgG1-SIRPα (N110Q) to cells expressing CD47 (CD47-transfected CHO cells).

The results show that anti-EGFR-huIgG1-SIRPαV1 (N110Q) bound to CD47 expressed on transfected CHO cells (FIG. 15). Unlike prior reports (Ogura et al., JBC 279: 13711, 2004), anti-EGFR-huIgG1-huSIRPα V1(N110Q) bound as well to CD47 as anti-EGFR-huIgG1-huSIRPαV1.

Example 9:
Anti-EGFR-huIgG1/anti-EGFR-LC-SIRPα Immunoglobulin Fusion Proteins

9(A) Construction and Expression of anti-EGFR-huIgG1/anti-EGFR-LC-SIRPα

The generation of an exemplary anti-EGFR-huIgG1/anti-EGFR-LC-SIRPα is based on the anti-EGFR C225 (cetuximab) monoclonal antibody (Kawamoto, PNAS 80:1337, 1983) and the SIRPα protein (Jiang et al, JBC 274: 559, 1999). The DNA and protein sequence of the Fab light chain for C225 are provided in SEQ ID NO:13 and SEQ ID NO:14, respectively. The DNA and protein sequence of the Fab heavy chain for C225 are provided in SEQ ID NO:15 and SEQ ID NO:16, respectively. The DNA and protein sequence of SIRPα allele V1 are provided in SEQ ID NO: 5 and SEQ ID NO:6, respectively, and the DNA and protein sequence of the IgV domain of SIRPα allele V2 are provided in SEQ ID NO:7 and SEQ ID NO:8, respectively. In a particular embodiment, anti-EGFR-huIgG1/anti-EGFR-LC-SIRPα is generated by linking the C-terminus of the anti-EGFR light chain polypeptide to the IgV domain of SIRPαV2 via a (G4S)₄ linker (SEQ ID NO: 201), and also can be fused directly without any linker or with (GXS)ᵧ, where X, Y=0, 1, 2, 3, 4, 5, 6, 7, 8 or more (SEQ ID NO: 205).

Figure 1F:
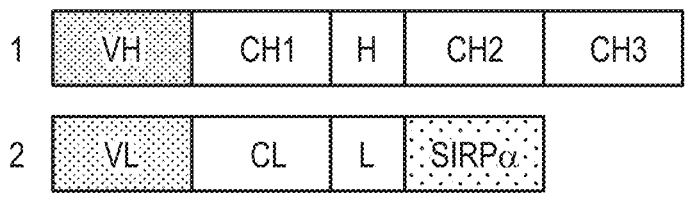
FIG. 1F is a schematic drawing of DNA constructs for the expression of an antibody-SIRPα. DNA construct 1 (top) encodes the heavy chain variable domain of antibody (VH) followed by heavy chain constant domains (CH1, hinge (H)-CH2-CH3). DNA construct 2 (bottom) encodes the light chain variable domain of antibody (VL) followed by light chain constant domain (CL) genetically fused via an optional linker (L) to SIRPα.
Figure 1G:
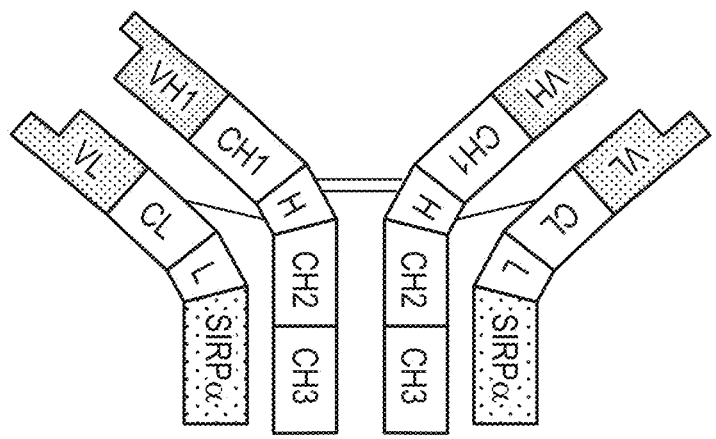
FIG. 1G is a schematic drawing of an antibody-SIRPα showing the tetrameric structure comprising the two polypeptide components encoded by the DNA construct shown in FIG. 1F.

For expression of anti-EGFR-huIgG1/anti-EGFR-LC-SIRPαV2, the following two gene constructs were assembled by standard recombinant DNA techniques and cloned into the mammalian expression vector pTT5 (containing the mouse light chain signal peptide sequence for secretion) as in FIG. 1F: (1) Construct VH(anti-EGFR)-CH1-H-CH2-CH3 (SEQ ID NO:45), encoding the following elements: anti-EGFR heavy chain variable domain, followed by human heavy chain constant domains 1-3 isotype IgG and (2) Construct VL(anti-EGFR)-CL-(G4S)₂-SIRPαV2 (SEQ ID NO:47) ("(G4S)₂" disclosed as SEQ ID NO: 206), encoding the following elements: anti-EGFR light chain variable domain, followed by human kappa light chain constant domain, followed by a (G4S)₄ linker (SEQ ID NO: 201) and the IgV domain of SIRPαV2. The corresponding amino acid sequences for these two constructs are shown in SEQ ID NO:46, and SEQ ID NO:48 respectively.

For expression of anti-EGFR-ds1-huIgG1/anti-EGFR-LC-SIRPαV2, the following two gene constructs were assembled by standard recombinant DNA techniques and cloned into the mammalian expression vector pTT5 (containing the mouse light chain signal peptide sequence for secretion) as in FIG. 1F: (1) Construct VH(anti-EGFR)(ds1-G44C)-CH1-H-CH2-CH3 (SEQ ID NO:73), encoding the following elements: anti-EGFR heavy chain variable domain with a stabilizing mutation (ds1: G44C) to compensate for destabilization of the light chain fusion (Orcutt et al., PEDS 23:221, 2010), followed by human heavy chain constant domains 1-3 isotype IgG and (2) Construct VL(anti-EGFR)(ds1-A100C)-CL-(G4S)₄-SIRPαV2 (SEQ ID NO:77) ("(G4S)₄" disclosed as SEQ ID NO: 201), encoding the following elements: anti-EGFR light chain variable domain with a stabilizing mutation (ds1: A100C), followed by human kappa light chain constant domain, followed by a (G4S)₄ linker (SEQ ID NO: 201) and the IgV domain of SIRPαV2. The corresponding amino acid sequences for these two constructs are shown in SEQ ID NO:74 and SEQ ID NO:78 respectively.

For expression of the anti-EGFR-ds2-huIgG1/anti-EGFR-LC-SIRPα, the following two gene constructs were assembled by standard recombinant DNA techniques and cloned into the mammalian expression vector pTT5 (containing the mouse light chain signal peptide sequence for secretion) as in FIG. 1F: (1) Construct VH(anti-EGFR)(ds2-Q105C)-CH1-H-CH2-CH3 (SEQ ID NO:75), encoding the following elements: anti-EGFR heavy chain variable domain with a stabilizing mutation (ds2: Q105C to compensate for destabilization of the light chain fusion (Orcutt et al, PEDS 23:221, 2010), followed by human heavy chain constant domains 1-3 isotype IgG and (2) Construct VL(anti-EGFR)(ds2-S43C)-CL-(G4S)$_4$-SIRPαV2 (SEQ ID NO:79) ("(G4S)$_4$" disclosed as SEQ ID NO: 201), encoding the following elements: anti-EGFR light chain variable domain with a stabilizing mutation (ds2: S43C), followed by human kappa light chain constant domain, followed by a (G4S)$_4$ linker (SEQ ID NO: 201) and the IgV domain of SIRPαV2. The corresponding amino acid sequences for these two constructs are shown in SEQ ID NO:76, and SEQ ID NO:80 respectively.

In addition, anti-EGFR and anti-CD47 in a standard monoclonal antibody format (anti-EGFR huIgG1 and anti-CD47 huIgG1) and SIRPα in an Fc-fusion protein format (SIRPαV2-Fc and Fc-SIRPαV2) (FIG. 1C) are generated as controls to compare with the anti-EGFR-huIgG1/anti-EGFR-LC-SIRPα format.

An alternate method of stabilization was examined by introducing the heavy and light chain disulfide pairing format of IgG4, by introducing two mutations (S131C and C222S in SEQ ID NO: 46) in the heavy chain CH1 domain. The light chain C-terminal cysteine which would have normally paired with the heavy chain C222 will now form a disulfide bond with C131. Additionally this mutated heavy chain can have either of the ds1 or ds2 mutation for even more stability enhancement and paired with the respective (ds1 or ds2) light chain.

Figure 21A:
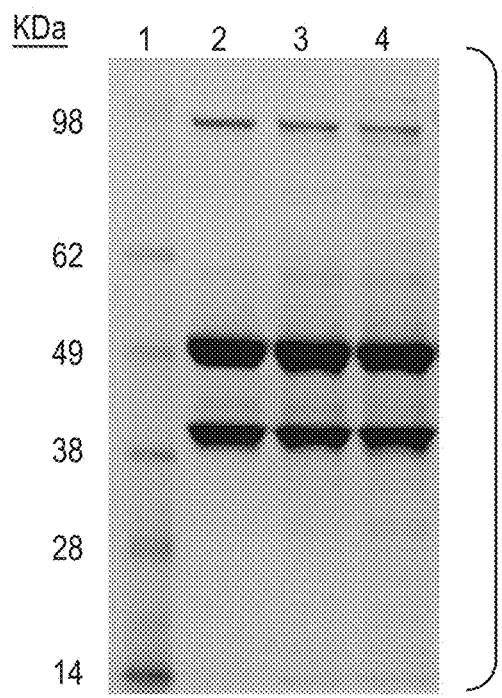
FIGS. 21A-C show the analysis of the expression of the two polypeptides of anti-EGFR-huIgG1/anti-EGFR-LC-SIRPαV2 by SDS-PAGE (FIG. 21A) and assembly of the full tetrameric molecule by size exclusion chromatography (SEC) (FIG. 21B) as described in Example 9, and the binding of anti-EGFR-huIgG1/anti-EGFR-LC-SIRPαV2 to cells expressing CD47 (CD47-transfected CHO cells, FIG. 21C).
Figure 21B:
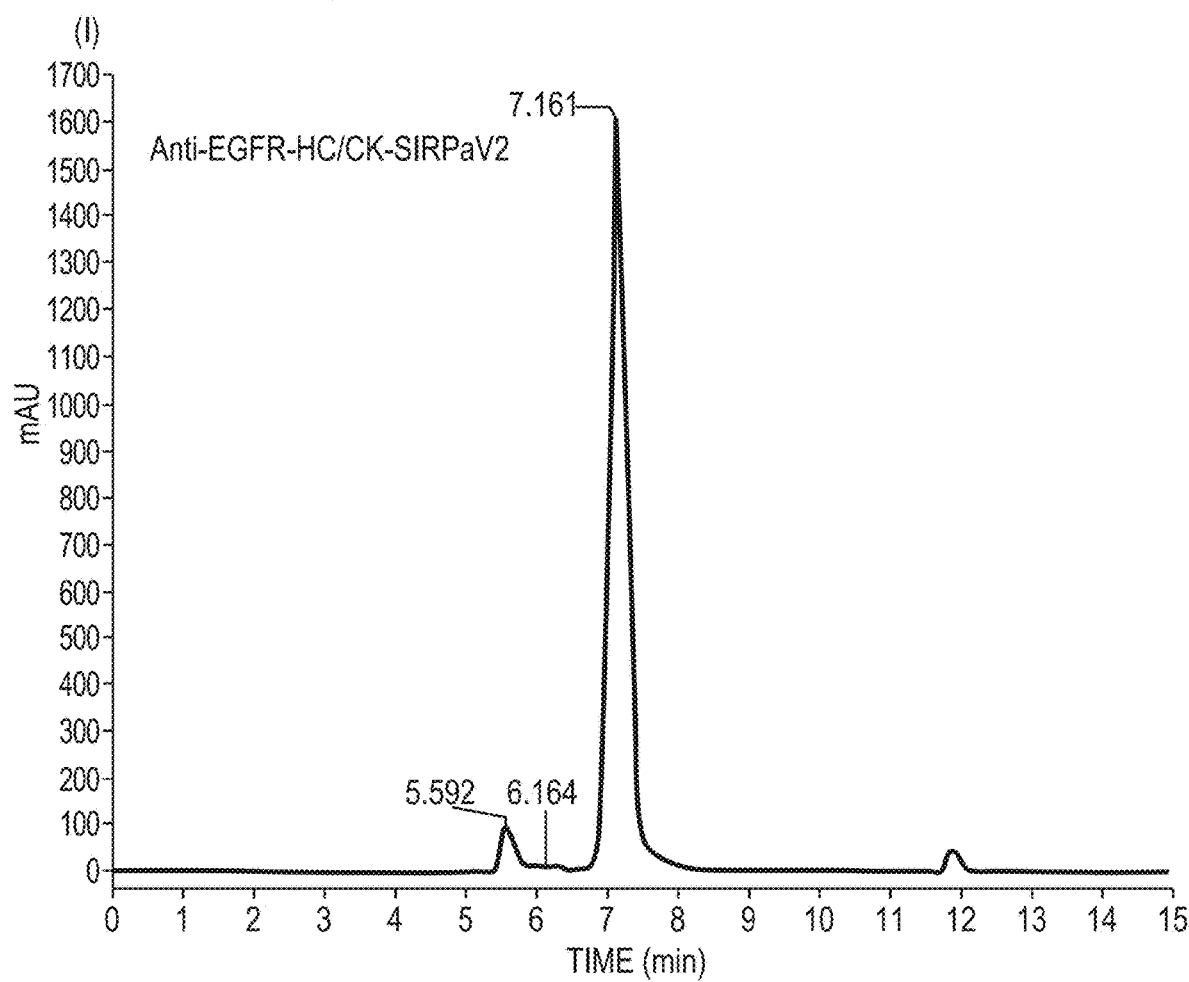
Figure 21B:
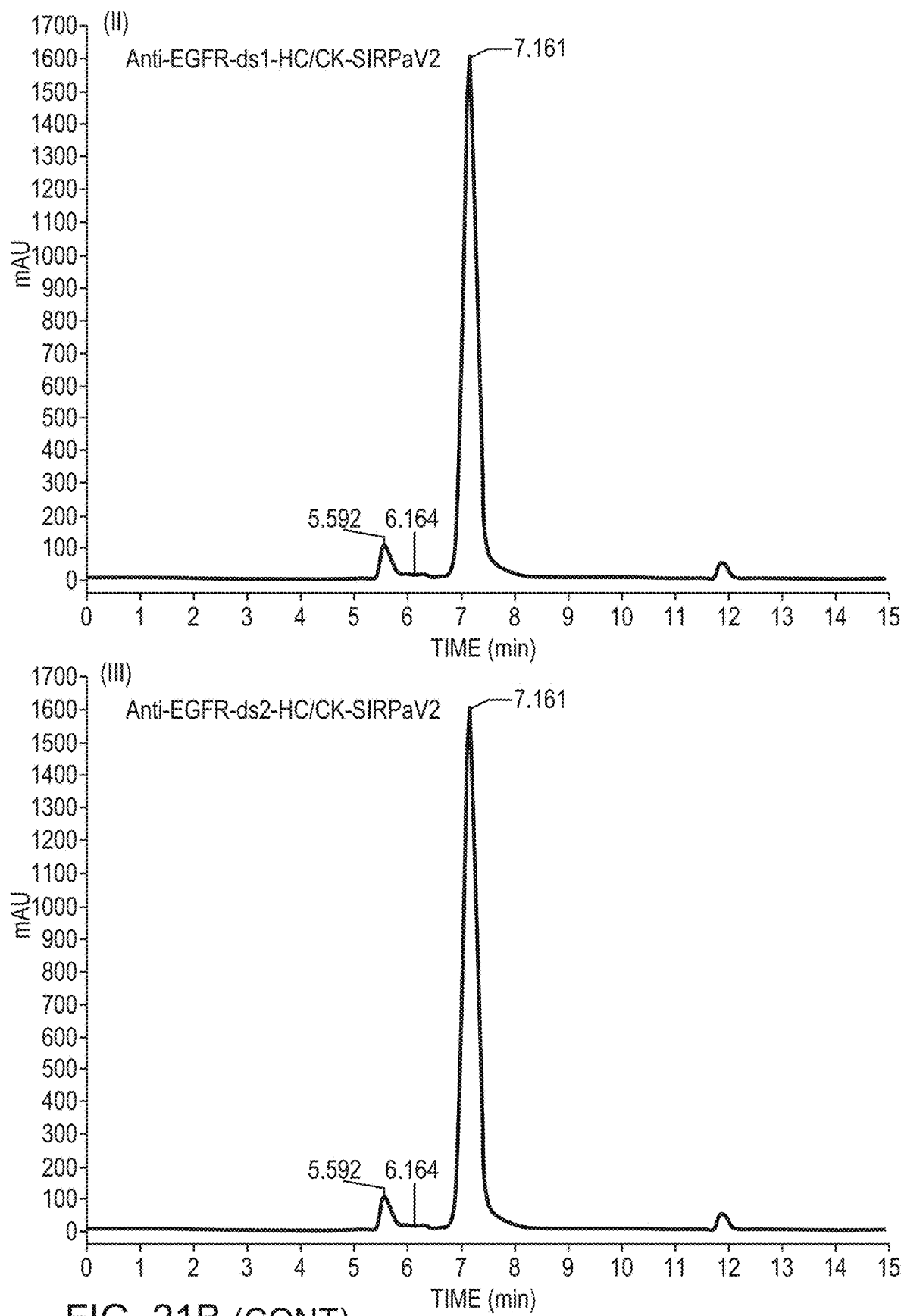

Each of the two vectors were co-transfected transiently into Expi293 cells using Expi293fectin (Life Technologies, Grand Island, N.Y.) for expression of anti-EGFR-huIgG1/anti-EGFR-LC-SIRPα. The proteins were purified in a single step by protein A affinity chromatography. Expression of the two polypeptides and assembly of the full tetrameric molecule were confirmed on sodium dodecyl sulfate-polyacrylamide gel electrophoresis (SDS-PAGE) and size exclusion chromatography (SEC). For SDS-PAGE, the purified protein samples were reduced with DTT and run on NuPAGE MES 4-12% Gel, 200V for 35 min, followed by Coomassie staining. The two major bands on the gel had the expected molecular weights (MW) and the correct stoichiometric ratio with >95% purity (FIG. 21A). In FIG. 21A, lane 1 shows the molecular weight (MW) marker, lane 2 shows the expected MW (49, 36 kDa) and the correct stoichiometric ratio (1:1) of the two polypeptides of anti-EGFR-huIgG1/anti-EGFR-LC-SIRPα, lane 3 shows the expected MW (49, 36 kDa) and the correct stoichiometric ratio (1:1) of the two polypeptides of anti-EGFR-ds1-huIgG1/anti-EGFR-LC-SIRPα, and lane 4 shows the expected MW (49, 36 kDa) and the correct stoichiometric ratio (1:1) of the two polypeptides of anti-EGFR-ds2-huIgG1/anti-EGFR-LC-SIRPα. The wild type sequences of the VH and VL domains had the least number of extra bands on the SDS PAGE, contrary to the expectation that the ds1 and ds2 mutations would stabilize the light chain fusion. For SEC, the purified protein samples were analyzed on a TSK-GEL Super SW3000 SEC column 4.6×300 mm (Tosoh Biosciences, Tokyo, Japan) that was equilibrated with 50 mM sodium phosphate, 400 mM sodium perchlorate, pH 6.3+0.1 and 38+2.0 mS/cm$^2$. Size exclusion chromatography showed a peak at the expected MW of about 172 kDa for the monomeric anti-EGFR-huIgG1/anti-EGFR-LC-SIRPα (FIG. 21B).

In addition, anti-EGFR and anti-CD47 in a standard monoclonal antibody format (anti-EGFR huIgG1 and anti-CD47 huIgG1) and SIRPα in an Fc-fusion protein format (SIRPαV2-Fc and Fc-SIRPαV2) (FIG. 1C) are generated as controls to compare with the anti-EGFR-huIgG1-SIRPα format.

9(B) Binding of anti-EGFR-huIgG1/anti-EGFR-LC-SIRPα to CD47 Expressed on Cells

Figure 21C:
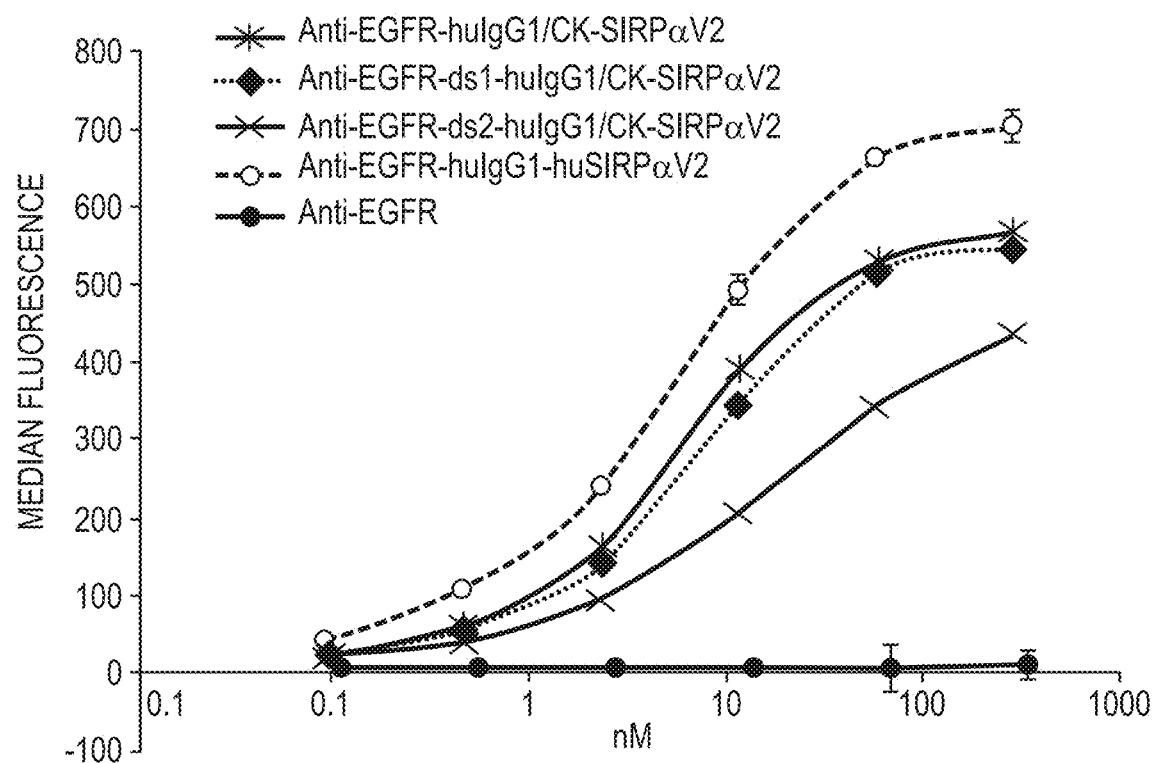

The ability of anti-EGFR-huIgG1/anti-EGFR-LC-SIRPαV2 to bind to CD47 overexpressed on the cell surface was measured, and compared to the control molecules. 2×10$^5$ CHO cells transfected with CD47 per well were incubated with varying concentrations of antibodies diluted in PBS+1% FBS in a 96 well plate for 60 min on ice. After washing with PBS+1% FBS, cells were incubated with FITC F(ab')2 goat Anti-Human IgG, Fcγ (Jackson ImmunoResearch, West Grove, Pa.) diluted 1:200 in PBS+1% FBS for 60 min on ice. After washing again, cells were fixed with 1% formaldehyde in PBS. Cells were analyzed by flow cytometry (MACSQuant, Miltenyi Biotec, Cologne, Germany). The results show that anti-EGFR-huIgG1/anti-EGFR-LC-SIRPαV2 bound to CD47 expressed on transfected CHO cells, but not as well as anti-EGFR-huIgG1-SIRPαV2 (FIG. 21C).

Example 10: SIRPα-Fc(huIgG1)-anti-EGFR(Fab) Immunoglobulin Fusion Protein

10(A) Construction and Expression of SIRPα-Fc(huIgG1)-anti-EGFR(Fab)

The generation of an exemplary SIRPα-Fc(huIgG1)-anti-EGFR(Fab) is based on the anti-EGFR C225 (cetuximab) monoclonal antibody (Kawamoto, PNAS 80:1337, 1983) and the SIRPα protein (Jiang et al, JBC 274: 559, 1999). The DNA and protein sequence of the Fab light chain for C225 are provided in SEQ ID NO:13 and SEQ ID NO:14, respectively. The DNA and protein sequence of the Fab heavy chain for C225 are provided in SEQ ID NO:15 and SEQ ID NO:16, respectively. The DNA and protein sequence of the IgV domain of SIRPα allele V2 are provided in SEQ ID NO: 7 and SEQ ID NO:8, respectively. SIRPα-Fc(huIgG1)-anti-EGFR(Fab) was generated by linking SIRPα to the N-terminus of the Fc heavy chain via a (G4S)$_2$ linker (SEQ ID NO: 206) followed by linking anti-EGFR Fab heavy chain to the C-terminus of the Fc heavy chain via a (G4S)$_4$ linker (SEQ ID NO: 201).

Figure 1H:
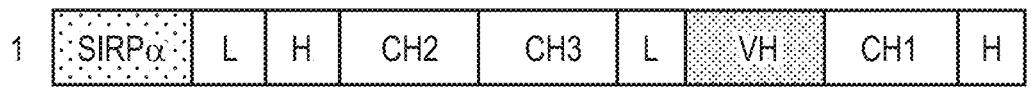
FIG. 1H is a schematic drawing of DNA constructs for the expression of a SIRPα-antibody. DNA construct 1 (top) encodes SIRPα genetically fused via an optional linker (L) to heavy chain constant domains (hinge (H)-CH2-CH3) genetically fused via an optional linker (L) to the heavy chain variable domain of antibody (VH) followed by heavy chain constant domain 1 (CH1), and an upper hinge region (H). DNA construct 2 (bottom) encodes the light chain variable domain of antibody (VL) followed by light chain constant domain (CL).
Figure 1H:
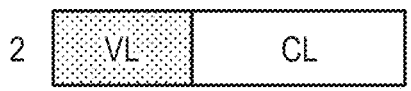
Figure 1I:
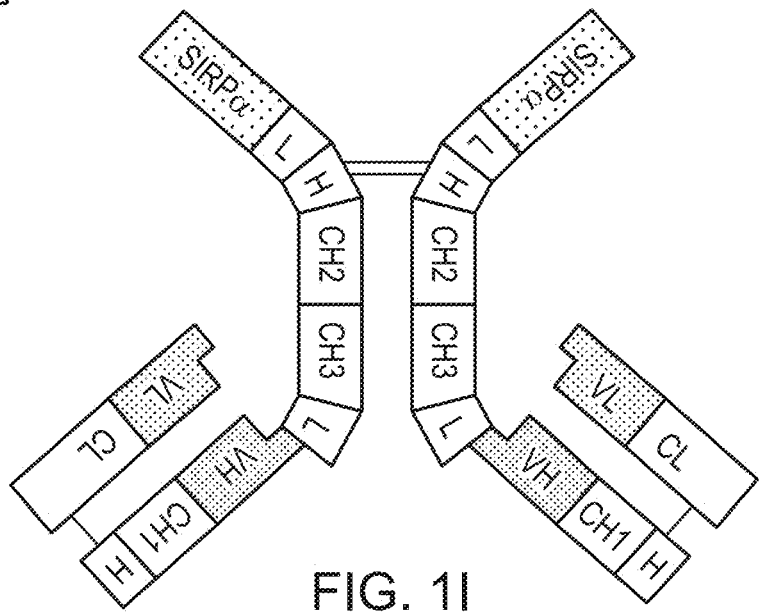
FIG. 1I is a schematic drawing of a SIRPα-antibody showing the tetrameric structure comprising the two polypeptide components encoded by the DNA construct shown in FIG. 1H.

For expression of the SIRPαV2-Fc(huIgG1)-anti-EGFR (Fab), the following two gene constructs were assembled by standard recombinant DNA techniques and cloned into the mammalian expression vector pTT5 (containing the mouse light chain signal peptide sequence for secretion), as in FIG. 1H: (1) Construct SIRPαV2-(G4S)$_2$-H-CH2-CH3-(G4S)$_4$-VH(anti-EGFR)-CH1 (SEQ ID NO:49) ("(G4S)$_2$" disclosed as SEQ ID NO: 206 and "(G4S)$_4$" disclosed as SEQ ID NO: 201), encoding the following elements: the IgV domain of SIRPαV2 followed by a (G4S)$_4$ linker (SEQ ID NO: 201) and human heavy chain hinge region with cysteine (which natively forms a disulfide bond with the light chain) mutated to a serine, (EPKSS, SEQ ID NO:50), followed by constant domains 2 and 3, followed by a (G4S)$_4$ linker (SEQ ID NO: 201), and anti-EGFR heavy chain variable domain followed by human heavy chain constant domain 1 followed by the hinge region (EPKSC, SEQ ID NO:51, to allow for a disulfide bridge with the anti-EGFR light chain) and (2) Construct VL(anti-EGFR)-CL (SEQ ID NO:13), encoding the following elements: anti-EGFR light chain variable domain followed by human kappa light chain constant domain. The corresponding amino acid sequences for these two constructs are shown in SEQ ID NO:52 and SEQ ID NO:14 respectively.

Figure 16A:
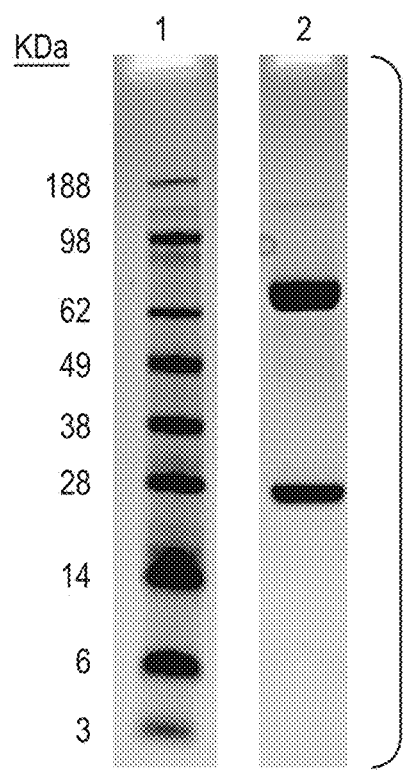
FIGS. 16A-B show the analysis of the expression of the two polypeptides of SIRPαV2-Fc(huIgG1)-anti-EGFR(Fab) by SDS-PAGE (FIG. 16A) and assembly of the full tetrameric molecule by size exclusion chromatography (SEC) (FIG. 16B) as described in Example 10.
Figure 16B:
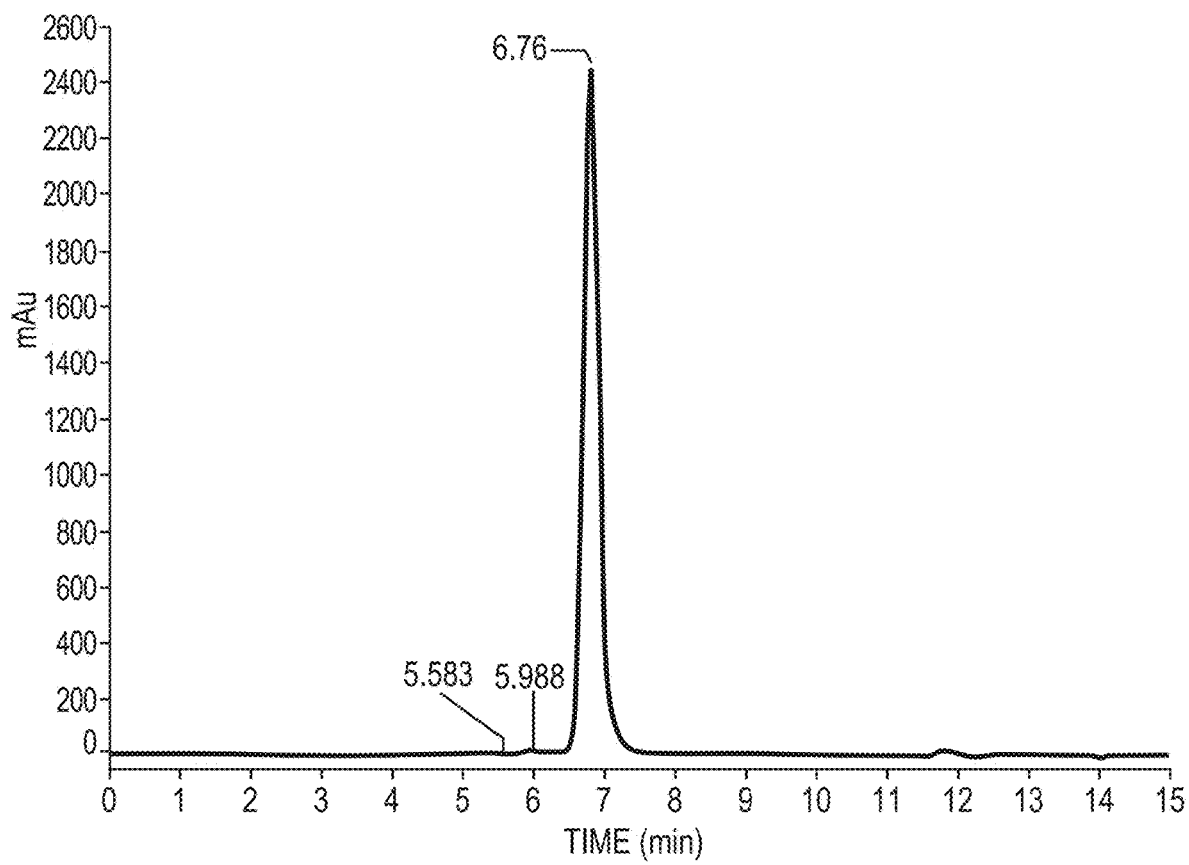

The two vectors were co-transfected transiently into Expi293 cells using Expi293fectin (Life Technologies, Grand Island, N.Y.) for expression of SIRPαV2-Fc(huIgG1)-anti-EGFR(Fab). The protein was purified in a single step by protein A affinity chromatography. Expression of the two polypeptides and assembly of the full tetrameric molecule were confirmed on sodium dodecyl sulfate-polyacrylamide gel electrophoresis (SDS-PAGE) and size exclusion chromatography (SEC). For SDS-PAGE, the purified protein samples were reduced with DTT and run on NuPAGE MES 4-12% Gel, 200V for 35 min, followed by Coomassie staining. The two major bands on the gel had the expected molecular weights (MW) and the correct stoichiometric ratio with >95% purity (FIG. 16A). In FIG. 16A, lane 1 shows the molecular weight (MW) marker and lane 2 shows the expected MW (64, 23 kDa) and the correct stoichiometric ratio (1:1) of the two polypeptides of SIRPα-Fc(huIgG1)-anti-EGFR(Fab). For SEC, the purified protein samples were analyzed on a TSK-GEL Super SW3000 SEC column 4.6× 300 mm (Tosoh Biosciences, Tokyo, Japan) that was equilibrated with 50 mM sodium phosphate, 400 mM sodium perchlorate, pH 6.3+0.1 and 38+2.0 mS/cm$^2$. Size exclusion chromatography showed a peak at the expected MW of about 173 kDa for the monomeric SIRPα-Fc(huIgG1)-anti-EGFR(Fab) (FIG. 16B).

In addition, anti-EGFR and anti-CD47 in a standard monoclonal antibody format (anti-EGFR huIgG1 and anti-CD47 huIgG1) and SIRPα in a Fc-fusion protein format (SIRPαV2-Fc and Fc-SIRPαV2) (FIG. 1C) are generated as controls to compare with the SIRPα-Fc(huIgG1)-anti-EGFR (Fab) format.

10(B) Binding of SIRPα-Fc(huIgG1)-anti-EGFR(Fab) to CD47 Expressed on Cells

The ability of SIRPα-Fc(huIgG1)-anti-EGFR(Fab) to bind to CD47 overexpressed on the cell surface was measured, and compared to the control molecules. 2×10$^5$ CHO cells transfected with CD47 per well were incubated with varying concentrations of antibodies diluted in PBS+1% FBS in a 96 well plate for 60 min on ice. After washing with PBS+1% FBS, cells were incubated with FITC F(ab')2 goat Anti-Human IgG, Fcγ (Jackson ImmunoResearch, West Grove, Pa.) diluted 1:200 in PBS+1% FBS for 60 min on ice. After washing again, cells were fixed with 1% formaldehyde in PBS. Cells were analyzed by flow cytometry (MACSQuant, Miltenyi Biotec, Cologne, Germany).

Figure 17A:
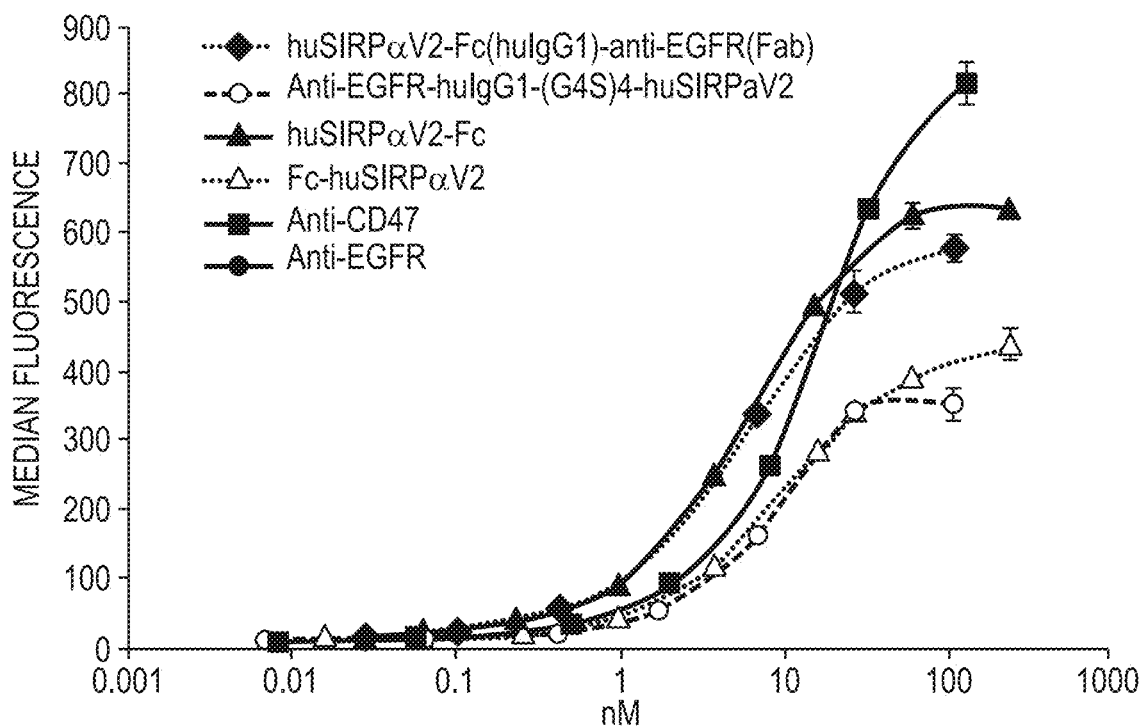
FIGS. 17A-B show binding of SIRPαV2-Fc(huIgG1)-anti-EGFR(Fab) to cells expressing CD47 (CD47-transfected CHO cells, FIG. 17A) and the in vitro activity of SIRPαV2-Fc(huIgG1)-anti-EGFR(Fab) in an ADCC assay using A549 target cells and engineered Jurkat effector cells (FIG. 17B), as described in Example 10.

The results show that SIRPα-Fc(huIgG1)-anti-EGFR (Fab) bound to CD47 expressed on CD47-transfected CHO cells (FIG. 17A). The binding of SIRPα-Fc(huIgG1)-anti-EGFR(Fab) or the control SIRPαV2-Fc was similar to that of anti-CD47, and better than that of anti-EGFR-huIgG1-huSIRPαV2 or Fc-SIRPαV2.

10(C)(i) In Vitro Biological Activities of SIRPα-Fc(huIgG1)-anti-EGFR(Fab)

The in vitro biological activity of SIRPα-Fc(huIgG1)-anti-EGFR(Fab) was shown in an antibody-dependent cell-mediated cytotoxicity (ADCC) assay. 6×10$^4$ human A549 epidermoid carcinoma cells were transferred to each well of a 96-well plate and incubated overnight at 37° C. The media from the cells was removed and replaced with serial dilutions of the recombinant antibodies for concentrations between 0.02-1600 ng/ml. After a 15-30 min incubation at 37° C., 1.5×10$^5$ effector cells (engineered Jurkat cells stably expressing the FcγRIIIa receptor, V158 (high affinity) variant, and an NFAT response element driving expression of firefly luciferase (Promega Madison, Wis.)) were added to each well of plates containing antibodies and A549 cells (effector-to-target cells ratio 2.5:1). After a 24-hour incubation, ADCC activity was measured via luciferase activity by adding Bio-Glo reagent (Promega Madison, Wis.) and measuring luminescence after 15 min incubation.

Figure 17B:
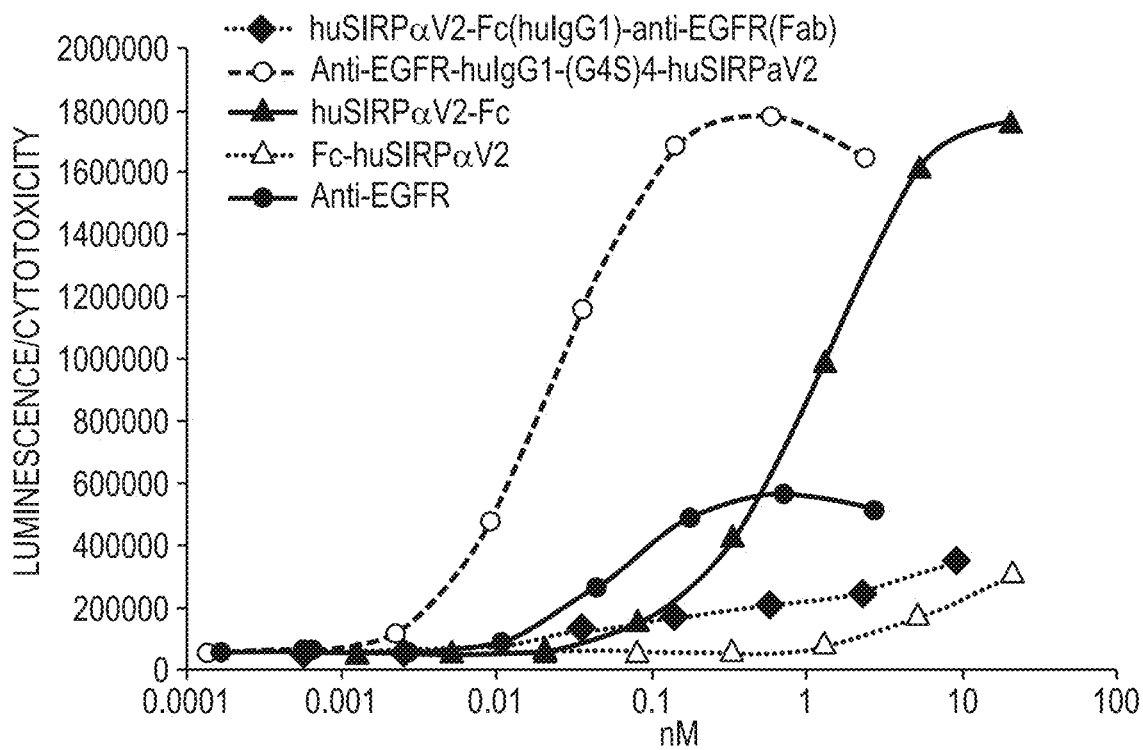

SIRPαV2-Fc(huIgG1)-anti-EGFR(Fab) was found to have lower ADCC activity than anti-EGFR, but higher ADCC activity than Fc-SIRPαV2 (FIG. 17B). The orientation of the binding domain relative to the Fc domain dictates the ADCC activity. Thus, SIRPα-FcV2 has higher activity than Fc-SIRPαV2 (FIG. 17B) and anti-EGFR has higher activity than Fc-anti-EGFR(Fab) (data not shown, but no activity observed). Without wishing to be bound by theory, since the anti-EGFR(Fab) moiety of SIRPαV2-Fc(huIgG1)-anti-EGFR(Fab) bound cells with higher affinity than the SIRPα moiety, it may position the Fc in an orientation for optimal ADCC activity.

10(C)(ii) In Vivo Biological Activities of SIRPα-Fc(huIgG1)-anti-EGFR(Fab)

The utility of SIRPαV2-Fc(huIgG1)-anti-EGFR(Fab) is shown by an in vivo experiment. In an orthotopic lung tumor model, NOD-SCID mice were injected i.v. with 2.5×10$^6$ human A549-luc epidermoid carcinoma cells, followed by i.p. injection of 400 μg/mouse of an antibody isotype control, 250 μg/mouse of anti-EGFR, combination of 250 μg/mouse of anti-EGFR and 136 μg/mouse of SIRPαV2-Fc, 298 μg/mouse of anti-EGFR-huIgG1-SIRPαV2, or 298 μg/mouse of SIRPαV2-Fc(huIgG1)-anti-EGFR(Fab), which is the equimolar amount of fusion protein. All the groups (n=7) received treatment twice a week for 3 weeks, and results were reported as bioluminescent signals from lungs, general health, e.g. paralysis, which preceded death by 10-14 days, and survival of mice.

Figure 18:
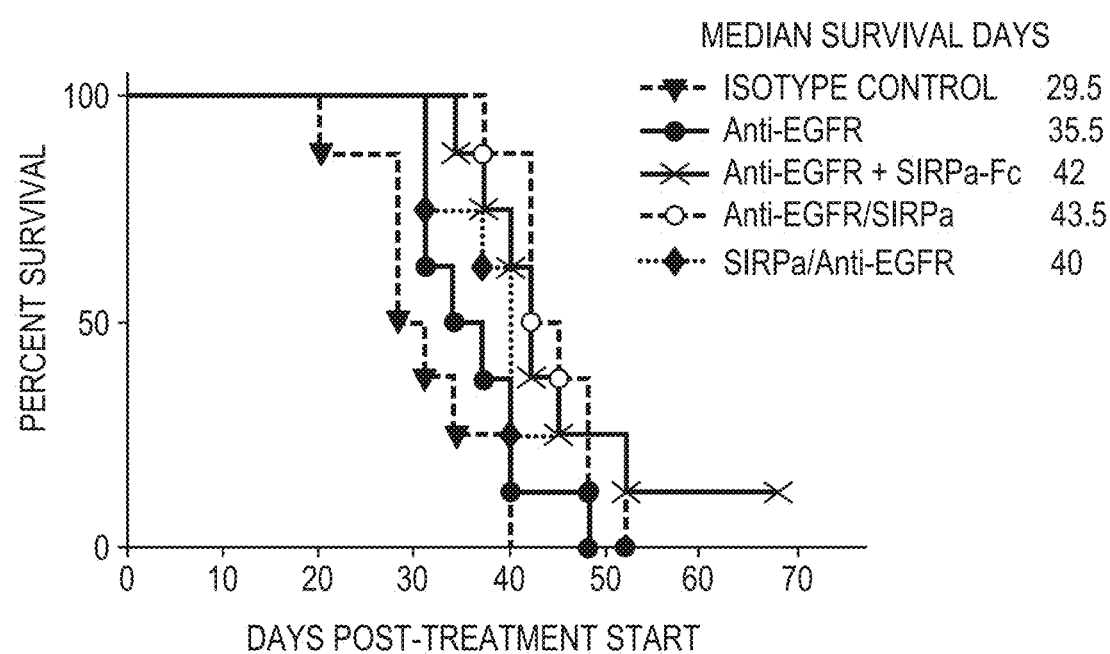
FIG. 18 shows the survival of mice after treatment with SIRPαV2-Fc(huIgG1)-anti-EGFR(Fab) in an orthotopic A549 lung tumor model (inverted filled triangle: isotype control; filled circle: anti-EGFR; cross: anti-EGFR and SIRPα-Fc; open circle: anti-EGFR-huIgG1-SIRPαV2; filled diamond: SIRPαV2-Fc(huIgG1)-anti-EGFR(Fab)).

Treatment with SIRPαV2-Fc(huIgG1)-anti-EGFR(Fab) fusion protein was found to be slightly inferior to the combination and anti-EGFR-huIgG1-SIRPαV2 (median survival 40 days, 42 days and 43.5 days respectively, FIG. 18), despite having similar binding to EGFR and superior binding to CD47. The reduction in ADCC shown in FIG. 17B may account for the decreased anti-tumor efficacy of SIRPαV2-Fc(huIgG1)-anti-EGFR(Fab) compared to anti-EGFR-huIgG1-SIRPαV2.

Example 11: SIRPα-Fc(huIgG1)-anti-EGFR(scFv) Immunoglobulin Fusion Proteins

The generation of an exemplary SIRPα-Fc(huIgG1)-anti-EGFR(scFv) is based on the SIRPα protein (Jiang et al, JBC 274: 559, 1999) and the anti-EGFR(scFv) C225 (U.S. Pat. No. 7,820,165). The DNA and protein sequence of the IgV domain of SIRPα allele V2 are provided in SEQ ID NO: 7 and SEQ ID NO: 8, respectively. The DNA and protein sequence of anti-EGFR(scFv) C225 are provided in SEQ ID NO:53 and SEQ ID NO:54, respectively. SIRPV2α-Fc (huIgG1)-anti-EGFR(scFv) is generated by linking the IgV domain of SIRPα to the N-terminus of the Fc heavy chain via a (G4S)$_2$ linker (SEQ ID NO: 206) followed by linking anti-EGFR(scFv) to the C-terminus of the Fc heavy chain via a (G4S)$_4$ linker (SEQ ID NO: 201).

Figure 1J:
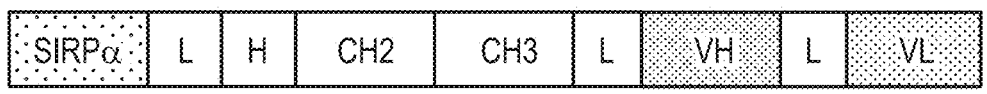
FIG. 1J is a schematic drawing of a DNA construct for the expression of a SIRPα-Fc-scFv are shown. DNA construct encodes SIRPα genetically fused via an optional linker (L) to heavy chain constant domains (hinge (H)-CH2-CH3) genetically fused via an optional linker (L) to the heavy chain variable domain of antibody (VH) genetically fused via an optional linker (L) to the light chain variable domain of antibody (VL).
Figure 1K:
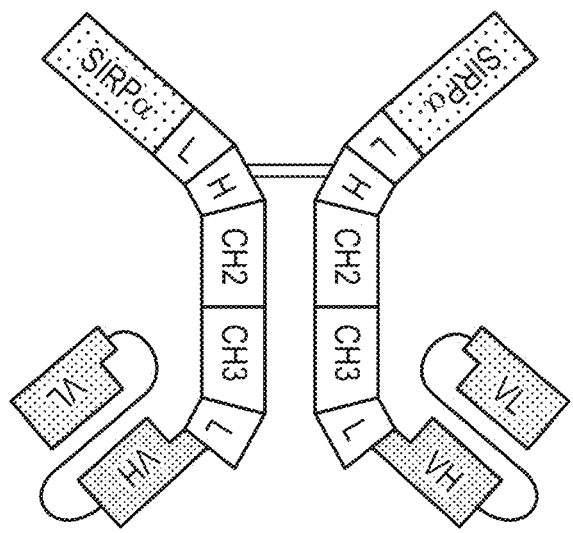
FIG. 1K is a schematic drawing of a SIRPα-Fc-scFv showing the dimeric structure comprising the polypeptide component encoded by the DNA construct shown in FIG. 1J.

For expression of the SIRPαV2-Fc(huIgG1)-anti-EGFR (scFv) C225, the following gene construct was assembled by standard recombinant DNA techniques and cloned into the mammalian expression vector pTT5 (containing the mouse light chain signal peptide sequence for secretion), as in FIG. 1J: Construct SIRPαV2-(G4S)$_2$—H-CH2-CH3-(G4S)$_4$—C225(VH)-(G4S)$_3$-C225(VL) (SEQ ID NO:55) ("(G4S)$_2$" disclosed as SEQ ID NO: 206 and "(G4S)$_4$" disclosed as SEQ ID NO: 201 and "(G4S)$_3$" as SEQ ID NO: 203), encoding the following elements: IgV domain of SIRPαV2 followed by a (G4S)$_4$ linker (SEQ ID NO: 201) and human heavy chain hinge region with cysteine (which natively forms a disulfide bond with the light chain) mutated to a serine, (EPKSS, SEQ ID NO:50), followed by constant domains 2 and 3, followed by a (G4S)$_4$ linker (SEQ ID NO: 201) and anti-EGFR heavy chain variable domain, followed by a (G4S)$_3$ linker (SEQ ID NO: 203) and anti-EGFR light chain variable domain. The corresponding amino acid sequence for this construct is shown in SEQ ID NO:56.

In addition, anti-EGFR and anti-CD47 in a standard monoclonal antibody format (anti-EGFR huIgG1 and anti-CD47 huIgG1), anti-EGFR in a scFv format (anti-EGFR (scFv)), and SIRPα in a Fc-fusion protein format (SIRPαV2-Fc and Fc-SIRPαV2) (FIG. 1C) were generated as controls to compare with the SIRPαV2-Fc(huIgG1)-anti-EGFR(scFv) format.

Example 12: Anti-EGFR(scFv)-Fc(huIgG1)-SIRPα Immunoglobulin Fusion Proteins

The generation of an exemplary anti-EGFR(scFv)-Fc (huIgG1)-SIRPα is based on the anti-EGFR(scFv) C225 (U.S. Pat. No. 7,820,165) and the SIRPα protein (Jiang et al, JBC 274: 559, 1999). The DNA and protein sequence of anti-EGFR(scFv) C225 are provided in SEQ ID NO:53 and SEQ ID NO:54, respectively. The DNA and protein sequence of the IgV domain of SIRPα allele V2 are provided in SEQ ID NO: 7 and SEQ ID NO:8, respectively. Anti-EGFR(scFv)-Fc(huIgG1)-SIRPαV2 is generated by linking anti-EGFR(scFv) to the N-terminus of the Fc heavy chain via a (G4S)$_2$ linker (SEQ ID NO: 206) followed by linking the IgV domain of SIRPαV2 to the C-terminus of the Fc heavy chain via a (G4S)$_4$ linker (SEQ ID NO: 201).

Figure 1L:
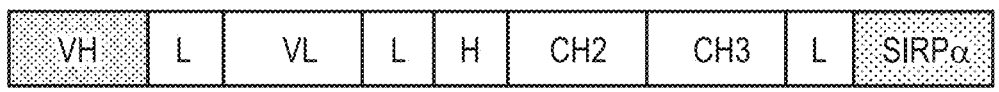
FIG. 1L is a schematic drawing of a DNA construct for the expression of a scFv-Fc-SIRPα are shown. The DNA construct encodes the heavy chain variable domain of antibody (VH) genetically fused via an optional linker (L) to the light chain variable domain of antibody (VL) genetically fused via an optional linker (L) to heavy chain constant domains (hinge (H)-CH2-CH3) genetically fused via an optional linker (L) to SIRPα.
Figure 1M:
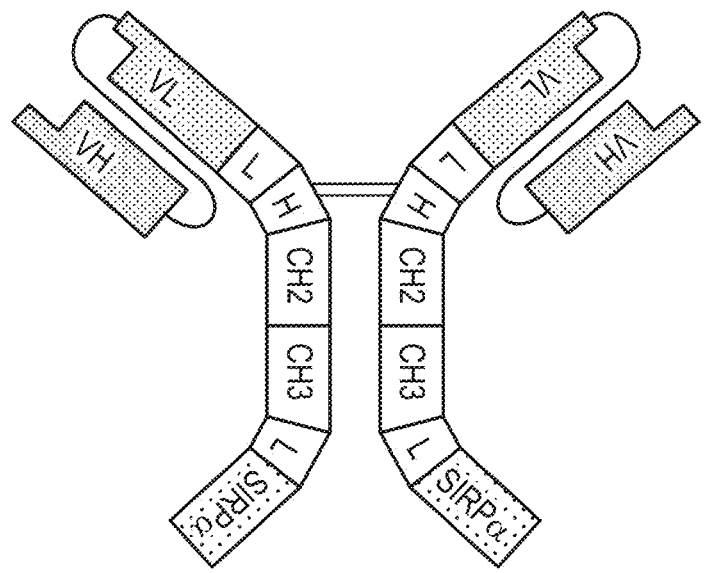
FIG. 1M is a schematic drawing of a scFv-Fc-SIRPα showing the dimeric structure comprising the polypeptide component encoded by the DNA construct shown in FIG. 1L.
Figure 1N:
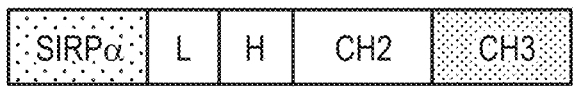
FIG. 1N is a schematic drawing of a DNA construct for the expression of a SIRPα-Fcab are shown. DNA construct encodes SIRPα genetically fused via an optional linker (L) to heavy chain constant domains (hinge (H)-CH2-CH3) with constant domain 3 modified to bind antigen.
Figure 1O:
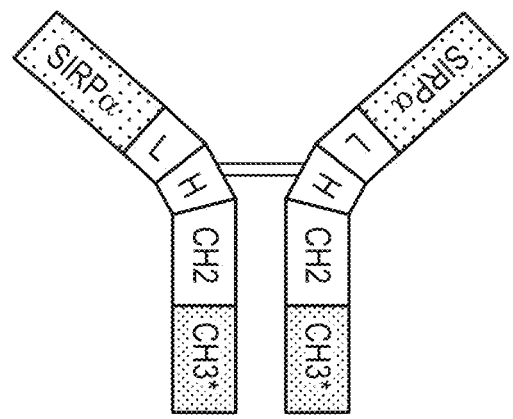

For expression of the anti-EGFR(scFv) C225-Fc (huIgG1)-SIRPαV2, the following gene construct was assembled by standard recombinant DNA techniques and cloned into the mammalian expression vector pTT5 (containing the mouse light chain signal peptide sequence for secretion), as in FIG. 1L: Construct C225(VH)-(G4S)$_3$-C225(VL)-(G4S)$_2$-H-CH2-CH3-(G4S)$_4$-SIRPαV2 (SEQ ID NO:57) ("(G4S)$_3$" disclosed as SEQ ID NO: 203 and "(G4S)$_2$" disclosed as SEQ ID NO: 206 and "(G4S)$_4$" as SEQ ID NO: 201), encoding the following elements: anti-EGFR heavy chain variable domain, followed by a (G4S)$_3$ linker (SEQ ID NO: 203) and anti-EGFR light chain variable domain followed by a (G4S)$_4$ linker (SEQ ID NO: 201) and human heavy chain hinge region with cysteine (which natively forms a disulfide bond with the light chain) mutated to a serine, (EPKSS, SEQ ID NO:50), followed by constant domains 2 and 3, followed by a (G4S)$_4$ linker (SEQ ID NO: 201) and the IgV domain of SIRPαV2. The corresponding amino acid sequence for this construct is shown in SEQ ID NO:58.

In addition, anti-EGFR and anti-CD47 in a standard monoclonal antibody format (anti-EGFR huIgG1 and anti-CD47 huIgG1), anti-EGFR in a scFv format (anti-EGFR (scFv)), and SIRPα in a Fc-fusion protein format (SIRPαV2-Fc and Fc-SIRPαV2) (FIG. 1C) were generated as controls to compare with the anti-EGFR(scFv)-Fc(huIgG1)-SIRPαV2 format.

Example 13: SIRPα-Fc(huIgG1)-anti-CD19(scFv) Immunoglobulin Fusion Proteins

The generation of SIRPα-Fc(huIgG1)-anti-CD19(scFv) is based on the SIRPα protein (Jiang et al, JBC 274: 559, 1999) and the anti-CD19(scFv) CHRI-19Fv1 (Nicholson et al, Molecular Immunology 34:1157, 1997). The DNA and protein sequence of the IgV domain of SIRPα allele V2 are provided in SEQ ID NO: 7 and SEQ ID NO: 8, respectively. The DNA and protein sequence of CHRI-19Fv1 are provided in SEQ ID NO:59 and SEQ ID NO:60, respectively. SIRPαV2-Fc(huIgG1)-anti-CD19(scFv) is generated by linking the IgV domain of SIRPαV2 to the N-terminus of the Fc heavy chain via a (G4S)$_2$ linker (SEQ ID NO: 206) followed by linking anti-CD19(scFv) to the C-terminus of the Fc heavy chain via a (G4S)$_4$ linker (SEQ ID NO: 201).

For expression of the SIRPαV2-Fc(huIgG1)-anti-CD19 (scFv), the following gene construct is assembled by standard recombinant DNA techniques and cloned into the mammalian expression vector pTT5 (containing the mouse light chain signal peptide sequence for secretion), as in FIG. 1J: Construct SIRPαV2-(G4S)$_2$—H-CH2-CH3-(G4S)$_4$-CHRI-19Fv1 (VH)-linker-CHRI-19Fv1 (VL) (SEQ ID NO:61) ("(G4S)$_2$" disclosed as SEQ ID NO: 206 and "(G4S)$_4$" disclosed as SEQ ID NO: 201), encoding the following elements: SIRPαV2 followed by a (G4S)$_4$ linker (SEQ ID NO: 201) and human heavy chain hinge region with cysteine (which natively forms a disulfide bond with the light chain) mutated to a serine, (EPKSS, SEQ ID NO:50), followed by constant domains 2 and 3, followed by a (G4S)$_4$ linker (SEQ ID NO: 201) and anti-CD19 heavy chain variable domain, followed by a (G4S)$_3$ linker (SEQ ID NO: 203) and anti-CD19 light chain variable domain. The corresponding amino acid sequences for this construct is shown in SEQ ID NO:62.

In addition, anti-CD47 in a standard monoclonal antibody format (anti-CD47 huIgG1), anti-CD19 in a scFv format (anti-CD19(scFv)), and SIRPα in a Fc-fusion protein format (SIRPαV2-Fc and Fc-SIRPαV2) (FIG. 1C) are generated as controls to compare with the SIRPαV2-Fc(huIgG1)-anti-CD19(scFv) format.

Example 14: Anti-CD19(scFv)-Fc(huIgG1)-SIRPα Immunoglobulin Fusion Proteins

The generation of an exemplary anti-CD19(scFv)-Fc(hu-IgG1)-SIRPα is based on the anti-CD19(scFv) CHRI-19Fv1 (Nicholson et al, Molecular Immunology 34:1157, 1997) and the SIRPα protein (Jiang et al, JBC 274: 559, 1999). The DNA and protein sequence of CHRI-19Fv1 are provided in SEQ ID NO:59 and SEQ ID NO:60, respectively. The DNA and protein sequence of the IgV domain of SIRPα allele V2 are provided in SEQ ID NO: 7 and SEQ ID NO:8, respectively. Anti-CD19(scFv)-Fc(huIgG1)-SIRPαV2 is generated by linking anti-CD19(scFv) to the N-terminus of the Fc heavy chain via a (G4S)$_2$ linker (SEQ ID NO: 206) followed by linking the IgV domain of SIRPαV2 to the C-terminus of the Fc heavy chain via a (G4S)$_4$ linker (SEQ ID NO: 201).

For expression of the anti-CD19(scFv)-Fc(huIgG1)-SIRPαV2, the following gene construct is assembled by standard recombinant DNA techniques and cloned into the mammalian expression vector pTT5 (containing the mouse light chain signal peptide sequence for secretion), as in FIG.

1L: Construct CHRI-19Fv1(VH)-linker-CHRI-19Fv1(VL)-(G4 S)$_2$—H-CH2-CH3-(G4S)$_4$-SIRPαV2 (SEQ ID NO:63) ("(G4S)$_2$" disclosed as SEQ ID NO: 206 and "(G4S)$_4$" disclosed as SEQ ID NO: 201), encoding the following elements: anti-CD19 heavy chain variable domain, followed by a (G4S)$_3$ linker (SEQ ID NO: 203) and anti-CD19 light chain variable domain, followed by a (G4S)$_4$ linker (SEQ ID NO: 201) and human heavy chain hinge region with cysteine (which natively forms a disulfide bond with the light chain) mutated to a serine, (EPKSS, SEQ ID NO:50), followed by constant domains 2 and 3, followed by a (G4S)$_4$ linker (SEQ ID NO: 201) and the IgV domain of SIRPαV2. The corresponding amino acid sequences for this construct is shown in SEQ ID NO:64.

In addition, anti-CD47 in a standard monoclonal antibody format (anti-CD47 huIgG1), anti-CD19 in a scFv format (anti-CD19(scFv)), and SIRPα in a Fc-fusion protein format (SIRPαV2-Fc and Fc-SIRPαV2) (FIG. 1C) are generated as controls to compare with the anti-CD19(scFv)-Fc(huIgG1)-SIRPαV2 format.

Example 15: SIRPα-Fcab(HER2) Immunoglobulin Fusion Proteins

15(A) Construction and Expression of SIRPα-Fcab(HER2)

The generation of an exemplary SIRPα-Fcab(HER2) is based on the SIRPα protein (Jiang et al, JBC 274: 559, 1999) and the anti-HER2 Fcab H10-03-6 (Wozniak-Knopp et al, PEDS 23:289, 2010). The DNA and protein sequence of the IgV domain of SIRPα allele V2 are provided in SEQ ID NO: 7 and SEQ ID NO:8, respectively. The DNA and protein sequence of Fcab(HER2) are provided in SEQ ID NO:65 and SEQ ID NO:66, respectively. SIRPαV2-Fcab(HER2) is generated by linking the IgV domain of SIRPαV2 to the N-terminus of Fcab(HER2) via a (G4S)$_2$ linker (SEQ ID NO: 206).

For expression of the SIRPαV2-Fcab(HER2), the following gene construct was assembled by standard recombinant DNA techniques and cloned into the mammalian expression vector pTT5 (containing the mouse light chain signal peptide sequence for secretion), as in FIG. 1F: Construct SIRPαV2-(G4S)$_2$-H-CH2-CH3(anti-HER2) (SEQ ID NO:67) ("(G4S)$_2$" disclosed as SEQ ID NO: 206), encoding the following elements: SIRPαV2 followed by a (G4S)$_4$ linker (SEQ ID NO: 201) and human heavy chain hinge region with cysteine (which natively forms a disulfide bond with the light chain) mutated to a serine, (EPKSS, SEQ ID NO:50), followed by constant domain 2 and constant domain 3 that has been modified to bind HER2 via the AB, CD, and EF loops. The corresponding amino acid sequences for this construct is shown in SEQ ID NO:68.

Figure 19A:
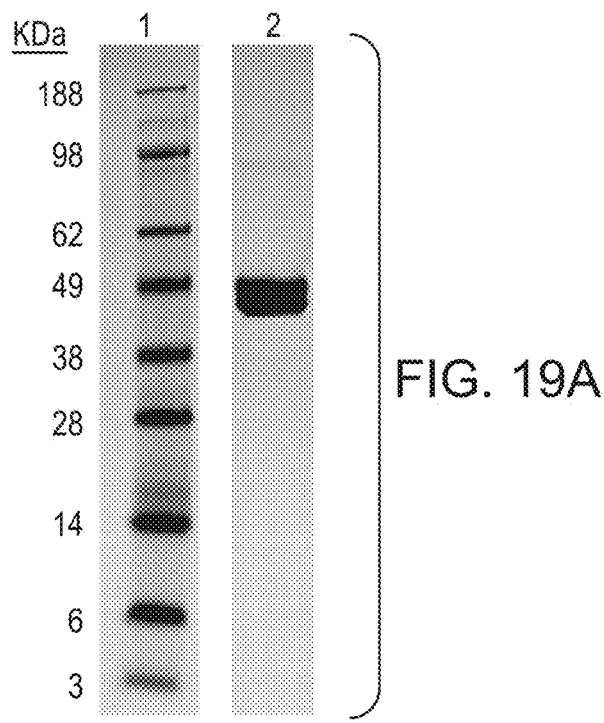
FIGS. 19A-B show the analysis of the expression of the polypeptide of SIRPαV2-Fcab(HER2) by SDS-PAGE (FIG. 19A) and assembly of the full dimeric molecule by size exclusion chromatography (SEC) (FIG. 19B) as described in Example 15.
Figure 19B:
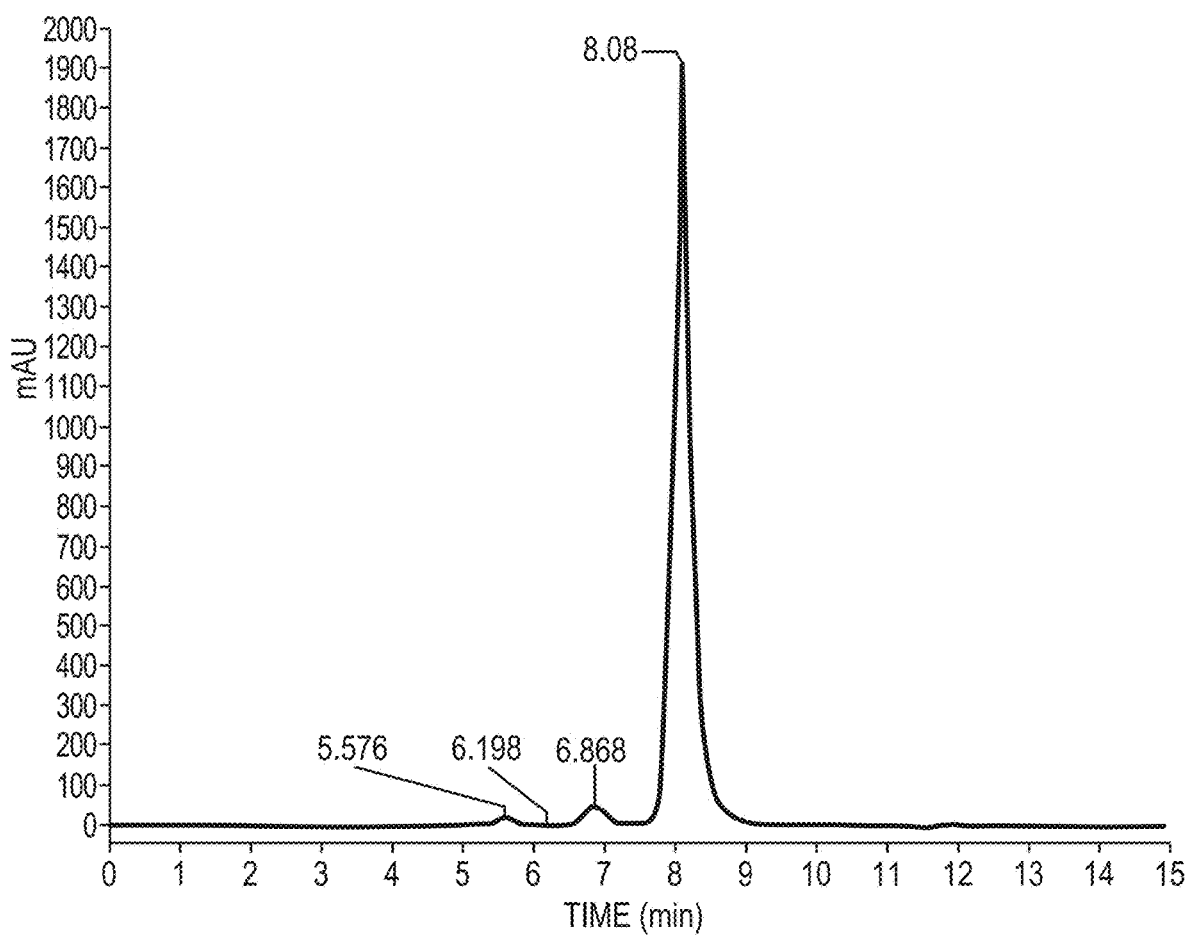

The vector was transfected transiently into Expi293 cells using Expi293fectin (Life Technologies, Grand Island, N.Y.) for expression of SIRPαV2-Fcab(HER2). The protein was purified in a single step by protein A affinity chromatography. Expression of the molecule was confirmed on sodium dodecyl sulfate-polyacrylamide gel electrophoresis (SDS-PAGE) and size exclusion chromatography (SEC). For SDS-PAGE, the purified protein sample was reduced with DTT and run on NuPAGE MES 4-12% Gel, 200V for 35 min, followed by Coomassie staining. The major band on the gel had the expected molecular weights (MW) with >95% purity (FIG. 19A). In FIG. 19A, lane 1 shows the molecular weight (MW) marker and lane 2 shows the expected MW (40 kDa) of SIRPαV2-Fcab(HER2). For SEC, the purified protein sample was analyzed on a TSK-GEL Super SW3000 SEC column 4.6×300 mm (Tosoh Biosciences, Tokyo, Japan) that was equilibrated with 50 mM sodium phosphate, 400 mM sodium perchlorate, pH 6.3+0.1 and 38+2.0 mS/cm$^2$. Size exclusion chromatography showed a peak at the expected MW of about 80 kDa for the monomeric SIRPαV2-Fcab(HER2) (FIG. 19B).

In addition, anti-HER2 and anti-CD47 in a standard monoclonal antibody format (anti-HER2 huIgG1 and anti-CD47 huIgG1), Fcab(HER2), and SIRPα in a Fc-fusion protein format (SIRPαV2-Fc and Fc-SIRPαV2) (FIG. 1C) were generated as controls to compare with the SIRPαV2-Fcab(HER2) format.

15(B)(i) Binding of SIRPα-Fcab(HER2) to CD47 Expressed on Cells

The ability of SIRPαV2-Fcab(HER2) to bind to CD47 expressed on the cell surface was measured, and compared to the control molecules. 2×10$^5$ CHO cells transfected with CD47 per well were incubated with varying concentrations of antibodies diluted in PBS+1% FBS in a 96 well plate for 60 min on ice. After washing with PBS+1% FBS, cells were incubated with FITC F(ab')2 goat Anti-Human IgG, Fcγ (Jackson ImmunoResearch, West Grove, Pa.) diluted 1:200 in PBS+1% FBS for 60 min on ice. After washing again, cells were fixed with 1% formaldehyde in PBS. Cells were analyzed by flow cytometry (MACSQuant, Miltenyi Biotec, Cologne, Germany).

Figure 20A:
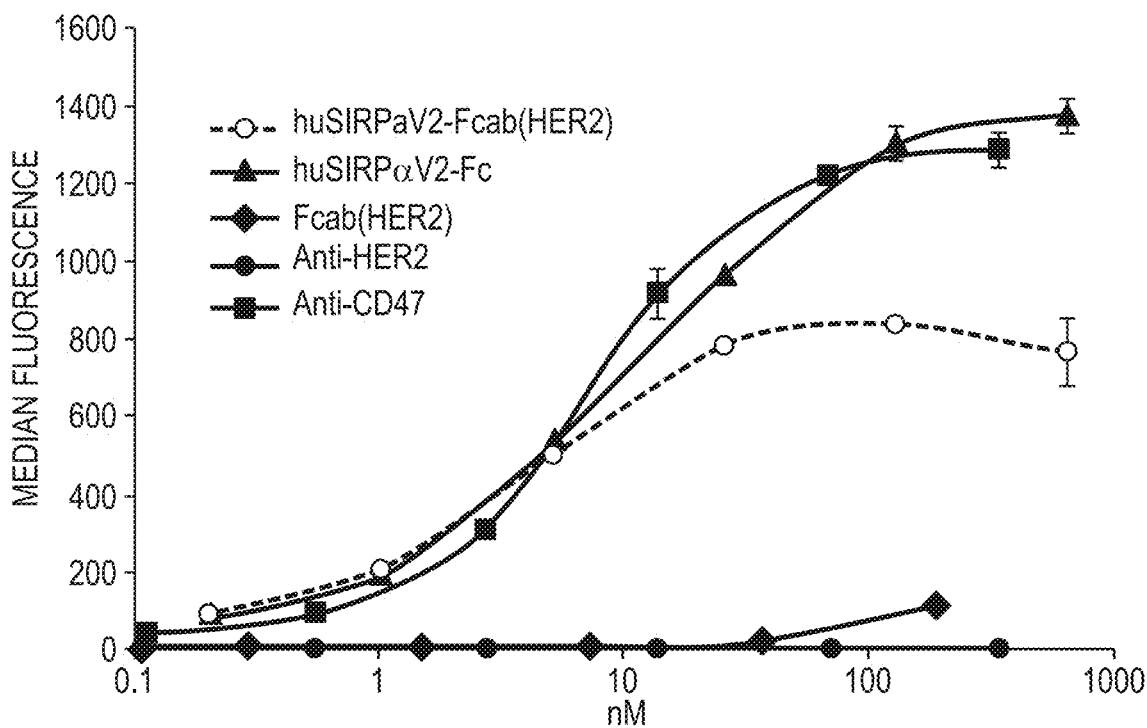
FIGS. 20A-B show binding of SIRPαV2-Fcab(HER2) to cells expressing CD47 (CD47-transfected CHO cells, FIG. 20A) or expressing both HER2 and CD47 (BT474 cells, FIG. 20B).

The results show that SIRPαV2-Fcab(HER2), anti-CD47, and SIRPα-Fc bound to CD47 expressed on transfected CHO cells, but anti-HER2 and Fcab(HER2) did not bind because HER2 is not expressed (FIG. 20A).

15(B) (ii) Binding Avidity of SIRPα-Fcab(HER2) on Cells Expressing Both Antigens The ability of SIRPαV2-Fcab(HER2) to bind with avidity to HER2 and CD47 on the cell surface was measured on human BT474 mammary gland/breast adenocarcinoma cells that overexpress HER2 and express CD47. 2×10$^5$ BT474 cells per well were incubated with varying concentrations of SIRPαV2-Fcab(HER2), SIRPαV2-Fc, Fcab(HER2), anti-HER2, and anti-CD47 diluted in PBS+1% FBS in a 96 well plate for 60 min on ice. After washing with PBS+1% FBS, cells were incubated with FITC F(ab')2 goat Anti-Human IgG, Fcγ (Jackson ImmunoResearch, West Grove, Pa.), diluted 1:200 in PBS+1% FBS for 60 min on ice. After washing again, cells were fixed with 1% formaldehyde in PBS. Cells were analyzed by flow cytometry (MACSQuant, Miltenyi Biotec, Cologne, Germany).

Figure 20B:
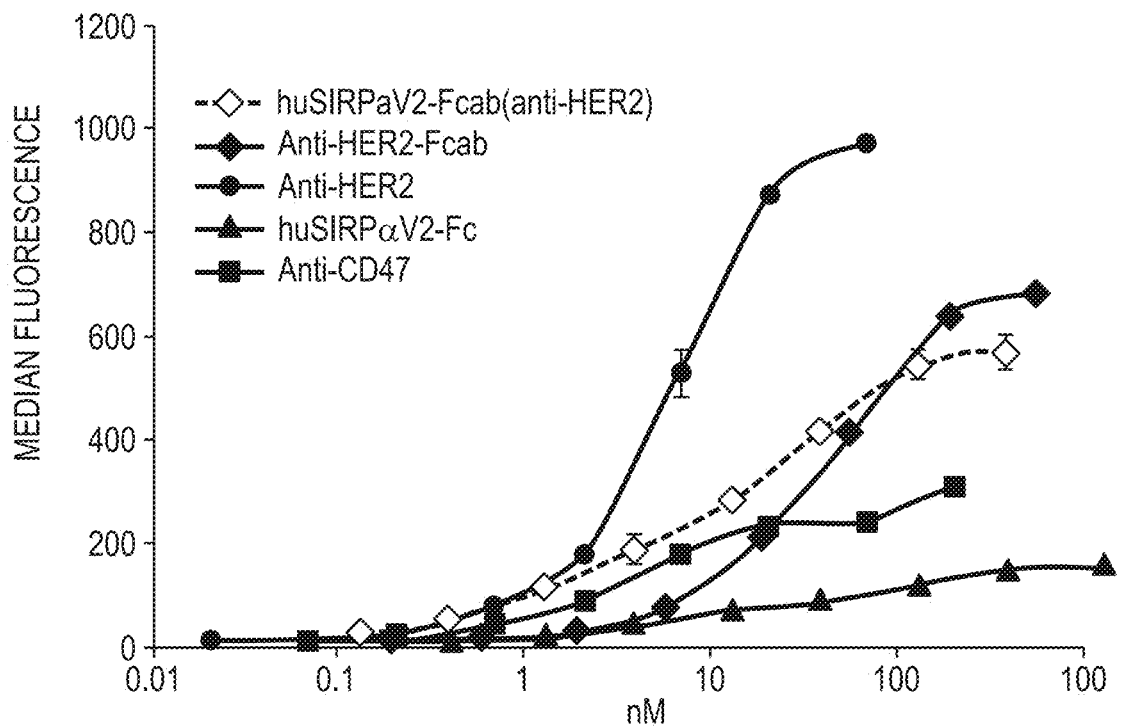

The results show that SIRPαV2-Fcab(HER2) binding to BT474 cells was enhanced compared to the binding of Fcab(HER2), particularly at lower concentrations (FIG. 20B), providing a strong evidence for avidity. The ability of SIRPαV2-Fcab(HER2) to harness the avidity of binding to the tumor cells by binding to two tumor targets on the same cell may result in more specific targeting and less side effects in vivo.

Example 16: Computational Methods to Identify SIRPα Residues Affecting CD47 Binding Computational methods familiar to those skilled in the art were used to identify SIRPα residues that may affect the binding of SIRPα to CD47, and to predict mutations with the potential to decrease or increase binding affinity of SIRPα to CD47 and identify candidates worth pursuing experimentally. Briefly, the crystal structure of the CD47/SIRPα complex was analyzed to identify SIRPα residue positions predicted to affect CD47 binding.

Computational mutagenesis was performed on the selected set of SIRPα positions to arrive at a value for the difference in binding energy of various putative mutations as compared to wild-type SIRPα, and a threshold value was set to categorize mutations predicted to have either reduced affinity or increased affinity for CD47 relative to wild-type SIRPα. Because the threshold value setting for the designation of reduced or increased affinity SIRPα variants overlapped, there was also significant overlap in the computationally predicted mutations listed in Table 1 and Table 2 (see below).

TABLE 1

SIRPα mutations predicted to reduce CD47 binding

| SIRPαV1 (SIRPαV2 if different) Residue | SEQ ID NO: 6 or SEQ ID NO: 8 Residue # | Computationally Designed Mutations (Total) in Either SIRPαV1 or SIRPαV2 |
|---|---|---|
| V | 6 | A, C, D, E, G, I, L, M, N, Q, S, T (12) |
| A (V) | 27 | C, D, G, H, L, N, S, T, V (9) |
| I | 31 | A, C, E, K, Q, R, T, V (8) |
| P | 35 | A, C, E, G, Q, S (6) |
| Q | 37 | A, C, E, G, H, K, L, M, N, R, S, T (12) |
| E | 47 | A, C, D, F, G, H, I, K, L, M, N, Q, R, S, T, V, W, Y (18) |
| Q | 52 | A, C, E, M (4) |
| E | 54 | D (1) |
| H | 56 | A, C, D, E, F, G, I, K, L, M, N, P, Q, R, S, T, V, W, Y (19) |
| L (S) | 66 | A, C, D, E, F, G, H, I, M, N, P, Q, S, T, V, W, Y (17) |
| T | 67 | A, C, D, E, F, G, H, I, L, M, N, Q, R, S, V, W, Y (17) |
| M | 72 | A, C, D, E, F, G, H, I, K, L, N, Q, R, S, T, V, W, Y (18) |
| V | 92 | A, C, D, E, G, I, M, N, Q, R, S, T (12) |

TABLE 2

SIRPα mutations that are predicted to have tighter CD47 binding compared to wild-type.

| SIRPαV1 (SIRPαV2 if different) Residue | SEQ ID NO: 6 or SEQ ID NO: 8 Residue # | Computationally Designed Mutations in Either SIRPαV1 or SIRPαV2 |
|---|---|---|
| V | 6 | A, D, I |
| A (V) | 27 | A, G, I, K, Q, R, S, T |
| I | 31 | C, K, R, T |
| P | 35 | G, N, Q, S |
| Q | 37 | A, G, H, W |
| E | 47 | G, S, W, Y |
| Q | 52 | E, H |
| E | 54 | P |
| H | 56 | C, I, P, Y |
| L (S) | 66 | A, C, D, E, F, H, K, L, M, N, P, Q, V, W |
| T | 67 | D, E, F, N, Q, W, Y |
| M | 72 | A, C, D, E, F, G, H, I, K, L, N, Q, R, S, W, Y |
| V | 92 | N |

33 SIRPα variants containing single point mutations, mainly from Table 2, were selected for further experimental characterization. (See Table 3 in Example 17).

Example 17: Anti-EGFR-huIgG1-SIRPα Variants

17(A) Construction and Expression of anti-EGFR-huIgG1-SIRPα Variants

Antibody-SIRPα variants were generated in the context of anti-EGFR-huIgG1-SIRPαV2 described in Example 4. The mutations in the IgV domain of SIRPα allele V2 are listed in Table 3 (with reference to SEQ ID NO: 8). Anti-EGFR-huIgG1-SIRPαV2 variants were generated by linking the C-terminus of the anti-EGFR heavy chain polypeptide to the IgV domain of variant SIRPαV2 via a (G4S)$_4$ linker (SEQ ID NO: 201).

For expression of each of the anti-EGFR-huIgG1-SIRPαV2 variants, the following two gene constructs were assembled by standard recombinant DNA techniques and cloned into the mammalian expression vector pTT5 (containing the mouse light chain signal peptide sequence for secretion) as in FIG. 1A: (1) Construct VH(anti-EGFR)-CH1-H-CH2-CH3-(G4S)$_4$—SIRPαV2 (SEQ ID NO:19) ("(G4S)$_4$" disclosed as SEQ ID NO: 201) with the sequence being modified to encode the particular mutation(s) listed in Table 3 for each variant; the construct encoded the following elements: anti-EGFR heavy chain variable domain followed by human heavy chain constant domains 1-3 isotype IgG1 followed by a (G4S)$_4$ linker (SEQ ID NO: 201) and IgV domain of variant SIRPαV2 and (2) Construct VL(anti-EGFR)-CL (SEQ ID NO:13), encoding the following elements: anti-EGFR light chain variable domain followed by human kappa light chain constant domain. The corresponding amino acid sequences for these two constructs are shown in SEQ ID NO:20 (which sequence must be modified to include the particular mutations listed in Table 3) and SEQ ID NO:14 respectively.

The set of two vectors for each of the anti-EGFR-huIgG1-SIRPαV2 variants were co-transfected transiently into Expi293 cells using Expi293fectin (Life Technologies, Grand Island, N.Y.) for expression of each of the anti-EGFR-huIgG1-SIRPαV2 variants. The proteins were purified in a single step by protein A affinity chromatography. Expression of the two polypeptides and assembly of the full tetrameric molecule was confirmed on size exclusion chromatography (SEC). For SEC, the purified protein samples were analyzed on a TSK-GEL Super SW3000 SEC column 4.6_300 mm (Tosoh Biosciences, Tokyo, Japan) that was equilibrated with 50 mM sodium phosphate, 400 mM sodium perchlorate, pH 6.3+0.1 and 38+2.0 mS/cm$^2$. Size exclusion chromatography showed a peak at the expected MW of about 173 kDa for the monomeric anti-EGFR-huIgG1-SIRPαV2. The percentage of the monomeric peak relative to all SEC peaks was reported for each variant in Table 3.

In addition, wild-type anti-EGFR-huIgG1-SIRPαV2 ("WT"), chimeric antibody B6H12/huIgG1 ("anti-CD47"), and anti-EGFR-huIgG1-SIRPαV2 with multiple mutations ("1D4" (V27I/K53R/S66T/K68R/F103V), (Weiskopf, Science 341:88, 2013); "AS2" (K53R/S66T/K68R); and "AS1" (L4V/V27I/I31T/K53R/S66T/K68R/F94L)) were generated as positive controls and anti-EGFR was generated as a negative control.

17(B) (i) Binding of anti-EGFR-huIgG1-SIRPα Variants to CD47 Expressed on Cells

The ability of anti-EGFR-huIgG1-SIRPαV2 variants to bind to CD47 overexpressed on the cell surface was measured, and compared to the control molecules. 2×10$^5$ CHO cells transfected to express high levels of CD47 per well were incubated with varying concentrations of antibodies diluted in PBS+1% FBS in a 96 well plate for 60 min on ice. After washing with PBS+1% FBS, cells were incubated with FITC F(ab')2 goat Anti-Human IgG, Fcγ (Jackson ImmunoResearch, West Grove, Pa.) diluted 1:200 in PBS+1% FBS for 60 min on ice. After washing again, cells were fixed with 1% formaldehyde in PBS. Cells were analyzed by flow cytometry (MACSQuant, Miltenyi Biotec, Cologne, Germany). An EC50 was calculated for each variant for binding to CD47 expressed on CHO cells by fitting data to a sigmoidal curve (log(agonist) vs. response—Variable slope (four parameters)) with Graph Pad Prism and reported in Table 3.

The results show that many anti-EGFR-huIgG1-SIRPαV2 variants, including V6I, V27I, I31R, I31T, Q37H, Q37W, H56P, and S66Q, bound to CD47 expressed on transfected CHO cells with greater affinity than wild-type anti-EGFR-huIgG1-SIRPαV2 (Table 3), whereas variants E54P and M72R bound with similar affinity. As expected, the positive controls anti-CD47, 1D4, AS2, and AS1 also bound to CD47 with greater affinity and the negative control anti-EGFR did not bind because EGFR is not expressed. The results show a single point mutation in SIRPα is sufficient to increase the affinity of SIRPα for CD47.

In order to compare the intrinsic binding affinity, i.e. minimize the avidity effect due to bivalent engagement that occurs at high receptor density, the binding of anti-EGFR-huIgG1-SIRPαV2 variants and control molecules to cells expressing low levels of CD47 was determined. $2 \times 10^5$ CD47$^{LO}$ human Ramos lymphoma cells per well were incubated with varying concentrations of antibodies diluted in PBS+1% FBS in a 96 well plate for 60 min on ice. After washing with PBS+1% FBS, cells were incubated with FITC F(ab')2 goat Anti-Human IgG, Fcγ (Jackson ImmunoResearch, West Grove, Pa.) diluted 1:200 in PBS+1% FBS for 60 min on ice. After washing again, cells were fixed with 1% formaldehyde in PBS. Cells were analyzed by flow cytometry (MACSQuant, Miltenyi Biotec, Cologne, Germany). An EC50 was calculated for each variant for binding to CD47 expressed on Ramos cells by fitting data to a sigmoidal curve (log(agonist) vs. response—Variable slope (four parameters)) with Graph Pad Prism and reported in Table 3.

The results show that many anti-EGFR-huIgG1-SIRPαV2 variants, including V6I, V27I, I31R, I31T, Q37H, Q37W, E54P, H56P, S66Q, and M72R, bound to CD47 expressed on Ramos cells with greater affinity than wild-type anti-EGFR-huIgG1-SIRPαV2 (Table 3), but the differences in EC50 values between the variants were greater compared to the differences seen with CD47$^{HI}$ cells. As expected, the positive controls anti-CD47, 1D4, AS2, and AS1 also bound to CD47 with greater affinity and the negative control anti-EGFR did not bind to Ramos cells because EGFR is not expressed.

The ability of the higher-affinity anti-EGFR-huIgG1-SIRPαV2 variants to bind to CD47 expressed on the cell surface of blood cells was measured, and compared to the control molecules. $2 \times 10^5$ fresh whole blood cells from healthy human donors per well were incubated with 50 μg/ml of proteins diluted in PBS+1% FBS in a 96 well plate for 60 min on ice. After washing with PBS+1% FBS, cells were incubated with a 1:200 dilution of FITC F(ab')2 goat Anti-Human IgG, Fcγ (Jackson ImmunoResearch, West Grove, Pa.) to detect binding of anti-EGFR-huIgG1-SIRPαV2 variants and a 1:100 dilution of PE mouse anti-human CD235a (BD Biosciences, San Jose, Calif.) to select for erythrocytes in PBS+1% FBS for 60 min on ice. After washing again, cells were fixed with 1% formaldehyde in PBS. Cells were analyzed by flow cytometry (MACSQuant, Miltenyi Biotec, Cologne, Germany). The median fluorescence intensity (MFI) at 50 μg/ml of each anti-EGFR-huIgG1-SIRPαV2 variant was determined and reported in Table 3. In addition, the degree of binding to erythrocytes was expressed as a % of the anti-CD47 MFI ((100×(MFI of protein)/(MFI of anti-CD47)).

The results confirmed that anti-CD47 bound to CD47 expressed on erythrocytes, but anti-EGFR-huIgG1-SIRPαV2 did not (Table 3), as shown before (FIG. 7B).

Several of the anti-EGFR-huIgG1-SIRPαV2 variants, including V6I, V27I, I31T, Q37H, E54P, and M72R, retained lack of binding to erythrocytes, similar to wild-type anti-EGFR-huIgG1-SIRPαV2 (3% or less of anti-CD47 binding). However, other variants, including I31R and S66Q, had some level of binding to erythrocytes (12% and 21% of anti-CD47 binding, respectively), as did the positive controls 1D4 (53%), AS2 (12%), and AS1 (37%). Q37W and H56P only bound weakly to erythrocytes (4% of anti-CD47 binding).

Table 3: List of anti-EGFR-huIgG1-SIRPαV2 variants, showing percent monomer by SEC, the EC50 (nM) of binding to CD47 expressed on CD47$^{HI}$ cells (CD47-transfected CHO cells) and CD47$^{LO}$ cells (Ramos cells), the MFI (mean fluorescence intensity) of the proteins at 50 μg/ml bound to human erythrocytes (RBC), and the % of RBC binding relative to anti-CD47 MFI (calculated as (100×(MFI of protein)/(MFI of anti-CD47)). Wild type anti-EGFR-huIgG1-SIRPαV2 ("WT"), positive control chimeric antibody B6H12/huIgG1 ("anti-CD47"), and negative control anti-EGFR are in bold and the higher affinity SIRPα positive controls ("1D4", "AS2" and "AS1") are in italics.

| Protein | % Monomer | CD47$^{HI}$ cells EC50 (nM) | CD47$^{LO}$ cells EC50 (nM) | RBC MFI | % RBC MFI of anti-CD47 |
|---|---|---|---|---|---|
| WT | 97 | 8 | 85 | 0.4 | 2% |
| Anti-CD47 | 96 | 7 | 6 | 23.3 | 100% |
| Anti-EGFR | 99 | NB | NB | 0.3 | 1% |
| *1D4* | 97 | 3 | 2 | 12.1 | 52% |
| *AS2* | 97 | 3 | 2 | 2.9 | 12% |
| *AS1* | 94 | 7 | 3 | 8.7 | 37% |
| V6I | 96 | 3 | 9 | 0.4 | 1% |
| V27I | 97 | 2 | 2 | 0.7 | 3% |
| V27Q | 93 | >100 | | | |
| I31R | 91 | 2 | 14 | 2.9 | 12% |
| I31T | 97 | 4 | 13 | 0.5 | 2% |
| P35G | 97 | 18 | | | |
| P35N | 97 | >100 | | | |
| Q37A | 96 | >100 | | | |
| Q37H | 96 | 6 | 71 | 0.3 | 2% |
| Q37V | 97 | 13 | | | |
| Q37W | 95 | 2 | 3 | 1 | 4% |
| E47Y | 97 | 10 | | | |
| Q52E | 88 | >100 | | | |
| Q52H | 90 | >100 | | | |
| E54P | 91 | 8 | 81 | 0.3 | 1% |
| H56P | 97 | 2 | 13 | 0.9 | 4% |
| H56Y | 90 | 12 | | | |
| S66E | 90 | 33 | | | |
| S66H | 86 | 25 | | | |
| S66Q | 90 | 5 | 2 | 4.9 | 21% |
| S66W | 97 | >100 | | | |
| T67E | 91 | >100 | | | |
| T67W | 91 | >100 | | | |
| K68A | 97 | >100 | | | |
| K68E | 97 | >100 | | | |
| K68H | 99 | 56 | | | |
| K68I | 97 | >100 | | | |
| K68T | 97 | >100 | | | |
| M72I | 96 | >100 | | | |
| M72N | 90 | 40 | | | |
| M72R | 87 | 8 | 84 | 0.3 | 1% |
| M72W | 96 | >100 | | | |
| V92N | 80 | 72 | | | |
| K53I + K68I | 97 | NB | | | |
| K53N + K68E | 98 | NB | | | |
| K53Q + K68T | 97 | NB | | | |
| K53T + K68A | 95 | NB | | | |
| K53V + K68H | 97 | NB | | | |

To potentially improve the therapeutic index of an anti-EGFR-huIgG1-SIRPα fusion protein in the treatment of cancer, it may be desirable to select an anti-EGFR-huIgG1-SIRPα variant with an optimal increase in binding to CD47 on CD47$^{HI}$ and CD47$^{LO}$ cells compared to anti-EGFR-huIgG1-SIRPα, and a relative lack of binding to erythrocytes (particularly compared to anti-CD47). For example, a variant may be chosen with an about 5-fold to an about 30-fold increase in binding to CD47$^{LO}$ cells compared to wild-type anti-EGFR-huIgG1-SIRPα, and an about 30% or less, an about 10% or less, an about 5% or less, or an about 3% or less binding to erythrocytes as compared to anti-CD47. Fulfilling such criteria, the biological activity of exemplary variant anti-EGFR-huIgG1-SIRPαV2(Q37W) was further characterized. It is contemplated that to improve the therapeutic index of an antibody-SIRPα fusion protein targeting a different tumor antigen, such as CD20 or HER2, analogous criteria may be used to choose the optimal SIRPα variant.

Example 18: Anti-EGFR-huIgG1-SIRPα(Q37W)

18(A) Construction and Expression of anti-EGFR-huIgG1-SIRPα(Q37W)

Figure 22A:
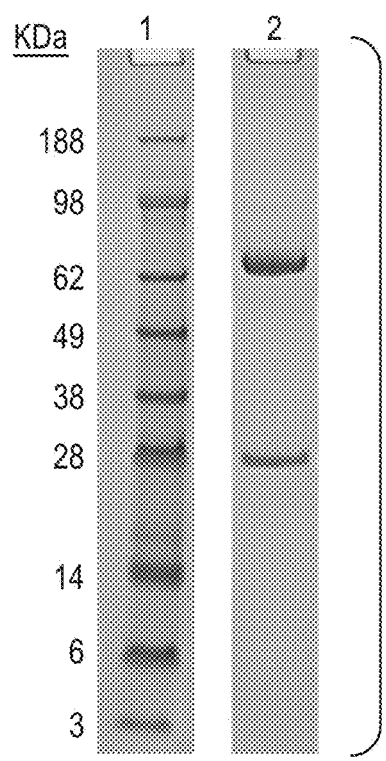
FIGS. 22A-B shows the analysis of the expression of the two polypeptides of anti-EGFR-huIgG1-SIRPαV2(Q37W) by SDS-PAGE (FIG. 22A) and assembly of the full tetrameric molecule by size exclusion chromatography (SEC) (FIG. 22B) as described in Example 18.
Figure 22B:
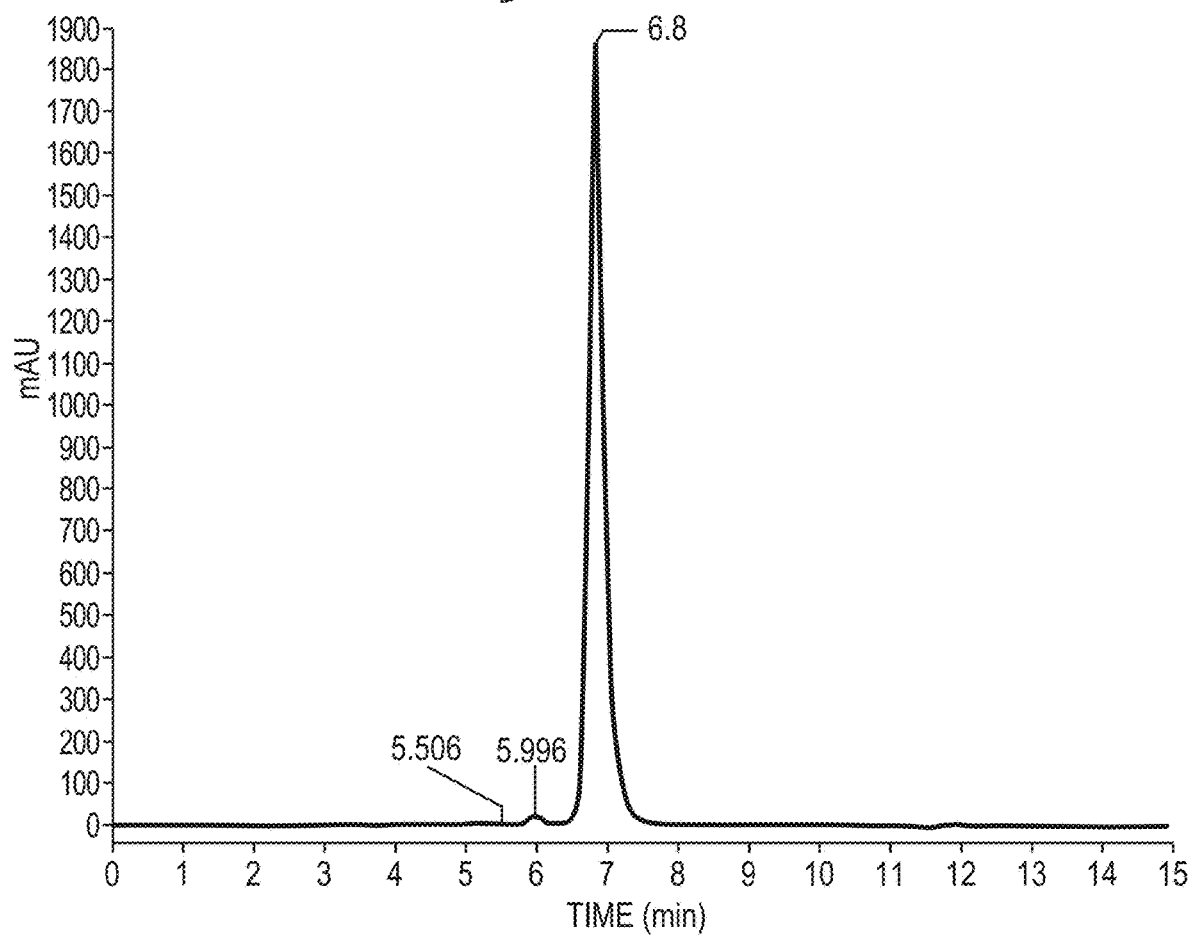

Anti-EGFR-huIgG1-SIRPαV2(Q37W) vectors from example 17 were co-transfected transiently into Expi293 cells using Expi293fectin (Life Technologies, Grand Island, N.Y.) for expression of anti-EGFR-huIgG1-SIRPαV2 (Q37W). The protein was purified in a single step by protein A affinity chromatography. Expression of the two polypeptides and assembly of the full tetrameric molecule were confirmed on sodium dodecyl sulfate-polyacrylamide gel electrophoresis (SDS-PAGE) and size exclusion chromatography (SEC). For SDS-PAGE, the purified protein samples were reduced with DTT and run on NuPAGE MES 4-12% Gel, 200V for 35 min, followed by Coomassie staining. The two major bands on the gel had the expected molecular weights (MW) and the correct stoichiometric ratio with >95% purity (FIG. 22A). In FIG. 22A, lane 1 shows the molecular weight (MW) marker and lane 2 shows the expected MW (64, 23 kDa) and the correct stoichiometric ratio (1:1) of the two polypeptides of anti-EGFR-huIgG1-SIRPαV2(Q37W). For SEC, the purified protein samples were analyzed on a TSK-GEL Super SW3000 SEC column 4.6_300 mm (Tosoh Biosciences, Tokyo, Japan) that was equilibrated with 50 mM sodium phosphate, 400 mM sodium perchlorate, pH 6.3+0.1 and 38+2.0 mS/cm². Size exclusion chromatography showed a peak at the expected MW of about 173 kDa for the monomeric anti-EGFR-huIgG1-SIRPαV2(Q37W) (FIG. 22B).

In addition, anti-EGFR and anti-CD47 in a standard monoclonal antibody format (anti-EGFR huIgG1 and anti-CD47 huIgG1) and SIRPα in a Fc-fusion protein format (SIRPαV2-Fc, Fc-SIRPαV2, and Fc-SIRPαV2(Q37W)) (FIG. 1C) and wild-type anti-EGFR-huIgG1-SIRPαV2 were generated as controls to compare with anti-EGFR-huIgG1-SIRPαV2(Q37W).

18(B) In Vitro Biological Activities of anti-EGFR-huIgG1-SIRPα(Q37W)

The ability for anti-EGFR-huIgG1-SIRPαV2(Q37W) to cause erythrocytes to hemagglutinate was determined, and compared to the control molecules. 30-50 µl of fresh human whole blood cells per well were incubated with 1, 3, 10 and 30 µg/ml of test proteins in a total volume of 100 µl of HBSS+0.5% BSA in a 96 well plate at 37° C. for 2-4 hours. The plates were centrifuged and the supernatant was removed. The cell pellets were resuspended with 100 µl of PBS. Wells were ranked between full solubilization of RBCs (no hemagglutination), partial pellet and solubilization (+hemagglutination) and dense pellet of cells with no solubilization (++hemagglutination).

The results confirmed that anti-CD47 causes erythrocytes to hemagglutinate (+hemagglutination at 3 µg/ml and ++hemagglutination at 10 and 30 µg/ml), but anti-EGFR-huIgG1-SIRPαV2 at all the concentrations tested did not hemagglutinate, correlating with the lack of erythrocyte binding shown in FIG. 7B (data not shown). Anti-EGFR-huIgG1-SIRPαV2(Q37W) at all the concentrations tested also did not cause erythrocytes to hemagglutinate, despite the increased binding of anti-EGFR-huIgG1-SIRPαV2(Q37W) to erythrocytes. This data provides further supporting evidence that anti-EGFR-huIgG1-SIRPαV2(Q37W) may achieve a better therapeutic index by increasing binding without increasing erythrocyte-related toxicity.

18(C) In Vivo Biological Activities of anti-EGFR-huIgG1-SIRPα(Q37W)

The utility of anti-EGFR-huIgG1-SIRPαV2(Q37W) is shown by an in vivo experiment. In an orthotopic lung tumor model, NOD-SCID mice were injected i.v. with 2.5×10⁶ human A549-luc epidermoid carcinoma cells, followed by i.p. injection of 400 µg/mouse of an antibody isotype control, 250 µg/mouse of anti-EGFR, 298 µg/mouse of anti-EGFR-huIgG1-SIRPαV2, or 298 µg/mouse of anti-EGFR-huIgG1-SIRPαV2(Q37W), which is the equimolar amount of fusion protein. All the groups (n=8) received treatment twice a week for 3 weeks, and results were reported as bioluminescent signals from lungs, general health, e.g. paralysis, which preceded death by 10-14 days, and survival of mice.

Figure 23:
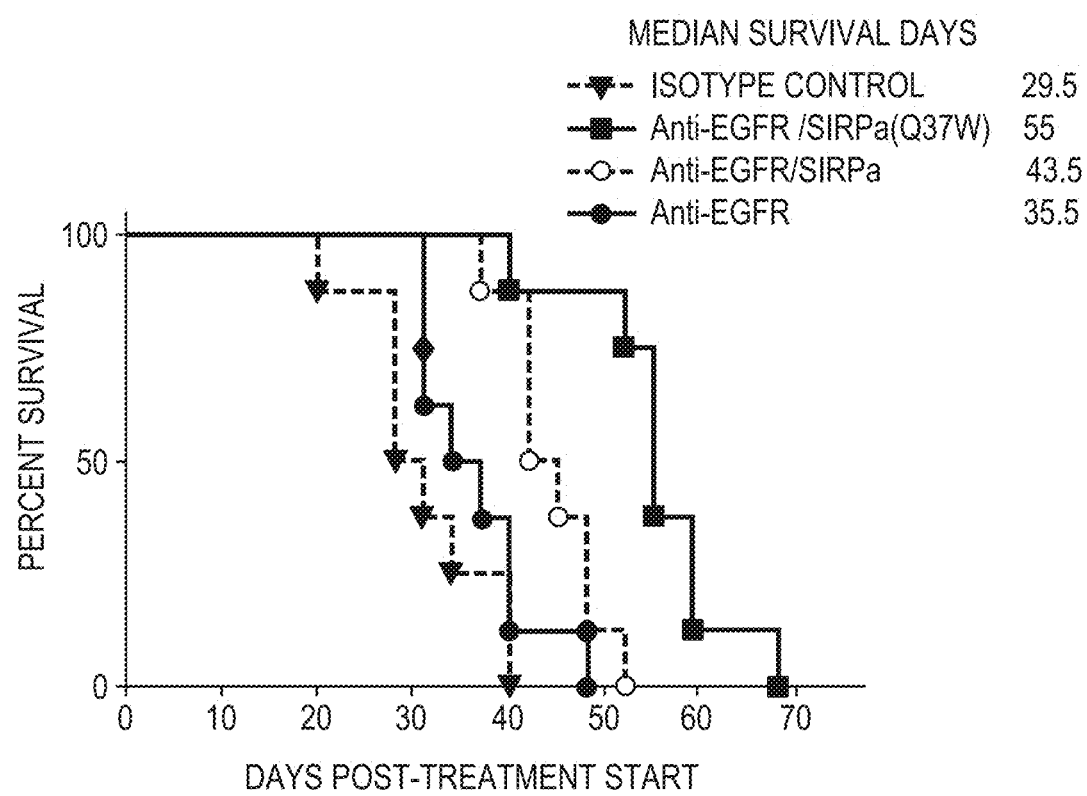
FIG. 23 shows the survival of mice after treatment with anti-EGFR-huIgG1-SIRPαV2 or anti-EGFR-huIgG1-SIRPαV2(Q37W) in an orthotopic A549 lung tumor model.

Treatment with anti-EGFR-huIgG1-SIRPαV2(Q37W) fusion protein was found to be superior to the two monotherapies and anti-EGFR-huIgG1-SIRPαV2 (FIG. 23). Introduction of a single Q37W mutation in the SIRPαV2 moiety of the fusion protein improved the median survival days from 43.5 days for the wild-type anti-EGFR-huIgG1-SIRPαV2 to 55 days, and the difference is highly significant (p=0.0019). The results clearly show that increasing the affinity of SIRPα for CD47 resulted in enhanced anti-tumor efficacy, which, without wishing to be bound by theory, can most easily be explained by the enhanced avidity-driven CD47 binding, and targeting of the A549 cells for elimination by immune cells. The wild-type anti-EGFR-huIgG1-SIRPαV2 in turn was more efficacious than the anti-EGFR antibody, prolonging the median survival day from 35.5 to 43.5 days (p=0.0187), confirming what was observed in a previous experiment (FIG. 9B). Thus, this data provides further supporting evidence that anti-EGFR-huIgG1-SIRPαV2(Q37W) may achieve a better therapeutic index by improving efficacy without increasing erythrocyte-related toxicity.

Example 19: Anti-CD20-huIgG1-SIRPα(Q37W)

19(A) Construction and Expression of anti-CD20-huIgG1-SIRPα(Q37W)

Exemplary anti-CD20-huIgG1-SIRPαV2(Q37W) is based on the anti-CD20-huIgG1-SIRPαV2 described in Example 2. Anti-CD20-huIgG1-SIRPαV2(Q37W) was generated by linking the C-terminus of the anti-CD20 heavy chain polypeptide to the IgV domain of variant SIRPαV2 containing the Q37W mutation via a (G4S)₄ linker (SEQ ID NO: 201).

For expression of anti-CD20-huIgG1-SIRPαV2, the following two gene constructs were assembled by standard recombinant DNA techniques and cloned into the mammalian expression vector pTT5 (containing the mouse light chain signal peptide sequence for secretion) as in FIG. 1A: (1) Construct VH(anti-CD20)-CH1-H-CH2-CH3-(G4S)$_4$-SIRPαV2(Q37W) (SEQ ID NO:11) ("(G4S)$_4$" disclosed as SEQ ID NO: 201) altered by the SIRPα allele V2 encoding mutation Q37W) encoding the following elements: anti-CD20 heavy chain variable domain followed by human heavy chain constant domains 1-3 isotype IgG1 followed by a (G4S)$_4$ linker (SEQ ID NO: 201) and the IgV domain of variant SIRPαV2 with mutation at Q37W and (2) Construct VL(anti-CD20)-CL (SEQ ID NO:1) encoding the anti-CD20 light chain variable domain followed by human kappa light chain constant domain. The corresponding amino acid sequences for these two constructs are shown in SEQ ID NO:12, additionally containing the SIRPα allele V2 mutation Q37W, and SEQ ID NO:2, respectively.

Figure 24A:
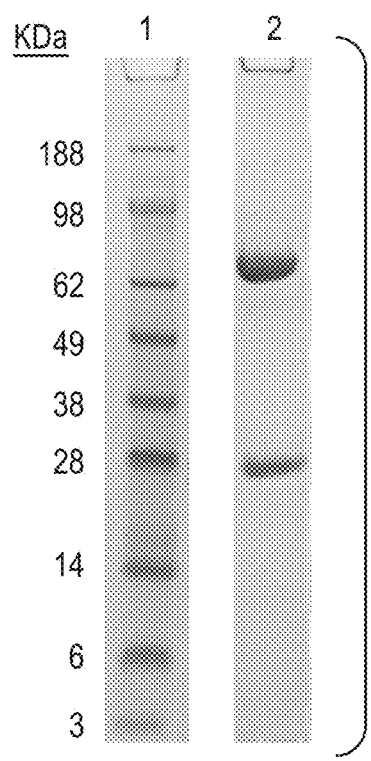
FIGS. 24A-B show the analysis of the expression of the two polypeptides of anti-CD20-huIgG1-SIRPαV2(Q37W) by SDS-PAGE (FIG. 24A) and assembly of the full tetrameric molecule by size exclusion chromatography (SEC) (FIG. 24B) as described in Example 19.
Figure 24B:
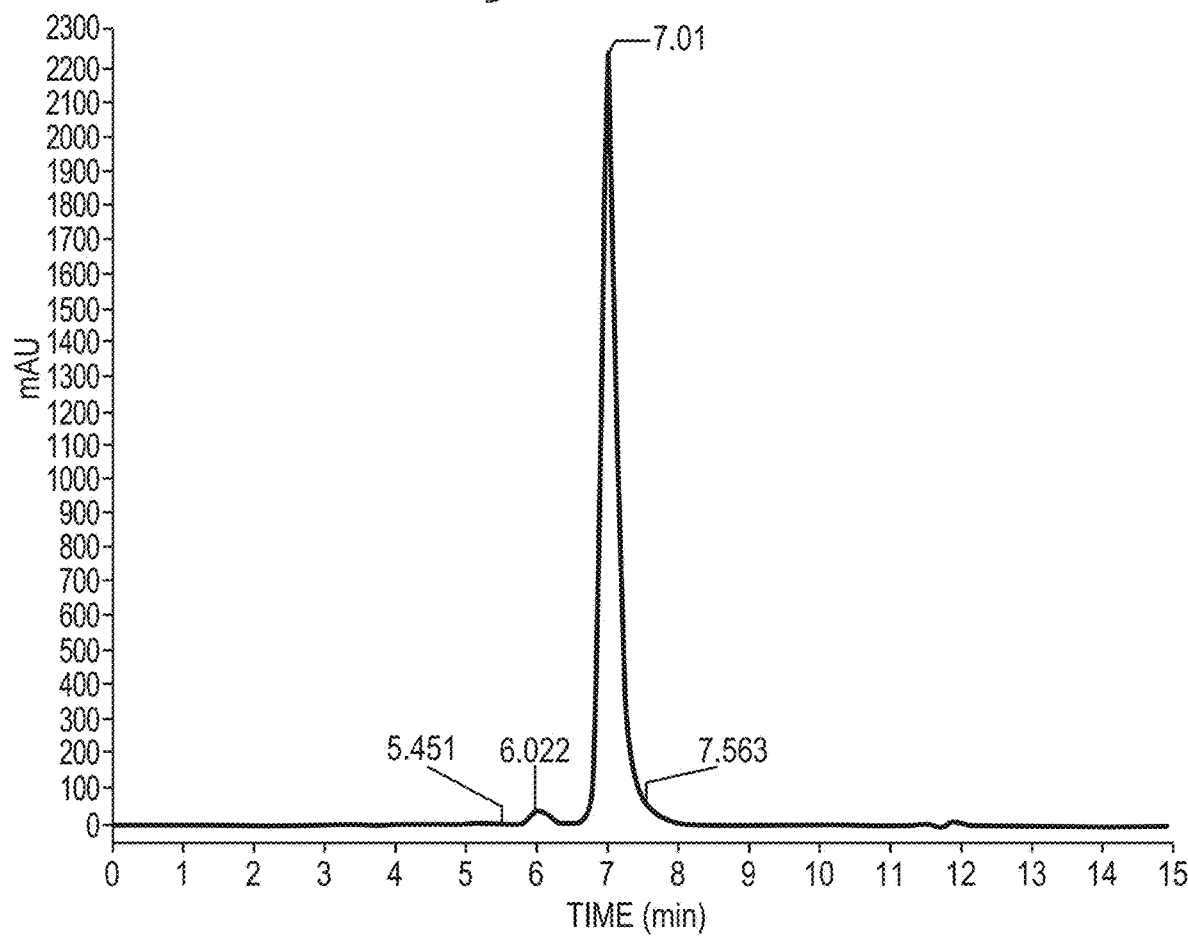

The set of two vectors for anti-CD20-huIgG1-SIRPαV2 (Q37W) expression was co-transfected transiently into Expi293 cells using Expi293fectin (Life Technologies, Grand Island, N.Y.). The protein was purified in a single step by protein A affinity chromatography. Expression of the two polypeptides and assembly of the full tetrameric molecule were confirmed on SDS-PAGE and SEC. For SDS-PAGE, the purified protein samples were reduced with DTT and run on NuPAGE MES 4-12% Gel, 200V for 35 min, followed by Coomassie staining. The two major bands on the gel had the expected MW and the correct stoichiometric ratio with >95% purity (FIG. 24A). In FIG. 24A, lane 1 shows the molecular weight (MW) marker and lane 2 shows the expected MW (63, 23 kDa) and the correct stoichiometric ratio (1:1) of the two polypeptides of anti-CD20-huIgG1-SIRPαV2. For SEC, the purified protein samples were analyzed on a TSK-GEL Super SW3000 SEC column 4.6× 300 mm (Tosoh Biosciences, Tokyo, Japan) that was equilibrated with 50 mM sodium phosphate, 400 mM sodium perchlorate, pH 6.3+0.1 and 38+2.0 mS/cm2. Size exclusion chromatography showed a peak at the expected MW of about 172 kDa for the monomeric anti-CD20-huIgG1-SIRPαV2(Q37W) (FIG. 24B).

In addition, anti-CD20 and anti-CD47 in a standard monoclonal antibody format (anti-CD20 huIgG1 and anti-CD47 huIgG1) and SIRPα in a Fc-fusion protein format (SIRPαV2-Fc, Fc-SIRPαV2, and Fc-SIRPαV2(Q37W)) (FIG. 1C) and wild-type anti-CD20-huIgG1-SIRPαV2 from Example 2 were generated as controls to compare with anti-CD20-huIgG1-SIRPαV2(Q37W).

19(B) In Vivo Biological Activity of the Combination of anti-CD20 with Fc-SIRPαV2(Q37W)

As an indication for the improved biological activity of anti-CD20-huIgG1-SIRPαV2(Q37W) as compared to anti-CD20-huIgG1-SIRPαV2, a disseminated lymphoma model in mouse was used to test the combination of anti-CD20 with either Fc-SIRPαV2 or Fc-SIRPαV2(Q37W). SCID mice were injected i.v. with 5×10$^6$ CD20+ human Daudi lymphoma cells, followed by i.p. injection of 25 µg/mouse of an antibody isotype control, 25 µg/mouse of anti-CD20, combination of 25 µg/mouse of anti-CD20 and 14 µg/mouse of Fc-SIRPαV2, or combination of 25 µg/mouse of anti-CD20 and 14 µg/mouse of Fc-SIRPαV2(Q37W). All groups (n=10) received treatment twice a week for 3 weeks, and results were reported as general health, e.g., paralysis, which preceded death by 10-14 days, and survival of mice.

Figure 25:
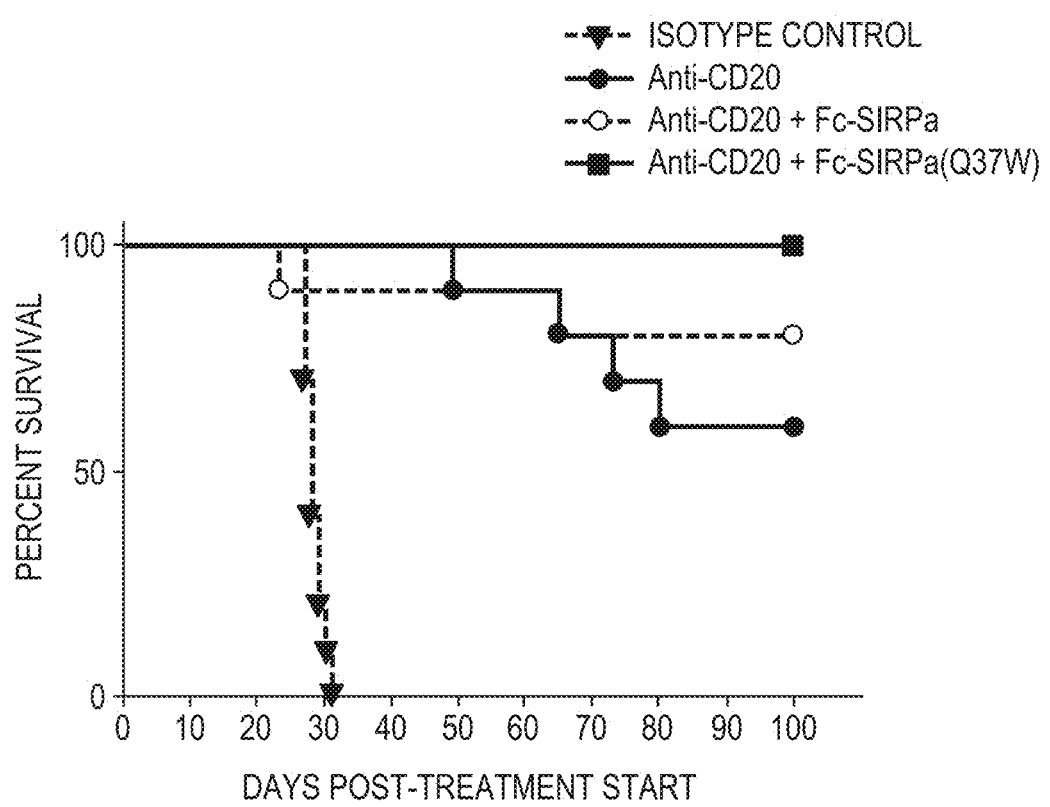
FIG. 25 shows the survival of mice after treatment with the combination of anti-CD20 and Fc-SIRPαV2 or Fc-SIRPαV2(Q37W) in a Daudi disseminated lymphoma model.

While the experiment has not yet concluded, it was found that at one hundred days after the start of treatment, 10 of 10 mice treated with the combination of anti-CD20 and Fc-SIRPαV2(Q37W), and 8 of 10 mice treated with the combination of anti-CD20 and Fc-SIRPαV2, were still alive, as compared to 6 of 10 mice treated with anti-CD20 alone (FIG. 25). Therefore, so far, treatment with the combination of anti-CD20 and Fc-SIRPαV2(Q37W) was found to be superior to the combination of anti-CD20 and Fc-SIRPαV2, which in turn was superior to the anti-CD20 monotherapy. It is expected that anti-CD20-huIgG1-SIRPαV2(Q37W) will also have improved activity as compared to anti-CD20-huIgG1-SIRPαV2.

TABLE 4

Amino Acid and Nucleic Acid Sequences

| SEQ ID NO: | Name | Description | Sequence |
|---|---|---|---|
| 1 | anti-CD20-LC | 2B8(VL)-CK | CAAATTGTTCTCTCCCAGTCTCCAGCAATCCTGTCTGCATCTCCA GGGGAGAAGGTCACAATGACTTGCAGGGCCAGCTCAAGTGTA AGTTACATCCACTGGTTCCAGCAGAAGCCAGGTTCCTCCCCCAA ACCCTGGATTTATGCCACATCCAACCTGGCTTCTGGAGTCCCTGT TCGCTTCAGTGGCAGTGGGTCTGGGACTTCTTACTCTCTCACCAT CAGCAGAGTGGAGGCTGAAGATGCTGCCACTTATTACTGCCAG CAGTGGACTAGTAACCCACCCACGTTCGGAGGGGGGACCAAGC TGGAAATCAAACGTACGGTGGCTGCACCATCTGTCTTCATCTTC CCGCCATCTGATGAGCAGTTGAAATCTGGAACTGCCTCTGTTGT GTGCCTGCTGAATAACTTCTATCCCAGAGAGGCCAAAGTACAG TGGAAGGTGGATAACGCCCTCCAATCGGGTAACTCCCAGGAGA GTGTCACAGAGCAGGACAGCAAGGACAGCACCTACAGCCTCAG CAGCACCCTGACGCTGAGCAAAGCAGACTACGAGAAACACAA AGTCTACGCCTGCGAAGTCACCCATCAGGGCCTGAGCTCGCCCG TCACAAAGAGCTTCAACAGGGGAGAGTGT |
| 2 | anti-CD20-LC | 2B8(VL)-CK | QIVLSQSPAILSASPGEKVTMTCRASSSVSYIHWFQQKPGSSPKP WIYATSNLASGVPVRFSGSGSGTSYSLTISRVEAEDAATYYCQQW TSNPPTFGGGTKLEIKRTVAAPSVFIFPPSDEQLKSGTASVVCLLNN FYPREAKVQWKVDNALQSGNSQESVTEQDSKDSTYSLSSTLTLSK ADYEKHKVYACEVTHQGLSSPVTKSFNRGEC |
| 3 | anti-CD20(VH)-CH1 | 2B8(VH)-CH1 | CAAGTCCAATTGCAGCAGCCCGGCGCCGAACTCGTGAAGCCGG GAGCTTCCGTGAAAATGAGCTGCAAGGCCTCCGGATACACCTT CACCTCCTACAACATGCACTGGGTGAAACAGACCCCAGGGAGG GGTCTGGAGTGGATTGGGCTATCTACCCGGGAAACGGCGAC |

TABLE 4-continued

Amino Acid and Nucleic Acid Sequences

| SEQ ID NO: | Name | Description | Sequence |
|---|---|---|---|
| | | | ACCAGCTATAACCAGAAGTTTAAGGGAAAGGCCACCCTGACTG<br>CCGACAAGTCCTCGTCGACTGCATACATGCAGCTCTCGAGCCTG<br>ACTTCCGAGGACAGCGCAGTGTATTACTGCGCACGCTCCACTTA<br>CTACGGCGGAGATTGGTACTTCAACGTCTGGGGCGCGGGCACC<br>ACTGTGACTGTGTCGGCCGCCTCCACTAAGGGCCCTAGCGTGTT<br>CCCCTTGGCGCCATCGTCAAAGTCCACCTCCGGTGGCACTGCCG<br>CCCTGGGATGCCTTGTGAAGGACTACTTCCCCGAACCTGTGACC<br>GTGTCCTGGAACTCGGGCGCACTGACTTCGGGGGTGCACACCT<br>TTCCTGCCGTCCTGCAATCGAGCGGTCTGTACTCCCTCTCGTCCG<br>TGGTCACCGTGCCGTCTAGCTCCCTCGGAACCCAGACCTACATC<br>TGCAACGTCAACCACAAGCCGAGCAACACCAAAGTGGATAAGA<br>GAGTGGAGCCGAAGTCATGC |
| 4 | anti-CD20(VH)-CH1 | 2B8(VH)-CH1 | QVQLQQPGAELVKPGASVKMSCKASGYTFTSYNMHWVKQTPG<br>RGLEWIGAIYPGNGDTSYNQKFKGKATLTADKSSSTAYMQLSSLT<br>SEDSAVYYCARSTYYGGDWNYFNVWGAGTTVTVSAASTKGPSVFP<br>LAPSSKSTSGGTAALGCLVKDYFPEPVTVSWNSGALTSGVHTFPA<br>VLQSSGLYSLSSVVTVPSSSLGTQTYICNVNHKPSNTKVDKRVEPK<br>SC |
| 5 | huSIRPαV1 | huSIRPa_ECD(V1-c1-C2)-transmembrane-CD | GAGGAGGAGCTGCAGGTGATTCAGCCTGACAAGTCCGTGTTGG<br>TTGCAGCTGGAGAGACAGCCACTCTGCGCTGCACTGCGACCTCT<br>CTGATCCCTGTGGGGCCCATCCAGTGGTTCAGAGGCGCTGGACC<br>AGGCCGGGAATTAATCTACAATCAAAAAGAAGGCCACTTCCCCC<br>GGGTAACAACTGTTTCAGACCTCACAAAGAGAAACAACATGGAC<br>TTTTCCATCCGCATCGGTAACATCACCCCAGCAGATGCCGGCACC<br>TACTACTGTGTGAAGTTCCGGAAAGGGAGCCCCGATGACGTGG<br>AGTTTAAGTCTGGAGCAGGCACTGAGCTGTCTGTGCGCGCCAAA<br>CCCTCTGCCCCCGTGGTATCGGGCCCTGCGGCGAGGGCCACACC<br>TCAGCACAGTGAGCTTCACCTGCGAGTCCCACGGCTTCTCACC<br>CAGAGACATCACCCTGAAATGGTTCAAAAATGGGAATGAGCTCT<br>CAGACTTCCAGACCAACGTGGACCCCGTAGGAGAGAGCGTGTCC<br>TACAGCATCCACAGCACAGCCAAGGTGGTGCTGACCCGCGAGG<br>ACGTTCACTCTCAAGTCATCTGCGAGGTGGCCCACGTCACCTTGC<br>AGGGGGGACCCTCTTCGTGGGACTGCCAACTTGTCTGAGACCATC<br>CGAGTTCCACCCACCCTTGGAGGTTACTCAACAGCCCGTGAGGGC<br>AGAGAACCAGGTGAATGTCACCTGCCAGGTGAGGAAGTTCTACC<br>CCCAGAGACTACAGCTGACCTGGTTGGAGAATGGAAACGTGTCC<br>CGGACAGAAACGGCCTCAACCGTTACAGAGAACAAGGATGGTA<br>CCTACAACTGGATGAGCTGGCTCCTGGTGAATGTATCTGCCCAC<br>AGGGATGATGTGAAGCTCACCTGCCAGGTGGAGCATGACGGGC<br>AGCCAGCGGTCAGCAAAAGCCATGACCTGAAGGTCTCAGCCCAC<br>CCGAAGGAGCAGGGCTCAAATACCGCCGCTGAGAACACTGGAT<br>CTAATGAACGGAACATCTATATTGTGGTGGGTGTGGTGTGCAC<br>TTGCTGGTGGCCCTACTGATGGCGGCCCTCTACCTCGTCCGAATC<br>AGACAGAAGAAAGCCCAGGGCTCCACTTCTTCTACAAGGTTGCA<br>TGAGCCCGAGAAGAATGCCAGAGAAATAACACAGGACACAAAT<br>GATATCACATATGCAGACCTGAACCTGCCCAAGGGGAAGAAGCC<br>TGCTCCCCAGGCTGCGGAGCCCAACAACCACACGGAGTATGCCA<br>GCATTCAGACCAGCCCGCAGCCCGCGTCGGAGGACACCCTCACC<br>TATGCTGACCTGGACATGGTCCACCTCAACCGGACCCCCAAGCA<br>GCCGGCCCCAAGCCTGAGCCGTCCTTCTCAGAGTACGCCAGCG<br>TCCAGGTCCCGAGGAAG |
| 6 | huSIRPαV1 | huSIRPa_ECD(V1-c1-C2)-transmembrane-CD | EEELQVIQPDKSVLVAAGETATLRCTATSLIPVGPIQWFRGAGPGR<br>ELIYNQKEGHFPRVTTVSDLTKRNNMDFSIRIGNITPADAGTYYCV<br>KFRKGSPDDVEFKSGAGTELSVRakpsapvvsgpaaratpqhtvsftcesh<br>gfsprditlkwfkngnelsdfqtnvdpvgesysysihstakvvltredvhsqviceva<br>hvtlqgdplrgtanlsetirvp*PTLEVTQQPVRAENQVNVTCQVRKFYPQ*<br>*RLQLTWLENGNVSRTETASTVTENKDGTYNWMSWLLVNVSAHR*<br>*DDVKLTCQVEHDGQPAVSKSHDLK*VSAHPKEQGSNTAAENTGS<br>NERNIYivvgvvctllvallmaalylvRIRQKKAQGSTSSTRLHEPEKNAREI<br>TQDTNDITYADLNLPKGKKPAPQAAEPNNHTEYASIQTSPQPASED<br>TLTYADLDMVHLNRTPKQPAPKPEPSFSEYASVQVPRK |
| 7 | huSIRPαaV2 (IgV) | huSIRPa_IgV(V2) | GAGGAAGAGCTGCAGGTCATCCAGCCTGACAAGTCAGTCAGCG<br>TGGCAGCTGGAGAGAGCGCCATTCTGCACTGCACAGTCACTTCC<br>CTGATCCCAGTGGGACCCATTCAGTGGTTCCGAGGCGCAGGACC<br>AGCAGGGAGACTGATCTACAACCAGAAGGAGGGCCATTTCCCCC<br>GCGTCACAACCGTGAGCGAATCTACCAAACGAGAGAATATGGAC<br>TTTAGTATCTCAATTAGCAACATTACTCCCGCTGATGCAGGCACC<br>TACTATTGCGTGAAGTTCCGGAAAGGAAGCCCTGACACTGAGTT<br>CAAGTCCGGGGCCGGCACCGAGCTGTCTGTGCGC |

TABLE 4-continued

Amino Acid and Nucleic Acid Sequences

| SEQ ID NO: | Name | Description | Sequence |
|---|---|---|---|
| 8 | huSIRPαV2 (IgV) | huSIRPa_IgV(V2) | EEELQVIQPDKSVSVAAGESAILHCTVTSLIPVGPIQWFRGAGPAR<br>ELIYNQKEGHFPRVTTVSESTKRENMDFSISISNITPADAGTYYCVK<br>FRKGSPDTEFKSGAGTELSVR |
| 9 | anti-CD20(VH)-CH1 | 2B8(VH)-ch1(huigg1m3)-HINGE(HUIGG1M3)-(huIgG1m3: ch2-CH3)-a-(g4s)x4-huSIRPa(V1) | CAAGTCCAATTGCAGCAGCCCGGCGCCGAACTCGTGAAGCCGG<br>GAGCTTCCGTGAAAATGAGCTGCAAGGCCTCCGGATACACCTTC<br>ACCTCCTACAACATGCACTGGGTGAAACAGACCCCAGGGAGGG<br>GTCTGGAGTGGATTGGGCGTATCTACCCGGGAAACGGCGACAC<br>CAGCTATAACCAGAAGTTTAAGGGAAAGGCCACCCTGACTGCCG<br>ACAAGTCCTCGTCGACTGCATACATGCAGCTCTCGAGCCTGACTT<br>CCGAGGACAGCGCAGTGTATTACTGCGCACGCTCCACTTACTAC<br>GGCGGAGATTGGTACTTCAACGTCTGGGGCGCGGGCACCACTG<br>TGACTGTGTCGGCCgcctccactaagggcccTAGCGTGTTCCCCTTGGCGCCAT<br>cgtcaaagtccacctccggtggcactgccgccctgggatgccttgtgaaggactactt<br>ccccgaacctgtgaccgtgtcctggaactcgggcgcactgacttcggggggtgcacac<br>ctttcctgccgtcctgcaatcgagcggtctgtactccctctcgtccgtggtcaccgtgc<br>cgtctagccctcggaacccagacctacatctgcaacgtcaaccacaagccgagc<br>aacaccaaagtggataagagagtgGAGCCGAAGTCATGCGACAAGACT<br>CATACTTGTCCCCCATGCCCCGCCCCGGAACTGCTGGGggcccat<br>ccgtgttcctgttcccgccgaaacctaaggacacctgatgatttcgagaactcc<br>ggaagtgacctgtgtggtggtcgacgtgtcccacgaggatccggaggtcaagt<br>tcaattggtacgtcgacggagtggaagtccacaacgccaagaccaagcccgg<br>gaggagcagtacaactccacttaccgggtggtgtccgtgctgaccgtgctgcat<br>caggattggctgaacggaaaggagtataagtgcaaagtgtcaaacaaggca<br>ttgcctgcgccaatcgaaaagaccattagcaaggccaag<br>GGAACCACAGGTGTACACTCTGCCCCCGTCCCGCGAAGAAATGA<br>CCAAGAACCAAGTGTCACTGACATGCCTCGTGAAGGGATTTTAC<br>CCGTCCGATATCGCCGTGGAATGGGAATCGAACGGTCAACCTGA<br>AAACAACTACAAGACGACCCCTCCGGTCCTGGACAGCGATGGCT<br>CATTCTTCCTGTACTCCAAGCTTACGGTGGACAAGTCCCGGTGGC<br>AACAGGGAAATGTGTTTTCGTGCTCCGTGATGCATGAGGCTCTG<br>CACAACCACTACACCCAGAAGTCACTCTCCCTGAGCCCCGGCgcg<br>gggggtggtggaagcggaggagggggtctgggggtggcggttccggcggcggcg<br>gatccGAGGAGGAACTTCAGGTCATCCAGCCCGACAAGAGCGTG<br>CTCGTGGCGGCCGGAGAAACCGCAACTCTGAGATGCACCGCTA<br>CCTCGCTGATTCCCGTGGGGCCTATCCAGTGGTTCCGCGGGGCC<br>GGACCCGGACGCGAGCTCATCTACAACCAGAAGGAGGGGCAC<br>TTCCCGAGGGTCACCACCGTGTCGGACCTCACCAAGCGCAACA<br>ACATGGACTTCAGCATTCGGATCGGCAACATCACCCCCGCCGAC<br>GCCGGCACCTATTACTGCGTGAAGTTCCGCAAGGGGCAGCCCTG<br>ACGACGTGGAGTTCAAAAGCGGAGCCGGAACCGAGCTGTCCG<br>TGAGA |
| 10 | anti-CD20-huIgG1-SIRPαV1 | 2B8(VH)-ch1(huigg1m3)-HINGE(HUIGG1M3)-(huIgG1m3: ch2-CH3)-a-(g4s)x4-huSIRPa(V1) | QVQLQQPGAELVKPGASVKMSCKASGYTFTSYNMHWVKQTPGR<br>GLEWIGAIYPGNGDTSYNQKFKGKATLTADKSSSTAYMQLSSLTSE<br>DSAVYYCARSTYYGGDWYFNVWGAGTTVTVSAastkgpsvfplapss<br>kstsggtaalgclvkdyfpepvtvswnsgaltsgvhtfpavlqssglyslssvvtvp<br>ssslgtqtyicnvnhkpsntkvdkrvEPKSCDKTHTCPPCPAPELLGgpsvfl<br>fppkpkdtlmisrtpevtcvvvdvshedpevkfnwyvdgvevhnakktkpreeq<br>ynstyrvvsvltvlhqdwlngkeykckvsnkalpapiektiskakGQPREPQV<br>YTLPPSREEMTKNQVSLTCLVKGFYPSDIAVEWESNGQPENNYKTT<br>PPVLDSDGSFFLYSKLTVDKSRWQQGNVFSCSVMHEALHNHYTQK<br>SLSLSPGagggsggggsggggsggggsEEELQVIQPDKSVLVAAGETAT<br>LRCTATSLIPVGPIQWFRGAGPGRELIYNQKEGHFPRVTTVSDLTK<br>RNNMDFSIRIGNITPADAGTYYCVKFRKGSPDDVEFKSGAGTELS<br>VR |
| 11 | anti-CD20-huIgG1-SIRPαV2 | 2B8(VH)-ch1(huigg1m3)-HINGE(HUIGG1M3)-(huIgG1m3: ch2-CH3)-a-(g4s)x4-huSIRPa(V2) | CAAGTCCAATTGCAGCAGCCCGGCGCCGAACTCGTGAAGCCGG<br>GAGCTTCCGTGAAAATGAGCTGCAAGGCCTCCGGATACACCTTC<br>ACCTCCTACAACATGCACTGGGTGAAACAGACCCCAGGGAGGG<br>GTCTGGAGTGGATTGGGCGTATCTACCCGGGAAACGGCGACAC<br>CAGCTATAACCAGAAGTTTAAGGGAAAGGCCACCCTGACTGCCG<br>ACAAGTCCTCGTCGACTGCATACATGCAGCTCTCGAGCCTGACTT<br>CCGAGGACAGCGCAGTGTATTACTGCGCACGCTCCACTTACTAC<br>GGCGGAGATTGGTACTTCAACGTCTGGGGCGCGGGCACCACTG<br>TGACTGTGTCGGCCgcctccactaagggcccTAGCGTGTTCCCCTTGGCGCCAT<br>cgtcaaagtccacctccggtggcactgccgccctgggatgccttgtgaaggactactt<br>ccccgaacctgtgaccgtgtcctggaactcgggcgcactgacttcggggggtgcacac<br>ctttcctgccgtcctgcaatcgagcggtctgtactccctctcgtccgtggtcaccgtgc<br>cgtctagccctcggaacccagacctacatctgcaacgtcaaccacaagccgagc<br>aacaccaaagtggataagagagtgGAGCCGAAGTCATGCGACAAGACT<br>CATACTTGTCCCCCATGCCCCGCCCCGGAACTGCTGGGggcccat<br>ccgtgttcctgttcccgccgaaacctaaggacacctgatgatttcgagaactcc<br>ggaagtgacctgtgtggtggtcgacgtgtcccacgaggatccggaggtcaagt |

TABLE 4-continued

Amino Acid and Nucleic Acid Sequences

| SEQ ID NO: | Name | Description | Sequence |
|---|---|---|---|
| | | | *tcaattggtacgtcgacggagtggaagtccacaacgccaagaccaagcccgg gaggagcagtacaactccacttaccgggtggtgtccgtgctgaccgtgctgcat caggattggctgaacggaaaggagtataagtgcaaagtgtcaaacaaggca ttgcctgcgccaatcgaaaagaccattagcaaggccaag*GGCCAGCCCAG GGAACCACAGGTGTACACTCTGCCCCCGTCCCGCGAAGAAATGA CCAAGAACCAAGTGTCACTGACATGCCTCGTGAAGGGATTTTAC CCGTCCGATATCGCCGTGGAATGGGAATCGAACGGTCAACCTGA AAACAACTACAAGACGACCCCTCCGGTCCTGGACAGCGATGGCT CATTCTTCCTGTACTCCAAGCTTACGGTGGACAAGTCCCGGTGGC AACAGGGAAATGTGTTTTCGTGCTCCGTGATGCATGAGGCTCTG CACAACCACTACACCCAGAAGTCACTCTCCCTGAGCCCCGGCgcg ggggggtggtggaagcggaggaggggggtctgggggtggcggttccggcggcggcg gatccGAGGAGGAGCTCCAGGTCATCCAGCTGACAAGTCCGTG TCGGTGGCCGCGGGAGAGTCCGCCATTCTGCACTGCACCGTGA CCTCCCTCATCCCCGTGGGACCTATCCAGTGGTTCAGAGGAGCC GGGCCCGCACGGGAACTGATCTATAACCAGAAGGAGGGCCATT TCCCCCGCGTGACCACCGTGTCCGAGAGCACCAAGAGGGAAAA CATGGACTTCAGCATTTCGATCAGCAACATCACTCCCGCTGACG CCGGGACCTACTACTGCGTGAAGTTCCGGAAAGGAAGCCCGGA CACCGAGTTCAAAAGCGGAGCCGGCACCGAACTGTCGGTCCGC |
| 12 | anti-CD20-huIgG1-SIRPαV2 | 2B8(VH)-ch1(huigg1m3)-HINGE(HUIGG1M3)-(huIgG1m3: ch2-CH3)-a-(g4s)x4-huSIRPa(V2) | QVQLQQPGAELVKPGASVKMSCKASGYTFTSYNMHWVKQTPGR GLEWIGAIYPGNGDTSYNQKFKGKATLTADKSSSTAYMQLSSLTSE DSAVYYCARSTYYGGDWYFNVWGAGTTVTVSA*astkgpsvfplapss ksstsggtaalgclvkdyfpepvtvswnsgaltsgvhtfpavlqssglyslssvvtvp ssslgtqtyicnvnhkpsntkvdkrv*EPKSCDKTHTCPPCPAPELLG*gpsvfl fppkpkdtlmisrtpevtcvvvdvshedpevkfnwyvdgvevhnaktkpreeq ynstyrvvsvltvlhqdwlngkeykckvsnkalpapiektiskak*GQPREPQV YTLPPSREEMTKNQVSLTCLVKGFYPSDIAVEWESNGQPENNYKTT PPVLDSDGSFFLYSKLTVDKSRWQQGNVFSCSVMHEALHNHYTQK SLSLSPG*agggggggggsggggsggggs*EEELQVIQPDKSVSVAAGESAI LHCTVTSLIPVGPIQWFRGAGPARELIYNQKEGHFPRVTTVSESTK RENMDFSISISNITPADAGTYYCVKFRKGSPDTEFKSGAGTELSVR |
| 13 | anti-EGFR-LC | C225 VL-CK | GACATCTTGCTGACTCAGTCTCCAGTCATCCTGTCTGTGAGTCCA GGAGAAAGAGTCAGTTTCTCCTGCAGGGCCAGTCAGAGTATTG GCACAAACATACACTGGTATCAGCAAAGAACAAATGGTTCTCC AAGGCTTCTCATAAAGTATGCTTCTGAGTCTATCTCTGGGATCC CTTCCAGGTTTAGTGGCAGTGGATCAGGGACAGATTTTACTCTT AGCATCAACAGTGTGGAGTCTGAAGATATTGCAGATTATTACT GTCAACAAAATAATAACTGGCCAACCACGTTCGGTGCTGGGAC CAAGCTGGAGCTGAAACGTACGGTGGCTGCACCATCTGTCTTC ATCTTCCCGCCATCTGATGAGCAGTTGAAATCTGGAACTGCCTC TGTTGTGTGCCTGCTGAATAACTTCTATCCCAGAGAGGCCAAAG TACAGTGGAAGGTGGATAACGCCCTCCAATCGGGTAACTCCCA GGAGAGTGTCACAGAGCAGGACAGCAAGGACAGCACCTACAG CCTCAGCAGCACCCTGACGCTGAGCAAAGCAGACTACGAGAAA CACAAAGTCTACGCCTGCGAAGTCACCCATCAGGGCCTGAGCTC GCCCGTCACAAAGAGCTTCAACAGGGGAGAGTGT |
| 14 | anti-EGFR-LC | C225VL-CK | DILLTQSPVILSVSPGERVSFSCRASQSIGTNIHWYQQRTNGSPRLL IKYASESISGIPSRFSGSGSGTDFTLSINSVESEDIADYYCQQNNNW PTTFGAGTKLELKRTVAAPSVFIFPPSDEQLKSGTASVVCLLNNFYP REAKVQWKVDNALQSGNSQESVTEQDSKDSTYSLSSTLTLSKADY EKHKVYACEVTHQGLSSPVTKSFNRGEC |
| 15 | anti-EGFR(VH)-CH1 | C225VH-CH1(huIgG1m3) | CAAGTCCAACTGAAGCAGTCCGGGCCGGGACTCGTGCAGCCGT CGCAGTCACTGTCCATCACTTGCACGGTGTCAGGCTTTTCCTTGA CCAACTACGGAGTGCACTGGGTGCGCCAGTCCCCTGGAAAGGG GCTGGAGTGGCTTGGCGTGATTTGGTCCGGAGGAAACACAGAC TACAACACTCCTTTCACCTCCCGCCTGAGCATTAACAAGGACAA CTCCAAGTCCCAAGTGTTCTTCAAGATGAACAGCCTGCAGACA ATGATACCGCCATCTACTATTGTGCCCGGGCTCTCACCTACTACG ACTACGAATTCGCCTACTGGGGACAGGGAACCCTGGTCACTGT CTCCGCGGCCTCCACTAAGGGCCCTAGCGTGTTCCCCTTGGCGC CATCGTCAAAGTCCACCTCCGGTGGCACTGCCGCCCTGGGATGC CTTGTGAAGGACTACTTCCCCGAACCTGTGACCGTGTCCTGGAA CTCGGGCGCACTGACTTCGGGGGTGCACACCTTTCCTGCCGTCC TGCAATCGAGCGGTCTGTACTCCCTCTCGTCCGTGGTCACCGTG CCGTCTAGCTCCCTCGGAACCCAGACCTACATCTGCAACGTCAA CCACAAGCCGAGCAACACCAAAGTGGATAAGAGAGTGGAGCC GAAGTCATGC |

TABLE 4-continued

Amino Acid and Nucleic Acid Sequences

| SEQ ID NO: | Name | Description | Sequence |
|---|---|---|---|
| 16 | anti-EGFR(VH)-CH1 | C225VH-CH1(huIgG1m3) CH1 | QVQLKQSGPGLVQPSQSLSITCTVSGFSLTNYGVHWVRQSPGKG<br>LEWLGVIWSGGNTDYNTPFTSRLSINKDNSKSQVFFKMNSLQSN<br>DTAIYYCARALTYYDYEFAYWGQGTLVTVSAASTKGPSVFPLAPSS<br>KSTSGGTAALGCLVKDYFPEPVTVSWNSGALTSGVHTFPAVLQSS<br>GLYSLSSVVTVPSSSLGTQTYICNVNHKPSNTKVDKRVEPKSC |
| 17 | anti-EGFR-huIgG1-SIRPαV1 | C225(VH)-ch1(huigg1m3)-HINGE(HUIGG1M3)-(huIgG1m3: ch2-CH3)-a-(g4s)x4-huSIRPa(V1) | CAAGTCCAACTGAAGCAGTCCGGGCCGGGACTCGTGCAGCCGTC<br>GCAGTCACTGTCCATCACTTGCACGGTGTCAGGCTTTTCCTTGAC<br>CAACTACGGAGTGCACTGGGTGCGCCAGTCCCCTGGAAAGGGG<br>CTGGAGTGGCTTGGCGTGATTTGGTCCGGAGGAAACACAGACT<br>ACAACACTCCTTTCACCTCCCGCCTGAGCATTAACAAGGACAACT<br>CCAAGTCCCAAGTGTTCTTCAAGATGAACAGCCTGCAGAGCAAT<br>GATACCGCCATCTACTATTGTGCCCGGGCTCTCACCTACTACGAC<br>TACGAATTCGCCTACTGGGGACAGGGAACCCTGGTCACTGTCTC<br>CGCGgcctccactaagggcccta gcgtgttcccctggcgccatcgtcaaagtcca<br>cctccggtggcactgccgccctgggatgccttgtgaaggactacttccccgaacctgt<br>gaccgtgtcctggaactcgggcgcactgacttcggggtgcacacctttcctgccgtc<br>ctgcaatcgagcggtctgtactccctctcgtccgtggtcaccgtgccgtctagctccct<br>cggaacccagacctacatctgcaacgtcaaccacaagccgagcaacaccaaagtg<br>gataagagagtgGAGCCGAAGTCATGCGACAAGACTCATACTTGTC<br>CCCCATGCCCCGCCCCGGAACTGCTGGGGggcccatccgtgttcctgtt<br>cccgccgaaacctaaggacacacctgatgatttcgagaactccggaagtgacctg<br>tgtggtggtcgacgtgtcccacgaggatccggaggtcaagttcaattggtacgt<br>cgacggagtggaagtccacaacgccaagaccaagccccgggaggagcagta<br>caactccacttaccgggtggtgtccgtgctgaccgtgctgcatcaggattggctg<br>aacggaaaggagtataagtgcaaagtgtcaaacaaggcattgcctgcgccaa<br>tcgaaaagaccattagcaaggccaagGGCCAGCCCAGGGAACCCACAG<br>GTGTACACTCTGCCCCCGTCCCGCGAAGAAATGACCAAGAACCA<br>AGTGTCACTGACATGCCTCGTGAAGGGATTTTACCCGTCCGATAT<br>CGCCGTGGAATGGGAATCGAACGGTCAACCTGAAAACAACTACA<br>AGACGACCCCTCCGGTCCTGGACAGCGATGGCTCATTCTTCCTGT<br>ACTCCAAGCTTACGGTGGACAAGTCCCGGTGGCAACAGGGAAA<br>TGTGTTTTCGTGCTCCGTGATGCATGAGGCTCTGCACAACCACTA<br>CACCCAGAAGTCACTCTCCCTGAGCCCCGGCgcggggggtggtggaag<br>cggaggaggggggtctgggggtggcggttccggcggcggcggatccGAGGAGG<br>AACTTCAGGTCATCCAGCCCGACAAGAGCGTGCTCGTGGCGGC<br>CGGAGAAACCGCAACTCTGAGATGCACCGCTACCTCGCTGATTC<br>CCGTGGGGCCTATCCAGTGGTTCCGCGGGGCCGGACCCGGACG<br>CGAGCTCATCTACAACCAGAAGGAGGGGCACTTCCCGAGGGTC<br>ACCACCGTGTCGGACCTCACCAAGCGCAACAACATGGACTTCA<br>GCATTCGGATCGGCAACATCACCCCCGCCGACGCCGGCACCTAT<br>TACTGCGTGAAGTTCCGGAAGGGCAGCCCTGACGACGTGGAGT<br>TCAAAAGCGGAGCCGGAACCGAGCTGTCCGTGAGA |
| 18 | anti-EGFR-huIgG1-SIRPαV1 | C225(VH)-ch1(huiggg1m3)-HINGE(HUIGG1M3)-(huIgG1m3: ch2-CH3)-a-(g4s)x4-huSIRPa(V1) | QVQLKQSGPGLVQPSQSLSITCTVSGFSLTNYGVHWVRQSPGKGLE<br>WLGVIWSGGNTDYNTPFTSRLSINKDNSKSQVFFKMNSLQSNDTAI<br>YYCARALTYYDYEFAYWGQGTLVTVSAastkgpsvfplapsskstsggta<br>algclvkdyfpepvtvswnsgaltsgvhtfpavlqssglyslssvvtvpsssslgtqty<br>icnvnhkpsntkvdkrvEPKSCDKTHTCPPCPAPELLGgpsvflfppkpkdt<br>lmisrtpevtcvvvdvshedpevkfnwyvdgvevhnaktkpreeqynstyrvv<br>svltvlhqdwlngkeykckvsnkalpapiektiskakGQPREPQVYTLPPSR<br>EEMTKNQVSLTCLVKGFYPSDIAVEWESNGQPENNYKTTPPVLDSD<br>GSFFLYSKLTVDKSRWQQGNVFSCSVMHEALHNHYTQKSLSLSPG<br>AGGGGSGGGGSGGGGSGGGGSEEELQVIQPDKSVLVAAGETATL<br>RCTATSLIPVGPIQWFRGAGPGRELIYNQKEGHFPRVTTVSDLTKR<br>NNMDFSIRIGNITPADAGTYYCVKFRKGSPDDVEFKSGAGTELSV<br>R |
| 19 | anti-EGFR-huIgG1-SIRPαV2 | C225(VH)-ch1(huiggg1m3)-HINGE(HUIGG1M3)-(huIgG1m3: ch2-CH3)-a-(g4s)x4-huSIRPa(V2) | CAAGTCCAACTGAAGCAGTCCGGGCCGGGACTCGTGCAGCCGTC<br>GCAGTCACTGTCCATCACTTGCACGGTGTCAGGCTTTTCCTTGAC<br>CAACTACGGAGTGCACTGGGTGCGCCAGTCCCCTGGAAAGGGG<br>CTGGAGTGGCTTGGCGTGATTTGGTCCGGAGGAAACACAGACT<br>ACAACACTCCTTTCACCTCCCGCCTGAGCATTAACAAGGACAACT<br>CCAAGTCCCAAGTGTTCTTCAAGATGAACAGCCTGCAGAGCAAT<br>GATACCGCCATCTACTATTGTGCCCGGGCTCTCACCTACTACGAC<br>TACGAATTCGCCTACTGGGGACAGGGAACCCTGGTCACTGTCTC<br>CGCGgcctccactaagggcccta gcgtgttcccctggcgccatcgtcaaagtcca<br>cctccggtggcactgccgccctgggatgccttgtgaaggactacttccccgaacctgt<br>gaccgtgtcctggaactcgggcgcactgacttcggggtgcacacctttcctgccgtc<br>ctgcaatcgagcggtctgtactccctctcgtccgtggtcaccgtgccgtctagctccct<br>cggaacccagacctacatctgcaacgtcaaccacaagccgagcaacaccaaagtg<br>gataagagagtgGAGCCGAAGTCATGCGACAAGACTCATACTTGTC<br>CCCCATGCCCCGCCCCGGAACTGCTGGGGggcccatccgtgttcctgtt<br>cccgccgaaacctaaggacacacctgatgatttcgagaactccggaagtgacctg |

TABLE 4-continued

Amino Acid and Nucleic Acid Sequences

| SEQ ID NO: | Name | Description | Sequence |
|---|---|---|---|
| | | | *tgtggtggtcgacgtgtcccacgaggatccggaggtcaagttcaattggtacgt cgacggagtggaagtccacaacgccaagaccaagccccgggaggagcagta caactccacttaccgggtggtgtccgtgctgaccgtgctgcatcaggattggctg aacggaaaggagtataagtgcaaagtgtcaaacaaggcattgcctgcgccaa tcgaaaagaccattagcaaggccaag*GGCCAGCCCAGGGAACCACAG GTGTACACTCTGCCCCCGTCCCGCGAAGAAATGACCAAGAACCA AGTGTCACTGACATGCCTCGTGAAGGGATTTTACCCGTCCGATAT CGCCGTGGAATGGGAATCGAACGGTCAACCTGAAAACAACTACA AGACGACCCCTCCGGTCCTGGACAGCGATGGCTCATTCTTCCTGT ACTCCAAGCTTACGGTGGACAAGTCCCGGTGGCAACAGGGAAA TGTGTTTTCGTGCTCCGTGATGCATGAGGCTCTGCACAACCACTA CACCCAGAAGTCACTCTCCCTGAGCCCCGGC*gcggggggtggtggaag cggaggagggggggtctgggggtggcggttccggcggcggcggatcc*GAGGAGG AGCTCCAGGTCATCCAGCCTGACAAGTCCGTGTCGGTGGCCGC GGGAGAGTCCGCCATTCTGCACTGCACCGTGACCTCCCTCATCC CCGTGGGACCTATCCAGTGGTTCAGAGGAGCCGGGCCCGCACG GGAACTGATCTATAACCAGAAGGAGGGCCATTTCCCCCGCGTG ACCACCGTGTCCGAGAGCACCAAGAGGGAAAACATGGACTTCA GCATTTCGATCAGCAACATCACTCCCGCTGACGCCGGGACCTAC TACTGCGTGAAGTTCCGGAAAGGAAGCCCGGACACCGAGTTCA AAGCGGAGCCGGCACCGAACTGTCGGTCCGC |
| 20 | anti-EGFR-huIgG1-SIRPαV2 | C225(VH)-ch1(huigg1m3)-HINGE(HUIGG1M3)-(huIgG1m3: ch2-CH3)-a-(g4s)x4-huSIRPa(V2) | QVQLKQSGPGLVQPSQSLSITCTVSGFSLTNYGVHWVRQSPGKGLE WLGVIWSGGNTDYNTPFTSRLSINKDNSKSQVFFKMNSLQSNDTAI YYCARALTYYDYEFAYWGQGTLVTVSA*astkgpsvfplapssksrsggta algclvkdyfpepvtvswnsgaltsgvhtfpavlqssglyslssvvtvpssslgtqty icnvnhkpsntkvdkrv*EPKSCDKTHTCPPCPAPELLG*gpsvflfppkpkdt lmisrtpevtcvvvdvshedpevkfnwyvdgvevhnaktkpreeqynstyrvv svltvlhqdwlngkeykckvsnkalpapiektiskak*GQPREPQVYTLPPSR+EE EEMTKNQVSLTCLVKGFYPSDIAVEWESNGQPENNYKTTPPVLDSD+EE GSFFLYSKLTVDKSRWQQGNVFSCSVMHEALHNHYTQKSLSLSPG+EE AGGGGSGGGGSGGGGSGGGGSEEELQVIQPDKSVSVAAGESAIL HCTVTSLIPVGPIQWFRGAGPARELIYNQKEGHFPRVTTVSESTKR ENMDFSISISNITPADAGTYYCVKFRKGSPDTEFKSGAGTELSVR |
| 21 | anti-HER2-LC | Herceptin(VL)-CK | GACATCCAGATGACCCAGAGCCCTAGCAGCCTGAGCGCAGCG TGGGCGACAGAGTGACAATCACCTGCAGGGCCAGCCAGGACG TGAATACCGCCGTGGCCTGGTACCAGCAGAAACCCGGCAAGGC CCCTAAGCTGCTGATCTACTCCGCCTCCTTCCTCTACAGCGGCGT GCCCAGCAGGTTTAGCGGCAGCAGGAGCGGCACAGATTTCACC CTGACCATCAGCAGCCTGCAGCCCGAGGACTTCGCCACCTACTA CTGCCAGCAGCATTACACCACCCCCCCCACCTTCGGCCAGGGAA CAAAGGTGGAGATCAAGCGTACGGTGGCCGCTCCCAGCGTGTT CATCTTCCCCCCCAGCGACGAGCAGCTGAAGAGCGGAACCGCC AGCGTGGTGTGCCTGCTGAACAACTTCTACCCCAGGGAGGCTA AGGTGCAGTGGAAGGTGGATAACGCCCTGCAGAGCGGCAATA GCCAGGAGTCCGTGACCGAACAGGACAGCAAGGACAGCACCT ACAGCCTGAGCAGCACCCTGACACTGAGCAAGGCCGACTACGA GAAGCACAAAGTGTACGCCTGCGAGGTGACCCACCAGGGACT GAGCAGCCCCGTGACCAAGTCCTTCAACAGGGGCGAGTGC |
| 22 | anti-HER2-LC | Herceptin(VL)-CK | DIQMTQSPSSLSASVGDRVTITCRASQDVNTAVAINYQQKPGKA PKLLIYSASFLYSGVPSRFSGSRSGTDFTLTISSLQPEDFATYYCQQH YTTPPTFGQGTKVEIKRTVAAPSVFIFPPSDEQLKSGTASVVCLLNN FYPREAKVQWKVDNALQSGNSQESVTEQDSKDSTYSLSSTLTLSK ADYEKHKVYACEVTHQGLSSPVTKSFNRGEC |
| 23 | anti-HER2(VH)-CH1 | Herceptin(VH)-CH1(huIgG1m3) | GAAGTCCAACTTGTGGAGAGCGGCGGGGGCCTGGTCCAGCCT GGAGGATCCCTGCGGCTGTCCTGCGCCGCTTCCGGATTCAACAT TAAGGATACCTACATTCACTGGGTCAGACAGGCCCCGGGAAAG GGGCTGGAATGGGTGGCCAGGATCTACCCGACCAACGGCTACA CTCGCTACGCCGACTCAGTGAAGGGTCGCTTCACCATCTCCGCC GACACGTCCAAGAACACAGCGTACCTCCAGATGAATTCACTGC GGGCCGAGGATACCGCTGTGTACTACTGTTCGCGATGGGCGG CGACGGATTCTATGCGATGGACTACTGGGGACAGGGAACCCTC GTGACTGTGTCCTCCGCCTCCACTAAGGGCCCTAGCGTGTTCCC CTTGGCGCCATCGTCAAAGTCCACCTCCGGTGGCACTGCCGCCC TGGGATGCCTTGTGAAGGACTACTTCCCGAACCTGTGACCGTG TCCTGGAACTCGGGCGCACTGACTTCGGGGGTGCACACCTTTCC TGCCGTCCTGCAATCGAGCGGTCTGTACTCCCTCTCGTCCGTGGT CACCGTGCCGTCTAGCTCCCTCGGAACCCAGACCTACATCTGCA ACGTCAACCACAAGCCGAGCAACACCAAAGTGGATAAGAGAG TGGAGCCGAAGTCATGC |

TABLE 4-continued

Amino Acid and Nucleic Acid Sequences

| SEQ ID NO: | Name | Description | Sequence |
|---|---|---|---|
| 24 | anti-HER2(VH)-CH1 | Herceptin(VH)-CH1(huIgG1m3) | EVQLVESGGGLVQPGGSLRLSCAASGFNIKDTYIHWVRQAPGKGL<br>EWVARIYPTNGYTRYADSVKGRFTISADTSKNTAYLQMNSLRAED<br>TAVYYCSRWGGDGFYAMDYWGQGTLVTVSSASTKGPSVFPLAP<br>SSKSTSGGTAALGCLVKDYFPEPVTVSWNSGALTSGVHTFPAVLQ<br>SSGLYSLSSVVTVPSSSLGTQTYICNVNHKPSNTKVDKRVEPKSC |
| 25 | anti-HER2-huIgG1-SIRPαV2 | Herceptin(VH)-ch1(huigg1m3)-HINGE(HUIGG1M3)-(huIgG1m3: ch2-CH3)-a-(g4s)x4-huSIRPa(V2) | GAAGTCCAACTTGTGGAGAGCGGCGGGGGCCTGGTCCAGCCTG<br>GAGGATCCCTGCGGCTGTCCTGCGCCGCTTCCGGATTCAACATTA<br>AGGATACCTACATTCACTGGGTCAGACAGGCCCCGGGAAAGGG<br>GCTGGAATGGGTGGCCAGGATCTACCCGACCAACGGCTACACTC<br>GCTACGCCGACTCAGTGAAGGGTCGCTTCACCATCTCCGCCGAC<br>ACGTCCAAGAACACAGCGTACCTCCAGATGAATTCACTGCGGGC<br>CGAGGATACCGCTGTGTACTACTGTTCGCGATGGGGCGGCGAC<br>GGATTCTATGCGATGGACTACTGGGGACAGGGAACCCTCGTGAC<br>TGTGTCCTCCgcctccactaagggcccctagcgtgttccccttggcgcgccatcgtca<br>aagtccacctccggtggcactgccgccctgggatgccttgtgaaggactacttcccg<br>aacctgtgaccgtgtcctggaactcgggcgcactgacttcggggggtgcacacctttcc<br>tgccgtcctgcaatcgagcggtctgtactccctctcgtccgtggtcaccgtgccgtcta<br>gctccctcggaacccagacctacatctgcaacgtcaaccacaagccgagcaacacc<br>aaagtggataagagagtgGAGCCGAAGTCATGCGACAAGACTCATAC<br>TTGTCCCCCATGCCCCGCCCCGGAACTGCTGGGggcccatccgtgtt<br>cctgttccgccgaaacctaaggacaccctgatgatttcgagaactccggaagt<br>gacctgtgtggtggtcgacgtgtcccacgaggaggtcaagttcaattg<br>gtacgtcgacggagtggaagtccacaacgccaagaccaagcccgggaggag<br>cagtacaaactccacttaccgggtggtgtccgtgctgaccgtgctgcatcaggatt<br>ggctgaacggaaaggagtataagtgcaaagtgtcaaacaaggcattgcctgc<br>gccaatcgaaaagaccattagcaaggccaagGGCCAGCCCAGGGAACC<br>ACAGGTGTACACTCTGCCCCCGTCCCGCGAAGAAATGACCAAGA<br>ACCAAGTGTCACTGACATGCCTCGTGAAGGGATTTTACCCGTCC<br>GATATCGCCGTGGAATGGGAATCGAACGGTCAACCTGAAAACA<br>ACTACAAGACGACCCCTCCGGTCCTGGACAGCGATGGCTCATTC<br>TTCCTGTACTCCAAGCTTACGGTGGACAAGTCCCGGTGGCAACA<br>GGGAAATGTGTTTTCGTGCTCCGTGATGCATGAGGCTCTGCACA<br>ACCACTACACCCAGAAGTCACTCTCCCTGAGCCCCGGCgcgggggg<br>tggtggaagcggaggaggggggtctgggggtggcggttccggcggcggcggatcc<br>GAGGAGGAGCTCCAGGTCATCCAGCCTGACAAGTCCGTGTCGG<br>TGGCCGCGGGAGAGTCCGCCATTCTGCACTGCACCGTGACCTCC<br>CTCATCCCCGTGGGACCTATCCAGTGGTTCAGAGGAGCCGGGC<br>CCGCACGGGAACTGATCTATAACCAGAAGGAGGCCATTTCCC<br>CCGCGTGACCACCGTGTCCGAGAGCACCAAGAGGGAAAACAT<br>GGACTTCAGCATTTCGATCAGCAACATCACTCCCGCTGACGCCG<br>GGACCTACTACTGCGTGAAGTTCCGGAAAGGAAGCCCGGACAC<br>CGAGTTCAAAAGCGGAGCCGGCACCGAACTGTCGGTCCGC |
| 26 | anti-HER2-huIgG1-SIRPαV2 | Herceptin(VH)-ch1(huiggm3)-HINGE(HUIGG1M3)-(huIgG1m3: ch2-CH3)-a-(g4s)x4-huSIRPa(V2) | EVQLVESGGGLVQPGGSLRLSCAASGFNIKDTYIHWVRQAPGKGLE<br>WVARIYPTNGYTRYADSVKGRFTISADTSKNTAYLQMNSLRAEDTA<br>VYYCSRWGGDGFYAMDYWGQGTLVTVSSastkgpsvfplapsskstsg<br>gtaalgclvkdyfpepvtvswnsgaltsgvhtfpavlqssglyslssvvtvpssslgt<br>qtyicnvnhkpsntkvdkrvEPKSCDKTHTCPPCPAPELLGgpsvflfppkp<br>kdtlmisrtpevtcvvvdvshedpevkfnwyvdgvevhnakttkpreeqynsty<br>rvvsvltvlhqdwlngkeykckvsnkalpapiektiskakGQPREPQVYTLPP<br>SREEMTKNQVSLTCLVKGFYPSDIAVEWESNGQPENNYKTTPPVLD<br>SDGSFFLYSKLTVDKSRWQQGNVFSCSVMHEALHNHYTQKSLSLSP<br>GAGGGGSGGGGSGGGGSGGGGSEEELQVIQPDKSVSVAAGESAI<br>LHCTVTSLIPVGPIQWFRGAGPARELIYNQKEGHFPRVTTVSESTK<br>RENMDFSISISNITPADAGTYYCVKFRKGSPDTEFKSGAGTELSVR |
| 27 | anti-GD2-LC | aGD2: 14.18(VL)-huCK | GACGTGGTGATGACCCAGACCCCCCTGAGCCTGCCCGTGACCCC<br>CGGCGAGCCCGCCAGCATCAGCTGCAGGAGCAGCCAGAGCCTG<br>GTGCACAGGAACGGCAACACCTACCTGCACTGGTACCTGCAGA<br>AGCCCGGCCAGAGCCCCAAGCTGCTGATCCACAAGGTGAGCAA<br>CAGGTTCAGCGGCGTGCCCGACAGGTTCAGCGGCAGCGGCAGC<br>GGCACCGACTTCACCCTGAAGATCAGCAGGGTGGAGGCCGAG<br>GACCTGGGCGTGTACTTCTGCAGCCAGAGCACCCACGTGCCCCC<br>CCTGACCTTCGGCGGCGGCACCAAGCTGGAGCTGAAGAGGACC<br>GTGGCCGCCCCCAGCGTGTTCATCTTCCCCCCCAGCGACGAGCA<br>GCTGAAGAGCGGCACCGCCAGCGTGGTGTGCCTGCTGAACAAC<br>TTCTACCCCAGGGAGGCCAAGGTGCAGTGGAAGGTGGACAAC<br>GCCCTGCAGAGCGGCAACAGCCAGGAGAGCGTGACCGAGCAG<br>GACAGCAAGGACAGCACCTACAGCCTGAGCAGCACCCTGACCC<br>TGAGCAAGGCCGACTACGAGAAGCACAAGGTGTACGCCTGCG<br>AGGTGACCCACCAGGGCCTGAGCAGCCCCGTGACCAAGAGCTT<br>CAACAGGGGCGAGTGC |

TABLE 4-continued

Amino Acid and Nucleic Acid Sequences

| SEQ ID NO: | Name | Description | Sequence |
|---|---|---|---|
| 28 | anti-GD2-LC | aGD2: 14.18(VQ-huCK) | DVVMTQTPLSLPVTPGEPASISCRSSQSLVHRNGNTYLHINYLQKP<br>GQSPKLLIHKVSNRFSGVPDRFSGSGSGTDFTLKISRVEAEDLGVYF<br>CSQSTHVPPLTFGAGTKLELKRTVAAPSVFIFPPSDEQLKSGTASVV<br>CLLNNFYPREAKVQWKVDNALQSGNSQESVTEQDSKDSTYSLSST<br>LTLSKADYEKHKVYACEVTHQGLSSPVTKSFNRGEC |
| 29 | anti-GD2 (VH)-CH1 | aGD2: 14.18(VH)-CH1(hUIgG1m3) | GAGGTGCAGCTGGTGCAGAGCGGCGCCGAGGTGGAGAAGCCC<br>GGCGCCAGCGTGAAGATCAGCTGCAAGGCCAGCGGCAGCAGC<br>TTCACCGGCTACAACATGAACTGGGTGAGGCAGAACATCGGCA<br>AGAGCCTGGAGTGGATCGGCGCCATCGACCCCTACTACGGCGG<br>CACCAGCTACAACCAGAAGTTCAAGGGCAGGGCCACCCTGACC<br>GTGGACAAGAGCACCAGCACCGCCTACATGCACCTGAAGAGCC<br>TGAGGAGCGAGGACACCGCCGTGTACTACTGCGTGAGCGGCAT<br>GGAGTACTGGGGCCAGGGCACCAGCGTGACCGTGAGCAGCGC<br>CAGCACCAAGGGCCCCAGCGTGTTCCCCCTGGCCCCCAGCAGCA<br>AGAGCACCAGCGGCGGCACCGCCGCCCTGGGCTGCCTGGTGAA<br>GGACTACTTCCCCGAGCCCGTGACCGTGAGCTGGAACAGCGGC<br>GCCCTGACCAGCGGCGTGCACACCTTCCCCGCCGTGCTGCAGAG<br>CAGCGGCCTGTACAGCCTGAGCAGCGTGGTGACCGTGCCCAGC<br>AGCAGCCTGGGCACCCAGACCTACATCTGCAACGTGAACCACA<br>AGCCCAGCAACACCAAGGTGGACAAGAAGGTGGAGCCCAAGA<br>GCTGC |
| 30 | anti-GD2 (VH)-CH1 | aGD2: 14.18(VH)-CH1(hUIgG1m3) | EVQLVQSGAEVEKPGASVKISCKASGSSFTGYNMNWVRQNIGKS<br>LEWIGAIDPYYGGTSYNQKFKGRATLTVDKSTSTAYMHLKSLRSE<br>DTAVYYCVSGMEYWGQGTSVTVSSASTKGPSVFPLAPSSKSTSG<br>GTAALGCLVKDYFPEPVTVSWNSGALTSGVHTFPAVLQSSGLYSL<br>SSVVTVPSSSLGTQTYICNVNHKPSNTKVDKKVEPKSC |
| 31 | anti-GD2-huIgG1-SIRPαV2 | aGD2: 14.18(VH)-ch1(huigg1m3)-HINGE(HUIGG1M3)-(huIg1m3: ch2-CH3)-a-(g4s)x4-huSIRPaV2 | GAGGTGCAGCTGGTGCAGAGCGGCGCCGAGGTGGAGAAGCCC<br>GGCGCCAGCGTGAAGATCAGCTGCAAGGCCAGCGGCAGCAGCT<br>TCACCGGCTACAACATGAACTGGGTGAGGCAGAACATCGGCAA<br>GAGCCTGGAGTGGATCGGCGCCATCGACCCCTACTACGGCGGC<br>ACCAGCTACAACCAGAAGTTCAAGGGCAGGGCCACCCTGACCGT<br>GGACAAGAGCACCAGCACCGCCTACATGCACCTGAAGAGCCTGA<br>GGAGCGAGGACACCGCCGTGTACTACTGCGTGAGCGGCATGGA<br>GTACTGGGGCCAGGGCACCAGCGTGACCGTGAGCAGC*gccagcac*<br>*caagggccccagcgtgttccccctggccccagcagcaagagcaccagcggcggca*<br>*ccgccgccctgggctgcctggtgaaggactacttccccgagcccgtgaccgtgagct*<br>*ggaacagcggcgcctgaccagcggcgtgcacaccttccccgccgtgctgcagagc*<br>*agcggcctgtacagcctgagcagcgtggtgaccgtgcccagcagcagcctgggcac*<br>*ccagacctacatctgcaacgtgaaccacaagcccagcaacaccaaggtggacaag*<br>*aaggtg*GAGCCCAAGAGCTGCGACAAGACCCACACCTGCCCCCCT<br>GCCCCCGCCCCCGAGCTGCTGGG*ggccccagcgtgttcctgttcccccca*<br>*agcccaaggacacccctgatgatcagcaggacccccgaggtgacctgcgtggtg*<br>*gtggacgtgagccacgaggaccccgaggtgaagttcaactggtacgtggacg*<br>*gcgtggaggtgcacaacgccaagaccaagcccagggaggagcagtacaaca*<br>*gcacctacagggtggtgagcgtcctgaccgtgctgcaccaggactggctgaac*<br>*ggcaaggagtacaagtgcaaggtgagcaacaaggccctgcccgcccccatcg*<br>*agaagaccatcagcaaggccaag*GGCCAGCCCAGGGAGCCCCAGGT<br>GTACACCCTGCCCCCAGCAGGGACGAGCTGACCAAGAACCAG<br>GTGAGCCTGACCTGCCTGGTGAAGGGCTTCTACCCCAGCGACAT<br>CGCCGTGGAGTGGGAGAGCAACGGCCAGCCCGAGAACAACTAC<br>AAGACCACCCCCCCCGTGCTGGACAGCGACGGCAGCTTCTTCCT<br>GTACAGCAAGCTGACCGTGGACAAGAGCAGGTGGCAGCAGGGC<br>AACGTGTTCAGCTGCAGCGTGATGCACGAGGCCCTGCACAACCA<br>CTACACCCAGAAGAGCCTGAGCCTGAGCCCCGGC*gccggcggcggc*<br>*ggcagcggcggcggcggcagcggcggcggcagcggcggcggcagc*GA<br>GGAGGAGCTGCAGGTGATCCAGCCCGACAAGAGCGTGAGCGT<br>GGCCGCCGGCGAGAGCGCCATCCTGCACTGCACCGTGACCAGC<br>CTGATCCCCGTGGGCCCCATCCAGTGGTTCAGGGGCGCCGGCCC<br>CGCCAGGGAGCTGATCTACAACCAGAAGGAGGGCCACTTCCCC<br>AGGGTGACCACCGTGAGCGAGAGCACCAAGAGGGAGAACATG<br>GACTTCAGCATCAGCATCAGCAACATCACCCCCGCCGACGCCGG<br>CACCTACTACTGCGTGAAGTTCAGGAAGGGCAGCCCCGACACC<br>GAGTTCAAGAGCGGCGCCGGCACCGAGCTGAGCGTGAGG |
| 32 | anti-GD2-huIgG1-SIRPαV2 | aGD2: 14.18(VH)-ch1(huigg1m3)-HINGE(HUIGG1M3)-(huIg1m3: ch2-CH3)-a-(g4s)x4-huSIRPaV2 | EVQLVQSGAEVEKPGASVKISCKASGSSFTGYNMNWVRQNIGKSL<br>EWIGAIDPYYGGTSYNQKFKGRATLTVDKSTSTAYMHLKSLRSEDTA<br>VYYCVSGMEYWGQGTSVTVSS*astkgpsvfplapssksstsggtaalgclvk*<br>*dyfpepvtvswnsgaltsgvhtfpavlqssglyslssvvtvpssslgtqtyicnvnh*<br>*kpsntkvdkkv*EPKSCDKTHTCPPCPAPELL*Ggpsvflfppkpkdtlmisrt*<br>*pevtcvvvdvshedpevkfnwyvdgvevhnaktkpreeqynstyrvvsvltvl*<br>*hqdwlngkeykckvsnkalpapiektiskak*GQPREPQVYTLPPSRDELTK |

TABLE 4-continued

Amino Acid and Nucleic Acid Sequences

| SEQ ID NO: | Name | Description | Sequence |
|---|---|---|---|
| | | | NQVSLTCLVKGFYPSDIAVEWESNGQPENNYKTTPPVLDSDGSFFL YSKLTVDKSRWQQGNVFSCSVMHEALHNHYTQKSLSLSPGaggggs ggggsggggsggggsEEELQVIQPDKSVSVAAGESAILHCTVTSLIPVG PIQWFRGAGPARELIYNQKEGHFPRVTTVSESTKRENMDFSISISN ITPADAGTYYCVKFRKGSPDTEFKSGAGTELSVR |
| 33 | anti-PDL1-LC | aPDL1(VL)-CL | <u>CAGAGCGCTTTGACTCAGCCTGCCTCCGTGTCTGGGTCTCCTGG ACAGTCGATCACCATCTCCTGCACTGGAACCAGCAGTGACGTTG GTGGCTATAATTATGTCTCCTGGTACCAACAACACCCAGGCAAA GCCCCCAAACTCATGATTTATGATGTCAGTAATCGGCCCTCAGG GGTTTCTAATCGCTTCTCTGGCTCCAAGTCTGGCAACACGGCCTC CCTGACCATCTCTGGGCTCCAGGCTGAGGACGAGGCTGATTACT ACTGCAGCTCATATACAAGCAGCAGCACTCGAGTCTTCGGAACT GGGACCAAGGTCACCGTCCTAGGT</u>CAGCCCAAGGCCAACCCCA CTGTCACTCTGTTCCCGCCCTCCTCTGAGGAGCTCCAAGCCAACA AGGCCACACTAGTGTGTCTGATCAGTGACTTCTACCCGGGAGCT GTGACAGTGGCCTGGAAGGCAGATGGCAGCCCCGTCAAGGCG GGAGTGGAGACCACCAAACCTCCAAACAGAGCAACAACAAG TACGCGGCCAGCAGCTACCTGAGCCTGACGCCTGAGCAGTGGA AGTCCCACAGAAGCTACAGCTGCCAGGTCACGCATGAAGGGAG CACCGTGGAGAAGACAGTGGCCCCTACAGAATGTTCA |
| 34 | anti-PDL1-LC | aPDL1(VL)-CL | <u>QSALTQPASVSGSPGQSITISCTGTSSDVGGYNYVSWYQQHPGK APKLMIYDVSNRPSGVSNRFSGSKSGNTASLTISGLQAEDEADYYC SSYTSSSTRVFGTGTKVTVLG</u>QPKANPTVTLFPPSSEELQANKATL VCLISDFYPGAVTVAWKADGSPVKAGVETTKPSKQSNNKYAASS YLSLTPEQWKSHRSYSCQVTHEGSTVEKTVAPTECS |
| 35 | anti-PDL1(VH)-CH1 | aPDL1(VH)-CH1 | <u>GAAGTTCAATTGTTAGAGTCTGGTGGCGGTCTTGTTCAGCCTGG TGGTTCTTTACGTCTTTCTTGCGCTGCTTCCGGATTCACTTTCTCT AGCTACATCATGATGTGGGTTCGCCAAGCTCCTGGTAAAGGTTT GGAGTGGGTTTCTTCTATCTATCCTTCTGGTGGCATTACTTTTTA TGCTGACACCGTTAAAGGTCGCTTCACTATCTCTAGAGACAACT CTAAGAATACTCTCTACTTGCAGATGAACAGCTTAAGGGCTGA GGACACAGCCGTGTATTACTGTGCACGGATCAAGTTGGGTACA GTAACTACGGTTGACTACTGGGGCCAGGGAACCCTGGTCACCG TCTCAAGCGCTAGCACCAAGGGCCCATCGGTCTTCCCCCTGGCA CCCTCCTCCAAGAGCACCTCTGGGGGCACAGCGGCCCTGGGCT GCCTGGTCAAGGACTACTTCCCCGAACCGGTGACGGTGTCGTG GAACTCAGGCGCCCTGACCAGCGGCGTGCACACCTTCCCGGCT GTCCTACAGTCCTCAGGACTCTACTCCCTCAGCAGCGTGGTGAC CGTGCCCTCCAGCAGCTTGGGCACCCAGACCTACATCTGCAACG TGAATCACAAGCCCAGCAACACCAAGGTGGACAAGAGAGTTG AGCCCAAATCTTGT</u> |
| 36 | anti-PDL1(VH)-CH1 | aPDL1(VH)-CH1 | <u>EVQLLESGGGLVQPGGSLRLSCAASGFTFSSYIMMWVRQAPGKG LEWVSSIYPSGGITFYADTVKGRFTISRDNSKNTLYLQMNSLRAED TAVYYCARIKLGTVTTVDYWGQGTLVTVSS</u>ASTKGPSVFPLAPSSK STSGGTAALGCLVKDYFPEPVTVSWNSGALTSGVHTFPAVLQSSG LYSLSSVVTVPSSSLGTQTYICNVNHKPSNTKVDKRVEPKSC |
| 37 | muSIRPα | muSIRPa_ECD(V-C1-C2)-transmembrane-CD | <u>AAGGAGCTGAAGGTGACCCAGCCCGAGAAGAGCGTGAGCGTG GCCGCCGGCGACAGCACCGTGCTGAACTGCACCCTGACCAGCC TGCTGCCCGTGGGCCCCATCAAGTGGTACAGGGGCGTGGGCCA GAGCAGGCTGCTGATCTACAGCTTCACCGGCGAGCACTTCCCCA GGGTGACCAACGTGAGCGACGGCACCAAGAGGAACAACATGG ACTTCAGCATCAGGATCAGCAACGTGACCCCCGAGGACGCCGG CACCTACTACTGCGTGAAGTTCCAGAAGGGCCCCAGCGAGCCC GACACCGAGATCCAGAGCGGCGGCGGCACCGAGGTGTACGTG CTGGCCAAG</u>cccagccccccgaggtgagcggccccgccgacagggcatccc cgaccagaaggtgaacttcacctgcaagagccacggcttcagccccaggaacatca cctgaagtggttcaaggacggccaggagctgcaccacctggagaccaccgtgaac ccagcggcaagaacgtgagctacaacatcagcagcaccgtgagggtggtgctgaa cagcatggacgtgcacagcaaggtgatctgcgaggtggcccacatcaccctggaca ggagcccctgaggggcatcgccaacctgagcaacttcatcagggtgagc*CCCAC CGTGAAGGTGACCCAGCCAGAGAGCCCCACCAGCATGAACCAGGTG AACCTGACCTGCAGGGCCGAGAGGTTCTACCCCGAGGACCTGC AGCTGATCTGGCTGGAGGAGAACGGCAAGGTGAGCAGGAACGACA CCCCCAAGAACCTGACCAAGAACACCGACGGCACCTACAACTAC ACCAGCCTGTTCCTGGTGAACAGCAGCGCCCACAGGGAGGACG TGGTGTTCACCTGCCAGGTGAAGCACGACCAGCAGCCCGCCATC ACCAGGAACACCACCGGCTGGGCTGGCCCACAGCAGCGACC AGGGCAGCATGCAGACCTTCCCCGGCAACAACGCCACCCACAAC*

TABLE 4-continued

Amino Acid and Nucleic Acid Sequences

| SEQ ID NO: | Name | Description | Sequence |
|---|---|---|---|
| | | | *TGGAAC**gtgttcatcggcgtgggcgtggcctgcgccctgctggtggtgctgctg*<br>*atggccgccctgtacc*,uns CTGCTGAGGATCAAGCAGAAGAAGGCCAAGG<br>GCAGCACCAGCAGCACCAGGCTGCACGAGCCCGAGAAGAACGC<br>CAGGGAGATCACCCAGGTGCAGAGCCTGATCCAGGACACCAAC<br>GACATCAACGACATCACCTACGCCGACCTGAACCTGCCCAAGGA<br>GAAGAAGCCCGCCCCCAGGGCCCCCGAGCCCAACAACCACACCG<br>AGTACGCCAGCATCGAGACCGGCAAGGTGCCCAGGCCCGAGGA<br>CACCCTGACCTACGCCGACCTGGACATGGTGCACCTGAGCAGGG<br>CCCAGCCCGCCCCCAAGCCCGAGCCCAGCTTCAGCGAGTACGCC<br>AGCGTGCAGGTGCAGAGGAA |
| 38 | muSIRPα | muSIRPa_ECD(V-<br>c1-C2)-<br>transmembrane-CD | KELKVTQPEKSVSVAAGDSTVLNCTLTSLLPVGPIKWYRGVGQSRL<br>LIYSFTGEHFPRVTNVSDATKRNNMDFSIRISNVTPEDAGTYYCVK<br>FQKGPSEPDTEIQSGGGTEVYVLAKpspevsgpadrgipdqkvnftcks<br>hgfsprnitlkwfkdgqehhlettvnpsgknysynisstvrvvlnsmdvhskvice<br>vahitldrsplrgianlsnfirvsPTVKVTQQSPTSMNQVNLTCRAERFYPE<br>DLQLIWLENGNVSRNDTPKNLTKNT*DGTYNYTSLFLVNSSAHRED<br>VVFTCQVKHDQQPAI*TRNHTVLGLAHSSDQGSMQTFPGNNATH<br>NWNv*figvgvacallvvllmaaly*LLRIKQKKAKGSTSSTRLHEPEKNAREI<br>TQVQSLIQDTNDINDITYADLNLPKEKKPAPRAPEPNNHTEYASIET<br>GKVPRPEDTLTYADLDMVHLSRAQPAPKPEPSFSEYASVQVQRK |
| 39 | anti-PDL1-<br>huIgG1-<br>SIRPαV1 | aPDL1(VH)-<br>ch1(huigg1m3)-<br>HINGE(HUIGG1M3)-<br>(huIgG1m3: ch2-<br>CH3)-a-(g4s)x4-<br>huSIRPaV1 | GAGGTGCAGCTGCTGGAGAGCGGCGGCGGCCTGGTGCAGCCCG<br>GCGGCAGCCTGAGGCTGAGCTGCGCCGCCAGCGGCTTCACCTTC<br>AGCAGCTACATCATGATGTGGGTGAGGCAGGCCCCCGGCAAGG<br>GCCTGGAGTGGGTGAGCAGCATCTACCCCAGCGGCGGCATCAC<br>CTTCTACGCCGACACCGTGAAGGGCAGGTTCACCATCAGCAGGG<br>ACAACAGCAAGAACACCCTGTACCTGCAGATGAACAGCCTGAGG<br>GCCGAGGACACCGCCGTGTACTACTGCGCCAGGATCAAGCTGG<br>GCACCGTGACCACCGTGGACTACTGGGGCCAGGGCACCCTGGT<br>GACCGTGAGCAGC*gccagcaccaagggcccagcgtgttccccctggcccca<br>gcagcaagagcaccagcggcaccgccgccctgggctgcctggtgaaggacta<br>cttccccgagcccgtgaccgtgagctggaacagcggcgccctgaccagcggcgtgc<br>acaccttccccgccgtgctgcagagcagcggcctgtacagcctgagcagcgtggtga<br>ccgtgcccagcagcagcctgggcacccagacctacatctgcaacgtgaaccacaag<br>cccagcaacaccaaggtggacaagaaggtg*GAGCCCAAGAGCTGCGACA<br>AGACCCACACCTGCCCCCCTGCCCCGCCCCCGAGCTGCTGGGCg<br>*gccccagcgtgttcctgttccccccaagcccaaggacacccctgatgatcagcag<br>gaccccgaggtgacctgcgtggtggtggacgtgagccacgaggaccccgag*<br>gtgaagttcaactggtacgtggacggcgtggaggtgcacaacgccaagacca<br>agccccaggggaggagcagtacaacagcacctacagggtggtgagcgtgctgac<br>cgtgctgcaccaggactggctgaacggcaaggagtacaagtgcaaggtgagc<br>aacaagggcctgccggccccatcgagaagaccatcagcaaggccaagGGCC<br>AGCCCAGGGAGCCCCAGGTGTACACCCTGCCCCCCAGCAGGGA<br>CGAGCTGACCAAGAACCAGGTGAGCCTGACCTGCCTGGTGAAG<br>GGCTTCTACCCCAGCGACATCGCCGTGGAGTGGGAGAGCAACG<br>GCCAGCCCGAGAACAACTACAAGACCACCCCCCCCGTGCTGGAC<br>AGCGACGGCAGCTTCTTCCTGTACAGCAAGCTGACCGTGGACAA<br>GAGCAGGTGGCAGCAGGGCAACGTGTTCAGCTGCAGCGTGATG<br>CACGAGGCCCTGCACAACCACTACACCCAGAAGAGCCTGAGCCT<br>GAGCCCCGGC*gccggcggcggcggcagcggcggcggcggcagcggcggcggc<br>ggcagcggcggcggcggcagc*GAGGAGGAGCTGCAGGTGATCCAGCC<br>CGACAAGAGCGTGCTGGTGGCCGCCGGCGAGACCGCCACCCTG<br>AGGTGCACCGCCACCAGCCTGATCCCCGTGGGCCCCATCCAGTG<br>GTTCAGGGGCGCCGGCCCCGGCAGGGAGCTGATCTACAACCAG<br>AAGGAGGGCCACTTCCCCAGGGTGACCACCGTGAGCGACCTGA<br>CCAAGAGGAACAACATGGACTTCAGCATCAGGATCGGCAACAT<br>CACCCCCGCCGACGCCGGCACCTACTACTGCGTGAAGTTCAGGA<br>AGGGCAGCCCCGACGACGTGGAGTTCAAGAGCGGCGCCGGCA<br>CCGAGCTGAGCGTGAGG |
| 40 | anti-PDL1-<br>huIgG1-<br>SIRPαV1 | aPDL1(VH)-<br>ch1(huigg1m3)-<br>HINGE(HUIGG1M3)-<br>(huIgG1m3: ch2-<br>CH3)-a-(g4s)x4-<br>huSIRPaV1 | EVQLLESGGGLVQPGGSLRLSCAASGFTFSSYIMMWVRQAPGKGL<br>EWVSSIYPSGGITFYADTVKGRFTISRDNSKNTLYLQMNSLRAEDTA<br>VYYCARIKLGTVTTVDYWGQGTLVTVSS*astkgpsvflapsskstsggta<br>algclvkdyfpepvtvswnsgaltsgvhtfpavlqssglyslssvvtvpssslgtqty<br>icnvnhkpsntkvdkkv*EPKSCDKTHTCPPCPAPELLG*gpsvflfppkpkd<br>tlmisrtpevtcvvvdvshedpevkfnwyvdgvevhnakttkpreegynstyrv<br>vsvltvlhqdwlngkeykckvsnkalpapiektiskak*GQPREPQVYTLPPS<br>RDELTKNQVSLTCLVKGFYPSDIAVEWESNGQPENNYKTTPPVLDS<br>DGSFFLYSKLTVDKSRWQQGNVFSCSVMHEALHNHYTQKSLSLSP<br>G*ggggsggggsggggsggggs*EEELQVIQPDKSVLVAAGETATLRCTA<br>TSLIPVGPIQWFRGAGPGRELIYNQKEGHFPRVTTVSDLTKRNNM<br>DFSIRIGNITPADGTYYCVKFRKGSPDDVEFKSGAGTELSVR |

TABLE 4-continued

Amino Acid and Nucleic Acid Sequences

| SEQ ID NO: | Name | Description | Sequence |
|---|---|---|---|
| 41 | anti-PDL1-huIgG1-muSIRPα | aPDL1(VH)-ch1(huigg1m3)-HINGE(HUIGG1M3)-(huIgG1m3: ch2-CH3)-a-(g4s)x4-MUSIRPa | GAAGTCCAACTCTTGGAGTCCGGCGGTGGCCTGGTGCAGCCAG<br>GGGGATCACTGCGCCTGAGCTGTGCCGCTTCCGGCTTTACTTTCT<br>CCTCCTACATTATGATGTGGGTGCGCCAGGCCCCGGGGAAGGG<br>ACTGGAATGGGTCAGCTCCATCTACCCTTCTGGTGGTATCACTTT<br>CTACGCCGACACGGTCAAGGGGAGATTCACCATCTCCCGGGACA<br>ACAGCAAGAACACCCTGTACCTCCAAATGAACTCCCTGCGCGCT<br>GAGGACACCGCCGTGTATTACTGCGCCCGGATCAAGCTGGGAAC<br>CGTGACCACCGTGGACTATTGGGGCCAGGGCACTCTGGTCACCG<br>TGTCGAGCgcctccactaagggaccctcagtgttcccactggcgcccagctcaaa<br>gagcacttccggaggcactgcggcgcttggatgtctcgtgaaggactacttccgga<br>gcctgtgaccgtgtcctggaactccggcgcactgacctccggcgtgcatacgttcccg<br>gcggtgctccagtcctccggtctgtactcgttgagctcggtggtcactgtgccgtcgtc<br>ctccctgggaacccagacttacatttgtaacgtgaaccataagccatccaacacaa<br>aggtcgacaaaaaggtcGAACCTAAGTCATGCGACAAGACCCACACTT<br>GCCCGCCATGCCCCGCCCCGAGCTGCTGGG*Aggaccatcggtgttc*<br>*ctctttccgccgaagccaaggacaccctgatgatcagccggaccccgaagtg*<br>*acctgtgtggtggtggatgtgtcgccacgaagatcggaggtcaagttcaattgg*<br>*tacgtggatggggtgaggtgcacaacgcaaaaactaaaccgagggaagaa*<br>*cagtacaattcgacctaccgcgtcgtgtccgtcttgactgtgctgcatcaggactg*<br>*gctgaatgggaaggagtacaagtgcaaagtgtcaaacaaggcccttcccgccc*<br>*ctattgaaaagactattagcaaggccaag*GGACAGCCCAGAGAACCGC<br>AAGTGTACACCCTGCCGCCCTCGAGGGACGAGCTTACTAAGAAC<br>CAAGTGTCCCTGACATGCCTCGTGAAGGGATTCTACCCTTCCGAC<br>ATTGCCGTGGAGTGGGAGTCTAACGGCCAGCCGGAAAACAACT<br>ACAAGACCACCCCACCGGTGTTGGATTCAGACGGCTCATTCTTCC<br>TGTACTCGAAGCTGACCGTGGACAAGTCCCGGTGGCAGCAGGG<br>GAACGTGTTCAGCTGCTCCGTCATGCACGAAGCGCTGCACAACC<br>ACTACACCCAGAAGTCCCTGTCGCTGTCCCCCGGAgccggggggagga<br>ggatccggtggtggtggcagcggcggaggaggctcaggcggcggagggtccAAG<br>GAGCTCAAAGTCACCCAGCCCGAAAAGAGCGTGTCAGTGGCCG<br>CCGGAGACTCAACTGTGCTGAACTGCACCCTCACCTCGCTGCTG<br>CCTGTGGGACCCATCAAGTGGTACCGCGGAGTGGGACAATCCA<br>GGCTGCTGATCTACTCCTTCACCGGGGAACACTTCCCTCGCGTG<br>ACCAACGTGTCGGACGCTACCAAGCGGAACAACATGGACTTTT<br>CGATCCGGATCTCCAATGTCACCCCTGAGGACGCCGGCACCTAC<br>TATTGCGTGAAGTTCCAAAAGGGACCTGGCGAACCTGATACTG<br>AGATCCAGTCCGGCGGCGGTACCGAGGTCTACGTGCTG |
| 42 | anti-PDL1-huIgG1-muSIRPα | aPDL1(VH)-ch1(huigg1m3)-HINGE(HUIGG1M3)-(huIgG1m3: ch2-CH3)-a-(g4s)x4-MUSIRPa | EVQLLESGGGLVQPGGSLRLSCAASGFTFSSYIMMWVRQAPGKGL<br>EWVSSIYPSGGITFYADTVKGRFTISRDNSKNTLYLQMNSLRAEDTA<br>VYYCARIKLGTVTTVDYWGQGTLVTVSS*astkgpsvfplapssstsggta*<br>*algclvkdyfpepvtvswnsgaltsgvhtfpavlqsssglyslssvvtvpssslgtqty*<br>*icnvnhkpsntkvdkkv*EPKSCDKTHTCPPCPAPELLG*gpsvflfppkpkd*<br>*tlmisrtpevtcvvvdvshedpevkfnwyvdvehnaktkpreegynstyrv*<br>*vsvltvlhqdwlngkeykckvank*GQPREPQVYTLPPS<br>RDELTKNQVSLTCLVKGFYPSDIAVEWESNGQPENNYKTTPPVLDS<br>DGSFFLYSKLTVDKSRWQQGNVFSCSVMHEALHNHYTQKSLSLSP<br>GaggggsggggsggggsggggsKELKVTQPEKSVSVAAGDSTVLNCTLT<br>SLLPVGPIKWYRGVGQSRLLIYSFTGEHFPRVTNVSDATKRNNMD<br>FSIRISNVTPEDAGTYYCVKFQKGPSEPDTEIQSGGGTEVYVL |
| 43 | anti-EGFR-huIgG1-SIRPαV1 (deglyco-sylated) | C225(VH)-ch1(huigg1m3)-HINGE(HUIGG1M3)-(huIgG1m3: ch2-CH3)-a-(g4s)x4-huSIRPaV1(N110Q) | CAAGTCCAACTGAAGCAGTCCGGGCCGGGACTCGTGCAGCCGTC<br>GCAGTCACTGTCCATCACTTGCACGGTGTCAGGCTTTTCCTTGAC<br>CAACTACGGAGTGCACTGGGTGCGCCAGTCCCCTGGAAAGGGG<br>CTGGAGTGGCTTGGCGTGATTTGGTCCGGAGGAAACACAGACT<br>ACAACACTCCTTTCACCTCCCGCCTGAGCATTAACAAGGACAACT<br>CCAAGTCCCAAGTGTTCTTCAAGATGAACAGCCTGCAGAGCAAT<br>GATACCGCCATCTACTATTGTGCCCGGGCTCTCACCTACTACGAC<br>TACGAATTCGCCTACTGGGGACAGGGAACCCTGGTCACTGTCTC<br>CGCGgcctccactaagggcccctagcgtgttccccttggcgccatcgtcaaagtcca<br>cctccggtggcactgccgccctgggatgccttgtggactacttccccgaaccgtgt<br>gaccgtgtcctggaactcgggcgcactgacttcgggggtgcacacctttcctgccgtc<br>ctgcaatcgagcggtctgtactccctctcgtccgtggtcaccgtgccgtctagctccct<br>cggaacccagacctacatctgcaacgtcaaccacaagccgagcaacaccaaagtg<br>gataagagagtgGAGCCGAAGTCATGCGACAAGACTCATACTTGTC<br>CCCCATGCCCCGCCCCGGAACTGCTGGG*ggccatccgtgttcctgtt*<br>*cccgccgaaacctaaggacaccctgatgatttcgagaactccggaagtgacctg*<br>*tgtggtggtcgacgtgtcccacgaggatccggaggtcaagttcaattggtacgt*<br>*cgacggagtggaagtgcacaacgcaagaccaagacccggaggagcagta*<br>*caactccacttaccgggtggtgtccgtgctgaccgtgctgcatcaggattggctg*<br>*aacggaaaggagtataagtgcaaagtgtcaaacaaggcattgcctgcgccaa*<br>*tgaaaagaccattagcaaggccaag*GGCCAGCCCAGGGAACCACAG<br>GTGTACACTCTGCCCCCGTCCCGCGAAGAAATGACCAAGAACCA<br>AGTGTCACTGACATGCCTCGTGAAGGGATTTTACCCGTCCGATAT |

TABLE 4-continued

Amino Acid and Nucleic Acid Sequences

| SEQ ID NO: | Name | Description | Sequence |
|---|---|---|---|
| | | | CGCCGTGGAATGGGAATCGAACGGTCAACCTGAAAACAACTACA<br>AGACGACCCCTCCGGTCCTGGACAGCGATGGCTCATTCTTCCTGT<br>ACTCCAAGCTTACGGTGGACAAGTCCCGGTGGCAACAGGGAAA<br>TGTGTTTTCGTGCTCCGTGATGCATGAGGCTCTGCACAACCACTA<br>CACCCAGAAGTCACTCTCCCTGAGCCCCGGCgcggggggtggtggaag<br>cggaggaggggggtctgggggtggcggttccggcggcggcggatccGAGGAGG<br>AACTTCAGGTCATCCAGCCCGACAAGAGCGTGCTCGTGGCCGGC<br>CGGAGAAACCGCAACTCTGAGATGCACCGCTACCTCGCTGATTC<br>CCGTGGGGCCTATCCAGTGGTTCCGCGGGGCCGGACCCGGACG<br>CGAGCTCATCTACAACCAGAAGGAGGGGCACTTCCCGAGGGTC<br>ACCACCGTGTCGGACCTCACCAAGCGCAACAACATGGACTTCA<br>GCATTCGGATCGGCCAAATCACCCCCGCCGACGCCGGCACCTAT<br>TACTGCGTGAAGTTCCGGAAGGGCAGCCCTGACGACGTGGAGT<br>TCAAAAGCGGAGCCGGAACCGAGCTGTCCGTGAGA |
| 44 | anti-EGFR-huIgG1-SIRPαV1 (deglyco-sylated) | C225(VH)-ch1(huigg1m3)-HINGE(HUIGG1M3)-(huIgG1m3:ch2-CH3)-a-(g4s)x4-huSIRPaV1 (N110Q) | QVQLKQSGPGLVQPSQSLSITCTVSGFSLTNYGVHWVRQSPGKGLE<br>WLGVIWSGGNTDYNTPFTSRLSINKDNSKSQVFFKMNSLQSNDTAI<br>YYCARALTYYDYEFAYWGQGTLVTVSAastkgpsvfplapssksttsggta<br>algclvkdyfpepvtvswnsgaltsgvhtfpavlqssglyslssvvtvpssslgtqty<br>icnvnhkpsntkvdkrv*EPKSCDKTHTCPPCPAPELLG*gpsvflfppkpkdt<br>lmisrtpevtcvvvdvshedpevkfnwyvdgvevhnaktkpreeqynstyrvv<br>svltvlhqdwlngkeykckvsnkalpapiektiskakGQPREPQVYTLPPSR<br>EEMTKNQVSLTCLVKGFYPSDIAVEWESNGQPENNYKTTPPVLDSD<br>GSFFLYSKLTVDKSRWQQGNVFSCSVMHEALHNHYTQKSLSLSPGa<br>gggggsggggsggggsggggsEEELQVIQPDKSVLVAAGETATLRCTATSL<br>IPVGPIQWFRGAGPGRELIYNQKEGHFPRVTTVSDLTKRNNMDF<br>SIRIGQITPADAGTYYCVKFRKGSPDDVEFKSGAGTELSVR |
| 45 | anti-EGFR-huIgG1 | C225(VH)-ch1(huigg1eu)-HINGE(HUIGG1EU)-(huIgG1eu: ch2-CH3) | CAGGTGCAGCTGAAGCAGAGCGGCCCCGGCCTGGTGCAGCCCA<br>GCCAGAGCCTGAGCATCACCTGCACCGTGAGCGGCTTCAGCCTG<br>ACCAACTACGGCGTGCACTGGGTGAGGCAGAGCCCCGGCAAGG<br>GCCTGGAGTGGCTGGGCGTGATCTGGAGCGGCGGCAACACCGA<br>CTACAACACCCCCTTCACCAGCAGGCTGAGCATCAACAAGGACA<br>ACAGCAAGAGCCAGGTGTTCTTCAAGATGAACAGCCTGCAGAGC<br>AACGACACCGCCATCTACTACTGCGCCAGGGCCCTGACCTACTAC<br>GACTACGAGTTCGCCTACTGGGGCCAGGGCACCCTGGTGACCGT<br>GAGCGCCGCCAGCACCAAGGGCCCCAGCGTGTTCCCCCTGGCCC<br>CCAGCAGCAAGAGCACCAGCGGCGGCACCGCCGCCCTGGGCTG<br>CCTGGTGAAGGACTACTTCCCCGAGCCCGTGACCGTGAGCTGGA<br>ACAGCGGCGCCCTGACCAGCGGCGTGCACACCTTCCCCGCCGTG<br>CTGCAGAGCAGCGGCCTGTACAGCCTGAGCAGCGTGGTGACCG<br>TGCCCAGCAGCAGCCTGGGCACCCAGACCTACATCTGCAACGTG<br>AACCACAAGCCCAGCAACACCAAGGTGGACAAGAGGGTGGAGC<br>CCAAGAGCTGCGACAAGACCCACACCTGCCCCCCCTGCCCCGCC<br>CCCGAGCTGCTGGGCGGCCCCAGCGTGTTCCTGTTCCCCCCCAA<br>GCCCAAGGACACCCTGATGATCAGCAGGACCCCCGAGGTGACCT<br>GCGTGGTGGTGGACGTGAGCCACGAGGACCCCGAGGTGAAGTT<br>CAACTGGTACGTGGACGGCGTGGAGGTGCACAACGCCAAGACC<br>AAGCCCAGGGAGGAGCAGTACAACAGCACCTACAGGGTGGTGA<br>GCGTGCTGACCGTGCTGCACCAGGACTGGCTGAACGGCAAGGA<br>GTACAAGTGCAAGGTGAGCAACAAGGCCCTGCCCGCCCCCATCG<br>AGAAGACCATCAGCAAGGCCAAGGGCCAGCCCAGGGAGCCCCA<br>GGTGTACACCCTGCCCCCCAGCAGGGAGGAGATGACCAAGAAC<br>CAGGTGAGCCTGACCTGCCTGGTGAAGGGCTTCTACCCCAGCGA<br>CATCGCCGTGGAGTGGGAGAGCAACGGCCAGCCCGAGAACAAC<br>TACAAGACCACCCCCCCCGTGCTGGACAGCGACGGCAGCTTCTT<br>CCTGTACAGCAAGCTGACCGTGGACAAGAGCAGGTGGCAGCAG<br>GGCAACGTGTTCAGCTGCAGCGTGATGCACGAGGCCCTGCACAA<br>CCACTACACCCAGAAGAGCCTGAGCCTGAGCCCCGGC |
| 46 | anti-EGFR-huIgG1 | C225(VH)-ch1(huigg1eu)-HINGE(HUIGG1EU)-(huIgG1eu: ch2-CH3) | QVQLKQSGPGLVQPSQSLSITCTVSGFSLTNYGVHWVRQSPGKGLE<br>WLGVIWSGGNTDYNTPFTSRLSINKDNSKSQVFFKMNSLQSNDTAI<br>YYCARALTYYDYEFAYWGQGTLVTVSAastkgpsvfplapssksttsggta<br>algclvkdyfpepvtvswnsgaltsgvhtfpavlqssglyslssvvtvpssslgtqty<br>icnvnhkpsntkvdkrv*EPKSCDKTHTCPPCPAPELLG*gpsvflfppkpkdt<br>lmisrtpevtcvvvdvshedpevkfnwyvdgvevhnaktkpreeqynstyrvv<br>svltvlhqdwlngkeykckvsnkalpapiektiskakGQPREPQVYTLPPSR<br>EEMTKNQVSLTCLVKGFYPSDIAVEWESNGQPENNYKTTPPVLDSD<br>GSFFLYSKLTVDKSRWQQGNVFSCSVMHEALHNHYTQKSLSLSPG |
| 47 | anti-EGFR(LC)-SIRPαV2 | C225(VL)-huck-(G4S)X2-sirpav2 | GACATTCTCCTGACACAGAGCCCCGTGATCCTGAGCGTGAGCCC<br>TGGCGAAAGGGTGAGCTTCAGCTGCAGGGCCAGCCAGAGCATC<br>GGCACCAACATCCACTGGTACCAGCAGAGGACAAACGGCAGCC<br>CTAGGCTGCTGATCAAGTACGCCAGCGAGAGCATCAGCGGCATC |

TABLE 4-continued

Amino Acid and Nucleic Acid Sequences

| SEQ ID NO: | Name | Description | Sequence |
|---|---|---|---|
| | | | CCCAGCAGGTTTAGCGGAAGCGGCAGCGGCACCGACTTCACCCT<br>GTCCATCAATTCCGTGGAGTCCGAGGACATCGCCGACTACTACT<br>GCCAGCAGAACAACAACTGGCCTACCACCTTCGGCGCCGGCACC<br>AAGCTGGAACTGAAGcgtacggtggccgccccagcgtgttcatctttccccc<br>cagcgacgagcagctgaaaagcggcaccgcctccgtggtgtgcctgctgaacaact<br>tctaccctagggaggccaaggtgcagtggaaggtggacaacgccctccagtccggc<br>aacagccaggagagcgtcaccgagcaggacagcaaggacagcacctacagcctg<br>agcagcaccctgaccctgagcaaggccgactacgagaagcacaaggtgtatgcct<br>gcgaggtgacccaccagggcctgagctcccctgtgaccaagtccttcaacaggggc<br>gagtgcGGGGAGGAGGCTCAGGGGGCGGAGGGTCAgaagaggaa<br>ctgcaagtgatccagcccgacaagtccgtgtctgtggcgctggcgagtctgcca<br>tcctgcactgcaccgtgacctccctgatcccgtgggacccatccagtggtttcgtg<br>gcgctggccctgccgtgagctgatctacaaccagaaagagggccacttcccc<br>gtgtgaccacgtgtccgagtccaccaagcgcgagaacatggacttctccatctc<br>catcagcaacatcaccctgccgatgccggcacctactactgcgtgaagttccgt<br>aagggctccccgacaccgagttcaagtctctggcgctggcaccgagctgtctgtg<br>cgt |
| 48 | anti-<br>EGFR(LC)-<br>SIRPαV2 | C225(VL)-huck-<br>(G4S)X2-sirpav2 | DILLTQSPVILSVSPGERVSFSCRASQSIGTNIHWYQQRTNGSPRLLIK<br>YASESISGIPSRFSGSGSGTDFTLSINSVESEDIADYYCQQNNNWPTT<br>FGAGTKLELKrtvaapsvfifppsdeqlksgtasvvclinnfypreakvqwkvd<br>nalqsgnsqesvteqdskdstyslsstltlskadyekhkvyacevthqgisspvtk<br>sfnrgecGGGGSGGGGSeeelqviqpdksvsaagesailhctvtslipvgpi<br>qwfrgagparellynqkeghfprvttvsestkrenmdfsisisnitpadagtyyc<br>vkfrkgspdtefksgagtelsvr |
| 49 | SIRPaV2-<br>Fc(huIgG1)-<br>anti_EGFR<br>(VH)-CH1 | huSIRPaV2-(g4s)x2-<br>HINGE(HUIGG1M3)-<br>(huIgG1m3: ch2-<br>CH3)-a-(g4s)x4-<br>C225(VH)-<br>ch1(huigg1m3) | GAGGAAGAACTCCAAGTGATCCAACCGGACAAATCCGTGAGCG<br>TGGCCGCCGGAGAAAGCGCCATCCTGCACTGCACCGTCACGTCA<br>CTGATTCCTGTGGGCCCAATTCAGTGGTTCAGAGGAGCGGGGCC<br>AGCCCGGGAACTGATCTACAACCAGAAGGAGGGTCACTTCCCTC<br>GGGTCACTACCGTGTCCGAGTCAACCAAGCGGGAAAACATGGA<br>CTTCTCGATCTCCATCTCCAACATTACCCCTGCGGACGCCGGCAC<br>ATACTATTGCGTCAAATTCCGCAAGGGTTCGCCGGACACCGAGT<br>TCAAGTCCGGAGCTGGTACCGAACTGAGCGTGCGG*ggggaggcg*<br>*gaagcggaggcggcggatcg*GAGCCCAAATCGTCTGACAAGACCCACA<br>CCTGTCCGCCCTGTCCTGCACCGGAACTTCTGGGggacttccgtgt<br>tcctgttcccaccctaagcctaaggacacctcatgatctcccggaccccggaggtc<br>acttgcgtggtggtggatgtgtcccacgaggacccggaagtgaagttcaattgg<br>tacgtggacggcgtggaagtccacaacgcaagaccaagccaagggaggaa<br>cagtacaacagcacctacagggtggtgtcagtgctcactgtgctgcatcaggac<br>tggctcaacgggaaagagtacaagtgcaagtctccaacaaggccttgccgc<br>tccaattgaaaagaccatttcgaaggccaagGGCCAGCCCAGAGAGCCG<br>CAAGTGTACACCCTGCCCCCGTCGCGCGAGGAGATGACCAAGAA<br>TCAAGTCTCCCTCACTTGTCTCGTGAAGGGCTTTTACCCTTCGGAT<br>ATCGCAGTGGAATGGGAATCCAACGGACAGCCGGAAAACAACT<br>ACAAGACGACCCCCGCCGTGCTGGATTCAGACGGCTCCTTCTTCT<br>TGTACTCAAAGCTGACGGTGGACAAGTCACGGTGGCAACAGGG<br>AAACGTCTTTTCCTGCTCCGTGATGCATGAAGCCCTGCACAACCA<br>TTACACTCAGAAGTCGCTGTCGCTTAGCCCTGGAgccggcggtggag<br>gttccggagggggtggaagcggcggaggaggaagcggggcgggggctccCAG<br>GTCCAACTGAAGCAGAGCGGTCCAGGACTGGTCCAGCCGTCCC<br>AGTCCCTGTCTATTACTTGCACCGTGTCCGGCTTTTCCCTGACTA<br>ACTATGGTGTCCACTGGGTGCGCCAGTCGCCCGGGAAGGGGCT<br>GGAGTGGCTGGGCGTGATCTGGAGCGGCGGGAACACCGACTA<br>TAACACTCCTTTCACTTCACGCCTGTCCATCAACAAGGATAACA<br>GCAAGAGCCAGGTGTTCTTTAAGATGAACTCACTCCAGTCCAAC<br>GACACCGCCATCTACTACTGCGCCCGCGCTCTCACCTACTACGAC<br>TACGAATTCGCCTACTGGGGACAAGGCACCCTGGTCACCGTGTC<br>GGCGgccagcaccaagggaccgtccgtgttcccctggcgcctcctcaaagtcca<br>cttccggcggcaccgctgccctgggatgcctcgtgaaggattatttcccggagcctgt<br>gaccgtgtcctggaactccggtgccctgacatccggcgtgcacaccttcctgcggtg<br>ctgcagtccagcggactgtactccctctcctcggtcgtgaccgtgccgtcctcgtccct<br>gggaactcagacttacatctgcaacgtgaaccataagcccctccaataccaaagtgga<br>caagagagtggagcccaagagctgc |
| 50 | mutated<br>hinge<br>region | mutated hinge<br>region | EPKSS |
| 51 | hinge<br>region | hinge region | EPKSC |

TABLE 4-continued

Amino Acid and Nucleic Acid Sequences

| SEQ ID NO: | Name | Description | Sequence |
|---|---|---|---|
| 52 | SIRPαV2-Fc(huIgG1)-anti_EGFR(VH)-CH1 | huSIRPaV2-(g4s)x2-HINGE(HUIGG1M3)-(huIgG1m3: ch2-CH3)-a-(g4s)x4-C225(VH)-ch1(huigg1m3) | EEELQVIQPDKSVSVAAGESAILHCTVTSLIPVGPIQWFRGAGPARE<br>LIYNQKEGHFPRVTTVSESTKRENMDFSISISNITPADAGTYYCVKFR<br>KGSPDTEFKSGAGTELSVR*ggggsggggs*EPKSSDKTHTCPPCPAPELL<br>G*gpsvflfppkpkdtlmisrtpevtcvvvdvshedpevkfnwyvdgvevhnak*<br>*tkpreeqynstyrvvsvltvlhqdwlngkeykckvsnkalpapiektiskak*GQ<br>PREPQVYTLPPSREEMTKNQVSLTCLVKGFYPSDIAVEWESNGQPE<br>NNYKTTPPVLDSDGSFFLYSKLTVDKSRWQQGNVFSCSVMHEALH+ee<br>NHYTQKSLSLSPGaggggsggggsggggsggggsQVQLKQSGPGLVQPS<br>QSLSITCTVSGFSLTNYGVHWVRQSPGKGLEWLGVIWSGGNTDY<br>NTPFTSRLSINKDNSKSQVFFKMNSLQSNDTAIYYCARALTYYDYE<br>FAYWGQGTLVTVSAastkgpsvfplapsskstsggtaalgclvkdyfpepvtv+ee<br>swnsqaltsqvhtfpavlqssqlyslssvvtvpssslqtqtyicnvnhkpsntkvdkrv<br>epksc |
| 53 | anti-EGFR(scFv) external-C225(VL) | externalC225(VH)-(g4s)x3- | CAGGTGCAGCTGAAGCAGAGCGGCCCCGGCCTGGTGCAGCCCA<br>GCCAGAGCCTGAGCATCACCTGCACCGTGAGCGGCTTCAGCCT<br>GACCAACTACGGCGTGCACTGGGTGAGGCAGAGCCCCGGCAA<br>GGGCCTGGAGTGGCTGGGCGTGATCTGGAGCGGCGGCAACAC<br>CGACTACAACACCCCCTTCACCAGCAGGCTGAGCATCAACAAG<br>GACAACAGCAAGAGCCAGGTGTTCTTCAAGATGAACAGCCTGC<br>AGAGCAACGACACCGCCATCTACTACTGCGCCAGGGCCCTGAC<br>CTACTACGACTACGAGTTCGCCTACTGGGGCCAGGGCACCCTG<br>GTGACCGTGAGCGCCggcggcggcggcagcggcggcggcagcggc<br>ggcggcggcagcGACATCCTGCTGACCCAGAGCCCCGTGATCCTGA<br>GCGTGAGCCCCGGCGAGAGGGTGAGCTTCAGCTGCAGGGCCAG<br>CCAGAGCATCGGCACCAACATCCACTGGTACCAGCAGAGGACCA<br>ACGGCAGCCCCAGGCTGCTGATCAAGTACGCCAGCGAGAGCATC<br>AGCGGCATCCCCAGCAGGTTCAGCGGCAGCGGCAGCGGCACCG<br>ACTTCACCCTGAGCATCAACAGCGTGGAGAGCGAGGACATCGCC<br>GACTACTACTGCCAGCAGAACAACAACTGGCCCACCACCTTCGGC<br>GCCGGCACCAAGCTGGAGCTGAAG |
| 54 | anti-EGFR(scFv) | externalC225(VH)-(g4s)x3-externalC225(VL) | QVQLKQSGPGLVQPSQSLSITCTVSGFSLTNYGVHWVRQSPGKG<br>LEWLGVIWSGGNTDYNTPFTSRLSINKDNSKSQVFFKMNSLQSN<br>DTAIYYCARALTYYDYEFAYWGQGTLVTVSAggggsggggsggggs<br>DILLTQSPVILSVSPGERVSFSCRASQSIGTNIHWYQQRTNGSPRLLIK<br>YASESISGIPSRFSGSGSGTDFTLSINSVESEDIADYYCQQNNNWPTT<br>FGAGTKLELK |
| 55 | SIRPαV2-Fc(huIgG1)-anti_EGFR(scFv) | huSIRPaV2-(g4s)x2-HINGE(HUIGG1M3-)(huIgG1m3: ch2-CH3)-a-(g4s)x4-externalC225(VH)-(g4s)x3-externalC225(VL) | GAGGAGGAGCTGCAGGTGATCCAGCCCGACAAGAGCGTGAGC<br>GTGGCCGCCGGCGAGAGCGCCATCCTGCACTGCACCGTGACCA<br>GCCTGATCCCCGTGGGCCCCATCCAGTGGTTCAGGGGCGCCGGC<br>CCCGCCAGGGAGCTGATCTACAACCAGAAGGAGGGCCACTTCCC<br>CAGGGTGACCACCGTGAGCGAGAGCACCAAGAGGGAGAACATG<br>GACTTCAGCATCAGCATCAGCAACATCACCCCCGCCGACGCCGG<br>CACCTACTACTGCGTGAAGTTCAGGAAGGGCAGCCCCGACACCG<br>AGTTCAAGAGCGGCGCCGGCACCGAGCTGAGCGTGAGGGGCG<br>GCGGCGGCAGCGGCGGCGGCGGCAGCGAGCCCAAGAGCAGCG<br>ACAAGACCCACACCTGCCCCCCCTGCCCCGCCCCCGAGCTGCTG<br>GGCGGCCCCAGCGTGTTCCTGTTCCCCCCCAAGCCCAAGGACAC<br>CCTGATGATCAGCAGGACCCCCGAGGTGACCTGCGTGGTGGTG<br>GACGTGAGCCACGAGGACCCCGAGGTGAAGTTCAACTGGTACG<br>TGGACGGCGTGGAGGTGCACAACGCCAAGACCAAGCCCAGGGA<br>GGAGCAGTACAACAGCACCTACAGGGTGGTGAGCGTGCTGACC<br>GTGCTGCACCAGGACTGGCTGAACGGCAAGGAGTACAAGTGCA<br>AGGTGAGCAACAAGGCCCTGCCCGCCCCCATCGAGAAGACCATC<br>AGCAAGGCCAAGGGCCAGCCCAGGGAGCCCCAGGTGTACACCC<br>TGCCCCCCAGCAGGGAGGAGATGACCAAGAACCAGGTGAGCCT<br>GACCTGCCTGGTGAAGGGCTTCTACCCCAGCGACATCGCCGTGG<br>AGTGGGAGAGCAACGGCCAGCCCGAGAACAACTACAAGACCAC<br>CCCCCCCGTGCTGGACAGCGACGGCAGCTTCTTCCTGTACAGCA<br>AGCTGACCGTGGACAAGAGCAGGTGGCAGCAGGGCAACGTGTT<br>CAGCTGCAGCGTGATGCACGAGGCCCTGCACAACCACTACACCC<br>AGAAGAGCCTGAGCCTGAGCCCCGGCGCCGGCGGCGGCGGCA<br>GCGGCGGCGGCAGCGGCGGCGGCGGCAGCGGCGGCGGC<br>GGCAGCCAGGTGCAGCTGAAGCAGAGCGGCCCCGGCCTGGTGC<br>AGCCCAGCCAGAGCCTGAGCATCACCTGCACCGTGAGCGGCTTC<br>AGCCTGACCAACTACGGCGTGCACTGGGTGAGGCAGAGCCCCG<br>GCAAGGGCCTGGAGTGGCTGGGCGTGATCTGGAGCGGCGGCAA<br>CACCGACTACAACACCCCCTTCACCAGCAGGCTGAGCATCAAC<br>AAGGACAACAGCAAGAGCCAGGTGTTCTTCAAGATGAACAGCCT<br>GCAGAGCAACGACACCGCCATCTACTACTGCGCCAGGGCCCTGA<br>CCTACTACGACTACGAGTTCGCCTACTGGGGCCAGGGCACCCTG<br>GTGACCGTGAGCGCCGGCGGCGGCGGCAGCGGCGGCGGC |

TABLE 4-continued

Amino Acid and Nucleic Acid Sequences

| SEQ ID NO: | Name | Description | Sequence |
|---|---|---|---|
| | | | AGCGGCGGCGGCAGCGACATCCTGCTGACCCAGAGCCCCG<br>TGATCCTGAGCGTGAGCCCCGGCGAGAGGGTGAGCTTCAGCTG<br>CAGGGCCAGCCAGAGCATCGGCACCAACATCCACTGGTACCAGC<br>AGAGGACCAACGGCAGCCCCAGGCTGCTGATCAAGTACGCCAG<br>CGAGAGCATCAGCGGCATCCCCAGCAGGTTCAGCGGCAGCGGC<br>AGCGGCACCGACTTCACCCTGAGCATCAACAGCGTGGAGAGCG<br>AGGACATCGCCGACTACTACTGCCAGCAGAACAACAACTGGCCC<br>ACCACCTTCGGCGCCGGCACCAAGCTGGAGCTGAAG |
| 56 | SIRPαV2-<br>Fc(huIgG1)-<br>anti_EGFR<br>(scFv) | huSIRPaV2-(g4s)x2-<br>HINGE(HUIGG1M3)-<br>(huIgG1m3: ch2-<br>CH3)-a-(g4s)x4-<br>externalC225(VH)-<br>(g4s)x3-<br>externalC225(VL) | EEELQVIQPDKSVSVAAGESAILHCTVTSLIPVGPIQWFRGAGPARE<br>LIYNQKEGHFPRVTTVSESTKRENMDFSISISNITPADAGTYYCVKFR<br>KGSPDTEFKSGAGTELSVR*ggggsggggs*EPKSSDKTHTCPPCPAPELL<br>G*gpsvflfppkpkdtlmisrtpevtcvvvdvshedpevkfnwyvdgvevhnak<br>tkpreeqynstyrvvsvltvlhqdwlngkeykckvsnkalpapiektiskak*GQ<br>PREPQVYTLPPSREEMTKNQVSLTCLVKGFYPSDIAVEWESNGQPE<br>NNYKTTPPVLDSDGSFFLYSKLTVDKSRWQQGNVFSCSVMHEALH<br>NHYTQKSLSLSPGa*ggggsggggsggggsggggs*QVQLKQSGPGLVQPS<br>QSLSITCTVSGFSLTNYGVHWVRQSPGKGLEWLGVIWSGGNTDY<br>NTPFTSRLSINKDNSKSQVFFKMNSLQSNDTAIYYCARALTYYDYE<br>FAYWGQGTLVTVSA*ggggsggggsggggsggggs*DILLTQSPVILSVSPGERV<br>SFSCRASQSIGTNIHWYQQRTNGSPRLLIKYASESISGIPSRFSGSGSG<br>TDFTLSINSVESEDIADYYCQQNNNWPTTFGAGTKLELK |
| 57 | anti-<br>EGFR(scFv)-<br>Fc(huIgG1)-<br>SIRPαV2 | C225(VH)-(g4s)x3-<br>C225(VL)-(g4s)x2-<br>HINGE(HUIGG1M3)-<br>(huIgG1m3: ch2-<br>CH3)-a-(g4s)x4-<br>huSIRPaV2 | CAGGTGCAGCTGAAGCAGAGCGGCCCCGGCCTGGTGCAGCCCA<br>GCCAGAGCCTGAGCATCACCTGCACCGTGAGCGGCTTCAGCCTG<br>ACCAACTACGGCGTGCACTGGGTGAGGCAGAGCCCCGGCAAGG<br>GCCTGGAGTGGCTGGGCGTGATCTGGAGCGGCGGCAACACCGA<br>CTACAACACCCCCTTCACCAGCAGGCTGAGCATCAACAAGGACA<br>ACAGCAAGAGCCAGGTGTTCTTCAAGATGAACAGCCTGCAGAGC<br>AACGACACCGCCATCTACTACTGCGCCAGGGCCCTGACCTACTAC<br>GACTACGAGTTCGCCTACTGGGGCCAGGGCACCCTGGTGACCGT<br>GAGCGCCGGCGGCGGCGGCAGCGGCGGCGGCGGCAGCGGCGG<br>CGGCGGCAGCGACATCCTGCTGACCCAGAGCCCCGTGATCCTGA<br>GCGTGAGCCCCGGCGAGAGGGTGAGCTTCAGCTGCAGGGCCAG<br>CCAGAGCATCGGCACCAACATCCACTGGTACCAGCAGAGGACCA<br>ACGGCAGCCCCAGGCTGCTGATCAAGTACGCCAGCGAGAGCAT<br>CAGCGGCATCCCCAGCAGGTTCAGCGGCAGCGGCAGCGGCACC<br>GACTTCACCCTGAGCATCAACAGCGTGGAGAGCGAGGACATCG<br>CCGACTACTACTGCCAGCAGAACAACAACTGGCCCACCACCTTCG<br>GCGCCGGCACCAAGCTGGAGCTGAAGGGCGGCGGCGGCAGCG<br>GCGGCGGCGGCAGCGAGCCCAAGAGCAGCGACAAGACCCACAC<br>CTGCCCCCCTGCCCCGCCCCCGAGCTGCTGGGCGGCCCCAGCG<br>TGTTCCTGTTCCCCCCCAAGCCCAAGGACACCCTGATGATCAGCA<br>GGACCCCCGAGGTGACCTGCGTGGTGGTGGACGTGAGCCACGA<br>GGACCCCGAGGTGAAGTTCAACTGGTACGTGGACGGCGTGGAG<br>GTGCACAACGCCAAGACCAAGCCCAGGGAGGAGCAGTACAACA<br>GCACCTACAGGGTGGTGAGCGTGCTGACCGTGCTGCACCAGGA<br>CTGGCTGAACGGCAAGGAGTACAAGTGCAAGGTGAGCAACAAG<br>GCCCTGCCCGCCCCCATCGAGAAGACCATCAGCAAGGCCAAGGG<br>CCAGCCCAGGGAGCCCCAGGTGTACACCCTGCCCCCCAGCAGGG<br>AGGAGATGACCAAGAACCAGGTGAGCCTGACCTGCCTGGTGAA<br>GGGCTTCTACCCCAGCGACATCGCCGTGGAGTGGGAGAGCAAC<br>GGCCAGCCCGAGAACAACTACAAGACCACCCCCCCCGTGCTGGA<br>CAGCGACGGCAGCTTCTTCCTGTACAGCAAGCTGACCGTGGACA<br>AGAGCAGGTGGCAGCAGGGCAACGTGTTCAGCTGCAGCGTGAT<br>GCACGAGGCCCTGCACAACCACTACACCCAGAAGAGCCTGAGCC<br>TGAGCCCCGGCGCCGGCGGCGGCGGCGGCGGCGGCGGCGGCA<br>GCGGCGGCGGCGGCAGCGGCGGCGGCGGCAGCGAGGAGGAG<br>CTGCAGGTGATCCAGCCCGACAAGAGCGTGAGCGTGGCCGCCG<br>GCGAGAGCGCCATCCTGCACTGCACCGTGACCAGCCTGATCCCC<br>GTGGGCCCCATCCAGTGGTTCAGGGGCGCCGGCCCCGCCAGGG<br>AGCTGATCTACAACCAGAAGGAGGGCCACTTCCCCAGGGTGACC<br>ACCGTGAGCGAGAGCACCAAGAGGGAGAACATGGACTTCAGCA<br>TCAGCATCAGCAACATCACCCCCGCCGACGCCGGCACCTACTACT<br>GCGTGAAGTTCAGGAAGGGCAGCCCCGACACCGAGTTCAAGAG<br>CGGCGCCGGCACCGAGCTGAGCGTGAGG |
| 58 | anti-<br>EGFR(scFv)-<br>Fc(huIgG1)-<br>SIRPαV2 | C225(VH)-(g4s)x3-<br>C225(VL)-(g4s)x2-<br>HINGE(HUIGG1M3)-<br>(huIgG1m3: ch2-<br>CH3)-a-(g4s)x4-<br>huSIRPaV2 | QVQLKQSGPGLVQPSQSLSITCTVSGFSLTNYGVHWVRQSPGKG<br>LEWLGVIWSGGNTDYNTPFTSRLSINKDNSKSQVFFKMNSLQSN<br>DTAIYYCARALTYYDYEFAYWGQGTLVTVSA*ggggsggggsggggsggggs*DI<br>LLTQSPVILSVSPGERVSFSCRASQSIGTNIHWYQQRTNGSPRLLIKY<br>ASESISGIPSRFSGSGSGTDFTLSINSVESEDIADYYCQQNNNWPTTF<br>GAGTKLELK*ggggsggggs*EPKSSDKTHTCPPCPAPELL*gpsvflfppkp<br>kdtlmisrtpevtcvvvdvshedpevkfnw*yvdgvevhnaktkpreeqynsty |

TABLE 4-continued

Amino Acid and Nucleic Acid Sequences

| SEQ ID NO: | Name | Description | Sequence |
|---|---|---|---|
| | | | *rvvsvltvlhqdwlngkeykckvsnkalpapiektiskak* GQPREPQVYTLPP SREEMTKNQVSLTCLVKGFYPSDIAVEWESNGQPENNYKTTPPVLD SDGSFFLYSKLTVDKSRWQQGNVFSCSVMHEALHNHYTQKSLSLSP G*ggggsggggsggggsggggs*EEELQVIQPDKSVSVAAGESAILHCTVT SLIPVGPIQWFRGAGPARELIYNQKEGHFPRVTTVSESTKRENMDF SISISNITPADAGTYYCVKFRKGSPDTEFKSGAGTELSVR |
| 59 | anti-CD19 (scFv) | aCD19(VH)-(g4s)x3- αCD19(VL) | GAGGTGAAGCTGCAGGAGAGCGGCCCCGGCCTGGTGGCCCCCA GCCAGAGCCTGAGCGTGACCTGCACCGTGAGCGGCGTGAGCCT GCCCGACTACGGCGTGAGCTGGATCAGGCAGCCCCCCAGGAAG GGCCTGGAGTGGCTGGGCGTGATCTGGGGCAGCGAGACCACCT ACTACAACAGCGCCCTGAAGAGCAGGCTGACCATCATCAAGGAC AACAGCAAGAGCCAGGTGTTCCTGAAGATGAACAGCCTGCAGA CCGACGACACCGCCATCTACTACTGCGCCAAGCACTACTACTACG GCGGCAGCTACGCCATGGACTACTGGGGCCAGGGCACCAGCGT GACCGTGAGCAGCGGCGGCGGCGGCAGCGGCGGCGGCGGCAG CGGCGGCGGCGGCAGCGACATCCAGATGACCCAGACCACCAGC AGCCTGAGCGCCAGCCTGGGCGACAGGGTGACCATCAGCTGCA GGGCCAGCCAGGACATCAGCAAGTACCTGAACTGGTACCAGCA GAAGCCCGACGGCACCGTGAAGCTGCTGATCTACCACACCAGCA GGCTGCACAGCGGCGTGCCCAGCAGGTTCAGCGGCAGCGGCAG CGGCACCGACTACAGCCTGACCATCAGCAACCTGGAGCAGGAG GACATCGCCACCTACTTCTGCCAGCAGGGCAACACCCTGCCCTAC ACCTTCGGCGGCGGCACCAAGCTGGAGATCACC |
| 60 | anti-CD19 (scFv) | aCD19(VH)-(g4s)x3- αCD19(VL) | EVKLQESGPGLVAPSQSLSVTCTVSGVSLPDYGVSWIRQPPRKGL EWLGVIWGSETTYYNSALKSRLTIIKDNSKSQVFLKMNSLQTDDT AIYYCAKHYYYGGSYAMDYWGQGTSVTVSS*ggggsggggsggggs* <u>DIQMTQTTSSLSASLGDRVTISCRASQDISKYLNWYQQKPDGTVKLL IYHTSRLHSGVPSRFSGSGSGTDYSLTISNLEQEDIATYFCQQGNTLP YTFGGGTKLEIT</u> |
| 61 | SIRPαV2- Fc(huIgG1)- anti_CD19 (scFv) | huSIRPaV2-(g4s)x2- HINGE(HUIGG1M3)- (huIgG1m3: ch2- CH3)-a-(g4S)x4- aCD19(VH)-(g4S)x3- αCD19(VL) | GAGGAGGAGCTGCAGGTGATCCAGCCCGACAAGAGCGTGAGC GTGGCCGCCGGCGAGAGCGCCATCCTGCACTGCACCGTGACCA GCCTGATCCCCGTGGGCCCCATCCAGTGGTTCAGGGGCGCCGGC CCCGCCAGGGAGCTGATCTACAACCAGAAGGAGGGCCACTTCCC CAGGGTGACCACCGTGAGCGAGAGCACCAAGAGGGAGAACATG GACTTCAGCATCAGCATCAGCAACATCACCCCCGCCGACGCCGG CACCTACTACTGCGTGAAGTTCAGGAAGGGCAGCCCCGACACCG AGTTCAAGAGCGGCGCCGGCACCGAGCTGAGCGTGAGGGGCG GCGGCGGCAGCGGCGGCGGCGGCAGCGAGCCCAAGAGCAGCG ACAAGACCCACACCTGCCCCCCCTGCCCCGCCCCCGAGCTGCTG GGCGGCCCCAGCGTGTTCCTGTTCCCCCCCAAGCCCAAGGACAC CCTGATGATCAGCAGGACCCCCGAGGTGACCTGCGTGGTGGTG GACGTGAGCCACGAGGACCCCGAGGTGAAGTTCAACTGGTACG TGGACGGCGTGGAGGTGCACAACGCCAAGACCAAGCCCAGGGA GGAGCAGTACAACAGCACCTACAGGGTGGTGAGCGTGCTGACC GTGCTGCACCAGGACTGGCTGAACGGCAAGGAGTACAAGTGCA AGGTGAGCAACAAGGCCCTGCCCGCCCCCATCGAGAAGACCATC AGCAAGGCCAAGGGCCAGCCCAGGGAGCCCCAGGTGTACACCC TGCCCCCCAGCAGGGAGGAGATGACCAAGAACCAGGTGAGCCT GACCTGCCTGGTGAAGGGCTTCTACCCCAGCGACATCGCCGTGG AGTGGGAGAGCAACGGCCAGCCCGAGAACAACTACAAGACCAC CCCCCCCGTGCTGGACAGCGACGGCAGCTTCTTCCTGTACAGCA AGCTGACCGTGGACAAGAGCAGGTGGCAGCAGGGCAACGTGTT CAGCTGCAGCGTGATGCACGAGGCCCTGCACAACCACTACACCC AGAAGAGCCTGAGCCTGAGCCCCGGCGCCGGCGGCGGCGGCA GCGGCGGCGGCGGCAGCGGCGGCGGCGGCAGCGGCGGCGGC GGCAGCGAGGTGAAGCTGCAGGAGAGCGGCCCCGGCCTGGTG GCCCCCAGCCAGAGCCTGAGCGTGACCTGCACCGTGAGCGGCG TGAGCCTGCCCGACTACGGCGTGAGCTGGATCAGGCAGCCCCCC AGGAAGGGCCTGGAGTGGCTGGGCGTGATCTGGGGCAGCGAG ACCACCTACTACAACAGCGCCCTGAAGAGCAGGCTGACCATCAT CAAGGACAACAGCAAGAGCCAGGTGTTCCTGAAGATGAACAGC CTGCAGACCGACGACACCGCCATCTACTACTGCGCCAAGCACTA CTACTACGGCGGCAGCTACGCCATGGACTACTGGGGCCAGGGC ACCAGCGTGACCGTGAGCAGCGGCGGCGGCGGCAGCGGCGGC GGCGGCAGCGGCGGCGGCAGCGACATCCAGATGACCCAG ACCACCAGCAGCCTGAGCGCCAGCCTGGGCGACAGGGTGACCA TCAGCTGCAGGGCCAGCCAGGACATCAGCAAGTACCTGAACTG GTACCAGCAGAAGCCCGACGGCACCGTGAAGCTGCTGATCTACC ACACCAGCAGGCTGCACAGCGGCGTGCCCAGCAGGTTCAGCGG |

TABLE 4-continued

Amino Acid and Nucleic Acid Sequences

| SEQ ID NO: | Name | Description | Sequence |
|---|---|---|---|
| | | | CAGCGGCAGCGGCACCGACTACAGCCTGACCATCAGCAACCTGG<br>AGCAGGAGGACATCGCCACCTACTTCTGCCAGCAGGGCAACACC<br>CTGCCCTACACCTTCGGCGGCGGCACCAAGCTGGAGATCACC |
| 62 | SIRPαV2-Fc(huIgG1)-anti_CD19 (scFv) | huSIRPaV2-(g4s)x2-HINGE(HUIGG1M3)-(huIgG1m3: ch2-CH3)-a-(g4s)x4-aCD19(VH)-(g4s)x3-αCD19(VL) | EEELQVIQPDKSVSVAAGESAILHCTVTSLIPVGPIQWFRGAGPARE<br>LIYNQKEGHFPRVTTVSESTKRENMDFSISISNITPADAGTYYCVKFR<br>KGSPDTEFKSGAGTELSVR*ggggsggggs*EPKSSDKTHTCPPCPAPELL<br>G*gpsvflfppkpkdtlmisrtpevtcvvvdvshedpevkfnwyvdgvevhnak<br>tkpreeqynstyrvvsvltvlhqdwlngkeykckvsnkalpapiektiskak*GQ<br>PREPQVYTLPPSREEMTKNQVSLTCLVKGFYPSDIAVEWESNGQPE<br>NNYKTTPPVLDSDGSFFLYSKLTVDKSRWQQGNVFSCSVMHEALH<br>NHYTQKSLSLSPGa***ggggsggggsggggsggggsggggs*EVKLQESGPGLVAPS<br>QSLSVTCTVSGVSLPDYGVSWIRQPPRKGLEWLGVIWGSETTYYN<br>SALKSRLTIIKDNSKSQVFLKMNSLQTDDTAIYYCAKHYYYGGSYA<br>MDYWGQGTSVTVSS***ggggsggggsggggsggggs*DIQMTQTTSSLSASLGD<br>RVTISCRASQDISKYLNWYQQKPDGTVKLLIYHTSRLHSGVPSRFSGS<br>GSGTDYSLTISNLEQEDIATYFCQQGNTLPYTFGGGTKLEIT* |
| 63 | anti-CD19(scFv)-Fc(huIgG1)-SIRPαV2 | aCD19(VH)-(g4s)x3-αCD19(VL)-(g4s)x2-HINGE(HUIGG1M3)-(huIgG1m3: ch2-CH3)-a-(g4s)x4-huSIRPaV2 | GAGGTGAAGCTGCAGGAGAGCGGCCCCGGCCTGGTGGCCCCCA<br>GCCAGAGCCTGAGCGTGACCTGCACCGTGAGCGGCGTGAGCCT<br>GCCCGACTACGGCGTGAGCTGGATCAGGCAGCCCCCCAGGAAG<br>GGCCTGGAGTGGCTGGGCGTGATCTGGGGCAGCGAGACCACCT<br>ACTACAACAGCGCCCTGAAGAGCAGGCTGACCATCATCAAGGAC<br>AACAGCAAGAGCCAGGTGTTCCTGAAGATGAACAGCCTGCAGA<br>CCGACGACACCGCCATCTACTACTGCGCCAAGCACTACTACTACG<br>GCGGCAGCTACGCCATGGACTACTGGGGCCAGGGCACCAGCGT<br>GACCGTGAGCAGCGGCGGCGGCGGCAGCGGCGGCGGCGGCAGC<br>GGCGGCGGCGGCAGCGACATCCAGATGACCCAGACCACCAGC<br>AGCCTGAGCGCCAGCCTGGGCGACAGGGTGACCATCAGCTGCA<br>GGGCCAGCCAGGACATCAGCAAGTACCTGAACTGGTACCAGCA<br>GAAGCCCGACGGCACCGTGAAGCTGCTGATCTACCACACCAGCA<br>GGCTGCACAGCGGCGTGCCCAGCAGGTTCAGCGGCAGCGGCAG<br>CGGCACCGACTACAGCCTGACCATCAGCAACCTGGAGCAGGAG<br>GACATCGCCACCTACTTCTGCCAGCAGGGCAACACCCTGCCCTAC<br>ACCTTCGGCGGCGGCACCAAGCTGGAGATCACCGGCGGCGGCG<br>GCAGCGGCGGCGGCGGCAGCGGCGAGCCCAAGAGCAGCGACAAGA<br>CCCACACCTGCCCCCCCTGCCCCGCCCCCGAGCTGCTGGGCGGC<br>CCCAGCGTGTTCCTGTTCCCCCCCAAGCCCAAGGACACCCTGATG<br>ATCAGCAGGACCCCCGAGGTGACCTGCGTGGTGGTGGACGTGA<br>GCCACGAGGACCCCGAGGTGAAGTTCAACTGGTACGTGGACGG<br>CGTGGAGGTGCACAACGCCAAGACCAAGCCCAGGGAGGAGCAG<br>TACAACAGCACCTACAGGGTGGTGAGCGTGCTGACCGTGCTGCA<br>CCAGGACTGGCTGAACGGCAAGGAGTACAAGTGCAAGGTGAGC<br>AACAAGGCCCTGCCCGCCCCCATCGAGAAGACCATCAGCAAGGC<br>CAAGGGCCAGCCCAGGGAGCCCCAGGTGTACACCCTGCCCCCCA<br>GCAGGGAGGAGATGACCAAGAACCAGGTGAGCCTGACCTGCCT<br>GGTGAAGGGCTTCTACCCCAGCGACATCGCCGTGGAGTGGGAG<br>AGCAACGGCCAGCCCGAGAACAACTACAAGACCACCCCCCCCGT<br>GCTGGACAGCGACGGCAGCTTCTTCCTGTACAGCAAGCTGACCG<br>TGGACAAGAGCAGGTGGCAGCAGGGCAACGTGTTCAGCTGCAG<br>CGTGATGCACGAGGCCCTGCACAACCACTACACCCAGAAGAGCC<br>TGAGCCTGAGCCCCGGCGCCGGCGGCGGCGGCAGCGGCGGCG<br>GCGGCAGCGGCGGCGGCGGCAGCGGCGGCGGCGGCAGCGAG<br>GAGGAGCTGCAGGTGATCCAGCCCGACAAGAGCGTGAGCGTGG<br>CCGCCGGCGAGAGCGCCATCCTGCACTGCACCGTGACCAGCCTG<br>ATCCCCGTGGGCCCCATCCAGTGGTTCAGGGGCGCCGGCCCCGC<br>CAGGGAGCTGATCTACAACCAGAAGGAGGGCCACTTCCCCAGG<br>GTGACCACCGTGAGCGAGAGCACCAAGAGGGAGAACATGGACT<br>TCAGCATCAGCATCAGCAACATCACCCCCGCCGACGCCGGCACC<br>TACTACTGCGTGAAGTTCAGGAAGGGCAGCCCCGACACCGAGTT<br>CAAGAGCGGCGCCGGCACCGAGCTGAGCGTGAGG |
| 64 | anti-CD19(scFv)-Fc(huIgG1)-SIRPαV2 | aCD19(VH)-(g4s)x3-αCD19(VL)-(g4s)x2-HINGE(HUIGG1M3)-(huIgG1m3: ch2-CH3)-a-(g4s)x4-huSIRPaV2 | EVKLQESGPGLVAPSQSLSVTCTVSGVSLPDYGVSWIRQPPRKGL<br>EWLGVIWGSETTYYNSALKSRLTIIKDNSKSQVFLKMNSLQTDDT<br>AIYYCAKHYYYGGSYAMDYWGQGTSVTVSS*ggggsggggsggggs*<br>*DIQMTQTTSSLSASLGDRVTISCRASQDISKYLNWYQQKPDGTVKLL<br>IYHTSRLHSGVPSRFSGSGSGTDYSLTISNLEQEDIATYFCQQGNTLP<br>YTFGGGTKLEIT***ggggsggggs*EPKSSDKTHTCPPCPAPELLG*gpsvflfp<br>pkpkdtlmisrtpevtcvvvdvshedpevkfnwyvdgvevhnaktkpreeqy<br>nstyrvvsvltvlhqdwlngkeykckvsnkalpapiektiskak*GQPREPQVY<br>TLPPSREEMTKNQVSLTCLVKGFYPSDIAVEWESNGQPENNYKTTP<br>PVLDSDGSFFLYSKLTVDKSRWQQGNVFSCSVMHEALHNHYTQKS |

TABLE 4-continued

Amino Acid and Nucleic Acid Sequences

| SEQ ID NO: | Name | Description | Sequence |
|---|---|---|---|
| | | | LSLSPGaggggsggggsggggsggggsEEELQVIQPDKSVSVAAGESAILH<br>CTVTSLIPVGPIQWFRGAGPARELIYNQKEGHFPRVTTVSESTKREN<br>MDFSISISNITPADAGTYYCVKFRKGSPDTEFKSGAGTELSVR |
| 65 | anti-HER2 (Fcab) | HINGE(HUIGG1M3)-(antiHER_Fcab_H10036: ch2-CH3) | GAGCCCAAGAGCAGCGACAAGACCCACACCTGCCCCCCCTGCCC<br>CGCCCCCGAGCTGCTGGGCGGCCCCAGCGTGTTCCTGTTCCCCCC<br>CAAGCCCAAGGACACCCTGATGATCAGCAGGACCCCCGAGGTG<br>ACCTGCGTGGTGGTGGACGTGAGCCACGAGGACCCCGAGGTGA<br>AGTTCAACTGGTACGTGGACGGCGTGGAGGTGCACAACGCCAA<br>GACCAAGCCCAGGGAGGAGCAGTACAACAGCACCTACAGGGTG<br>GTGAGCGTGCTGACCGTGCTGCACCAGGACTGGCTGAACGGCA<br>AGGAGTACAAGTGCAAGGTGAGCAACAAGGCCCTGCCCGCCCC<br>CATCGAGAAGACCATCAGCAAGGCCAAGGGCCAGCCCAGGGAG<br>CCCCAGGTGTACACCCTGCCCCCCAGCAGGGACGAGTACCTGTA<br>CGGCGACGTGAGCCTGACCTGCCTGGTGAAGGGCTTCTACCCCA<br>GCGACATCGCCGTGGAGTGGGAGAGCAACGGCCAGCCCGAGAA<br>CAACTACAAGACCACCCCCCCCGTGCTGGACAGCGACGGCAGCT<br>TCTTCCTGTACAGCAAGCTGACCGTGCCCAGGCACAGCGCCAGG<br>ATGTGGAGGTGGGCCCACGGCAACGTGTTCAGCTGCAGCGTGA<br>TGCACGAGGCCCTGCACAACCACTACACCCAGAAGAGCCTGAGC<br>CTGAGCCCCGGCAAG |
| 66 | anti-HER2 (Fcab) | HINGE(HUIGG1M3)-(antiHER_Fcab_H10036: ch2-CH3) | *EPKSSDKTHTCPPCPAPELLG*gpsvflfppkpkdtlmisrtpevtcvvvdvsh edpevkfnwyvdgvevhnaktkpreeqynstyrvvsvltvlhqdwlngkeykc kvsnkalpapiektiskakGQPREPQVYTLPPSRDEYLYGDVSLTCLVKG FYPSDIAVEWESNGQPENNYKTTPPVLDSDGSFFLYSKLTVPRHSAR MWRWAHGNVFSCSVMHEALHNHYTQKSLSLSPGK |
| 67 | SIRPαV2-anti_HER2 (Fcab) | huSIRPαV2-(g4s)x2-HINGE(HUIGG1M3)-(antiHER_Fcab_H10036: ch2-CH3) | GAGGAGGAGCTGCAGGTGATCCAGCCCGACAAGAGCGTGAGC<br>GTGGCCGCCGGCGAGAGCGCCATCCTGCACTGCACCGTGACCA<br>GCCTGATCCCCGTGGGCCCCATCCAGTGGTTCAGGGGCGCCGGC<br>CCCGCCAGGGAGCTGATCTACAACCAGAAGGAGGGCCACTTCC<br>CAGGGTGACCACCGTGAGCGAGAGCACCAAGAGGGAGAACATG<br>GACTTCAGCATCAGCATCAGCAACATCACCCCCGCCGACGCCGG<br>CACCTACTACTGCGTGAAGTTCAGGAAGGGCAGCCCCGACACCG<br>AGTTCAAGAGCGGCGCCGGCACCGAGCTGAGCGTGAGGGGCA<br>GCGGCGGCAGCGGCGGCGGCGGCAGCGAGCCCAAGAGCAGCG<br>ACAAGACCCACACCTGCCCCCCCTGCCCCGCCCCCGAGCTGCTG<br>GGCGGCCCCAGCGTGTTCCTGTTCCCCCCCAAGCCCAAGGACAC<br>CCTGATGATCAGCAGGACCCCCGAGGTGACCTGCGTGGTGGTG<br>GACGTGAGCCACGAGGACCCCGAGGTGAAGTTCAACTGGTACG<br>TGGACGGCGTGGAGGTGCACAACGCCAAGACCAAGCCCAGGGA<br>GGAGCAGTACAACAGCACCTACAGGGTGGTGAGCGTGCTGACC<br>GTGCTGCACCAGGACTGGCTGAACGGCAAGGAGTACAAGTGCA<br>AGGTGAGCAACAAGGCCCTGCCCGCCCCCATCGAGAAGACCATC<br>AGCAAGGCCAAGGGCCAGCCCAGGGAGCCCCAGGTGTACACCC<br>TGCCCCCCAGCAGGGACGAGTACCTGTACGGCGACGTGAGCCT<br>GACCTGCCTGGTGAAGGGCTTCTACCCCAGCGACATCGCCGTGG<br>AGTGGGAGAGCAACGGCCAGCCCGAGAACAACTACAAGACCAC<br>CCCCCCCGTGCTGGACAGCGACGGCAGCTTCTTCCTGTACAGCA<br>AGCTGACCGTGCCCAGGCACAGCGCCAGGATGTGGAGGTGGGC<br>CCACGGCAACGTGTTCAGCTGCAGCGTGATGCACGAGGCCCTGC<br>ACAACCACTACACCCAGAAGAGCCTGAGCCTGAGCCCCGGCAAG |
| 68 | SIRPαV2-anti_HER2 (Fcab) | huSIRPαV2-(g4s)x2-HINGE(HUIGG1M3)-(antiHER_Fcab_H10036: ch2-CH3) | EEELQVIQPDKSVSVAAGESAILHCTVTSLIPVGPIQWFRGAGPARE<br>LIYNQKEGHFPRVTTVSESTKRENMDFSISISNITPADAGTYYCVKFR<br>KGSPDTEFKSGAGTELSVRggggsggggs*EPKSSDKTHTCPPCPAPELL G*gpsvflfppkpkdtlmisrtpevtcvvvdvshedpevkfnwyvdgvevhnak tkpreeqynstyrvvsvltvlhqdwlngkeykckvsnkalpapiektiskakGQ PREPQVYTLPPSRDEYLYGDVSLTCLVKGFYPSDIAVEWESNGQPEN NYKTTPPVLDSDGSFFLYSKLTVPRHSARMWRWAHGNVFSCSVM HEALHNHYTQKSLSLSPGK |
| 69 | anti-EGFR-huIgG1-(G4S)3-SIRPαV2 | C225(VH)-ch1(huigg1m3)-HINGE(HUIGG1M3)-(huIgg1m3: ch2-CH3)-a-(g4s)x3-huSIRPαa(V2) | CAAGTCCAACTGAAGCAGTCCGGGCCGGGACTCGTGCAGCCGTC<br>GCAGTCACTCTCCATCACTTGCACGGTGTCGGGCTTTTCCTTGAC<br>CAACTACGGAGTGCACTGGGTGCGACAGTCCCCTGGAAAGGGG<br>CTGGAGTGGCTTGGCGTGATTGGTCCGAGGGAAACACAGACT<br>ACAACACTCCTTTCACCTCCCGCCTGAGCATTAACAAGGACAACT<br>CCAAGTCCCAAGTGTTCTTCAAGATGAACAGCCTGCAGAGCAAT<br>GATACCGCCATCTACTATTGTGCCCGGGCTCTCACCTACTACGAC<br>TACGAATTCGCCTACTGGGGACAGGGAACCCTGGTCACTGTCTC<br>CGCGgcctccactaagggcccatcggtgttccccttggcgccatcgtcaaagtcca cctccggtggcactgccgccctgggatgcctgtgaaggactacttccccgaacctgt gaccgtgtcctggaactcgggcgcactgacttcggggggtgcacacctttcctgccgtc TABLE 4-continued Amino Acid and Nucleic Acid Sequences

| SEQ ID NO: | Name | Description | Sequence |
|---|---|---|---|
| | | | ctgcaatcgagcggtctgtactccctctcgtccgtggtcaccgtgccgtctagctccct cggaacccagacctacatctgcaacgtcaaccacaagccgagcaacaccaaagtg gataagagagtg*GAGCCGAAGTCATGCGACAAGACTCATACTTGTC CCCCATGCCCCGCCCCGGAACTGCTGGG*ggcccatccgtgttcctgtt ccgcgcgaaacctaaggacaccctgatgatttcgagaactccggaagtgacctg tgtggtggtcgacgtgtcccacgaggatccggaggtcaagttcaattggtacgt cgacggagtggaagtccacaacgccaagaccaagcccgggaggagcagta caactccacttacggggtggtgtccgtgctgaccgtgctgcatcaggattggctg aacggaaaggagtataagtgcaaagtgtcaaacaaggcattgcctgcgccaa tcgaaaagaccattagcaaggccaagGGCCAGCCCAGGGAACCACAG GTGTACACTCTGCCCCCGTCCCGCGAAGAAATGACCAAGAACCA AGTGTCACTGACATGCCTCGTGAAGGGATTTTACCCGTCCGATAT CGCCGTGGAATGGGAATCGAACGGTCAACCTGAAAACAACTACA AGACGACCCCTCCGGTCCTGGACAGCGATGGCTCATTCTTCCTGT ACTCCAAGCTTACGGTGGACAAGTCCCGGTGGCAACAGGGAAA TGTGTTTTCGTGCTCCGTGATGCATGAGGCTCTGCACAACCACTA CACCCAGAAGTCACTCTCCCTGAGCCCCGGCgcggggggtggtggaag cggaggagggggtctgggggtggcggttccGAGGAGGAGCTCCAGGTCA TCCAGCCTGACAAGTCCGTGTCGGTGGCCGCGGGAGAGTCCGC CATTCTGCACTGCACCGTGACCTCCCTCATCCCCGTGGGACCTAT CCAGTGGTTCAGAGGAGCCGGGCCCGCACGGGAACTGATCTAT AACCAGAAGGAGGGCCATTTCCCCCGCGTGACCACCGTGTCCG AGAGCACCAAGAGGGAAAAACATGGACTTCAGCATTTCGATCAG CAACATCACTCCCGCTGACGCCGGGACCTACTACTGCGTGAAGT TCCGGAAAGGAAGCCCGGACACCGAGTTCAAAAGCGGAGCCG GCACCGAACTGTCGGTCCGC |
| 70 | anti-EGFR-huIgG1-(G4S)3-SIRPαV2 | C225(VH)-ch1(huigg1m3)-HINGE(HUIGG1M3)-(huIgG1m3: ch2-CH3)-a-(g4s)x3-huSIRPa(V2) | QVQLKQSGPGLVQPSQSLSITCTVSGFSLTNYGVHWVRQSPGKGLE WLGVIWSGGNTDYNTPFTSRLSINKDNSKSQVFFKMNSLQSNDTAI YYCARALTYYDYEFAYWGQGTLVTVSA*astkgpsvfplapsskstsggta algclvkdyfpepvtvswnsgaltsgvhtfpavlqssglyslssvvtvpssslgtqty icnvnhkpsntkvdkrv*EPKSCDKTHTCPPCPAPELLG*gpsvflfppkpkdt lmisrtpevtcvvvdvshedpevkfnwyvdgvevhnaktkpreeqynstyrvv svltvlhqdwlngkeykckvsnkalpapiektiskakGQPREPQVYTLPPSR EEMTKNQVSLTCLVKGFYPSDIAVEWESNGQPENNYKTTPPVLDSD GSFFLYSKLTVDKSRWQQGNVFSCSVMHEALHNHYTQKSLSLSPG AGGGGSGGGGSGGGGSEEELQVIQPDKSVSVAAGESAILHCTVTS LIPVGPIQWFRGAGPARELIYNQKEGHFPRVTTVSESTKRENMDF SISISNITPADAGTYYCVKFRKGSPDTEFKSGAGTELSVR |
| 71 | anti-EGFR-huIgG1-(G4S)5-SIRPαV2 | C225(VH)-ch1(huigg1m3)-HINGE(HUIGG1M3)-(huIgG1m3: ch2-CH3)-a-(g4s)x5-huSIRPa(V2) | CAAGTCCAACTGAAGCAGTCCGGGCCGGGACTCGTGCAGCCGTC GCAGTCACTGTCCATCACTTGCACGGTGTCAGGCTTTTCCTTGAC CAACTACGGAGTGCACTGGGTGCGCCAGTCCCCTGGAAAGGGG CTGGAGTGGCTTGGCGTGATTTGGTCCGGAGGAAACACAGACT ACAACACTCCTTTCACCTCCCGCCTGAGCATTAACAAGGACAACT CCAGTCCCAAGTGTTCTTCAAGATGAACAGCCTGCAGAGCAAT GATACCGCCATCTACTATTGTGCCCGGGCTCTCACCTACTACGAC TACGAATTCGCCTACTGGGGACAGGGAACCCTGGTCACTGTCTC CGCG*gcctccactaagggcccctagcgtgttcccccttggcgccatcgtcaaagtcca cctccggtggcactgcgccctgggatgccttgtgaaggactactt*ccccgaacctgt gaccgtgtcctggaactcgggcgcactgacttcggggggtgcacaccttcctgccgtc ctgcaatcgagcggtctgtactccctctcgtccgtggtcaccgtgccgtctagctccct cggaacccagacctacatctgcaacgtcaaccacaagccgagcaacaccaaagtg gataagagagtg*GAGCCGAAGTCATGCGACAAGACTCATACTTGTC CCCCATGCCCCGCCCCGGAACTGCTGGG*ggcccatccgtgttcctgtt ccgcgcgaaacctaaggacaccctgatgatttcgagaactccggaagtgacctg tgtggtggtcgacgtgtcccacgaggatccggaggtcaagttcaattggtacgt cgacggagtggaagtccacaacgccaagaccaagcccgggaggagcagta caactccacttacggggtggtgtccgtgctgaccgtgctgcatcaggattggctg aacggaaaggagtataagtgcaaagtgtcaaacaaggcattgcctgcgccaa tcgaaaagaccattagcaaggccaagGGCCAGCCCAGGGAACCACAG GTGTACACTCTGCCCCCGTCCCGCGAAGAAATGACCAAGAACCA AGTGTCACTGACATGCCTCGTGAAGGGATTTTACCCGTCCGATAT CGCCGTGGAATGGGAATCGAACGGTCAACCTGAAAACAACTACA AGACGACCCCTCCGGTCCTGGACAGCGATGGCTCATTCTTCCTGT ACTCCAAGCTTACGGTGGACAAGTCCCGGTGGCAACAGGGAAA TGTGTTTTCGTGCTCCGTGATGCATGAGGCTCTGCACAACCACTA CACCCAGAAGTCACTCTCCCTGAGCCCCGGCgcggggggtggtggaag cggaggagggtggcggttccggcggcggcggatccggcggcgcg gatccGAGGAGGAGCTCCAGGTCATCCAGCCTGACAAGTCCGTG TCGGTGGCCGCGGGAGAGTCCGCCATTCTGCACTGCACCGTGA CCTCCCTCATCCCCGTGGGACCTATCCAGTGGTTCAGAGGAGCC GGGCCCGCACGGGAACTGATCTATAACCAGAAGGAGGGCCATT TCCCCCGCGTGACCACCGTGTCCGAGAGCACCAAGAGGGAAAA |

TABLE 4-continued

Amino Acid and Nucleic Acid Sequences

| SEQ ID NO: | Name | Description | Sequence |
|---|---|---|---|
| | | | CATGGACTTCAGCATTTCGATCAGCAACATCACTCCCGCTGACG<br>CCGGGACCTACTACTGCGTGAAGTTCCGGAAAGGAAGCCCGGA<br>CACCGAGTTCAAAAGCGGAGCCGGCACCGAACTGTCGGTCCGC |
| 72 | anti-EGFR-huIgG1-(G4S)5-SIRPαV2 | C225(VH)-ch1(huigg1m3)-HINGE(HUIGG1M3)-(huIgG1m3: ch2-CH3)-a-(g4s)x5-huSIRPa(V2) | QVQLKQSGPGLVQPSQSLSITCTVSGFSLTNYGVHWVRQSPGKGLE<br>WLGVIWSGGNTDYNTPFTSRLSINKDNSKSQVFFKMNSLQSNDTAI<br>YYCARALTYYDYEFAYWGQGTLVTVSAastkgpsvfplapssskstsggta<br>algclvkdyfpepvtvswnsgaltsgvhtfpavlqssglyslssvvtvpssslgtqty<br>icnvnhkpsntkvdkrv*EPKSCDKTHTCPPCPAPELL*gpsvflfppkpkdt*<br>*lmisrtpevtcvvvdvshedpevkfnwyvdgvevhnakktkpreeqynstyrvv*<br>*svltvlhqdwlngkeykckvsnkalpapiektiskak*GQPREPQVYTLPPSR<br>EEMTKNQVSLTCLVKGFYPSDIAVEWESNGQPENNYKTTPPVLDSD<br>GSFFLYSKLTVDKSRWQQGNVFSCSVMHEALHNHYTQKSLSLSPG<br>AGGGGSGGGGSGGGGSGGGGSGGGGSEEELQVIQPDKSVSVAA<br>GESAILHCTVTSLIPVGPIQWFRGAGPARELIYNQKEGHFPRVTTV<br>SESTKRENMDFSISISNITPADAGTYYCVKFRKGSPDTEFKSGAGTE<br>LSVR |
| 73 | anti-EGFR(VH_ds1_G44C)-huIgG1 | C225(VH_ds1_G44C)-ch1(huigg1m3)-HINGE(HUIGG1M3)-(huIgG1m3: ch2-CH3) | CAGGTGCAGCTGAAGCAGAGCGGCCCCGGCCTGGTGCAGCCCA<br>GCCAGAGCCTGAGCATCACCTGCACCGTGAGCGGCTTCAGCCTG<br>ACCAACTACGGCGTGCACTGGGTGAGGCAGAGCCCCGGCAAGT<br>GCCTGGAGTGGCTGGGCGTGATCTGGAGCGGCGGCAACACCGA<br>CTACAACACCCCCTTCACCAGCAGGCTGAGCATCAACAAGGACA<br>ACAGCAAGAGCCAGGTGTTCTTCAAGATGAACAGCCTGCAGAGC<br>AACGACACCGCCATCTACTACTGCGCCAGGGCCCTGACCTACTAC<br>GACTACGAGTTCGCCTACTGGGGCCAGGGCACCCTGGTGACCGT<br>GAGCGCCGCCAGCACCAAGGGCCCCAGCGTGTTCCCCCTGGCCC<br>CCAGCAGCAAGAGCACCAGCGGCGGCACCGCCGCCCTGGGCTG<br>CCTGGTGAAGGACTACTTCCCCGAGCCCGTGACCGTGAGCTGGA<br>ACAGCGGCGCCCTGACCAGCGGCGTGCACACCTTCCCCGCCGTG<br>CTGCAGAGCAGCGGCCTGTACAGCCTGAGCAGCGTGGTGACCG<br>TGCCCAGCAGCAGCCTGGGCACCCAGACCTACATCTGCAACGTG<br>AACCACAAGCCCAGCAACACCAAGGTGGACAAGAGGGTGGAGC<br>CCAAGAGCTGCGACAAGACCCACACCTGCCCCCCCTGCCCCGCC<br>CCCGAGCTGCTGGGCGGCCCCAGCGTGTTCCTGTTCCCCCCCAA<br>GCCCAAGGACACCCTGATGATCAGCAGGACCCCCGAGGTGACCT<br>GCGTGGTGGTGGACGTGAGCCACGAGGACCCCGAGGTGAAGTT<br>CAACTGGTACGTGGACGGCGTGGAGGTGCACAACGCCAAGACC<br>AAGCCCAGGGAGGAGCAGTACAACAGCACCTACAGGGTGGTGA<br>GCGTGCTGACCGTGCTGCACCAGGACTGGCTGAACGGCAAGGA<br>GTACAAGTGCAAGGTGAGCAACAAGGCCCTGCCCGCCCCCATCG<br>AGAAGACCATCAGCAAGGCCAAGGGCCAGCCCAGGGAGCCCCA<br>GGTGTACACCCTGCCCCCCAGCAGGGAGGAGATGACCAAGAAC<br>CAGGTGAGCCTGACCTGCCTGGTGAAGGGCTTCTACCCCAGCGA<br>CATCGCCGTGGAGTGGGAGAGCAACGGCCAGCCCGAGAACAAC<br>TACAAGACCACCCCCCCCGTGCTGGACAGCGACGGCAGCTTCTT<br>CCTGTACAGCAAGCTGACCGTGGACAAGAGCAGGTGGCAGCAG<br>GGCAACGTGTTCAGCTGCAGCGTGATGCACGAGGCCCTGCACAA<br>CCACTACACCCAGAAGAGCCTGAGCCTGAGCCCCGGC |
| 74 | anti-EGFR(VH_ds1_G44C)-huIgG1 | C225(VH_ds1_G44C)-ch1(huigg1m3)-HINGE(HUIGG1M31)(huIgG1m3: ch2-CH3) | QVQLKQSGPGLVQPSQSLSITCTVSGFSLTNYGVHWVRQSPGKCLE<br>WLGVIWSGGNTDYNTPFTSRLSINKDNSKSQVFFKMNSLQSNDTAI<br>YYCARALTYYDYEFAYWGQGTLVTVSAastkgpsvfplapssskstsggta<br>algclvkdyfpepvtvswnsgaltsgvhtfpavlqssglvslssvvtvpssslgtqty<br>icnvnhkpsntkvdkrv*EPKSCDKTHTCPPCPAPELLG*gpsvflfppkpkdt<br>lmisrtpevtcvvvdvshedpevkfnwyvdgvevhnakktkpreeqynstyrvv<br>svltvlhqdwlngkeykckvsnkalpapiektiskakGQPREPQVYTLPPSR<br>EEMTKNQVSLTCLVKGFYPSDIAVEWESNGQPENNYKTTPPVLDSD<br>GSFFLYSKLTVDKSRWQQGNVFSCSVMHEALHNHYTQKSLSLSPG |
| 75 | anti-EGFR(VH_ds2_Q105C)-huIgG1 | C225(VH_ds2_Q105C)-ch1(huigg1m3)-HINGE(HUIGG1M3)-(huIgG1m3: ch2-CH3) | CAGGTGCAGCTGAAGCAGAGCGGCCCCGGCCTGGTGCAGCCCA<br>GCCAGAGCCTGAGCATCACCTGCACCGTGAGCGGCTTCAGCCTG<br>ACCAACTACGGCGTGCACTGGGTGAGGCAGAGCCCCGGCAAGG<br>GCCTGGAGTGGCTGGGCGTGATCTGGAGCGGCGGCAACACCGA<br>CTACAACACCCCCTTCACCAGCAGGCTGAGCATCAACAAGGACA<br>ACAGCAAGAGCCAGGTGTTCTTCAAGATGAACAGCCTGCAGAGC<br>AACGACACCGCCATCTACTACTGCGCCAGGGCCCTGACCTACTAC<br>GACTACGAGTTCGCCTACTGGGGCTGCGGCACCCTGGTGACCGT<br>GAGCGCCGCCAGCACCAAGGGCCCCAGCGTGTTCCCCCTGGCCC<br>CCAGCAGCAAGAGCACCAGCGGCGGCACCGCCGCCCTGGGCTG<br>CCTGGTGAAGGACTACTTCCCCGAGCCCGTGACCGTGAGCTGGA<br>ACAGCGGCGCCCTGACCAGCGGCGTGCACACCTTCCCCGCCGTG<br>CTGCAGAGCAGCGGCCTGTACAGCCTGAGCAGCGTGGTGACCG<br>TGCCCAGCAGCAGCCTGGGCACCCAGACCTACATCTGCAACGTG |

TABLE 4-continued

Amino Acid and Nucleic Acid Sequences

| SEQ ID NO: | Name | Description | Sequence |
|---|---|---|---|
| | | | AACCACAAGCCCAGCAACACCAAGGTGGACAAGAGGGTGGAGC<br>CCAAGAGCTGCGACAAGACCCACACCTGCCCCCCCTGCCCCGCC<br>CCCGAGCTGCTGGGCGGCCCCAGCGTGTTCCTGTTCCCCCCCAA<br>GCCCAAGGACACCCTGATGATCAGCAGGACCCCCGAGGTGACCT<br>GCGTGGTGGTGGACGTGAGCCACGAGGACCCCGAGGTGAAGTT<br>CAACTGGTACGTGGACGGCGTGGAGGTGCACAACGCCAAGACC<br>AAGCCCAGGGAGGAGCAGTACAACAGCACCTACAGGGTGGTGA<br>GCGTGCTGACCGTGCTGCACCAGGACTGGCTGAACGGCAAGGA<br>GTACAAGTGCAAGGTGAGCAACAAGGCCCTGCCCGCCCCCATCG<br>AGAAGACCATCAGCAAGGCCAAGGGCCAGCCCAGGGAGCCCCA<br>GGTGTACACCCTGCCCCCCAGCAGGGAGGAGATGACCAAGAAC<br>CAGGTGAGCCTGACCTGCCTGGTGAAGGGCTTCTACCCCAGCGA<br>CATCGCCGTGGAGTGGGAGAGCAACGGCCAGCCCGAGAACAAC<br>TACAAGACCACCCCCCCCGTGCTGGACAGCGACGGCAGCTTCTT<br>CCTGTACAGCAAGCTGACCGTGGACAAGAGCAGGTGGCAGCAG<br>GGCAACGTGTTCAGCTGCAGCGTGATGCACGAGGCCCTGCACAA<br>CCACTACACCCAGAAGAGCCTGAGCCTGAGCCCCGGC |
| 76 | anti-EGFR(VH_ds2_Q105C)-huIgG1 | C225(VH_ds2_Q105C)-ch1(huigg1m3)-HINGE(HUIGG1M3)-(huIgG1m3: ch2-CH3) | QVQLKQSGPGLVQPSQSLSITCTVSGFSLTNYGVHWVRQSPGKGLE<br>WLGVIWSGGNTDYNTPFTSRLSINKDNSKSQVFFKMNSLQSNDTAI<br>YYCARALTYYDYEFAYWGCGTLVTVSAastkgpsvfplapsskstsggtaa<br>lgclvkdyfpepvtvswnsgaltsgvhtfpavlqssglyslssvvtvpssslgtqtyi<br>cnvnhkpsntkvdkrv*EPKSCDKTHTCPPCPAPELLG*gpsvflfppkpkdtl<br>misrtpevtcvvvdvshedpevkfnwyvdgvevhnaktkpreeqynstyrvv<br>svltvlhqdwlngkeykckvsnkalpapiektiskakGQPREPQVYTLPPSR<br>EEMTKNQVSLTCLVKGFYPSDIAVEWESNGQPENNYKTTPPVLDSD<br>GSFFLYSKLTVDKSRWQQGNVFSCSVMHEALHNHYTQKSLSLSPG |
| 77 | anti-EGFR(VL_ds1_A100C)-huCK-SIRPαV2 | C225(VL_ds1_A100C)-huck-(G4S)X2-sirpav2 | GACATCCTGCTGACCCAGAGCCCCGTGATCCTGAGCGTGAGCCC<br>CGGCGAGAGGGTGAGCTTCAGCTGCAGGGCCAGCCAGAGCATC<br>GGCACCAACATCCACTGGTACCAGCAGAGGACCAACGGCAGCCC<br>CAGGCTGCTGATCAAGTACGCCAGCGAGAGCATCAGCGGCATCC<br>CCAGCAGGTTCAGCGGCAGCGGCAGCGGCACCGACTTCACCCTG<br>AGCATCAACAGCGTGGAGAGCGAGGACATCGCCGACTACTACT<br>GCCAGCAGAACAACAACTGGCCCACCACCTTCGGCTGCGGCACC<br>AAGCTGGAGCTGAAGAGGACCGTGGCCGCCCCCAGCGTGTTCA<br>TCTTCCCCCCCAGCGACGAGCAGCTGAAGAGCGGCACCGCCAGC<br>GTGGTGTGCCTGCTGAACAACTTCTACCCCAGGGAGGCCAAGGT<br>GCAGTGGAAGGTGGACAACGCCCTGCAGAGCGGCAACAGCCAG<br>GAGAGCGTGACCGAGCAGGACAGCAAGGACAGCACCTACAGCC<br>TGAGCAGCACCCTGACCCTGAGCAAGGCCGACTACGAGAAGCA<br>CAAGGTGTACGCCTGCGAGGTGACCCACCAGGGCCTGAGCAGC<br>CCCGTGACCAAGAGCTTCAACAGGGGCGAGTGCGGCGGCGGCG<br>GCAGCGGCGGCGGCGGCAGCGAGGAGGAGCTGCAGGTGATCC<br>AGCCCGACAAGAGCGTGAGCGTGGCCGCCGGCGAGAGCGCCAT<br>CCTGCACTGCACCGTGACCAGCCTGATCCCCGTGGGCCCCATCCA<br>GTGGTTCAGGGGCGCCGGCCCCGCCAGGGAGCTGATCTACAAC<br>CAGAAGGAGGGCCACTTCCCCAGGGTGACCACCGTGAGCGAGA<br>GCACCAAGAGGGAGAACATGGACTTCAGCATCAGCATCAGCAA<br>CATCACCCCCGCCGACGCCGGCACCTACTACTGCGTGAAGTTCA<br>GGAAGGGCAGCCCCGACACCGAGTTCAAGAGCGGCGCCGGCAC<br>CGAGCTGAGCGTGAGG |
| 78 | anti-EGFR(VL_ds1_A100C)-huCK-SIRPαV2 | C225(VL_ds1_A100C)-huck-(G4S)X2-sirpav2 | DILLTQSPVILSVSPGERVSFSCRASQSIGTNIHWYQQRTNGSPRLLIK<br>YASESISGIPSRFSGSGSGTDFTLSINSVESEDIADYYCQQNNNWPTT<br>FGCGTKLELKrtvaapsvfifppsdeqlksgtasvvcllnnfypreakvqwkvd<br>nalqsgnsqesvteqdskdstyslsstltlskadyekhkvyacevthqglsspvtk<br>sfnrgec*GGGGSGGGGS*nkalpapiektiskakailhctvtslipvgpi<br>qwfrgagparelieynqkeghfprvttvsestkrenmdfsisisnitpadagtyyc<br>vkfrkgspdtefksgagtelsvr |
| 79 | anti-EGFR(VL_ds2_S43C)-huCK-SIRPαV2 | C225(VL_ds2_S43C)-huck-(G4S)X2-sirpav2 | GACATCCTGCTGACCCAGAGCCCCGTGATCCTGAGCGTGAGCCC<br>CGGCGAGAGGGTGAGCTTCAGCTGCAGGGCCAGCCAGAGCATC<br>GGCACCAACATCCACTGGTACCAGCAGAGGACCAACGGCTGCCC<br>CAGGCTGCTGATCAAGTACGCCAGCGAGAGCATCAGCGGCATCC<br>CCAGCAGGTTCAGCGGCAGCGGCAGCGGCACCGACTTCACCCTG<br>AGCATCAACAGCGTGGAGAGCGAGGACATCGCCGACTACTACT<br>GCCAGCAGAACAACAACTGGCCCACCACCTTCGGCGCCGGCACC<br>AAGCTGGAGCTGAAGAGGACCGTGGCCGCCCCCAGCGTGTTCA<br>TCTTCCCCCCCAGCGACGAGCAGCTGAAGAGCGGCACCGCCAGC<br>GTGGTGTGCCTGCTGAACAACTTCTACCCCAGGGAGGCCAAGGT<br>GCAGTGGAAGGTGGACAACGCCCTGCAGAGCGGCAACAGCCAG<br>GAGAGCGTGACCGAGCAGGACAGCAAGGACAGCACCTACAGCC<br>TGAGCAGCACCCTGACCCTGAGCAAGGCCGACTACGAGAAGCA |

TABLE 4-continued

Amino Acid and Nucleic Acid Sequences

| SEQ ID NO: | Name | Description | Sequence |
|---|---|---|---|
| | | | CAAGGTGTACGCCTGCGAGGTGACCCACCAGGGCCTGAGCAGC CCCGTGACCAAGAGCTTCAACAGGGGCGAGTGCGGCGGCGGCG GCAGCGGCGGCGGCGGCAGCGAGGAGGAGCTGCAGGTGATCC AGCCCGACAAGAGCGTGAGCGTGGCCGCCGGCGAGAGCGCCAT CCTGCACTGCACCGTGACCAGCCTGATCCCCGTGGGCCCCATCC AGTGGTTCAGGGGCGCCGGCCCCGCCAGGGAGCTGATCTACAAC CAGAAGGAGGGCCACTTCCCCAGGGTGACCACCGTGAGCGAGA GCACCAAGAGGGAGAACATGGACTTCAGCATCAGCATCAGCAA CATCACCCCCGCCGACGCCGGCACCTACTACTGCGTGAAGTTCA GGAAGGGCAGCCCCGACACCGAGTTCAAGAGCGGCGCCGGCAC CGAGCTGAGCGTGAGG |
| 80 | anti-EGFR(VL ds2_S43C)-huCK-SIRPaV2 | C225(VL_ds2_S43C)-huck-(G4S)X2-sirpav2 | DILLTQSPVILSVSPGERVSFSCRASQSIGTNIHWYQQRTNGCPRLLI KYASESISGIPSRFSGSGSGTDFTLSINSVESEDIADYYCQQNNNWPT TFGAGTKLELKrtvaapsvfifppsdeqlksgtasvvcllnnfypreakvqwkv dnalqsgnsqesvteqdskdstyslsstltlskadyekhkvyacevthqgisspvt ksfnrgecGGGGSGGGGSeeelqviqpdksvsvaagesailhctvtslipvgpi qwfrgagpareliynqkeghfprvttvsestkrenmdfsisisnitpadagtyyc vkfrkgspdtefksgagtelsvr |
| 81 | Cetuximab (HC) | anti-EGFR: HC | QVQLKQSGPGLVQPSQSLSITCTVSGFSLTNYGVHWVRQSPGKGLE WLGVIWSGGNTDYNTPFTSRLSINKDNSKSQVFFKMNSLQSNDTAI YYCARALTYYDYEFAYWGQGTLVTVSAASTKGPSVFPLAPSSKSTSG GTAALGCLVKDYFPEPVTVSWNSGALTSGVHTFPAVLQSSGLYSLSS VVTVPSSSLGTQTYICNVNHKPSNTKVDKRVEPKSCDKTHTCPP CPAPELLGGPSVFLFPPKPKDTLMISRTPEVTCVVVDVSHEDPEVKF NWYVDGVEVHNAKTKPREEQYNSTYRVVSVLTVLHQDWLNGKEY KCKVSNKALPAPIEKTISKAKGQPREPQVYTLPPSRDELTKNQVSLTC LVKGFYPSDIAVEWESNGQPENNYKTTPPVLDSDGSFFLYSKLTVDK SRWQQGNVFSCSVMHEALHNHYTQKSLSLSPGK |
| 82 | Cetuximab (LC) | anti-EGFR: LC | DILLTQSPVILSVSPGERVSFSCRASQSIGTNIHWYQQRTNGSPRLLIK YASESISGIPSRFSGSGSGTDFTLSINSVESEDIADYYCQQNNNWPTT FGAGTKLELKRTVAAPSVFIFPPSDEQLKSGTASVVCLLNNFYPREAK VQWKVDNALQSGNSQESVTEQDSKDSTYSLSSTLTLSKADYEKHKV YACEVTHQGLSSPVTKSFNRGA |
| 83 | Panitumumab (HC) | anti-EGFR: HC | QVQLQESGPGLVKPSETLSLTCTVSGGSVSSGDYYWTWIRQSPGKG LEWIGHIYYSGNTNYNPSLKSRLTISIDTSKTQFSLKLSSVTAADTAIYY CVRDRVTGAFDIWGQGTMVTVSSASTKGPSVFPLAPCSRSTSESTA ALGCLVKDYFPEPVTVSWNSGALTSGVHTFPAVLQSSGLYSLSSVVT VPSSNFGTQTYTCNVDHKPSNTKVDKTVERKCCVECPPCPAPPVAG PSVFLFPPKPKDTLMISRTPEVTCVVVDVSHEDPEVQFNWYVDGVE VHNAKTKPREEQFNSTFRVVSVLTVVHQDWLNGKEYKCKVSNKGL PAPIEKTISKTKGQPREPQVYTLPPSREEMTKNQVSLTCLVKGFYPSD IAVEWESNGQPENNYKTTPPMLDSDGSFFLYSKLTVDKSRWQQGN VFSCSVMHEALHNHYTQKSLSLSPGK |
| 84 | Panitumumab (LC) | anti-EGFR: LC | DIQMTQSPSSLSASVGDRVTITCQASQDISNYLNWYQQKPGKAPKL LIYDASNLETGVPSRFSGSGSGTDFTFTISSLQPEDIATYFCQHFDHLP LAFGGGTKVEIKRTVAAPSVFIFPPSDEQLKSGTASVVCLLNNFYPRE AKVQWKVDNALQSGNSQESVTEQDSKDSTYSLSSTLTLSKADYEKH KVYACEVTHQGLSSPVTKSFNRGEC |
| 85 | Nimotuzumab (HC) | anti-EGFR: Fab(H) | QVQLQQSGAEVKKPGSSVKVSCKASGYTFTNYYIYWVRQAPGQGL EWIGGINPTSGGSNFNEKFKTRVTITADESSTTAYMELSSLRSEDTAF YFCTRQGLWFDSDGRGFDFWGQGTTVTVSSASTKGPSVFPLAPSS KSTSGGTAALGCLVKDYFPEPVTVSWNSGALTSGVHTFPAVLQSSG LYSLSSVVTVPSSSLGTQTYICNVNHKPSNTKVDKKVP |
| 86 | Nimotuzumab (LC) | anti-EGFR: Fab(L) | DIQMTQSPSSLSASVGDRVTITCRSSQNIVHSNGNTYLDWYQQTP GKAPKLLIYKVSNRFSGVPSRFSGSGSGTDFTFTISSLQPEDIATYYCF QYSHVPWTFGQGTKLQITREVAAPSVFIFPPSDEQLKSGTASVVCLL NNFYPREAKVQWKVDNALQSGNSQESVTEQDSKDSTYSLSSTLTLS KADYEKHKVYACEVTHQGLSSPVTKSFNRGEC |
| 87 | Matuzumab (HC) | anti-EGFR: Fab(H) | QVQLVQSGAEVKKPGASVKVSCKASGYTFTSHWMHWVRQAPGQ GLEWIGEFNPSNGRTNYNEKFKSKATMTVDTSTNTAYMELSSLRSE DTAVYYCASRDYDYDGRYFDYWGQGTLVTVSSASTKGPSVFPLAPS SKSTSGGTAALGCLVKDYFPEPVTVSWNSGALTSGVHTFPAVLQSS GLYSLSSVVTVPSSSLGTQTYICNVNHKPSNTKVDKKVEPKS |
| 88 | Matuzumab (LC) | anti-EGFR: Fab(L) | DIQMTQSPSSLSASVGDRVTITCSASSSVTYMYWYQQKPGKAPKLLI YDTSNLASGVPSRFSGSGSGTDYTFTISSLQPEDIATYYCQQWSSHIF |

TABLE 4-continued

Amino Acid and Nucleic Acid Sequences

| SEQ ID NO: | Name | Description | Sequence |
|---|---|---|---|
| | | | TFGQGTKVEIKRTVAAPSVFIFPPSDEQLKSGTASVVCLLNNFYPREA KVQWKVDNALQSGNSQESVTEQDSKDSTYSLSSTLTLSKADYEKHK VYACEVTHQGLSSPVTKSFNRGE |
| 89 | Futuximab (HC) | anti-EGFR: HC | EVQLQQPGSELVRPGASVKLSCKASGYTFTSYWMHWVKQRPGQG LEWIGNIYPGSRSTNYDEKFKSKATLTVDTSSSTAYMQLSSLTSEDSA VYYCTRNGDYYVSSGDAMDYWGQGTSVTVSSASTKGPSVFPLAPS SKSTSGGTAALGCLVKDYFPEPVTVSWNSGALTSGVHTFPAVLQSS GLYSLSSVVTVPSSSLGTQTYICNVNHKPSNTKVDKRVEPKSCDKTH TCPPCPAPELLGGPSVFLFPPKPKDTLMISRTPEVTCVVVDVSHEDP EVKFNWYVDGVEVHNAKTKPREEQYNSTYRVVSVLTVLHQDWLN GKEYKCKVSNKALPAPIEKTISKAKGQPREPQVYTLPPSREEMTKNQ VSLTCLVKGFYPSDIAVEWESNGQPENNYKTTPPVLDSDGSFFLYSK LTVDKSRWQQGNVFSCSVMHEALHNHYTQKSLSLSPG |
| 90 | Futuximab (LC) | anti-EGFR: LC | DIQMTQTTSSLSASLGDRVTISCRTSQDIGNYLNWYQQKPDGTVKL LIYYTSRLHSGVPSRFSGSGSGTDFSLTINNVEQEDVATYFCQHYNTV PPTFGGGTKLEIKRTVAAPSVFIFPPSDEQLKSGTASVVCLLNNFYPR EAKVQWKVDNALQSGNSQESVTEQDSKDSTYSLSSTLTLSKADYEK HKVYACEVTHQGLSSPVTKSFNRGEC |
| 91 | Modotuximab (HC) | anti-EGFR: HC | QVQLQQPGAELVEPGGSVKLSCKASGYTFTSHWMHWVKQRPGQ GLEWIGEINPSSGRNNYNEKFKSKATLTVDKSSSTAYMQFSSLTSED SAVYYCVRYYGYDEAMDYWGQGTSVTVSSASTKGPSVFPPLAPSSKS TSGGTAALGCLVKDYFPEPVTVSWNSGALTSGVHTFPAVLQSSGLY SLSSVVTVPSSSLGTQTYICNVNHKPSNTKVDKRVEPKSCDKTHTCP PCPAPELLGGPSVFLFPPKPKDTLMISRTPEVTCVVVDVSHEDPEVK FNWYVDGVEVHNAKTKPREEQYNSTYRVVSVLTVLHQDWLNGKE YKCKVSNKALPAPIEKTISKAKGQPREPQVYTLPPSREEMTKNQVSL TCLVKGFYPSDIAVEWESNGQPENNYKTTPPVLDSDGSFFLYSKLTV DKSRWQQGNVFSCSVMHEALHNHYTQKSLSLSPG |
| 92 | Modotuximab (LC) | anti-EGFR: LC | DIVMTQAAFSNPVTLGTSASISCRSSKSLLHSNGITYLYWYLQKPGQ SPQLLIYQMSNLASGVPDRFSSSGSGTDFTLRISRVEAEDVGVYYCA QNLELPYTFGGGTKLEIKRTVAAPSVFIFPPSDEQLKSGTASVVCLLN NFYPREAKVQWKVDNALQSGNSQESVTEQDSKDSTYSLSSTLTLSK ADYEKHKVYACEVTHQGLSSPVTKSFNRGEC |
| 93 | Imgatuzumab (HC) | anti-EGFR: HC | QVQLVQSGAEVKKPGSSVKVSCKASGFTFTDYKIHWVRQAPGQGL EWMGYFNPNSGYSTYAQKFQGRVTITADKSTSTAYMELSSLRSED AVYYCARLSPGGYYVMDAWGQGTTVTVSSASTKGPSVFPLAPSSKS TSGGTAALGCLVKDYFPEPVTVSWNSGALTSGVHTFPAVLQSSGLY SLSSVVTVPSSSLGTQTYICNVNHKPSNTKVDKKVEPKSCDKTHTCP PCPAPELLGGPSVFLFPPKPKDTLMISRTPEVTCVVVDVSHEDPEVK FNWYVDGVEVHNAKTKPREEQYNSTYRVVSVLTVLHQDWLNGKE YKCKVSNKALPAPIEKTISKAKGQPREPQVYTLPPSRDELTKNQVSLT CLVKGFYPSDIAVEWESNGQPENNYKTTPPVLDSDGSFFLYSKLTVD KSRWQQGNVFSCSVMHEALHNHYTQKSLSLSPG |
| 94 | Imgatuzumab (LC) | anti-EGFR: LC | DIQMTQSPSSLSASVGDRVTITCRASQGINNYLNWYQQKPGKAPK RLIYNTNNLQTGVPSRFSGSGSGTEFTLTISSLQPEDFATYYCLQHNS FPTFGQGTKLEIKRTVAAPSVFIFPPSDEQLKSGTASVVCLLNNFYPR EAKVQWKVDNALQSGNSQESVTEQDSKDSTYSLSSTLTLSKADYEK HKVYACEVTHQGLSSPVTKSFNRGEC |
| 95 | Necitumumab (HC) | anti-EGFR: HC | QVQLQESGPGLVKPSQTLSLTCTVSGGSISSGDYYWSWIRQPPGKG LEWIGYIYYSGSTDYNPSLKSRVTMSVDTSKNQFSLKVNSVTAADTA VYYCARVSIFGVGTFDYWGQGTLVTVSSASTKGPSVLPLAPSSKSTS GGTAALGCLVKDYFPEPVTVSWNSGALTSGVHTFPAVLQSSGLYSL SSVVTVPSSSLGTQTYICNVNHKPSNTKVDKRVEPKSCDKTHTCPPC PAPELLGGPSVFLFPPKPKDTLMISRTPEVTCVVVDVSHEDPEVKFN WYVDGVEVHNAKTKPREEQYNSTYRVVSVLTVLHQDWLNGKEYK CKVSNKALPAPIEKTISKAKGQPREPQVYTLPPSREEMTKNQVSLTC LVKGFYPSDIAVEWESNGQPENNYKTTPPVLDSDGSFFLYSKLTVDK SRWQQGNVFSCSVMHEALHNHYTQKSLSLSPGK |
| 96 | Necitumumab (LC) | anti-EGFR: LC | EIVMTQSPATLSLSPGERATLSCRASQSVSSYLAWYQQKPGQAPRL LIYDASNRATGIPARFSGSGSGTDFTLTISSLEPEDFAVYYCHQYGSTP LTFGGGTKAEIKRTVAAPSVFIFPPSDEQLKSGTASVVCLLNNFYPRE AKVQWKVDNALQSGNSQESVTEQDSKDSTYSLSSTLTLSKADYEKH KVYACEVTHQGLSSPVTKSFNRGEC |
| 97 | Rituximab (HC) | anti-CD20: HC | QVQLQQPGAELVKPGASVKMSCKASGYTFTSYNMHWVKQTPGR GLEWIGAIYPGNGDTSYNQKFKGKATLTADKSSSTAYMQLSSLTSE |

TABLE 4-continued

Amino Acid and Nucleic Acid Sequences

| SEQ ID NO: | Name | Description | Sequence |
|---|---|---|---|
| | | | DSAVYYCARSTYYGGDWYFNVWGAGTTVTVSAASTKGPSVFPLAP SSKSTSGGTAALGCLVKDYFPEPVTVSWNSGALTSGVHTFPAVLQS SGLYSLSSVVTVPSSSLGTQTYICNVNHKPSNTKVDKKVEPKSCDKT HTCPPCPAPELLGGPSVFLFPPKPKDTLMISRTPEVTCVVVDVSHED PEVKFNWYVDGVEVHNAKTKPREEQYNSTYRVVSVLTVLHQDWL NGKEYKCKVSNKALPAPIEKTISKAKGQPREPQVYTLPPSRDELTKN QVSLTCLVKGFYPSDIAVEWESNGQPENNYKTTPPVLDSDGSFFLYS KLTVDKSRWQQGNVFSCSVMHEALHNHYTQKSLSLSPGK |
| 98 | Rituximab (LC) | anti-CD20: LC | QIVLSQSPAILSASPGEKVTMTCRASSSVSYIHWFQQKPGSSPKPWI YATSNLASGVPVRFSGSGSGTSYSLTISRVEAEDAATYYCQQWTSNP PTFGGGTKLEIKRTVAAPSVFIFPPSDEQLKSGTASVVCLLNNFYPRE AKVQWKVDNALQSGNSQESVTEQDSKDSTYSLSSTLTLSKADYEKH KVYACEVTHQGLSSPVTKSFNRGEC |
| 99 | Ofatumumab (HC) | anti-CD20: Fab(H) | EVQLVESGGGLVQPGRSLRLSCAASGFTFNDYAMHWVRQAPGKG LEWVSTISWNSGSIGYADSVKGRFTISRDNAKKSLYLQMNSLRAED TALYYCAKDIQYGNYYYGMDVWGQGTTVTVSSASTKGPSVFPLAP GSSKSTSGGTAALGCLVKDYFPEPVTVSWNSGALTSGVHTFPAVLQS SGLYSLSSVVTVPSSSLGTQTYICNVNHKPSNTKVDKKVEP |
| 100 | Ofatumumab | anti-CD20: Fab(L) | EIVLTQSPATLSLSPGERATLSCRASQSVSSYLAWYQQKPGQAPRLLI YDASNRATGIPARFSGSGSGTDFTLTISSLEPEDFAVYYCQQRSNWP ITFGQGTRLEIKRTVAAPSVFIFPPSDEQLKSGTASVVCLLNNFYPRE AKVQWKVDNALQSGNSQESVTEQDSKDSTYSLSSTLTLSKADYEKH KVYACEVTHQGLSSPVTKSFNR |
| 101 | Obinutuzumab (HC) | anti-CD20: HC | QVQLVQSGAEVKKPGSSVKVSCKASGYAFSYSWINWVRQAPGQG LEWMGRIFPGDGDTDYNGKFKGRVTITADKSTSTAYMELSSLRSED TAVYYCARNVFDGYWLVYWGQGTLVTVSSASTKGPSVFPLAPSSKS TSGGTAALGCLVKDYFPEPVTVSWNSGALTSGVHTFPAVLQSSGLY SLSSVVTVPSSSLGTQTYICNVNHKPSNTKVDKKVEPKSCDKTHTCP PCPAPELLGGPSVFLFPPKPKDTLMISRTPEVTCVVVDVSHEDPEVK FNWYVDGVEVHNAKTKPREEQYNSTYRVVSVLTVLHQDWLNGKE YKCKVSNKALPAPIEKTISKAKGQPREPQVYTLPPSRDELTKNQVSLT CLVKGFYPSDIAVEWESNGQPENNYKTTPPVLDSDGSFFLYSKLTVD KSRWQQGNVFSCSVMHEALHNHYTQKSLSLSPGK |
| 102 | Obinutuzumab (LC) | anti-CD20: LC | DIVMTQTPLSLPVTPGEPASISCRSSKSLLHSNGITYLYWYLQKPGQS PQLLIYQMSNLVSGVPDRFSGSGSGTDFTLKISRVEAEDVGVYCAQ NLELPYTFGGGTKVEIKRTVAAPSVFIFPPSDEQLKSGTASVVCLLNN FYPREAKVQWKVDNALQSGNSQESVTEQDSKDSTYSLSSTLTLSKA DYEKHKVYACEVTHQGLSSPVTKSFNRGEC |
| 103 | Ibritumomab tiuxetan (HC) | anti-CD20: HC | QAYLQQSGAELVRPGASVKMSCKASGYTFTSYNMHWVKQTPRQG LEWIGAIYPGNGDTSYNQKFKGKATLTVDKSSSTAYMQLSSLTSEDS AVYFCARVVYYSNSYWYFDVWGTGTTVTVSAPSVYPLAPVCGDTT GSSVTLGCLVKGYFPEPVTLTWNSGSLSSGVHTFPAVLQSDLYTLSSS VTVTSSTWPSQSITCNVAHPASSTKVDKKIEPRGPTIKPCPPCKCPAP NLLGGPSVFIFPPKIKDVLMISLSPIVTCVVVDVSEDDPDVQISWFVN NVEVHTAQTQTHREDYNSTLRVVSALPIQHQDWMSGKEFKCKVN NKDLPAPIERTISKPKGSVRAPQVYVLPPPEEEMTKKQVTLTCMVTD FMPEDIYVEWTNNGKTELNYKNTEPVLDSDGSYFMYSKLRVEKKN WVERNSYSCSVVHEGLHNHHTTKSFSR |
| 104 | Ibritumomab tiuxetan (LC) | anti-CD20: LC | QIVLSQSPAILSASPGEKVTMTCRASSSVSYMHWYQQKPGSSPKP WIYAPSNLASGVPARFSGSGSGTSYSLTISRVEAEDAATYYCQQWSF NPPTFGAGTKLELKRADAAPTVFIFPPSDEQLKSGTASVVCLLNNFY PREAKVQWKVDNALQSGNSQESVTEQDSKDSTYSLSSTLTLSKADY EKHKVYACEVTHQGLSSPVTKSFN |
| 105 | Ocaratuzumab (HC) | anti-CD20: HC | EVQLVQSGAEVKKPGESLKISCKGSGRTFTSYNMHWVRQMPGKGL EWMGAIYPLTGDTSYNQKSKLQVTISADKSISTAYLQWSSLKASDTA MYYCARSTYVGGDWQFDVWGKGTTVTVSSASTKGPSVFPLAPSSK STSGGTAALGCLVKDYFPEPVTVSWNSGALTSGVHTFPAVLQSSGL YSLSSVVTVPSSSLGTQTYICNVNHKPSNTKVDKKVEPKSCDKTHTC PPCPAPELLGGPSVFLFPPKIKDTLMISRTPEVTCVVVDVSHEDPEVK FNWYVDGVEVHNAKTKPREEQYNSTYRVVSVLTVLHQDWLNGKE YKCKVSNKALPAPIEKTISKAKGQPREPQVYTLPPSRDELTKNQVSLT CLVKGFYPSDIAVEWESNGQPENNYKTTPPVLDSDGSFFLYSKLTVD KSRWQQGNVFSCSVMHEALHNHYTQKSLSLSPG |
| 106 | Ocaratuzumab (LC) | anti-CD20: LC | EIVLTQSPGTLSLSPGERATLSCRASSSVPYIHWYQQKPGQAPRLLIY ATSALASGIPDRFSGSGSGTDFTLTISRLEPEDFAVYYCQQWLSNPPT |

TABLE 4-continued

Amino Acid and Nucleic Acid Sequences

| SEQ ID NO: | Name | Description | Sequence |
|---|---|---|---|
| | | | FGQGTKLEIKRTVAAPSVFIFPPSDEQLKSGTASVVCLLNNFYPREAK VQWKVDNALQSGNSQESVTEQDSKDSTYSLSSTLTLSKADYEKHKV YACEVTHQGLSSPVTKSFNRGEC |
| 107 | Ocrelizumab (HC) | anti-CD20: HC | EVQLVESGGGLVQPGGSLRLSCAASGYTFTSYNMHWVRQAPGKG LEWVGAIYPGNGDTSYNQKFKGRFTISVDKSKNTLYLQMNSLRAED TAVYYCARVVYYSNSYWYFDVWGQGTLVTVSSASTKGPSVFPLAPS SKSTSGGTAALGCLVKDYFPEPVTVSWNSGALTSGVHTFPAVLQSS GLYSLSSVVTVPSSSLGTQTYICNVNHKPSNTKVDKKVEPKSCDKTH TCPPCPAPELLGGPSVFLFPPKPKDTLMISRTPEVTCVVVDVSHEDP EVKFNWYVDGVEVHNAKTKPREEQYNSTYRVVSVLTVLHQDWLN GKEYKCKVSNKALPAPIEKTISKAKGQPREPQVYTLPPSREEMTKNQ VSLTCLVKGFYPSDIAVEWESNGQPENNYKTTPPVLDSDGSFFLYSK LTVDKSRWQQGNVFSCSVMHEALHNHYTQKSLSLSPGK |
| 108 | Ocrelizumab (LC) | anti-CD20: LC | DIQMTQSPSSLSASVGDRVTITCRASSSVSYMHWYQQKPGKAPKP LIYAPSNLASGVPSRFSGSGSGTDFTLTISSLQPEDFATYYCQQWSFN PPTFGQGTKVEIKRTVAAPSVFIFPPSDEQLKSGTASVVCLLNNFYPR EAKVQWKVDNALQSGNSQESVTEQDSKDSTYSLSSTLTLSKADYEK HKVYACEVTHQGLSSPVTKSFNRGEC |
| 109 | Tositumomab I-131 (HC) | anti-CD20: HC | QAYLQQSGAELVRPGASVKMSCKASGYTFTSYNMHWVKQTPRQG LEWIGAIYPGNGDTSYNQKFKGKATLTVDKSSSTAYMQLSSLTSEDS AVYFCARVVYYSNSYWYFDVWGTGTTVTVSGPSVFPLAPSSKSTSG GTAALGCLVKDYFPEPVTVSWNSGALTSGVHTFPAVLQSSGLYSLSS VVTVPSSSLGTQTYICNVNHKPSNTKVDKKAEPKSCDKTHTCPPCPA PELLGGPSVFLFPPKPKDTLMISRTPEVTCVVVDVSHEDPEVKFNWY VDGVEVHNAKTKPREEQYNSTYRVVSVLTVLHQDWLNGKEYKCKV SNKALPAPIEKTISKAKGQPREPQVYTLPPSRDELTKNQVSLTCLVKG FYPSDIAVEWESNGQPENNYKTTPPVLDSDGSFFLYSKLTVDKSRW QQGNVFSCSVMHEALHNHYTQKSLSLSPGK |
| 110 | Tositumomab I-131 (LC) | anti-CD20: LC | QIVLSQSPAILSASPGEKVTMTCRASSSVSYMHWYQQKPGSSPKP WIYAPSNLASGVPARFSGSGSGTSYSLTISRVEAEDAATYYCQQWSF NPPTFGAGTKLELKRTVAAPSVFIFPPSDEQLKSGTASVVCLLNNFYP REAKVQWKVDNALQSGNSQESVTEQDSKDSTYSLSSTLTLSKADYE KHKVYACEVTHQGLSSPVTKSFNR |
| 111 | Ublituximab (HC) | anti-CD20: HC | QAYLQQSGAELVRPGASVKMSCKASGYTFTSYNMHWVKQTPRQG LEWIGGIYPGNGDTSYNQKFKGKATLTVGKSSSTAYMQLSSLTSEDS AVYFCARYDYNYAMDYWGQGTSVTVSSASTKGPSVFPLAPSSKSTS GGTAALGCLVKDYFPEPVTVSWNSGALTSGVHTFPAVLQSSGLYSL SSVVTVPSSSLGTQTYICNVNHKPSNTKVDKKVEPKSCDKTHTCPPC PAPELLGGPSVFLFPPKPKDTLMISRTPEVTCVVVDVSHEDPEVKFN WYVDGVEVHNAKTKPREEQYNSTYRVVSVLTVLHQDWLNGKEYK CKVSNKALPAPIEKTISKAKGQPREPQVYTLPPSRDELTKNQVSLTCL VKGFYPSDIAVEWESNGQPENNYKTTPPVLDSDGSFFLYSKLTVDKS RWQQGNVFSCSVMHEALHNHYTQKSLSLSPGK |
| 112 | Ublituximab (LC) | anti-CD20: LC | QIVLSQSPAILSASPGEKVTMTCRASSSVSYMHWYQQKPGSSPKP WIYATSNLASGVPARFSGSGSGTSYSFTISRVEAEDAATYYCQQWTF NPPTFGGGTRLEIKRTVAAPSVFIFPPSDEQLKSGTASVVCLLNNFYP REAKVQWKVDNALQSGNSQESVTEQDSKDSTYSLSSTLTLSKADYE KHKVYACEVTHQGLSSPVTKSFNRGEC |
| 113 | Veltuzumab (HC) | anti-CD20: HC | QVQLQQSGAEVKKPGSSVKVSCKASGYTFTSYNMHWVKQAPGQ GLEWIGAIYPGNGDTSYNQKFKGKATLTADESTNTAYMELSSLRSE DTAFYYCARSTYYGGDWYFDVWGQGTTVTVSSASTKGPSVFPLAP SSKSTSGGTAALGCLVKDYFPEPVTVSWNSGALTSGVHTFPAVLQS SGLYSLSSVVTVPSSSLGTQTYICNVNHKPSNTKVDKRVEPKSCDKT HTCPPCPAPELLGGPSVFLFPPKPKDTLMISRTPEVTCVVVDVSHED PEVKFNWYVDGVEVHNAKTKPREEQYNSTYRVVSVLTVLHQDWL NGKEYKCKVSNKALPAPIEKTISKAKGQPREPQVYTLPPSREEMTKN QVSLTCLVKGFYPSDIAVEWESNGQPENNYKTTPPVLDSDGSFFLYS KLTVDKSRWQQGNVFSCSVMHEALHNHYTQKSLSLSPGK |
| 114 | Veltuzumab (LC) | anti-CD20: LC | DIQLTQSPSSLSASVGDRVTMTCRASSSVSYIHWFQQKPGKAPKP WIYATSNLASGVPRFSGSGSGTDYTFTISSLQPEDIATYYCQQWTS NPPTFGGGTKLEIKRTVAAPSVFIFPPSDEQLKSGTASVVCLLNNFYP REAKVQWKVDNALQSGNSQESVTEQDSKDSTYSLSSTLTLSKADYE KHKVYACEVTHQGLSSPVTKSFNRGEC |
| 115 | Transtuzumab (HC) | anti-HER2: HC | EVQLVESGGGLVQPGGSLRLSCAASGFNIKDTYIHWVRQAPGKGLE WVARIYPTNGYTRYADSVKGRFTISADTSKNTAYLQMNSLRAEDTA |

TABLE 4-continued

Amino Acid and Nucleic Acid Sequences

| SEQ ID NO: | Name | Description | Sequence |
|---|---|---|---|
| | | | VYYCSRWGGDGFYAMDYWGQGTLVTVSSASTKGPSVFPLAPSSKS TSGGTAALGCLVKDYFPEPVTVSWNSGALTSGVHTFPAVLQSSGLY SLSSVVTVPSSSLGTQTYICNVNHKPSNTKVDKKVEPPKSCDKTHTC PPCPAPELLGGPSVFLFPPKPKDTLMISRTPEVTCVVVDVSHEDPEV KFNWYVDGVEVHNAKTKPREEQYNSTYRVVSVLTVLHQDWLNGK EYKCKVSNKALPAPIEKTISKAKGQPREPQVYTLPPSRDELTKNQVSL TCLVKGFYPSDIAVEWESNGQPENNYKTTPPVLDSDGSFFLYSKLTV DKSRWQQGNVFSCSVMHEALHNHYTQKSLSLSPGK |
| 116 | Transtuzumab (LC) | anti-HER2: LC | DIQMTQSPSSLSASVGDRVTITCRASQDVNTAVAWYQQKPGKAPK LLIYSASFLYSGVPSRFSGSRSGTDFTLTISSLQPEDFATYYCQQHYTT PPTFGQGTKVEIKRTVAAPSVFIFPPSDEQLKSGTASVVCLLNNFYPR EAKVQWKVDNALQSGNSQESVTEQDSKDSTYSLSSTLTLSKADYEK HKVYACEVTHQGLSSPVTKSFNRGEC |
| 117 | Pertuzumab (HC) | anti-HER2: HC | EVQLVESGGGLVQPGGSLRLSCAASGFTFTDYTMDWVRQAPGKG LEWVADVNPNSGGSIYNQRFKGRFTLSVDRSKNTLYLQMNSLRAE DTAVYYCARNLGPSFYFDYWGQGTLVTVSSASTKGPSVFPLAPSSKS TSGGTAALGCLVKDYFPEPVTVSWNSGALTSGVHTFPAVLQSSGLY SLSSVVTVPSSSLGTQTYICNVNHKPSNTKVDKKVEPKSCDKTHTCP PCPAPELLGGPSVFLFPPKPKDTLMISRTPEVTCVVVDVSHEDPEVK FNWYVDGVEVHNAKTKPREEQYNSTYRVVSVLTVLHQDWLNGKE YKCKVSNKALPAPIEKTISKAKGQPREPQVYTLPPSREEMTKNQVSL TCLVKGFYPSDIAVEWESNGQPENNYKTTPPVLDSDGSFFLYSKLTV DKSRWQQGNVFSCSVMHEALHNHYTQKSLSLSPG |
| 118 | Pertuzumab (LC) | anti-HER2: LC | DIQMTQSPSSLSASVGDRVTITCKASQDVSIGVAWYQQKPGKAPKL LIYSASYRYTGVPSRFSGSGSGTDFTLTISSLQPEDFATYYCQQYYIYP YTFGQGTKVEIKRTVAAPSVFIFPPSDEQLKSGTASVVCLLNNFYPRE AKVQWKVDNALQSGNSQESVTEQDSKDSTYSLSSTLTLSKADYEKH KVYACEVTHQGLSSPVTKSFNRGEC |
| 119 | Margetuximab (HC) | anti-HER2: HC | QVQLQQSGPELVKPGASLKLSCTASGFNIKDTYIHWVKQRPEQGLE WIGRIYPTNGYTRYDPKFQDKATITADTSSNTAYLQVSRLTSEDTAV YYCSRWGGDGFYAMDYWGQGASVTVSSASTKGPSVFPLAPSSKST SGGTAALGCLVKDYFPEPVTVSWNSGALTSGVHTFPAVLQSSGLYS LSSVVTVPSSSLGTQTYICNVNHKPSNTKVDKRVEPKSCDKTHTCPP CPAPELVGGPSVFLLPPKPKDTLMISRTPEVTCVVVDVSHEDPEVKF NWYVDGVEVHNAKTKPPEEQYNSTLRVVSVLTVLHQDWLNGKEY KCKVSNKALPAPIEKTISKAKGQPREPQVYTLPPSRDELTKNQVSLTC LVKGFYPSDIAVEWESNGQPENNYKTTPLVLDSDGSFFLYSKLTVDK SRWQQGNVFSCSVMHEALHNHYTQKSLSLSPGK |
| 120 | Margetuximab (LC) | anti-HER2: LC | DIVMTQSHKFMSTSVGDRVSITCKASQDVNTAVAWYQQKPGHSP KLLIYSASFRYTGVPDRFTGSRSGTDFTFTISSVQAEDLAVYYCQQHY TTPPTFGGGTKVEIKRTVAAPSVFIFPPSDEQLKSGTASVVCLLNNFY PREAKVQWKVDNALQSGNSQESVTEQDSKDSTYSLSSTLTLSKADY EKHKVYACEVTHQGLSSPVTKSFNRGEC |
| 121 | Atezolizumab (HC) | anti-PDL1: HC | EVQLVESGGGLVQPGGSLRLSCAASGFTFSDSWIHWVRQAPGKGL EWVAWISPYGGSTYYADSVKGRFTISADTSKNTAYLQMNSLRAEDT AVYYCARRHWPGGFDYWGQGTLVTVSSASTKGPSVFPLAPSSKST SGGTAALGCLVKDYFPEPVTVSWNSGALTSGVHTFPAVLQSSGLYS LSSVVTVPSSSLGTQTYICNVNHKPSNTKVDKKVEPKSCDKTHTCPP CPAPELLGGPSVFLFPPKPKDTLMISRTPEVTCVVVDVSHEDPEVKF NWYVDGVEVHNAKTKPREEQYASTYRVVSVLTVLHQDWLNGKEY KCKVSNKALPAPIEKTISKAKGQPREPQVYTLPPSREEMTKNQVSLT CLVKGFYPSDIAVEWESNGQPENNYKTTPPVLDSDGSFFLYSKLTVD KSRWQQGNVFSCSVMHEALHNHYTQKSLSLSPGK |
| 122 | Atezolizumab (LC) | anti-PDL1: LC | DIQMTQSPSSLSASVGDRVTITCRASQDVSTAVAWYQQKPGKAPK LLIYSASFLYSGVPSRFSGSGSGTDFTLTISSLQPEDFATYYCQQYLYH PATFGQGTKVEIKRTVAAPSVFIFPPSDEQLKSGTASVVCLLNNFYPR EAKVQWKVDNALQSGNSQESVTEQDSKDSTYSLSSTLTLSKADYEK HKVYACEVTHQGLSSPVTKSFNRGEC |
| 123 | Durvalumab (HC) | anti-PDL1: HC | EVQLVESGGGLVQPGGSLRLSCAASGFTFSRYWMSWVRQAPGKG LEWVANIKQDGSEKYYVDSVKGRFTISRDNAKNSLYLQMNSLRAED TAVYYCAREGGWFGELAFDYWGQGTLVTVSSASTKGPSVFPLAPSS KSTSGGTAALGCLVKDYFPEPVTVSWNSGALTSGVHTFPAVLQSSG LYSLSSVVTVPSSSLGTQTYICNVNHKPSNTKVDKRVEPKSCDKTHTC PPCPAPEFEGGPSVFLFPPKPKDTLMISRTPEVTCVVVDVSHEDPEV KFNWYVDGVEVHNAKTKPREEQYNSTYRVVSVLTVLHQDWLNGK EYKCKVSNKALPASIEKTISKAKGQPREPQVYTLPPSREEMTKNQVS |

TABLE 4-continued

Amino Acid and Nucleic Acid Sequences

| SEQ ID NO: | Name | Description | Sequence |
|---|---|---|---|
| | | | LTCLVKGFYPSDIAVEWESNGQPENNYKTTPPVLDSDGSFFLYSKLT VDKSRWQQGNVFSCSVMHEALHNHYTQKSLSLSPGK |
| 124 | Durvalumab (LC) | anti-PDL1: LC | EIVLTQSPGTLSLSPGERATLSCRASQRVSSSYLAWYQQKPGQAPRL LIYDASSRATGIPDRFSGSGSGTDFTLTISRLEPEDFAVYYCQQYGSLP WTFGQGTKVEIKRTVAAPSVFIFPPSDEQLKSGTASVVCLLNNFYPR EAKVQWKVDNALQSGNSQESVTEQDSKDSTYSLSSTLTLSKADYEK HKVYACEVTHQGLSSPVTKSFNRGEC |
| 125 | huSIRPαV1 (A27I) | huSIRPαV1 (V1 domain with A27I) | EEELQVIQPDKSVLVAAGETATLRCTITSLIPVGPIQWFRGAGPGREL IYNQKEGHFPRVTTVSDLTKRNNMDFSIRIGNITPADAGTYYCVKFR KGSPDDVEFKSGAGTELSVR |
| 126 | huSIRPαV2 (V27I) | huSIRPαV2 (V2 domain with V27I) | EEELQVIQPDKSVSVAAGESAILHCTITSLIPVGPIQWFRGAGPARELI YNQKEGHFPRVTTVSESTKRENMDFSISISNITPADAGTYYCVKFRK GSPDTEFKSGAGTELSVR |
| 127 | huSIRPαV1 (H56P) | huSIRPαV1 (V1 domain with H56P) | EEELQVIQPDKSVLVAAGETATLRCTATSLIPVGPIQWFRGAGPGRE LIYNQKEGPFPRVTTVSDLTKRNNMDFSIRIGNITPADAGTYYCVKF RKGSPDDVEFKSGAGTELSVR |
| 128 | huSIRPαV2 (H56P) | huSIRPαV2 (V2 domain with H56P) | EEELQVIQPDKSVSVAAGESAILHCTVTSLIPVGPIQWFRGAGPARE LIYNQKEGPFPRVTTVSESTKRENMDFSISISNITPADAGTYYCVKFR KGSPDTEFKSGAGTELSVR |
| 129 | huSIRPαV1 (V6I) | huSIRPαV1 (V1 domain with V6I) | EEELQIIQPDKSVLVAAGETATLRCTATSLIPVGPIQWFRGAGPGREL IYNQKEGHFPRVTTVSDLTKRNNMDFSIRIGNITPADAGTYYCVKFR KGSPDDVEFKSGAGTELSVR |
| 130 | huSIRPαV2 (V6I) | huSIRPαV2 (V2 domain with V6I) | EEELQIIQPDKSVSVAAGESAILHCTVTSLIPVGPIQWFRGAGPARELI YNQKEGHFPRVTTVSESTKRENMDFSISISNITPADAGTYYCVKFRK GSPDTEFKSGAGTELSVR |
| 131 | huSIRPαV1 (I31T) | huSIRPαV1 (V1 domain with I31T) | EEELQVIQPDKSVLVAAGETATLRCTATSLTPVGPIQWFRGAGPGR ELIYNQKEGHFPRVTTVSDLTKRNNMDFSIRIGNITPADAGTYYCVK FRKGSPDDVEFKSGAGTELSVR |
| 132 | huSIRPαV2 (I31T) | huSIRPαV2 (V2 domain with I31T) | EEELQVIQPDKSVSVAAGESAILHCTVTSLTPVGPIQWFRGAGPARE LIYNQKEGHFPRVTTVSESTKRENMDFSISISNITPADAGTYYCVKFR KGSPDTEFKSGAGTELSVR |
| 133 | huSIRPαV1 (I31R) | huSIRPαV1 (V1 domain with I31R) | EEELQVIQPDKSVLVAAGETATLRCTATSLRPVGPIQWFRGAGPGR ELIYNQKEGHFPRVTTVSDLTKRNNMDFSIRIGNITPADAGTYYCVK FRKGSPDDVEFKSGAGTELSVR |
| 134 | huSIRPαV2 (I31R) | huSIRPαV2 (V2 domain with I31R) | EEELQVIQPDKSVSVAAGESAILHCTVTSLRPVGPIQWFRGAGPARE LIYNQKEGHFPRVTTVSESTKRENMDFSISISNITPADAGTYYCVKFR KGSPDTEFKSGAGTELSVR |
| 135 | huSIRPαV1 (Q37W) | huSIRPαV1 (V1 domain with Q37W) | EEELQVIQPDKSVLVAAGETATLRCTATSLIPVGPIWWFRGAGPGR ELIYNQKEGHFPRVTTVSDLTKRNNMDFSIRIGNITPADAGTYYCVK FRKGSPDDVEFKSGAGTELSVR |
| 136 | huSIRPαV2 (Q37W) | huSIRPαV2 (V2 domain with Q37W) | EEELQVIQPDKSVSVAAGESAILHCTVTSLIPVGPIWWFRGAGPARE LIYNQKEGHFPRVTTVSESTKRENMDFSISISNITPADAGTYYCVKFR KGSPDTEFKSGAGTELSVR |
| 137 | huSIRPαV1 (L66Q) | huSIRPαV1 (V1 domain with L66Q) | EEELQVIQPDKSVLVAAGETATLRCTATSLIPVGPIQWFRGAGPGRE LIYNQKEGHFPRVTTVSDQTKRNNMDFSIRIGNITPADAGTYYCVKF RKGSPDDVEFKSGAGTELSVR |
| 138 | huSIRPαV2 (S66Q) | huSIRPαV2 (V2 domain with S66Q) | EEELQVIQPDKSVSVAAGESAILHCTVTSLIPVGPIQWFRGAGPARE LIYNQKEGHFPRVTTVSEQTKRENMDFSISISNITPADAGTYYCVKFR KGSPDTEFKSGAGTELSVR |
| 139 | huSIRPαV1 (Q37H) | huSIRPαV1 (V1 domain with Q37H) | EEELQVIQPDKSVLVAAGETATLRCTATSLIPVGPIHWFRGAGPGRE LIYNQKEGHFPRVTTVSDLTKRNNMDFSIRIGNITPADAGTYYCVKF RKGSPDDVEFKSGAGTELSVR |
| 140 | huSIRPαV2 (Q37H) | huSIRPαV2 (V2 domain with Q37H) | EEELQVIQPDKSVSVAAGESAILHCTVTSLIPVGPIHWFRGAGPAREL IYNQKEGHFPRVTTVSESTKRENMDFSISISNITPADAGTYYCVKFRK GSPDTEFKSGAGTELSVR |

TABLE 4-continued

Amino Acid and Nucleic Acid Sequences

| SEQ ID NO: | Name | Description | Sequence |
|---|---|---|---|
| 141 | huSIRPαV1 (E54P) | huSIRPαV1 (V1 domain with E54P) | EEELQVIQPDKSVLVAAGETATLRCTATSLIPVGPIQWFRGAGPGRE LIYNQKPGHFPRVTTVSDLTKRNNMDFSIRIGNITPADAGTYYCVKF RKGSPDDVEFKSGAGTELSVR |
| 142 | huSIRPαV2 (E54P) | huSIRPαV2 (V2 domain with E54P) | EEELQVIQPDKSVSVAAGESAILHCTVTSLIPVGPIQWFRGAGPARE LIYNQKPGHFPRVTTVSESTKRENMDFSISISNITPADAGTYYCVKFR KGSPDTEFKSGAGTELSVR |
| 143 | huSIRPαV1 (M72R) | huSIRPαV1 (V1 domain with M72R) | EEELQVIQPDKSVLVAAGETATLRCTATSLIPVGPIQWFRGAGPGRE LIYNQKEGHFPRVTTVSDLTKRNNRDFSIRIGNITPADAGTYYCVKFR KGSPDDVEFKSGAGTELSVR |
| 144 | huSIRPαV2 (M27R) | huSIRPαV2 (V2 domain with M72R) | EEELQVIQPDKSVSVAAGESAILHCTVTSLIPVGPIQWFRGAGPARE LIYNQKEGHFPRVTTVSESTKRENRDFSISISNITPADAGTYYCVKFRK GSPDTEFKSGAGTELSVR |
| 145 | anti-CD47-LC | B6H12(VL)-CK | <u>GATATTGTGATGACTCAGTCTCCAGCCACCCTGTCTGTGACTCCA GGAGATAGAGTCTCTCTTTCCTGCAGGGCCAGCCAGACTATTAGee CGACTACTTACACTGGTATCAACAAAAATCACATGAGTCTCcaac GCTTCTCATCAAATTTGCTTCCCAATCCATTTCTGGGATCCCCTCCee AGGTTCAGTGGCAGTGGATCAGGCTCAGATTTCACTCTCAGTATee CAACAGTGTGGAACCTGAAGATGTTGGAGTGTATTACTGTCAAAee ATGGTCACGGCTTTCCTCGGACGTTCGGTGGAGGGACCAAGCTGee GAAATAAAACGTACGGTGGCTGCACCATCTGTCTTCATCTTCCCG</u> CCATCTGATGAGCAGCTTAAGTCTGGAACTGCCTCTGTTGTGTGC CTGCTGAATAACTTCTATCCCAGAGAGGCCAAAGTACAGTGGAA GGTGGATAACGCCCTCCAATCGGGTAACTCCCAGGAGAGTGTCA CAGAGCAGGACAGCAAGGACAGCACCTACAGCCTCAGCAGCAC CCTGACGCTGAGCAAAGCAGACTACGAGAAACACAAAGTCTACG CCTGCGAAGTCACCCATCAGGGCCTGAGCTCGCCCGTCACAAAG AGCTTCAACAGGGGAGAGTGT |
| 146 | anti-CD47-LC | B6H12(VL)-CK | <u>DIVITQSPATLSVTPGDRVSLSCRASQTISDYLHWYQQKSHESPRLLI KFASQSISGIPSRFSGSGSGSDFTLSINSVEPEDVGVYYCQNGHGFPR TFGGGTKLEIKRTVAAPSVFIFPPSDEQLKSGTASVVCLLNNFYPREA KVQWKVDNALQSGNSQESVTEQDSKDSTYSLSSTLTLSKADYEKHK VYACEVTHQGLSSPVTKSFNRGEC</u> |
| 147 | anti-CD47-huIgG1 | B6H12(VH)-ch1(huigg1m3)-HINGE(HUIGG1M3)-(huIgG1m3: ch2-CH3) | GAGGTGCAGCTGGTGGAGTCTGGGGGAGACTTAGTGAAGCCTG GAGGGTCCCTGAAACTCTCCTGTGCAGCCTCTGGATTCACTTTCA GTGGCTATGGCATGTCTTGGGTTCGCCAGACTCCAGACAAGAGG CTGGAGTGGGTCGCAACCATTACTAGTGGTGGTACTTACACCTA CTATCCAGACAGTGTGAAGGGGCGATTCACCATCTCCAGAGACA ATGCCAAGAACACCCTGTACCTGCAAATAGACAGTCTGAAGTCT GAGGATACAGCCATATATTTCTGTGCAAGATCCCTCGCGGGAAA TGCTATGGACTACTGGGGTCAAGGGACCAGCGTCACCGTCTCCT CAgctagcaccaagggcccatcggtcttccccctggcaccctcctccaagagcacct ctggggggcacagcggccctgggctgcctggtcaaggactacttccccgaaccggtg acggtgtcgtggaactcaggcgccctgaccagcggcgtgcacaccttcccggctgtc ctacagtcctcaggactctactccctcagcagcgtggtgaccgtgccctccagcagct tgggcacccagacctacatctgcaacgtgaatcacaagcccagcaacaccaaggtg gacaagagagtt<i>GAGCCCAAATCTTGTGACAAAACTCACACATGCCC ACCGTGCCCAGCACCTGAACTCCTGGGG</i>gacacgtcagtcttcctcttcc cccaaaacccaaggacaccctcatgatctcccggacccctgaggtcacatgcgt ggtggtggacgtgagccacgaagaccctgaggtcaagttcaactggtacgtgg acggcgtggaggtgcataatgccaagacaaagccgcgggaggagcagtaca acagcacgtaccgtgtggtcagcgtcctcaccgtcctgcaccaggactggctga atggcaaggagtacaagtgcaaggtctccaacaaagccctcccagcccccatc gagaaaaccatctccaaagccaaa<u>GGGCAGCCCCGAGAACCACAGGT GTACACCCTGCCCCCATCCCGGGAGGAGATGACCAAGAACCAGG TCAGCCTGACCTGCCTGGTCAAAGGCTTCTATCCCAGCGACATCG CCGTGGAGTGGGAGAGCAATGGGCAGCCGGAGAACAACTACAA GACCACGCCTCCCGTGCTGGACTCCGACGGCTCCTTCTTCCTCTA TAGCAAGCTCACCGTGGACAAGAGCAGGTGGCAGCAGGGGAAC GTCTTCTCATGCTCCGTGATGCATGAGGCTCTGCACAACCACTAC ACGCAGAAGAGCCTCTCCCTGTCCCCGGGTAAA</u> |
| 148 | anti-CD47-huIgG1 | B6H12(VH)-ch1(huigg1m3)-HINGE(HUIGG1M3)-(huIgG1m3: ch2-CH3) | EVQLQESGGDLVKPGGSLKLSCAASGFTFSGYGMSWVRQTPDKRL EWVATITSGGTYTYYPDSVKGRFTISRDNAKNTLYLQIDSLKSEDTAI YFCARSLAGNAMDYWGQGTTVTVSSastkgpsvflplapsskstsggtaal gclvkdyfpepvtvswnsgaltsgvhtfpavlqssglyslssvvtvpssslgtqtylc nvnhkpsntkvdkrv<i>EPKSCDKTHTCPPCPAPELLG</i>gpsvflfppkpkdtl misrtpevtcvvvdvshedpevkfnwyvdgvevhnaktkpreeqynstyrvvs vltvlhqdwlngkeykckvsnkalpapiektis<u>KAKGQPREPQVYTLPPSRE</u> |

TABLE 4-continued

Amino Acid and Nucleic Acid Sequences

| SEQ ID NO: | Name | Description | Sequence |
|---|---|---|---|
| | | | EMTKNQVSLTCLVKGFYPSDIAVEWESNGQPENNYKTTPPVLDSD<br>GSFFLYSKLTVDKSRWQQGNVFSCSVMHEALHNHYTQKSLSLSPGK |
| 149 | anti-EGFR-huIgG1-SIRPαV2(1D4) | C225(VH)-ch1(huigg1m3)-HINGE(HUIGG1M3-)(huIgG1m3: ch2-CH3)-a-(g4s)x4-huSIRPa(V2: 1D4) | QVQLKQSGPGLVQPSQSLSITCTVSGFSLTNYGVHWVRQSPGKGLE<br>WLGVIWSGGNTDYNTPFTSRLSINKDNSKSQVFFKMNSLQSNDTAI<br>YYCARALTYYDYEFAYWGQGTLVTVSAastkgpsvfplapsskstsggta<br>algclvkdyfpepvtvswnsngaltsgvhtfpavlqssglyslssvvtvpssslgtqty<br>icnvnhkpsntkvdkrvEPKSCDKTHTCPPCPAPELLGgpsvflfppkpkdt<br>lmisrtpevtcvvvdvshedpevkfnwyvdgvevhnaktkpreeqynstyrvv<br>svltvlhqdwlngkeykckvsnkalpapiektiskakGQPREPQVYTLPPSR<br>EEMTKNQVSLTCLVKGFYPSDIAVEWESNGQPENNYKTTPPVLDSD<br>GSFFLYSKLTVDKSRWQQGNVFSCSVMHEALHNHYTQKSLSLSPG<br>AGGGGSGGGGSGGGGSGGGGSEEELQVIQPDKSVSVAAGESAIL<br>HCTITSLIPVGPIQWFRGAGPARELIYNQREGHFPRVTTVSETTRRE<br>NMDFSISISNITPADAGTYYCVKFRKGSPDTEVKSGAGTELSVR |
| 150 | anti-EGFR-huIgG1-SIRPαV2(6Ang) | C225(VH)-ch1(huigg1lm3)-HINGE(HUIGG1M3-)(huIgG1m3: ch2-CH3)-a-(g4s)x4-huSIRPa(V2: 6Ang) | QVQLKQSGPGLVQPSQSLSITCTVSGFSLTNYGVHWVRQSPGKGLE<br>WLGVIWSGGNTDYNTPFTSRLSINKDNSKSQVFFKMNSLQSNDTAI<br>YYCARALTYYDYEFAYWGQGTLVTVSAastkgpsvfplapsskstsggta<br>algclvkdyfpepvtvswnsngaltsgvhtfpavlqssglyslssvvtvpssslgtqty<br>icnvnhkpsntkvdkrvEPKSCDKTHTCPPCPAPELLGgpsvflfppkpkdt<br>lmisrtpevtcvvvdvshedpevkfnwyvdgvevhnaktkpreeqynstyrvv<br>svltvlhqdwlngkeykckvsnkalpapiektiskakGQPREPQVYTLPPSR<br>EEMTKNQVSLTCLVKGFYPSDIAVEWESNGQPENNYKTTPPVLDSD<br>GSFFLYSKLTVDKSRWQQGNVFSCSVMHEALHNHYTQKSLSLSPG<br>AGGGGSGGGGSGGGGSGGGGSEEELQVIQPDKSVSVAAGESAIL<br>HCTVTVSLTPVGPIQWFRGAGPARELIYNQREGHFPRVTTVSETTRR<br>ENMDFSISISNITPADAGTYYCVKFRKGSPDTEFKSGAGTELSVR |
| 151 | anti-EGFR-huIgG1-SIRPαV2(8Ang) | C225(VH)-ch1(huigg1m3)-HINGE(HUIGG1M3-)(huIgG1m3: ch2-CH3)-a-(g4s)x4-huSIRPa(V2: 8Ang) | QVQLKQSGPGLVQPSQSLSITCTVSGFSLTNYGVHWVRQSPGKGLE<br>WLGVIWSGGNTDYNTPFTSRLSINKDNSKSQVFFKMNSLQSNDTAI<br>YYCARALTYYDYEFAYWGQGTLVTVSAastkgpsvfplapsskstsggta<br>algclvkdyfpepvtvswnsngaltsgvhtfpavlqssglyslssvvtvpssslgtqty<br>icnvnhkpsntkvdkrvEPKSCDKTHTCPPCPAPELLGgpsvflfppkpkdt<br>lmisrtpevtcvvvdvshedpevkfnwyvdgvevhnaktkpreeqynstyrvv<br>svltvlhqdwlngkeykckvsnkalpapiektiskakGQPREPQVYTLPPSR<br>EEMTKNQVSLTCLVKGFYPSDIAVEWESNGQPENNYKTTPPVLDSD<br>GSFFLYSKLTVDKSRWQQGNVFSCSVMHEALHNHYTQKSLSLSPG<br>AGGGGSGGGGSGGGGSGGGGSEEEVQVIQPDKSVSVAAGESAIL<br>HCTITSLTPVGPIQWFRGAGPARELIYNQRGHFPRVTTVSETTRR<br>ENMDFSISISNITPADAGTYYCVKLRKGSPDTEFKSGAGTELSVR |
| 152 | anti-EGFR-huIgG1-SIRPαV2(V6I) | C225(VH)-ch1(huigg1m3)-HINGE(HUIGG1M3-)(huIgG1m3: ch2-CH3)-a-(g4s)x4-huSIRPa(V2: V6I) | QVQLKQSGPGLVQPSQSLSITCTVSGFSLTNYGVHWVRQSPGKGLE<br>WLGVIWSGGNTDYNTPFTSRLSINKDNSKSQVFFKMNSLQSNDTAI<br>YYCARALTYYDYEFAYWGQGTLVTVSAastkgpsvfplapsskstsggta<br>algclvkdyfpepvtvswnsngaltsgvhtfpavlqssglyslssvvtvpssslgtqty<br>icnvnhkpsntkvdkrvEPKSCDKTHTCPPCPAPELLGgpsvflfppkpkdt<br>lmisrtpevtcvvvdvshedpevkfnwyvdgvevhnaktkpreeqynstyrvv<br>svltvlhqdwlngkeykckvsnkalpapiektiskakGQPREPQVYTLPPSR<br>EEMTKNQVSLTCLVKGFYPSDIAVEWESNGQPENNYKTTPPVLDSD<br>GSFFLYSKLTVDKSRWQQGNVFSCSVMHEALHNHYTQKSLSLSPG<br>AGGGGSGGGGSGGGGSGGGGSEEELQIIQPDKSVSVAAGESAILH<br>CTVTSLIPVGPIQWFRGAGPARELIYNQKEGHFPRVTTVSESTKRE<br>NMDFSISISNITPADAGTYYCVKFRKGSPDTEFKSGAGTELSVR |
| 153 | anti-EGFR-huIgG1-SIRPαV2(V27I) | C225(VH)-ch1(huigg1m3)-HINGE(HUIGG1M3-)(huIgG1m3: ch2-CH3)-a-(g4s)x4-huSIRPa(V2: V27I) | QVQLKQSGPGLVQPSQSLSITCTVSGFSLTNYGVHWVRQSPGKGLE<br>WLGVIWSGGNTDYNTPFTSRLSINKDNSKSQVFFKMNSLQSNDTAI<br>YYCARALTYYDYEFAYWGQGTLVTVSAastkgpsvfplapsskstsggta<br>algclvkdyfpepvtvswnsngaltsgvhtfpavlqssglyslssvvtvpssslgtqty<br>icnvnhkpsntkvdkrvEPKSCDKTHTCPPCPAPELLGgpsvflfppkpkdt<br>lmisrtpevtcvvvdvshedpevkfnwyvdgvevhnaktkpreeqynstyrvv<br>svltvlhqdwlngkeykckvsnrkalpapiektiskakGQPREPQVYTLPPSR<br>EEMTKNQVSLTCLVKGFYPSDIAVEWESNGQPENNYKTTPPVLDSD<br>GSFFLYSKLTVDKSRWQQGNVFSCSVMHEALHNHYTQKSLSLSPG<br>AGGGGSGGGGSGGGGSGGGGSEEELQVIQPDKSVSVAAGESAIL<br>HCTITSLIPVGPIQWFRGAGPARELIYNQKEGHFPRVTTVSESTKRE<br>NMDFSISISNITPADAGTYYCVKFRKGSPDTEFKSGAGTELSVR |
| 154 | anti-EGFR-huIgG1-SIRPαV2(V27Q) | C225(VH)-ch1(huigg1m3)-HINGE(HUIGG1M3-)(huIgG1m3: ch2-CH3)-a-(g4s)x4-huSIRPa(V2: V27Q) | QVQLKQSGPGLVQPSQSLSITCTVSGFSLTNYGVHWVRQSPGKGLE<br>WLGVIWSGGNTDYNTPFTSRLSINKDNSKSQVFFKMNSLQSNDTAI<br>YYCARALTYYDYEFAYWGQGTLVTVSAastkgpsvfplapsskstsggta<br>algclvkdyfpepvtvswnsngaltsgvhtfpavlqssglyslssvvtvpssslgtqty<br>icnvnhkpsntkvdkrvEPKSCDKTHTCPPCPAPELLGgpsvflfppkpkdt<br>lmisrtpevtcvvvdvshedpevkfnwyvdgvevhnaktkpreeqynstyrvv |

TABLE 4-continued

Amino Acid and Nucleic Acid Sequences

| SEQ ID NO: | Name | Description | Sequence |
|---|---|---|---|
| | | | *svltvlhqdwlngkeykckvsnkalpapiektiskak*GQPREPQVYTLPPSR<br>EEMTKNQVSLTCLVKGFYPSDIAVEWESNGQPENNYKTTPPVLDSD<br>GSFFLYSKLTVDKSRWQQGNVFSCSVMHEALHNHYTQKSLSLSPG<br>AGGGGSGGGGSGGGGSGGGGSEEELQVIQPDKSVSVAAGESAIL<br>HCTQTSLIPVGPIQWFRGAGPARELIYNQKEGHFPRVTTVSESTKR<br>ENMDFSISISNITPADAGTYYCVKFRKGSPDTEFKSGAGTELSVR |
| 155 | anti-EGFR-huIgG1-SIRPαV2 (I31R) | C225(VH)-ch1(huigg1m3)-HINGE(HUIGG1M3)-(huIgG1m3:ch2-CH3)-a-(g4s)x4-huSIRPa(V2: I31R) | QVQLKQSGPGLVQPSQSLSITCTVSGFSLTNYGVHWVRQSPGKGLE<br>WLGVIWSGGNTDYNTPFTSRLSINKDNSKSQVFFKMNSLQSNDTAI<br>YYCARALTYYDYEFAYWGQGTLVTVSA*astkgpsvfplapsskstsggta<br>algclvkdyfpepvtvswnsgaltsgvhtfpavlqssglyslssvvtypssslgtqty<br>icnvnhkpsntkvdkrv*EPKSCDKTHTCPPCPAPELLG*gpsvflfppkpkdt<br>lmisrtpevtcvvvdvshedpevkfnwyvdgvevhnaktkpreeqynstyrvv<br>svltvlhqdwlngkeykckvsnkalpapiektiskak*GQPREPQVYTLPPSR<br>EEMTKNQVSLTCLVKGFYPSDIAVEWESNGQPENNYKTTPPVLDSD<br>GSFFLYSKLTVDKSRWQQGNVFSCSVMHEALHNHYTQKSLSLSPG<br>AGGGGSGGGGSGGGGSGGGGSEEELQVIQPDKSVSVAAGESAIL<br>HCTVTSLRPVGPIQWFRGAGPARELIYNQKEGHFPRVTTVSESTK<br>RENMDFSISISNITPADAGTYYCVKFRKGSPDTEFKSGAGTELSVR |
| 156 | anti-EGFR-huIgG1-SIRPαV2 (I31T) | C225(VH)-ch1(huigg1m3)-HINGE(HUIGG1M3)-(huIgG1m3:ch2-CH3)-a-(g4s)x4-huSIRPa(V2: I31T) | QVQLKQSGPGLVQPSQSLSITCTVSGFSLTNYGVHWVRQSPGKGLE<br>WLGVIWSGGNTDYNTPFTSRLSINKDNSKSQVFFKMNSLQSNDTAI<br>YYCARALTYYDYEFAYWGQGTLVTVSA*astkgpsvfplapsskstsggta<br>algclvkdyfpepvtvswnsgaltsgvhtfpavlqssglyslssvvtypssslgtqty<br>icnvnhkpsntkvdkrv*EPKSCDKTHTCPPCPAPELLG*gpsvflfppkpkdt<br>lmisrtpevtcvvvdvshedpevkfnwyvdgvevhnaktkpreeqynstyrvv<br>svltvlhqdwlngkeykckvsnkalpapiektiskak*GQPREPQVYTLPPSR<br>EEMTKNQVSLTCLVKGFYPSDIAVEWESNGQPENNYKTTPPVLDSD<br>GSFFLYSKLTVDKSRWQQGNVFSCSVMHEALHNHYTQKSLSLSPG<br>AGGGGSGGGGSGGGGSGGGGSEEELQVIQPDKSVSVAAGESAIL<br>HCTVTSLTPVGPIQWFRGAGPARELIYNQKEGHFPRVTTVSESTK<br>RENMDFSISISNITPADAGTYYCVKFRKGSPDTEFKSGAGTELSVR |
| 157 | anti-EGFR-huIgG1-SIRPαV2 (P35G) | C225(VH)-ch1(huigg1m3)-HINGE(HUIGG1M3)-(huIgG1m3:ch2-CH3)-a-(g4s)x4-huSIRPa(V2: P35G) | QVQLKQSGPGLVQPSQSLSITCTVSGFSLTNYGVHWVRQSPGKGLE<br>WLGVIWSGGNTDYNTPFTSRLSINKDNSKSQVFFKMNSLQSNDTAI<br>YYCARALTYYDYEFAYWGQGTLVTVSA*astkgpsvfplapsskstsggta<br>algclvkdyfpepvtvswnsgaltsgvhtfpavlqssglvslssvvtypssslgtqty<br>icnvnhkpsntkvdkrv*EPKSCDKTHTCPPCPAPELLG*gpsvflfppkpkdt<br>lmisrtpevtcvvvdvshedpevkfnwyvdgvevhnaktkpreeqynstyrvv<br>svltvlhqdwlngkeykckvsnkalpapiektiskak*GQPREPQVYTLPPSR<br>EEMTKNQVSLTCLVKGFYPSDIAVEWESNGQPENNYKTTPPVLDSD<br>GSFFLYSKLTVDKSRWQQGNVFSCSVMHEALHNHYTQKSLSLSPG<br>AGGGGSGGGGSGGGGSGGGGSEEELQVIQPDKSVSVAAGESAIL<br>HCTVTSLIPVGGIQWFRGAGPARELIYNQKEGHFPRVTTVSESTKR<br>ENMDFSISISNITPADAGTYYCVKFRKGSPDTEFKSGAGTELSVR |
| 158 | anti-EGFR-huIgG1-SIRPαV2 (P35N) | C225(VH)-ch1(huigg1m3)-HINGE(HUIGG1M3)-(huIgG1m3:ch2-CH3)-a-(g4s)x4-huSIRPa(V2: P35N) | QVQLKQSGPGLVQPSQSLSITCTVSGFSLTNYGVHWVRQSPGKGLE<br>WLGVIWSGGNTDYNTPFTSRLSINKDNSKSQVFFKMNSLQSNDTAI<br>YYCARALTYYDYEFAYWGQGTLVTVSA*astkgpsvfplapsskstsggta<br>algclvkdyfpepvtvswnsgaltsgvhtfpavlqssglvslssvvtypssslgtqty<br>icnvnhkpsntkvdkrv*EPKSCDKTHTCPPCPAPELLG*gpsvflfppkpkdt<br>lmisrtpevtcvvvdvshedpevkfnwyvdgvevhnaktkpreeqynstyrvv<br>svltvlhqdwlngkeykckvsnkalpapiektiskak*GQPREPQVYTLPPSR<br>EEMTKNQVSLTCLVKGFYPSDIAVEWESNGQPENNYKTTPPVLDSD<br>GSFFLYSKLTVDKSRWQQGNVFSCSVMHEALHNHYTQKSLSLSPG<br>AGGGGSGGGGSGGGGSGGGGSEEELQVIQPDKSVSVAAGESAIL<br>HCTVTSLIPVGNIQWFRGAGPARELIYNQKEGHFPRVTTVSESTKR<br>ENMDFSISISNITPADAGTYYCVKFRKGSPDTEFKSGAGTELSVR |
| 159 | anti-EGFR-huIgG1-SIRPαV2 (Q37A) | C225(VH)-ch1(huigg1m3)-HINGE(HUIGG1M3)-(huIgG1m3:ch2-CH3)-a-(g4s)x4-huSIRPa(V2: Q37A) | QVQLKQSGPGLVQPSQSLSITCTVSGFSLTNYGVHWVRQSPGKGLE<br>WLGVIWSGGNTDYNTPFTSRLSINKDNSKSQVFFKMNSLQSNDTAI<br>YYCARALTYYDYEFAYWGQGTLVTVSA*astkgpsvfplapsskstsggta<br>algclvkdyfpepvtvswnsgaltsgvhtfpavlqssglyslssvvtypssslgtqty<br>icnvnhkpsntkvdkrv*EPKSCDKTHTCPPCPAPELLG*gpsvflfppkpkdt<br>lmisrtpevtcvvvdvshedpevkfnwyvdgvevhnaktkpreeqynstyrvv<br>svltvlhqdwlngkeykckvsnkalpapiektiskak*GQPREPQVYTLPPSR<br>EEMTKNQVSLTCLVKGFYPSDIAVEWESNGQPENNYKTTPPVLDSD<br>GSFFLYSKLTVDKSRWQQGNVFSCSVMHEALHNHYTQKSLSLSPG<br>AGGGGSGGGGSGGGGSGGGGSEEELQVIQPDKSVSVAAGESAIL<br>HCTVTSLIPVGPIAWFRGAGPARELIYNQKEGHFPRVTTVSESTKR<br>ENMDFSISISNITPADAGTYYCVKFRKGSPDTEFKSGAGTELSVR |
| 160 | anti-EGFR-huIgG1- | C225(VH)-ch1(huigg1m3)- | QVQLKQSGPGLVQPSQSLSITCTVSGFSLTNYGVHWVRQSPGKGLE<br>WLGVIWSGGNTDYNTPFTSRLSINKDNSKSQVFFKMNSLQSNDTAI |

TABLE 4-continued

Amino Acid and Nucleic Acid Sequences

| SEQ ID NO: | Name | Description | Sequence |
|---|---|---|---|
| | SIRPαV2 (Q37H) | HINGE(HUIGG1M3)-(huIgG1m3: ch2-CH3)-a-(g4s)x4-huSIRPa(V2: Q37H) | YYCARALTYYDYEFAYWGQGTLVTVSA*astkgpsvfplapssskstsggta algclvkdyfpepvtvswnsgaltsgvhtfpavlqgssglyslssvvtypssslgtqty icnvnhkpsntkvdkrv*EPKSCDKTHTCPPCPAPELLG*gpsvflfppkpkdt lmisrtpevtcvvvdvshedpevkfnwyvdgvevhnaktkpreeqynstyrvv svltvlhqdwlngkeykckvsnkalpapiektiskak*GQPREPQVYTLPPSR EEMTKNQVSLTCLVKGFYPSDIAVEWESNGQPENNYKTTPPVLDSD GSFFLYSKLTVDKSRWQQGNVFSCSVMHEALHNHYTQKSLSLSPG AGGGGSGGGGSGGGGSGGGGSEEELQVIQPDKSVSVAAGESAIL HCTVTSLIPVGPIHWFRGAGPARELIYNQKEGHFPRVTTVSESTKR ENMDFSISISNITPADAGTYYCVKFRKGSPDTEFKSGAGTELSVR |
| 161 | anti-EGFR-huIgG1-SIRPαV2 (Q37V) | C225(VH)-ch1(huigg1m3)-HINGE(HUIGG1M3)-(huIgG1m3: ch2-CH3)-a-(g4s)x4-huSIRPa(V2: Q37v) | QVQLKQSGPGLVQPSQSLSITCTVSGFSLTNYGVHWVRQSPGKGLE WLGVIWSGGNTDYNTPFTSRLSINKDNSKSQVFFKMNSLQSNDTAI YYCARALTYYDYEFAYWGQGTLVTVSA*astkgpsvfplapssskstsggta algclvkdyfpepvtvswnsgaltsgvhtfpavlqgssglyslssvvtypssslgtqty icnvnhkpsntkvdkrv*EPKSCDKTHTCPPCPAPELLG*gpsvflfppkpkdt lmisrtpevtcvvvdvshedpevkfnwyvdgvevhnaktkpreeqynstyrvv svltvlhqdwlngkeykckvsnkalpapiektiskak*GQPREPQVYTLPPSR EEMTKNQVSLTCLVKGFYPSDIAVEWESNGQPENNYKTTPPVLDSD GSFFLYSKLTVDKSRWQQGNVFSCSVMHEALHNHYTQKSLSLSPG AGGGGSGGGGSGGGGSGGGGSEEELQVIQPDKSVSVAAGESAIL HCTVTSLIPVGPIVWFRGAGPARELIYNQKEGHFPRVTTVSESTKR ENMDFSISISNITPADAGTYYCVKFRKGSPDTEFKSGAGTELSVR |
| 162 | anti-EGFR-huIgG1-SIRPαV2 (Q37W) | C225(VH)-ch1(huigg1m3)-HINGE(HUIGG1M3)-(huIgG1m3: ch2-CH3)-a-(g4s)x4-huSIRPa(V2: Q37w) | QVQLKQSGPGLVQPSQSLSITCTVSGFSLTNYGVHWVRQSPGKGLE WLGVIWSGGNTDYNTPFTSRLSINKDNSKSQVFFKMNSLQSNDTAI YYCARALTYYDYEFAYWGQGTLVTVSA*astkgpsvfplapssskstsggta algclvkdyfpepvtvswnsgaltsgvhtfpavlqgssglyslssvvtypssslgtqty icnvnhkpsntkvdkrv*EPKSCDKTHTCPPCPAPELLG*gpsvflfppkpkdt lmisrtpevtcvvvdvshedpevkfnwyvdgvevhnaktkpreeqynstyrvv svltvlhqdwlngkeykckvsnkalpapiektiskak*GQPREPQVYTLPPSR EEMTKNQVSLTCLVKGFYPSDIAVEWESNGQPENNYKTTPPVLDSD GSFFLYSKLTVDKSRWQQGNVFSCSVMHEALHNHYTQKSLSLSPG AGGGGSGGGGSGGGGSGGGGSEEELQVIQPDKSVSVAAGESAIL HCTVTSLIPVGPIWWFRGAGPARELIYNQKEGHFPRVTTVSESTKR ENMDFSISISNITPADAGTYYCVKFRKGSPDTEFKSGAGTELSVR |
| 163 | anti-EGFR-huIgG1-SIRPαV2 (E47Y) | C225(VH)-ch1(huigg1m3)-HINGE(HUIGG1M3)-(huIgG1m3: ch2-CH3)-a-(g4s)x4-huSIRPa(V2: E47Y) | QVQLKQSGPGLVQPSQSLSITCTVSGFSLTNYGVHWVRQSPGKGLE WLGVIWSGGNTDYNTPFTSRLSINKDNSKSQVFFKMNSLQSNDTAI YYCARALTYYDYEFAYWGQGTLVTVSA*astkgpsvfplapssskstsggta algclvkdyfpepvtvswnsgaltsgvhtfpavlqgssglyslssvvtypssslgtqty icnvnhkpsntkvdkrv*EPKSCDKTHTCPPCPAPELLG*gpsvflfppkpkdt lmisrtpevtcvvvdvshedpevkfnwyvdgvevhnaktkpreeqynstyrvv svltvlhqdwlngkeykckvsnkalpapiektiskak*GQPREPQVYTLPPSR EEMTKNQVSLTCLVKGFYPSDIAVEWESNGQPENNYKTTPPVLDSD GSFFLYSKLTVDKSRWQQGNVFSCSVMHEALHNHYTQKSLSLSPG AGGGGSGGGGSGGGGSGGGGSEEELQVIQPDKSVSVAAGESAIL HCTVTSLIPVGPIQWFRGAGPARYLIYNQKEGHFPRVTTVSESTKR ENMDFSISISNITPADAGTYYCVKFRKGSPDTEFKSGAGTELSVR |
| 164 | anti-EGFR-huIgG1-SIRPαV2 (Q52E) | C225(VH)-ch1(huigg1m3)-HINGE(HUIGG1M3)-(huIgG1m3: ch2-CH3)-a-(g4s)x4-huSIRPa(V2: Q52E) | QVQLKQSGPGLVQPSQSLSITCTVSGFSLTNYGVHWVRQSPGKGLE WLGVIWSGGNTDYNTPFTSRLSINKDNSKSQVFFKMNSLQSNDTAI YYCARALTYYDYEFAYWGQGTLVTVSA*astkgpsvfplapssskstsggta algclvkdyfpepvtvswnsgaltsgvhtfpavlqgssglyslssvvtypssslgtqty icnvnhkpsntkvdkrv*EPKSCDKTHTCPPCPAPELLG*gpsvflfppkpkdt lmisrtpevtcvvvdvshedpevkfnwyvdgvevhnaktkpreeqynstyrvv svltvlhqdwlngkeykckvsnkalpapiektiskak*GQPREPQVYTLPPSR EEMTKNQVSLTCLVKGFYPSDIAVEWESNGQPENNYKTTPPVLDSD GSFFLYSKLTVDKSRWQQGNVFSCSVMHEALHNHYTQKSLSLSPG AGGGGSGGGGSGGGGSGGGGSEEELQVIQPDKSVSVAAGESAIL HCTVTSLIPVGPIQWFRGAGPARELIYNEKEGHFPRVTTVSESTKR ENMDFSISISNITPADAGTYYCVKFRKGSPDTEFKSGAGTELSVR |
| 165 | anti-EGFR-huIgG1-SIRPαV2 (Q52H) | C225(VH)-ch1(huigg1m3)-HINGE(HUIGG1M3)-(huIgG1m3: ch2-CH3)-a-(g4s)x4-huSIRPa(V2: Q52H) | QVQLKQSGPGLVQPSQSLSITCTVSGFSLTNYGVHWVRQSPGKGLE WLGVIWSGGNTDYNTPFTSRLSINKDNSKSQVFFKMNSLQSNDTAI YYCARALTYYDYEFAYWGQGTLVTVSA*astkgpsvfplapssskstsggta algclvkdyfpepvtvswnsgaltsgvhtfpavlqgssglyslssvvtypssslgtqty icnvnhkpsntkvdkrv*EPKSCDKTHTCPPCPAPELLG*gpsvflfppkpkdt lmisrtpevtcvvvdvshedpevkfnwyvdgvevhnaktkpreeqynstyrvv svltvlhqdwlngkeykckvsnkalpapiektiskak*GQPREPQVYTLPPSR EEMTKNQVSLTCLVKGFYPSDIAVEWESNGQPENNYKTTPPVLDSD GSFFLYSKLTVDKSRWQQGNVFSCSVMHEALHNHYTQKSLSLSPG |

TABLE 4-continued

Amino Acid and Nucleic Acid Sequences

| SEQ ID NO: | Name | Description | Sequence |
|---|---|---|---|
| | | | AGGGGSGGGGSGGGGSGGGGSEEELQVIQPDKSVSVAAGESAIL HCTVTSLIPVGPIQWFRGAGPARELIYNHKEGHFPRVTTVSESTKR ENMDFSISISNITPADAGTYYCVKFRKGSPDTEFKSGAGTELSVR |
| 166 | anti-EGFR-huIgG1-SIRPαV2 (E54P) | C225(VH)-ch1(huigg1m3)-HINGE(HUIGG1M3)-(huIgG1m3: ch2-CH3)-a-(g4s)x4-huSIRPa(V2: E54P) | QVQLKQSGPGLVQPSQSLSITCTVSGFSLTNYGVHWVRQSPGKGLE WLGVIWSGGNTDYNTPFTSRLSINKDNSKSQVFFKMNSLQSNDTAI YYCARALTYYDYEFAYWGQGTLVTVSA*astkgpsvfplapssksttsggta algclvkdyfpepvtvswnsgaltsgvhtfpavlqssglyslssvvtypsssIgtqty icnvnhkpsntkvdkrv*EPKSCDKTHTCPPCPAPELLG*gpsvflfppkpkdt lmisrtpevtcvvvdvshedpevkfnwyvdgvevhnaktkpreeqynstyrvv svltvlhqdwlngkeykckvsnkalpapiektiskak*GQPREPQVYTLPPSR EEMTKNQVSLTCLVKGFYPSDIAVEWESNGQPENNYKTTPPVLDSD GSFFLYSKLTVDKSRWQQGNVFSCSVMHEALHNHYTQKSLSLSPG AGGGGSGGGGSGGGGSGGGGSEEELQVIQPDKSVSVAAGESAIL HCTVTSLIPVGPIQWFRGAGPARELIYNQPGHFPRVTTVSESTKR ENMDFSISISNITPADAGTYYCVKFRKGSPDTEFKSGAGTELSVR |
| 167 | anti-EGFR-huIgG1-SIRPαV2 (H56P) | C225(VH)-ch1(huigg1m3)-HINGE(HUIGG1M3)-(huIgG1m3: ch2-CH3)-a-(g4s)x4-huSIRPa(V2: H56P) | QVQLKQSGPGLVQPSQSLSITCTVSGFSLTNYGVHWVRQSPGKGLE WLGVIWSGGNTDYNTPFTSRLSINKDNSKSQVFFKMNSLQSNDTAI YYCARALTYYDYEFAYWGQGTLVTVSA*astkgpsvfplapssksttsggta algclvkdyfpepvtvswnsgaltsgvhtfpavlqssglyslssvvtypsssIgtqty icnvnhkpsntkvdkrv*EPKSCDKTHTCPPCPAPELLG*gpsvflfppkpkdt lmisrtpevtcvvvdvshedpevkfnwyvdgvevhnaktkpreeqynstyrvv svltvlhqdwlngkeykckvsnkalpapiektiskak*GQPREPQVYTLPPSR EEMTKNQVSLTCLVKGFYPSDIAVEWESNGQPENNYKTTPPVLDSD GSFFLYSKLTVDKSRWQQGNVFSCSVMHEALHNHYTQKSLSLSPG AGGGGSGGGGSGGGGSGGGGSEEELQVIQPDKSVSVAAGESAIL HCTVTSLIPVGPIQWFRGAGPARELIYNQKEGPPFPRVTTVSESTKR ENMDFSISISNITPADAGTYYCVKFRKGSPDTEFKSGAGTELSVR |
| 168 | anti-EGFR-huIgG1-SIRPαV2 (H56Y) | C225(VH)-ch1(huigg1m3)-HINGE(HUIGG1M3)-(huIgG1m3: ch2-CH3)-a-(g4s)x4-huSIRPa(V2: H56Y) | QVQLKQSGPGLVQPSQSLSITCTVSGFSLTNYGVHWVRQSPGKGLE WLGVIWSGGNTDYNTPFTSRLSINKDNSKSQVFFKMNSLQSNDTAI YYCARALTYYDYEFAYWGQGTLVTVSA*astkgpsvfplapssksttsggta algclvkdyfpepvtvswnsgaltsgvhtfpavlqssglyslssvvtypsssIgtqty icnvnhkpsntkvdkrv*EPKSCDKTHTCPPCPAPELLG*gpsvflfppkpkdt lmisrtpevtcvvvdvshedpevkfnwyvdgvevhnaktkpreeqynstyrvv svltvlhqdwlngkeykckvsnkalpapiektiskak*GQPREPQVYTLPPSR EEMTKNQVSLTCLVKGFYPSDIAVEWESNGQPENNYKTTPPVLDSD GSFFLYSKLTVDKSRWQQGNVFSCSVMHEALHNHYTQKSLSLSPG AGGGGSGGGGSGGGGSGGGGSEEELQVIQPDKSVSVAAGESAIL HCTVTSLIPVGPIQWFRGAGPARELIYNQKEGYFPRVTTVSESTKR ENMDFSISISNITPADAGTYYCVKFRKGSPDTEFKSGAGTELSVR |
| 169 | anti-EGFR-huIgG1-SIRPαV2 (S66E) | C225(VH)-ch1(huigg1m3)-HINGE(HUIGG1M3)-(huIgG1m3: ch2-CH3)-a-(g4s)x4-huSIRPa(V2: S66E) | QVQLKQSGPGLVQPSQSLSITCTVSGFSLTNYGVHWVRQSPGKGLE WLGVIWSGGNTDYNTPFTSRLSINKDNSKSQVFFKMNSLQSNDTAI YYCARALTYYDYEFAYWGQGTLVTVSA*astkgpsvfplapssksttsggta algclvkdyfpepvtvswnsgaltsgvhtfpavlqssglyslssvvtypsssIgtqty icnvnhkpsntkvdkrv*EPKSCDKTHTCPPCPAPELLG*gpsvflfppkpkdt lmisrtpevtcvvvdvshedpevkfnwyvdgvevhnaktkpreeqynstyrvv svltvlhqdwlngkeykckvsnkalpapiektiskak*GQPREPQVYTLPPSR EEMTKNQVSLTCLVKGFYPSDIAVEWESNGQPENNYKTTPPVLDSD GSFFLYSKLTVDKSRWQQGNVFSCSVMHEALHNHYTQKSLSLSPG AGGGGSGGGGSGGGGSGGGGSEEELQVIQPDKSVSVAAGESAIL HCTVTSLIPVGPIQWFRGAGPARELIYNQKEGHFPRVTTVSEETKR ENMDFSISISNITPADAGTYYCVKFRKGSPDTEFKSGAGTELSVR |
| 170 | anti-EGFR-huIgG1-SIRPαV2 (S66H) | C225(VH)-ch1(huigg1m3)-HINGE(HUIGG1M3)-(huIgG1m3: ch2-CH3)-a-(g4s)x4-huSIRPa(V2: S66H) | QVQLKQSGPGLVQPSQSLSITCTVSGFSLTNYGVHWVRQSPGKGLE WLGVIWSGGNTDYNTPFTSRLSINKDNSKSQVFFKMNSLQSNDTAI YYCARALTYYDYEFAYWGQGTLVTVSA*astkgpsvfplapssksttsggta algclvkdyfpepvtvswnsgaltsgvhtfpavlqssglyslssvvtypsssIgtqty icnvnhkpsntkvdkrv*EPKSCDKTHTCPPCPAPELLG*gpsvflfppkpkdt lmisrtpevtcvvvdvshedpevkfnwyvdgvevhnaktkpreeqynstyrvv svltvlhqdwlngkeykckvsnkalpapiektiskak*GQPREPQVYTLPPSR EEMTKNQVSLTCLVKGFYPSDIAVEWESNGQPENNYKTTPPVLDSD GSFFLYSKLTVDKSRWQQGNVFSCSVMHEALHNHYTQKSLSLSPG AGGGGSGGGGSGGGGSGGGGSEEELQVIQPDKSVSVAAGESAIL HCTVTSLIPVGPIQWFRGAGPARELIYNQKEGHFPRVTTVSEHTKR ENMDFSISISNITPADAGTYYCVKFRKGSPDTEFKSGAGTELSVR |
| 171 | anti-EGFR-huIgG1-SIRPαV2 (S66Q) | C225(VH)-ch1(huigg1m3)-HINGE(HUIGG1M3)-(huIgG1m3: ch2-CH3)-a-(g4s)x4- | QVQLKQSGPGLVQPSQSLSITCTVSGFSLTNYGVHWVRQSPGKGLE WLGVIWSGGNTDYNTPFTSRLSINKDNSKSQVFFKMNSLQSNDTAI YYCARALTYYDYEFAYWGQGTLVTVSA*astkgpsvfplapssksttsggta algclvkdyfpepvtvswnsgaltsgvhtfpavlqssglyslssvvtypsssIgtqty icnvnhkpsntkvdkrv*EPKSCDKTHTCPPCPAPELLG*gpsvflfppkpkdt* |

TABLE 4-continued

Amino Acid and Nucleic Acid Sequences

| SEQ ID NO: | Name | Description | Sequence |
|---|---|---|---|
| | | | huSIRPa(V2: S66Q)<br>*lmisrtpevtcvvvdvshedpevkfnwyvdgvevhnaktkpreeqynstyrvv svltvlhqdwlngkeykckvsrkalpapiektiskak*GQPREPQVYTLPPSR<br>EEMTKNQVSLTCLVKGFYPSDIAVEWESNGQPENNYKTTPPVLDSD<br>GSFFLYSKLTVDKSRWQQGNVFSCSVMHEALHNHYTQKSLSLSPG<br>AGGGGSGGGGSGGGGSGGGGSEEELQVIQPDKSVSVAAGESAIL<br>HCTVTSLIPVGPIQWFRGAGPARELIYNQKEGHFPRVTTVSEQTKR<br>ENMDFSISISNITPADAGTYYCVKFRKGSPDTEFKSGAGTELSVR |
| 172 | anti-EGFR-huIgG1-SIRPαV2 (S66W) | C225(VH)-ch1(huigg1m3)-HINGE(HUIGG1M3)-(huIgG1m3: ch2-CH3)-a-(g4s)x4-huSIRPa(V2: S66W) | QVQLKQSGPGLVQPSQSLSITCTVSGFSLTNYGVHWVRQSPGKGLE<br>WLGVIWSGGNTDYNTPFTSRLSINKDNSKSQVFFKMNSLQSNDTAI<br>YYCARALTYYDYEFAYWGQGTLVTVSA*astkgpsvfplapssskstsggta<br>algclvkdyfpepvtvswnsgaltsgvhtfpavlqssglyslssvvtypsssslgtqty<br>icnvnhkpsntkvdkrv*EPKSCDKTHTCPPCPAPELLG*gpsvflfppkpkdt<br>lmisrtpevtcvvvdvshedpevkfnwyvdgvevhnaktkpreeqynstyrvv svltvlhqdwlngkeykckvsrkalpapiektiskak*GQPREPQVYTLPPSR<br>EEMTKNQVSLTCLVKGFYPSDIAVEWESNGQPENNYKTTPPVLDSD<br>GSFFLYSKLTVDKSRWQQGNVFSCSVMHEALHNHYTQKSLSLSPG<br>AGGGGSGGGGSGGGGSGGGGSEEELQVIQPDKSVSVAAGESAIL<br>HCTVTSLIPVGPIQWFRGAGPARELIYNQKEGHFPRVTTVSEWTK<br>RENMDFSISISNITPADAGTYYCVKFRKGSPDTEFKSGAGTELSVR |
| 173 | anti-EGFR-huIgG1-SIRPαV2 (T67E) | C225(VH)-ch1(huigg1m3)-HINGE(HUIGG1M3)-(huIgG1m3: ch2-CH3)-a-(g4s)x4-huSIRPa(V2: T67E) | QVQLKQSGPGLVQPSQSLSITCTVSGFSLTNYGVHWVRQSPGKGLE<br>WLGVIWSGGNTDYNTPFTSRLSINKDNSKSQVFFKMNSLQSNDTAI<br>YYCARALTYYDYEFAYWGQGTLVTVSA*astkgpsvfplapssskstsggta<br>algclvkdyfpepvtvswnsgaltsgvhtfpavlqssglyslssvvtypsssslgtqty<br>icnvnhkpsntkvdkrv*EPKSCDKTHTCPPCPAPELLG*gpsvflfppkpkdt<br>lmisrtpevtcvvvdvshedpevkfnwyvdgvevhnaktkpreeqynstyrvv svltvlhqdwlngkeykckvsrkalpapiektiskak*GQPREPQVYTLPPSR<br>EEMTKNQVSLTCLVKGFYPSDIAVEWESNGQPENNYKTTPPVLDSD<br>GSFFLYSKLTVDKSRWQQGNVFSCSVMHEALHNHYTQKSLSLSPG<br>AGGGGSGGGGSGGGGSGGGGSEEELQVIQPDKSVSVAAGESAIL<br>HCTVTSLIPVGPIQWFRGAGPARELIYNQKEGHFPRVTTVSESEKR<br>ENMDFSISISNITPADAGTYYCVKFRKGSPDTEFKSGAGTELSVR |
| 174 | anti-EGFR-huIgG1-SIRPαV2 (T67W) | C225(VH)-ch1(huigg1m3)-HINGE(HUIGG1M3)-(huIgG1m3: ch2-CH3)-a-(g4s)x4-huSIRPa(V2: T67W) | QVQLKQSGPGLVQPSQSLSITCTVSGFSLTNYGVHWVRQSPGKGLE<br>WLGVIWSGGNTDYNTPFTSRLSINKDNSKSQVFFKMNSLQSNDTAI<br>YYCARALTYYDYEFAYWGQGTLVTVSA*astkgpsvfplapssskstsggta<br>algclvkdyfpepvtvswnsgaltsgvhtfpavlqssglyslssvvtypsssslgtqty<br>icnvnhkpsntkvdkrv*EPKSCDKTHTCPPCPAPELLG*gpsvflfppkpkdt<br>lmisrtpevtcvvvdvshedpevkfnwyvdgvevhnaktkpreeqynstyrvv svltvlhqdwlngkeykckvsrkalpapiektiskak*GQPREPQVYTLPPSR<br>EEMTKNQVSLTCLVKGFYPSDIAVEWESNGQPENNYKTTPPVLDSD<br>GSFFLYSKLTVDKSRWQQGNVFSCSVMHEALHNHYTQKSLSLSPG<br>AGGGGSGGGGSGGGGSGGGGSEEELQVIQPDKSVSVAAGESAIL<br>HCTVTSLIPVGPIQWFRGAGPARELIYNQKEGHFPRVTTVSESWK<br>RENMDFSISISNITPADAGTYYCVKFRKGSPDTEFKSGAGTELSVR |
| 175 | anti-EGFR-huIgG1-SIRPαV2 (K68A) | C225(VH)-ch1(huigg1m3)-HINGE(HUIGG1M3)-(huIgG1m3: ch2-CH3)-a-(g4s)x4-huSIRPa(V2: K68A) | QVQLKQSGPGLVQPSQSLSITCTVSGFSLTNYGVHWVRQSPGKGLE<br>WLGVIWSGGNTDYNTPFTSRLSINKDNSKSQVFFKMNSLQSNDTAI<br>YYCARALTYYDYEFAYWGQGTLVTVSA*astkgpsvfplapssskstsggta<br>algclvkdyfpepvtvswnsgaltsgvhtfpavlqssglyslssvvtypsssslgtqty<br>icnvnhkpsntkvdkrv*EPKSCDKTHTCPPCPAPELLG*gpsvflfppkpkdt<br>lmisrtpevtcvvvdvshedpevkfnwyvdgvevhnaktkpreeqynstyrvv svltvlhqdwlngkeykckvsrkalpapiektiskak*GQPREPQVYTLPPSR<br>EEMTKNQVSLTCLVKGFYPSDIAVEWESNGQPENNYKTTPPVLDSD<br>GSFFLYSKLTVDKSRWQQGNVFSCSVMHEALHNHYTQKSLSLSPG<br>AGGGGSGGGGSGGGGSGGGGSEEELQVIQPDKSVSVAAGESAIL<br>HCTVTSLIPVGPIQWFRGAGPARELIYNQKEGHFPRVTTVSESTAR<br>ENMDFSISISNITPADAGTYYCVKFRKGSPDTEFKSGAGTELSVR |
| 176 | anti-EGFR-huIgG1-SIRPαV2 (K68E) | C225(VH)-ch1(huigg1m3)-HINGE(HUIGG1M3)-(huIgG1m3: ch2-CH3)-a-(g4s)x4-huSIRPa(V2: K68E) | QVQLKQSGPGLVQPSQSLSITCTVSGFSLTNYGVHWVRQSPGKGLE<br>WLGVIWSGGNTDYNTPFTSRLSINKDNSKSQVFFKMNSLQSNDTAI<br>YYCARALTYYDYEFAYWGQGTLVTVSA*astkgpsvfplapssskstsggta<br>algclvkdyfpepvtvswnsgaltsgvhtfpavlqssglyslssvvtypsssslgtqty<br>icnvnhkpsntkvdkrv*EPKSCDKTHTCPPCPAPELLG*gpsvflfppkpkdt<br>lmisrtpevtcvvvdvshedpevkfnwyvdgvevhnaktkpreeqynstyrvv svltvlhqdwlngkeykckvsrkalpapiektiskak*GQPREPQVYTLPPSR<br>EEMTKNQVSLTCLVKGFYPSDIAVEWESNGQPENNYKTTPPVLDSD<br>GSFFLYSKLTVDKSRWQQGNVFSCSVMHEALHNHYTQKSLSLSPG<br>AGGGGSGGGGSGGGGSGGGGSEEELQVIQPDKSVSVAAGESAIL<br>HCTVTSLIPVGPIQWFRGAGPARELIYNQKEGHFPRVTTVSESTER<br>ENMDFSISISNITPADAGTYYCVKFRKGSPDTEFKSGAGTELSVR |

TABLE 4-continued

Amino Acid and Nucleic Acid Sequences

| SEQ ID NO: | Name | Description | Sequence |
|---|---|---|---|
| 177 | anti-EGFR-huIgG1-SIRPαV2 (K68H) | C225(VH)-ch1(huigg1m3)-HINGE(HUIGG1M3)-(huIgG1m3:ch2-CH3)-a-(g4s)x4-huSIRPa(V2:K68H) | QVQLKQSGPGLVQPSQSLSITCTVSGFSLTNYGVHWVRQSPGKGLE<br>WLGVIWSGGNTDYNTPFTSRLSINKDNSKSQVFFKMNSLQSNDTAI<br>YYCARALTYYDYEFAYWGQGTLVTVSAastkgpsvfplapssksstggta<br>algclvkdyfpepvtvswnsgaltsgvhtfpavlqssglyslssvvtypssslgtqty<br>icnvnhkpsntkvdkrvEPKSCDKTHTCPPCPAPELLGgpsvflfppkpkdt<br>lmisrtpevtcvvvdvshedpevkfnwyvdgvevhnaktkpreeqynstyrvv<br>svltvlhqdwlngkeykckvsnkalpapiektiskakGQPREPQVYTLPPSR<br>EEMTKNQVSLTCLVKGFYPSDIAVEWESNGQPENNYKTTPPVLDSD<br>GSFFLYSKLTVDKSRWQQGNVFSCSVMHEALHNHYTQKSLSLSPG<br>AGGGGSGGGGSGGGGSGGGGSEEELQVIQPDKSVSVAAGESAIL<br>HCTVTSLIPVGPIQWFRGAGPARELIYNQKEGHFPRVTTVSESTHR<br>ENMDFSISISNITPADAGTYYCVKFRKGSPDTEFKSGAGTELSVR |
| 178 | anti-EGFR-huIgG1-SIRPαV2 (K68I) | C225(VH)-ch1(huigg1m3)-HINGE(HUIGG1M3)-(huIgG1m3:ch2-CH3)-a-(g4s)x4-huSIRPa(V2:K68I) | QVQLKQSGPGLVQPSQSLSITCTVSGFSLTNYGVHWVRQSPGKGLE<br>WLGVIWSGGNTDYNTPFTSRLSINKDNSKSQVFFKMNSLQSNDTAI<br>YYCARALTYYDYEFAYWGQGTLVTVSAastkgpsvfplapssksstggta<br>algclvkdyfpepvtvswnsgaltsgvhtfpavlqssglyslssvvtypssslgtqty<br>icnvnhkpsntkvdkrvEPKSCDKTHTCPPCPAPELLGgpsvflfppkpkdt<br>lmisrtpevtcvvvdvshedpevkfnwyvdgvevhnaktkpreeqynstyrvv<br>svltvlhqdwlngkeykckvsnkalpapiektiskakGQPREPQVYTLPPSR<br>EEMTKNQVSLTCLVKGFYPSDIAVEWESNGQPENNYKTTPPVLDSD<br>GSFFLYSKLTVDKSRWQQGNVFSCSVMHEALHNHYTQKSLSLSPG<br>AGGGGSGGGGSGGGGSGGGGSEEELQVIQPDKSVSVAAGESAIL<br>HCTVTSLIPVGPIQWFRGAGPARELIYNQKEGHFPRVTTVSESTIRE<br>NMDFSISISNITPADAGTYYCVKFRKGSPDTEFKSGAGTELSVR |
| 179 | anti-EGFR-huIgG1-SIRPαV2 (K68T) | C225(VH)-ch1(huigg1m3)-HINGE(HUIGG1M3)-(huIgG1m3:ch2-CH3)-a-(g4s)x4-huSIRPa(V2:K68T) | QVQLKQSGPGLVQPSQSLSITCTVSGFSLTNYGVHWVRQSPGKGLE<br>WLGVIWSGGNTDYNTPFTSRLSINKDNSKSQVFFKMNSLQSNDTAI<br>YYCARALTYYDYEFAYWGQGTLVTVSAastkgpsvfplapssksstggta<br>algclvkdyfpepvtvswnsgaltsgvhtfpavlqssglyslssvvtypssslgtqty<br>icnvnhkpsntkvdkrvEPKSCDKTHTCPPCPAPELLGgpsvflfppkpkdt<br>lmisrtpevtcvvvdvshedpevkfnwyvdgvevhnaktkpreeqynstyrvv<br>svltvlhqdwlngkeykckvsnkalpapiektiskakGQPREPQVYTLPPSR<br>EEMTKNQVSLTCLVKGFYPSDIAVEWESNGQPENNYKTTPPVLDSD<br>GSFFLYSKLTVDKSRWQQGNVFSCSVMHEALHNHYTQKSLSLSPG<br>AGGGGSGGGGSGGGGSGGGGSEEELQVIQPDKSVSVAAGESAIL<br>HCTVTSLIPVGPIQWFRGAGPARELIYNQKEGHFPRVTTVSESTTR<br>ENMDFSISISNITPADAGTYYCVKFRKGSPDTEFKSGAGTELSVR |
| 180 | anti-EGFR-huIgG1-SIRPαV2 (M72I) | C225(VH)-ch1(huigg1m3)-HINGE(HUIGG1M3)-(huIgG1m3:ch2-CH3)-a-(g4s)x4-huSIRPa(V2:M72I) | QVQLKQSGPGLVQPSQSLSITCTVSGFSLTNYGVHWVRQSPGKGLE<br>WLGVIWSGGNTDYNTPFTSRLSINKDNSKSQVFFKMNSLQSNDTAI<br>YYCARALTYYDYEFAYWGQGTLVTVSAastkgpsvfplapssksstggta<br>algclvkdyfpepvtvswnsgaltsgvhtfpavlqssglyslssvvtypssslgtqty<br>icnvnhkpsntkvdkrvEPKSCDKTHTCPPCPAPELLGgpsvflfppkpkdt<br>lmisrtpevtcvvvdvshedpevkfnwyvdgvevhnaktkpreeqynstyrvv<br>svltvlhqdwlngkeykckvsnkalpapiektiskakGQPREPQVYTLPPSR<br>EEMTKNQVSLTCLVKGFYPSDIAVEWESNGQPENNYKTTPPVLDSD<br>GSFFLYSKLTVDKSRWQQGNVFSCSVMHEALHNHYTQKSLSLSPG<br>AGGGGSGGGGSGGGGSGGGGSEEELQVIQPDKSVSVAAGESAIL<br>HCTVTSLIPVGPIQWFRGAGPARELIYNQKEGHFPRVTTVSESTKR<br>ENIDFSISISNITPADAGTYYCVKFRKGSPDTEFKSGAGTELSVR |
| 181 | anti-EGFR-huIgG1-SIRPαV2 (M72N) | C225(VH)-ch1(huigg1m3)-HINGE(HUIGG1M3)-(huIgG1m3:ch2-CH3)-a-(g4s)x4-huSIRPa(V2:M72N) | QVQLKQSGPGLVQPSQSLSITCTVSGFSLTNYGVHWVRQSPGKGLE<br>WLGVIWSGGNTDYNTPFTSRLSINKDNSKSQVFFKMNSLQSNDTAI<br>YYCARALTYYDYEFAYWGQGTLVTVSAastkgpsvfplapssksstggta<br>algclvkdyfpepvtvswnsgaltsgvhtfpavlqssglyslssvvtypssslgtqty<br>icnvnhkpsntkvdkrvEPKSCDKTHTCPPCPAPELLGgpsvflfppkpkdt<br>lmisrtpevtcvvvdvshedpevkfnwyvdgvevhnaktkpreeqynstyrvv<br>svltvlhqdwlngkeykckvsnkalpapiektiskakGQPREPQVYTLPPSR<br>EEMTKNQVSLTCLVKGFYPSDIAVEWESNGQPENNYKTTPPVLDSD<br>GSFFLYSKLTVDKSRWQQGNVFSCSVMHEALHNHYTQKSLSLSPG<br>AGGGGSGGGGSGGGGSGGGGSEEELQVIQPDKSVSVAAGESAIL<br>HCTVTSLIPVGPIQWFRGAGPARELIYNQKEGHFPRVTTVSESTKR<br>ENNDFSISISNITPADAGTYYCVKFRKGSPDTEFKSGAGTELSVR |
| 182 | anti-EGFR-huIgG1-SIRPαV2 (M72R) | C225(VH)-ch1(huigg1m3)-HINGE(HUIGG1M3)-(huIgG1m3:ch2-CH3)-a-(g4s)x4-huSIRPa(V2:M72R) | QVQLKQSGPGLVQPSQSLSITCTVSGFSLTNYGVHWVRQSPGKGLE<br>WLGVIWSGGNTDYNTPFTSRLSINKDNSKSQVFFKMNSLQSNDTAI<br>YYCARALTYYDYEFAYWGQGTLVTVSAastkgpsvfplapssksstggta<br>algclvkdyfpepvtvswnsgaltsgvhtfpavlqssglyslssvvtypssslgtqty<br>icnvnhkpsntkvdkrvEPKSCDKTHTCPPCPAPELLGgpsvflfppkpkdt<br>lmisrtpevtcvvvdvshedpevkfnwyvdgvevhnaktkpreeqynstyrvv<br>svltvlhqdwlngkeykckvsnkalpapiektiskakGQPREPQVYTLPPSR<br>EEMTKNQVSLTCLVKGFYPSDIAVEWESNGQPENNYKTTPPVLDSD<br>GSFFLYSKLTVDKSRWQQGNVFSCSVMHEALHNHYTQKSLSLSPG |

TABLE 4-continued

Amino Acid and Nucleic Acid Sequences

| SEQ ID NO: | Name | Description | Sequence |
|---|---|---|---|
| | | | AGGGGSGGGGSGGGGSGGGGSEEELQVIQPDKSVSVAAGESAIL HCTVTSLIPVGPIQWFRGAGPARELIYNQKEGHFPRVTTVSESTKR ENRDFSISISNITPADAGTYYCVKFRKGSPDTEFKSGAGTELSVR |
| 183 | anti-EGFR-huIgG1-SIRPαV2 (M72W) | C225(VH)-ch1(huigg1m3)-HINGE(HUIGG1M3)-(huIgG1m3: ch2-CH3)-a-(g4s)x4-huSIRPa(V2: M72W) | QVQLKQSGPGLVQPSQSLSITCTVSGFSLTNYGVHWVRQSPGKGLE WLGVIWSGGNTDYNTPFTSRLSINKDNSKSQVFFKMNSLQSNDTAI YYCARALTYYDYEFAYWGQGTLVTVSA*astkgpsvfplapssktsggta algclvkdyfpepvtvswnsgaltsgvhtfpavlqsssglyslssvvtypssslgtqty icnvnhkpsntkvdkrv*EPKSCDKTHTCPPCPAPELLG*gpsvflfppkpkdt lmisrtpevtcvvvdvshedpevkfnwyvdgvevhnaktkpreeqynstyrvv svltvlhqdwlngkeykckvsnkalpapiektiskak*GQPREPQVYTLPPSR EEMTKNQVSLTCLVKGFYPSDIAVEWESNGQPENNYKTTPPVLDSD GSFFLYSKLTVDKSRWQQGNVFSCSVMHEALHNHYTQKSLSLSPG AGGGGSGGGGSGGGGSGGGGSEEELQVIQPDKSVSVAAGESAIL HCTVTSLIPVGPIQWFRGAGPARELIYNQKEGHFPRVTTVSESTKR ENWDFSISISNITPADAGTYYCVKFRKGSPDTEFKSGAGTELSVR |
| 184 | anti-EGFR-huIgG1-SIRPαV2 (V92N) | C225(VH)-ch1(huigg1m3)-HINGE(HUIGG1M3)-(huIgG1m3: ch2-CH3)-a-(g4s)x4-huSIRPa(V2: V92N) | QVQLKQSGPGLVQPSQSLSITCTVSGFSLTNYGVHWVRQSPGKGLE WLGVIWSGGNTDYNTPFTSRLSINKDNSKSQVFFKMNSLQSNDTAI YYCARALTYYDYEFAYWGQGTLVTVSA*astkgpsvfplapssktsggta algclvkdyfpepvtvswnsgaltsgvhtfpavlqsssglyslssvvtypssslgtqty icnvnhkpsntkvdkrv*EPKSCDKTHTCPPCPAPELLG*gpsvflfppkpkdt lmisrtpevtcvvvdvshedpevkfnwyvdgvevhnaktkpreeqynstyrvv svltvlhqdwlngkeykckvsnkalpapiektiskak*GQPREPQVYTLPPSR EEMTKNQVSLTCLVKGFYPSDIAVEWESNGQPENNYKTTPPVLDSD GSFFLYSKLTVDKSRWQQGNVFSCSVMHEALHNHYTQKSLSLSPG AGGGGSGGGGSGGGGSGGGGSEEELQVIQPDKSVSVAAGESAIL HCTVTSLIPVGPIQWFRGAGPARELIYNQKEGHFPRVTTVSESTKR ENMDFSISISNITPADAGTYYCNK**FRKGSPDTEFKSGAGTELSVR |
| 185 | anti-EGFR-huIgG1-SIRPαV2 (K53 + K68I) | C225(VH)-ch1(huigg1m3)-HINGE(HUIGG1M3)-(huIgG1m3: ch2-CH3)-a-(g4s)x4-huSIRPa(V2: K53I + K68I) | QVQLKQSGPGLVQPSQSLSITCTVSGFSLTNYGVHWVRQSPGKGLE WLGVIWSGGNTDYNTPFTSRLSINKDNSKSQVFFKMNSLQSNDTAI YYCARALTYYDYEFAYWGQGTLVTVSA*astkgpsvfplapssktsggta algclvkdyfpepvtvswnsgaltsgvhtfpavlqsssglyslssvvtypssslgtqty icnvnhkpsntkvdkrv*EPKSCDKTHTCPPCPAPELLG*gpsvflfppkpkdt lmisrtpevtcvvvdvshedpevkfnwyvdgvevhnaktkpreeqynstyrvv svltvlhqdwlngkeykckvsnkalpapiektiskak*GQPREPQVYTLPPSR EEMTKNQVSLTCLVKGFYPSDIAVEWESNGQPENNYKTTPPVLDSD GSFFLYSKLTVDKSRWQQGNVFSCSVMHEALHNHYTQKSLSLSPG AGGGGSGGGGSGGGGSGGGGSEEELQVIQPDKSVSVAAGESAIL HCTVTSLIPVGPIQWFRGAGPARELIYNQIEGHFPRVTTVSESTIR**E NMDFSISISNITPADAGTYYCVKFRKGSPDTEFKSGAGTELSVR |
| 186 | anti-EGFR-huIgG1-SIRPαV2 (K53N + K68E) | C225(VH)-ch1(huigg1m3)-HINGE(HUIGG1M3)-(huIgG1m3: ch2-CH3)-a-(g4s)x4-huSIRPa(V2: K53N + K68E) | QVQLKQSGPGLVQPSQSLSITCTVSGFSLTNYGVHWVRQSPGKGLE WLGVIWSGGNTDYNTPFTSRLSINKDNSKSQVFFKMNSLQSNDTAI YYCARALTYYDYEFAYWGQGTLVTVSA*astkgpsvfplapssktsggta algclvkdyfpepvtvswnsgaltsgvhtfpavlqsssglyslssvvtypssslgtqty icnvnhkpsntkvdkrv*EPKSCDKTHTCPPCPAPELLG*gpsvflfppkpkdt lmisrtpevtcvvvdvshedpevkfnwyvdgvevhnaktkpreeqynstyrvv svltvlhqdwlngkeykckvsnkalpapiektiskak*GQPREPQVYTLPPSR EEMTKNQVSLTCLVKGFYPSDIAVEWESNGQPENNYKTTPPVLDSD GSFFLYSKLTVDKSRWQQGNVFSCSVMHEALHNHYTQKSLSLSPG AGGGGSGGGGSGGGGSGGGGSEEELQVIQPDKSVSVAAGESAIL HCTVTSLIPVGPIQWFRGAGPARELIYNQNEGHFPRVTTVSESTER** ENMDFSISISNITPADAGTYYCVKFRKGSPDTEFKSGAGTELSVR |
| 187 | anti-EGFR-huIgG1-SIRPαV2 (K53Q + K68T) | C225(VH)-ch1(huigg1m3)-HINGE(HUIGG1M3)-(huIgG1m3: ch2-CH3)-a-(g4s)x4-huSIRPa(V2: K53Q + K68T) | QVQLKQSGPGLVQPSQSLSITCTVSGFSLTNYGVHWVRQSPGKGLE WLGVIWSGGNTDYNTPFTSRLSINKDNSKSQVFFKMNSLQSNDTAI YYCARALTYYDYEFAYWGQGTLVTVSA*astkgpsvfplapssktsggta algclvkdyfpepvtvswnsgaltsgvhtfpavlqsssglyslssvvtypssslgtqty icnvnhkpsntkvdkrv*EPKSCDKTHTCPPCPAPELLG*gpsvflfppkpkdt lmisrtpevtcvvvdvshedpevkfnwyvdgvevhnaktkpreeqynstyrvv svltvlhqdwlngkeykckvsnkalpapiektiskak*GQPREPQVYTLPPSR EEMTKNQVSLTCLVKGFYPSDIAVEWESNGQPENNYKTTPPVLDSD GSFFLYSKLTVDKSRWQQGNVFSCSVMHEALHNHYTQKSLSLSPG AGGGGSGGGGSGGGGSGGGGSEEELQVIQPDKSVSVAAGESAIL HCTVTSLIPVGPIQWFRGAGPARELIYNQQEGHFPRVTTVSESTTR ENMDFSISISNITPADAGTYYCVKFRKGSPDTEFKSGAGTELSVR |
| 188 | anti-EGFR-huIgG1-SIRPαV2 (K53T + K68A) | C225(VH)-ch1(huigg1m3)-HINGE(HUIGG1M3)-(huIgG1m3: ch2-CH3)-a-(g4s)x4-huSIRPa(V2: K53T + K68A) | QVQLKQSGPGLVQPSQSLSITCTVSGFSLTNYGVHWVRQSPGKGLE WLGVIWSGGNTDYNTPFTSRLSINKDNSKSQVFFKMNSLQSNDTAI YYCARALTYYDYEFAYWGQGTLVTVSA*astkgpsvfplapssktsggta algclvkdyfpepvtvswnsgaltsgvhtfpavlqsssglyslssvvtypssslgtqty icnvnhkpsntkvdkrv*EPKSCDKTHTCPPCPAPELLG*gpsvflfppkpkdt |

TABLE 4-continued

Amino Acid and Nucleic Acid Sequences

| SEQ ID NO: | Name | Description | Sequence |
|---|---|---|---|
| | | huSIRPa(V2: K53T + K68A) | *lmisrtpevtcvvvdvshedpevkfnwyvdgvevhnaktkpreeqynstyrvv svltvlhqdwlngkeykckvsrkalpapiektiskak*GQPREPQVYTLPPSR EEMTKNQVSLTCLVKGFYPSDIAVEWESNGQPENNYKTTPPVLDSD GSFFLYSKLTVDKSRWQQGNVFSCSVMHEALHNHYTQKSLSLSPG AGGGGSGGGGSGGGGSGGGGSEEELQVIQPDKSVSVAAGESAIL HCTVTSLIPVGPIQWFRGAGPARELIYNQTEGHFPRVTTVSESTAR ENMDFSISISNITPADAGTYYCVKFRKGSPDTEFKSGAGTELSVR |
| 189 | anti-EGFR-huIgG1-SIRPαV2 (K53V + K68H) | C225(VH)-ch1(huigg1m3)-HINGE(HUIGG1M3)-(huIgG1m3: ch2-CH3)-a-(g4s)x4-huSIRPa(V2: K53V + K68H) | QVQLKQSGPGLVQPSQSLSITCTVSGFSLTNYGVHWVRQSPGKGLE WLGVIWSGGNTDYNTPFTSRLSINKDNSKSQVFFKMNSLQSNDTAI YYCARALTYYDYEFAYWGQGTLVTVSA*astkgpsvfplapsskstsggta algclvkdyfpepvtvswnsgaltsgvhtfpavlqssglyslssvvtypssslgtqty icnvnhkpsntkvdkrv*EPKSCDKTHTCPPCPAPELLG*gpsvflfppkpkdt lmisrtpevtcvvvdvshedpevkfnwyvdgvevhnaktkpreeqynstyrvv svltvlhqdwlngkeykckvsrkalpapiektiskak*GQPREPQVYTLPPSR EEMTKNQVSLTCLVKGFYPSDIAVEWESNGQPENNYKTTPPVLDSD GSFFLYSKLTVDKSRWQQGNVFSCSVMHEALHNHYTQKSLSLSPG AGGGGSGGGGSGGGGSGGGGSEEELQVIQPDKSVSVAAGESAIL HCTVTSLIPVGPIQWFRGAGPARELIYNQVEGHFPRVTTVSESTHR ENMDFSISISNITPADAGTYYCVKFRKGSPDTEFKSGAGTELSVR |
| 190 | SIRPα IgV Alleles | SIRPa IgV where $X_1$ is E or G; $X_2$ is F or S; $X_3$ is L or S; $X_4$ is S or T; $X_5$ is I or T; $X_6$ is H, L or R; $X_7$ is A or V; $X_8$ is A or G; $X_9$ is D or E; $X_{10}$ is L or S; $X_{11}$ is E or N; $X_{12}$ is P or S; $X_{13}$ is R or S; $X_{14}$ is G or S; $X_{15}$ is missing residue (deletion) or D; $X_{16}$ is T or V; $X_{18}$ is A or G. | EEX$_1$LQVIQPDKX$_2$VX$_3$VAAGEX$_4$AX$_5$LX$_6$CTX$_7$TSLIPVGPIQWFRGA GPX$_8$RELIYNQKEGHFPRVTTVSX$_9$X$_{10}$DLTKRX$_{11}$NMDFX$_{12}$IX$_{13}$IX$_{14}$N ITPADAGTYYCVKFRKGSPDX$_{15}$X$_{16}$EFKSGAGTELSVR |
| 191 | Fc-SIRPαV2CC | HINGE(HUIGG1M3: ESMUTATION)-ch2(huigg1m3)-CH3(HUIGG1M3)-a(g4s)x4-HUSIRPAV2-c1-C2 | GAACCGAAGTCCTCCGACAAGACTCACACTTGTCCCCCATGCCCG GCCCCTGAGCTGCTGGGA*ggccatccgtgttcctgttcccgccgaaaccta aggacaccctgatgatttcgagaactccggaagtgacctgtgtggtggtcgacgtgtc ccacgaggatccggaggtcaagttcaattggtacgtcgacggagtggaagtccacaa cgccaagaccaagccccggagggagcagtacaactccacttaccgggtggtgtccgt gctgaccgtgctgcatcaggattggctgaacggaaaggagtataagtgcaaagtgtc aaacaaggcattgcctgcgccaatcgaaaagaccattagcaagctgcaag*GGCCA GCCCAGGGAACCCAGGTGTACACTCTGCCCCCGTCCCGCGAA GAAATGACCAAGAACCAAGTGTCACTGACATGCCTCGTGAAGG GATTTTACCCGTCCGATATCGCCGTGGAATGGGAATCGAACGG TCAACCTGAAAACAACTACAAGACGACCCCTCCGGTCCTGGACA GCGATGGCTCATTCTTCCTGTACTCCAAGCTTACGGTGGACAAG TCCCGGTGGCAACAGGGAAATGTGTTTTCGTGCTCCGTGATGC ATGAGGCTCTGCACAACCACTACACCCAGAAGTCACTCTCCCTG AGCCCCGGC*gcggggggtggtggaagcggaggagggggtctggggtggcg gttccggcggcggcggatcc*GAGGAGGAGCTCCAGGTCATCCAGCCTG ACAAGTCCGTGTCGGTGGCCGCGGGAGAGTCCGCCATTCTGCAC TGCACCGTGACCTCCCTCATCCCCGTGGGACCTATCCAGTGGTTC AGAGGAGCCGGGCCCGCACGGGAACTGATCTATAACCAGAAGG AGGGCCATTTCCCCCGCGTGACCACCGTGTCCGAGAGCACCAAG AGGGAAAACATGGACTTCAGCATTTCGATCAGCAACATCACTCC CGCTGACGCCGGGACCTACTACTGCGTGAAGTTCCGGAAAGGA AGCCCGGACACCGAGTTCAAAAGCGGAGCCGGCACCGAACTGT CGGTCCGC*gccaagccttccgccccggtggtgtcaggaccggccgcccgagcaa ctccgcaacacactgtgtcttttacttgcgaatcccacgggttcagccctcgggacatt accctgaagtggttcaagaacgggaacgaactgagcgacttccagaccaacgtgga cccagtgggcgaatcagtgtcctactcgatccattcgaccgccaagtcgtgttgacc cgcgaggatgtgcactcccaagtcatctgcgaggtggcccacgtgacactccaggc gaccccctgagaggcaccgcgaacctgtccgaaaccattcgcgtgccc*CCTACGC TCGAAGTGACCCAGCAGCCAGTCCGCGCCGAAAACCAGGTCAA CGTGACCTGTCAAGTCCGCAAGTTCTACCCGCAACGGCTGCAGC |

TABLE 4-continued

Amino Acid and Nucleic Acid Sequences

| SEQ ID NO: | Name | Description | Sequence |
|---|---|---|---|
| | | | TTACCTGGCTGGAGAACGGCAACGTGTCCCGGACCGAGACTGC GAGCACCGTCACCGAGAACAAGGATGGAACCTACAATTGGAT GTCCTGGCTTCTCGTGAATGTGTCGGCGCATAGGGACGACGTG AAGCTGACTTGCCAGGTCGAACACGACGGACAGCCCGCTGTGT CCAAGTCACACGATCTCAAAGTGTCCGCCCACCCGAAGGAGCA GGGAAGCAACACTGCTGCCGAGAACACCGGTTCCAACGAAAG AAACATCTAC |
| 192 | Fc-SIRPαV2CC | HINGE(HUIGG1M3: ES MUTATION)-ch2(huigg1m3)-CH3(HUIGG1M3)-a(g4s)x4-HUSIRPAV2-c1-C2 | EPKSSDKTHTCPPCPAPELLGgpsvflfppkpkdtlmisrtpevtcvvvdvsh edpevkfnwyvdgvevhnaktkpreeqynstyrvvsvltvlhqdwlngkeykck vsnkalpapiektiskakGQPREPQVYTLPPSREEMTKNQVSLTCLVKG FYPSDIAVEWESNGQPENNYKTTPPVLDSDGSFFLYSKLTVDKSR WQQGNVFSCSVMHEALHNHYTQKSLSLSPGaggggsggggsggggs ggggsEEELQVIQPDKSVSVAAGESAILHCTVTSLIPVGPIQWFRGAG PARELIYNQKEGHFPRVTTVSESTKRENMDFSISISNITPADAGTYYC VKFRKGSPDTEFKSGAGTELSVRakpsapvvsgpaaratpqhtvsftcesh gfsprditlkwfkngnelsdfqtnvdpvgesvsysihstakvvltredvhsqviceva hvtlqgdplrgtanlsetirvpPTLEVTQQPVRAENQVNVTCQVRKFYPQ RLQLTWLENGNVSRTETASTVTENKDGTYNWMSWLLVNVSAHR DDVKLTCQVEHDGQPAVSKSHDLKVSAHPKEQGSNTAAENTGS NERNIY |
| 193 | huSIRPα IgV(V3) | huSIRPα IgV(V3) | EEELQVIQPDKSVSVAAGESAILLCTVTSLIPVGPIQWFRGAGPAREL IYNQKEGHFPRVTTVSESTKRENMDFSISISNITPADAGTYYCVKFRK GSPDTEFKSGAGTELSVR |
| 194 | huSIRPα IgV(4) | huSIRPα IgV(4) | EEGLQVIQPDKSVSVAAGESAILHCTATSLIPVGPIQWFRGAGPGRE LIYNQKEGHFPRVTTVSDLTKRNNMDFSIRIGNITPADAGTYYCVKF RKGSPDDVEFKSGAGTELSVR |
| 195 | huSIRPα IgV(5) | huSIRPα IgV(5) | EEELQVIQPDKFVLVAAGETATLRCTATSLIPVGPIQWFRGAGPGRE LIYNQKEGHFPRVTTVSDLTKRNNMDFSIRIGNITPADAGTYYCVKF RKGSPDDVEFKSGAGTELSVR |
| 196 | huSIRPα IgV(6) | huSIRPα IgV(6) | EEELQVIQPDKSVLVAAGETATLRCTATSLIPVGPIQWFRGAGPGRE LIYNQKEGHFPRVTTVSDLTKRNNMDFPIRIGNITPADAGTYYCVKF RKGSPDDVEFKSGAGTELSVR |
| 197 | huSIRPα IgV(7) | huSIRPα IgV(7) | EEELQVIQPDKSVSVAAGESAILHCTVTSLIPVGPIQWFRGAGPARE LIYNQKEGHFPRVTTVSESTKRENMDFSISISNITPADAGTYYCVKFR KGSPDTEFKSGAGTELSVR |
| 198 | huSIRPα IgV(8) | huSIRPα IgV(8) | EEELQVIQPDKSVLVAAGETATLRCTATSLIPVGPIQWFRGAGPARE LIYNQKEGHFPRVTTVSESTKRENMDFSISISNITPADAGTYYCVKFR KGSPDTEFKSGAGTELSVR |
| 199 | huSIRPα IgV(9) | huSIRPα IgV(9) | EEELQVIQPDKSVLVAAGETATLRCTATSLIPVGPIQWFRGAGPGRE LIYNQKEGHFPRVTTVSDLTKRNNMDFSIRISNITPADAGTYYCVKF RKGSPDDVEFKSGAGTELSVR |
| 200 | huSIRPα IgV(10) | huSIRPα IgV(10) | EEELQVIQPDKSVSVAAGESAILHCTVTSLIPVGPIQWFRGAGPARE LIYNQKEGHFPRVTTVSESTKRENMDFSISISNITPADAGTYYCVKFR KGSPDTEFKSGAGTELSVR |

What is claimed is:

1. A SIRPα antibody fusion protein comprising:
an IgV extracellular domain of SIRPα comprising an amino acid sequence at least 95% identical to residues 3-115 of SEQ ID NO:6, to residues 3-114 of SEQ ID NO:8, or to residues 1-115 of SEQ ID NO:190, and comprising a substitution at one or more positions corresponding to positions 37, 54, or 72 of SEQ ID NO:6, SEQ ID NO:8, or SEQ ID NO:190, wherein the substitution at one or more positions is selected from the group consisting of: Q37W, Q37H, E54P, and M72R; and
an antibody or antigen-binding fragment thereof that binds to a surface antigen on a tumor cell.

2. The SIRPα antibody fusion protein of claim 1, wherein the surface antigen is a tumor antigen.

3. The SIRPα antibody fusion protein of claim 1, wherein the IgV extracellular domain of SIRPα comprises an amino acid sequence at least 95% identical to residues 1-115 of SEQ ID NO:6 or to residues 1-114 of SEQ ID NO:8.

4. The SIRPα antibody fusion protein of claim 1, wherein the IgV extracellular domain of SIRPα comprises an amino acid sequence at least 95% identical to a sequence selected from the group consisting of: residues 1-114 of SEQ ID NO:193, residues 1-115 of SEQ ID NO:194, residues 1-115 of SEQ ID NO:195, residues 1-115 of SEQ ID NO:196, residues 1-114 of SEQ ID NO:197, residues 1-114 of SEQ ID NO:198, residues 1-115 of SEQ ID NO:199, and residues 1-114 of SEQ ID NO:200.

5. The SIRPα antibody fusion protein of claim 1, wherein the IgV extracellular domain of SIRPα comprises an amino acid sequence at least 95% identical to residues 1-343 of SEQ ID NO:6.

6. A pharmaceutical composition comprising a pharmaceutically effective amount of the SIRPα antibody fusion protein of claim 1 and a pharmaceutically acceptable carrier.

7. The SIRPα antibody fusion protein of claim 2, wherein the tumor antigen is selected from the group consisting of HER2, HER3, EGFR, CD20, GD2, PD-L1, and CD19.

8. The SIRPα antibody fusion protein of claim 1, wherein the antibody or antigen-binding fragment thereof is an anti-EGFR antibody.

9. The SIRPα antibody fusion protein of claim 1, wherein the substitution is Q37W.

10. The SIRPα antibody fusion protein of claim 1, wherein the substitution is E54P.

11. The SIRPα antibody fusion protein of claim 1, wherein the IgV extracellular domain of SIRPα comprises the amino acid sequence of SEQ ID NO:135 or SEQ ID NO:136.

12. The SIRPα antibody fusion protein of claim 1, wherein the IgV extracellular domain of SIRPα comprises the amino acid sequence of SEQ ID NO:141 or SEQ ID NO:142.

13. The SIRPα antibody fusion protein of claim 1, wherein the IgV extracellular domain of SIRPα is connected to a heavy chain of the antibody or portion thereof.

14. The SIRPα antibody fusion protein of claim 1, wherein the IgV extracellular domain of SIRPα is connected to a light chain of the antibody or portion thereof.

15. The SIRPα antibody fusion protein of claim 1, wherein the IgV extracellular domain of SIRPα is connected at its N-terminus to the antibody or antigen-binding fragment thereof.

16. The SIRPα antibody fusion protein of claim 1, wherein the IgV extracellular domain of SIRPα is connected at its C-terminus to the antibody or antigen-binding fragment thereof.

17. The SIRPα antibody fusion protein of claim 1, wherein the IgV extracellular domain of SIRPα is connected to an N-terminus of the antibody of antigen-binding fragment thereof.

18. The SIRPα antibody fusion protein of claim 1, wherein the IgV extracellular domain of SIRPα is connected to a C-terminus of the antibody or antigen-binding fragment thereof.

19. The SIRPα antibody fusion protein of claim 1, wherein the substitution is Q37H.

20. The SIRPα antibody fusion protein of claim 1, wherein the substitution is M72R.

* * * * *

SEQUENCE LISTING

<160> NUMBER OF SEQ ID NOS: 206

<210> SEQ ID NO 1
<211> LENGTH: 639
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 1
caaattgttc tctcccagtc tccagcaatc ctgtctgcat ctccagggga gaaggtcaca    60

-continued

```
atgacttgca gggccagctc aagtgtaagt tacatccact ggttccagca gaagccaggt      120
tcctccccca aaccctggat ttatgccaca tccaacctgg cttctggagt ccctgttcgc      180
ttcagtggca gtgggtctgg gacttcttac tctctcacca tcagcagagt ggaggctgaa      240
gatgctgcca cttattactg ccagcagtgg actagtaacc cacccacgtt cggagggggg      300
accaagctgg aaatcaaacg tacggtggct gcaccatctg tcttcatctt cccgccatct      360
gatgagcagt tgaaatctgg aactgcctct gttgtgtgcc tgctgaataa cttctatccc      420
agagaggcca agtacagtg gaaggtggat aacgccctcc aatcgggtaa ctcccaggag       480
agtgtcacag agcaggacag caaggacagc acctacagcc tcagcagcac cctgacgctg      540
agcaaagcag actacgagaa acacaaagtc tacgcctgcg aagtcaccca tcagggcctg      600
agctcgcccg tcacaaagag cttcaacagg ggagagtgt                             639
```

<210> SEQ ID NO 2
<211> LENGTH: 213
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 2

```
Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Ile
            20                  25                  30

His Trp Phe Gln Gln Lys Pro Gly Ser Ser Pro Lys Pro Trp Ile Tyr
        35                  40                  45

Ala Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Thr Ser Asn Pro Pro Thr
                85                  90                  95

Phe Gly Gly Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210
```

<210> SEQ ID NO 3
<211> LENGTH: 672
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3

```
caagtccaat tgcagcagcc cggcgccgaa ctcgtgaagc cgggagcttc cgtgaaaatg      60
agctgcaagg cctccggata caccttcacc tcctacaaca tgcactgggt gaaacagacc     120
ccagggaggg gtctggagtg gattggggct atctacccgg gaaacggcga caccagctat     180
aaccagaagt ttaagggaaa ggccaccctg actgccgaca gtcctcgtc gactgcatac      240
atgcagctct cgagcctgac ttccgaggac agcgcagtgt attactgcgc acgtccact      300
tactacggcg gagattggta cttcaacgtc tggggcgcgg gcaccactgt gactgtgtcg     360
gccgcctcca ctaagggccc tagcgtgttc cccttggcgc catcgtcaaa gtccacctcc     420
ggtggcactg ccgccctggg atgccttgtg aaggactact cccccgaacc tgtgaccgtg     480
tcctggaact cgggcgcact gacttcgggg gtgcacacct ttcctgccgt cctgcaatcg     540
agcggtctgt actccctctc gtccgtggtc accgtgccgt ctagctccct cggaacccag     600
acctacatct gcaacgtcaa ccacaagccg agcaacacca agtggataa gagagtggag      660
ccgaagtcat gc                                                         672
```

<210> SEQ ID NO 4
<211> LENGTH: 224
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

```
Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Arg Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Ala Asp Lys Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Thr Tyr Tyr Gly Gly Asp Trp Tyr Phe Asn Val Trp Gly
            100                 105                 110

Ala Gly Thr Thr Val Thr Val Ser Ala Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205
```

Lys Pro Ser Asn Thr Lys Val Asp Lys Arg Val Glu Pro Lys Ser Cys
            210                 215                 220

<210> SEQ ID NO 5
<211> LENGTH: 1422
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5

| | | | | | |
|---|---|---|---|---|---|
| gaggaggagc | tgcaggtgat | tcagcctgac | aagtccgtgt | tggttgcagc | tggagagaca | 60 |
| gccactctgc | gctgcactgc | gacctctctg | atccctgtgg | ggcccatcca | gtggttcaga | 120 |
| ggagctggac | caggccggga | attaatctac | aatcaaaaag | aaggccactt | ccccccgggta | 180 |
| acaactgttt | cagacctcac | aaagagaaac | aacatggact | tttccatccg | catcggtaac | 240 |
| atcaccccag | cagatgccgg | cacctactac | tgtgtgaagt | tccggaaagg | agcccccgat | 300 |
| gacgtggagt | ttaagtctgg | agcaggcact | gagctgtctg | tgcgcgccaa | accctctgcc | 360 |
| cccgtggtat | cggcccctgc | ggcgagggcc | acacctcagc | acacagtgag | cttcacctgc | 420 |
| gagtcccacg | gcttctcacc | cagagacatc | accctgaaat | ggttcaaaaa | tgggaatgag | 480 |
| ctctcagact | tccagaccaa | cgtggacccc | gtaggagaga | gcgtgtccta | cagcatccac | 540 |
| agcacagcca | aggtggtgct | gacccgcgag | gacgttcact | ctcaagtcat | ctgcgaggtg | 600 |
| gcccacgtca | ccttgcaggg | ggaccctctt | cgtgggactg | ccaacttgtc | tgagaccatc | 660 |
| cgagttccac | ccaccttgga | ggttactcaa | cagcccgtga | gggcagagaa | ccaggtgaat | 720 |
| gtcacctgcc | aggtgaggaa | gttctacccc | cagagactac | agctgacctg | gttggagaat | 780 |
| ggaaacgtgt | cccggacaga | aacggcctca | accgttacag | agaacaagga | tggtacctac | 840 |
| aactggatga | gctggctcct | ggtgaatgta | tctgcccaca | gggatgatgt | gaagctcacc | 900 |
| tgccaggtgg | agcatgacgg | gcagccagcg | gtcagcaaaa | gccatgacct | gaaggtctca | 960 |
| gcccacccga | aggagcaggg | ctcaaatacc | gccgctgaga | cactggatc | taatgaacgg | 1020 |
| aacatctata | ttgtggtggg | tgtggtgtgc | accttgctgg | tggccctact | gatggcggcc | 1080 |
| ctctacctcg | tccgaatcag | acagaagaaa | gcccagggct | ccacttcttc | tacaaggttg | 1140 |
| catgagcccg | agaagaatgc | cagagaaata | cacaggaca | caaatgatat | cacatatgca | 1200 |
| gacctgaacc | tgcccaaggg | gaagaagcct | gctccccagg | ctgcggagcc | aacaaccac | 1260 |
| acggagtatg | ccagcattca | gaccagcccg | cagcccgcgt | cggaggacac | cctcacctat | 1320 |
| gctgacctgg | acatggtcca | cctcaaccgg | accccaagc | agccggcccc | caagcctgag | 1380 |
| ccgtccttct | cagagtacgc | cagcgtccag | gtcccgagga | ag | | 1422 |

<210> SEQ ID NO 6
<211> LENGTH: 474
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Glu Glu Glu Leu Gln Val Ile Gln Pro Asp Lys Ser Val Leu Val Ala
1               5                   10                  15

Ala Gly Glu Thr Ala Thr Leu Arg Cys Thr Ala Thr Ser Leu Ile Pro
            20                  25                  30

```
Val Gly Pro Ile Gln Trp Phe Arg Gly Ala Gly Pro Gly Arg Glu Leu
         35                  40                  45

Ile Tyr Asn Gln Lys Glu Gly His Phe Pro Arg Val Thr Thr Val Ser
 50                  55                  60

Asp Leu Thr Lys Arg Asn Asn Met Asp Phe Ser Ile Arg Ile Gly Asn
 65                  70                  75                  80

Ile Thr Pro Ala Asp Ala Gly Thr Tyr Tyr Cys Val Lys Phe Arg Lys
                 85                  90                  95

Gly Ser Pro Asp Asp Val Glu Phe Lys Ser Gly Ala Gly Thr Glu Leu
                100                 105                 110

Ser Val Arg Ala Lys Pro Ser Ala Pro Val Val Ser Gly Pro Ala Ala
                115                 120                 125

Arg Ala Thr Pro Gln His Thr Val Ser Phe Thr Cys Glu Ser His Gly
            130                 135                 140

Phe Ser Pro Arg Asp Ile Thr Leu Lys Trp Phe Lys Asn Gly Asn Glu
145                 150                 155                 160

Leu Ser Asp Phe Gln Thr Asn Val Asp Pro Val Gly Glu Ser Val Ser
                165                 170                 175

Tyr Ser Ile His Ser Thr Ala Lys Val Val Leu Thr Arg Glu Asp Val
            180                 185                 190

His Ser Gln Val Ile Cys Glu Val Ala His Val Thr Leu Gln Gly Asp
            195                 200                 205

Pro Leu Arg Gly Thr Ala Asn Leu Ser Glu Thr Ile Arg Val Pro Pro
            210                 215                 220

Thr Leu Glu Val Thr Gln Gln Pro Val Arg Ala Glu Asn Gln Val Asn
225                 230                 235                 240

Val Thr Cys Gln Val Arg Lys Phe Tyr Pro Gln Arg Leu Gln Leu Thr
                245                 250                 255

Trp Leu Glu Asn Gly Asn Val Ser Arg Thr Glu Thr Ala Ser Thr Val
                260                 265                 270

Thr Glu Asn Lys Asp Gly Thr Tyr Asn Trp Met Ser Trp Leu Leu Val
            275                 280                 285

Asn Val Ser Ala His Arg Asp Asp Val Lys Leu Thr Cys Gln Val Glu
            290                 295                 300

His Asp Gly Gln Pro Ala Val Ser Lys Ser His Asp Leu Lys Val Ser
305                 310                 315                 320

Ala His Pro Lys Glu Gln Gly Ser Asn Thr Ala Ala Glu Asn Thr Gly
                325                 330                 335

Ser Asn Glu Arg Asn Ile Tyr Ile Val Val Gly Val Val Cys Thr Leu
                340                 345                 350

Leu Val Ala Leu Leu Met Ala Ala Leu Tyr Leu Val Arg Ile Arg Gln
            355                 360                 365

Lys Lys Ala Gln Gly Ser Thr Ser Ser Thr Arg Leu His Glu Pro Glu
370                 375                 380

Lys Asn Ala Arg Glu Ile Thr Gln Asp Thr Asn Asp Ile Thr Tyr Ala
385                 390                 395                 400

Asp Leu Asn Leu Pro Lys Gly Lys Lys Pro Ala Pro Gln Ala Ala Glu
                405                 410                 415

Pro Asn Asn His Thr Glu Tyr Ala Ser Ile Gln Thr Ser Pro Gln Pro
            420                 425                 430

Ala Ser Glu Asp Thr Leu Thr Tyr Ala Asp Leu Asp Met Val His Leu
            435                 440                 445
```

Asn Arg Thr Pro Lys Gln Pro Ala Pro Lys Pro Glu Pro Ser Phe Ser
    450                 455                 460

Glu Tyr Ala Ser Val Gln Val Pro Arg Lys
465                 470

<210> SEQ ID NO 7
<211> LENGTH: 342
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7
gaggaagagc tgcaggtcat ccagcctgac aagtcagtca gcgtggcagc tggagagagc      60
gccattctgc actgcacagt cacttccctg atcccagtgg gacccattca gtggttccga     120
ggcgcaggac cagccaggga actgatctac aaccagaagg agggccattt ccccgcgtc     180 acaaccgtga gcgaatctac caaacgagag aatatggact ttagtatctc aattagcaac     240
attactcccg ctgatgcagg cacctactat tgcgtgaagt tccggaaagg aagccctgac     300
actgagttca gtccggggc cggcaccgag ctgtctgtgc gc                          342

<210> SEQ ID NO 8
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Glu Glu Glu Leu Gln Val Ile Gln Pro Asp Lys Ser Val Ser Val Ala
1               5                   10                  15

Ala Gly Glu Ser Ala Ile Leu His Cys Thr Val Thr Ser Leu Ile Pro
            20                  25                  30

Val Gly Pro Ile Gln Trp Phe Arg Gly Ala Gly Pro Ala Arg Glu Leu
        35                  40                  45

Ile Tyr Asn Gln Lys Glu Gly His Phe Pro Arg Val Thr Thr Val Ser
    50                  55                  60

Glu Ser Thr Lys Arg Glu Asn Met Asp Phe Ser Ile Ser Ile Ser Asn
65                  70                  75                  80

Ile Thr Pro Ala Asp Ala Gly Thr Tyr Tyr Cys Val Lys Phe Arg Lys
                85                  90                  95

Gly Ser Pro Asp Thr Glu Phe Lys Ser Gly Ala Gly Thr Glu Leu Ser
            100                 105                 110

Val Arg

<210> SEQ ID NO 9
<211> LENGTH: 1758
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9
caagtccaat tgcagcagcc cggcgccgaa ctcgtgaagc cgggagcttc cgtgaaaatg      60
agctgcaagg cctccggata caccttcacc tcctacaaca tgcactgggt gaaacagacc     120
ccagggaggg gtctggagtg gattgggct atctacccgg gaaacggcga caccagctat     180

-continued

```
aaccagaagt taagggaaa ggccaccctg actgccgaca agtcctcgtc gactgcatac      240
atgcagctct cgagcctgac ttccgaggac agcgcagtgt attactgcgc acgtccact      300
tactacggcg agattggta cttcaacgtc tggggcgcgg gcaccactgt gactgtgtcg      360
gccgcctcca ctaagggccc tagcgtgttc cccttggcgc atcgtcaaa gtccacctcc      420
ggtggcactg ccgccctggg atgccttgtg aaggactact cccccgaacc tgtgaccgtg      480
tcctggaact cgggcgcact gacttcgggg gtgcacacct tcctgccgt cctgcaatcg      540
agcggtctgt actccctctc gtccgtggtc accgtgccgt ctagctccct cggaacccag      600
acctacatct gcaacgtcaa ccacaagccg agcaacacca agtggataa agagtggag      660
ccgaagtcat gcgacaagac tcatacttgt ccccatgcc ccgccccgga actgctgggg      720
ggcccatccg tgttcctgtt cccgccgaaa cctaaggaca ccctgatgat ttcgagaact      780
ccggaagtga cctgtgtggt ggtcgacgtg tcccacgagg atccggaggt caagttcaat      840
tggtacgtcg acggagtgga agtccacaac gccaagacca gccccgggga ggagcagtac      900
aactccactt accgggtggt gtccgtgctg accgtgctgc atcaggattg gctgaacgga      960
aaggagtata agtgcaaagt gtcaaacaag gcattgcctg cgccaatcga aaagaccatt     1020
agcaaggcca agggccagcc cagggaacca caggtgtaca ctctgccccc gtcccgcgaa     1080
gaaatgacca gaaccaagt gtcactgaca tgcctcgtga agggatttta cccgtccgat     1140
atcgccgtgg aatgggaatc gaacggtcaa cctgaaaaca actacaagac gaccccctccg    1200
gtcctggaca gcgatggctc attcttcctg tactccaagc ttacggtgga caagtcccgg     1260
tggcaacagg gaaatgtgtt ttcgtgctcc gtgatgcatg aggctctgca caaccactac     1320
acccagaagt cactctccct gagcccccggc gcggggggtg gtggaagcgg aggagggggg     1380
tctgggggtg gcggttccgg cggcggcgga tccgaggagg aacttcaggt catccagccc     1440
gacaagagcg tgctcgtggc ggccggagaa accgcaactc tgagatgcac cgctacctcg     1500
ctgattcccg tggggcctat ccagtggttc cgcggggccg gacccggacg cgagctcatc     1560
tacaaccaga aggagggggca cttcccgagg gtcaccaccg tgtcggacct caccaagcgc     1620
aacaacatgg acttcagcat tcggatcggc aacatcaccc ccgccgacgc cggcacctat     1680
tactgcgtga agttccggaa gggcagcccct gacgacgtgg agttcaaaag cggagccgga     1740
accgagctgt ccgtgaga                                                   1758
```

```
<210> SEQ ID NO 10
<211> LENGTH: 586
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Arg Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Ala Asp Lys Ser Ser Ser Thr Ala Tyr
```

```
                65                  70                  75                  80
        Met Gln Leu Ser Ser Leu Thr Ser Glu Asp Ser Ala Val Tyr Tyr Cys
                            85                  90                  95

Ala Arg Ser Thr Tyr Tyr Gly Gly Asp Trp Tyr Phe Asn Val Trp Gly
                        100                 105                 110

Ala Gly Thr Thr Val Thr Val Ser Ala Ala Ser Thr Lys Gly Pro Ser
                        115                 120                 125

Val Phe Pro Leu Ala Pro Ser Ser Lys Ser Thr Ser Gly Gly Thr Ala
                    130                 135                 140

Ala Leu Gly Cys Leu Val Lys Asp Tyr Phe Pro Glu Pro Val Thr Val
        145                 150                 155                 160

Ser Trp Asn Ser Gly Ala Leu Thr Ser Gly Val His Thr Phe Pro Ala
                            165                 170                 175

Val Leu Gln Ser Ser Gly Leu Tyr Ser Leu Ser Ser Val Val Thr Val
                        180                 185                 190

Pro Ser Ser Ser Leu Gly Thr Gln Thr Tyr Ile Cys Asn Val Asn His
                        195                 200                 205

Lys Pro Ser Asn Thr Lys Val Asp Lys Arg Val Glu Pro Lys Ser Cys
                    210                 215                 220

Asp Lys Thr His Thr Cys Pro Pro Cys Pro Ala Pro Glu Leu Leu Gly
        225                 230                 235                 240

Gly Pro Ser Val Phe Leu Phe Pro Pro Lys Pro Lys Asp Thr Leu Met
                            245                 250                 255

Ile Ser Arg Thr Pro Glu Val Thr Cys Val Val Val Asp Val Ser His
                        260                 265                 270

Glu Asp Pro Glu Val Lys Phe Asn Trp Tyr Val Asp Gly Val Glu Val
                    275                 280                 285

His Asn Ala Lys Thr Lys Pro Arg Glu Glu Gln Tyr Asn Ser Thr Tyr
                    290                 295                 300

Arg Val Val Ser Val Leu Thr Val Leu His Gln Asp Trp Leu Asn Gly
        305                 310                 315                 320

Lys Glu Tyr Lys Cys Lys Val Ser Asn Lys Ala Leu Pro Ala Pro Ile
                            325                 330                 335

Glu Lys Thr Ile Ser Lys Ala Lys Gly Gln Pro Arg Glu Pro Gln Val
                        340                 345                 350

Tyr Thr Leu Pro Pro Ser Arg Glu Glu Met Thr Lys Asn Gln Val Ser
                    355                 360                 365

Leu Thr Cys Leu Val Lys Gly Phe Tyr Pro Ser Asp Ile Ala Val Glu
        370                 375                 380

Trp Glu Ser Asn Gly Gln Pro Glu Asn Asn Tyr Lys Thr Thr Pro Pro
        385                 390                 395                 400

Val Leu Asp Ser Asp Gly Ser Phe Phe Leu Tyr Ser Lys Leu Thr Val
                            405                 410                 415

Asp Lys Ser Arg Trp Gln Gln Gly Asn Val Phe Ser Cys Ser Val Met
                        420                 425                 430

His Glu Ala Leu His Asn His Tyr Thr Gln Lys Ser Leu Ser Leu Ser
                    435                 440                 445

Pro Gly Ala Gly Gly Gly Ser Gly Gly Gly Ser Gly Gly Gly
                    450                 455                 460

Gly Ser Gly Gly Gly Ser Glu Glu Leu Gln Val Ile Gln Pro
        465                 470                 475                 480

Asp Lys Ser Val Leu Val Ala Ala Gly Glu Thr Ala Thr Leu Arg Cys
                        485                 490                 495
```

```
         Thr Ala Thr Ser Leu Ile Pro Val Gly Pro Ile Gln Trp Phe Arg Gly
                     500                 505                 510

Ala Gly Pro Gly Arg Glu Leu Ile Tyr Asn Gln Lys Glu Gly His Phe
                 515                 520                 525

Pro Arg Val Thr Thr Val Ser Asp Leu Thr Lys Arg Asn Asn Met Asp
             530                 535                 540

Phe Ser Ile Arg Ile Gly Asn Ile Thr Pro Ala Asp Ala Gly Thr Tyr
         545                 550                 555                 560

Tyr Cys Val Lys Phe Arg Lys Gly Ser Pro Asp Asp Val Glu Phe Lys
                         565                 570                 575

Ser Gly Ala Gly Thr Glu Leu Ser Val Arg
                     580                 585

<210> SEQ ID NO 11
<211> LENGTH: 1755
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11
caagtccaat tgcagcagcc cggcgccgaa ctcgtgaagc cgggagcttc cgtgaaaatg      60
agctgcaagg cctccggata caccttcacc tcctacaaca tgcactgggt gaaacagacc     120
ccagggaggg gtctggagtg gattggggct atctacccgg aaacggcga caccagctat      180 aaccagaagt ttaagggaaa ggccaccctg actgccgaca gtcctcgtc gactgcatac      240 atgcagctct cgagcctgac ttccgaggac agcgcagtgt attactgcgc acgtccact      300 tactacggcg gagattggta cttcaacgtc tggggcgcgg caccactgt gactgtgtcg      360 gccgcctcca ctaagggccc tagcgtgttc cccttggcgc atcgtcaaa gtccacctcc     420 ggtggcactg ccgccctggg atgccttgtg aaggactact ccccgaacc tgtgaccgtg     480 tcctggaact cgggcgcact gacttcgggg gtgcacacct ttcctgccgt cctgcaatcg    540
agcggtctgt actccctctc gtccgtggtc accgtgccgt ctagctccct cggaacccag    600
acctacatct gcaacgtcaa ccacaagccg agcaacacca agtggataa gagagtggag    660 ccgaagtcat gcgacaagac tcatacttgt cccccatgcc ccgccccgga actgctgggg   720
ggcccatccg tgttcctgtt cccgccgaaa cctaaggaca cctgatgat ttcgagaact    780 ccggaagtga cctgtgtggt ggtcgacgtg tcccacgagg atccggaggt caagttcaat    840
tggtacgtcg acggagtgga agtccacaac gccaagacca gccccggga ggagcagtac    900 aactccactt accgggtggt gtccgtgctg accgtgctgc atcaggattg gctgaacgga    960
aaggagtata agtgcaaagt gtcaaacaag gcattgcctg cgccaatcga aaagaccatt   1020
agcaaggcca agggccagcc cagggaacca caggtgtaca ctctgccccc gtcccgcgaa    1080
gaaatgacca gaaccaagt gtcactgaca tgcctcgtga agggatttta cccgtccgat   1140
atcgccgtgg aatgggaatc gaacggtcaa cctgaaaaca actacaagac gacccctccg    1200
gtcctggaca gcgatggctc attcttcctg tactccaagc ttacggtgga caagtcccgg    1260
tggcaacagg gaaatgtgtt tcgtgctcc gtgatgcatg aggctctgca caaccactac    1320
acccagaagt cactctccct gagccccggc gcgggggtg gtggaagcgg aggagggggg   1380
tctgggggtg gcggttccgg cggcggcgga tccgaggag agctccaggt catccagcct    1440
gacaagtccg tgtcggtggc cgcgggagag tccgccattc tgcactgcac cgtgacctcc    1500
```

-continued

```
ctcatccccg tgggacctat ccagtggttc agaggagccg ggcccgcacg ggaactgatc    1560
tataaccaga aggagggcca tttcccccgc gtgaccaccg tgtccgagag caccaagagg    1620
gaaaacatgg acttcagcat ttcgatcagc aacatcactc ccgctgacgc cgggacctac    1680
tactgcgtga agttccggaa aggaagcccg gacaccgagt tcaaaagcgg agccggcacc    1740
gaactgtcgg tccgc                                                     1755
```

<210> SEQ ID NO 12
<211> LENGTH: 585
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 12

```
Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Arg Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Thr Tyr Tyr Gly Gly Asp Trp Tyr Phe Asn Val Trp Gly
            100                 105                 110

Ala Gly Thr Thr Val Thr Val Ser Ala Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300
```

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Ala Gly Gly Gly Gly Ser Gly Gly Gly Ser Gly Gly Gly
    450                 455                 460

Gly Ser Gly Gly Gly Ser Glu Glu Glu Leu Gln Val Ile Gln Pro
465                 470                 475                 480

Asp Lys Ser Val Ser Val Ala Ala Gly Glu Ser Ala Ile Leu His Cys
                485                 490                 495

Thr Val Thr Ser Leu Ile Pro Val Gly Pro Ile Gln Trp Phe Arg Gly
            500                 505                 510

Ala Gly Pro Ala Arg Glu Leu Ile Tyr Asn Gln Lys Glu Gly His Phe
        515                 520                 525

Pro Arg Val Thr Thr Val Ser Glu Ser Thr Lys Arg Glu Asn Met Asp
    530                 535                 540

Phe Ser Ile Ser Ile Ser Asn Ile Thr Pro Ala Asp Ala Gly Thr Tyr
545                 550                 555                 560

Tyr Cys Val Lys Phe Arg Lys Gly Ser Pro Asp Thr Glu Phe Lys Ser
                565                 570                 575

Gly Ala Gly Thr Glu Leu Ser Val Arg
            580                 585

<210> SEQ ID NO 13
<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 13
gacatcttgc tgactcagtc tccagtcatc ctgtctgtga gtccaggaga aagagtcagt      60
ttctcctgca gggccagtca gagtattggc acaaacatac actggtatca gcaaagaaca     120
aatggttctc caaggcttct cataaagtat gcttctgagt ctatctctgg gatcccttcc     180
aggtttagtg gcagtggatc aggacagatt ttactcttag catcaacagt gtggagtct      240 gaagatattg cagattatta ctgtcaacaa aataataact ggccaaccac gttcggtgct     300
gggaccaagc tggagctgaa acgtacggtg gctgcaccat ctgtcttcat cttcccgcca     360
tctgatgagc agttgaaatc tggaactgcc tctgttgtgt gcctgctgaa taacttctat     420

```
cccagagagg ccaaagtaca gtggaaggtg ataacgccc tccaatcggg taactcccag      480
gagagtgtca cagagcagga cagcaaggac agcacctaca gcctcagcag caccctgacg      540
ctgagcaaag cagactacga gaaacacaaa gtctacgcct gcgaagtcac ccatcagggc      600
ctgagctcgc ccgtcacaaa gagcttcaac aggggagagt gt                        642
```

```
<210> SEQ ID NO 14
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Asp Ile Leu Leu Thr Gln Ser Pro Val Ile Leu Ser Val Ser Pro Gly
1               5                   10                  15

Glu Arg Val Ser Phe Ser Cys Arg Ala Ser Gln Ser Ile Gly Thr Asn
            20                  25                  30

Ile His Trp Tyr Gln Gln Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Asn Asn Asn Trp Pro Thr
                85                  90                  95

Thr Phe Gly Ala Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

```
<210> SEQ ID NO 15
<211> LENGTH: 666
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 15
caagtccaac tgaagcagtc cgggccggga ctcgtgcagc cgtcgcagtc actgtccatc      60
acttgcacgg tgtcaggctt ttccttgacc aactacggag tgcactgggt gcgccagtcc     120
cctggaaagg ggctggagtg gcttggcgtg atttggtccg gaggaaacac agactacaac     180 actccttca cctcccgcct gagcattaac aaggacaact ccaagtccca gtgttcttc      240
```

```
aagatgaaca gcctgcagag caatgatacc gccatctact attgtgcccg ggctctcacc    300
tactacgact acgaattcgc ctactgggga cagggaaccc tggtcactgt ctccgcggcc    360
tccactaagg gccctagcgt gttccccttg cgccatcgt caaagtccac ctccggtggc    420
actgccgccc tgggatgcct tgtgaaggac tacttcccg aacctgtgac cgtgtcctgg    480
aactcgggcg cactgacttc ggggtgcac acctttcctg ccgtcctgca atcgagcggt    540
ctgtactccc tctcgtccgt ggtcaccgtg ccgtctagct ccctcggaac ccagacctac    600
atctgcaacg tcaaccacaa gccgagcaac accaaagtgg ataagagagt ggagccgaag    660
tcatgc                                                                666
```

```
<210> SEQ ID NO 16
<211> LENGTH: 222
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys
    210                 215                 220

<210> SEQ ID NO 17
<211> LENGTH: 1752
<212> TYPE: DNA
<213> ORGANISM: Artificial Sequence
<220> FEATURE:
<223> OTHER INFORMATION: Description of Artificial Sequence: Synthetic
      polynucleotide
```

<400> SEQUENCE: 17

```
caagtccaac tgaagcagtc cgggccggga ctcgtgcagc cgtcgcagtc actgtccatc      60
acttgcacgg tgtcaggctt ttccttgacc aactacggag tgcactgggt gcgccagtcc    120
cctggaaagg ggctggagtg gcttggcgtg atttggtccg gaggaaacac agactacaac    180
actcctttca cctcccgcct gagcattaac aaggacaact ccaagtccca agtgttcttc    240
aagatgaaca gcctgcagag caatgatacc gccatctact attgtgcccg ggctctcacc    300
tactacgact acgaattcgc ctactgggga cagggaaccc tggtcactgt ctccgcggcc    360
tccactaagg gcctagcgt gttccccttg gcgccatcgt caaagtccac ctccggtggc    420
actgccgccc tgggatgcct tgtgaaggac tacttccccg aacctgtgac cgtgtcctgg    480
aactcgggcg cactgacttc gggggtgcac acctttcctg ccgtcctgca atcgagcggt    540
ctgtactccc tctcgtccgt ggtcaccgtg ccgtctagct ccctcggaac ccagacctac    600
atctgcaacg tcaaccacaa gccgagcaac accaaagtgg ataagagagt ggagccgaag    660
tcatgcgaca agactcatac ttgtccccca tgccccgccc cggaactgct gggggggccca    720
tccgtgttcc tgttcccgcc gaaacctaag gacaccctga tgatttcgag aactccggaa    780
gtgacctgtg tggtggtcga cgtgtcccac gaggatccgg aggtcaagtt caattggtac    840
gtcgacggag tggaagtcca caacgccaag accaagcccc gggaggagca gtacaactcc    900
acttaccggg tggtgtccgt gctgaccgtg ctgcatcagg attggctgaa cggaaaggag    960
tataagtgca agtgtcaaa caaggcattg cctgcgccaa tcgaaaagac cattagcaag   1020
gccaaggggc agcccaggga accacaggtg tacactctgc ccccgtcccg cgaagaaatg   1080
accaagaacc aagtgtcact gacatgcctc gtgaagggat tttacccgtc cgatatcgcc   1140
gtggaatggg aatcgaacgg tcaacctgaa acaactaca agacgacccc tccggtcctg   1200
gacagcgatg gctcattctt cctgtactcc aagcttacgg tggacaagtc ccggtggcaa   1260
cagggaaatg tgttttcgtg ctccgtgatg catgaggctc tgcacaacca ctacacccag   1320
aagtcactct ccctgagccc cggcgcgggg ggtggtggaa gcggaggagg ggggtctggg   1380
ggtggcggtt ccggcggcgg cggatccgag gaggaacttc aggtcatcca gcccgacaag   1440
agcgtgctcg tggcggccgg agaaaccgca actctgagat gcaccgctac ctcgctgatt   1500
cccgtggggc ctatccagtg gttccgcggg gccggacccg gacgcgagct catctacaac   1560
cagaaggagg ggcacttccc gagggtcacc accgtgtcgg acctcaccaa gcgcaacaac   1620
atggacttca gcattcggat cggcaacatc accccgccg acgccggcac ctattactgc   1680
gtgaagttcc ggaagggcag ccctgacgac gtggagttca aaagcggagc cggaaccgag   1740
ctgtccgtga ga                                                        1752
```

<210> SEQ ID NO 18
<211> LENGTH: 584
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 18

```
Gln Val Gln Leu Lys Gln Ser Gly Pro Gly Leu Val Gln Pro Ser Gln
1               5                   10                  15
Ser Leu Ser Ile Thr Cys Thr Val Ser Gly Phe Ser Leu Thr Asn Tyr
            20                  25                  30
```

```
Gly Val His Trp Val Arg Gln Ser Pro Gly Lys Gly Leu Glu Trp Leu
          35                  40                  45
Gly Val Ile Trp Ser Gly Gly Asn Thr Asp Tyr Asn Thr Pro Phe Thr
 50                  55                  60
Ser Arg Leu Ser Ile Asn Lys Asp Asn Ser Lys Ser Gln Val Phe Phe
 65                  70                  75                  80
Lys Met Asn Ser Leu Gln Ser Asn Asp Thr Ala Ile Tyr Tyr Cys Ala
                 85                  90                  95
Arg Ala Leu Thr Tyr Tyr Asp Tyr Glu Phe Ala Tyr Trp Gly Gln Gly
                 100                 105                 110
Thr Leu Val Thr Val Ser Ala Ala Ser Thr Lys Gly Pro Ser Val Phe
             115                 120                 125
Pro Leu Ala Pro Ser Ser Lys Ser Thr Ser Gly Gly Thr Ala Ala Leu
 130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                 165                 170                 175
Gln Ser Ser Gly Leu Tyr Ser Leu Ser Ser Val Val Thr Val Pro Ser
             180                 185                 190
Ser Ser Leu Gly Thr Gln Thr Tyr Ile Cys Asn Val Asn His Lys Pro
         195                 200                 205
Ser Asn Thr Lys Val Asp Lys Arg Val Glu Pro Lys Ser Cys Asp Lys
     210                 215                 220
Thr His Thr Cys Pro Pro Cys Pro Ala Pro Glu Leu Leu Gly Gly Pro
225                 230                 235                 240
Ser Val Phe Leu Phe Pro Pro Lys Pro Lys Asp Thr Leu Met Ile Ser
                 245                 250                 255
Arg Thr Pro Glu Val Thr Cys Val Val Val Asp Val Ser His Glu Asp
             260                 265                 270
Pro Glu Val Lys Phe Asn Trp Tyr Val Asp Gly Val Glu Val His Asn
         275                 280                 285
Ala Lys Thr Lys Pro Arg Glu Glu Gln Tyr Asn Ser Thr Tyr Arg Val
     290                 295                 300
Val Ser Val Leu Thr Val Leu His Gln Asp Trp Leu Asn Gly Lys Glu
305                 310                 315                 320
Tyr Lys Cys Lys Val Ser Asn Lys Ala Leu Pro Ala Pro Ile Glu Lys
                 325                 330                 335
Thr Ile Ser Lys Ala Lys Gly Gln Pro Arg Glu Pro Gln Val Tyr Thr
             340                 345                 350
Leu Pro Pro Ser Arg Glu Glu Met Thr Lys Asn Gln Val Ser Leu Thr
         355                 360                 365
Cys Leu Val Lys Gly Phe Tyr Pro Ser Asp Ile Ala Val Glu Trp Glu
370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
                 405                 410                 415
Ser Arg Trp Gln Gln Gly Asn Val Phe Ser Cys Ser Val Met His Glu
             420                 425                 430
Ala Leu His Asn His Tyr Thr Gln Lys Ser Leu Ser Leu Ser Pro Gly
         435                 440                 445
Ala Gly Gly Gly Gly Ser Gly Gly Gly Gly Ser Gly Gly Gly Gly Ser
```

```
                   450                 455                 460
Gly Gly Gly Gly Ser Glu Glu Leu Gln Val Ile Gln Pro Asp Lys
465                 470                 475                 480

Ser Val Leu Val Ala Ala Gly Glu Thr Ala Thr Leu Arg Cys Thr Ala
                485                 490                 495

Thr Ser Leu Ile Pro Val Gly Pro Ile Gln Trp Phe Arg Gly Ala Gly
                500                 505                 510

Pro Gly Arg Glu Leu Ile Tyr Asn Gln Lys Glu Gly His Phe Pro Arg
            515                 520                 525

Val Thr Thr Val Ser Asp Leu Thr Lys Arg Asn Asn Met Asp Phe Ser
        530                 535                 540

Ile Arg Ile Gly Asn Ile Thr Pro Ala Asp Ala Gly Thr Tyr Tyr Cys
545                 550                 555                 560

Val Lys Phe Arg Lys Gly Ser Pro Asp Asp Val Glu Phe Lys Ser Gly
                565                 570                 575

Ala Gly Thr Glu Leu Ser Val Arg
                580
```

<210> SEQ ID NO 19
<211> LENGTH: 1749
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 19

```
caagtccaac tgaagcagtc cgggccggga ctcgtgcagc cgtcgcagtc actgtccatc    60
acttgcacgg tgtcaggctt ttccttgacc aactacggag tgcactgggt gcgccagtcc   120
cctggaaagg ggctggagtg gcttggcgtg atttggtccg gaggaaacac agactacaac   180 actccttttca cctcccgcct gagcattaac aaggacaact ccaagtccca agtgttcttc   240
aagatgaaca gcctgcagag caatgatacc gccatctact attgtgcccg ggctctcacc   300
tactacgact acgaattcgc ctactgggga cagggaaccc tggtcactgt ctccgcggcc   360
tccactaagg gccctagcgt gttccccttg cgccatcgt caaagtccac ctccggtggc   420
actgccgccc tgggatgcct tgtgaaggac tacttccccg aacctgtgac cgtgtcctgg   480
aactcgggcg cactgacttc gggggtgcac acctttcctg ccgtcctgca atcgagcggt   540
ctgtactccc tctcgtccgt ggtcaccgtg ccgtctagct ccctcggaac ccagacctac   600
atctgcaacg tcaaccacaa gccgagcaac accaaagtgg ataagagagt ggagccgaag   660
tcatgcgaca gactcatac ttgtccccca tgccccgccc cggaactgct gggggggccca   720 tccgtgttcc tgttcccgcc gaaacctaag gacaccctga tgatttcgag aactccggaa   780
gtgacctgtg tggtggtcga cgtgtcccac gaggatccgg aggtcaagtt caattggtac   840
gtcgacggag tggaagtcca caacgccaag accaagcccc gggaggagca gtacaactcc   900
acttaccggg tggtgtccgt gctgaccgtg ctgcatcagg attggctgaa cggaaaggag   960
tataagtgca agtgtcaaa caaggcattg cctgcgccaa tcgaaaagac cattagcaag  1020
gccaagggcc agcccaggga accacaggtg tacactctgc ccccgtcccg cgaagaaatg  1080
accaagaacc aagtgtcact gacatgcctc gtgaagggat tttacccgtc cgatatcgcc  1140
gtggaatggg aatcgaacgg tcaacctgaa acaactaca agacgacccc tccggtcctg  1200
gacagcgatg gctcattctt cctgtactcc aagcttacgg tggacaagtc ccggtggcaa  1260
```

-continued

```
cagggaaatg tgttttcgtg ctccgtgatg catgaggctc tgcacaacca ctacacccag    1320
aagtcactct ccctgagccc cggcgcgggg ggtggtggaa gcggaggagg ggggtctggg    1380
ggtggcggtt ccggcggcgg cggatccgag gaggagctcc aggtcatcca gcctgacaag    1440
tccgtgtcgg tggccgcggg agagtccgcc attctgcact gcaccgtgac ctccctcatc    1500
cccgtgggac ctatccagtg gttcagagga gccgggcccg cacgggaact gatctataac    1560
cagaaggagg ccatttccc cgcgtgacc accgtgtccg agagcaccaa gagggaaaac     1620
atggacttca gcatttcgat cagcaacatc actcccgctg acgccgggac ctactactgc    1680
gtgaagttcc ggaaggaag cccggacacc gagttcaaaa gcggagccgg caccgaactg    1740
tcggtccgc                                                          1749
```

<210> SEQ ID NO 20
<211> LENGTH: 583
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

```
Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270
```

```
Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Ala Gly Gly Gly Gly Ser Gly Gly Gly Ser Gly Gly Gly Gly Ser
    450                 455                 460

Gly Gly Gly Gly Ser Glu Glu Leu Gln Val Ile Gln Pro Asp Lys
465                 470                 475                 480

Ser Val Ser Val Ala Ala Gly Glu Ser Ala Ile Leu His Cys Thr Val
                485                 490                 495

Thr Ser Leu Ile Pro Val Gly Pro Ile Gln Trp Phe Arg Gly Ala Gly
            500                 505                 510

Pro Ala Arg Glu Leu Ile Tyr Asn Gln Lys Glu Gly His Phe Pro Arg
        515                 520                 525

Val Thr Thr Val Ser Glu Ser Thr Lys Arg Glu Asn Met Asp Phe Ser
530                 535                 540

Ile Ser Ile Ser Asn Ile Thr Pro Ala Asp Ala Gly Thr Tyr Tyr Cys
545                 550                 555                 560

Val Lys Phe Arg Lys Gly Ser Pro Asp Thr Glu Phe Lys Ser Gly Ala
                565                 570                 575

Gly Thr Glu Leu Ser Val Arg
            580

<210> SEQ ID NO 21
<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 21
gacatccaga tgacccagag ccctagcagc ctgagcgcga gcgtgggcga cagagtgaca    60
atcacctgca gggccagcca ggacgtgaat accgccgtgg cctggtacca gcagaaaccc   120
ggcaaggccc ctaagctgct gatctactcc gcctccttcc tctacagcgg cgtgcccagc   180
aggtttagcg gcagcaggag cggcacagat ttcaccctga ccatcagcag cctgcagccc   240
gaggacttcg ccacctacta ctgccagcag cattacacca ccccccccac cttcggccag   300
ggaacaaagg tggagatcaa gcgtacggtg gccgctccca gcgtgttcat cttcccccc    360 agcgacgagc agctgaagag cggaaccgcc agcgtggtgt gcctgctgaa caacttctac   420
```

```
ctgagcaagg ccgactacga gaagcacaaa gtgtacgcct gcgaggtgac ccaccaggga    600
ctgagcagcc ccgtgaccaa gtccttcaac aggggcgagt gc                      642
```

<210> SEQ ID NO 22
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 23
<211> LENGTH: 669
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 23

```
gaagtccaac ttgtggagag cggcgggggc ctggtccagc ctggaggatc cctgcggctg    60
tcctgcgccg cttccggatt caacattaag gataccctaca ttcactgggt cagacaggcc   120
ccgggaaagg ggctggaatg ggtggccagg atctacccga ccaacggcta cactcgctac   180
gccgactcag tgaagggtcg cttcaccatc tccgccgaca cgtccaagaa cacagcgtac   240
ctccagatga attcactgcg ggccgaggat accgctgtgt actactgttc gcatgggcgc   300
ggcgacggat tctatgcgat ggactactgg ggacagggaa ccctcgtgac tgtgtcctcc   360
```

```
gcctccacta agggccctag cgtgttcccc ttggcgccat cgtcaaagtc cacctccggt    420
ggcactgccg ccctgggatg ccttgtgaag gactacttcc ccgaacctgt gaccgtgtcc    480
tggaactcgg gcgcactgac ttcggggggtg cacacctttc ctgccgtcct gcaatcgagc    540
ggtctgtact ccctctcgtc cgtggtcacc gtgccgtcta gctccctcgg aacccagacc    600
tacatctgca acgtcaacca caagccgagc aacaccaaag tggataagag agtggagccg    660
aagtcatgc                                                             669
```

<210> SEQ ID NO 24
<211> LENGTH: 223
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys
    210                 215                 220
```

<210> SEQ ID NO 25
<211> LENGTH: 1752
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 25

```
gaagtccaac ttgtggagag cggcggggc ctggtccagc ctggaggatc cctgcggctg     60
```

-continued

| | |
|---|---|
| tcctgcgccg cttccggatt caacattaag gatacctaca ttcactgggt cagacaggcc | 120 |
| ccgggaaagg ggctggaatg ggtggccagg atctacccga ccaacggcta cactcgctac | 180 |
| gccgactcag tgaagggtcg cttcaccatc tccgccgaca cgtccaagaa cacagcgtac | 240 |
| ctccagatga attcactgcg ggccgaggat accgctgtgt actactgttc gcgatggggc | 300 |
| ggcgacggat tctatgcgat ggactactgg ggacagggaa ccctcgtgac tgtgtcctcc | 360 |
| gcctccacta agggcctag cgtgttcccc ttggcgccat cgtcaaagtc cacctccggt | 420 |
| ggcactgccg ccctgggatg ccttgtgaag gactacttcc ccgaacctgt gaccgtgtcc | 480 |
| tggaactcgg gcgcactgac ttcggggtg cacacctttc ctgccgtcct gcaatcgagc | 540 |
| ggtctgtact ccctctcgtc cgtggtcacc gtgccgtcta gctccctcgg aacccagacc | 600 |
| tacatctgca acgtcaacca caagccgagc aacaccaaag tggataagag agtggagccg | 660 |
| aagtcatgcg acaagactca tacttgtccc ccatgccccg ccccggaact gctgggggc | 720 |
| ccatccgtgt tcctgttccc gccgaaacct aaggacaccc tgatgatttc gagaactccg | 780 |
| gaagtgacct gtgtggtggt cgacgtgtcc cacgaggatc cggaggtcaa gttcaattgg | 840 |
| tacgtcgacg gagtggaagt ccacaacgcc aagaccaagc cccgggagga gcagtacaac | 900 |
| tccacttacc gggtggtgtc cgtgctgacc gtgctgcatc aggattggct gaacggaaag | 960 |
| gagtataagt gcaaagtgtc aaacaaggca ttgcctgcgc caatcgaaaa gaccattagc | 1020 |
| aaggccaagg gccagcccag ggaaccacag gtgtacactc tgccccccgtc cgcgaagaa | 1080 |
| atgaccaaga accaagtgtc actgacatgc ctcgtgaagg gattttaccc gtccgatatc | 1140 |
| gccgtggaat gggaatcgaa cggtcaacct gaaaacaact acaagacgac ccctccggtc | 1200 |
| ctggacagcg atggctcatt cttcctgtac tccaagctta cggtggacaa gtcccggtgg | 1260 |
| caacaggaa atgtgttttc gtgctccgtg atgcatgagg ctctgcacaa ccactacacc | 1320 |
| cagaagtcac tctccctgag ccccggcgcg ggggtggtg gaagcggagg agggggtct | 1380 |
| gggggtggcg gttccggcgg cggcggatcc gaggaggagc tccaggtcat ccagcctgac | 1440 |
| aagtccgtgt cggtggccgc gggagagtcc gccattctgc actgcaccgt gacctccctc | 1500 |
| atccccgtgg gacctatcca gtggttcaga ggagccgggc ccgcacggga actgatctat | 1560 |
| aaccagaagg agggccattt ccccgcgtg accaccgtgt ccgagagcac caagagggaa | 1620 |
| aacatggact tcagcatttc gatcagcaac atcactcccg ctgacgccgg gacctactac | 1680 |
| tgcgtgaagt tccggaaagg aagcccggac accgagttca aaagcggagc cggcaccgaa | 1740 |
| ctgtcggtcc gc | 1752 |

<210> SEQ ID NO 26
<211> LENGTH: 584
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val

-continued

```
                50                  55                  60
Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ser Arg Trp Gly Gly Asp Gly Phe Tyr Ala Met Asp Tyr Trp Gly Gln
                100                 105                 110

Gly Thr Leu Val Thr Val Ser Ser Ala Ser Thr Lys Gly Pro Ser Val
                115                 120                 125

Phe Pro Leu Ala Pro Ser Ser Lys Ser Thr Ser Gly Gly Thr Ala Ala
                130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
                195                 200                 205

Pro Ser Asn Thr Lys Val Asp Lys Arg Val Glu Pro Lys Ser Cys Asp
                210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
                275                 280                 285

Asn Ala Lys Thr Lys Pro Arg Glu Glu Gln Tyr Asn Ser Thr Tyr Arg
                290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Arg Glu Glu Met Thr Lys Asn Gln Val Ser Leu
                355                 360                 365

Thr Cys Leu Val Lys Gly Phe Tyr Pro Ser Asp Ile Ala Val Glu Trp
                370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
                435                 440                 445

Gly Ala Gly Gly Gly Ser Gly Gly Gly Ser Gly Gly Gly
                450                 455                 460

Ser Gly Gly Gly Gly Ser Glu Glu Glu Leu Gln Val Ile Gln Pro Asp
465                 470                 475                 480
```

```
Lys Ser Val Ser Val Ala Ala Gly Glu Ser Ala Ile Leu His Cys Thr
                485                 490                 495

Val Thr Ser Leu Ile Pro Val Gly Pro Ile Gln Trp Phe Arg Gly Ala
            500                 505                 510

Gly Pro Ala Arg Glu Leu Ile Tyr Asn Gln Lys Glu Gly His Phe Pro
        515                 520                 525

Arg Val Thr Thr Val Ser Glu Ser Thr Lys Arg Glu Asn Met Asp Phe
    530                 535                 540

Ser Ile Ser Ile Ser Asn Ile Thr Pro Ala Asp Ala Gly Thr Tyr Tyr
545                 550                 555                 560

Cys Val Lys Phe Arg Lys Gly Ser Pro Asp Thr Glu Phe Lys Ser Gly
                565                 570                 575

Ala Gly Thr Glu Leu Ser Val Arg
            580
```

<210> SEQ ID NO 27
<211> LENGTH: 660
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 27

```
gacgtggtga tgacccagac ccccctgagc ctgcccgtga ccccggcga gcccgccagc      60
atcagctgca ggagcagcca gagcctggtg cacaggaacg gcaacaccta cctgcactgg    120
tacctgcaga gcccggcca gagccccaag ctgctgatcc acaaggtgag caacaggttc     180
agcggcgtgc ccgacaggtt cagcggcagc ggcagcggca ccgacttcac cctgaagatc    240
agcagggtgg aggccgagga cctgggcgtg tacttctgca gccagagcac ccacgtgccc    300
cccctgacct tcggcgccgg caccaagctg gagctgaaga ggaccgtggc cgcccccagc    360
gtgttcatct tcccccccag cgacgagcag ctgaagagcg gcaccgccag cgtggtgtgc    420
ctgctgaaca acttctaccc cagggaggcc aaggtgcagt ggaaggtgga caacgccctg    480
cagagcggca cagccagga gcgtgacc gagcaggaca gcaaggacag cacctacagc       540
ctgagcagca ccctgaccct gagcaaggcc gactacgaga gcacaaggt gtacgcctgc    600
gaggtgaccc accagggcct gagcagcccc gtgaccaaga gcttcaacag gggcgagtgc    660
```

<210> SEQ ID NO 28
<211> LENGTH: 220
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

```
Asp Val Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Val His Arg
            20                  25                  30

Asn Gly Asn Thr Tyr Leu His Trp Tyr Leu Gln Lys Pro Gly Gln Ser
        35                  40                  45

Pro Lys Leu Leu Ile His Lys Val Ser Asn Arg Phe Ser Gly Val Pro
    50                  55                  60

Asp Arg Phe Ser Gly Ser Gly Ser Gly Thr Asp Phe Thr Leu Lys Ile
```

```
                65                  70                  75                  80
Ser Arg Val Glu Ala Glu Asp Leu Gly Val Tyr Phe Cys Ser Gln Ser
                    85                  90                  95

Thr His Val Pro Pro Leu Thr Phe Gly Ala Gly Thr Lys Leu Glu Leu
                100                 105                 110

Lys Arg Thr Val Ala Ala Pro Ser Val Phe Ile Phe Pro Pro Ser Asp
                115                 120                 125

Glu Gln Leu Lys Ser Gly Thr Ala Ser Val Val Cys Leu Leu Asn Asn
            130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
                180                 185                 190

Glu Lys His Lys Val Tyr Ala Cys Glu Val Thr His Gln Gly Leu Ser
            195                 200                 205

Ser Pro Val Thr Lys Ser Phe Asn Arg Gly Glu Cys
    210                 215                 220
```

<210> SEQ ID NO 29
<211> LENGTH: 648
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 29

```
gaggtgcagc tggtgcagag cggcgccgag gtggagaagc ccggcgccag cgtgaagatc    60
agctgcaagg ccagcggcag cagcttcacc ggctacaaca tgaactgggt gaggcagaac   120
atcggcaaga gcctggagtg gatcggcgcc atcgacccct actacggcgg caccagctac   180
aaccagaagt tcaagggcag ggccaccctg accgtggaca gagcaccag caccgcctac   240
atgcacctga gagcctgag gagcgaggac accgccgtgt actactgcgt gagcggcatg   300
gagtactggg gccagggcac cagcgtgacc gtgagcagcg ccagcaccaa gggccccagc   360
gtgttccccc tggcccccag cagcaagagc accagcggcg gcaccgccgc cctgggctgc   420
ctggtgaagg actacttccc cgagcccgtg accgtgagct ggaacagcgg cgccctgacc   480
agcggcgtgc acaccttccc cgccgtgctg cagagcagcg gcctgtacag cctgagcagc   540
gtggtgaccg tgcccagcag cagcctgggc acccagacct acatctgcaa cgtgaaccac   600
aagcccagca acaccaaggt ggacaagaag gtggagccca gagctgc                  648
```

<210> SEQ ID NO 30
<211> LENGTH: 216
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 30

```
Glu Val Gln Leu Val Gln Ser Gly Ala Glu Val Glu Lys Pro Gly Ala
1               5                   10                  15

Ser Val Lys Ile Ser Cys Lys Ala Ser Gly Ser Ser Phe Thr Gly Tyr
            20                  25                  30
```

Asn Met Asn Trp Val Arg Gln Asn Ile Gly Lys Ser Leu Glu Trp Ile
            35                  40                  45

Gly Ala Ile Asp Pro Tyr Tyr Gly Gly Thr Ser Tyr Asn Gln Lys Phe
 50                  55                  60

Lys Gly Arg Ala Thr Leu Thr Val Asp Lys Ser Thr Ser Thr Ala Tyr
 65                  70                  75                  80

Met His Leu Lys Ser Leu Arg Ser Glu Asp Thr Ala Val Tyr Tyr Cys
                 85                  90                  95

Val Ser Gly Met Glu Tyr Trp Gly Gln Gly Thr Ser Val Thr Val Ser
                100                 105                 110

Ser Ala Ser Thr Lys Gly Pro Ser Val Phe Pro Leu Ala Pro Ser Ser
            115                 120                 125

Lys Ser Thr Ser Gly Gly Thr Ala Ala Leu Gly Cys Leu Val Lys Asp
        130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Gln
            180                 185                 190

Thr Tyr Ile Cys Asn Val Asn His Lys Pro Ser Asn Thr Lys Val Asp
        195                 200                 205

Lys Lys Val Glu Pro Lys Ser Cys
    210                 215

<210> SEQ ID NO 31
<211> LENGTH: 1731
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 31
gaggtgcagc tggtgcagag cggcgccgag gtggagaagc ccggcgccag cgtgaagatc      60
agctgcaagg ccagcggcag cagcttcacc ggctacaaca tgaactgggt gaggcagaac     120
atcggcaaga gcctggagtg gatcggcgcc atcgacccct actacggcgg caccagctac     180
aaccagaagt tcaagggcag ggccaccctg accgtggaca agagcaccag caccgcctac     240
atgcacctga gagcctgaga gagcgaggac accgccgtgt actactgcgt gagcggcatg     300
gagtactggg gccagggcac cagcgtgacc gtgagcagcg ccagcaccaa gggccccagc     360
gtgttccccc tggcccccag cagcaagagc accagcggcg gcaccgccgc cctgggctgc     420
ctggtgaagg actacttccc cgagcccgtg accgtgagct ggaacagcgg cgccctgacc     480
agcggcgtgc acaccttccc cgccgtgctg cagagcagcg gcctgtacag cctgagcagc     540
gtggtgaccg tgcccagcag cagcctgggc acccagacct acatctgcaa cgtgaaccac     600
aagcccagca acaccaaggt ggacaagaag gtggagccca gagctgcga caagacccac     660 acctgccccc cctgccccgc ccccgagctg ctgggcggcc ccagcgtgtt cctgttcccc     720
cccaagccca aggacaccct gatgatcagc aggacccccg aggtgacctg cgtggtggtg     780
gacgtgagcc acgaggaccc cgaggtgaag ttcaactggt acgtggacgg cgtggaggtg     840
cacaacgcca agaccaagcc cagggaggag cagtacaaca gcacctacag gg tggtgagc     900 gtgctgaccg tgctgcacca ggactggctg aacggcaagg agtacaagtg caaggtgagc     960

```
aacaaggccc tgcccgcccc catcgagaag accatcagca aggccaaggg ccagcccagg    1020 gagcccagg tgtacaccct gcccccagc agggacgagc tgaccaagaa ccaggtgagc      1080
ctgacctgcc tggtgaaggg cttctacccc agcgacatcg ccgtggagtg ggagagcaac    1140
ggccagcccg agaacaacta caagaccacc cccccgtgc tggacagcga cggcagcttc     1200
ttcctgtaca gcaagctgac cgtggacaag agcaggtggc agcagggcaa cgtgttcagc    1260
tgcagcgtga tgcacgaggc cctgcacaac cactacaccc agaagagcct gagcctgagc    1320
cccggcgccg gcggcggcgg cagcggcggc ggcggcagcg gcggcggcgg cagcggcggc    1380
ggcggcagcg aggaggagct gcaggtgatc cagcccgaca gagcgtgag cgtggccgcc     1440 ggcgagagcg ccatcctgca ctgcaccgtg accagcctga tccccgtggg ccccatccag    1500
tggttcaggg gcgccggccc cgccaggag ctgatctaca accagaagga gggccacttc     1560
cccagggtga ccaccgtgag cgagagcacc aagagggaga acatggactt cagcatcagc    1620
atcagcaaca tcacccccgc cgacgccggc acctactact gcgtgaagtt caggaagggc    1680
agccccgaca ccgagttcaa gagcggcgcc ggcaccgagc tgagcgtgag g             1731

<210> SEQ ID NO 32
<211> LENGTH: 577
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Glu Val Gln Leu Val Gln Ser Gly Ala Glu Val Glu Lys Pro Gly Ala
1               5                   10                  15

Ser Val Lys Ile Ser Cys Lys Ala Ser Gly Ser Ser Phe Thr Gly Tyr
            20                  25                  30

Asn Met Asn Trp Val Arg Gln Asn Ile Gly Lys Ser Leu Glu Trp Ile
        35                  40                  45

Gly Ala Ile Asp Pro Tyr Tyr Gly Gly Thr Ser Tyr Asn Gln Lys Phe
    50                  55                  60

Lys Gly Arg Ala Thr Leu Thr Val Asp Lys Ser Thr Ser Thr Ala Tyr
65                  70                  75                  80

Met His Leu Lys Ser Leu Arg Ser Glu Asp Thr Ala Val Tyr Tyr Cys
                85                  90                  95

Val Ser Gly Met Glu Tyr Trp Gly Gln Gly Thr Ser Val Thr Val Ser
            100                 105                 110

Ser Ala Ser Thr Lys Gly Pro Ser Val Phe Pro Leu Ala Pro Ser Ser
        115                 120                 125

Lys Ser Thr Ser Gly Gly Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Gln
            180                 185                 190

Thr Tyr Ile Cys Asn Val Asn His Lys Pro Ser Asn Thr Lys Val Asp
        195                 200                 205

Lys Lys Val Glu Pro Lys Ser Cys Asp Lys Thr His Thr Cys Pro Pro
    210                 215                 220
```

Cys Pro Ala Pro Glu Leu Leu Gly Gly Pro Ser Val Phe Leu Phe Pro
225                 230                 235                 240

Pro Lys Pro Lys Asp Thr Leu Met Ile Ser Arg Thr Pro Glu Val Thr
            245                 250                 255

Cys Val Val Asp Val Ser His Glu Asp Pro Glu Val Lys Phe Asn
        260                 265                 270

Trp Tyr Val Asp Gly Val Glu Val His Asn Ala Lys Thr Lys Pro Arg
        275                 280                 285

Glu Glu Gln Tyr Asn Ser Thr Tyr Arg Val Val Ser Val Leu Thr Val
    290                 295                 300

Leu His Gln Asp Trp Leu Asn Gly Lys Glu Tyr Lys Cys Lys Val Ser
305                 310                 315                 320

Asn Lys Ala Leu Pro Ala Pro Ile Glu Lys Thr Ile Ser Lys Ala Lys
                325                 330                 335

Gly Gln Pro Arg Glu Pro Gln Val Tyr Thr Leu Pro Pro Ser Arg Asp
            340                 345                 350

Glu Leu Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
370                 375                 380

Asn Asn Tyr Lys Thr Thr Pro Pro Val Leu Asp Ser Asp Gly Ser Phe
385                 390                 395                 400

Phe Leu Tyr Ser Lys Leu Thr Val Asp Lys Ser Arg Trp Gln Gln Gly
                405                 410                 415

Asn Val Phe Ser Cys Ser Val Met His Glu Ala Leu His Asn His Tyr
            420                 425                 430

Thr Gln Lys Ser Leu Ser Leu Ser Pro Gly Ala Gly Gly Gly Gly Ser
        435                 440                 445

Gly Gly Gly Gly Ser Gly Gly Gly Ser Gly Gly Gly Gly Ser Glu
450                 455                 460

Glu Glu Leu Gln Val Ile Gln Pro Asp Lys Ser Val Ser Val Ala Ala
465                 470                 475                 480

Gly Glu Ser Ala Ile Leu His Cys Thr Val Thr Ser Leu Ile Pro Val
                485                 490                 495

Gly Pro Ile Gln Trp Phe Arg Gly Ala Gly Pro Ala Arg Glu Leu Ile
            500                 505                 510

Tyr Asn Gln Lys Glu Gly His Phe Pro Arg Val Thr Thr Val Ser Glu
        515                 520                 525

Ser Thr Lys Arg Glu Asn Met Asp Phe Ser Ile Ser Ile Ser Asn Ile
530                 535                 540

Thr Pro Ala Asp Ala Gly Thr Tyr Tyr Cys Val Lys Phe Arg Lys Gly
545                 550                 555                 560

Ser Pro Asp Thr Glu Phe Lys Ser Gly Ala Gly Thr Glu Leu Ser Val
                565                 570                 575

Arg

<210> SEQ ID NO 33
<211> LENGTH: 648
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 33

```
cagagcgctt tgactcagcc tgcctccgtg tctgggtctc ctggacagtc gatcaccatc      60
tcctgcactg gaaccagcag tgacgttggt ggctataatt atgtctcctg gtaccaacaa     120
cacccaggca aagcccccaa actcatgatt tatgatgtca gtaatcggcc ctcaggggtt     180
tctaatcgct tctctggctc caagtctggc aacacggcct ccctgaccat ctctgggctc     240
caggctgagg acgaggctga ttactactgc agctcatata aagcagcag cactcgagtc      300 ttcggaactg ggaccaaggt caccgtccta ggtcagccca aggccaaccc cactgtcact     360
ctgttcccgc cctcctctga ggagctccaa gccaacaagg ccacactagt gtgtctgatc     420
agtgacttct acccgggagc tgtgacagtg gcctggaagg cagatggcag ccccgtcaag     480
gcgggagtgg agaccaccaa accctccaaa cagagcaaca acaagtacgc ggccagcagc     540
tacctgagcc tgacgcccga gcagtggaag tcccacagaa gctacagctg ccaggtcacg     600
catgaaggga gcaccgtgga agacagtg gcccctacag aatgttca                    648
```

<210> SEQ ID NO 34
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

```
Gln Ser Ala Leu Thr Gln Pro Ala Ser Val Ser Gly Ser Pro Gly Gln
  1               5                  10                  15

Ser Ile Thr Ile Ser Cys Thr Gly Thr Ser Ser Asp Val Gly Gly Tyr
                 20                  25                  30

Asn Tyr Val Ser Trp Tyr Gln Gln His Pro Gly Lys Ala Pro Lys Leu
             35                  40                  45

Met Ile Tyr Asp Val Ser Asn Arg Pro Ser Gly Val Ser Asn Arg Phe
         50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ser Ser Tyr Thr Ser Ser
                 85                  90                  95

Ser Thr Arg Val Phe Gly Thr Gly Thr Lys Val Thr Val Leu Gly Gln
                100                 105                 110

Pro Lys Ala Asn Pro Thr Val Thr Leu Phe Pro Pro Ser Ser Glu Glu
            115                 120                 125

Leu Gln Ala Asn Lys Ala Thr Leu Val Cys Leu Ile Ser Asp Phe Tyr
        130                 135                 140

Pro Gly Ala Val Thr Val Ala Trp Lys Ala Asp Gly Ser Pro Val Lys
145                 150                 155                 160

Ala Gly Val Glu Thr Thr Lys Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215
```

<210> SEQ ID NO 35
<211> LENGTH: 669
<212> TYPE: DNA

<213> ORGANISM: Artificial Sequence
<220> FEATURE:
<223> OTHER INFORMATION: Description of Artificial Sequence: Synthetic polynucleotide

<400> SEQUENCE: 35

```
gaagttcaat tgttagagtc tggtggcggt cttgttcagc ctggtggttc tttacgtctt      60
tcttgcgctg cttccggatt cactttctct agctacatca tgatgtgggt tcgccaagct     120
cctggtaaag gtttggagtg ggtttcttct atctatcctt ctggtggcat tactttttat     180
gctgacaccg ttaaaggtcg cttcactatc tctagagaca actctaagaa tactctctac     240
ttgcagatga acagcttaag ggctgaggac acagccgtgt attactgtgc acggatcaag     300
ttgggtacag taactacggt tgactactgg ggccagggaa ccctggtcac cgtctcaagc     360
gctagcacca agggcccatc ggtcttcccc ctggcaccct cctccaagag cacctctggg     420
ggcacagcgg ccctgggctg cctggtcaag gactacttcc ccgaaccggt gacggtgtcg     480
tggaactcag gcgccctgac cagcggcgtg cacaccttcc cggctgtcct acagtcctca     540
ggactctact ccctcagcag cgtggtgacc gtgccctcca gcagcttggg cacccagacc     600
tacatctgca acgtgaatca caagcccagc aacaccaagg tggacaagag agttgagccc     660
aaatcttgt                                                             669
```

<210> SEQ ID NO 36
<211> LENGTH: 223
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 36

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ile Met Met Trp Val Arg Gln Ala Pro Gly Lys Gly Leu Glu Trp Val
        35                  40                  45

Ser Ser Ile Tyr Pro Ser Gly Gly Ile Thr Phe Tyr Ala Asp Thr Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile Lys Leu Gly Thr Val Thr Thr Val Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
```

```
                195                 200                 205
Pro Ser Asn Thr Lys Val Asp Lys Arg Val Glu Pro Lys Ser Cys
    210                 215                 220

<210> SEQ ID NO 37
<211> LENGTH: 1445
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 37
aaggagctga aggtgaccca gcccgagaag agcgtgagcg tggccgccgg cgacagcacc     60
gtgctgaact gcaccctgac cagcctgctg cccgtgggcc ccatcaagtg gtacaggggc    120
gtgggccaga gcaggctgct gatctacagc ttcaccggcg agcacttccc cagggtgacc    180
aacgtgagcg acgccaccaa gaggaacaac atggacttca gcatcaggat cagcaacgtg    240 accccccgagg acgccggcac ctactactgc gtgaagttcc agaagggccc cagcgagccc    300
gacaccgaga tccagagcgg cggcggcacc gaggtgtacg tgctggccaa gcccagcccc    360
cccgaggtga gcgccccccgc cgacaggggc atccccgacc agaaggtgaa cttcacctgc    420
aagagccacg gcttcagccc caggaacatc accctgaagt ggttcaagga cggccaggag    480
ctgcaccacc tggagaccac cgtgaacccc agcggcaaga acgtgagcta acacatcagc    540
agcaccgtga gggtggtgct gaacagcatg gacgtgcaca gcaaggtgat ctgcgaggtg    600
gcccacatca ccctggacag gagcccccctg aggggcatcg ccaacctgag caacttcatc    660
agggtgagcc ccaccgtgaa ggtgacccag cagagcccca ccagcatgaa ccaggtgaac    720
ctgacctgca gggccgagag gttctacccc gaggacctgc agctgatctg gctggagaac    780
ggcaacgtga gcaggaacga caccccccaag aacctgacca gaacaccga cggcacctac    840 aactacacca gcctgttcct ggtgaacagc agcgcccaca gggaggacgt ggtgttcacc    900
tgccaggtga agcacgacca gcagcccgcc atcaccagga ccacaccgt gctgggcctg    960 gcccacagca gcgaccaggg cagcatgcag accttccccg caacaacgc cacccacaac   1020 tggaacgtgt tcatcggcgt gggcgtggcc tgcgccctgc tggtggtgct gctgatggcc   1080
gccctgtacc tgctgaggat caagcagaag aaggccaagg gcagcaccag cagcaccagg   1140
ctgcacgagc ccgagaagaa cgccagggag atcacccagg tgcagagcct gatccaggac   1200
accaacgaca tcaacgacat cacctacgcc gacctgaacc tgcccaagga agaagagccc   1260 gccccccaggg ccccccgagcc caacaaccac accgagtacg ccagcatcga gaccggcaag   1320
gtgcccaggc ccgaggacac cctgacctac gccgacctgg acatggtgca cctgagcagg   1380
gcccagcccg ccccccaagcc cgagcccagc ttcagcgagt acgccagcgt gcaggtgcag   1440
aggaa                                                                1445

<210> SEQ ID NO 38
<211> LENGTH: 482
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Lys Glu Leu Lys Val Thr Gln Pro Glu Lys Ser Val Ser Val Ala Ala
1               5                   10                  15
```

-continued

Gly Asp Ser Thr Val Leu Asn Cys Thr Leu Thr Ser Leu Leu Pro Val
                20                  25                  30

Gly Pro Ile Lys Trp Tyr Arg Gly Val Gly Gln Ser Arg Leu Leu Ile
                35                  40                  45

Tyr Ser Phe Thr Gly Glu His Phe Pro Arg Val Thr Asn Val Ser Asp
    50                  55                  60

Ala Thr Lys Arg Asn Asn Met Asp Phe Ser Ile Arg Ile Ser Asn Val
65                  70                  75                  80

Thr Pro Glu Asp Ala Gly Thr Tyr Tyr Cys Val Lys Phe Gln Lys Gly
                85                  90                  95

Pro Ser Glu Pro Asp Thr Glu Ile Gln Ser Gly Gly Thr Glu Val
                100                 105                 110

Tyr Val Leu Ala Lys Pro Ser Pro Glu Val Ser Gly Pro Ala Asp
                115                 120                 125

Arg Gly Ile Pro Asp Gln Lys Val Asn Phe Thr Cys Lys Ser His Gly
130                 135                 140

Phe Ser Pro Arg Asn Ile Thr Leu Lys Trp Phe Lys Asp Gly Gln Glu
145                 150                 155                 160

Leu His His Leu Glu Thr Thr Val Asn Pro Ser Gly Lys Asn Val Ser
                165                 170                 175

Tyr Asn Ile Ser Ser Thr Val Arg Val Val Leu Asn Ser Met Asp Val
                180                 185                 190

His Ser Lys Val Ile Cys Glu Val Ala His Ile Thr Leu Asp Arg Ser
                195                 200                 205

Pro Leu Arg Gly Ile Ala Asn Leu Ser Asn Phe Ile Arg Val Ser Pro
                210                 215                 220

Thr Val Lys Val Thr Gln Gln Ser Pro Thr Ser Met Asn Gln Val Asn
225                 230                 235                 240

Leu Thr Cys Arg Ala Glu Arg Phe Tyr Pro Glu Asp Leu Gln Leu Ile
                245                 250                 255

Trp Leu Glu Asn Gly Asn Val Ser Arg Asn Asp Thr Pro Lys Asn Leu
                260                 265                 270

Thr Lys Asn Thr Asp Gly Thr Tyr Asn Tyr Thr Ser Leu Phe Leu Val
                275                 280                 285

Asn Ser Ser Ala His Arg Glu Asp Val Val Phe Thr Cys Gln Val Lys
                290                 295                 300

His Asp Gln Gln Pro Ala Ile Thr Arg Asn His Thr Val Leu Gly Leu
305                 310                 315                 320

Ala His Ser Ser Asp Gln Gly Ser Met Gln Thr Phe Pro Gly Asn Asn
                325                 330                 335

Ala Thr His Asn Trp Asn Val Phe Ile Gly Val Gly Val Ala Cys Ala
                340                 345                 350

Leu Leu Val Val Leu Leu Met Ala Ala Leu Tyr Leu Leu Arg Ile Lys
                355                 360                 365

Gln Lys Lys Ala Lys Gly Ser Thr Ser Ser Thr Arg Leu His Glu Pro
                370                 375                 380

Glu Lys Asn Ala Arg Glu Ile Thr Gln Val Gln Ser Leu Ile Gln Asp
385                 390                 395                 400

Thr Asn Asp Ile Asn Asp Ile Thr Tyr Ala Asp Leu Asn Leu Pro Lys
                405                 410                 415

Glu Lys Lys Pro Ala Pro Arg Ala Pro Glu Pro Asn Asn His Thr Glu
                420                 425                 430

```
Tyr Ala Ser Ile Glu Thr Gly Lys Val Pro Arg Pro Glu Asp Thr Leu
            435                 440                 445
Thr Tyr Ala Asp Leu Asp Met Val His Leu Ser Arg Ala Gln Pro Ala
    450                 455                 460
Pro Lys Pro Glu Pro Ser Phe Ser Glu Tyr Ala Ser Val Gln Val Gln
465                 470                 475                 480
Arg Lys

<210> SEQ ID NO 39
<211> LENGTH: 1755
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 39
```

| | | |
|---|---|---|
| gaggtgcagc tgctggagag cggcggcggc ctggtgcagc ccggcggcag cctgaggctg | 60 |
| agctgcgccg ccagcggctt caccttcagc agctacatca tgatgtgggt gaggcaggcc | 120 |
| cccggcaagg gcctggagtg ggtgagcagc atctacccca gcggcggcat caccttctac | 180 |
| gccgacaccg tgaagggcag gttcaccatc agcagggaca cagcaagaa caccctgtac | 240 |
| ctgcagatga acagcctgag ggccgaggac accgccgtgt actactgcgc caggatcaag | 300 |
| ctgggcaccg tgaccaccgt ggactactgg ggccagggca ccctggtgac cgtgagcagc | 360 |
| gccagcacca agggcccag cgtgttcccc ctggccccca gcagcaagag caccagcggc | 420 |
| ggcaccgccg ccctgggctg cctggtgaag gactacttcc ccgagcccgt gaccgtgagc | 480 |
| tggaacagcg gcgccctgac cagcggcgtg cacaccttcc ccgccgtgct gcagagcagc | 540 |
| ggcctgtaca gcctgagcag cgtggtgacc gtgcccagca gcagcctggg cacccagacc | 600 |
| tacatctgca acgtgaacca caagcccagc aacaccaagg tggacaagaa ggtggagccc | 660 |
| aagagctgcg acaagaccca cacctgcccc cctgccccg cccccgagct gctgggcggc | 720 |
| cccagcgtgt tcctgttccc ccccaagccc aaggacaccc tgatgatcag caggaccccc | 780 |
| gaggtgacct gcgtggtggt ggacgtgagc cacgaggacc ccgaggtgaa gttcaactgg | 840 |
| tacgtggacg gcgtggaggt gcacaacgcc aagaccaagc ccagggagga gcagtacaac | 900 |
| agcacctaca gggtggtgag cgtgctgacc gtgctgcacc aggactggct gaacggcaag | 960 |
| gagtacaagt gcaaggtgag caacaaggcc ctgcccgccc ccatcgagaa gaccatcagc | 1020 |
| aaggccaagg gccagcccag ggagcccag gtgtacaccc tgcccccag cagggacgag | 1080 |
| ctgaccaaga accaggtgag cctgacctgc ctggtgaagg gcttctaccc cagcgacatc | 1140 |
| gccgtggagt gggagagcaa cggccagccc gagaacaact acaagaccac cccccccgtg | 1200 |
| ctggacagcg acggcagctt cttcctgtac agcaagctga ccgtggacaa gagcaggtgg | 1260 |
| cagcagggca acgtgttcag ctgcagcgtg atgcacgagg ccctgcacaa ccactacacc | 1320 |
| cagaagagcc tgagcctgag ccccggcgcc ggcggcggcg cagcggcgg cggcggcagc | 1380 |
| ggcggcggcg gcagcggcgg cggcggcagc gaggaggagc tgcaggtgat ccagcccgac | 1440 |
| aagagcgtgc tggtggccgc cggcgagacc gccaccctga ggtgcaccgc caccagcctg | 1500 |
| atccccgtgg gccccatcca gtggttcagg ggcgccggcc ccggcaggga gctgatctac | 1560 |
| aaccagaagg agggccactt ccccaggggtg accaccgtga gcgacctgac caagaggaac | 1620 |
| aacatggact tcagcatcag gatcggcaac atcaccccg ccgacgccgg cacctactac | 1680 |
| tgcgtgaagt tcaggaaggg cagccccgac gacgtggagt tcaagagcgg cgccggcacc | 1740 | gagctgagcg tgagg                                                            1755

<210> SEQ ID NO 40
<211> LENGTH: 585
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ile Met Met Trp Val Arg Gln Ala Pro Gly Lys Gly Leu Glu Trp Val
        35                  40                  45

Ser Ser Ile Tyr Pro Ser Gly Gly Ile Thr Phe Tyr Ala Asp Thr Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile Lys Leu Gly Thr Val Thr Thr Val Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

```
Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Ala Gly Gly Gly Ser Gly Gly Gly Ser Gly Gly Gly Gly Gly Gly
    450                 455                 460

Ser Gly Gly Gly Gly Ser Glu Glu Glu Leu Gln Val Ile Gln Pro Asp
465                 470                 475                 480

Lys Ser Val Leu Val Ala Ala Gly Glu Thr Ala Thr Leu Arg Cys Thr
                485                 490                 495

Ala Thr Ser Leu Ile Pro Val Gly Pro Ile Gln Trp Phe Arg Gly Ala
            500                 505                 510

Gly Pro Gly Arg Glu Leu Ile Tyr Asn Gln Lys Glu Gly His Phe Pro
        515                 520                 525

Arg Val Thr Thr Val Ser Asp Leu Thr Lys Arg Asn Asn Met Asp Phe
    530                 535                 540

Ser Ile Arg Ile Gly Asn Ile Thr Pro Ala Asp Ala Gly Thr Tyr Tyr
545                 550                 555                 560

Cys Val Lys Phe Arg Lys Gly Ser Pro Asp Asp Val Glu Phe Lys Ser
                565                 570                 575

Gly Ala Gly Thr Glu Leu Ser Val Arg
            580                 585

<210> SEQ ID NO 41
<211> LENGTH: 1755
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 41
gaagtccaac tcttggagtc cggcggtggc ctggtgcagc caggggggatc actgcgcctg      60 agctgtgccg cttccggctt tactttctcc tcctacatta tgatgtgggt cgcccaggcc     120
ccggggaagg gactggaatg ggtcagctcc atctaccctt ctggtggtat cactttctac     180
gccgacacgg tcaaggggag attcaccatc tcccgggaca acagcaagaa caccctgtac     240
ctccaaatga actccctgcg cgctgaggat accgccgtgt attactgcgc ccggatcaag     300
ctgggaaccg tgaccaccgt ggactattgg ggccagggca ctctggtcac cgtgtcgagc     360
gcctccacta agggaccctc agtgttccca ctggcgccca gctcaaagag cacttccgga     420
ggcactgcgg cgcttggatg tctcgtgaag gactacttcc cggagcctgt gaccgtgtcc     480
tggaactccg gcgcactgac ctccggcgtg catacgttcc cggcggtgct ccagtcctcc     540
ggtctgtact cgttgagctc ggtggtcact gtgccgtcgt cctccctggg aacccagact     600
tacatttgta acgtgaacca taagccatcc aacacaaagg tcgacaaaaa ggtcgaacct     660
```

```
aagtcatgcg acaagaccca cacttgcccg ccatgccccg cccccgagct gctgggagga    720
ccatcggtgt tcctctttcc gccgaagccc aaggacaccc tgatgatcag ccggaccccc    780
gaagtgacct gtgtggtggt ggatgtgtcg cacgaagatc cggaggtcaa gttcaattgg    840
tacgtggatg gggtggaggt gcacaacgca aaaactaaac cgagggaaga acagtacaat    900
tcgacctacc gcgtcgtgtc cgtcttgact gtgctgcatc aggactggct gaatgggaag    960
gagtacaagt gcaaagtgtc aaacaaggcc cttcccgccc ctattgaaaa gactattagc   1020
aaggccaagg gacagcccag agaaccgcaa gtgtacaccc tgccgccctc gagggacgag   1080
cttactaaga accaagtgtc cctgacatgc ctcgtgaagg gattctaccc ttccgacatt   1140
gccgtggagt gggagtctaa cggccagccg gaaaacaact acaagaccac cccaccggtg   1200
ttggattcag acggctcatt cttcctgtac tcgaagctga ccgtggacaa gtcccggtgg   1260 cagcaggga acgtgttcag ctgctccgtc atgcacgaag cgctgcacaa ccactacacc   1320
cagaagtccc tgtcgctgtc ccccggagcc gggggaggag gatccggtgg tggtggcagc   1380
ggcggaggag gctcaggcgg cggagggtcc aaggagctca agtcaccca gcccgaaaag   1440 agcgtgtcag tggccgccgg agactcaact gtgctgaact gcaccctcac ctcgctgctg   1500
cctgtgggac ccatcaagtg gtaccgcgga gtgggacaat ccaggctgct gatctactcc   1560
ttcaccgggg aacacttccc tcgcgtgacc aacgtgtcgg acgctaccaa gcggaacaac   1620
atggactttt cgatccggat ctccaatgtc accctgagg acgccggcac ctactattgc   1680
gtgaagttcc aaaagggacc tagcgaacct gatactgaga tccagtccgg cggcggtacc   1740
gaggtctacg tgctg                                                   1755

<210> SEQ ID NO 42
<211> LENGTH: 585
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ile Met Met Trp Val Arg Gln Ala Pro Gly Lys Gly Leu Glu Trp Val
        35                  40                  45

Ser Ser Ile Tyr Pro Ser Gly Gly Ile Thr Phe Tyr Ala Asp Thr Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile Lys Leu Gly Thr Val Thr Thr Val Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160
```

```
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
            180                 185                 190
Ser Ser Ser Leu Gly Thr Gln Thr Tyr Ile Cys Asn Val Asn His Lys
        195                 200                 205
Pro Ser Asn Thr Lys Val Asp Lys Lys Val Glu Pro Lys Ser Cys Asp
    210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
            260                 265                 270
Asp Pro Glu Val Lys Phe Asn Trp Tyr Val Asp Gly Val Glu Val His
        275                 280                 285
Asn Ala Lys Thr Lys Pro Arg Glu Glu Gln Tyr Asn Ser Thr Tyr Arg
    290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
            340                 345                 350
Thr Leu Pro Pro Ser Arg Asp Glu Leu Thr Lys Asn Gln Val Ser Leu
        355                 360                 365
Thr Cys Leu Val Lys Gly Phe Tyr Pro Ser Asp Ile Ala Val Glu Trp
    370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro
        435                 440                 445
Gly Ala Gly Gly Gly Gly Ser Gly Gly Gly Gly Ser Gly Gly Gly Gly
    450                 455                 460
Ser Gly Gly Gly Gly Ser Lys Glu Leu Lys Val Thr Gln Pro Glu Lys
465                 470                 475                 480
Ser Val Ser Val Ala Ala Gly Asp Ser Thr Val Leu Asn Cys Thr Leu
                485                 490                 495
Thr Ser Leu Leu Pro Val Gly Pro Ile Lys Trp Tyr Arg Gly Val Gly
            500                 505                 510
Gln Ser Arg Leu Leu Ile Tyr Ser Phe Thr Gly Glu His Phe Pro Arg
        515                 520                 525
Val Thr Asn Val Ser Asp Ala Thr Lys Arg Asn Asn Met Asp Phe Ser
    530                 535                 540
Ile Arg Ile Ser Asn Val Thr Pro Glu Asp Ala Gly Thr Tyr Tyr Cys
545                 550                 555                 560
Val Lys Phe Gln Lys Gly Pro Ser Glu Pro Asp Thr Glu Ile Gln Ser
                565                 570                 575
Gly Gly Gly Thr Glu Val Tyr Val Leu
```

580          585

<210> SEQ ID NO 43
<211> LENGTH: 1752
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 43

```
caagtccaac tgaagcagtc cgggccggga ctcgtgcagc cgtcgcagtc actgtccatc      60
acttgcacgg tgtcaggctt ttccttgacc aactacggag tgcactgggt gcgccagtcc     120
cctggaaagg ggctggagtg gcttggcgtg atttggtccg gaggaaacac agactacaac     180
actcctttca cctcccgcct gagcattaac aaggacaact ccaagtccca agtgttcttc     240
aagatgaaca gcctgcagag caatgatacc gccatctact attgtgcccg ggctctcacc     300
tactacgact acgaattcgc ctactgggga cagggaaccc tggtcactgt ctccgcggcc     360
tccactaagg gccctagcgt gttccccttg cgccatcgt caaagtccac ctccggtggc     420
actgccgccc tgggatgcct tgtgaaggac tacttccccg aacctgtgac cgtgtcctgg     480
aactcgggcg cactgacttc ggggggtgcac acctttcctg ccgtcctgca atcgagcggt     540
ctgtactccc tctcgtccgt ggtcaccgtg ccgtctagct ccctcggaac ccagacctac     600
atctgcaacg tcaaccacaa gccgagcaac accaaagtgg ataagagagt ggagccgaag     660
tcatgcgaca agactcatac ttgtccccca tgccccgccc cggaactgct gggggggccca     720
tccgtgttcc tgttcccgcc gaaacctaag gacaccctga tgatttcgag aactccggaa     780
gtgacctgtg tggtggtcga cgtgtcccac gaggatccgg aggtcaagtt caattggtac     840
gtcgacggag tggaagtcca caacgccaag accaagcccc gggaggagca gtacaactcc     900
acttaccggg tggtgtccgt gctgaccgtg ctgcatcagg attggctgaa cggaaaggag     960
tataagtgca aagtgtcaaa caaggcattg cctgcgccaa tcgaaaagac cattagcaag    1020
gccaagggcc agcccaggga accacaggtg tacactctgc ccccgtcccg cgaagaaatg    1080
accaagaacc aagtgtcact gacatgcctc gtgaagggat tttacccgtc cgatatcgcc    1140
gtggaatggg aatcgaacgg tcaacctgaa acaactaca agacgacccc tccggtcctg    1200
gacagcgatg gctcattctt cctgtactcc aagcttacgg tggacaagtc ccggtggcaa    1260
cagggaaatg tgttttcgtg ctccgtgatg catgaggctc tgcacaacca ctacacccag    1320
aagtcactct ccctgagccc cggcgcgggg ggtggtggaa gcggaggagg ggggtctggg    1380
ggtggcggtt ccggcggcgg cggatccgag gaggaacttc aggtcatcca gcccgacaag    1440
agcgtgctcg tggcggccgg agaaaccgca actctgagat gcaccgctac ctcgctgatt    1500
cccgtggggc ctatccagtg gttccgcggg gccggacccg gacgcgagct catctacaac    1560
cagaaggagg ggcacttccc gagggtcacc accgtgtcgg acctcaccaa gcgcaacaac    1620
atggacttca gcattcggat cggccaaatc accccgccg acgccggcac ctattactgc    1680
gtgaagttcc ggaagggcag ccctgacgac gtggagttca aaagcggagc cggaaccgag    1740
ctgtccgtga ga                                                       1752
```

<210> SEQ ID NO 44
<211> LENGTH: 584
<212> TYPE: PRT
<213> ORGANISM: Artificial Sequence
<220> FEATURE:

<223> OTHER INFORMATION: Description of Artificial Sequence: Synthetic polypeptide

<400> SEQUENCE: 44

| | | | | | | | | | | | | | | | |
|---|---|---|---|---|---|---|---|---|---|---|---|---|---|---|---|
| Gln | Val | Gln | Leu | Lys | Gln | Ser | Gly | Pro | Gly | Leu | Val | Gln | Pro | Ser | Gln |
| 1 | | | | 5 | | | | | 10 | | | | | 15 | |
| Ser | Leu | Ser | Ile | Thr | Cys | Thr | Val | Ser | Gly | Phe | Ser | Leu | Thr | Asn | Tyr |
| | | | | 20 | | | | | 25 | | | | | 30 | |
| Gly | Val | His | Trp | Val | Arg | Gln | Ser | Pro | Gly | Lys | Gly | Leu | Glu | Trp | Leu |
| | | | 35 | | | | | 40 | | | | | 45 | | |
| Gly | Val | Ile | Trp | Ser | Gly | Gly | Asn | Thr | Asp | Tyr | Asn | Thr | Pro | Phe | Thr |
| | 50 | | | | | 55 | | | | | 60 | | | | |
| Ser | Arg | Leu | Ser | Ile | Asn | Lys | Asp | Asn | Ser | Lys | Ser | Gln | Val | Phe | Phe |
| 65 | | | | | 70 | | | | | 75 | | | | | 80 |
| Lys | Met | Asn | Ser | Leu | Gln | Ser | Asn | Asp | Thr | Ala | Ile | Tyr | Tyr | Cys | Ala |
| | | | | 85 | | | | | 90 | | | | | 95 | |
| Arg | Ala | Leu | Thr | Tyr | Tyr | Asp | Tyr | Glu | Phe | Ala | Tyr | Trp | Gly | Gln | Gly |
| | | | 100 | | | | | 105 | | | | | 110 | | |
| Thr | Leu | Val | Thr | Val | Ser | Ala | Ala | Ser | Thr | Lys | Gly | Pro | Ser | Val | Phe |
| | | | 115 | | | | | 120 | | | | | 125 | | |
| Pro | Leu | Ala | Pro | Ser | Ser | Lys | Ser | Thr | Ser | Gly | Gly | Thr | Ala | Ala | Leu |
| | 130 | | | | | 135 | | | | | 140 | | | | |
| Gly | Cys | Leu | Val | Lys | Asp | Tyr | Phe | Pro | Glu | Pro | Val | Thr | Val | Ser | Trp |
| 145 | | | | | 150 | | | | | 155 | | | | | 160 |
| Asn | Ser | Gly | Ala | Leu | Thr | Ser | Gly | Val | His | Thr | Phe | Pro | Ala | Val | Leu |
| | | | | 165 | | | | | 170 | | | | | 175 | |
| Gln | Ser | Ser | Gly | Leu | Tyr | Ser | Leu | Ser | Ser | Val | Val | Thr | Val | Pro | Ser |
| | | | 180 | | | | | 185 | | | | | 190 | | |
| Ser | Ser | Leu | Gly | Thr | Gln | Thr | Tyr | Ile | Cys | Asn | Val | Asn | His | Lys | Pro |
| | | | 195 | | | | | 200 | | | | | 205 | | |
| Ser | Asn | Thr | Lys | Val | Asp | Lys | Arg | Val | Glu | Pro | Lys | Ser | Cys | Asp | Lys |
| | 210 | | | | | 215 | | | | | 220 | | | | |
| Thr | His | Thr | Cys | Pro | Pro | Cys | Pro | Ala | Pro | Glu | Leu | Leu | Gly | Gly | Pro |
| 225 | | | | | 230 | | | | | 235 | | | | | 240 |
| Ser | Val | Phe | Leu | Phe | Pro | Pro | Lys | Pro | Lys | Asp | Thr | Leu | Met | Ile | Ser |
| | | | | 245 | | | | | 250 | | | | | 255 | |
| Arg | Thr | Pro | Glu | Val | Thr | Cys | Val | Val | Val | Asp | Val | Ser | His | Glu | Asp |
| | | | 260 | | | | | 265 | | | | | 270 | | |
| Pro | Glu | Val | Lys | Phe | Asn | Trp | Tyr | Val | Asp | Gly | Val | Glu | Val | His | Asn |
| | | | 275 | | | | | 280 | | | | | 285 | | |
| Ala | Lys | Thr | Lys | Pro | Arg | Glu | Glu | Gln | Tyr | Asn | Ser | Thr | Tyr | Arg | Val |
| | 290 | | | | | 295 | | | | | 300 | | | | |
| Val | Ser | Val | Leu | Thr | Val | Leu | His | Gln | Asp | Trp | Leu | Asn | Gly | Lys | Glu |
| 305 | | | | | 310 | | | | | 315 | | | | | 320 |
| Tyr | Lys | Cys | Lys | Val | Ser | Asn | Lys | Ala | Leu | Pro | Ala | Pro | Ile | Glu | Lys |
| | | | | 325 | | | | | 330 | | | | | 335 | |
| Thr | Ile | Ser | Lys | Ala | Lys | Gly | Gln | Pro | Arg | Glu | Pro | Gln | Val | Tyr | Thr |
| | | | 340 | | | | | 345 | | | | | 350 | | |
| Leu | Pro | Pro | Ser | Arg | Glu | Glu | Met | Thr | Lys | Asn | Gln | Val | Ser | Leu | Thr |
| | | | 355 | | | | | 360 | | | | | 365 | | |
| Cys | Leu | Val | Lys | Gly | Phe | Tyr | Pro | Ser | Asp | Ile | Ala | Val | Glu | Trp | Glu |
| | 370 | | | | | 375 | | | | | 380 | | | | |
| Ser | Asn | Gly | Gln | Pro | Glu | Asn | Asn | Tyr | Lys | Thr | Thr | Pro | Pro | Val | Leu |
| 385 | | | | | 390 | | | | | 395 | | | | | 400 |

```
Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Ala Gly Gly Gly Ser Gly Gly Gly Ser Gly Gly Gly Gly Ser
        450                 455                 460

Gly Gly Gly Gly Ser Glu Glu Glu Leu Gln Val Ile Gln Pro Asp Lys
465                 470                 475                 480

Ser Val Leu Val Ala Ala Gly Glu Thr Ala Thr Leu Arg Cys Thr Ala
            485                 490                 495

Thr Ser Leu Ile Pro Val Gly Pro Ile Gln Trp Phe Arg Gly Ala Gly
            500                 505                 510

Pro Gly Arg Glu Leu Ile Tyr Asn Gln Lys Glu Gly His Phe Pro Arg
            515                 520                 525

Val Thr Thr Val Ser Asp Leu Thr Lys Arg Asn Asn Met Asp Phe Ser
            530                 535                 540

Ile Arg Ile Gly Gln Ile Thr Pro Ala Asp Ala Gly Thr Tyr Tyr Cys
545                 550                 555                 560

Val Lys Phe Arg Lys Gly Ser Pro Asp Asp Val Glu Phe Lys Ser Gly
            565                 570                 575

Ala Gly Thr Glu Leu Ser Val Arg
            580

<210> SEQ ID NO 45
<211> LENGTH: 1344
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 45
caggtgcagc tgaagcagag cggccccggc ctggtgcagc ccagccagag cctgagcatc      60
acctgcaccg tgagcggctt cagcctgacc aactacggcg tgcactgggt gaggcagagc     120
cccggcaagg gcctggagtg gctgggcgtg atctggagcg gcggcaacac cgactacaac     180
acccccttca ccagcaggct gagcatcaac aaggacaaca gcaagagcca ggtgttcttc     240
aagatgaaca gcctgcagag caacgacacc gccatctact actgcgccag ggccctgacc     300
tactacgact acgagttcgc ctactggggc cagggcaccc tggtgaccgt gagcgccgcc     360
agcaccaagg gccccagcgt gttcccctg gccccagca gcaagagcac cagcggcggc      420
accgccgccc tgggctgcct ggtgaaggac tacttccccg agcccgtgac cgtgagctgg     480
aacagcggcg ccctgaccag cggcgtgcac accttccccg ccgtgctgca gagcagcggc     540
ctgtacagcc tgagcagcgt ggtgaccgtg cccagcagca gcctgggcac ccagacctac     600
atctgcaacg tgaaccacaa gcccagcaac accaaggtgg acaagagggt ggagcccaag     660
agctgcgaca gacccacac tgccccccc tgccccgccc ccgagctgct gggcggcccc      720
agcgtgttcc tgttcccccc caagcccaag gacaccctga tgatcagcag gacccccgag     780
gtgacctgcg tggtggtgga cgtgagccac gaggaccccg aggtgaagtt caactggtac     840
gtggacggcg tggaggtgca caacgccaag accaagccca gggaggagca gtacaacagc     900
acctacaggg tggtgagcgt gctgaccgtg ctgcaccagg actggctgaa cggcaaggag     960
```

-continued

```
tacaagtgca aggtgagcaa caaggccctg cccgccccca tcgagaagac catcagcaag    1020
gccaagggcc agcccaggga gccccaggtg tacaccctgc cccccagcag ggaggagatg    1080
accaagaacc aggtgagcct gacctgcctg gtgaagggct tctacccag cgacatcgcc     1140 gtggagtggg agagcaacgg ccagcccgag aacaactaca agaccacccc ccccgtgctg    1200
gacagcgacg gcagcttctt cctgtacagc aagctgaccg tggacaagag caggtggcag    1260
cagggcaacg tgttcagctg cagcgtgatg cacgaggccc tgcacaacca ctacacccag    1320
aagagcctga gcctgagccc cggc                                           1344
```

<210> SEQ ID NO 46
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

<210> SEQ ID NO 47
<211> LENGTH: 1013
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 47
gacattctcc tgacacagag ccccgtgatc ctgagcgtga gccctggcga aagggtgagc    60
ttcagctgca gggccagcca gagcatcggc accaacatcc actggtacca gcagaggaca   120
aacggcagcc ctaggctgct gatcaagtac gccagcgaga gcatcagcgg catccccagc   180
aggtttagcg gaagcggcag cggcaccgac ttcaccctgt ccatcaattc cgtggagtcc   240
gaggacatcg ccgactacta ctgccagcag aacaacaact ggcctaccac cttcggcgcc   300
ggcaccaagc tggaactgaa gcgtacggtg ccgccccca gcgtgttcat ctttccccc    360
agcgacgagc agctgaaaag cggcaccgcc tccgtggtgt gcctgctgaa caacttctac   420
cctagggagg ccaaggtgca gtggaaggtg acaacgccc tccagtccgg caacagccag   480
gagagcgtca ccgagcagga cagcaaggac agcacctaca gcctgagcag caccctgacc   540
ctgagcaagg ccgactacga gaagcacaag gtgtatgcct gcgaggtgac ccaccagggc   600
ctgagctccc ctgtgaccaa gtccttcaac aggggcgagt gcggggagga ggctcagggg   660
gcggagggtc agaagaggaa ctgcaagtga tccagcccga caagtccgtg tctgtggccg   720
ctggcgagtc tgccatcctg cactgcaccg tgacctccct gatccccgtg ggacccatcc   780
agtggtttcg tggcgctggc cctgcccgtg agctgatcta caaccagaaa gagggccact   840
tcccccgtgt gaccaccgtg tccgagtcca ccaagcgcga aacatggac ttctccatct   900
ccatcagcaa catcaccct gccgatgccg gcacctacta ctgcgtgaag ttccgtaagg   960
gctcccccga caccgagttc aagtctggcg ctggcaccga gctgtctgtg cgt         1013

<210> SEQ ID NO 48
<211> LENGTH: 338

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Asp Ile Leu Leu Thr Gln Ser Pro Val Ile Leu Ser Val Ser Pro Gly
1               5                   10                  15

Glu Arg Val Ser Phe Ser Cys Arg Ala Ser Gln Ser Ile Gly Thr Asn
            20                  25                  30

Ile His Trp Tyr Gln Gln Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Asn Asn Asn Trp Pro Thr
                85                  90                  95

Thr Phe Gly Ala Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Gly Gly Ser Gly Gly Gly Gly Ser
    210                 215                 220

Glu Glu Glu Leu Gln Val Ile Gln Pro Asp Lys Ser Val Ser Val Ala
225                 230                 235                 240

Ala Gly Glu Ser Ala Ile Leu His Cys Thr Val Thr Ser Leu Ile Pro
                245                 250                 255

Val Gly Pro Ile Gln Trp Phe Arg Gly Ala Gly Pro Ala Arg Glu Leu
            260                 265                 270

Ile Tyr Asn Gln Lys Glu Gly His Phe Pro Arg Val Thr Thr Val Ser
        275                 280                 285

Glu Ser Thr Lys Arg Glu Asn Met Asp Phe Ser Ile Ser Ile Ser Asn
    290                 295                 300

Ile Thr Pro Ala Asp Ala Gly Thr Tyr Tyr Cys Val Lys Phe Arg Lys
305                 310                 315                 320

Gly Ser Pro Asp Thr Glu Phe Lys Ser Gly Ala Gly Thr Glu Leu Ser
                325                 330                 335

Val Arg

<210> SEQ ID NO 49
<211> LENGTH: 1794
<212> TYPE: DNA
<213> ORGANISM: Artificial Sequence
<220> FEATURE:

<223> OTHER INFORMATION: Description of Artificial Sequence: Synthetic
      polynucleotide

<400> SEQUENCE: 49

```
gaggaagaac tccaagtgat ccaaccggac aaatccgtga gcgtggccgc cggagaaagc      60
gccatcctgc actgcaccgt cacgtcactg attcctgtgg gcccaattca gtggttcaga     120
ggagcgggc cagcccggga actgatctac aaccagaagg agggtcactt ccctcgggtc      180
actaccgtgt ccgagtcaac caagcgggaa acatggact tctcgatctc catctccaac      240
attacccctg cggacgccgg cacatactat tgcgtcaaat ccgcaaggg ttcgccggac      300
accgagttca gtccggagc tggtaccgaa ctgagcgtgc gggggggagg cggaagcgga      360
ggcggcggat cggagcccaa atcgtctgac aagacccaca cctgtccgcc ctgtcctgca      420
ccggaacttc tgggcggacc ttccgtgttc ctgttcccac ctaagcctaa ggacaccctc      480
atgatctccc ggaccccgga ggtcacttgc gtggtggtgg atgtgtccca cgaggacccg      540
gaagtgaagt tcaattggta cgtggacggc gtggaagtcc acaacgcaaa gaccaagcca      600
agggaggaac agtacaacag cacctacagg gtggtgtcag tgctcactgt gctgcatcag      660
gactggctca acgggaaaga gtacaagtgc aaagtctcca acaaggcctt gcccgctcca      720
attgaaaaga ccatttcgaa ggccaagggc cagcccagag agccgcaagt gtacaccctg      780
ccccccgtcgc gcgaggagat gaccaagaat caagtctccc tcacttgtct cgtgaagggc      840
ttttacccctt cggatatcgc agtggaatgg gaatccaacg gacagccgga aaacaactac      900
aagacgaccc cgcccgtgct ggattcagac ggctccttct tcttgtactc aaagctgacg      960
gtggacaagt cacggtggca cagggaaac gtctttttcct gctccgtgat gcatgaagcc     1020
ctgcacaacc attacactca gaagtcgctg tcgcttagcc ctggagccgg cggtggaggt     1080
tccggagggg gtggaagcgg cggaggagga agcggggggcg ggggctccca ggtccaactg     1140
aagcagagcg gtccaggact ggtccagccg tcccagtccc tgtctattac ttgcaccgtg     1200
tccggcttt ccctgactaa ctatggtgtc cactgggtgc gccagtcgcc cgggaagggg     1260
ctggagtggc tgggcgtgat ctggagcggc gggaacaccg actataacac tcctttcact     1320
tcacgcctgt ccatcaacaa ggataacagc aagagccagg tgttctttaa gatgaactca     1380
ctccagtcca cgacaccgc catctactac tgcgcccgcg ctctcaccta ctacgactac     1440
gaattcgcct actggggaca aggcaccctg gtcaccgtgt cggcggccag caccaaggga     1500
ccgtccgtgt tccccctggc gccgtcctca agtccactt ccggcggcac cgctgccctg     1560
ggatgcctcg tgaaggatta tttcccggag cctgtgaccg tgtcctggaa ctccggtgcc     1620
ctgacatccg gcgtgcacac cttccctgcg gtgctgcagt ccagcggact gtactccctc     1680
tcctcggtcg tgaccgtgcc gtcctcgtcc ctgggaactc agacttacat ctgcaacgtg     1740
aaccataagc cctccaatac caaagtggac aagagagtgg agcccaagag ctgc           1794
```

<210> SEQ ID NO 50
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Glu Pro Lys Ser Ser
1               5

<210> SEQ ID NO 51
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Glu Pro Lys Ser Cys
1               5

<210> SEQ ID NO 52
<211> LENGTH: 598
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Glu Glu Glu Leu Gln Val Ile Gln Pro Asp Lys Ser Val Ser Val Ala
1               5                   10                  15

Ala Gly Glu Ser Ala Ile Leu His Cys Thr Val Thr Ser Leu Ile Pro
            20                  25                  30

Val Gly Pro Ile Gln Trp Phe Arg Gly Ala Gly Pro Ala Arg Glu Leu
        35                  40                  45

Ile Tyr Asn Gln Lys Glu Gly His Phe Pro Arg Val Thr Thr Val Ser
    50                  55                  60

Glu Ser Thr Lys Arg Glu Asn Met Asp Phe Ser Ile Ser Ile Ser Asn
65                  70                  75                  80

Ile Thr Pro Ala Asp Ala Gly Thr Tyr Tyr Cys Val Lys Phe Arg Lys
                85                  90                  95

Gly Ser Pro Asp Thr Glu Phe Lys Ser Gly Ala Gly Thr Glu Leu Ser
            100                 105                 110

Val Arg Gly Gly Gly Gly Ser Gly Gly Gly Gly Ser Glu Pro Lys Ser
        115                 120                 125

Ser Asp Lys Thr His Thr Cys Pro Pro Cys Pro Ala Pro Glu Leu Leu
    130                 135                 140

Gly Gly Pro Ser Val Phe Leu Phe Pro Pro Lys Pro Lys Asp Thr Leu
145                 150                 155                 160

Met Ile Ser Arg Thr Pro Glu Val Thr Cys Val Val Val Asp Val Ser
                165                 170                 175

His Glu Asp Pro Glu Val Lys Phe Asn Trp Tyr Val Asp Gly Val Glu
            180                 185                 190

Val His Asn Ala Lys Thr Lys Pro Arg Glu Glu Gln Tyr Asn Ser Thr
        195                 200                 205

Tyr Arg Val Val Ser Val Leu Thr Val Leu His Gln Asp Trp Leu Asn
    210                 215                 220

Gly Lys Glu Tyr Lys Cys Lys Val Ser Asn Lys Ala Leu Pro Ala Pro
225                 230                 235                 240

Ile Glu Lys Thr Ile Ser Lys Ala Lys Gly Gln Pro Arg Glu Pro Gln
                245                 250                 255

Val Tyr Thr Leu Pro Pro Ser Arg Glu Glu Met Thr Lys Asn Gln Val
            260                 265                 270

Ser Leu Thr Cys Leu Val Lys Gly Phe Tyr Pro Ser Asp Ile Ala Val
        275                 280                 285

Glu Trp Glu Ser Asn Gly Gln Pro Glu Asn Asn Tyr Lys Thr Thr Pro
    290                 295                 300

Pro Val Leu Asp Ser Asp Gly Ser Phe Phe Leu Tyr Ser Lys Leu Thr
305                 310                 315                 320

Val Asp Lys Ser Arg Trp Gln Gln Gly Asn Val Phe Ser Cys Ser Val
                325                 330                 335

Met His Glu Ala Leu His Asn His Tyr Thr Gln Lys Ser Leu Ser Leu
            340                 345                 350

Ser Pro Gly Ala Gly Gly Gly Ser Gly Gly Gly Ser Gly Gly
        355                 360                 365

Gly Gly Ser Gly Gly Gly Ser Gln Val Gln Leu Lys Gln Ser Gly
    370                 375                 380

Pro Gly Leu Val Gln Pro Ser Gln Ser Leu Ser Ile Thr Cys Thr Val
385                 390                 395                 400

Ser Gly Phe Ser Leu Thr Asn Tyr Gly Val His Trp Val Arg Gln Ser
                405                 410                 415

Pro Gly Lys Gly Leu Glu Trp Leu Gly Val Ile Trp Ser Gly Gly Asn
            420                 425                 430

Thr Asp Tyr Asn Thr Pro Phe Thr Ser Arg Leu Ser Ile Asn Lys Asp
        435                 440                 445

Asn Ser Lys Ser Gln Val Phe Phe Lys Met Asn Ser Leu Gln Ser Asn
450                 455                 460

Asp Thr Ala Ile Tyr Tyr Cys Ala Arg Ala Leu Thr Tyr Tyr Asp Tyr
465                 470                 475                 480

Glu Phe Ala Tyr Trp Gly Gln Gly Thr Leu Val Thr Val Ser Ala Ala
                485                 490                 495

Ser Thr Lys Gly Pro Ser Val Phe Pro Leu Ala Pro Ser Ser Lys Ser
            500                 505                 510

Thr Ser Gly Gly Thr Ala Ala Leu Gly Cys Leu Val Lys Asp Tyr Phe
        515                 520                 525

Pro Glu Pro Val Thr Val Ser Trp Asn Ser Gly Ala Leu Thr Ser Gly
530                 535                 540

Val His Thr Phe Pro Ala Val Leu Gln Ser Ser Gly Leu Tyr Ser Leu
545                 550                 555                 560

Ser Ser Val Val Thr Val Pro Ser Ser Ser Leu Gly Thr Gln Thr Tyr
                565                 570                 575

Ile Cys Asn Val Asn His Lys Pro Ser Asn Thr Lys Val Asp Lys Arg
            580                 585                 590

Val Glu Pro Lys Ser Cys
        595

<210> SEQ ID NO 53
<211> LENGTH: 723
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 53
caggtgcagc tgaagcagag cggccccggc ctggtgcagc ccagccagag cctgagcatc       60
acctgcaccg tgagcggctt cagcctgacc aactacggcg tgcactgggt gaggcagagc      120
cccggcaagg gcctggagtg gctgggcgtg atctggagcg gcggcaacac cgactacaac      180
acccccttca ccagcaggct gagcatcaac aaggacaaca gcaagagcca ggtgttcttc      240

-continued

```
aagatgaaca gcctgcagag caacgacacc gccatctact actgcgccag ggccctgacc    300
tactacgact acgagttcgc ctactggggc cagggcaccc tggtgaccgt gagcgccggc    360
ggcggcggca gcggcggcgg cggcagcggc ggcggcggca gcgacatcct gctgacccag    420
agccccgtga tcctgagcgt gagccccggc gagagggtga gcttcagctg cagggccagc    480
cagagcatcg gcaccaacat ccactggtac cagcagagga ccaacggcag ccccaggctg    540
ctgatcaagt acgccagcga gagcatcagc ggcatcccca gcaggttcag cggcagcggc    600
agcggcaccg acttcaccct gagcatcaac agcgtggaga gcgaggacat cgccgactac    660
tactgccagc agaacaacaa ctggcccacc accttcggcg ccggcaccaa gctggagctg    720
aag                                                                  723
```

<210> SEQ ID NO 54
<211> LENGTH: 241
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 54

```
Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala Gly Gly Gly Ser Gly Gly Gly Gly
        115                 120                 125

Ser Gly Gly Gly Ser Asp Ile Leu Leu Thr Gln Ser Pro Val Ile
    130                 135                 140

Leu Ser Val Ser Pro Gly Glu Arg Val Ser Phe Ser Cys Arg Ala Ser
145                 150                 155                 160

Gln Ser Ile Gly Thr Asn Ile His Trp Tyr Gln Gln Arg Thr Asn Gly
                165                 170                 175

Ser Pro Arg Leu Leu Ile Lys Tyr Ala Ser Glu Ser Ile Ser Gly Ile
            180                 185                 190

Pro Ser Arg Phe Ser Gly Ser Gly Ser Gly Thr Asp Phe Thr Leu Ser
        195                 200                 205

Ile Asn Ser Val Glu Ser Glu Asp Ile Ala Asp Tyr Tyr Cys Gln Gln
    210                 215                 220

Asn Asn Asn Trp Pro Thr Thr Phe Gly Ala Gly Thr Lys Leu Glu Leu
225                 230                 235                 240

Lys
```

<210> SEQ ID NO 55
<211> LENGTH: 1851

<212> TYPE: DNA
<213> ORGANISM: Artificial Sequence
<220> FEATURE:
<223> OTHER INFORMATION: Description of Artificial Sequence: Synthetic
     polynucleotide

<400> SEQUENCE: 55

```
gaggaggagc tgcaggtgat ccagcccgac aagagcgtga gcgtggccgc cggcgagagc      60
gccatcctgc actgcaccgt gaccagcctg atccccgtgg ccccatcca gtggttcagg     120
ggcgccggcc ccgccaggga gctgatctac aaccagaagg agggccactt ccccagggtg     180
accaccgtga gcgagagcac caagagggag aacatggact tcagcatcag catcagcaac     240
atcaccccg ccgacgccgg cacctactac tgcgtgaagt tcaggaaggg cagccccgac     300
accgagttca gagcggcgc cggcaccgag ctgagcgtga ggggcggcgg cggcagcggc     360
ggcggcggca gcgagcccaa gagcagcgac aagacccaca cctgccccc ctgccccgcc     420
cccgagctgc tgggcggccc cagcgtgttc ctgttccccc ccaagcccaa ggacaccctg     480
atgatcagca ggacccccga ggtgacctgc gtggtggtgg acgtgagcca cgaggacccc     540
gaggtgaagt tcaactggta cgtggacggc gtggaggtgc acaacgccaa gaccaagccc     600
agggaggagc agtacaacag cacctacagg gtggtgagcg tgctgaccgt gctgcaccag     660
gactggctga acggcaagga gtacaagtgc aaggtgagca caaggccct gcccgccccc     720
atcgagaaga ccatcagcaa ggccaagggc cagcccaggg agccccaggt gtacaccctg     780
ccccccagca gggaggagat gaccaagaac caggtgagcc tgacctgcct ggtgaagggc     840
ttctacccca gcgacatcgc cgtggagtgg gagagcaacg gccagcccga gaacaactac     900
aagaccaccc cccccgtgct ggacagcgac ggcagcttct tcctgtacag caagctgacc     960
gtggacaaga gcaggtggca gcagggcaac gtgttcagct gcagcgtgat gcacgaggcc    1020
ctgcacaacc actacaccca gaagagcctg agcctgagcc ccggcgccgg cggcggcggc    1080
agcggcggcg gcggcagcgg cggcggcggc agcggcggcg gcggcagcca ggtgcagctg    1140
aagcagagcg gccccggcct ggtgcagccc agccagagcc tgagcatcac ctgcaccgtg    1200
agcggcttca gcctgaccaa ctacggcgtg cactgggtga ggcagagccc cggcaagggc    1260
ctggagtggc tgggcgtgat ctggagcggc ggcaacaccg actacaacac cccttcacc    1320
agcaggctga gcatcaacaa ggacaacagc aagagccagg tgttcttcaa gatgaacagc    1380
ctgcagagca cgacaccgc catctactac tgcgccaggg ccctgaccta ctacgactac    1440
gagttcgcct actggggcca gggcaccctg gtgaccgtga gcgccggcgg cggcggcagc    1500
ggcggcggcg cagcggcgg cggcggcagc gacatcctgc tgacccagag ccccgtgatc    1560
ctgagcgtga gccccggcga gagggtgagc ttcagctgca gggccagcca gagcatcggc    1620
accaacatcc actggtacca gcagaggacc aacggcagcc ccaggctgct gatcaagtac    1680
gccagcgaga gcatcagcgg catccccagc aggttcagcg gcagcggcag cggcaccgac    1740
ttcaccctga gcatcaacag cgtggagagc gaggacatcg ccgactacta ctgccagcag    1800
aacaacaact ggcccaccac cttcggcgcc ggcaccaagc tggagctgaa g             1851
```

<210> SEQ ID NO 56
<211> LENGTH: 617
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 56

Glu Glu Glu Leu Gln Val Ile Gln Pro Asp Lys Ser Val Ser Val Ala
1               5                   10                  15

Ala Gly Glu Ser Ala Ile Leu His Cys Thr Val Thr Ser Leu Ile Pro
            20                  25                  30

Val Gly Pro Ile Gln Trp Phe Arg Gly Ala Gly Pro Ala Arg Glu Leu
        35                  40                  45

Ile Tyr Asn Gln Lys Glu Gly His Phe Pro Arg Val Thr Thr Val Ser
    50                  55                  60

Glu Ser Thr Lys Arg Glu Asn Met Asp Phe Ser Ile Ser Ile Ser Asn
65                  70                  75                  80

Ile Thr Pro Ala Asp Ala Gly Thr Tyr Tyr Cys Val Lys Phe Arg Lys
                85                  90                  95

Gly Ser Pro Asp Thr Glu Phe Lys Ser Gly Ala Gly Thr Glu Leu Ser
            100                 105                 110

Val Arg Gly Gly Gly Gly Ser Gly Gly Gly Ser Glu Pro Lys Ser
        115                 120                 125

Ser Asp Lys Thr His Thr Cys Pro Pro Cys Pro Ala Pro Glu Leu Leu
    130                 135                 140

Gly Gly Pro Ser Val Phe Leu Phe Pro Pro Lys Pro Lys Asp Thr Leu
145                 150                 155                 160

Met Ile Ser Arg Thr Pro Glu Val Thr Cys Val Val Val Asp Val Ser
                165                 170                 175

His Glu Asp Pro Glu Val Lys Phe Asn Trp Tyr Val Asp Gly Val Glu
            180                 185                 190

Val His Asn Ala Lys Thr Lys Pro Arg Glu Glu Gln Tyr Asn Ser Thr
        195                 200                 205

Tyr Arg Val Val Ser Val Leu Thr Val Leu His Gln Asp Trp Leu Asn
    210                 215                 220

Gly Lys Glu Tyr Lys Cys Lys Val Ser Asn Lys Ala Leu Pro Ala Pro
225                 230                 235                 240

Ile Glu Lys Thr Ile Ser Lys Ala Lys Gly Gln Pro Arg Glu Pro Gln
                245                 250                 255

Val Tyr Thr Leu Pro Pro Ser Arg Glu Glu Met Thr Lys Asn Gln Val
            260                 265                 270

Ser Leu Thr Cys Leu Val Lys Gly Phe Tyr Pro Ser Asp Ile Ala Val
        275                 280                 285

Glu Trp Glu Ser Asn Gly Gln Pro Glu Asn Asn Tyr Lys Thr Thr Pro
    290                 295                 300

Pro Val Leu Asp Ser Asp Gly Ser Phe Phe Leu Tyr Ser Lys Leu Thr
305                 310                 315                 320

Val Asp Lys Ser Arg Trp Gln Gln Gly Asn Val Phe Ser Cys Ser Val
                325                 330                 335

Met His Glu Ala Leu His Asn His Tyr Thr Gln Lys Ser Leu Ser Leu
            340                 345                 350

Ser Pro Gly Ala Gly Gly Gly Ser Gly Gly Gly Ser Gly Gly
        355                 360                 365

Gly Gly Ser Gly Gly Gly Ser Gln Val Gln Leu Lys Gln Ser Gly
    370                 375                 380

Pro Gly Leu Val Gln Pro Ser Gln Ser Leu Ser Ile Thr Cys Thr Val
385                 390                 395                 400

Ser Gly Phe Ser Leu Thr Asn Tyr Gly Val His Trp Val Arg Gln Ser
                405                 410                 415

```
Pro Gly Lys Gly Leu Glu Trp Leu Gly Val Ile Trp Ser Gly Gly Asn
        420                 425                 430

Thr Asp Tyr Asn Thr Pro Phe Thr Ser Arg Leu Ser Ile Asn Lys Asp
    435                 440                 445

Asn Ser Lys Ser Gln Val Phe Phe Lys Met Asn Ser Leu Gln Ser Asn
450                 455                 460

Asp Thr Ala Ile Tyr Tyr Cys Ala Arg Ala Leu Thr Tyr Tyr Asp Tyr
465                 470                 475                 480

Glu Phe Ala Tyr Trp Gly Gln Gly Thr Leu Val Thr Val Ser Ala Gly
                485                 490                 495

Gly Gly Gly Ser Gly Gly Gly Ser Gly Gly Gly Ser Asp Ile
            500                 505                 510

Leu Leu Thr Gln Ser Pro Val Ile Leu Ser Val Ser Pro Gly Glu Arg
        515                 520                 525

Val Ser Phe Ser Cys Arg Ala Ser Gln Ser Ile Gly Thr Asn Ile His
    530                 535                 540

Trp Tyr Gln Gln Arg Thr Asn Gly Ser Pro Arg Leu Leu Ile Lys Tyr
545                 550                 555                 560

Ala Ser Glu Ser Ile Ser Gly Ile Pro Ser Arg Phe Ser Gly Ser Gly
                565                 570                 575

Ser Gly Thr Asp Phe Thr Leu Ser Ile Asn Ser Val Glu Ser Glu Asp
            580                 585                 590

Ile Ala Asp Tyr Tyr Cys Gln Gln Asn Asn Asn Trp Pro Thr Thr Phe
        595                 600                 605

Gly Ala Gly Thr Lys Leu Glu Leu Lys
        610                 615

<210> SEQ ID NO 57
<211> LENGTH: 1851
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 57
caggtgcagc tgaagcagag cggccccggc ctggtgcagc ccagccagag cctgagcatc      60
acctgcaccg tgagcggctt cagcctgacc aactacggcg tgcactgggt gaggcagagc     120
cccggcaagg gcctggagtg gctgggcgtg atctggagcg gcggcaacac cgactacaac     180
acccccttca ccagcaggct gagcatcaac aaggacaaca gcaagagcca ggtgttcttc     240
aagatgaaca gcctgcagag caacgacacc gccatctact actgcgccag ggccctgacc     300
tactacgact acgagttcgc ctactggggc cagggcaccc tggtgaccgt gagcgccggc     360
ggcggcggca gcggcggcgg cggcagcggc ggcggcggca gcgacatcct gctgacccag     420
agccccgtga tcctgagcgt gagccccggc gagagggtga gcttcagctg cagggccagc     480
cagagcatcg gcaccaacat ccactggtac cagcagagga ccaacggcag ccccaggctg     540
ctgatcaagt acgccagcga gagcatcagc ggcatcccca gcaggttcag cggcagcggc     600
agcggcaccg acttcaccct gagcatcaac agcgtggaga gcgaggacat cgccgactac     660
tactgccagc agaacaacaa ctggccccac cccttcggcg ccggcaccaa gctggagctg     720
aagggcggcg gcggcagcgg cggcggcggc agcgagccca gagcagcga caagacccac     780 acctgccccc cctgccccgc ccccgagctg ctgggcggcc ccagcgtgtt cctgttcccc     840
```

```
cccaagccca aggacaccct gatgatcagc aggaccccg aggtgacctg cgtggtggtg    900
gacgtgagcc acgaggaccc cgaggtgaag ttcaactggt acgtggacgg cgtggaggtg    960
cacaacgcca agaccaagcc cagggaggag cagtacaaca gcacctacag ggtggtgagc   1020
gtgctgaccg tgctgcacca ggactggctg aacggcaagg agtacaagtg caaggtgagc   1080
aacaaggccc tgcccgcccc catcgagaag accatcagca aggccaaggg ccagcccagg   1140
gagcccagg tgtacaccct gccccccagc agggaggaga tgaccaagaa ccaggtgagc   1200
ctgacctgcc tggtgaaggg cttctacccc agcgacatcg ccgtggagtg ggagagcaac   1260
ggccagcccg agaacaacta caagaccacc cccccgtgc tggacagcga cggcagcttc   1320
ttcctgtaca gcaagctgac cgtggacaag agcaggtggc agcagggcaa cgtgttcagc   1380
tgcagcgtga tgcacgaggc cctgcacaac cactacaccc agaagagcct gagcctgagc   1440
cccggcgccg gcggcggcgg cagcggcggc ggcggcagcg gcggcggcgg cagcggcggc   1500
ggcggcagcg aggaggagct gcaggtgatc cagcccgaca gagcgtgag cgtggccgcc   1560
ggcgagagcg ccatcctgca ctgcaccgtg accagcctga tccccgtggg ccccatccag   1620
tggttcaggg gcgccggccc cgccagggag ctgatctaca accagaagga gggccacttc   1680
cccagggtga ccaccgtgag cgagagcacc aagagggaga catggacttt cagcatcagc   1740
atcagcaaca tcacccccgc cgacgccggc acctactact gcgtgaagtt caggaagggc   1800
agcccccgaca ccgagttcaa gagcggcgcc ggcaccgagc tgagcgtgag g         1851
```

<210> SEQ ID NO 58
<211> LENGTH: 617
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

```
Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala Gly Gly Gly Gly Ser Gly Gly Gly Gly
        115                 120                 125

Ser Gly Gly Gly Gly Ser Asp Ile Leu Leu Thr Gln Ser Pro Val Ile
    130                 135                 140

Leu Ser Val Ser Pro Gly Glu Arg Val Ser Phe Ser Cys Arg Ala Ser
145                 150                 155                 160

Gln Ser Ile Gly Thr Asn Ile His Trp Tyr Gln Gln Arg Thr Asn Gly
                165                 170                 175

Ser Pro Arg Leu Leu Ile Lys Tyr Ala Ser Glu Ser Ile Ser Gly Ile
```

```
                    180                 185                 190
Pro Ser Arg Phe Ser Gly Ser Gly Ser Gly Thr Asp Phe Thr Leu Ser
            195                 200                 205
Ile Asn Ser Val Glu Ser Glu Asp Ile Ala Asp Tyr Tyr Cys Gln Gln
            210                 215                 220
Asn Asn Asn Trp Pro Thr Thr Phe Gly Ala Gly Thr Lys Leu Glu Leu
225                 230                 235                 240
Lys Gly Gly Gly Ser Gly Gly Gly Ser Glu Pro Lys Ser Ser
            245                 250                 255
Asp Lys Thr His Thr Cys Pro Pro Cys Pro Ala Pro Glu Leu Leu Gly
            260                 265                 270
Gly Pro Ser Val Phe Leu Phe Pro Pro Lys Pro Lys Asp Thr Leu Met
            275                 280                 285
Ile Ser Arg Thr Pro Glu Val Thr Cys Val Val Val Asp Val Ser His
            290                 295                 300
Glu Asp Pro Glu Val Lys Phe Asn Trp Tyr Val Asp Gly Val Glu Val
305                 310                 315                 320
His Asn Ala Lys Thr Lys Pro Arg Glu Glu Gln Tyr Asn Ser Thr Tyr
            325                 330                 335
Arg Val Val Ser Val Leu Thr Val Leu His Gln Asp Trp Leu Asn Gly
            340                 345                 350
Lys Glu Tyr Lys Cys Lys Val Ser Asn Lys Ala Leu Pro Ala Pro Ile
            355                 360                 365
Glu Lys Thr Ile Ser Lys Ala Lys Gly Gln Pro Arg Glu Pro Gln Val
            370                 375                 380
Tyr Thr Leu Pro Pro Ser Arg Glu Glu Met Thr Lys Asn Gln Val Ser
385                 390                 395                 400
Leu Thr Cys Leu Val Lys Gly Phe Tyr Pro Ser Asp Ile Ala Val Glu
            405                 410                 415
Trp Glu Ser Asn Gly Gln Pro Glu Asn Asn Tyr Lys Thr Thr Pro Pro
            420                 425                 430
Val Leu Asp Ser Asp Gly Ser Phe Phe Leu Tyr Ser Lys Leu Thr Val
            435                 440                 445
Asp Lys Ser Arg Trp Gln Gln Gly Asn Val Phe Ser Cys Ser Val Met
            450                 455                 460
His Glu Ala Leu His Asn His Tyr Thr Gln Lys Ser Leu Ser Leu Ser
465                 470                 475                 480
Pro Gly Ala Gly Gly Gly Gly Ser Gly Gly Gly Gly Ser Gly Gly Gly
            485                 490                 495
Gly Ser Gly Gly Gly Gly Ser Glu Glu Glu Leu Gln Val Ile Gln Pro
            500                 505                 510
Asp Lys Ser Val Ser Val Ala Ala Gly Glu Ser Ala Ile Leu His Cys
            515                 520                 525
Thr Val Thr Ser Leu Ile Pro Val Gly Pro Ile Gln Trp Phe Arg Gly
            530                 535                 540
Ala Gly Pro Ala Arg Glu Leu Ile Tyr Asn Gln Lys Glu Gly His Phe
545                 550                 555                 560
Pro Arg Val Thr Thr Val Ser Glu Ser Thr Lys Arg Glu Asn Met Asp
            565                 570                 575
Phe Ser Ile Ser Ile Ser Asn Ile Thr Pro Ala Asp Ala Gly Thr Tyr
            580                 585                 590
Tyr Cys Val Lys Phe Arg Lys Gly Ser Pro Asp Thr Glu Phe Lys Ser
            595                 600                 605
```

Gly Ala Gly Thr Glu Leu Ser Val Arg
        610             615

<210> SEQ ID NO 59
<211> LENGTH: 726
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 59
gaggtgaagc tgcaggagag cggccccggc ctggtggccc ccagccagag cctgagcgtg      60
acctgcaccg tgagcggcgt gagcctgccc gactacggcg tgagctggat caggcagccc     120
cccaggaagg cctggagtg gctgggcgtg atctggggca gcgagaccac ctactacaac      180
agcgccctga agagcaggct gaccatcatc aaggacaaca gcaagagcca ggtgttcctg     240
aagatgaaca gcctgcagac cgacgacacc gccatctact actgcgccaa gcactactac     300
tacggcggca gctacgccat ggactactgg ggccagggca ccagcgtgac cgtgagcagc     360
ggcggcggcg gcagcggcgg cggcggcagc ggcggcggcg gcagcgacat ccagatgacc     420
cagaccacca gcagcctgag cgccagcctg ggcgacaggg tgaccatcag ctgcagggcc     480
agccaggaca tcagcaagta cctgaactgg taccagcaga agcccgacgg caccgtgaag     540
ctgctgatct accacaccag caggctgcac agcggcgtgc ccagcaggtt cagcggcagc     600
ggcagcggca ccgactacag cctgaccatc agcaacctgg agcaggagga catcgccacc     660
tacttctgcc agcagggcaa caccctgccc tacaccttcg gcggcggcac caagctggag     720
atcacc                                                                726

<210> SEQ ID NO 60
<211> LENGTH: 242
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Glu Val Lys Leu Gln Glu Ser Gly Pro Gly Leu Val Ala Pro Ser Gln
1               5                   10                  15

Ser Leu Ser Val Thr Cys Thr Val Ser Gly Val Ser Leu Pro Asp Tyr
            20                  25                  30

Gly Val Ser Trp Ile Arg Gln Pro Pro Arg Lys Gly Leu Glu Trp Leu
        35                  40                  45

Gly Val Ile Trp Gly Ser Glu Thr Thr Tyr Tyr Asn Ser Ala Leu Lys
    50                  55                  60

Ser Arg Leu Thr Ile Ile Lys Asp Asn Ser Lys Ser Gln Val Phe Leu
65                  70                  75                  80

Lys Met Asn Ser Leu Gln Thr Asp Asp Thr Ala Ile Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Ser Val Thr Val Ser Ser Gly Gly Gly Gly Ser Gly Gly Gly
        115                 120                 125

Gly Ser Gly Gly Gly Gly Ser Asp Ile Gln Met Thr Gln Thr Thr Ser
    130                 135                 140

```
Ser Leu Ser Ala Ser Leu Gly Asp Arg Val Thr Ile Ser Cys Arg Ala
145                 150                 155                 160

Ser Gln Asp Ile Ser Lys Tyr Leu Asn Trp Tyr Gln Gln Lys Pro Asp
            165                 170                 175

Gly Thr Val Lys Leu Leu Ile Tyr His Thr Ser Arg Leu His Ser Gly
        180                 185                 190

Val Pro Ser Arg Phe Ser Gly Ser Gly Ser Gly Thr Asp Tyr Ser Leu
    195                 200                 205

Thr Ile Ser Asn Leu Glu Gln Glu Asp Ile Ala Thr Tyr Phe Cys Gln
        210                 215                 220

Gln Gly Asn Thr Leu Pro Tyr Thr Phe Gly Gly Gly Thr Lys Leu Glu
225                 230                 235                 240

Ile Thr

<210> SEQ ID NO 61
<211> LENGTH: 1854
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 61
gaggaggagc tgcaggtgat ccagcccgac aagagcgtga gcgtggccgc cggcgagagc      60
gccatcctgc actgcaccgt gaccagcctg atccccgtgg cccccatcca gtggttcagg     120
ggcgccggcc cgccagggga gctgatctac aaccagaagg agggccactt ccccagggtg     180
accaccgtga gcgagagcac caagagggag aacatggact tcagcatcag catcagcaac     240
atcacccccg ccgacgccgg cacctactac tgcgtgaagt tcaggaaggg cagccccgac     300
accgagttca gagcggcgc cggcaccgag ctgagcgtga gggcggcgg cggcagcggc      360 ggcggcggca gcgagcccaa gagcagcgac aagacccaca cctgcccccc ctgccccgcc     420
cccgagctgc tgggcggccc cagcgtgttc ctgttccccc caagcccaa ggacaccctg      480 atgatcagca ggacccccga ggtgacctgc gtggtggtgg acgtgagcca cgaggacccc     540
gaggtgaagt tcaactggta cgtggacggc gtggaggtgc acaacgccaa gaccaagccc     600
agggaggagc agtacaacag cacctacagg gtggtgagcg tgctgaccgt gctgcaccag     660
gactggctga acggcaagga gtacaagtgc aaggtgagca caaggccct gcccgccccc      720 atcgagaaga ccatcagcaa ggccaagggc cagcccaggg agccccaggt gtacaccctg     780
ccccccagca gggaggagat gaccaagaac caggtgagcc tgacctgcct ggtgaagggc     840
ttctaccccc gcgacatcgc cgtggagtgg gagagcaacg gccagcccga gaacaactac     900
aagaccaccc ccccgtgct ggacagcgac ggcagcttct cctgtacag caagctgacc       960 gtggacaaga gcaggtggca gcagggcaac gtgttcagct gcagcgtgat gcacgaggcc    1020
ctgcacaacc actacaccca gaagagcctg agcctgagcc ccggcgccgg cggcggcggc    1080
agcggcggcg gcggcagcgg cggcggcggc agcggcggcg gcggcagcga ggtgaagctg    1140
caggagagcg gccccggcct ggtggccccc agccagagcc tgagcgtgac cctgaccgtg    1200
agcggcgtga gcctgcccga ctacggcgtg agctggatca ggcagccccc caggaagggc    1260
ctggagtggc tgggcgtgat ctggggcagc gagaccacct actacaacag cgccctgaag    1320
agcaggctga ccatcatcaa ggacaacagc aagagccagg tgttcctgaa gatgaacagc    1380
ctgcagaccg acgacaccgc catctactac tgcgccaagc actactacta cggcggcagc    1440
```

```
tacgccatgg actactgggg ccagggcacc agcgtgaccg tgagcagcgg cggcggcggc    1500
agcggcggcg gcggcagcgg cggcggcggc agcgacatcc agatgaccca gaccaccagc    1560
agcctgagcg ccagcctggg cgacagggtg accatcagct gcagggccag ccaggacatc    1620
agcaagtacc tgaactggta ccagcagaag cccgacggca ccgtgaagct gctgatctac    1680
cacaccagca ggctgcacag cggcgtgccc agcaggttca gcggcagcgg cagcggcacc    1740
gactacagcc tgaccatcag caacctggag caggaggaca tcgccaccta cttctgccag    1800
cagggcaaca ccctgcccta caccttcggc ggcggcacca agctggagat cacc          1854
```

<210> SEQ ID NO 62
<211> LENGTH: 618
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

```
Glu Glu Glu Leu Gln Val Ile Gln Pro Asp Lys Ser Val Ser Val Ala
1               5                   10                  15

Ala Gly Glu Ser Ala Ile Leu His Cys Thr Val Thr Ser Leu Ile Pro
            20                  25                  30

Val Gly Pro Ile Gln Trp Phe Arg Gly Ala Gly Pro Ala Arg Glu Leu
        35                  40                  45

Ile Tyr Asn Gln Lys Glu Gly His Phe Pro Arg Val Thr Thr Val Ser
    50                  55                  60

Glu Ser Thr Lys Arg Glu Asn Met Asp Phe Ile Ser Ile Ser Asn
65                  70                  75                  80

Ile Thr Pro Ala Asp Ala Gly Thr Tyr Tyr Cys Val Lys Phe Arg Lys
                85                  90                  95

Gly Ser Pro Asp Thr Glu Phe Lys Ser Gly Ala Gly Thr Glu Leu Ser
            100                 105                 110

Val Arg Gly Gly Gly Ser Gly Gly Gly Ser Glu Pro Lys Ser
        115                 120                 125

Ser Asp Lys Thr His Thr Cys Pro Pro Cys Pro Ala Pro Glu Leu Leu
    130                 135                 140

Gly Gly Pro Ser Val Phe Leu Phe Pro Pro Lys Pro Lys Asp Thr Leu
145                 150                 155                 160

Met Ile Ser Arg Thr Pro Glu Val Thr Cys Val Val Val Asp Val Ser
                165                 170                 175

His Glu Asp Pro Glu Val Lys Phe Asn Trp Tyr Val Asp Gly Val Glu
            180                 185                 190

Val His Asn Ala Lys Thr Lys Pro Arg Glu Glu Gln Tyr Asn Ser Thr
        195                 200                 205

Tyr Arg Val Val Ser Val Leu Thr Val Leu His Gln Asp Trp Leu Asn
    210                 215                 220

Gly Lys Glu Tyr Lys Cys Lys Val Ser Asn Lys Ala Leu Pro Ala Pro
225                 230                 235                 240

Ile Glu Lys Thr Ile Ser Lys Ala Lys Gly Gln Pro Arg Glu Pro Gln
                245                 250                 255

Val Tyr Thr Leu Pro Pro Ser Arg Glu Glu Met Thr Lys Asn Gln Val
            260                 265                 270

Ser Leu Thr Cys Leu Val Lys Gly Phe Tyr Pro Ser Asp Ile Ala Val
        275                 280                 285
```

Glu Trp Glu Ser Asn Gly Gln Pro Glu Asn Asn Tyr Lys Thr Thr Pro
290                 295                 300

Pro Val Leu Asp Ser Asp Gly Ser Phe Phe Leu Tyr Ser Lys Leu Thr
305                 310                 315                 320

Val Asp Lys Ser Arg Trp Gln Gln Gly Asn Val Phe Ser Cys Ser Val
            325                 330                 335

Met His Glu Ala Leu His Asn His Tyr Thr Gln Lys Ser Leu Ser Leu
            340                 345                 350

Ser Pro Gly Ala Gly Gly Gly Ser Gly Gly Gly Ser Gly Gly
            355                 360                 365

Gly Gly Ser Gly Gly Gly Ser Glu Val Lys Leu Gln Glu Ser Gly
370                 375                 380

Pro Gly Leu Val Ala Pro Ser Gln Ser Leu Ser Val Thr Cys Thr Val
385                 390                 395                 400

Ser Gly Val Ser Leu Pro Asp Tyr Gly Val Ser Trp Ile Arg Gln Pro
            405                 410                 415

Pro Arg Lys Gly Leu Glu Trp Leu Gly Val Ile Trp Gly Ser Glu Thr
            420                 425                 430

Thr Tyr Tyr Asn Ser Ala Leu Lys Ser Arg Leu Thr Ile Ile Lys Asp
            435                 440                 445

Asn Ser Lys Ser Gln Val Phe Leu Lys Met Asn Ser Leu Gln Thr Asp
450                 455                 460

Asp Thr Ala Ile Tyr Tyr Cys Ala Lys His Tyr Tyr Gly Gly Ser
465                 470                 475                 480

Tyr Ala Met Asp Tyr Trp Gly Gln Gly Thr Ser Val Thr Val Ser Ser
            485                 490                 495

Gly Gly Gly Gly Ser Gly Gly Gly Ser Gly Gly Gly Ser Asp
            500                 505                 510

Ile Gln Met Thr Gln Thr Thr Ser Ser Leu Ser Ala Ser Leu Gly Asp
            515                 520                 525

Arg Val Thr Ile Ser Cys Arg Ala Ser Gln Asp Ile Ser Lys Tyr Leu
530                 535                 540

Asn Trp Tyr Gln Gln Lys Pro Asp Gly Thr Val Lys Leu Leu Ile Tyr
545                 550                 555                 560

His Thr Ser Arg Leu His Ser Gly Val Pro Ser Arg Phe Ser Gly Ser
            565                 570                 575

Gly Ser Gly Thr Asp Tyr Ser Leu Thr Ile Ser Asn Leu Glu Gln Glu
            580                 585                 590

Asp Ile Ala Thr Tyr Phe Cys Gln Gln Gly Asn Thr Leu Pro Tyr Thr
            595                 600                 605

Phe Gly Gly Gly Thr Lys Leu Glu Ile Thr
610                 615

<210> SEQ ID NO 63
<211> LENGTH: 1854
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 63
gaggtgaagc tgcaggagag cggccccggc ctggtggccc ccagccagag cctgagcgtg      60
acctgcaccg tgagcggcgt gagcctgccc gactacggcg tgagctggat caggcagccc     120
cccaggaagg gcctggagtg gctgggcgtg atctggggca gcgagaccac ctactacaac     180

| | | |
|---|---|---|
| agcgccctga agagcaggct gaccatcatc aaggacaaca gcaagagcca ggtgttcctg | 240 | |
| aagatgaaca gcctgcagac cgacgacacc gccatctact actgcgccaa gcactactac | 300 | |
| tacggcggca gctacgccat ggactactgg ggccagggca ccagcgtgac cgtgagcagc | 360 | |
| ggcggcggcg gcagcggcgg cggcggcagc ggcggcggcg gcagcgacat ccagatgacc | 420 | |
| cagaccacca gcagcctgag cgccagcctg ggcgacaggg tgaccatcag ctgcagggcc | 480 | |
| agccaggaca tcagcaagta cctgaactgg taccagcaga agcccgacgg caccgtgaag | 540 | |
| ctgctgatct accacaccag caggctgcac agcggcgtgc ccagcaggtt cagcggcagc | 600 | |
| ggcagcggca ccgactacag cctgaccatc agcaacctgg agcaggagga catcgccacc | 660 | |
| tacttctgcc agcagggcaa caccctgccc tacaccttcg gcggcggcac caagctggag | 720 | |
| atcaccggcg gcggcggcag cggcggcggc ggcagcgagc ccaagagcag cgacaagacc | 780 | |
| cacacctgcc cccctgccc cgcccccgag ctgctgggcg gccccagcgt gttcctgttc | 840 | |
| cccccaagc caaggacac cctgatgatc agcaggaccc ccgaggtgac ctgcgtggtg | 900 | |
| gtggacgtga gccacgagga cccccgaggtg aagttcaact ggtacgtgga cggcgtggag | 960 | |
| gtgcacaacg ccaagaccaa gccccaggag gagcagtaca acagcaccta cagggtggtg | 1020 | |
| agcgtgctga ccgtgctgca ccaggactgg ctgaacggca aggagtacaa gtgcaaggtg | 1080 | |
| agcaacaagg ccctgcccgc ccccatcgag aagaccatca gcaaggccaa gggccagccc | 1140 | |
| agggagcccc aggtgtacac cctgccccc agcagggagg agatgaccaa gaaccaggtg | 1200 | |
| agcctgacct gcctggtgaa gggcttctac cccagcgaca tcgccgtgga gtgggagagc | 1260 | |
| aacggccagc ccgagaacaa ctacaagacc accccccccg tgctggacag cgacggcagc | 1320 | |
| ttcttcctgt acagcaagct gaccgtggac aagagcaggt ggcagcaggg caacgtgttc | 1380 | |
| agctgcagcg tgatgcacga ggccctgcac aaccactaca cccagaagag cctgagcctg | 1440 | |
| agccccggcg ccggcggcgg cggcagcggc ggcggcggca gcggcggcgg cggcagcggc | 1500 | |
| ggcggcggca gcgaggagga gctgcaggtg atccagcccg acaagagcgt gagcgtggcc | 1560 | |
| gccggcgaga gcgccatcct gcactgcacc gtgaccagcc tgatccccgt gggccccatc | 1620 | |
| cagtggttca ggggcgccgg ccccgccagg gagctgatct acaaccagaa ggagggccac | 1680 | |
| ttccccaggg tgaccaccgt gagcgagagc accaagaggg agaacatgga cttcagcatc | 1740 | |
| agcatcagca acatcacccc cgccgacgcc ggcacctact actgcgtgaa gttcaggaag | 1800 | |
| ggcagccccg acaccgagtt caagagcggc gccggcaccg agctgagcgt gagg | 1854 | |

<210> SEQ ID NO 64
<211> LENGTH: 618
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 64

Glu Val Lys Leu Gln Glu Ser Gly Pro Gly Leu Val Ala Pro Ser Gln
1               5                   10                  15

Ser Leu Ser Val Thr Cys Thr Val Ser Gly Val Ser Leu Pro Asp Tyr
            20                  25                  30

Gly Val Ser Trp Ile Arg Gln Pro Pro Arg Lys Gly Leu Glu Trp Leu
        35                  40                  45

Gly Val Ile Trp Gly Ser Glu Thr Thr Tyr Tyr Asn Ser Ala Leu Lys
    50                  55                  60

```
Ser Arg Leu Thr Ile Ile Lys Asp Asn Ser Lys Ser Gln Val Phe Leu
 65                  70                  75                  80

Lys Met Asn Ser Leu Gln Thr Asp Asp Thr Ala Ile Tyr Tyr Cys Ala
                 85                  90                  95

Lys His Tyr Tyr Tyr Gly Gly Ser Tyr Ala Met Asp Tyr Trp Gly Gln
            100                 105                 110

Gly Thr Ser Val Thr Val Ser Ser Gly Gly Gly Gly Ser Gly Gly Gly
        115                 120                 125

Gly Ser Gly Gly Gly Gly Ser Asp Ile Gln Met Thr Gln Thr Thr Ser
    130                 135                 140

Ser Leu Ser Ala Ser Leu Gly Asp Arg Val Thr Ile Ser Cys Arg Ala
145                 150                 155                 160

Ser Gln Asp Ile Ser Lys Tyr Leu Asn Trp Tyr Gln Gln Lys Pro Asp
                165                 170                 175

Gly Thr Val Lys Leu Leu Ile Tyr His Thr Ser Arg Leu His Ser Gly
            180                 185                 190

Val Pro Ser Arg Phe Ser Gly Ser Gly Ser Gly Thr Asp Tyr Ser Leu
        195                 200                 205

Thr Ile Ser Asn Leu Glu Gln Glu Asp Ile Ala Thr Tyr Phe Cys Gln
210                 215                 220

Gln Gly Asn Thr Leu Pro Tyr Thr Phe Gly Gly Gly Thr Lys Leu Glu
225                 230                 235                 240

Ile Thr Gly Gly Gly Gly Ser Gly Gly Gly Gly Ser Glu Pro Lys Ser
                245                 250                 255

Ser Asp Lys Thr His Thr Cys Pro Pro Cys Pro Ala Pro Glu Leu Leu
                260                 265                 270

Gly Gly Pro Ser Val Phe Leu Phe Pro Pro Lys Pro Lys Asp Thr Leu
            275                 280                 285

Met Ile Ser Arg Thr Pro Glu Val Thr Cys Val Val Val Asp Val Ser
        290                 295                 300

His Glu Asp Pro Glu Val Lys Phe Asn Trp Tyr Val Asp Gly Val Glu
305                 310                 315                 320

Val His Asn Ala Lys Thr Lys Pro Arg Glu Glu Gln Tyr Asn Ser Thr
                325                 330                 335

Tyr Arg Val Val Ser Val Leu Thr Val Leu His Gln Asp Trp Leu Asn
            340                 345                 350

Gly Lys Glu Tyr Lys Cys Lys Val Ser Asn Lys Ala Leu Pro Ala Pro
        355                 360                 365

Ile Glu Lys Thr Ile Ser Lys Ala Lys Gly Gln Pro Arg Glu Pro Gln
    370                 375                 380

Val Tyr Thr Leu Pro Pro Ser Arg Glu Glu Met Thr Lys Asn Gln Val
385                 390                 395                 400

Ser Leu Thr Cys Leu Val Lys Gly Phe Tyr Pro Ser Asp Ile Ala Val
                405                 410                 415

Glu Trp Glu Ser Asn Gly Gln Pro Glu Asn Asn Tyr Lys Thr Thr Pro
            420                 425                 430

Pro Val Leu Asp Ser Asp Gly Ser Phe Phe Leu Tyr Ser Lys Leu Thr
        435                 440                 445

Val Asp Lys Ser Arg Trp Gln Gln Gly Asn Val Phe Ser Cys Ser Val
    450                 455                 460

Met His Glu Ala Leu His Asn His Tyr Thr Gln Lys Ser Leu Ser Leu
465                 470                 475                 480
```

Ser Pro Gly Ala Gly Gly Gly Gly Ser Gly Gly Gly Ser Gly Gly
            485                 490                 495

Gly Gly Ser Gly Gly Gly Ser Glu Glu Leu Gln Val Ile Gln
            500                 505                 510

Pro Asp Lys Ser Val Ser Val Ala Ala Gly Glu Ser Ala Ile Leu His
        515                 520                 525

Cys Thr Val Thr Ser Leu Ile Pro Val Gly Pro Ile Gln Trp Phe Arg
    530                 535                 540

Gly Ala Gly Pro Ala Arg Glu Leu Ile Tyr Asn Gln Lys Glu Gly His
545                 550                 555                 560

Phe Pro Arg Val Thr Thr Val Ser Glu Ser Thr Lys Arg Glu Asn Met
                565                 570                 575

Asp Phe Ser Ile Ser Ile Ser Asn Ile Thr Pro Ala Asp Ala Gly Thr
            580                 585                 590

Tyr Tyr Cys Val Lys Phe Arg Lys Gly Ser Pro Asp Thr Glu Phe Lys
        595                 600                 605

Ser Gly Ala Gly Thr Glu Leu Ser Val Arg
    610                 615

<210> SEQ ID NO 65
<211> LENGTH: 711
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 65
gagcccaaga gcagcgacaa gacccacacc tgcccccccct gccccgcccc cgagctgctg      60
ggcggcccca gcgtgttcct gttcccccccc aagcccaagg acaccctgat gatcagcagg     120 accccccgagg tgacctgcgt ggtggtggac gtgagccacg aggaccccga ggtgaagttc     180
aactggtacg tggacggcgt ggaggtgcac aacgccaaga ccaagcccag ggaggagcag     240
tacaacagca cctacagggt ggtgagcgtg ctgaccgtgc tgcaccagga ctggctgaac     300
ggcaaggagt acaagtgcaa ggtgagcaac aaggcccctg ccgcccccat cgagaagacc     360
atcagcaagg ccaagggcca gccccagggag ccccaggtgt acaccctgcc ccccagcagg     420
gacgagtacc tgtacggcga cgtgagcctg acctgcctgg tgaagggctt ctaccccagc     480
gacatcgccg tggagtggga gagcaacggc cagcccgaga caactacaa gaccacccccc      540 cccgtgctgg acagcgacgg cagcttcttc ctgtacagca agctgaccgt gcccaggcac     600
agcgccagga tgtggaggtg ggcccacggc aacgtgttca gctgcagcgt gatgcacgag     660
gccctgcaca accactacac ccagaagagc ctgagcctga gccccggcaa g              711

<210> SEQ ID NO 66
<211> LENGTH: 237
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
            35                  40                  45

Val Asp Val Ser His Glu Asp Pro Glu Val Lys Phe Asn Trp Tyr Val
 50                  55                  60

Asp Gly Val Glu Val His Asn Ala Lys Thr Lys Pro Arg Glu Glu Gln
 65                  70                  75                  80

Tyr Asn Ser Thr Tyr Arg Val Val Ser Val Leu Thr Val Leu His Gln
                 85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Tyr Leu
    130                 135                 140

Tyr Gly Asp Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Pro Arg His Ser Ala Arg Met Trp Arg Trp Ala
        195                 200                 205

His Gly Asn Val Phe Ser Cys Ser Val Met His Glu Ala Leu His Asn
    210                 215                 220

His Tyr Thr Gln Lys Ser Leu Ser Leu Ser Pro Gly Lys
225                 230                 235

<210> SEQ ID NO 67
<211> LENGTH: 1083
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 67
gaggaggagc tgcaggtgat ccagcccgac aagagcgtga gcgtggccgc cggcgagagc      60
gccatcctgc actgcaccgt gaccagcctg atccccgtgg cccccatcca gtggttcagg     120
ggcgccggcc ccgccaggga gctgatctac aaccagaagg agggccactt ccccagggtg     180
accaccgtga gcgagagcac caagagggag aacatggact tcagcatcag catcagcaac     240
atcacccccg ccgacgccgg cacctactac tgcgtgaagt tcaggaaggg cagccccgac     300
accgagttca gagcggcgc cggcaccgag ctgagcgtga gggcggcgg cggcagcggc     360 ggcggcggca gcgagcccaa gagcagcgac aagacccaca cctgcccccc ctgccccgcc     420
cccgagctgc tgggcggccc cagcgtgttc ctgttcccc caagcccaa ggacaccctg     480 atgatcagca ggaccccga ggtgacctgc gtggtggtgg acgtgagcca cgaggacccc     540
gaggtgaagt tcaactggta cgtggacggc gtggaggtgc acaacgccaa gaccaagccc     600
agggaggagc agtacaacag cacctacagg gtggtgagcg tgctgaccgt gctgcaccag     660
gactggctga acggcaagga gtacaagtgc aaggtgagca caaggccct gcccgccccc     720 atcgagaaga ccatcagcaa ggccaagggc cagcccaggg agccccaggt gtacaccctg     780 cccccagca gggacgagta cctgtacggg gacgtgagcc tgacctgcct ggtgaagggc     840
ttctacccca gcgacatcgc cgtggagtgg gagagcaacg gccagcccga gaacaactac     900

```
aagaccaccc ccccgtgct ggacagcgac ggcagcttct tcctgtacag caagctgacc    960
gtgcccaggc acagcgccag gatgtggagg tgggcccacg caacgtgttt cagctgcagc  1020
gtgatgcacg aggccctgca caaccactac acccagaaga gcctgagcct gagccccggc  1080
aag                                                                1083
```

<210> SEQ ID NO 68
<211> LENGTH: 361
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

```
Glu Glu Glu Leu Gln Val Ile Gln Pro Asp Lys Ser Val Ser Val Ala
1               5                   10                  15

Ala Gly Glu Ser Ala Ile Leu His Cys Thr Val Thr Ser Leu Ile Pro
            20                  25                  30

Val Gly Pro Ile Gln Trp Phe Arg Gly Ala Gly Pro Ala Arg Glu Leu
        35                  40                  45

Ile Tyr Asn Gln Lys Glu Gly His Phe Pro Arg Val Thr Thr Val Ser
    50                  55                  60

Glu Ser Thr Lys Arg Glu Asn Met Asp Phe Ser Ile Ser Ile Ser Asn
65                  70                  75                  80

Ile Thr Pro Ala Asp Ala Gly Thr Tyr Tyr Cys Val Lys Phe Arg Lys
                85                  90                  95

Gly Ser Pro Asp Thr Glu Phe Lys Ser Gly Ala Gly Thr Glu Leu Ser
            100                 105                 110

Val Arg Gly Gly Gly Ser Gly Gly Gly Ser Glu Pro Lys Ser
        115                 120                 125

Ser Asp Lys Thr His Thr Cys Pro Pro Cys Pro Ala Pro Glu Leu Leu
    130                 135                 140

Gly Gly Pro Ser Val Phe Leu Phe Pro Pro Lys Pro Lys Asp Thr Leu
145                 150                 155                 160

Met Ile Ser Arg Thr Pro Glu Val Thr Cys Val Val Val Asp Val Ser
                165                 170                 175

His Glu Asp Pro Glu Val Lys Phe Asn Trp Tyr Val Asp Gly Val Glu
            180                 185                 190

Val His Asn Ala Lys Thr Lys Pro Arg Glu Glu Gln Tyr Asn Ser Thr
        195                 200                 205

Tyr Arg Val Val Ser Val Leu Thr Val Leu His Gln Asp Trp Leu Asn
    210                 215                 220

Gly Lys Glu Tyr Lys Cys Lys Val Ser Asn Lys Ala Leu Pro Ala Pro
225                 230                 235                 240

Ile Glu Lys Thr Ile Ser Lys Ala Lys Gly Gln Pro Arg Glu Pro Gln
                245                 250                 255

Val Tyr Thr Leu Pro Pro Ser Arg Asp Glu Leu Tyr Gly Asp Val
            260                 265                 270

Ser Leu Thr Cys Leu Val Lys Gly Phe Tyr Pro Ser Asp Ile Ala Val
        275                 280                 285

Glu Trp Glu Ser Asn Gly Gln Pro Glu Asn Asn Tyr Lys Thr Thr Pro
    290                 295                 300

Pro Val Leu Asp Ser Asp Gly Ser Phe Phe Leu Tyr Ser Lys Leu Thr
305                 310                 315                 320
```

Val Pro Arg His Ser Ala Arg Met Trp Arg Trp Ala His Gly Asn Val
             325                 330                 335

Phe Ser Cys Ser Val Met His Glu Ala Leu His Asn His Tyr Thr Gln
             340                 345                 350

Lys Ser Leu Ser Leu Ser Pro Gly Lys
             355                 360

<210> SEQ ID NO 69
<211> LENGTH: 1734
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 69

| | | |
|---|---|---|
| caagtccaac tgaagcagtc cgggccggga ctcgtgcagc cgtcgcagtc actgtccatc | 60 |
| acttgcacgg tgtcaggctt ttccttgacc aactacggag tgcactgggt gcgccagtcc | 120 |
| cctggaaagg ggctggagtg gcttggcgtg atttggtccg gaggaaacac agactacaac | 180 |
| actcctttca cctcccgcct gagcattaac aaggacaact ccaagtccca agtgttcttc | 240 |
| aagatgaaca gcctgcagag caatgatacc gccatctact attgtgcccg ggctctcacc | 300 |
| tactacgact acgaattcgc ctactgggga caggaacccc tggtcactgt ctccgcggcc | 360 |
| tccactaagg gccctagcgt gttccccttg cgccatcgt caaagtccac ctccggtggc | 420 |
| actgccgccc tgggatgcct tgtgaaggac tacttccccg aacctgtgac cgtgtcctgg | 480 |
| aactcgggcg cactgacttc ggggtgcac acctttcctg ccgtcctgca atcgagcggt | 540 |
| ctgtactccc tctcgtccgt ggtcaccgtg ccgtctagct ccctcggaac ccagacctac | 600 |
| atctgcaacg tcaaccacaa gccgagcaac accaaagtgg ataagagagt ggagccgaag | 660 |
| tcatgcgaca agactcatac ttgtccccca tgccccgccc cggaactgct gggggggccca | 720 |
| tccgtgttcc tgttcccgcc gaaacctaag gacaccctga tgatttcgag aactccggaa | 780 |
| gtgacctgtg tggtggtcga cgtgtcccac gaggatccgg aggtcaagtt caattggtac | 840 |
| gtcgacggag tggaagtcca caacgccaag accaagcccc gggaggagca gtacaactcc | 900 |
| acttaccggg tggtgtccgt gctgaccgtg ctgcatcagg attggctgaa cggaaaggag | 960 |
| tataagtgca agtgtcaaa caaggcattg cctgcgccaa tcgaaaagac cattagcaag | 1020 |
| gccaagggcc agcccaggga accacaggtg tacactctgc cccgtcccg gaagaaatg | 1080 |
| accaagaacc aagtgtcact gacatgcctc gtgaaggat tttacccgtc cgatatcgcc | 1140 |
| gtggaatggg aatcgaacgg tcaacctgaa acaactaca agacgacccc tccggtcctg | 1200 |
| gacagcgatg gctcattctt cctgtactcc aagcttacgg tggacaagtc ccggtggcaa | 1260 |
| caggaaaatg tgttttcgtg ctccgtgatg catgaggctc tgcacaacca ctacacccag | 1320 |
| aagtcactct ccctgagccc cggcgcgggg ggtggtggaa gcgaggagg ggggtctggg | 1380 |
| ggtggcggtt ccgaggagga gctccaggtc atccagcctg acaagtccgt gtcggtggcc | 1440 |
| gcggagagt ccgccattct gcactgcacc gtgacctccc tcatcccgt gggacctatc | 1500 |
| cagtggttca gggagccgg gccgcacgg gaactgatct ataaccagaa ggagggccat | 1560 |
| ttcccccgcg tgaccaccgt gtccgagagc accaagaggg aaaacatgga cttcagcatt | 1620 |
| tcgatcagca acatcactcc cgctgacgcc gggacctact actgcgtgaa gttcggaaaa | 1680 |
| ggaagcccgg acaccgagtt caaaagcgga gccggcaccg aactgtcggt ccgc | 1734 |

```
<210> SEQ ID NO 70
<211> LENGTH: 578
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70
```

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Ala Gly Gly Gly Ser Gly Gly Gly Ser Gly Gly Gly Ser
450                 455                 460

Glu Glu Glu Leu Gln Val Ile Gln Pro Asp Lys Ser Val Ser Val Ala
465                 470                 475                 480

Ala Gly Glu Ser Ala Ile Leu His Cys Thr Val Thr Ser Leu Ile Pro
                485                 490                 495

Val Gly Pro Ile Gln Trp Phe Arg Gly Ala Gly Pro Ala Arg Glu Leu
            500                 505                 510

Ile Tyr Asn Gln Lys Glu Gly His Phe Pro Arg Val Thr Thr Val Ser
        515                 520                 525

Glu Ser Thr Lys Arg Glu Asn Met Asp Phe Ser Ile Ser Ile Ser Asn
530                 535                 540

Ile Thr Pro Ala Asp Ala Gly Thr Tyr Tyr Cys Val Lys Phe Arg Lys
545                 550                 555                 560

Gly Ser Pro Asp Thr Glu Phe Lys Ser Gly Ala Gly Thr Glu Leu Ser
                565                 570                 575

Val Arg

<210> SEQ ID NO 71
<211> LENGTH: 1764
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 71
caagtccaac tgaagcagtc cgggccggga ctcgtgcagc cgtcgcagtc actgtccatc     60
acttgcacgg tgtcaggctt ttccttgacc aactacggag tgcactgggt gcgccagtcc    120
cctggaaagg ggctggagtg gcttggcgtg atttggtccg gaggaaacac agactacaac    180
actcctttca cctcccgcct gagcattaac aaggacaact ccaagtccca agtgttcttc    240
aagatgaaca gcctgcagag caatgatacc gccatctact attgtgcccg ggctctcacc    300
tactacgact acgaattcgc ctactgggga cagggaaccc tggtcactgt ctccgcggcc    360
tccactaagg gcctagcgt gttccccttg cgccatcgt caaagtccac ctccggtggc    420
actgccgccc tgggatgcct tgtgaaggac tacttccccg aacctgtgac cgtgtcctgg    480
aactcgggcg cactgacttc gggggtgcac acctttcctg ccgtcctgca atcgagcggt    540
ctgtactccc tctcgtccgt ggtcaccgtg ccgtctagct ccctcggaac ccagacctac    600
atctgcaacg tcaaccacaa gccgagcaac accaaagtgg ataagagagt ggagccgaag    660
tcatgcgaca agactcatac ttgtccccca tgccccgccc cggaactgct ggggggccca    720
tccgtgttcc tgttcccgcc gaaacctaag gacaccctga tgatttcgag aactccggaa    780

```
gtgacctgtg tggtggtcga cgtgtcccac gaggatccgg aggtcaagtt caattggtac    840
gtcgacggag tggaagtcca caacgccaag accaagcccc gggaggagca gtacaactcc    900
acttaccggg tggtgtccgt gctgaccgtg ctgcatcagg attggctgaa cggaaaggag    960
tataagtgca aagtgtcaaa caaggcattg cctgcgccaa tcgaaaagac cattagcaag   1020
gccaagggcc agcccaggga accacaggtg tacactctgc ccccgtcccg cgaagaaatg   1080
accaagaacc aagtgtcact gacatgcctc gtgaagggat tttacccgtc cgatatcgcc   1140
gtggaatggg aatcgaacgg tcaacctgaa aacaactaca agacgacccc tccggtcctg   1200
gacagcgatg gctcattctt cctgtactcc aagcttacgg tggacaagtc ccggtggcaa   1260
cagggaaatg tgttttcgtg ctccgtgatg catgaggctc tgcacaacca ctacacccag   1320
aagtcactct ccctgagccc cggcgcgggg ggtggtggaa gcggaggagg ggggtctggg   1380
ggtggcggtt ccggcggcgg cggatccggc ggcggcggat ccgaggagga gctccaggtc   1440
atccagcctg acaagtccgt gtcggtggcc gcgggagagt ccgccattct gcactgcacc   1500
gtgacctccc tcatccccgt gggacctatc cagtggttca gaggagccgg gccgcacgg   1560 gaactgatct ataaccagaa ggagggccat ttccccgcg tgaccaccgt gtccgagagc   1620
accaagaggg aaaacatgga cttcagcatt tcgatcagca acatcactcc cgctgacgcc   1680
gggacctact actgcgtgaa gttccggaaa ggaagcccgg acaccgagtt caaaagcgga   1740
gccggcaccg aactgtcggt ccgc                                           1764
```

<210> SEQ ID NO 72
<211> LENGTH: 588
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser

-continued

```
                180                 185                 190
Ser Ser Leu Gly Thr Gln Thr Tyr Ile Cys Asn Val Asn His Lys Pro
            195                 200                 205
Ser Asn Thr Lys Val Asp Lys Arg Val Glu Pro Lys Ser Cys Asp Lys
            210                 215                 220
Thr His Thr Cys Pro Pro Cys Pro Ala Pro Glu Leu Leu Gly Gly Pro
225                 230                 235                 240
Ser Val Phe Leu Phe Pro Pro Lys Pro Lys Asp Thr Leu Met Ile Ser
                245                 250                 255
Arg Thr Pro Glu Val Thr Cys Val Val Val Asp Val Ser His Glu Asp
            260                 265                 270
Pro Glu Val Lys Phe Asn Trp Tyr Val Asp Gly Val Glu Val His Asn
            275                 280                 285
Ala Lys Thr Lys Pro Arg Glu Glu Gln Tyr Asn Ser Thr Tyr Arg Val
            290                 295                 300
Val Ser Val Leu Thr Val Leu His Gln Asp Trp Leu Asn Gly Lys Glu
305                 310                 315                 320
Tyr Lys Cys Lys Val Ser Asn Lys Ala Leu Pro Ala Pro Ile Glu Lys
                325                 330                 335
Thr Ile Ser Lys Ala Lys Gly Gln Pro Arg Glu Pro Gln Val Tyr Thr
                340                 345                 350
Leu Pro Pro Ser Arg Glu Glu Met Thr Lys Asn Gln Val Ser Leu Thr
            355                 360                 365
Cys Leu Val Lys Gly Phe Tyr Pro Ser Asp Ile Ala Val Glu Trp Glu
370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
                405                 410                 415
Ser Arg Trp Gln Gln Gly Asn Val Phe Ser Cys Ser Val Met His Glu
            420                 425                 430
Ala Leu His Asn His Tyr Thr Gln Lys Ser Leu Ser Leu Ser Pro Gly
            435                 440                 445
Ala Gly Gly Gly Gly Ser Gly Gly Gly Gly Ser Gly Gly Gly Gly Ser
            450                 455                 460
Gly Gly Gly Gly Ser Gly Gly Gly Gly Ser Glu Glu Leu Gln Val
465                 470                 475                 480
Ile Gln Pro Asp Lys Ser Val Ser Val Ala Ala Gly Glu Ser Ala Ile
                485                 490                 495
Leu His Cys Thr Val Thr Ser Leu Ile Pro Val Gly Pro Ile Gln Trp
                500                 505                 510
Phe Arg Gly Ala Gly Pro Ala Arg Glu Leu Ile Tyr Asn Gln Lys Glu
            515                 520                 525
Gly His Phe Pro Arg Val Thr Thr Val Ser Glu Ser Thr Lys Arg Glu
            530                 535                 540
Asn Met Asp Phe Ser Ile Ser Ile Ser Asn Ile Thr Pro Ala Asp Ala
545                 550                 555                 560
Gly Thr Tyr Tyr Cys Val Lys Phe Arg Lys Gly Ser Pro Asp Thr Glu
                565                 570                 575
Phe Lys Ser Gly Ala Gly Thr Glu Leu Ser Val Arg
            580                 585
```

<210> SEQ ID NO 73

<211> LENGTH: 1344
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 73

```
caggtgcagc tgaagcagag cggccccggc ctggtgcagc ccagccagag cctgagcatc      60
acctgcaccg tgagcggctt cagcctgacc aactacggcg tgcactgggt gaggcagagc     120
cccggcaagt gcctggagtg gctgggcgtg atctggagcg gcggcaacac cgactacaac     180
acccccttca ccagcaggct gagcatcaac aaggacaaca gcaagagcca ggtgttcttc     240
aagatgaaca gcctgcagag caacgacacc gccatctact actgcgccag ggccctgacc     300
tactacgact acgagttcgc ctactggggc cagggcaccc tggtgaccgt gagcgccgcc     360
agcaccaagg gccccagcgt gttccccctg gcccccagca gcaagagcac cagcggcggc     420
accgccgccc tgggctgcct ggtgaaggac tacttccccg agcccgtgac cgtgagctgg     480
aacagcggcg ccctgaccag cggcgtgcac accttccccg ccgtgctgca gagcagcggc     540
ctgtacagcc tgagcagcgt ggtgaccgtg cccagcagca gcctgggcac ccagacctac     600
atctgcaacg tgaaccacaa gcccagcaac accaaggtgg acaagagggt ggagcccaag     660
agctgcgaca gacccacac tgcccccccc tgccccgccc ccgagctgct gggcggcccc     720
agcgtgttcc tgttcccccc caagcccaag gacaccctga tgatcagcag gacccccgag     780
gtgacctgcg tggtggtgga cgtgagccac gaggaccccg aggtgaagtt caactggtac     840
gtggacggcg tggaggtgca caacgccaag accaagccca gggaggagca gtacaacagc     900
acctacaggg tggtgagcgt gctgaccgtg ctgcaccagg actggctgaa cggcaaggag     960
tacaagtgca aggtgagcaa caaggccctg cccgccccca tcgagaagac catcagcaag    1020
gccaagggcc agcccaggga gccccaggtg tacaccctgc cccccagcag ggaggagatg    1080
accaagaacc aggtgagcct gacctgcctg gtgaagggct tctaccccag cgacatcgcc    1140
gtggagtggg agagcaacgg ccagcccgag aacaactaca agaccacccc ccccgtgctg    1200
gacagcgacg gcagcttctt cctgtacagc aagctgaccg tggacaagag caggtggcag    1260
cagggcaacg tgttcagctg cagcgtgatg cacgaggccc tgcacaacca ctacacccag    1320
aagagcctga gcctgagccc cggc                                           1344
```

<210> SEQ ID NO 74
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Cys Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe

```
                65                  70                  75                  80
Lys Met Asn Ser Leu Gln Ser Asn Asp Thr Ala Ile Tyr Tyr Cys Ala
                    85                  90                  95

Arg Ala Leu Thr Tyr Tyr Asp Tyr Glu Phe Ala Tyr Trp Gly Gln Gly
                100                 105                 110

Thr Leu Val Thr Val Ser Ala Ala Ser Thr Lys Gly Pro Ser Val Phe
                115                 120                 125

Pro Leu Ala Pro Ser Ser Lys Ser Thr Ser Gly Gly Thr Ala Ala Leu
            130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
            195                 200                 205

Ser Asn Thr Lys Val Asp Lys Arg Val Glu Pro Lys Ser Cys Asp Lys
        210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
            435                 440                 445

<210> SEQ ID NO 75
<211> LENGTH: 1344
<212> TYPE: DNA
<213> ORGANISM: Artificial Sequence
<220> FEATURE:
<223> OTHER INFORMATION: Description of Artificial Sequence: Synthetic
      polynucleotide
```

<400> SEQUENCE: 75

```
caggtgcagc tgaagcagag cggccccggc ctggtgcagc ccagccagag cctgagcatc    60
acctgcaccg tgagcggctt cagcctgacc aactacggcg tgcactgggt gaggcagagc   120
cccggcaagg gcctggagtg gctgggcgtg atctggagcg gcggcaacac cgactacaac   180
accccccttca ccagcaggct gagcatcaac aaggacaaca gcaagagcca ggtgttcttc   240
aagatgaaca gcctgcagag caacgacacc gccatctact actgcgccag ggccctgacc   300
tactacgact acgagttcgc ctactggggc tgcggcaccc tggtgaccgt gagcgccgcc   360
agcaccaagg gcccagcgt gttcccctg gcccccagca gcaagagcac cagcggcggc   420
accgccgccc tgggctgcct ggtgaaggac tacttccccg agccgtgac cgtgagctgg   480
aacagcggcg ccctgaccag cggcgtgcac accttccccg ccgtgctgca gagcagcggc   540
ctgtacagcc tgagcagcgt ggtgaccgtg cccagcagca gcctgggcac ccagacctac   600
atctgcaacg tgaaccacaa gcccagcaac accaaggtgg acaagagggt ggagcccaag   660
agctgcgaca gacccacac ctgcccccc tgccccgccc ccgagctgct gggcggcccc   720
agcgtgttcc tgttcccccc caagcccaag gacacccctga tgatcagcag gaccccggag   780
gtgacctgcg tggtggtgga cgtgagccac gaggaccccg aggtgaagtt caactggtac   840
gtggacggcg tggaggtgca caacgccaag accaagccca gggaggagca gtacaacagc   900
acctacaggg tggtgagcgt gctgaccgtg ctgcaccagg actggctgaa cggcaaggag   960
tacaagtgca aggtgagcaa caaggccctg cccgccccca tcgagaagac catcagcaag  1020
gccaagggcc agccccaggga gccccaggtg tacaccctgc ccccagcag ggaggagatg  1080
accaagaacc aggtgagcct gacctgcctg gtgaagggct tctacccag cgacatcgcc  1140
gtggagtggg agagcaacgg ccagcccgag aacaactaca agaccaccc ccccgtgctg  1200
gacagcgacg gcagcttctt cctgtacagc aagctgaccg tggacaagag caggtggcag  1260
cagggcaacg tgttcagctg cagcgtgatg cacgaggccc tgcacaacca ctacacccag  1320
aagagcctga gcctgagccc cggc                                         1344
```

<210> SEQ ID NO 76
<211> LENGTH: 448
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 76

```
Gln Val Gln Leu Lys Gln Ser Gly Pro Gly Leu Val Gln Pro Ser Gln
1               5                  10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Cys Gly
```

```
            100                 105                 110
Thr Leu Val Thr Val Ser Ala Ala Ser Thr Lys Gly Pro Ser Val Phe
            115                 120                 125

Pro Leu Ala Pro Ser Ser Lys Ser Thr Ser Gly Gly Thr Ala Ala Leu
            130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Arg Val Glu Pro Lys Ser Cys Asp Lys
            210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
            290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

<210> SEQ ID NO 77
<211> LENGTH: 1014
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 77
gacatcctgc tgacccagag ccccgtgatc ctgagcgtga gccccggcga gagggtgagc      60
ttcagctgca gggccagcca gagcatcggc accaacatcc actggtacca gcagaggacc     120
```

```
aacggcagcc ccaggctgct gatcaagtac gccagcgaga gcatcagcgg catccccagc    180
aggttcagcg gcagcggcag cggcaccgac ttcaccctga gcatcaacag cgtggagagc    240
gaggacatcg ccgactacta ctgccagcag aacaacaact ggcccaccac cttcggctgc    300
ggcaccaagc tggagctgaa gaggaccgtg gccgccccca gcgtgttcat cttcccccc     360 agcgacgagc agctgaagag cggcaccgcc agcgtggtgt gcctgctgaa caacttctac    420
cccagggagg ccaaggtgca gtggaaggtg acaacgccc tgcagagcgg caacagccag     480
gagagcgtga ccgagcagga cagcaaggac agcacctaca gcctgagcag cacccctgacc   540 ctgagcaagg ccgactacga gaagcacaag gtgtacgcct gcgaggtgac ccaccagggc    600
ctgagcagcc ccgtgaccaa gagcttcaac aggggcgagt gcggcggcgg cggcagcggc    660
ggcggcggca gcgaggagga gctgcaggtg atccagcccg acaagagcgt gagcgtggcc    720
gccggcgaga gcgccatcct gcactgcacc gtgaccagcc tgatccccgt gggccccatc    780
cagtggttca ggggcgccgg ccccgccagg gagctgatct acaaccagaa ggagggccac    840
ttccccaggg tgaccaccgt gagcgagagc accaagaggg agaacatgga cttcagcatc    900
agcatcagca acatcacccc cgccgacgcc ggcacctact actgcgtgaa gttcaggaag    960
ggcagccccg acaccgagtt caagagcggc gccggcaccg agctgagcgt gagg         1014
```

<210> SEQ ID NO 78
<211> LENGTH: 338
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

```
Asp Ile Leu Leu Thr Gln Ser Pro Val Ile Leu Ser Val Ser Pro Gly
1               5                   10                  15

Glu Arg Val Ser Phe Ser Cys Arg Ala Ser Gln Ser Ile Gly Thr Asn
            20                  25                  30

Ile His Trp Tyr Gln Gln Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Asn Asn Asn Trp Pro Thr
                85                  90                  95

Thr Phe Gly Cys Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
```

```
                195                 200                 205
Phe Asn Arg Gly Glu Cys Gly Gly Gly Gly Gly Gly Gly Ser
            210                 215                 220

Glu Glu Glu Leu Gln Val Ile Gln Pro Asp Lys Ser Val Ser Val Ala
225                 230                 235                 240

Ala Gly Glu Ser Ala Ile Leu His Cys Thr Val Ser Leu Ile Pro
                245                 250                 255

Val Gly Pro Ile Gln Trp Phe Arg Gly Ala Gly Pro Ala Arg Glu Leu
            260                 265                 270

Ile Tyr Asn Gln Lys Glu Gly His Phe Pro Arg Val Thr Thr Val Ser
                275                 280                 285

Glu Ser Thr Lys Arg Glu Asn Met Asp Phe Ser Ile Ser Ile Ser Asn
290                 295                 300

Ile Thr Pro Ala Asp Ala Gly Thr Tyr Tyr Cys Val Lys Phe Arg Lys
305                 310                 315                 320

Gly Ser Pro Asp Thr Glu Phe Lys Ser Gly Ala Gly Thr Glu Leu Ser
                325                 330                 335

Val Arg

<210> SEQ ID NO 79
<211> LENGTH: 1014
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 79
gacatcctgc tgacccagag ccccgtgatc ctgagcgtga gccccggcga gagggtgagc      60
ttcagctgca gggccagcca gagcatcggc accaacatcc actggtacca gcagaggacc     120
aacggctgcc ccaggctgct gatcaagtac gccagcgaga gcatcagcgg catccccagc     180
aggttcagcg gcagcggcag cggcaccgac ttcaccctga gcatcaacag cgtggagagc     240
gaggacatcg ccgactacta ctgccagcag aacaacaact ggcccaccac cttcggcgcc     300
ggcaccaagc tggagctgaa gaggaccgtg gccgccccca gcgtgttcat cttccccccc     360
agcgacgagc agctgaagag cggcaccgcc agcgtggtgt gcctgctgaa caacttctac     420
cccagggagg ccaaggtgca gtggaaggtg gacaacgccc tgcagagcgg caacagccag     480
gagagcgtga ccgagcagga cagcaaggac agcacctaca gcctgagcag cacccttgacc     540 ctgagcaagg ccgactacga aagcacaag gtgtacgcct gcgaggtgac ccaccagggc     600
ctgagcagcc ccgtgaccaa gagcttcaac aggggcgagt gcggcggcgg cggcagcggc     660
ggcggcggca gcgaggagga gctgcaggtg atccagcccg acaagagcgt gagcgtggcc     720
gccggcgaga gcgccatcct gcactgcacc gtgaccagcc tgatccccgt gggccccatc     780
cagtggttca gggcgccgg ccccgccagg gagctgatct acaaccagaa ggagggccac     840
ttccccaggg tgaccaccgt gagcgagagc accaagaggg agaacatgga cttcagcatc     900
agcatcagca acatcacccc cgccgacgcc ggcacctact actgcgtgaa gttcaggaag     960
ggcagccccg acaccgagtt caagagcggc gccggcaccg agctgagcgt gagg          1014

<210> SEQ ID NO 80
<211> LENGTH: 338
<212> TYPE: PRT
<213> ORGANISM: Artificial Sequence
<220> FEATURE:
```

<223> OTHER INFORMATION: Description of Artificial Sequence: Synthetic
       polypeptide

<400> SEQUENCE: 80

Asp Ile Leu Leu Thr Gln Ser Pro Val Ile Leu Ser Val Ser Pro Gly
1               5                   10                  15

Glu Arg Val Ser Phe Ser Cys Arg Ala Ser Gln Ser Ile Gly Thr Asn
            20                  25                  30

Ile His Trp Tyr Gln Gln Arg Thr Asn Gly Cys Pro Arg Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Asn Asn Asn Trp Pro Thr
                85                  90                  95

Thr Phe Gly Ala Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Gly Ser Gly Gly Gly Gly Ser
    210                 215                 220

Glu Glu Glu Leu Gln Val Ile Gln Pro Asp Lys Ser Val Ser Val Ala
225                 230                 235                 240

Ala Gly Glu Ser Ala Ile Leu His Cys Thr Val Thr Ser Leu Ile Pro
                245                 250                 255

Val Gly Pro Ile Gln Trp Phe Arg Gly Ala Gly Pro Ala Arg Glu Leu
            260                 265                 270

Ile Tyr Asn Gln Lys Glu Gly His Phe Pro Arg Val Thr Thr Val Ser
        275                 280                 285

Glu Ser Thr Lys Arg Glu Asn Met Asp Phe Ser Ile Ser Ile Ser Asn
    290                 295                 300

Ile Thr Pro Ala Asp Ala Gly Thr Tyr Tyr Cys Val Lys Phe Arg Lys
305                 310                 315                 320

Gly Ser Pro Asp Thr Glu Phe Lys Ser Gly Ala Gly Thr Glu Leu Ser
                325                 330                 335

Val Arg

<210> SEQ ID NO 81
<211> LENGTH: 452
<212> TYPE: PRT
<213> ORGANISM: Artificial Sequence
<220> FEATURE:
<223> OTHER INFORMATION: Description of Artificial Sequence: Synthetic
       polypeptide

<400> SEQUENCE: 81

```
Gln Val Gln Leu Lys Gln Ser Gly Pro Gly Leu Val Gln Pro Ser Gln
1               5                   10                  15
Ser Leu Ser Ile Thr Cys Thr Val Ser Gly Phe Ser Leu Thr Asn Tyr
            20                  25                  30
Gly Val His Trp Val Arg Gln Ser Pro Gly Lys Gly Leu Glu Trp Leu
        35                  40                  45
Gly Val Ile Trp Ser Gly Gly Asn Thr Asp Tyr Asn Thr Pro Phe Thr
    50                  55                  60
Ser Arg Leu Ser Ile Asn Lys Asp Asn Ser Lys Ser Gln Val Phe Phe
65                  70                  75                  80
Lys Met Asn Ser Leu Gln Ser Asn Asp Thr Ala Ile Tyr Tyr Cys Ala
                85                  90                  95
Arg Ala Leu Thr Tyr Tyr Asp Tyr Glu Phe Ala Tyr Trp Gly Gln Gly
            100                 105                 110
Thr Leu Val Thr Val Ser Ala Ala Ser Thr Lys Gly Pro Ser Val Phe
        115                 120                 125
Pro Leu Ala Pro Ser Ser Lys Ser Thr Ser Gly Gly Thr Ala Ala Leu
    130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
            180                 185                 190
Ser Ser Leu Gly Thr Gln Thr Tyr Ile Cys Asn Val Asn His Lys Pro
        195                 200                 205
Ser Asn Thr Lys Val Asp Lys Arg Val Glu Pro Lys Ser Pro Lys Ser
    210                 215                 220
Cys Asp Lys Thr His Thr Cys Pro Pro Cys Pro Ala Pro Glu Leu Leu
225                 230                 235                 240
Gly Gly Pro Ser Val Phe Leu Phe Pro Pro Lys Pro Lys Asp Thr Leu
                245                 250                 255
Met Ile Ser Arg Thr Pro Glu Val Thr Cys Val Val Val Asp Val Ser
            260                 265                 270
His Glu Asp Pro Glu Val Lys Phe Asn Trp Tyr Val Asp Gly Val Glu
        275                 280                 285
Val His Asn Ala Lys Thr Lys Pro Arg Glu Glu Gln Tyr Asn Ser Thr
    290                 295                 300
Tyr Arg Val Val Ser Val Leu Thr Val Leu His Gln Asp Trp Leu Asn
305                 310                 315                 320
Gly Lys Glu Tyr Lys Cys Lys Val Ser Asn Lys Ala Leu Pro Ala Pro
                325                 330                 335
Ile Glu Lys Thr Ile Ser Lys Ala Lys Gly Gln Pro Arg Glu Pro Gln
            340                 345                 350
Val Tyr Thr Leu Pro Pro Ser Arg Asp Glu Leu Thr Lys Asn Gln Val
        355                 360                 365
Ser Leu Thr Cys Leu Val Lys Gly Phe Tyr Pro Ser Asp Ile Ala Val
    370                 375                 380
Glu Trp Glu Ser Asn Gly Gln Pro Glu Asn Asn Tyr Lys Thr Thr Pro
385                 390                 395                 400
Pro Val Leu Asp Ser Asp Gly Ser Phe Phe Leu Tyr Ser Lys Leu Thr
                405                 410                 415
```

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450

<210> SEQ ID NO 82
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

Asp Ile Leu Leu Thr Gln Ser Pro Val Ile Leu Ser Val Ser Pro Gly
1               5                   10                  15

Glu Arg Val Ser Phe Ser Cys Arg Ala Ser Gln Ser Ile Gly Thr Asn
            20                  25                  30

Ile His Trp Tyr Gln Gln Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Asn Asn Trp Pro Thr
                85                  90                  95

Thr Phe Gly Ala Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Ala
    210

<210> SEQ ID NO 83
<211> LENGTH: 445
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Val Ser Ser Gly
            20                  25                  30

-continued

Asp Tyr Tyr Trp Thr Trp Ile Arg Gln Ser Pro Gly Lys Gly Leu Glu
         35                  40                  45

Trp Ile Gly His Ile Tyr Tyr Ser Gly Asn Thr Asn Tyr Asn Pro Ser
 50                  55                  60

Leu Lys Ser Arg Leu Thr Ile Ser Ile Asp Thr Ser Lys Thr Gln Phe
 65                  70                  75                  80

Ser Leu Lys Leu Ser Ser Val Thr Ala Ala Asp Thr Ala Ile Tyr Tyr
                 85                  90                  95

Cys Val Arg Asp Arg Val Thr Gly Ala Phe Asp Ile Trp Gly Gln Gly
             100                 105                 110

Thr Met Val Thr Val Ser Ser Ala Ser Thr Lys Gly Pro Ser Val Phe
             115                 120                 125

Pro Leu Ala Pro Cys Ser Arg Ser Thr Ser Glu Ser Thr Ala Ala Leu
         130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                 165                 170                 175

Gln Ser Ser Gly Leu Tyr Ser Leu Ser Ser Val Val Thr Val Pro Ser
             180                 185                 190

Ser Asn Phe Gly Thr Gln Thr Tyr Thr Cys Asn Val Asp His Lys Pro
         195                 200                 205

Ser Asn Thr Lys Val Asp Lys Thr Val Glu Arg Lys Cys Cys Val Glu
     210                 215                 220

Cys Pro Pro Cys Pro Ala Pro Pro Val Ala Gly Pro Ser Val Phe Leu
225                 230                 235                 240

Phe Pro Pro Lys Pro Lys Asp Thr Leu Met Ile Ser Arg Thr Pro Glu
                 245                 250                 255

Val Thr Cys Val Val Val Asp Val Ser His Glu Asp Pro Glu Val Gln
             260                 265                 270

Phe Asn Trp Tyr Val Asp Gly Val Glu Val His Asn Ala Lys Thr Lys
         275                 280                 285

Pro Arg Glu Glu Gln Phe Asn Ser Thr Phe Arg Val Val Ser Val Leu
     290                 295                 300

Thr Val Val His Gln Asp Trp Leu Asn Gly Lys Glu Tyr Lys Cys Lys
305                 310                 315                 320

Val Ser Asn Lys Gly Leu Pro Ala Pro Ile Glu Lys Thr Ile Ser Lys
                 325                 330                 335

Thr Lys Gly Gln Pro Arg Glu Pro Gln Val Tyr Thr Leu Pro Pro Ser
             340                 345                 350

Arg Glu Glu Met Thr Lys Asn Gln Val Ser Leu Thr Cys Leu Val Lys
         355                 360                 365

Gly Phe Tyr Pro Ser Asp Ile Ala Val Glu Trp Glu Ser Asn Gly Gln
     370                 375                 380

Pro Glu Asn Asn Tyr Lys Thr Thr Pro Pro Met Leu Asp Ser Asp Gly
385                 390                 395                 400

Ser Phe Phe Leu Tyr Ser Lys Leu Thr Val Asp Lys Ser Arg Trp Gln
                 405                 410                 415

Gln Gly Asn Val Phe Ser Cys Ser Val Met His Glu Ala Leu His Asn
             420                 425                 430

His Tyr Thr Gln Lys Ser Leu Ser Leu Ser Pro Gly Lys
         435                 440                 445

```
<210> SEQ ID NO 84
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Phe Cys Gln His Phe Asp His Leu Pro Leu
                85                  90                  95

Ala Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 85
<211> LENGTH: 222
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 85

Gln Val Gln Leu Gln Gln Ser Gly Ala Glu Val Lys Lys Pro Gly Ser
1               5                   10                  15

Ser Val Lys Val Ser Cys Lys Ala Ser Gly Tyr Thr Phe Thr Asn Tyr
            20                  25                  30

Tyr Ile Tyr Trp Val Arg Gln Ala Pro Gly Gln Gly Leu Glu Trp Ile
        35                  40                  45

Gly Gly Ile Asn Pro Thr Ser Gly Gly Ser Asn Phe Asn Glu Lys Phe
    50                  55                  60

Lys Thr Arg Val Thr Ile Thr Ala Asp Glu Ser Ser Thr Thr Ala Tyr
65                  70                  75                  80
```

```
Met Glu Leu Ser Ser Leu Arg Ser Glu Asp Thr Ala Phe Tyr Phe Cys
                85                  90                  95

Thr Arg Gln Gly Leu Trp Phe Asp Ser Asp Gly Arg Gly Phe Asp Phe
            100                 105                 110

Trp Gly Gln Gly Thr Thr Val Thr Val Ser Ser Ala Ser Thr Lys Gly
            115                 120                 125

Pro Ser Val Phe Pro Leu Ala Pro Ser Ser Lys Ser Thr Ser Gly Gly
            130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
            195                 200                 205

Asn His Lys Pro Ser Asn Thr Lys Val Asp Lys Lys Val Pro
            210                 215                 220

<210> SEQ ID NO 86
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 86

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Asn Ile Val His Ser
            20                  25                  30

Asn Gly Asn Thr Tyr Leu Asp Trp Tyr Gln Gln Thr Pro Gly Lys Ala
        35                  40                  45

Pro Lys Leu Leu Ile Tyr Lys Val Ser Asn Arg Phe Ser Gly Val Pro
    50                  55                  60

Ser Arg Phe Ser Gly Ser Gly Ser Gly Thr Asp Phe Thr Phe Thr Ile
65                  70                  75                  80

Ser Ser Leu Gln Pro Glu Asp Ile Ala Thr Tyr Tyr Cys Phe Gln Tyr
                85                  90                  95

Ser His Val Pro Trp Thr Phe Gly Gln Gly Thr Lys Leu Gln Ile Thr
            100                 105                 110

Arg Glu Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys
            210                 215
```

<210> SEQ ID NO 87
<211> LENGTH: 223
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser His
            20                  25                  30

Trp Met His Trp Val Arg Gln Ala Pro Gly Gln Gly Leu Glu Trp Ile
        35                  40                  45

Gly Glu Phe Asn Pro Ser Asn Gly Arg Thr Asn Tyr Asn Glu Lys Phe
    50                  55                  60

Lys Ser Lys Ala Thr Met Thr Val Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Ser Arg Asp Tyr Asp Tyr Asp Gly Arg Tyr Phe Asp Tyr Trp Gly
            100                 105                 110

Gln Gly Thr Leu Val Thr Val Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser
    210                 215                 220

<210> SEQ ID NO 88
<211> LENGTH: 212
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Ser Val Thr Tyr Met
            20                  25                  30

Tyr Trp Tyr Gln Gln Lys Pro Gly Lys Ala Pro Lys Leu Leu Ile Tyr
        35                  40                  45

Asp Thr Ser Asn Leu Ala Ser Gly Val Pro Ser Arg Phe Ser Gly Ser
    50                  55                  60

Gly Ser Gly Thr Asp Tyr Thr Phe Thr Ile Ser Ser Leu Gln Pro Glu
65                  70                  75                  80

```
Asp Ile Ala Thr Tyr Tyr Cys Gln Gln Trp Ser Ser His Ile Phe Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu
    210

<210> SEQ ID NO 89
<211> LENGTH: 452
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 89

Glu Val Gln Leu Gln Gln Pro Gly Ser Glu Leu Val Arg Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Asn Ile Tyr Pro Gly Ser Arg Ser Thr Asn Tyr Asp Glu Lys Phe
    50                  55                  60

Lys Ser Lys Ala Thr Leu Thr Val Asp Thr Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Thr Arg Asn Gly Asp Tyr Tyr Val Ser Ser Gly Asp Ala Met Asp Tyr
            100                 105                 110

Trp Gly Gln Gly Thr Ser Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Arg Val Glu Pro Lys
```

```
                  210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly
    450

<210> SEQ ID NO 90
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 90

Asp Ile Gln Met Thr Gln Thr Thr Ser Ser Leu Ser Ala Ser Leu Gly
1               5                   10                  15

Asp Arg Val Thr Ile Ser Cys Arg Thr Ser Gln Asp Ile Gly Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Phe Ser Leu Thr Ile Asn Asn Val Glu Gln
65                  70                  75                  80

Glu Asp Val Ala Thr Tyr Phe Cys Gln His Tyr Asn Thr Val Pro Pro
                85                  90                  95

Thr Phe Gly Gly Gly Thr Lys Leu Glu Ile Lys Arg Thr Val Ala Ala
            100                 105                 110
```

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 91
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 91

Gln Val Gln Leu Gln Gln Pro Gly Ala Glu Leu Val Glu Pro Gly Gly
1               5                   10                  15

Ser Val Lys Leu Ser Cys Lys Ala Ser Gly Tyr Thr Phe Thr Ser His
            20                  25                  30

Trp Met His Trp Val Lys Gln Arg Pro Gly Gln Gly Leu Glu Trp Ile
        35                  40                  45

Gly Glu Ile Asn Pro Ser Ser Gly Arg Asn Asn Tyr Asn Glu Lys Phe
    50                  55                  60

Lys Ser Lys Ala Thr Leu Thr Val Asp Lys Ser Ser Ser Thr Ala Tyr
65                  70                  75                  80

Met Gln Phe Ser Ser Leu Thr Ser Glu Asp Ser Ala Val Tyr Tyr Cys
                85                  90                  95

Val Arg Tyr Tyr Gly Tyr Asp Glu Ala Met Asp Tyr Trp Gly Gln Gly
            100                 105                 110

Thr Ser Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

```
Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
            290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
            370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

<210> SEQ ID NO 92
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 92

Asp Ile Val Met Thr Gln Ala Ala Phe Ser Asn Pro Val Thr Leu Gly
1               5                   10                  15

Thr Ser Ala Ser Ile Ser Cys Arg Ser Ser Lys Ser Leu Leu His Ser
            20                  25                  30

Asn Gly Ile Thr Tyr Leu Tyr Trp Tyr Leu Gln Lys Pro Gly Gln Ser
        35                  40                  45

Pro Gln Leu Leu Ile Tyr Gln Met Ser Asn Leu Ala Ser Gly Val Pro
    50                  55                  60

Asp Arg Phe Ser Ser Ser Gly Ser Gly Thr Asp Phe Thr Leu Arg Ile
65                  70                  75                  80

Ser Arg Val Glu Ala Glu Asp Val Gly Val Tyr Tyr Cys Ala Gln Asn
                85                  90                  95

Leu Glu Leu Pro Tyr Thr Phe Gly Gly Gly Thr Lys Leu Glu Ile Lys
            100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
```

```
                    165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
        210                 215

<210> SEQ ID NO 93
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 93

Gln Val Gln Leu Val Gln Ser Gly Ala Glu Val Lys Lys Pro Gly Ser
1               5                   10                  15

Ser Val Lys Val Ser Cys Lys Ala Ser Gly Phe Thr Phe Thr Asp Tyr
            20                  25                  30

Lys Ile His Trp Val Arg Gln Ala Pro Gly Gln Gly Leu Glu Trp Met
        35                  40                  45

Gly Tyr Phe Asn Pro Asn Ser Gly Tyr Ser Thr Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Ser Pro Gly Gly Tyr Tyr Val Met Asp Ala Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300
```

```
Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
            370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
                435                 440                 445

Gly

<210> SEQ ID NO 94
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 94

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Asn Asn Tyr
            20                  25                  30

Leu Asn Trp Tyr Gln Gln Lys Pro Gly Lys Ala Pro Lys Arg Leu Ile
        35                  40                  45

Tyr Asn Thr Asn Asn Leu Gln Thr Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Phe Pro Thr
                85                  90                  95

Phe Gly Gln Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205
```

-continued

```
Asn Arg Gly Glu Cys
    210

<210> SEQ ID NO 95
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 95

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Asp Tyr Tyr Trp Ser Trp Ile Arg Gln Pro Pro Gly Lys Gly Leu Glu
        35                  40                  45

Trp Ile Gly Tyr Ile Tyr Tyr Ser Gly Ser Thr Asp Tyr Asn Pro Ser
    50                  55                  60

Leu Lys Ser Arg Val Thr Met Ser Val Asp Thr Ser Lys Asn Gln Phe
65                  70                  75                  80

Ser Leu Lys Val Asn Ser Val Thr Ala Ala Asp Thr Ala Val Tyr Tyr
                85                  90                  95

Cys Ala Arg Val Ser Ile Phe Gly Val Gly Thr Phe Asp Tyr Trp Gly
            100                 105                 110

Gln Gly Thr Leu Val Thr Val Ser Ser Ala Ser Thr Lys Gly Pro Ser
        115                 120                 125

Val Leu Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350
```

```
Tyr Thr Leu Pro Pro Ser Arg Glu Glu Met Thr Lys Asn Gln Val Ser
            355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
            435                 440                 445

Pro Gly Lys
    450

<210> SEQ ID NO 96
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 96

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys His Gln Tyr Gly Ser Thr Pro Leu
                85                  90                  95

Thr Phe Gly Gly Gly Thr Lys Ala Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 97
<211> LENGTH: 451
<212> TYPE: PRT
```

<213> ORGANISM: Artificial Sequence
<220> FEATURE:
<223> OTHER INFORMATION: Description of Artificial Sequence: Synthetic polypeptide

<400> SEQUENCE: 97

```
Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Arg Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Thr Tyr Tyr Gly Gly Asp Trp Tyr Phe Asn Val Trp Gly
            100                 105                 110

Ala Gly Thr Thr Val Thr Val Ser Ala Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380
```

```
Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
            405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Lys
    450
```

<210> SEQ ID NO 98
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 98

```
Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Ile
            20                  25                  30

His Trp Phe Gln Gln Lys Pro Gly Ser Ser Pro Lys Pro Trp Ile Tyr
        35                  40                  45

Ala Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Thr Ser Asn Pro Pro Thr
                85                  90                  95

Phe Gly Gly Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210
```

<210> SEQ ID NO 99
<211> LENGTH: 222
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 99

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asn Asp Tyr
            20                  25                  30

Ala Met His Trp Val Arg Gln Ala Pro Gly Lys Gly Leu Glu Trp Val
        35                  40                  45

Ser Thr Ile Ser Trp Asn Ser Gly Ser Ile Gly Tyr Ala Asp Ser Val
    50                  55                  60

Lys Gly Arg Phe Thr Ile Ser Arg Asp Asn Ala Lys Lys Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Ile Gln Tyr Gly Asn Tyr Tyr Tyr Gly Met Asp Val Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Gly Ser Ser Lys Ser Thr Ser Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro
    210                 215                 220

<210> SEQ ID NO 100
<211> LENGTH: 211
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 100

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Ile
                85                  90                  95

Thr Phe Gly Gln Gly Thr Arg Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

```
Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg
    210

<210> SEQ ID NO 101
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 101

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Tyr Ser
            20                  25                  30

Trp Ile Asn Trp Val Arg Gln Ala Pro Gly Gln Gly Leu Glu Trp Met
        35                  40                  45

Gly Arg Ile Phe Pro Gly Asp Gly Asp Thr Asp Tyr Asn Gly Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Val Phe Asp Gly Tyr Trp Leu Val Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
```

```
                    275                 280                 285
Ala Lys Thr Lys Pro Arg Glu Glu Gln Tyr Asn Ser Thr Tyr Arg Val
            290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
                355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 102
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 102

Asp Ile Val Met Thr Gln Thr Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Gly Ile Thr Tyr Leu Tyr Trp Tyr Leu Gln Lys Pro Gly Gln Ser
        35                  40                  45

Pro Gln Leu Leu Ile Tyr Gln Met Ser Asn Leu Val Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Tyr Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
```

-continued

```
                180                 185                 190
Lys His Lys Val Tyr Ala Cys Glu Val Thr His Gln Gly Leu Ser Ser
            195                 200                 205

Pro Val Thr Lys Ser Phe Asn Arg Gly Glu Cys
        210                 215

<210> SEQ ID NO 103
<211> LENGTH: 443
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 103

Gln Ala Tyr Leu Gln Gln Ser Gly Ala Glu Leu Val Arg Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Arg Gln Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Val Val Tyr Tyr Ser Asn Ser Tyr Trp Tyr Phe Asp Val Trp
            100                 105                 110

Gly Thr Gly Thr Thr Val Thr Val Ser Ala Pro Ser Val Tyr Pro Leu
        115                 120                 125

Ala Pro Val Cys Gly Asp Thr Thr Gly Ser Ser Val Thr Leu Gly Cys
    130                 135                 140

Leu Val Lys Gly Tyr Phe Pro Glu Pro Val Thr Leu Thr Trp Asn Ser
145                 150                 155                 160

Gly Ser Leu Ser Ser Gly Val His Thr Phe Pro Ala Val Leu Gln Ser
                165                 170                 175

Asp Leu Tyr Thr Leu Ser Ser Ser Val Thr Val Thr Ser Ser Thr Trp
            180                 185                 190

Pro Ser Gln Ser Ile Thr Cys Asn Val Ala His Pro Ala Ser Ser Thr
        195                 200                 205

Lys Val Asp Lys Lys Ile Glu Pro Arg Gly Pro Thr Ile Lys Pro Cys
    210                 215                 220

Pro Pro Cys Lys Cys Pro Ala Pro Asn Leu Leu Gly Gly Pro Ser Val
225                 230                 235                 240

Phe Ile Phe Pro Pro Lys Ile Lys Asp Val Leu Met Ile Ser Leu Ser
                245                 250                 255

Pro Ile Val Thr Cys Val Val Val Asp Val Ser Glu Asp Asp Pro Asp
            260                 265                 270

Val Gln Ile Ser Trp Phe Val Asn Asn Val Glu Val His Thr Ala Gln
        275                 280                 285

Thr Gln Thr His Arg Glu Asp Tyr Asn Ser Thr Leu Arg Val Val Ser
    290                 295                 300

Ala Leu Pro Ile Gln His Gln Asp Trp Met Ser Gly Lys Glu Phe Lys
305                 310                 315                 320
```

```
Cys Lys Val Asn Asn Lys Asp Leu Pro Ala Pro Ile Glu Arg Thr Ile
                325                 330                 335

Ser Lys Pro Lys Gly Ser Val Arg Ala Pro Gln Val Tyr Val Leu Pro
            340                 345                 350

Pro Pro Glu Glu Glu Met Thr Lys Lys Gln Val Thr Leu Thr Cys Met
            355                 360                 365

Val Thr Asp Phe Met Pro Glu Asp Ile Tyr Val Glu Trp Thr Asn Asn
370                 375                 380

Gly Lys Thr Glu Leu Asn Tyr Lys Asn Thr Glu Pro Val Leu Asp Ser
385                 390                 395                 400

Asp Gly Ser Tyr Phe Met Tyr Ser Lys Leu Arg Val Glu Lys Lys Asn
                405                 410                 415

Trp Val Glu Arg Asn Ser Tyr Ser Cys Ser Val Val His Glu Gly Leu
            420                 425                 430

His Asn His His Thr Thr Lys Ser Phe Ser Arg
            435                 440

<210> SEQ ID NO 104
<211> LENGTH: 209
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 104

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Met
            20                  25                  30

His Trp Tyr Gln Gln Lys Pro Gly Ser Ser Pro Lys Pro Trp Ile Tyr
        35                  40                  45

Ala Pro Ser Asn Leu Ala Ser Gly Val Pro Ala Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Ser Phe Asn Pro Pro Thr
                85                  90                  95

Phe Gly Ala Gly Thr Lys Leu Glu Leu Lys Arg Ala Asp Ala Ala Pro
            100                 105                 110

Thr Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn

<210> SEQ ID NO 105
<211> LENGTH: 450
```

<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 105

| Glu | Val | Gln | Leu | Val | Gln | Ser | Gly | Ala | Glu | Val | Lys | Lys | Pro | Gly | Glu |
|---|---|---|---|---|---|---|---|---|---|---|---|---|---|---|---|
| 1 | | | | 5 | | | | | 10 | | | | | 15 | |

| Ser | Leu | Lys | Ile | Ser | Cys | Lys | Gly | Ser | Gly | Arg | Thr | Phe | Thr | Ser | Tyr |
|---|---|---|---|---|---|---|---|---|---|---|---|---|---|---|---|
| | | | 20 | | | | | 25 | | | | | 30 | | |

| Asn | Met | His | Trp | Val | Arg | Gln | Met | Pro | Gly | Lys | Gly | Leu | Glu | Trp | Met |
|---|---|---|---|---|---|---|---|---|---|---|---|---|---|---|---|
| | | 35 | | | | | 40 | | | | | 45 | | | |

| Gly | Ala | Ile | Tyr | Pro | Leu | Thr | Gly | Asp | Thr | Ser | Tyr | Asn | Gln | Lys | Ser |
|---|---|---|---|---|---|---|---|---|---|---|---|---|---|---|---|
| | 50 | | | | | 55 | | | | | 60 | | | | |

| Lys | Leu | Gln | Val | Thr | Ile | Ser | Ala | Asp | Lys | Ser | Ile | Ser | Thr | Ala | Tyr |
|---|---|---|---|---|---|---|---|---|---|---|---|---|---|---|---|
| 65 | | | | | 70 | | | | | 75 | | | | | 80 |

| Leu | Gln | Trp | Ser | Ser | Leu | Lys | Ala | Ser | Asp | Thr | Ala | Met | Tyr | Tyr | Cys |
|---|---|---|---|---|---|---|---|---|---|---|---|---|---|---|---|
| | | | | 85 | | | | | 90 | | | | | 95 | |

| Ala | Arg | Ser | Thr | Tyr | Val | Gly | Gly | Asp | Trp | Gln | Phe | Asp | Val | Trp | Gly |
|---|---|---|---|---|---|---|---|---|---|---|---|---|---|---|---|
| | | | 100 | | | | | 105 | | | | | 110 | | |

| Lys | Gly | Thr | Thr | Val | Thr | Val | Ser | Ser | Ala | Ser | Thr | Lys | Gly | Pro | Ser |
|---|---|---|---|---|---|---|---|---|---|---|---|---|---|---|---|
| | | 115 | | | | | 120 | | | | | 125 | | | |

| Val | Phe | Pro | Leu | Ala | Pro | Ser | Ser | Lys | Ser | Thr | Ser | Gly | Gly | Thr | Ala |
|---|---|---|---|---|---|---|---|---|---|---|---|---|---|---|---|
| | 130 | | | | | 135 | | | | | 140 | | | | |

| Ala | Leu | Gly | Cys | Leu | Val | Lys | Asp | Tyr | Phe | Pro | Glu | Pro | Val | Thr | Val |
|---|---|---|---|---|---|---|---|---|---|---|---|---|---|---|---|
| 145 | | | | | 150 | | | | | 155 | | | | | 160 |

| Ser | Trp | Asn | Ser | Gly | Ala | Leu | Thr | Ser | Gly | Val | His | Thr | Phe | Pro | Ala |
|---|---|---|---|---|---|---|---|---|---|---|---|---|---|---|---|
| | | | | 165 | | | | | 170 | | | | | 175 | |

| Val | Leu | Gln | Ser | Ser | Gly | Leu | Tyr | Ser | Leu | Ser | Ser | Val | Val | Thr | Val |
|---|---|---|---|---|---|---|---|---|---|---|---|---|---|---|---|
| | | | 180 | | | | | 185 | | | | | 190 | | |

| Pro | Ser | Ser | Ser | Leu | Gly | Thr | Gln | Thr | Tyr | Ile | Cys | Asn | Val | Asn | His |
|---|---|---|---|---|---|---|---|---|---|---|---|---|---|---|---|
| | | 195 | | | | | 200 | | | | | 205 | | | |

| Lys | Pro | Ser | Asn | Thr | Lys | Val | Asp | Lys | Lys | Val | Glu | Pro | Lys | Ser | Cys |
|---|---|---|---|---|---|---|---|---|---|---|---|---|---|---|---|
| | 210 | | | | | 215 | | | | | 220 | | | | |

| Asp | Lys | Thr | His | Thr | Cys | Pro | Pro | Cys | Pro | Ala | Pro | Glu | Leu | Leu | Gly |
|---|---|---|---|---|---|---|---|---|---|---|---|---|---|---|---|
| 225 | | | | | 230 | | | | | 235 | | | | | 240 |

| Gly | Pro | Ser | Val | Phe | Leu | Phe | Pro | Pro | Lys | Ile | Lys | Asp | Thr | Leu | Met |
|---|---|---|---|---|---|---|---|---|---|---|---|---|---|---|---|
| | | | | 245 | | | | | 250 | | | | | 255 | |

| Ile | Ser | Arg | Thr | Pro | Glu | Val | Thr | Cys | Val | Val | Val | Asp | Val | Ser | His |
|---|---|---|---|---|---|---|---|---|---|---|---|---|---|---|---|
| | | | 260 | | | | | 265 | | | | | 270 | | |

| Glu | Asp | Pro | Glu | Val | Lys | Phe | Asn | Trp | Tyr | Val | Asp | Gly | Val | Glu | Val |
|---|---|---|---|---|---|---|---|---|---|---|---|---|---|---|---|
| | | 275 | | | | | 280 | | | | | 285 | | | |

| His | Asn | Ala | Lys | Thr | Lys | Pro | Arg | Glu | Glu | Gln | Tyr | Asn | Ser | Thr | Tyr |
|---|---|---|---|---|---|---|---|---|---|---|---|---|---|---|---|
| | 290 | | | | | 295 | | | | | 300 | | | | |

| Arg | Val | Val | Ser | Val | Leu | Thr | Val | Leu | His | Gln | Asp | Trp | Leu | Asn | Gly |
|---|---|---|---|---|---|---|---|---|---|---|---|---|---|---|---|
| 305 | | | | | 310 | | | | | 315 | | | | | 320 |

| Lys | Glu | Tyr | Lys | Cys | Lys | Val | Ser | Asn | Lys | Ala | Leu | Pro | Ala | Pro | Ile |
|---|---|---|---|---|---|---|---|---|---|---|---|---|---|---|---|
| | | | | 325 | | | | | 330 | | | | | 335 | |

| Glu | Lys | Thr | Ile | Ser | Lys | Gln | Lys | Gly | Gln | Pro | Arg | Glu | Pro | Gln | Val |
|---|---|---|---|---|---|---|---|---|---|---|---|---|---|---|---|
| | | | 340 | | | | | 345 | | | | | 350 | | |

| Tyr | Thr | Leu | Pro | Pro | Ser | Arg | Asp | Glu | Leu | Thr | Lys | Asn | Gln | Val | Ser |
|---|---|---|---|---|---|---|---|---|---|---|---|---|---|---|---|
| | | 355 | | | | | 360 | | | | | 365 | | | |

| Leu | Thr | Cys | Leu | Val | Lys | Gly | Phe | Tyr | Pro | Ser | Asp | Ile | Ala | Val | Glu |
|---|---|---|---|---|---|---|---|---|---|---|---|---|---|---|---|
| | 370 | | | | | 375 | | | | | 380 | | | | |

```
Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly
    450

<210> SEQ ID NO 106
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 106

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Ser Val Pro Tyr Ile
            20                  25                  30

His Trp Tyr Gln Gln Lys Pro Gly Gln Ala Pro Arg Leu Leu Ile Tyr
        35                  40                  45

Ala Thr Ser Ala Leu Ala Ser Gly Ile Pro Asp Arg Phe Ser Gly Ser
    50                  55                  60

Gly Ser Gly Thr Asp Phe Thr Leu Thr Ile Ser Arg Leu Glu Pro Glu
65                  70                  75                  80

Asp Phe Ala Val Tyr Tyr Cys Gln Gln Trp Leu Ser Asn Pro Pro Thr
                85                  90                  95

Phe Gly Gln Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 107
<211> LENGTH: 452
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 107
```

-continued

```
Glu Val Gln Leu Val Glu Ser Gly Gly Leu Val Gln Pro Gly Gly
1               5                   10                  15

Ser Leu Arg Leu Ser Cys Ala Ala Ser Gly Tyr Thr Phe Thr Ser Tyr
            20                  25                  30

Asn Met His Trp Val Arg Gln Ala Pro Gly Lys Gly Leu Glu Trp Val
        35                  40                  45

Gly Ala Ile Tyr Pro Gly Asn Gly Asp Thr Ser Tyr Asn Gln Lys Phe
    50                  55                  60

Lys Gly Arg Phe Thr Ile Ser Val Asp Lys Ser Lys Asn Thr Leu Tyr
65              70                  75                  80

Leu Gln Met Asn Ser Leu Arg Ala Glu Asp Thr Ala Val Tyr Tyr Cys
                85                  90                  95

Ala Arg Val Val Tyr Tyr Ser Asn Ser Tyr Trp Tyr Phe Asp Val Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
            165                 170                 175

Ala Val Leu Gln Ser Ser Gly Leu Tyr Ser Leu Ser Ser Val Val Thr
        180                 185                 190

Val Pro Ser Ser Ser Leu Gly Thr Gln Thr Tyr Ile Cys Asn Val Asn
    195                 200                 205

His Lys Pro Ser Asn Thr Lys Val Asp Lys Lys Val Glu Pro Lys Ser
210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
            245                 250                 255

Met Ile Ser Arg Thr Pro Glu Val Thr Cys Val Val Val Asp Val Ser
        260                 265                 270

His Glu Asp Pro Glu Val Lys Phe Asn Trp Tyr Val Asp Gly Val Glu
    275                 280                 285

Val His Asn Ala Lys Thr Lys Pro Arg Glu Glu Gln Tyr Asn Ser Thr
290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
            325                 330                 335

Ile Glu Lys Thr Ile Ser Lys Ala Lys Gly Gln Pro Arg Glu Pro Gln
        340                 345                 350

Val Tyr Thr Leu Pro Pro Ser Arg Glu Glu Met Thr Lys Asn Gln Val
    355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
            405                 410                 415
```

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
            435                 440                 445

Ser Pro Gly Lys
    450

<210> SEQ ID NO 108
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 108

Asp Ile Gln Met Thr Gln Ser Pro Ser Ser Leu Ser Ala Ser Val Gly
1               5                   10                  15

Asp Arg Val Thr Ile Thr Cys Arg Ala Ser Ser Ser Val Ser Tyr Met
            20                  25                  30

His Trp Tyr Gln Gln Lys Pro Gly Lys Ala Pro Lys Pro Leu Ile Tyr
        35                  40                  45

Ala Pro Ser Asn Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Ser Phe Asn Pro Pro Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 109
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 109

Gln Ala Tyr Leu Gln Gln Ser Gly Ala Glu Leu Val Arg Pro Gly Ala
1               5                   10                  15

Ser Val Lys Met Ser Cys Lys Ala Ser Gly Tyr Thr Phe Thr Ser Tyr
            20                  25                  30

```
Asn Met His Trp Val Lys Gln Thr Pro Arg Gln Gly Leu Glu Trp Ile
         35                  40                  45

Gly Ala Ile Tyr Pro Gly Asn Gly Asp Thr Ser Tyr Asn Gln Lys Phe
 50                  55                  60

Lys Gly Lys Ala Thr Leu Thr Val Asp Lys Ser Ser Ser Thr Ala Tyr
 65                  70                  75                  80

Met Gln Leu Ser Ser Leu Thr Ser Glu Asp Ser Ala Val Tyr Phe Cys
                 85                  90                  95

Ala Arg Val Val Tyr Tyr Ser Asn Ser Tyr Trp Tyr Phe Asp Val Trp
            100                 105                 110

Gly Thr Gly Thr Thr Val Thr Val Ser Gly Pro Ser Val Phe Pro Leu
        115                 120                 125

Ala Pro Ser Ser Lys Ser Thr Ser Gly Gly Thr Ala Ala Leu Gly Cys
        130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Ala Glu Pro Lys Ser Cys Asp Lys Thr His
        210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
        290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445
```

-continued

```
<210> SEQ ID NO 110
<211> LENGTH: 210
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 110

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Met
            20                  25                  30

His Trp Tyr Gln Gln Lys Pro Gly Ser Ser Pro Lys Pro Trp Ile Tyr
        35                  40                  45

Ala Pro Ser Asn Leu Ala Ser Gly Val Pro Ala Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Ser Phe Asn Pro Pro Thr
                85                  90                  95

Phe Gly Ala Gly Thr Lys Leu Glu Leu Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg
    210

<210> SEQ ID NO 111
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 111

Gln Ala Tyr Leu Gln Gln Ser Gly Ala Glu Leu Val Arg Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Arg Gln Gly Leu Glu Trp Ile
        35                  40                  45

Gly Gly Ile Tyr Pro Gly Asn Gly Asp Thr Ser Tyr Asn Gln Lys Phe
    50                  55                  60

Lys Gly Lys Ala Thr Leu Thr Val Gly Lys Ser Ser Ser Thr Ala Tyr
65                  70                  75                  80

Met Gln Leu Ser Ser Leu Thr Ser Glu Asp Ser Ala Val Tyr Phe Cys
```

```
                         85                  90                  95
Ala Arg Tyr Asp Tyr Asn Tyr Ala Met Asp Tyr Trp Gly Gln Gly Thr
                100                 105                 110

Ser Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
                180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Lys Thr
        210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
                260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
        290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 112
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 112
```

```
Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Val Ser Tyr Met
            20                  25                  30

His Trp Tyr Gln Gln Lys Pro Gly Ser Ser Pro Lys Pro Trp Ile Tyr
            35                  40                  45

Ala Thr Ser Asn Leu Ala Ser Gly Val Pro Ala Arg Phe Ser Gly Ser
    50                  55                  60

Gly Ser Gly Thr Ser Tyr Ser Phe Thr Ile Ser Arg Val Glu Ala Glu
65                  70                  75                  80

Asp Ala Ala Thr Tyr Tyr Cys Gln Gln Trp Thr Phe Asn Pro Pro Thr
                85                  90                  95

Phe Gly Gly Gly Thr Arg Leu Glu Ile Lys Arg Thr Val Ala Ala Pro
            100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
            130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
            195                 200                 205

Asn Arg Gly Glu Cys
    210

<210> SEQ ID NO 113
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 113

Gln Val Gln Leu Gln Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
            20                  25                  30

Asn Met His Trp Val Lys Gln Ala Pro Gly Gln Gly Leu Glu Trp Ile
            35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Ala Asp Glu Ser Thr Asn Thr Ala Tyr
65                  70                  75                  80

Met Glu Leu Ser Ser Leu Arg Ser Glu Asp Thr Ala Phe Tyr Tyr Cys
                85                  90                  95

Ala Arg Ser Thr Tyr Tyr Gly Gly Asp Trp Tyr Phe Asp Val Trp Gly
            100                 105                 110

Gln Gly Thr Thr Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
            130                 135                 140
```

```
Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
            165                 170                 175

Val Leu Gln Ser Ser Gly Leu Tyr Ser Leu Ser Ser Val Val Thr Val
        180                 185                 190

Pro Ser Ser Ser Leu Gly Thr Gln Thr Tyr Ile Cys Asn Val Asn His
    195                 200                 205

Lys Pro Ser Asn Thr Lys Val Asp Lys Arg Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 114
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 114

Asp Ile Gln Leu Thr Gln Ser Pro Ser Ser Leu Ser Ala Ser Val Gly
1               5                   10                  15

Asp Arg Val Thr Met Thr Cys Arg Ala Ser Ser Ser Val Ser Tyr Ile
            20                  25                  30

His Trp Phe Gln Gln Lys Pro Gly Lys Ala Pro Lys Pro Trp Ile Tyr
```

```
                35                  40                  45
Ala Thr Ser Asn Leu Ala Ser Gly Val Pro Val Arg Phe Ser Gly Ser
        50                  55                  60

Gly Ser Gly Thr Asp Tyr Thr Phe Thr Ile Ser Ser Leu Gln Pro Glu
65                  70                  75                  80

Asp Ile Ala Thr Tyr Tyr Cys Gln Gln Trp Thr Ser Asn Pro Pro Thr
                85                  90                  95

Phe Gly Gly Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
        130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
            195                 200                 205

Asn Arg Gly Glu Cys
        210

<210> SEQ ID NO 115
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 115

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175
```

```
Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Pro Lys Ser Cys
        210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 116
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 116

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80
```

```
Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 117
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 117

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Gly Ser Ile Tyr Asn Gln Arg Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
```

```
                210                 215                 220
Thr His Thr Cys Pro Pro Cys Pro Ala Pro Glu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
                275                 280                 285

Ala Lys Thr Lys Pro Arg Glu Glu Gln Tyr Asn Ser Thr Tyr Arg Val
                290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Glu Glu Met Thr Lys Asn Gln Val Ser Leu Thr
                355                 360                 365

Cys Leu Val Lys Gly Phe Tyr Pro Ser Asp Ile Ala Val Glu Trp Glu
                370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
                435                 440                 445

<210> SEQ ID NO 118
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 118

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
                20                  25                  30

Val Ala Trp Tyr Gln Gln Lys Pro Gly Lys Ala Pro Lys Leu Leu Ile
                35                  40                  45

Tyr Ser Ala Ser Tyr Arg Tyr Thr Gly Val Pro Ser Arg Phe Ser Gly
                50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Tyr
                85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
                115                 120                 125
```

```
Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 119
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 119

Gln Val Gln Leu Gln Gln Ser Gly Pro Glu Leu Val Lys Pro Gly Ala
1               5                   10                  15

Ser Leu Lys Leu Ser Cys Thr Ala Ser Gly Phe Asn Ile Lys Asp Thr
            20                  25                  30

Tyr Ile His Trp Val Lys Gln Arg Pro Glu Gln Gly Leu Glu Trp Ile
        35                  40                  45

Gly Arg Ile Tyr Pro Thr Asn Gly Tyr Thr Arg Tyr Asp Pro Lys Phe
    50                  55                  60

Gln Asp Lys Ala Thr Ile Thr Ala Asp Thr Ser Ser Asn Thr Ala Tyr
65                  70                  75                  80

Leu Gln Val Ser Arg Leu Thr Ser Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Ala Ser Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Val Gly Gly
225                 230                 235                 240

Pro Ser Val Phe Leu Leu Pro Pro Lys Pro Lys Asp Thr Leu Met Ile
                245                 250                 255

Ser Arg Thr Pro Glu Val Thr Cys Val Val Val Asp Val Ser His Glu
            260                 265                 270
```

```
Asp Pro Glu Val Lys Phe Asn Trp Tyr Val Asp Gly Val Glu Val His
            275                 280                 285

Asn Ala Lys Thr Lys Pro Pro Glu Glu Gln Tyr Asn Ser Thr Leu Arg
        290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Leu Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 120
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 120

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Asn Thr Ala
            20                  25                  30

Val Ala Trp Tyr Gln Gln Lys Pro Gly His Ser Pro Lys Leu Leu Ile
        35                  40                  45

Tyr Ser Ala Ser Phe Arg Tyr Thr Gly Val Pro Asp Arg Phe Thr Gly
    50                  55                  60

Ser Arg Ser Gly Thr Asp Phe Thr Phe Thr Ile Ser Ser Val Gln Ala
65                  70                  75                  80

Glu Asp Leu Ala Val Tyr Tyr Cys Gln Gln His Tyr Thr Thr Pro Pro
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
```

```
                    165                 170                 175
Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 121
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 121

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Ala Ser Thr Tyr Arg Val Val
    290                 295                 300
```

```
Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 122
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 122

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Tyr His Pro Ala
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

-continued

```
<210> SEQ ID NO 123
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 123

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Gly Trp Phe Gly Glu Leu Ala Phe Asp Tyr Trp Gly
            100                 105                 110

Gln Gly Thr Leu Val Thr Val Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Phe Glu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Ser Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
```

```
                355                 360                 365
Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
                435                 440                 445

Pro Gly Lys
    450

<210> SEQ ID NO 124
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 124

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Arg Val Ser Ser Ser
                20                  25                  30

Tyr Leu Ala Trp Tyr Gln Gln Lys Pro Gly Gln Ala Pro Arg Leu Leu
            35                  40                  45

Ile Tyr Asp Ala Ser Ser Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Leu Pro
                85                  90                  95

Trp Thr Phe Gly Gln Gly Thr Lys Val Glu Ile Lys Arg Thr Val Ala
                100                 105                 110

Ala Pro Ser Val Phe Ile Phe Pro Pro Ser Asp Glu Gln Leu Lys Ser
            115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
                180                 185                 190

Tyr Ala Cys Glu Val Thr His Gln Gly Leu Ser Ser Pro Val Thr Lys
            195                 200                 205

Ser Phe Asn Arg Gly Glu Cys
    210                 215

<210> SEQ ID NO 125
<211> LENGTH: 115
<212> TYPE: PRT
<213> ORGANISM: Artificial Sequence
<220> FEATURE:
```

<223> OTHER INFORMATION: Description of Artificial Sequence: Synthetic
     polypeptide

<400> SEQUENCE: 125

Glu Glu Glu Leu Gln Val Ile Gln Pro Asp Lys Ser Val Leu Val Ala
1               5                   10                  15

Ala Gly Glu Thr Ala Thr Leu Arg Cys Thr Ile Thr Ser Leu Ile Pro
            20                  25                  30

Val Gly Pro Ile Gln Trp Phe Arg Gly Ala Gly Pro Gly Arg Glu Leu
        35                  40                  45

Ile Tyr Asn Gln Lys Glu Gly His Phe Pro Arg Val Thr Thr Val Ser
    50                  55                  60

Asp Leu Thr Lys Arg Asn Asn Met Asp Phe Ser Ile Arg Ile Gly Asn
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg
        115

<210> SEQ ID NO 126
<211> LENGTH: 114
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 126

Glu Glu Glu Leu Gln Val Ile Gln Pro Asp Lys Ser Val Ser Val Ala
1               5                   10                  15

Ala Gly Glu Ser Ala Ile Leu His Cys Thr Ile Thr Ser Leu Ile Pro
            20                  25                  30

Val Gly Pro Ile Gln Trp Phe Arg Gly Ala Gly Pro Ala Arg Glu Leu
        35                  40                  45

Ile Tyr Asn Gln Lys Glu Gly His Phe Pro Arg Val Thr Thr Val Ser
    50                  55                  60

Glu Ser Thr Lys Arg Glu Asn Met Asp Phe Ser Ile Ser Ile Ser Asn
65                  70                  75                  80

Ile Thr Pro Ala Asp Ala Gly Thr Tyr Tyr Cys Val Lys Phe Arg Lys
                85                  90                  95

Gly Ser Pro Asp Thr Glu Phe Lys Ser Gly Ala Gly Thr Glu Leu Ser
            100                 105                 110

Val Arg

<210> SEQ ID NO 127
<211> LENGTH: 115
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 127

Glu Glu Glu Leu Gln Val Ile Gln Pro Asp Lys Ser Val Leu Val Ala
1               5                   10                  15

Ala Gly Glu Thr Ala Thr Leu Arg Cys Thr Ala Thr Ser Leu Ile Pro
            20                  25                  30

```
Val Gly Pro Ile Gln Trp Phe Arg Gly Ala Gly Pro Gly Arg Glu Leu
        35                  40                  45

Ile Tyr Asn Gln Lys Glu Gly Pro Phe Pro Arg Val Thr Thr Val Ser
    50                  55                  60

Asp Leu Thr Lys Arg Asn Asn Met Asp Phe Ser Ile Arg Ile Gly Asn
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
                100                 105                 110

Ser Val Arg
        115

<210> SEQ ID NO 128
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 128

Glu Glu Glu Leu Gln Val Ile Gln Pro Asp Lys Ser Val Ser Val Ala
1               5                   10                  15

Ala Gly Glu Ser Ala Ile Leu His Cys Thr Val Thr Ser Leu Ile Pro
            20                  25                  30

Val Gly Pro Ile Gln Trp Phe Arg Gly Ala Gly Pro Ala Arg Glu Leu
        35                  40                  45

Ile Tyr Asn Gln Lys Glu Gly Pro Phe Pro Arg Val Thr Thr Val Ser
    50                  55                  60

Glu Ser Thr Lys Arg Glu Asn Met Asp Phe Ser Ile Ser Ile Ser Asn
65                  70                  75                  80

Ile Thr Pro Ala Asp Ala Gly Thr Tyr Tyr Cys Val Lys Phe Arg Lys
                85                  90                  95

Gly Ser Pro Asp Thr Glu Phe Lys Ser Gly Ala Gly Thr Glu Leu Ser
                100                 105                 110

Val Arg

<210> SEQ ID NO 129
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 129

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ala Thr Ser Leu Ile Pro
            20                  25                  30

Val Gly Pro Ile Gln Trp Phe Arg Gly Ala Gly Pro Gly Arg Glu Leu
        35                  40                  45

Ile Tyr Asn Gln Lys Glu Gly His Phe Pro Arg Val Thr Thr Val Ser
    50                  55                  60

Asp Leu Thr Lys Arg Asn Asn Met Asp Phe Ser Ile Arg Ile Gly Asn
65                  70                  75                  80
```

```
Ile Thr Pro Ala Asp Ala Gly Thr Tyr Tyr Cys Val Lys Phe Arg Lys
                85                  90                  95

Gly Ser Pro Asp Val Glu Phe Lys Ser Gly Ala Gly Thr Glu Leu
            100                 105                 110

Ser Val Arg
        115

<210> SEQ ID NO 130
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 130

Glu Glu Glu Leu Gln Ile Ile Gln Pro Asp Lys Ser Val Ser Val Ala
1               5                   10                  15

Ala Gly Glu Ser Ala Ile Leu His Cys Thr Val Thr Ser Leu Ile Pro
            20                  25                  30

Val Gly Pro Ile Gln Trp Phe Arg Gly Ala Gly Pro Ala Arg Glu Leu
        35                  40                  45

Ile Tyr Asn Gln Lys Glu Gly His Phe Pro Arg Val Thr Thr Val Ser
    50                  55                  60

Glu Ser Thr Lys Arg Glu Asn Met Asp Phe Ser Ile Ser Ile Ser Asn
65                  70                  75                  80

Ile Thr Pro Ala Asp Ala Gly Thr Tyr Tyr Cys Val Lys Phe Arg Lys
                85                  90                  95

Gly Ser Pro Asp Thr Glu Phe Lys Ser Gly Ala Gly Thr Glu Leu Ser
            100                 105                 110

Val Arg

<210> SEQ ID NO 131
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 131

Glu Glu Glu Leu Gln Val Ile Gln Pro Asp Lys Ser Val Leu Val Ala
1               5                   10                  15

Ala Gly Glu Thr Ala Thr Leu Arg Cys Thr Ala Thr Ser Leu Thr Pro
            20                  25                  30

Val Gly Pro Ile Gln Trp Phe Arg Gly Ala Gly Pro Gly Arg Glu Leu
        35                  40                  45

Ile Tyr Asn Gln Lys Glu Gly His Phe Pro Arg Val Thr Thr Val Ser
    50                  55                  60

Asp Leu Thr Lys Arg Asn Asn Met Asp Phe Ser Ile Arg Ile Gly Asn
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg
        115
```

```
<210> SEQ ID NO 132
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 132

Glu Glu Glu Leu Gln Val Ile Gln Pro Asp Lys Ser Val Ser Val Ala
1               5                   10                  15

Ala Gly Glu Ser Ala Ile Leu His Cys Thr Val Thr Ser Leu Thr Pro
            20                  25                  30

Val Gly Pro Ile Gln Trp Phe Arg Gly Ala Gly Pro Ala Arg Glu Leu
        35                  40                  45

Ile Tyr Asn Gln Lys Glu Gly His Phe Pro Arg Val Thr Thr Val Ser
    50                  55                  60

Glu Ser Thr Lys Arg Glu Asn Met Asp Phe Ser Ile Ser Ile Ser Asn
65                  70                  75                  80

Ile Thr Pro Ala Asp Ala Gly Thr Tyr Tyr Cys Val Lys Phe Arg Lys
                85                  90                  95

Gly Ser Pro Asp Thr Glu Phe Lys Ser Gly Ala Gly Thr Glu Leu Ser
            100                 105                 110

Val Arg

<210> SEQ ID NO 133
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 133

Glu Glu Glu Leu Gln Val Ile Gln Pro Asp Lys Ser Val Leu Val Ala
1               5                   10                  15

Ala Gly Glu Thr Ala Thr Leu Arg Cys Thr Ala Thr Ser Leu Arg Pro
            20                  25                  30

Val Gly Pro Ile Gln Trp Phe Arg Gly Ala Gly Pro Gly Arg Glu Leu
        35                  40                  45

Ile Tyr Asn Gln Lys Glu Gly His Phe Pro Arg Val Thr Thr Val Ser
    50                  55                  60

Asp Leu Thr Lys Arg Asn Asn Met Asp Phe Ser Ile Arg Ile Gly Asn
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg
        115

<210> SEQ ID NO 134
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 134
```

-continued

Glu Glu Glu Leu Gln Val Ile Gln Pro Asp Lys Ser Val Ser Val Ala
1               5                   10                  15

Ala Gly Glu Ser Ala Ile Leu His Cys Thr Val Thr Ser Leu Arg Pro
            20                  25                  30

Val Gly Pro Ile Gln Trp Phe Arg Gly Ala Gly Pro Ala Arg Glu Leu
        35                  40                  45

Ile Tyr Asn Gln Lys Glu Gly His Phe Pro Arg Val Thr Thr Val Ser
    50                  55                  60

Glu Ser Thr Lys Arg Glu Asn Met Asp Phe Ile Ser Ile Ser Asn
65                  70                  75                  80

Ile Thr Pro Ala Asp Ala Gly Thr Tyr Tyr Cys Val Lys Phe Arg Lys
                85                  90                  95

Gly Ser Pro Asp Thr Glu Phe Lys Ser Gly Ala Gly Thr Glu Leu Ser
            100                 105                 110

Val Arg

<210> SEQ ID NO 135
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 135

Glu Glu Glu Leu Gln Val Ile Gln Pro Asp Lys Ser Val Leu Val Ala
1               5                   10                  15

Ala Gly Glu Thr Ala Thr Leu Arg Cys Thr Ala Thr Ser Leu Ile Pro
            20                  25                  30

Val Gly Pro Ile Trp Trp Phe Arg Gly Ala Gly Pro Gly Arg Glu Leu
        35                  40                  45

Ile Tyr Asn Gln Lys Glu Gly His Phe Pro Arg Val Thr Thr Val Ser
    50                  55                  60

Asp Leu Thr Lys Arg Asn Asn Met Asp Phe Ser Ile Arg Ile Gly Asn
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg
    115

<210> SEQ ID NO 136
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 136

Glu Glu Glu Leu Gln Val Ile Gln Pro Asp Lys Ser Val Ser Val Ala
1               5                   10                  15

Ala Gly Glu Ser Ala Ile Leu His Cys Thr Val Thr Ser Leu Ile Pro
            20                  25                  30

Val Gly Pro Ile Trp Trp Phe Arg Gly Ala Gly Pro Ala Arg Glu Leu
        35                  40                  45

Ile Tyr Asn Gln Lys Glu Gly His Phe Pro Arg Val Thr Thr Val Ser

```
                    50                  55                  60

Glu Ser Thr Lys Arg Glu Asn Met Asp Phe Ser Ile Ser Ile Ser Asn
 65                  70                  75                  80

Ile Thr Pro Ala Asp Ala Gly Thr Tyr Tyr Cys Val Lys Phe Arg Lys
                    85                  90                  95

Gly Ser Pro Asp Thr Glu Phe Lys Ser Gly Ala Gly Thr Glu Leu Ser
                100                 105                 110

Val Arg

<210> SEQ ID NO 137
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 137

Glu Glu Glu Leu Gln Val Ile Gln Pro Asp Lys Ser Val Leu Val Ala
  1               5                  10                  15

Ala Gly Glu Thr Ala Thr Leu Arg Cys Thr Ala Thr Ser Leu Ile Pro
                 20                  25                  30

Val Gly Pro Ile Gln Trp Phe Arg Gly Ala Gly Pro Gly Arg Glu Leu
             35                  40                  45

Ile Tyr Asn Gln Lys Glu Gly His Phe Pro Arg Val Thr Thr Val Ser
 50                  55                  60

Asp Gln Thr Lys Arg Asn Asn Met Asp Phe Ser Ile Arg Ile Gly Asn
 65                  70                  75                  80

Ile Thr Pro Ala Asp Ala Gly Thr Tyr Tyr Cys Val Lys Phe Arg Lys
                 85                  90                  95

Gly Ser Pro Asp Asp Val Glu Phe Lys Ser Gly Ala Gly Thr Glu Leu
                100                 105                 110

Ser Val Arg
        115

<210> SEQ ID NO 138
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 138

Glu Glu Glu Leu Gln Val Ile Gln Pro Asp Lys Ser Val Ser Val Ala
  1               5                  10                  15

Ala Gly Glu Ser Ala Ile Leu His Cys Thr Val Thr Ser Leu Ile Pro
                 20                  25                  30

Val Gly Pro Ile Gln Trp Phe Arg Gly Ala Gly Pro Ala Arg Glu Leu
             35                  40                  45

Ile Tyr Asn Gln Lys Glu Gly His Phe Pro Arg Val Thr Thr Val Ser
 50                  55                  60

Glu Gln Thr Lys Arg Glu Asn Met Asp Phe Ser Ile Ser Ile Ser Asn
 65                  70                  75                  80

Ile Thr Pro Ala Asp Ala Gly Thr Tyr Tyr Cys Val Lys Phe Arg Lys
                 85                  90                  95

Gly Ser Pro Asp Thr Glu Phe Lys Ser Gly Ala Gly Thr Glu Leu Ser
                100                 105                 110
```

Val Arg

<210> SEQ ID NO 139
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 139

```
Glu Glu Glu Leu Gln Val Ile Gln Pro Asp Lys Ser Val Leu Val Ala
1               5                   10                  15

Ala Gly Glu Thr Ala Thr Leu Arg Cys Thr Ala Thr Ser Leu Ile Pro
            20                  25                  30

Val Gly Pro Ile His Trp Phe Arg Gly Ala Gly Pro Gly Arg Glu Leu
        35                  40                  45

Ile Tyr Asn Gln Lys Glu Gly His Phe Pro Arg Val Thr Thr Val Ser
50                  55                  60

Asp Leu Thr Lys Arg Asn Asn Met Asp Phe Ser Ile Arg Ile Gly Asn
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg
        115
```

<210> SEQ ID NO 140
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 140

```
Glu Glu Glu Leu Gln Val Ile Gln Pro Asp Lys Ser Val Ser Val Ala
1               5                   10                  15

Ala Gly Glu Ser Ala Ile Leu His Cys Thr Val Thr Ser Leu Ile Pro
            20                  25                  30

Val Gly Pro Ile His Trp Phe Arg Gly Ala Gly Pro Ala Arg Glu Leu
        35                  40                  45

Ile Tyr Asn Gln Lys Glu Gly His Phe Pro Arg Val Thr Thr Val Ser
50                  55                  60

Glu Ser Thr Lys Arg Glu Asn Met Asp Phe Ser Ile Ser Ile Ser Asn
65                  70                  75                  80

Ile Thr Pro Ala Asp Ala Gly Thr Tyr Tyr Cys Val Lys Phe Arg Lys
                85                  90                  95

Gly Ser Pro Asp Thr Glu Phe Lys Ser Gly Ala Gly Thr Glu Leu Ser
            100                 105                 110

Val Arg
```

<210> SEQ ID NO 141
<211> LENGTH: 115
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 141

Glu Glu Glu Leu Gln Val Ile Gln Pro Asp Lys Ser Val Leu Val Ala
1               5                   10                  15

Ala Gly Glu Thr Ala Thr Leu Arg Cys Thr Ala Thr Ser Leu Ile Pro
            20                  25                  30

Val Gly Pro Ile Gln Trp Phe Arg Gly Ala Gly Pro Gly Arg Glu Leu
        35                  40                  45

Ile Tyr Asn Gln Lys Pro Gly His Phe Pro Arg Val Thr Thr Val Ser
    50                  55                  60

Asp Leu Thr Lys Arg Asn Asn Met Asp Phe Ser Ile Arg Ile Gly Asn
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg
        115

<210> SEQ ID NO 142
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 142

Glu Glu Glu Leu Gln Val Ile Gln Pro Asp Lys Ser Val Ser Val Ala
1               5                   10                  15

Ala Gly Glu Ser Ala Ile Leu His Cys Thr Val Thr Ser Leu Ile Pro
            20                  25                  30

Val Gly Pro Ile Gln Trp Phe Arg Gly Ala Gly Pro Ala Arg Glu Leu
        35                  40                  45

Ile Tyr Asn Gln Lys Pro Gly His Phe Pro Arg Val Thr Thr Val Ser
    50                  55                  60

Glu Ser Thr Lys Arg Glu Asn Met Asp Phe Ser Ile Ser Ile Ser Asn
65                  70                  75                  80

Ile Thr Pro Ala Asp Ala Gly Thr Tyr Tyr Cys Val Lys Phe Arg Lys
                85                  90                  95

Gly Ser Pro Asp Thr Glu Phe Lys Ser Gly Ala Gly Thr Glu Leu Ser
            100                 105                 110

Val Arg

<210> SEQ ID NO 143
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 143

Glu Glu Glu Leu Gln Val Ile Gln Pro Asp Lys Ser Val Leu Val Ala
1               5                   10                  15

Ala Gly Glu Thr Ala Thr Leu Arg Cys Thr Ala Thr Ser Leu Ile Pro
            20                  25                  30

Val Gly Pro Ile Gln Trp Phe Arg Gly Ala Gly Pro Gly Arg Glu Leu
            35                  40                  45

Ile Tyr Asn Gln Lys Glu Gly His Phe Pro Arg Val Thr Thr Val Ser
 50                  55                  60

Asp Leu Thr Lys Arg Asn Asn Arg Asp Phe Ser Ile Arg Ile Gly Asn
 65                  70                  75                  80

Ile Thr Pro Ala Asp Ala Gly Thr Tyr Tyr Cys Val Lys Phe Arg Lys
                 85                  90                  95

Gly Ser Pro Asp Asp Val Glu Phe Lys Ser Gly Ala Gly Thr Glu Leu
                100                 105                 110

Ser Val Arg
        115

<210> SEQ ID NO 144
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 144

Glu Glu Glu Leu Gln Val Ile Gln Pro Asp Lys Ser Val Ser Val Ala
 1               5                  10                  15

Ala Gly Glu Ser Ala Ile Leu His Cys Thr Val Thr Ser Leu Ile Pro
                20                  25                  30

Val Gly Pro Ile Gln Trp Phe Arg Gly Ala Gly Pro Ala Arg Glu Leu
            35                  40                  45

Ile Tyr Asn Gln Lys Glu Gly His Phe Pro Arg Val Thr Thr Val Ser
 50                  55                  60

Glu Ser Thr Lys Arg Glu Asn Arg Asp Phe Ser Ile Ser Ile Ser Asn
 65                  70                  75                  80

Ile Thr Pro Ala Asp Ala Gly Thr Tyr Tyr Cys Val Lys Phe Arg Lys
                 85                  90                  95

Gly Ser Pro Asp Thr Glu Phe Lys Ser Gly Ala Gly Thr Glu Leu Ser
                100                 105                 110

Val Arg

<210> SEQ ID NO 145
<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 145
gatattgtga tgactcagtc tccagccacc ctgtctgtga ctccaggaga tagagtctct      60
ctttcctgca gggccagcca gactattagc gactacttac actggtatca acaaaaatca    120
catgagtctc caaggcttct catcaaattt gcttcccaat ccatttctgg gatcccctcc    180
aggttcagtg gcagtggatc aggctcagat tcactctcag tatcaacagt gtggaacct    240 gaagatgttg gagtgtatta ctgtcaaaat ggtcacggct tcctcggac gttcggtgga    300 gggaccaagc tggaaataaa acgtacggtg gctgcaccat ctgtcttcat cttcccgcca    360
tctgatgagc agcttaagtc tggaactgcc tctgttgtgt gcctgctgaa taacttctat    420
cccagagagg ccaaagtaca gtggaaggtg gataacgccc tccaatcggg taactcccag    480

```
gagagtgtca cagagcagga cagcaaggac agcacctaca gcctcagcag caccctgacg    540
ctgagcaaag cagactacga gaaacacaaa gtctacgcct gcgaagtcac ccatcagggc    600
ctgagctcgc ccgtcacaaa gagcttcaac aggggagagt gt                      642

<210> SEQ ID NO 146
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 146

Asp Ile Val Ile Thr Gln Ser Pro Ala Thr Leu Ser Val Thr Pro Gly
1               5                   10                  15

Asp Arg Val Ser Leu Ser Cys Arg Ala Ser Gln Thr Ile Ser Asp Tyr
            20                  25                  30

Leu His Trp Tyr Gln Gln Lys Ser His Glu Ser Pro Arg Leu Leu Ile
        35                  40                  45

Lys Phe Ala Ser Gln Ser Ile Ser Gly Ile Pro Ser Arg Phe Ser Gly
    50                  55                  60

Ser Gly Ser Gly Ser Asp Phe Thr Leu Ser Ile Asn Ser Val Glu Pro
65                  70                  75                  80

Glu Asp Val Gly Val Tyr Tyr Cys Gln Asn Gly His Gly Phe Pro Arg
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 147
<211> LENGTH: 1344
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 147
gaggtgcagc tggtggagtc tgggggagac ttagtgaagc ctggagggtc cctgaaactc    60
tcctgtgcag cctctggatt cactttcagt ggctatggca tgtcttgggt tcgccagact    120
ccagacaaga ggctggagtg ggtcgcaacc attactagtg gtggtactta cacctactat    180
ccagacagtg tgaaggggcg attcaccatc tccagagaca tgccaagaa caccctgtac    240 ctgcaaatag acagtctgaa gtctgaggat acagccatat atttctgtgc aagatccctc    300
```

```
gcgggaaatg ctatggacta ctggggtcaa gggaccagcg tcaccgtctc ctcagctagc      360
accaagggcc catcggtctt ccccctggca ccctcctcca gagcacctc tgggggcaca       420 gcggccctgg gctgcctggt caaggactac ttccccgaac cggtgacggt gtcgtggaac      480
tcaggcgccc tgaccagcgg cgtgcacacc ttcccggctg tcctacagtc ctcaggactc      540
tactccctca gcagcgtggt gaccgtgccc tccagcagct gggcaccca gacctacatc       600 tgcaacgtga atcacaagcc cagcaacacc aaggtggaca gagagttga cccaaatct        660 tgtgacaaaa ctcacacatg cccaccgtgc ccagcacctg aactcctggg gggaccgtca      720
gtcttcctct ccccccaaa acccaaggac accctcatga tctcccggac ccctgaggtc       780
acatgcgtgg tggtggacgt gagccacgaa gaccctgagg tcaagttcaa ctggtacgtg      840
gacggcgtgg aggtgcataa tgccaagaca aagccgcggg aggagcagta caacagcacg      900
taccgtgtgg tcagcgtcct caccgtcctg caccaggact ggctgaatgg caaggagtac      960
aagtgcaagg tctccaacaa agccctccca gcccccatcg agaaaaccat ctccaaagcc     1020
aaagggcagc cccgagaacc acaggtgtac accctgcccc catcccggga ggagatgacc     1080
aagaaccagg tcagcctgac ctgcctggtc aaaggcttct atcccagcga catcgccgtg     1140
gagtgggaga gcaatgggca gccggagaac aactacaaga ccacgcctcc cgtgctggac     1200
tccgacggct ccttcttcct ctatagcaag ctcaccgtgg acaagagcag gtggcagcag     1260
gggaacgtct tctcatgctc cgtgatgcat gaggctctgc acaaccacta cacgcagaag     1320
agcctctccc tgtccccggg taaa                                            1344
```

<210> SEQ ID NO 148
<211> LENGTH: 448
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 148

```
Glu Val Gln Leu Gln Glu Ser Gly Gly Asp Leu Val Lys Pro Gly Gly
1               5                   10                  15

Ser Leu Lys Leu Ser Cys Ala Ala Ser Gly Phe Thr Phe Ser Gly Tyr
            20                  25                  30

Gly Met Ser Trp Val Arg Gln Thr Pro Asp Lys Arg Leu Glu Trp Val
        35                  40                  45

Ala Thr Ile Thr Ser Gly Gly Thr Tyr Thr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Ile Asp Ser Leu Lys Ser Glu Asp Thr Ala Ile Tyr Phe Cys
                85                  90                  95

Ala Arg Ser Leu Ala Gly Asn Ala Met Asp Tyr Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
```

```
                     165                 170                 175
Ser Ser Gly Leu Tyr Ser Leu Ser Ser Val Thr Val Pro Ser Ser
                180                 185                 190

Ser Leu Gly Thr Gln Thr Tyr Ile Cys Asn Val Asn His Lys Pro Ser
            195                 200                 205

Asn Thr Lys Val Asp Lys Arg Val Glu Pro Lys Ser Cys Asp Lys Thr
        210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Asp Val Ser His Glu Asp Pro
                260                 265                 270

Glu Val Lys Phe Asn Trp Tyr Val Asp Gly Val Glu Val His Asn Ala
                275                 280                 285

Lys Thr Lys Pro Arg Glu Glu Gln Tyr Asn Ser Thr Tyr Arg Val Val
            290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
        370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 149
<211> LENGTH: 583
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 149

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80
```

```
Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala Ala Ser Thr Lys Gly Pro Ser Val Phe
            115                 120                 125

Pro Leu Ala Pro Ser Ser Lys Ser Thr Ser Gly Gly Thr Ala Ala Leu
            130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
            195                 200                 205

Ser Asn Thr Lys Val Asp Lys Arg Val Glu Pro Lys Ser Cys Asp Lys
            210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
            290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Ala Gly Gly Gly Gly Ser Gly Gly Gly Gly Ser Gly Gly Gly Gly Ser
450                 455                 460

Gly Gly Gly Gly Ser Glu Glu Leu Gln Val Ile Gln Pro Asp Lys
465                 470                 475                 480

Ser Val Ser Val Ala Ala Gly Glu Ser Ala Ile Leu His Cys Thr Ile
            485                 490                 495

Thr Ser Leu Ile Pro Val Gly Pro Ile Gln Trp Phe Arg Gly Ala Gly
```

```
                500                 505                 510
Pro Ala Arg Glu Leu Ile Tyr Asn Gln Arg Glu Gly His Phe Pro Arg
            515                 520                 525

Val Thr Thr Val Ser Glu Thr Thr Arg Arg Glu Asn Met Asp Phe Ser
    530                 535                 540

Ile Ser Ile Ser Asn Ile Thr Pro Ala Asp Ala Gly Thr Tyr Tyr Cys
545                 550                 555                 560

Val Lys Phe Arg Lys Gly Ser Pro Asp Thr Glu Val Lys Ser Gly Ala
            565                 570                 575

Gly Thr Glu Leu Ser Val Arg
            580

<210> SEQ ID NO 150
<211> LENGTH: 583
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 150

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270
```

```
Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Ala Gly Gly Gly Ser Gly Gly Gly Ser Gly Gly Gly Ser
    450                 455                 460

Gly Gly Gly Ser Glu Glu Glu Leu Gln Val Ile Gln Pro Asp Lys
465                 470                 475                 480

Ser Val Ser Val Ala Ala Gly Glu Ser Ala Ile Leu His Cys Thr Val
                485                 490                 495

Thr Ser Leu Ile Pro Val Gly Pro Ile Gln Trp Phe Arg Gly Ala Gly
            500                 505                 510

Pro Ala Arg Glu Leu Ile Tyr Asn Gln Arg Glu Gly His Phe Pro Arg
        515                 520                 525

Val Thr Thr Val Ser Glu Thr Thr Arg Arg Glu Asn Met Asp Phe Ser
530                 535                 540

Ile Ser Ile Ser Asn Ile Thr Pro Ala Asp Ala Gly Thr Tyr Tyr Cys
545                 550                 555                 560

Val Lys Phe Arg Lys Gly Ser Pro Asp Thr Glu Phe Lys Ser Gly Ala
                565                 570                 575

Gly Thr Glu Leu Ser Val Arg
            580
```

```
<210> SEQ ID NO 151
<211> LENGTH: 583
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 151

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45
```

```
Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                    85                  90                  95

Arg Ala Leu Thr Tyr Tyr Asp Tyr Glu Phe Ala Tyr Trp Gly Gln Gly
                100                 105                 110

Thr Leu Val Thr Val Ser Ala Ala Ser Thr Lys Gly Pro Ser Val Phe
            115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
            195                 200                 205

Ser Asn Thr Lys Val Asp Lys Arg Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Ala Gly Gly Gly Gly Ser Gly Gly Gly Ser Gly Gly Gly Gly Ser
    450                 455                 460
```

```
Gly Gly Gly Gly Ser Glu Glu Val Gln Val Ile Gln Pro Asp Lys
465                 470                 475                 480

Ser Val Ser Val Ala Ala Gly Glu Ser Ala Ile Leu His Cys Thr Ile
            485                 490                 495

Thr Ser Leu Thr Pro Val Gly Pro Ile Gln Trp Phe Arg Gly Ala Gly
            500                 505                 510

Pro Ala Arg Glu Leu Ile Tyr Asn Gln Arg Glu Gly His Phe Pro Arg
            515                 520                 525

Val Thr Thr Val Ser Glu Thr Arg Arg Glu Asn Met Asp Phe Ser
            530                 535                 540

Ile Ser Ile Ser Asn Ile Thr Pro Ala Asp Ala Gly Thr Tyr Tyr Cys
545                 550                 555                 560

Val Lys Leu Arg Lys Gly Ser Pro Asp Thr Glu Phe Lys Ser Gly Ala
            565                 570                 575

Gly Thr Glu Leu Ser Val Arg
            580

<210> SEQ ID NO 152
<211> LENGTH: 583
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 152

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240
```

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
        260                 265                 270

Pro Glu Val Lys Phe Asn Trp Tyr Val Asp Gly Val Glu Val His Asn
    275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Ala Gly Gly Gly Ser Gly Gly Gly Ser Gly Gly Gly Ser
    450                 455                 460

Gly Gly Gly Ser Glu Glu Glu Leu Gln Ile Ile Gln Pro Asp Lys
465                 470                 475                 480

Ser Val Ser Val Ala Ala Gly Glu Ser Ala Ile Leu His Cys Thr Val
                485                 490                 495

Thr Ser Leu Ile Pro Val Gly Pro Ile Gln Trp Phe Arg Gly Ala Gly
            500                 505                 510

Pro Ala Arg Glu Leu Ile Tyr Asn Gln Lys Glu Gly His Phe Pro Arg
        515                 520                 525

Val Thr Thr Val Ser Glu Ser Thr Lys Arg Glu Asn Met Asp Phe Ser
    530                 535                 540

Ile Ser Ile Ser Asn Ile Thr Pro Ala Asp Ala Gly Thr Tyr Tyr Cys
545                 550                 555                 560

Val Lys Phe Arg Lys Gly Ser Pro Asp Thr Glu Phe Lys Ser Gly Ala
                565                 570                 575

Gly Thr Glu Leu Ser Val Arg
            580

<210> SEQ ID NO 153
<211> LENGTH: 583
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 153

Gln Val Gln Leu Lys Gln Ser Gly Pro Gly Leu Val Gln Pro Ser Gln

-continued

```
1               5                   10                  15
Ser Leu Ser Ile Thr Cys Thr Val Ser Gly Phe Ser Leu Thr Asn Tyr
            20                  25                  30
Gly Val His Trp Val Arg Gln Ser Pro Gly Lys Gly Leu Glu Trp Leu
            35                  40                  45
Gly Val Ile Trp Ser Gly Gly Asn Thr Asp Tyr Asn Thr Pro Phe Thr
            50                  55                  60
Ser Arg Leu Ser Ile Asn Lys Asp Asn Ser Lys Ser Gln Val Phe Phe
65                  70                  75                  80
Lys Met Asn Ser Leu Gln Ser Asn Asp Thr Ala Ile Tyr Tyr Cys Ala
            85                  90                  95
Arg Ala Leu Thr Tyr Tyr Asp Tyr Glu Phe Ala Tyr Trp Gly Gln Gly
            100                 105                 110
Thr Leu Val Thr Val Ser Ala Ala Ser Thr Lys Gly Pro Ser Val Phe
            115                 120                 125
Pro Leu Ala Pro Ser Ser Lys Ser Thr Ser Gly Gly Thr Ala Ala Leu
130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
            165                 170                 175
Gln Ser Ser Gly Leu Tyr Ser Leu Ser Ser Val Val Thr Val Pro Ser
            180                 185                 190
Ser Ser Leu Gly Thr Gln Thr Tyr Ile Cys Asn Val Asn His Lys Pro
            195                 200                 205
Ser Asn Thr Lys Val Asp Lys Arg Val Glu Pro Lys Ser Cys Asp Lys
210                 215                 220
Thr His Thr Cys Pro Pro Cys Pro Ala Pro Glu Leu Leu Gly Gly Pro
225                 230                 235                 240
Ser Val Phe Leu Phe Pro Pro Lys Pro Lys Asp Thr Leu Met Ile Ser
            245                 250                 255
Arg Thr Pro Glu Val Thr Cys Val Val Val Asp Val Ser His Glu Asp
            260                 265                 270
Pro Glu Val Lys Phe Asn Trp Tyr Val Asp Gly Val Glu Val His Asn
            275                 280                 285
Ala Lys Thr Lys Pro Arg Glu Glu Gln Tyr Asn Ser Thr Tyr Arg Val
            290                 295                 300
Val Ser Val Leu Thr Val Leu His Gln Asp Trp Leu Asn Gly Lys Glu
305                 310                 315                 320
Tyr Lys Cys Lys Val Ser Asn Lys Ala Leu Pro Ala Pro Ile Glu Lys
            325                 330                 335
Thr Ile Ser Lys Ala Lys Gly Gln Pro Arg Glu Pro Gln Val Tyr Thr
            340                 345                 350
Leu Pro Pro Ser Arg Glu Glu Met Thr Lys Asn Gln Val Ser Leu Thr
            355                 360                 365
Cys Leu Val Lys Gly Phe Tyr Pro Ser Asp Ile Ala Val Glu Trp Glu
            370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
            405                 410                 415
Ser Arg Trp Gln Gln Gly Asn Val Phe Ser Cys Ser Val Met His Glu
            420                 425                 430
```

Ala Leu His Asn His Tyr Thr Gln Lys Ser Leu Ser Leu Ser Pro Gly
            435                 440                 445

Ala Gly Gly Gly Ser Gly Gly Gly Ser Gly Gly Gly Ser
    450                 455                 460

Gly Gly Gly Gly Ser Glu Glu Leu Gln Val Ile Gln Pro Asp Lys
465                 470                 475                 480

Ser Val Ser Val Ala Ala Gly Glu Ser Ala Ile Leu His Cys Thr Ile
                485                 490                 495

Thr Ser Leu Ile Pro Val Gly Pro Ile Gln Trp Phe Arg Gly Ala Gly
            500                 505                 510

Pro Ala Arg Glu Leu Ile Tyr Asn Gln Lys Glu Gly His Phe Pro Arg
            515                 520                 525

Val Thr Thr Val Ser Glu Ser Thr Lys Arg Glu Asn Met Asp Phe Ser
            530                 535                 540

Ile Ser Ile Ser Asn Ile Thr Pro Ala Asp Ala Gly Thr Tyr Tyr Cys
545                 550                 555                 560

Val Lys Phe Arg Lys Gly Ser Pro Asp Thr Glu Phe Lys Ser Gly Ala
                565                 570                 575

Gly Thr Glu Leu Ser Val Arg
            580

<210> SEQ ID NO 154
<211> LENGTH: 583
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 154

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro

```
                195                 200                 205
Ser Asn Thr Lys Val Asp Lys Arg Val Glu Pro Lys Ser Cys Asp Lys
210                 215                 220
Thr His Thr Cys Pro Pro Cys Pro Ala Pro Glu Leu Leu Gly Gly Pro
225                 230                 235                 240
Ser Val Phe Leu Phe Pro Pro Lys Pro Lys Asp Thr Leu Met Ile Ser
                245                 250                 255
Arg Thr Pro Glu Val Thr Cys Val Val Val Asp Val Ser His Glu Asp
            260                 265                 270
Pro Glu Val Lys Phe Asn Trp Tyr Val Asp Gly Val Glu Val His Asn
        275                 280                 285
Ala Lys Thr Lys Pro Arg Glu Glu Gln Tyr Asn Ser Thr Tyr Arg Val
    290                 295                 300
Val Ser Val Leu Thr Val Leu His Gln Asp Trp Leu Asn Gly Lys Glu
305                 310                 315                 320
Tyr Lys Cys Lys Val Ser Asn Lys Ala Leu Pro Ala Pro Ile Glu Lys
                325                 330                 335
Thr Ile Ser Lys Ala Lys Gly Gln Pro Arg Glu Pro Gln Val Tyr Thr
            340                 345                 350
Leu Pro Pro Ser Arg Glu Glu Met Thr Lys Asn Gln Val Ser Leu Thr
        355                 360                 365
Cys Leu Val Lys Gly Phe Tyr Pro Ser Asp Ile Ala Val Glu Trp Glu
370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
                405                 410                 415
Ser Arg Trp Gln Gln Gly Asn Val Phe Ser Cys Ser Val Met His Glu
            420                 425                 430
Ala Leu His Asn His Tyr Thr Gln Lys Ser Leu Ser Leu Ser Pro Gly
        435                 440                 445
Ala Gly Gly Gly Gly Ser Gly Gly Gly Gly Ser Gly Gly Gly Gly Ser
    450                 455                 460
Gly Gly Gly Gly Ser Glu Glu Glu Leu Gln Val Ile Gln Pro Asp Lys
465                 470                 475                 480
Ser Val Ser Val Ala Ala Gly Glu Ser Ala Ile Leu His Cys Thr Gln
                485                 490                 495
Thr Ser Leu Ile Pro Val Gly Pro Ile Gln Trp Phe Arg Gly Ala Gly
            500                 505                 510
Pro Ala Arg Glu Leu Ile Tyr Asn Gln Lys Glu Gly His Phe Pro Arg
        515                 520                 525
Val Thr Thr Val Ser Glu Ser Thr Lys Arg Glu Asn Met Asp Phe Ser
    530                 535                 540
Ile Ser Ile Ser Asn Ile Thr Pro Ala Asp Ala Gly Thr Tyr Tyr Cys
545                 550                 555                 560
Val Lys Phe Arg Lys Gly Ser Pro Asp Thr Glu Phe Lys Ser Gly Ala
                565                 570                 575
Gly Thr Glu Leu Ser Val Arg
            580

<210> SEQ ID NO 155
<211> LENGTH: 583
<212> TYPE: PRT
<213> ORGANISM: Artificial Sequence
```

<220> FEATURE:
<223> OTHER INFORMATION: Description of Artificial Sequence: Synthetic
      polypeptide

<400> SEQUENCE: 155

```
Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65              70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
```

```
                385                 390                 395                 400
        Asp Ser Asp Gly Ser Phe Phe Leu Tyr Ser Lys Leu Thr Val Asp Lys
                        405                 410                 415

Ser Arg Trp Gln Gln Gly Asn Val Phe Ser Cys Ser Val Met His Glu
                        420                 425                 430

Ala Leu His Asn His Tyr Thr Gln Lys Ser Leu Ser Leu Ser Pro Gly
                        435                 440                 445

Ala Gly Gly Gly Ser Gly Gly Gly Ser Gly Gly Gly Ser
                450                 455                 460

Gly Gly Gly Ser Glu Glu Glu Leu Gln Val Ile Gln Pro Asp Lys
        465                 470                 475                 480

Ser Val Ser Val Ala Ala Gly Glu Ser Ala Ile Leu His Cys Thr Val
                        485                 490                 495

Thr Ser Leu Arg Pro Val Gly Pro Ile Gln Trp Phe Arg Gly Ala Gly
                        500                 505                 510

Pro Ala Arg Glu Leu Ile Tyr Asn Gln Lys Glu Gly His Phe Pro Arg
                        515                 520                 525

Val Thr Thr Val Ser Glu Ser Thr Lys Arg Glu Asn Met Asp Phe Ser
                        530                 535                 540

Ile Ser Ile Ser Asn Ile Thr Pro Ala Asp Ala Gly Thr Tyr Tyr Cys
        545                 550                 555                 560

Val Lys Phe Arg Lys Gly Ser Pro Asp Thr Glu Phe Lys Ser Gly Ala
                        565                 570                 575

Gly Thr Glu Leu Ser Val Arg
                        580

<210> SEQ ID NO 156
<211> LENGTH: 583
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 156

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
                20                  25                  30

Gly Val His Trp Val Arg Gln Ser Pro Gly Lys Gly Leu Glu Trp Leu
            35                  40                  45

Gly Val Ile Trp Ser Gly Gly Asn Thr Asp Tyr Asn Thr Pro Phe Thr
        50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
                100                 105                 110

Thr Leu Val Thr Val Ser Ala Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160
```

```
Asn Ser Gly Ala Leu Thr Ser Gly Val His Thr Phe Pro Ala Val Leu
            165                 170                 175
Gln Ser Ser Gly Leu Tyr Ser Leu Ser Ser Val Val Thr Val Pro Ser
        180                 185                 190
Ser Ser Leu Gly Thr Gln Thr Tyr Ile Cys Asn Val Asn His Lys Pro
    195                 200                 205
Ser Asn Thr Lys Val Asp Lys Arg Val Glu Pro Lys Ser Cys Asp Lys
210                 215                 220
Thr His Thr Cys Pro Pro Cys Pro Ala Pro Glu Leu Leu Gly Gly Pro
225                 230                 235                 240
Ser Val Phe Leu Phe Pro Pro Lys Pro Lys Asp Thr Leu Met Ile Ser
            245                 250                 255
Arg Thr Pro Glu Val Thr Cys Val Val Val Asp Val Ser His Glu Asp
            260                 265                 270
Pro Glu Val Lys Phe Asn Trp Tyr Val Asp Gly Val Glu Val His Asn
        275                 280                 285
Ala Lys Thr Lys Pro Arg Glu Glu Gln Tyr Asn Ser Thr Tyr Arg Val
    290                 295                 300
Val Ser Val Leu Thr Val Leu His Gln Asp Trp Leu Asn Gly Lys Glu
305                 310                 315                 320
Tyr Lys Cys Lys Val Ser Asn Lys Ala Leu Pro Ala Pro Ile Glu Lys
            325                 330                 335
Thr Ile Ser Lys Ala Lys Gly Gln Pro Arg Glu Pro Gln Val Tyr Thr
            340                 345                 350
Leu Pro Pro Ser Arg Glu Glu Met Thr Lys Asn Gln Val Ser Leu Thr
        355                 360                 365
Cys Leu Val Lys Gly Phe Tyr Pro Ser Asp Ile Ala Val Glu Trp Glu
370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
            405                 410                 415
Ser Arg Trp Gln Gln Gly Asn Val Phe Ser Cys Ser Val Met His Glu
        420                 425                 430
Ala Leu His Asn His Tyr Thr Gln Lys Ser Leu Ser Leu Ser Pro Gly
    435                 440                 445
Ala Gly Gly Gly Gly Ser Gly Gly Gly Gly Ser Gly Gly Gly Gly Ser
450                 455                 460
Gly Gly Gly Gly Ser Glu Glu Glu Leu Gln Val Ile Gln Pro Asp Lys
465                 470                 475                 480
Ser Val Ser Val Ala Ala Gly Glu Ser Ala Ile Leu His Cys Thr Val
            485                 490                 495
Thr Ser Leu Thr Pro Val Gly Pro Ile Gln Trp Phe Arg Gly Ala Gly
            500                 505                 510
Pro Ala Arg Glu Leu Ile Tyr Asn Gln Lys Glu Gly His Phe Pro Arg
        515                 520                 525
Val Thr Thr Val Ser Glu Ser Thr Lys Arg Glu Asn Met Asp Phe Ser
    530                 535                 540
Ile Ser Ile Ser Asn Ile Thr Pro Ala Asp Ala Gly Thr Tyr Tyr Cys
545                 550                 555                 560
Val Lys Phe Arg Lys Gly Ser Pro Asp Thr Glu Phe Lys Ser Gly Ala
            565                 570                 575
Gly Thr Glu Leu Ser Val Arg
```

<210> SEQ ID NO 157
<211> LENGTH: 583
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 157

```
Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350
```

```
Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
            435                 440                 445

Ala Gly Gly Gly Ser Gly Gly Gly Ser Gly Gly Gly Gly Ser
    450                 455                 460

Gly Gly Gly Gly Ser Glu Glu Glu Leu Gln Val Ile Gln Pro Asp Lys
465                 470                 475                 480

Ser Val Ser Val Ala Ala Gly Glu Ser Ala Ile Leu His Cys Thr Val
                485                 490                 495

Thr Ser Leu Ile Pro Val Gly Gly Ile Gln Trp Phe Arg Gly Ala Gly
            500                 505                 510

Pro Ala Arg Glu Leu Ile Tyr Asn Gln Lys Glu Gly His Phe Pro Arg
        515                 520                 525

Val Thr Thr Val Ser Glu Ser Thr Lys Arg Glu Asn Met Asp Phe Ser
        530                 535                 540

Ile Ser Ile Ser Asn Ile Thr Pro Ala Asp Ala Gly Thr Tyr Tyr Cys
545                 550                 555                 560

Val Lys Phe Arg Lys Gly Ser Pro Asp Thr Glu Phe Lys Ser Gly Ala
                565                 570                 575

Gly Thr Glu Leu Ser Val Arg
            580

<210> SEQ ID NO 158
<211> LENGTH: 583
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 158

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
                20                  25                  30

Gly Val His Trp Val Arg Gln Ser Pro Gly Lys Gly Leu Glu Trp Leu
            35                  40                  45

Gly Val Ile Trp Ser Gly Gly Asn Thr Asp Tyr Asn Thr Pro Phe Thr
        50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala Ala Ser Thr Lys Gly Pro Ser Val Phe
        115                 120                 125
```

```
Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Ala Gly Gly Gly Ser Gly Gly Gly Ser Gly Gly Gly Ser
    450                 455                 460

Gly Gly Gly Ser Glu Glu Glu Leu Gln Val Ile Gln Pro Asp Lys
465                 470                 475                 480

Ser Val Ser Val Ala Ala Gly Glu Ser Ala Ile Leu His Cys Thr Val
                485                 490                 495

Thr Ser Leu Ile Pro Val Gly Asn Ile Gln Trp Phe Arg Gly Ala Gly
            500                 505                 510

Pro Ala Arg Glu Leu Ile Tyr Asn Gln Lys Glu Gly His Phe Pro Arg
        515                 520                 525

Val Thr Thr Val Ser Glu Ser Thr Lys Arg Glu Asn Met Asp Phe Ser
    530                 535                 540
```

```
Ile Ser Ile Ser Asn Ile Thr Pro Ala Asp Ala Gly Thr Tyr Tyr Cys
545                 550                 555                 560

Val Lys Phe Arg Lys Gly Ser Pro Asp Thr Glu Phe Lys Ser Gly Ala
                565                 570                 575

Gly Thr Glu Leu Ser Val Arg
                580

<210> SEQ ID NO 159
<211> LENGTH: 583
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 159

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
                20                  25                  30

Gly Val His Trp Val Arg Gln Ser Pro Gly Lys Gly Leu Glu Trp Leu
            35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320
```

```
Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Ala Gly Gly Gly Ser Gly Gly Gly Ser Gly Gly Gly Ser
    450                 455                 460

Gly Gly Gly Ser Glu Glu Leu Gln Val Ile Gln Pro Asp Lys
465                 470                 475                 480

Ser Val Ser Val Ala Ala Gly Glu Ser Ala Ile Leu His Cys Thr Val
                485                 490                 495

Thr Ser Leu Ile Pro Val Gly Pro Ile Ala Trp Phe Arg Gly Ala Gly
            500                 505                 510

Pro Ala Arg Glu Leu Ile Tyr Asn Gln Lys Gly His Phe Pro Arg
        515                 520                 525

Val Thr Thr Val Ser Glu Ser Thr Lys Arg Glu Asn Met Asp Phe Ser
    530                 535                 540

Ile Ser Ile Ser Asn Ile Thr Pro Ala Asp Ala Gly Thr Tyr Tyr Cys
545                 550                 555                 560

Val Lys Phe Arg Lys Gly Ser Pro Asp Thr Glu Phe Lys Ser Gly Ala
                565                 570                 575

Gly Thr Glu Leu Ser Val Arg
            580

<210> SEQ ID NO 160
<211> LENGTH: 583
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 160

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
```

```
                    85                  90                  95
Arg Ala Leu Thr Tyr Tyr Asp Tyr Glu Phe Ala Tyr Trp Gly Gln Gly
                100                 105                 110

Thr Leu Val Thr Val Ser Ala Ala Ser Thr Lys Gly Pro Ser Val Phe
                115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
            195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
    435                 440                 445

Ala Gly Gly Gly Gly Ser Gly Gly Gly Gly Ser Gly Gly Gly Gly Ser
    450                 455                 460

Gly Gly Gly Gly Ser Glu Glu Leu Gln Val Ile Gln Pro Asp Lys Ser
465                 470                 475                 480

Ser Val Ser Val Ala Ala Gly Glu Ser Ala Ile Leu His Cys Thr Val
                485                 490                 495

Thr Ser Leu Ile Pro Val Gly Pro Ile His Trp Phe Arg Gly Ala Gly
            500                 505                 510
```

Pro Ala Arg Glu Leu Ile Tyr Asn Gln Lys Glu Gly His Phe Pro Arg
            515                 520                 525

Val Thr Thr Val Ser Glu Ser Thr Lys Arg Glu Asn Met Asp Phe Ser
            530                 535                 540

Ile Ser Ile Ser Asn Ile Thr Pro Ala Asp Ala Gly Thr Tyr Tyr Cys
545                 550                 555                 560

Val Lys Phe Arg Lys Gly Ser Pro Asp Thr Glu Phe Lys Ser Gly Ala
                565                 570                 575

Gly Thr Glu Leu Ser Val Arg
            580

<210> SEQ ID NO 161
<211> LENGTH: 583
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 161

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
            35                  40                  45

Gly Val Ile Trp Ser Gly Gly Asn Thr Asp Tyr Asn Thr Pro Phe Thr
        50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn

```
                275                 280                 285
Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Ala Gly Gly Gly Ser Gly Gly Gly Ser Gly Gly Gly Ser
    450                 455                 460

Gly Gly Gly Ser Glu Glu Glu Leu Gln Val Ile Gln Pro Asp Lys
465                 470                 475                 480

Ser Val Ser Val Ala Ala Gly Glu Ser Ala Ile Leu His Cys Thr Val
                485                 490                 495

Thr Ser Leu Ile Pro Val Gly Pro Ile Val Trp Phe Arg Gly Ala Gly
            500                 505                 510

Pro Ala Arg Glu Leu Ile Tyr Asn Gln Lys Glu Gly His Phe Pro Arg
        515                 520                 525

Val Thr Thr Val Ser Glu Ser Thr Lys Arg Glu Asn Met Asp Phe Ser
    530                 535                 540

Ile Ser Ile Ser Asn Ile Thr Pro Ala Asp Ala Gly Thr Tyr Tyr Cys
545                 550                 555                 560

Val Lys Phe Arg Lys Gly Ser Pro Asp Thr Glu Phe Lys Ser Gly Ala
                565                 570                 575

Gly Thr Glu Leu Ser Val Arg
            580

<210> SEQ ID NO 162
<211> LENGTH: 583
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 162

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45
```

-continued

```
Gly Val Ile Trp Ser Gly Gly Asn Thr Asp Tyr Asn Thr Pro Phe Thr
 50               55                  60
Ser Arg Leu Ser Ile Asn Lys Asp Asn Ser Lys Ser Gln Val Phe Phe
 65                  70                  75                  80
Lys Met Asn Ser Leu Gln Ser Asn Asp Thr Ala Ile Tyr Tyr Cys Ala
                 85                  90                  95
Arg Ala Leu Thr Tyr Tyr Asp Tyr Glu Phe Ala Tyr Trp Gly Gln Gly
                100                 105                 110
Thr Leu Val Thr Val Ser Ala Ala Ser Thr Lys Gly Pro Ser Val Phe
            115                 120                 125
Pro Leu Ala Pro Ser Ser Lys Ser Thr Ser Gly Gly Thr Ala Ala Leu
130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
            180                 185                 190
Ser Ser Leu Gly Thr Gln Thr Tyr Ile Cys Asn Val Asn His Lys Pro
        195                 200                 205
Ser Asn Thr Lys Val Asp Lys Arg Val Glu Pro Lys Ser Cys Asp Lys
210                 215                 220
Thr His Thr Cys Pro Pro Cys Pro Ala Pro Glu Leu Leu Gly Gly Pro
225                 230                 235                 240
Ser Val Phe Leu Phe Pro Pro Lys Pro Lys Asp Thr Leu Met Ile Ser
                245                 250                 255
Arg Thr Pro Glu Val Thr Cys Val Val Val Asp Val Ser His Glu Asp
            260                 265                 270
Pro Glu Val Lys Phe Asn Trp Tyr Val Asp Gly Val Glu Val His Asn
        275                 280                 285
Ala Lys Thr Lys Pro Arg Glu Glu Gln Tyr Asn Ser Thr Tyr Arg Val
290                 295                 300
Val Ser Val Leu Thr Val Leu His Gln Asp Trp Leu Asn Gly Lys Glu
305                 310                 315                 320
Tyr Lys Cys Lys Val Ser Asn Lys Ala Leu Pro Ala Pro Ile Glu Lys
                325                 330                 335
Thr Ile Ser Lys Ala Lys Gly Gln Pro Arg Glu Pro Gln Val Tyr Thr
            340                 345                 350
Leu Pro Pro Ser Arg Glu Glu Met Thr Lys Asn Gln Val Ser Leu Thr
        355                 360                 365
Cys Leu Val Lys Gly Phe Tyr Pro Ser Asp Ile Ala Val Glu Trp Glu
370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
                405                 410                 415
Ser Arg Trp Gln Gln Gly Asn Val Phe Ser Cys Ser Val Met His Glu
            420                 425                 430
Ala Leu His Asn His Tyr Thr Gln Lys Ser Leu Ser Leu Ser Pro Gly
        435                 440                 445
Ala Gly Gly Gly Ser Gly Gly Gly Ser Gly Gly Gly Ser
450                 455                 460
Gly Gly Gly Gly Ser Glu Glu Glu Leu Gln Val Ile Gln Pro Asp Lys
```

465                 470                 475                 480
Ser Val Ser Val Ala Ala Gly Glu Ser Ala Ile Leu His Cys Thr Val
                        485                 490                 495

Thr Ser Leu Ile Pro Val Gly Pro Ile Trp Trp Phe Arg Gly Ala Gly
                500                 505                 510

Pro Ala Arg Glu Leu Ile Tyr Asn Gln Lys Gly His Phe Pro Arg
        515                 520                 525

Val Thr Thr Val Ser Glu Ser Thr Lys Arg Glu Asn Met Asp Phe Ser
530                 535                 540

Ile Ser Ile Ser Asn Ile Thr Pro Ala Asp Ala Gly Thr Tyr Tyr Cys
545                 550                 555                 560

Val Lys Phe Arg Lys Gly Ser Pro Asp Thr Glu Phe Lys Ser Gly Ala
                565                 570                 575

Gly Thr Glu Leu Ser Val Arg
            580

<210> SEQ ID NO 163
<211> LENGTH: 583
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 163

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
                20                  25                  30

Gly Val His Trp Val Arg Gln Ser Pro Gly Lys Gly Leu Glu Trp Leu
            35                  40                  45

Gly Val Ile Trp Ser Gly Gly Asn Thr Asp Tyr Asn Thr Pro Phe Thr
        50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala Ala Ser Thr Lys Gly Pro Ser Val Phe
        115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

```
Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Ala Gly Gly Gly Gly Ser Gly Gly Gly Gly Ser Gly Gly Gly Gly Ser
    450                 455                 460

Gly Gly Gly Gly Ser Glu Glu Glu Leu Gln Val Ile Gln Pro Asp Lys
465                 470                 475                 480

Ser Val Ser Val Ala Ala Gly Glu Ser Ala Ile Leu His Cys Thr Val
                485                 490                 495

Thr Ser Leu Ile Pro Val Gly Pro Ile Gln Trp Phe Arg Gly Ala Gly
            500                 505                 510

Pro Ala Arg Tyr Leu Ile Tyr Asn Gln Lys Glu Gly His Phe Pro Arg
        515                 520                 525

Val Thr Thr Val Ser Glu Ser Thr Lys Arg Glu Asn Met Asp Phe Ser
    530                 535                 540

Ile Ser Ile Ser Asn Ile Thr Pro Ala Asp Ala Gly Thr Tyr Tyr Cys
545                 550                 555                 560

Val Lys Phe Arg Lys Gly Ser Pro Asp Thr Glu Phe Lys Ser Gly Ala
                565                 570                 575

Gly Thr Glu Leu Ser Val Arg
            580

<210> SEQ ID NO 164
<211> LENGTH: 583
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 164

Gln Val Gln Leu Lys Gln Ser Gly Pro Gly Leu Val Gln Pro Ser Gln
1               5                   10                  15
```

-continued

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Ala Gly Gly Gly Gly Ser Gly Gly Gly Ser Gly Gly Gly Gly Ser
450                 455                 460

Gly Gly Gly Gly Ser Glu Glu Glu Leu Gln Val Ile Gln Pro Asp Lys
465                 470                 475                 480

Ser Val Ser Val Ala Ala Gly Glu Ser Ala Ile Leu His Cys Thr Val
                485                 490                 495

Thr Ser Leu Ile Pro Val Gly Pro Ile Gln Trp Phe Arg Gly Ala Gly
            500                 505                 510

Pro Ala Arg Glu Leu Ile Tyr Asn Glu Lys Glu Gly His Phe Pro Arg
        515                 520                 525

Val Thr Thr Val Ser Glu Ser Thr Lys Arg Glu Asn Met Asp Phe Ser
    530                 535                 540

Ile Ser Ile Ser Asn Ile Thr Pro Ala Asp Ala Gly Thr Tyr Tyr Cys
545                 550                 555                 560

Val Lys Phe Arg Lys Gly Ser Pro Asp Thr Glu Phe Lys Ser Gly Ala
                565                 570                 575

Gly Thr Glu Leu Ser Val Arg
            580

<210> SEQ ID NO 165
<211> LENGTH: 583
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 165

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

-continued

```
Ser Asn Thr Lys Val Asp Lys Arg Val Glu Pro Lys Ser Cys Asp Lys
        210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
                275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Glu Glu Met Thr Lys Asn Gln Val Ser Leu Thr
                355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
                435                 440                 445

Ala Gly Gly Gly Gly Ser Gly Gly Gly Ser Gly Gly Gly Gly Ser
450                 455                 460

Gly Gly Gly Gly Ser Glu Glu Leu Gln Val Ile Gln Pro Asp Lys
465                 470                 475                 480

Ser Val Ser Val Ala Ala Gly Glu Ser Ala Ile Leu His Cys Thr Val
                485                 490                 495

Thr Ser Leu Ile Pro Val Gly Pro Ile Gln Trp Phe Arg Gly Ala Gly
                500                 505                 510

Pro Ala Arg Glu Leu Ile Tyr Asn His Lys Glu Gly His Phe Pro Arg
                515                 520                 525

Val Thr Thr Val Ser Glu Ser Thr Lys Arg Glu Asn Met Asp Phe Ser
                530                 535                 540

Ile Ser Ile Ser Asn Ile Thr Pro Ala Asp Ala Gly Thr Tyr Tyr Cys
545                 550                 555                 560

Val Lys Phe Arg Lys Gly Ser Pro Asp Thr Glu Phe Lys Ser Gly Ala
                565                 570                 575

Gly Thr Glu Leu Ser Val Arg
                580
```

<210> SEQ ID NO 166
<211> LENGTH: 583
<212> TYPE: PRT
<213> ORGANISM: Artificial Sequence
<220> FEATURE:

<223> OTHER INFORMATION: Description of Artificial Sequence: Synthetic
polypeptide

<400> SEQUENCE: 166

```
Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400
```

```
Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
        420                 425                 430

Ala Leu His Asn His Tyr Thr Gln Lys Ser Leu Ser Leu Ser Pro Gly
    435                 440                 445

Ala Gly Gly Gly Ser Gly Gly Gly Ser Gly Gly Gly Gly Ser
450                 455                 460

Gly Gly Gly Gly Ser Glu Glu Leu Gln Val Ile Gln Pro Asp Lys
465                 470                 475                 480

Ser Val Ser Val Ala Ala Gly Glu Ser Ala Ile Leu His Cys Thr Val
            485                 490                 495

Thr Ser Leu Ile Pro Val Gly Pro Ile Gln Trp Phe Arg Gly Ala Gly
            500                 505                 510

Pro Ala Arg Glu Leu Ile Tyr Asn Gln Lys Pro Gly His Phe Pro Arg
            515                 520                 525

Val Thr Thr Val Ser Glu Ser Thr Lys Arg Glu Asn Met Asp Phe Ser
            530                 535                 540

Ile Ser Ile Ser Asn Ile Thr Pro Ala Asp Ala Gly Thr Tyr Tyr Cys
545                 550                 555                 560

Val Lys Phe Arg Lys Gly Ser Pro Asp Thr Glu Phe Lys Ser Gly Ala
                565                 570                 575

Gly Thr Glu Leu Ser Val Arg
                580

<210> SEQ ID NO 167
<211> LENGTH: 583
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 167

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
```

```
                    165                 170                 175
Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Arg Val Glu Pro Lys Ser Cys Asp Lys
        210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Ala Gly Gly Gly Ser Gly Gly Gly Ser Gly Gly Gly Ser
    450                 455                 460

Gly Gly Gly Gly Ser Glu Glu Glu Leu Gln Val Ile Gln Pro Asp Lys
465                 470                 475                 480

Ser Val Ser Val Ala Ala Gly Glu Ser Ala Ile Leu His Cys Thr Val
                485                 490                 495

Thr Ser Leu Ile Pro Val Gly Pro Ile Gln Trp Phe Arg Gly Ala Gly
            500                 505                 510

Pro Ala Arg Glu Leu Ile Tyr Asn Gln Lys Glu Gly Pro Phe Pro Arg
        515                 520                 525

Val Thr Thr Val Ser Glu Ser Thr Lys Arg Glu Asn Met Asp Phe Ser
    530                 535                 540

Ile Ser Ile Ser Asn Ile Thr Pro Ala Asp Ala Gly Thr Tyr Tyr Cys
545                 550                 555                 560

Val Lys Phe Arg Lys Gly Ser Pro Asp Thr Glu Phe Lys Ser Gly Ala
                565                 570                 575

Gly Thr Glu Leu Ser Val Arg
            580
```

<210> SEQ ID NO 168
<211> LENGTH: 583
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 168

```
Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
```

```
                355                 360                 365
Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Ala Gly Gly Gly Ser Gly Gly Gly Ser Gly Gly Gly Gly Ser
    450                 455                 460

Gly Gly Gly Gly Ser Glu Glu Leu Gln Val Ile Gln Pro Asp Lys
465                 470                 475                 480

Ser Val Ser Val Ala Ala Gly Glu Ser Ala Ile Leu His Cys Thr Val
                485                 490                 495

Thr Ser Leu Ile Pro Val Gly Pro Ile Gln Trp Phe Arg Gly Ala Gly
            500                 505                 510

Pro Ala Arg Glu Leu Ile Tyr Asn Gln Lys Glu Gly Tyr Phe Pro Arg
        515                 520                 525

Val Thr Thr Val Ser Glu Ser Thr Lys Arg Glu Asn Met Asp Phe Ser
    530                 535                 540

Ile Ser Ile Ser Asn Ile Thr Pro Ala Asp Ala Gly Thr Tyr Tyr Cys
545                 550                 555                 560

Val Lys Phe Arg Lys Gly Ser Pro Asp Thr Glu Phe Lys Ser Gly Ala
                565                 570                 575

Gly Thr Glu Leu Ser Val Arg
            580

<210> SEQ ID NO 169
<211> LENGTH: 583
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 169

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala Ala Ser Thr Lys Gly Pro Ser Val Phe
        115                 120                 125
```

```
Pro Leu Ala Pro Ser Ser Lys Ser Thr Ser Gly Gly Thr Ala Ala Leu
    130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
            180                 185                 190
Ser Ser Leu Gly Thr Gln Thr Tyr Ile Cys Asn Val Asn His Lys Pro
        195                 200                 205
Ser Asn Thr Lys Val Asp Lys Arg Val Glu Pro Lys Ser Cys Asp Lys
    210                 215                 220
Thr His Thr Cys Pro Pro Cys Pro Ala Pro Glu Leu Leu Gly Gly Pro
225                 230                 235                 240
Ser Val Phe Leu Phe Pro Pro Lys Pro Lys Asp Thr Leu Met Ile Ser
                245                 250                 255
Arg Thr Pro Glu Val Thr Cys Val Val Val Asp Val Ser His Glu Asp
                260                 265                 270
Pro Glu Val Lys Phe Asn Trp Tyr Val Asp Gly Val Glu Val His Asn
            275                 280                 285
Ala Lys Thr Lys Pro Arg Glu Glu Gln Tyr Asn Ser Thr Tyr Arg Val
        290                 295                 300
Val Ser Val Leu Thr Val Leu His Gln Asp Trp Leu Asn Gly Lys Glu
305                 310                 315                 320
Tyr Lys Cys Lys Val Ser Asn Lys Ala Leu Pro Ala Pro Ile Glu Lys
                325                 330                 335
Thr Ile Ser Lys Ala Lys Gly Gln Pro Arg Glu Pro Gln Val Tyr Thr
                340                 345                 350
Leu Pro Pro Ser Arg Glu Glu Met Thr Lys Asn Gln Val Ser Leu Thr
        355                 360                 365
Cys Leu Val Lys Gly Phe Tyr Pro Ser Asp Ile Ala Val Glu Trp Glu
    370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
                405                 410                 415
Ser Arg Trp Gln Gln Gly Asn Val Phe Ser Cys Ser Val Met His Glu
            420                 425                 430
Ala Leu His Asn His Tyr Thr Gln Lys Ser Leu Ser Leu Ser Pro Gly
        435                 440                 445
Ala Gly Gly Gly Ser Gly Gly Gly Ser Gly Gly Gly Ser
    450                 455                 460
Gly Gly Gly Gly Ser Glu Glu Leu Gln Val Ile Gln Pro Asp Lys
465                 470                 475                 480
Ser Val Ser Val Ala Ala Gly Glu Ser Ala Ile Leu His Cys Thr Val
                485                 490                 495
Thr Ser Leu Ile Pro Val Gly Pro Ile Gln Trp Phe Arg Gly Ala Gly
                500                 505                 510
Pro Ala Arg Glu Leu Ile Tyr Asn Gln Lys Glu Gly His Phe Pro Arg
            515                 520                 525
Val Thr Thr Val Ser Glu Glu Thr Lys Arg Glu Asn Met Asp Phe Ser
        530                 535                 540
Ile Ser Ile Ser Asn Ile Thr Pro Ala Asp Ala Gly Thr Tyr Tyr Cys
```

```
                  545                 550                 555                 560
            Val Lys Phe Arg Lys Gly Ser Pro Asp Thr Glu Phe Lys Ser Gly Ala
                              565                 570                 575

Gly Thr Glu Leu Ser Val Arg
                              580

<210> SEQ ID NO 170
<211> LENGTH: 583
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 170

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320
```

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Ala Gly Gly Gly Ser Gly Gly Gly Ser Gly Gly Gly Ser
    450                 455                 460

Gly Gly Gly Ser Glu Glu Glu Leu Gln Val Ile Gln Pro Asp Lys
465                 470                 475                 480

Ser Val Ser Val Ala Ala Gly Glu Ser Ala Ile Leu His Cys Thr Val
                485                 490                 495

Thr Ser Leu Ile Pro Val Gly Pro Ile Gln Trp Phe Arg Gly Ala Gly
            500                 505                 510

Pro Ala Arg Glu Leu Ile Tyr Asn Gln Lys Glu Gly His Phe Pro Arg
        515                 520                 525

Val Thr Thr Val Ser Glu His Thr Lys Arg Glu Asn Met Asp Phe Ser
    530                 535                 540

Ile Ser Ile Ser Asn Ile Thr Pro Ala Asp Ala Gly Thr Tyr Tyr Cys
545                 550                 555                 560

Val Lys Phe Arg Lys Gly Ser Pro Asp Thr Glu Phe Lys Ser Gly Ala
                565                 570                 575

Gly Thr Glu Leu Ser Val Arg
            580

<210> SEQ ID NO 171
<211> LENGTH: 583
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 171

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
                20                  25                  30

Gly Val His Trp Val Arg Gln Ser Pro Gly Lys Gly Leu Glu Trp Leu
            35                  40                  45

Gly Val Ile Trp Ser Gly Gly Asn Thr Asp Tyr Asn Thr Pro Phe Thr
        50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

```
Arg Ala Leu Thr Tyr Tyr Asp Tyr Glu Phe Ala Tyr Trp Gly Gln Gly
            100                 105                 110

Thr Leu Val Thr Val Ser Ala Ser Thr Lys Gly Pro Ser Val Phe
            115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
            195                 200                 205

Ser Asn Thr Lys Val Asp Lys Arg Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
            290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Ala Gly Gly Gly Gly Ser Gly Gly Gly Ser Gly Gly Gly Gly Ser
            450                 455                 460

Gly Gly Gly Gly Ser Glu Glu Glu Leu Gln Val Ile Gln Pro Asp Lys
465                 470                 475                 480

Ser Val Ser Val Ala Ala Gly Glu Ser Ala Ile Leu His Cys Thr Val
                485                 490                 495

Thr Ser Leu Ile Pro Val Gly Pro Ile Gln Trp Phe Arg Gly Ala Gly
            500                 505                 510
```

```
Pro Ala Arg Glu Leu Ile Tyr Asn Gln Lys Gly His Phe Pro Arg
            515                 520                 525

Val Thr Thr Val Ser Glu Gln Thr Lys Arg Glu Asn Met Asp Phe Ser
530                 535                 540

Ile Ser Ile Ser Asn Ile Thr Pro Ala Asp Ala Gly Thr Tyr Tyr Cys
545                 550                 555                 560

Val Lys Phe Arg Lys Gly Ser Pro Asp Thr Glu Phe Lys Ser Gly Ala
                565                 570                 575

Gly Thr Glu Leu Ser Val Arg
            580

<210> SEQ ID NO 172
<211> LENGTH: 583
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 172

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285
```

```
Ala Lys Thr Lys Pro Arg Glu Glu Gln Tyr Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Ala Gly Gly Gly Ser Gly Gly Gly Ser Gly Gly Gly Gly Ser
450                 455                 460

Gly Gly Gly Gly Ser Glu Glu Glu Leu Gln Val Ile Gln Pro Asp Lys
465                 470                 475                 480

Ser Val Ser Val Ala Ala Gly Glu Ser Ala Ile Leu His Cys Thr Val
                485                 490                 495

Thr Ser Leu Ile Pro Val Gly Pro Ile Gln Trp Phe Arg Gly Ala Gly
            500                 505                 510

Pro Ala Arg Glu Leu Ile Tyr Asn Gln Lys Glu Gly His Phe Pro Arg
        515                 520                 525

Val Thr Thr Val Ser Glu Trp Thr Lys Arg Glu Asn Met Asp Phe Ser
530                 535                 540

Ile Ser Ile Ser Asn Ile Thr Pro Ala Asp Ala Gly Thr Tyr Tyr Cys
545                 550                 555                 560

Val Lys Phe Arg Lys Gly Ser Pro Asp Thr Glu Phe Lys Ser Gly Ala
                565                 570                 575

Gly Thr Glu Leu Ser Val Arg
            580

<210> SEQ ID NO 173
<211> LENGTH: 583
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 173

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
                20                  25                  30

Gly Val His Trp Val Arg Gln Ser Pro Gly Lys Gly Leu Glu Trp Leu
            35                  40                  45

Gly Val Ile Trp Ser Gly Gly Asn Thr Asp Tyr Asn Thr Pro Phe Thr
```

```
                50                  55                  60
Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
                100                 105                 110

Thr Leu Val Thr Val Ser Ala Ala Ser Thr Lys Gly Pro Ser Val Phe
                115                 120                 125

Pro Leu Ala Pro Ser Ser Lys Ser Thr Ser Gly Gly Thr Ala Ala Leu
                130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
                195                 200                 205

Ser Asn Thr Lys Val Asp Lys Arg Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
                275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Glu Glu Met Thr Lys Asn Gln Val Ser Leu Thr
                355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
                435                 440                 445

Ala Gly Gly Gly Gly Ser Gly Gly Gly Gly Ser Gly Gly Gly Gly Ser
                450                 455                 460

Gly Gly Gly Gly Ser Glu Glu Glu Leu Gln Val Ile Gln Pro Asp Lys
465                 470                 475                 480
```

```
Ser Val Ser Val Ala Ala Gly Glu Ser Ala Ile Leu His Cys Thr Val
                485                 490                 495

Thr Ser Leu Ile Pro Val Gly Pro Ile Gln Trp Phe Arg Gly Ala Gly
                500                 505                 510

Pro Ala Arg Glu Leu Ile Tyr Asn Gln Lys Glu Gly His Phe Pro Arg
                515                 520                 525

Val Thr Thr Val Ser Glu Ser Glu Lys Arg Glu Asn Met Asp Phe Ser
                530                 535                 540

Ile Ser Ile Ser Asn Ile Thr Pro Ala Asp Ala Gly Thr Tyr Tyr Cys
545                 550                 555                 560

Val Lys Phe Arg Lys Gly Ser Pro Asp Thr Glu Phe Lys Ser Gly Ala
                565                 570                 575

Gly Thr Glu Leu Ser Val Arg
                580

<210> SEQ ID NO 174
<211> LENGTH: 583
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 174

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
                20                  25                  30

Gly Val His Trp Val Arg Gln Ser Pro Gly Lys Gly Leu Glu Trp Leu
                35                  40                  45

Gly Val Ile Trp Ser Gly Gly Asn Thr Asp Tyr Asn Thr Pro Phe Thr
            50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
                100                 105                 110

Thr Leu Val Thr Val Ser Ala Ala Ser Thr Lys Gly Pro Ser Val Phe
                115                 120                 125

Pro Leu Ala Pro Ser Ser Lys Ser Thr Ser Gly Gly Thr Ala Ala Leu
                130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
                195                 200                 205

Ser Asn Thr Lys Val Asp Lys Arg Val Glu Pro Lys Ser Cys Asp Lys
                210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
```

```
                        245                 250                 255
Arg Thr Pro Glu Val Thr Cys Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Ala Gly Gly Gly Gly Ser Gly Gly Gly Ser Gly Gly Gly Gly Ser
    450                 455                 460

Gly Gly Gly Gly Ser Glu Glu Leu Gln Val Ile Gln Pro Asp Lys
465                 470                 475                 480

Ser Val Ser Val Ala Ala Gly Glu Ser Ala Ile Leu His Cys Thr Val
                485                 490                 495

Thr Ser Leu Ile Pro Val Gly Pro Ile Gln Trp Phe Arg Gly Ala Gly
            500                 505                 510

Pro Ala Arg Glu Leu Ile Tyr Asn Gln Lys Glu Gly His Phe Pro Arg
        515                 520                 525

Val Thr Thr Val Ser Glu Ser Trp Lys Arg Glu Asn Met Asp Phe Ser
    530                 535                 540

Ile Ser Ile Ser Asn Ile Thr Pro Ala Asp Ala Gly Thr Tyr Tyr Cys
545                 550                 555                 560

Val Lys Phe Arg Lys Gly Ser Pro Asp Thr Glu Phe Lys Ser Gly Ala
                565                 570                 575

Gly Thr Glu Leu Ser Val Arg
            580

<210> SEQ ID NO 175
<211> LENGTH: 583
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 175

Gln Val Gln Leu Lys Gln Ser Gly Pro Gly Leu Val Gln Pro Ser Gln
1               5                   10                  15
```

-continued

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly

```
                    435                 440                 445
Ala Gly Gly Gly Ser Gly Gly Gly Ser Gly Gly Gly Ser
        450                 455                 460

Gly Gly Gly Ser Glu Glu Leu Gln Val Ile Gln Pro Asp Lys
465                 470                 475                 480

Ser Val Ser Val Ala Ala Gly Glu Ser Ala Ile Leu His Cys Thr Val
                    485                 490                 495

Thr Ser Leu Ile Pro Val Gly Pro Ile Gln Trp Phe Arg Gly Ala Gly
            500                 505                 510

Pro Ala Arg Glu Leu Ile Tyr Asn Gln Lys Glu Gly His Phe Pro Arg
                515                 520                 525

Val Thr Thr Val Ser Glu Ser Thr Ala Arg Glu Asn Met Asp Phe Ser
        530                 535                 540

Ile Ser Ile Ser Asn Ile Thr Pro Ala Asp Ala Gly Thr Tyr Tyr Cys
545                 550                 555                 560

Val Lys Phe Arg Lys Gly Ser Pro Asp Thr Glu Phe Lys Ser Gly Ala
                565                 570                 575

Gly Thr Glu Leu Ser Val Arg
            580
```

<210> SEQ ID NO 176
<211> LENGTH: 583
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 176

```
Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205
```

```
Ser Asn Thr Lys Val Asp Lys Arg Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Ala Gly Gly Gly Gly Ser Gly Gly Gly Ser Gly Gly Gly Gly Gly Ser
450                 455                 460

Gly Gly Gly Gly Ser Glu Glu Glu Leu Gln Val Ile Gln Pro Asp Lys
465                 470                 475                 480

Ser Val Ser Val Ala Ala Gly Glu Ser Ala Ile Leu His Cys Thr Val
            485                 490                 495

Thr Ser Leu Ile Pro Val Gly Pro Ile Gln Trp Phe Arg Gly Ala Gly
            500                 505                 510

Pro Ala Arg Glu Leu Ile Tyr Asn Gln Lys Glu Gly His Phe Pro Arg
        515                 520                 525

Val Thr Thr Val Ser Glu Ser Thr Glu Arg Glu Asn Met Asp Phe Ser
530                 535                 540

Ile Ser Ile Ser Asn Ile Thr Pro Ala Asp Ala Gly Thr Tyr Tyr Cys
545                 550                 555                 560

Val Lys Phe Arg Lys Gly Ser Pro Asp Thr Glu Phe Lys Ser Gly Ala
            565                 570                 575

Gly Thr Glu Leu Ser Val Arg
            580

<210> SEQ ID NO 177
<211> LENGTH: 583
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 177

```
Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400
```

```
Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
        420                 425                 430

Ala Leu His Asn His Tyr Thr Gln Lys Ser Leu Ser Leu Ser Pro Gly
            435                 440                 445

Ala Gly Gly Gly Ser Gly Gly Gly Ser Gly Gly Gly Gly Ser
450                 455                 460

Gly Gly Gly Gly Ser Glu Glu Leu Gln Val Ile Gln Pro Asp Lys
465                 470                 475                 480

Ser Val Ser Val Ala Ala Gly Glu Ser Ala Ile Leu His Cys Thr Val
                485                 490                 495

Thr Ser Leu Ile Pro Val Gly Pro Ile Gln Trp Phe Arg Gly Ala Gly
            500                 505                 510

Pro Ala Arg Glu Leu Ile Tyr Asn Gln Lys Glu Gly His Phe Pro Arg
        515                 520                 525

Val Thr Thr Val Ser Glu Ser Thr His Arg Glu Asn Met Asp Phe Ser
    530                 535                 540

Ile Ser Ile Ser Asn Ile Thr Pro Ala Asp Ala Gly Thr Tyr Tyr Cys
545                 550                 555                 560

Val Lys Phe Arg Lys Gly Ser Pro Asp Thr Glu Phe Lys Ser Gly Ala
                565                 570                 575

Gly Thr Glu Leu Ser Val Arg
            580
```

<210> SEQ ID NO 178
<211> LENGTH: 583
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 178

```
Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175
```

```
Gln Ser Ser Gly Leu Tyr Ser Leu Ser Ser Val Val Thr Val Pro Ser
            180                 185                 190
Ser Ser Leu Gly Thr Gln Thr Tyr Ile Cys Asn Val Asn His Lys Pro
            195                 200                 205
Ser Asn Thr Lys Val Asp Lys Arg Val Glu Pro Lys Ser Cys Asp Lys
210                 215                 220
Thr His Thr Cys Pro Pro Cys Pro Ala Pro Glu Leu Leu Gly Gly Pro
225                 230                 235                 240
Ser Val Phe Leu Phe Pro Pro Lys Pro Lys Asp Thr Leu Met Ile Ser
                245                 250                 255
Arg Thr Pro Glu Val Thr Cys Val Val Val Asp Val Ser His Glu Asp
                260                 265                 270
Pro Glu Val Lys Phe Asn Trp Tyr Val Asp Gly Val Glu Val His Asn
            275                 280                 285
Ala Lys Thr Lys Pro Arg Glu Glu Gln Tyr Asn Ser Thr Tyr Arg Val
290                 295                 300
Val Ser Val Leu Thr Val Leu His Gln Asp Trp Leu Asn Gly Lys Glu
305                 310                 315                 320
Tyr Lys Cys Lys Val Ser Asn Lys Ala Leu Pro Ala Pro Ile Glu Lys
                325                 330                 335
Thr Ile Ser Lys Ala Lys Gly Gln Pro Arg Glu Pro Gln Val Tyr Thr
                340                 345                 350
Leu Pro Pro Ser Arg Glu Glu Met Thr Lys Asn Gln Val Ser Leu Thr
            355                 360                 365
Cys Leu Val Lys Gly Phe Tyr Pro Ser Asp Ile Ala Val Glu Trp Glu
            370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
                405                 410                 415
Ser Arg Trp Gln Gln Gly Asn Val Phe Ser Cys Ser Val Met His Glu
                420                 425                 430
Ala Leu His Asn His Tyr Thr Gln Lys Ser Leu Ser Leu Ser Pro Gly
            435                 440                 445
Ala Gly Gly Gly Gly Ser Gly Gly Gly Gly Ser Gly Gly Gly Gly Ser
450                 455                 460
Gly Gly Gly Gly Ser Glu Glu Glu Leu Gln Val Ile Gln Pro Asp Lys
465                 470                 475                 480
Ser Val Ser Val Ala Ala Gly Glu Ser Ala Ile Leu His Cys Thr Val
                485                 490                 495
Thr Ser Leu Ile Pro Val Gly Pro Ile Gln Trp Phe Arg Gly Ala Gly
                500                 505                 510
Pro Ala Arg Glu Leu Ile Tyr Asn Gln Lys Glu Gly His Phe Pro Arg
            515                 520                 525
Val Thr Thr Val Ser Glu Ser Thr Ile Arg Glu Asn Met Asp Phe Ser
            530                 535                 540
Ile Ser Ile Ser Asn Ile Thr Pro Ala Asp Ala Gly Thr Tyr Tyr Cys
545                 550                 555                 560
Val Lys Phe Arg Lys Gly Ser Pro Asp Thr Glu Phe Lys Ser Gly Ala
                565                 570                 575
Gly Thr Glu Leu Ser Val Arg
            580
```

<210> SEQ ID NO 179
<211> LENGTH: 583
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 179

```
Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365
```

```
Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
        420                 425                 430

Ala Leu His Asn His Tyr Thr Gln Lys Ser Leu Ser Leu Ser Pro Gly
            435                 440                 445

Ala Gly Gly Gly Ser Gly Gly Gly Ser Gly Gly Gly Ser
450                 455                 460

Gly Gly Gly Ser Glu Glu Glu Leu Gln Val Ile Gln Pro Asp Lys
465                 470                 475                 480

Ser Val Ser Val Ala Ala Gly Glu Ser Ala Ile Leu His Cys Thr Val
                485                 490                 495

Thr Ser Leu Ile Pro Val Gly Pro Ile Gln Trp Phe Arg Gly Ala Gly
            500                 505                 510

Pro Ala Arg Glu Leu Ile Tyr Asn Gln Lys Glu Gly His Phe Pro Arg
        515                 520                 525

Val Thr Thr Val Ser Glu Ser Thr Thr Arg Glu Asn Met Asp Phe Ser
530                 535                 540

Ile Ser Ile Ser Asn Ile Thr Pro Ala Asp Ala Gly Thr Tyr Tyr Cys
545                 550                 555                 560

Val Lys Phe Arg Lys Gly Ser Pro Asp Thr Glu Phe Lys Ser Gly Ala
                565                 570                 575

Gly Thr Glu Leu Ser Val Arg
            580

<210> SEQ ID NO 180
<211> LENGTH: 583
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 180

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
                20                  25                  30

Gly Val His Trp Val Arg Gln Ser Pro Gly Lys Gly Leu Glu Trp Leu
            35                  40                  45

Gly Val Ile Trp Ser Gly Gly Asn Thr Asp Tyr Asn Thr Pro Phe Thr
        50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala Ala Ser Thr Lys Gly Pro Ser Val Phe
        115                 120                 125

Pro Leu Ala Pro Ser Ser Lys Ser Thr Ser Gly Gly Thr Ala Ala Leu
```

-continued

```
                130                 135                 140
Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Arg Val Glu Pro Lys Ser Cys Asp Lys
        210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Ala Gly Gly Gly Gly Ser Gly Gly Gly Gly Ser Gly Gly Gly Gly Ser
450                 455                 460

Gly Gly Gly Gly Ser Glu Glu Leu Gln Val Ile Gln Pro Asp Lys Ser
465                 470                 475                 480

Val Ser Val Ala Ala Gly Glu Ser Ala Ile Leu His Cys Thr Val Thr
                485                 490                 495

Ser Leu Ile Pro Val Gly Pro Ile Gln Trp Phe Arg Gly Ala Gly Pro
            500                 505                 510

Ala Arg Glu Leu Ile Tyr Asn Gln Lys Glu Gly His Phe Pro Arg Val
        515                 520                 525

Thr Thr Val Ser Glu Ser Thr Lys Arg Glu Asn Ile Asp Phe Ser Ile
530                 535                 540

Ser Ile Ser Asn Ile Thr Pro Ala Asp Ala Gly Thr Tyr Tyr Cys
545                 550                 555                 560
```

Val Lys Phe Arg Lys Gly Ser Pro Asp Thr Glu Phe Lys Ser Gly Ala
565 570 575

Gly Thr Glu Leu Ser Val Arg
580

<210> SEQ ID NO 181
<211> LENGTH: 583
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 181

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys

```
                    325                 330                 335
Thr Ile Ser Lys Ala Lys Gly Gln Pro Arg Glu Pro Gln Val Tyr Thr
                340                 345                 350

Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Ala Gly Gly Gly Gly Ser Gly Gly Gly Gly Ser Gly Gly Gly Gly Ser
    450                 455                 460

Gly Gly Gly Gly Ser Glu Glu Glu Leu Gln Val Ile Gln Pro Asp Lys
465                 470                 475                 480

Ser Val Ser Val Ala Ala Gly Glu Ser Ala Ile Leu His Cys Thr Val
                485                 490                 495

Thr Ser Leu Ile Pro Val Gly Pro Ile Gln Trp Phe Arg Gly Ala Gly
            500                 505                 510

Pro Ala Arg Glu Leu Ile Tyr Asn Gln Lys Glu Gly His Phe Pro Arg
        515                 520                 525

Val Thr Thr Val Ser Glu Ser Thr Lys Arg Glu Asn Asn Asp Phe Ser
    530                 535                 540

Ile Ser Ile Ser Asn Ile Thr Pro Ala Asp Ala Gly Thr Tyr Tyr Cys
545                 550                 555                 560

Val Lys Phe Arg Lys Gly Ser Pro Asp Thr Glu Phe Lys Ser Gly Ala
                565                 570                 575

Gly Thr Glu Leu Ser Val Arg
            580

<210> SEQ ID NO 182
<211> LENGTH: 583
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 182

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95
```

-continued

Arg Ala Leu Thr Tyr Tyr Asp Tyr Glu Phe Ala Tyr Trp Gly Gln Gly
              100                 105                 110

Thr Leu Val Thr Val Ser Ala Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Ala Gly Gly Gly Gly Ser Gly Gly Gly Gly Ser Gly Gly Gly Gly Ser
    450                 455                 460

Gly Gly Gly Gly Ser Glu Glu Glu Leu Gln Val Ile Gln Pro Asp Lys
465                 470                 475                 480

Ser Val Ser Val Ala Ala Gly Glu Ser Ala Ile Leu His Cys Thr Val
                485                 490                 495

Thr Ser Leu Ile Pro Val Gly Pro Ile Gln Trp Phe Arg Gly Ala Gly
            500                 505                 510

Pro Ala Arg Glu Leu Ile Tyr Asn Gln Lys Glu Gly His Phe Pro Arg

```
            515                 520                 525
Val Thr Thr Val Ser Glu Ser Thr Lys Arg Glu Asn Arg Asp Phe Ser
        530                 535                 540

Ile Ser Ile Ser Asn Ile Thr Pro Ala Asp Ala Gly Thr Tyr Tyr Cys
545                 550                 555                 560

Val Lys Phe Arg Lys Gly Ser Pro Asp Thr Glu Phe Lys Ser Gly Ala
                565                 570                 575

Gly Thr Glu Leu Ser Val Arg
            580

<210> SEQ ID NO 183
<211> LENGTH: 583
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 183

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285
```

```
Ala Lys Thr Lys Pro Arg Glu Glu Gln Tyr Asn Ser Thr Tyr Arg Val
    290                 295                 300
Val Ser Val Leu Thr Val Leu His Gln Asp Trp Leu Asn Gly Lys Glu
305                 310                 315                 320
Tyr Lys Cys Lys Val Ser Asn Lys Ala Leu Pro Ala Pro Ile Glu Lys
                325                 330                 335
Thr Ile Ser Lys Ala Lys Gly Gln Pro Arg Glu Pro Gln Val Tyr Thr
            340                 345                 350
Leu Pro Pro Ser Arg Glu Glu Met Thr Lys Asn Gln Val Ser Leu Thr
        355                 360                 365
Cys Leu Val Lys Gly Phe Tyr Pro Ser Asp Ile Ala Val Glu Trp Glu
370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
                405                 410                 415
Ser Arg Trp Gln Gln Gly Asn Val Phe Ser Cys Ser Val Met His Glu
            420                 425                 430
Ala Leu His Asn His Tyr Thr Gln Lys Ser Leu Ser Leu Ser Pro Gly
        435                 440                 445
Ala Gly Gly Gly Ser Gly Gly Gly Ser Gly Gly Gly Gly Ser
450                 455                 460
Gly Gly Gly Gly Ser Glu Glu Leu Gln Val Ile Gln Pro Asp Lys
465                 470                 475                 480
Ser Val Ser Val Ala Ala Gly Glu Ser Ala Ile Leu His Cys Thr Val
                485                 490                 495
Thr Ser Leu Ile Pro Val Gly Pro Ile Gln Trp Phe Arg Gly Ala Gly
            500                 505                 510
Pro Ala Arg Glu Leu Ile Tyr Asn Gln Lys Glu Gly His Phe Pro Arg
        515                 520                 525
Val Thr Thr Val Ser Glu Ser Thr Lys Arg Glu Asn Trp Asp Phe Ser
530                 535                 540
Ile Ser Ile Ser Asn Ile Thr Pro Ala Asp Ala Gly Thr Tyr Tyr Cys
545                 550                 555                 560
Val Lys Phe Arg Lys Gly Ser Pro Asp Thr Glu Phe Lys Ser Gly Ala
                565                 570                 575
Gly Thr Glu Leu Ser Val Arg
            580

<210> SEQ ID NO 184
<211> LENGTH: 583
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 184

Gln Val Gln Leu Lys Gln Ser Gly Pro Gly Leu Val Gln Pro Ser Gln
1               5                   10                  15
Ser Leu Ser Ile Thr Cys Thr Val Ser Gly Phe Ser Leu Thr Asn Tyr
            20                  25                  30
Gly Val His Trp Val Arg Gln Ser Pro Gly Lys Gly Leu Glu Trp Leu
        35                  40                  45
Gly Val Ile Trp Ser Gly Gly Asn Thr Asp Tyr Asn Thr Pro Phe Thr
    50                  55                  60
```

```
Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Ala Gly Gly Gly Gly Ser Gly Gly Gly Gly Ser Gly Gly Gly Gly Ser
    450                 455                 460

Gly Gly Gly Gly Ser Glu Glu Glu Leu Gln Val Ile Gln Pro Asp Lys
465                 470                 475                 480
```

-continued

```
Ser Val Ser Val Ala Gly Glu Ser Ala Ile Leu His Cys Thr Val
            485                 490                 495

Thr Ser Leu Ile Pro Val Gly Pro Ile Gln Trp Phe Arg Gly Ala Gly
        500                 505                 510

Pro Ala Arg Glu Leu Ile Tyr Asn Gln Lys Glu Gly His Phe Pro Arg
        515                 520                 525

Val Thr Thr Val Ser Glu Ser Thr Lys Arg Glu Asn Met Asp Phe Ser
    530                 535                 540

Ile Ser Ile Ser Asn Ile Thr Pro Ala Asp Ala Gly Thr Tyr Tyr Cys
545                 550                 555                 560

Asn Lys Phe Arg Lys Gly Ser Pro Asp Thr Glu Phe Lys Ser Gly Ala
                565                 570                 575

Gly Thr Glu Leu Ser Val Arg
            580

<210> SEQ ID NO 185
<211> LENGTH: 583
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 185

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255
```

Arg Thr Pro Glu Val Thr Cys Val Val Val Asp Val Ser His Glu Asp
        260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
            370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Ala Gly Gly Gly Gly Ser Gly Gly Gly Ser Gly Gly Gly Gly Ser
            450                 455                 460

Gly Gly Gly Gly Ser Glu Glu Glu Leu Gln Val Ile Gln Pro Asp Lys
465                 470                 475                 480

Ser Val Ser Val Ala Ala Gly Glu Ser Ala Ile Leu His Cys Thr Val
                485                 490                 495

Thr Ser Leu Ile Pro Val Gly Pro Ile Gln Trp Phe Arg Gly Ala Gly
            500                 505                 510

Pro Ala Arg Glu Leu Ile Tyr Asn Gln Ile Glu Gly His Phe Pro Arg
            515                 520                 525

Val Thr Thr Val Ser Glu Ser Thr Ile Arg Glu Asn Met Asp Phe Ser
            530                 535                 540

Ile Ser Ile Ser Asn Ile Thr Pro Ala Asp Ala Gly Thr Tyr Tyr Cys
545                 550                 555                 560

Val Lys Phe Arg Lys Gly Ser Pro Asp Thr Glu Phe Lys Ser Gly Ala
                565                 570                 575

Gly Thr Glu Leu Ser Val Arg
            580

<210> SEQ ID NO 186
<211> LENGTH: 583
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 186

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr

-continued

```
                20                  25                  30
Gly Val His Trp Val Arg Gln Ser Pro Gly Lys Gly Leu Glu Trp Leu
            35                  40                  45
Gly Val Ile Trp Ser Gly Gly Asn Thr Asp Tyr Asn Thr Pro Phe Thr
        50                  55                  60
Ser Arg Leu Ser Ile Asn Lys Asp Asn Ser Lys Ser Gln Val Phe Phe
65                  70                  75                  80
Lys Met Asn Ser Leu Gln Ser Asn Asp Thr Ala Ile Tyr Tyr Cys Ala
                85                  90                  95
Arg Ala Leu Thr Tyr Tyr Asp Tyr Glu Phe Ala Tyr Trp Gly Gln Gly
            100                 105                 110
Thr Leu Val Thr Val Ser Ala Ala Ser Thr Lys Gly Pro Ser Val Phe
        115                 120                 125
Pro Leu Ala Pro Ser Ser Lys Ser Thr Ser Gly Gly Thr Ala Ala Leu
    130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
            180                 185                 190
Ser Ser Leu Gly Thr Gln Thr Tyr Ile Cys Asn Val Asn His Lys Pro
        195                 200                 205
Ser Asn Thr Lys Val Asp Lys Arg Val Glu Pro Lys Ser Cys Asp Lys
    210                 215                 220
Thr His Thr Cys Pro Pro Cys Pro Ala Pro Glu Leu Leu Gly Gly Pro
225                 230                 235                 240
Ser Val Phe Leu Phe Pro Pro Lys Pro Lys Asp Thr Leu Met Ile Ser
                245                 250                 255
Arg Thr Pro Glu Val Thr Cys Val Val Val Asp Val Ser His Glu Asp
            260                 265                 270
Pro Glu Val Lys Phe Asn Trp Tyr Val Asp Gly Val Glu Val His Asn
        275                 280                 285
Ala Lys Thr Lys Pro Arg Glu Glu Gln Tyr Asn Ser Thr Tyr Arg Val
    290                 295                 300
Val Ser Val Leu Thr Val Leu His Gln Asp Trp Leu Asn Gly Lys Glu
305                 310                 315                 320
Tyr Lys Cys Lys Val Ser Asn Lys Ala Leu Pro Ala Pro Ile Glu Lys
                325                 330                 335
Thr Ile Ser Lys Ala Lys Gly Gln Pro Arg Glu Pro Gln Val Tyr Thr
            340                 345                 350
Leu Pro Pro Ser Arg Glu Glu Met Thr Lys Asn Gln Val Ser Leu Thr
        355                 360                 365
Cys Leu Val Lys Gly Phe Tyr Pro Ser Asp Ile Ala Val Glu Trp Glu
    370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
                405                 410                 415
Ser Arg Trp Gln Gln Gly Asn Val Phe Ser Cys Ser Val Met His Glu
            420                 425                 430
Ala Leu His Asn His Tyr Thr Gln Lys Ser Leu Ser Leu Ser Pro Gly
        435                 440                 445
```

```
Ala Gly Gly Gly Gly Ser Gly Gly Gly Ser Gly Gly Gly Ser
        450                 455                 460

Gly Gly Gly Gly Ser Glu Glu Leu Gln Val Ile Gln Pro Asp Lys
465                 470                 475                 480

Ser Val Ser Val Ala Ala Gly Glu Ser Ala Ile Leu His Cys Thr Val
                485                 490                 495

Thr Ser Leu Ile Pro Val Gly Pro Ile Gln Trp Phe Arg Gly Ala Gly
                500                 505                 510

Pro Ala Arg Glu Leu Ile Tyr Asn Gln Asn Glu Gly His Phe Pro Arg
            515                 520                 525

Val Thr Thr Val Ser Glu Ser Thr Glu Arg Glu Asn Met Asp Phe Ser
    530                 535                 540

Ile Ser Ile Ser Asn Ile Thr Pro Ala Asp Ala Gly Thr Tyr Tyr Cys
545                 550                 555                 560

Val Lys Phe Arg Lys Gly Ser Pro Asp Thr Glu Phe Lys Ser Gly Ala
                565                 570                 575

Gly Thr Glu Leu Ser Val Arg
            580

<210> SEQ ID NO 187
<211> LENGTH: 583
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 187

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
                20                  25                  30

Gly Val His Trp Val Arg Gln Ser Pro Gly Lys Gly Leu Glu Trp Leu
            35                  40                  45

Gly Val Ile Trp Ser Gly Gly Asn Thr Asp Tyr Asn Thr Pro Phe Thr
        50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
```

```
                210                 215                 220
Thr His Thr Cys Pro Pro Cys Pro Ala Pro Glu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
                275                 280                 285

Ala Lys Thr Lys Pro Arg Glu Glu Gln Tyr Asn Ser Thr Tyr Arg Val
                290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Glu Glu Met Thr Lys Asn Gln Val Ser Leu Thr
                355                 360                 365

Cys Leu Val Lys Gly Phe Tyr Pro Ser Asp Ile Ala Val Glu Trp Glu
                370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
                435                 440                 445

Ala Gly Gly Gly Gly Ser Gly Gly Gly Gly Ser Gly Gly Gly Gly Ser
450                 455                 460

Gly Gly Gly Gly Ser Glu Glu Glu Leu Gln Val Ile Gln Pro Asp Lys
465                 470                 475                 480

Ser Val Ser Val Ala Ala Gly Glu Ser Ala Ile Leu His Cys Thr Val
                485                 490                 495

Thr Ser Leu Ile Pro Val Gly Pro Ile Gln Trp Phe Arg Gly Ala Gly
                500                 505                 510

Pro Ala Arg Glu Leu Ile Tyr Asn Gln Gln Glu Gly His Phe Pro Arg
                515                 520                 525

Val Thr Thr Val Ser Glu Ser Thr Arg Glu Asn Met Asp Phe Ser
                530                 535                 540

Ile Ser Ile Ser Asn Ile Thr Pro Ala Asp Ala Gly Thr Tyr Tyr Cys
545                 550                 555                 560

Val Lys Phe Arg Lys Gly Ser Pro Asp Thr Glu Phe Lys Ser Gly Ala
                565                 570                 575

Gly Thr Glu Leu Ser Val Arg
                580
```

<210> SEQ ID NO 188
<211> LENGTH: 583
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 188

| | | | | | | | | | | | | | | |
|---|---|---|---|---|---|---|---|---|---|---|---|---|---|---|
| Gln | Val | Gln | Leu | Lys | Gln | Ser | Gly | Pro | Gly | Leu | Val | Gln | Pro | Ser | Gln |
| 1 | | | | 5 | | | | | 10 | | | | | 15 | |
| Ser | Leu | Ser | Ile | Thr | Cys | Thr | Val | Ser | Gly | Phe | Ser | Leu | Thr | Asn | Tyr |
| | | | 20 | | | | | 25 | | | | | 30 | | |
| Gly | Val | His | Trp | Val | Arg | Gln | Ser | Pro | Gly | Lys | Gly | Leu | Glu | Trp | Leu |
| | | 35 | | | | | 40 | | | | | 45 | | | |
| Gly | Val | Ile | Trp | Ser | Gly | Gly | Asn | Thr | Asp | Tyr | Asn | Thr | Pro | Phe | Thr |
| | 50 | | | | | 55 | | | | | 60 | | | | |
| Ser | Arg | Leu | Ser | Ile | Asn | Lys | Asp | Asn | Ser | Lys | Ser | Gln | Val | Phe | Phe |
| 65 | | | | | 70 | | | | | 75 | | | | | 80 |
| Lys | Met | Asn | Ser | Leu | Gln | Ser | Asn | Asp | Thr | Ala | Ile | Tyr | Tyr | Cys | Ala |
| | | | | 85 | | | | | 90 | | | | | 95 | |
| Arg | Ala | Leu | Thr | Tyr | Tyr | Asp | Tyr | Glu | Phe | Ala | Tyr | Trp | Gly | Gln | Gly |
| | | | 100 | | | | | 105 | | | | | 110 | | |
| Thr | Leu | Val | Thr | Val | Ser | Ala | Ala | Ser | Thr | Lys | Gly | Pro | Ser | Val | Phe |
| | | 115 | | | | | 120 | | | | | 125 | | | |
| Pro | Leu | Ala | Pro | Ser | Ser | Lys | Ser | Thr | Ser | Gly | Gly | Thr | Ala | Ala | Leu |
| | 130 | | | | | 135 | | | | | 140 | | | | |
| Gly | Cys | Leu | Val | Lys | Asp | Tyr | Phe | Pro | Glu | Pro | Val | Thr | Val | Ser | Trp |
| 145 | | | | | 150 | | | | | 155 | | | | | 160 |
| Asn | Ser | Gly | Ala | Leu | Thr | Ser | Gly | Val | His | Thr | Phe | Pro | Ala | Val | Leu |
| | | | | 165 | | | | | 170 | | | | | 175 | |
| Gln | Ser | Ser | Gly | Leu | Tyr | Ser | Leu | Ser | Ser | Val | Val | Thr | Val | Pro | Ser |
| | | | 180 | | | | | 185 | | | | | 190 | | |
| Ser | Ser | Leu | Gly | Thr | Gln | Thr | Tyr | Ile | Cys | Asn | Val | Asn | His | Lys | Pro |
| | | 195 | | | | | 200 | | | | | 205 | | | |
| Ser | Asn | Thr | Lys | Val | Asp | Lys | Arg | Val | Glu | Pro | Lys | Ser | Cys | Asp | Lys |
| | 210 | | | | | 215 | | | | | 220 | | | | |
| Thr | His | Thr | Cys | Pro | Pro | Cys | Pro | Ala | Pro | Glu | Leu | Leu | Gly | Gly | Pro |
| 225 | | | | | 230 | | | | | 235 | | | | | 240 |
| Ser | Val | Phe | Leu | Phe | Pro | Pro | Lys | Pro | Lys | Asp | Thr | Leu | Met | Ile | Ser |
| | | | | 245 | | | | | 250 | | | | | 255 | |
| Arg | Thr | Pro | Glu | Val | Thr | Cys | Val | Val | Val | Asp | Val | Ser | His | Glu | Asp |
| | | | 260 | | | | | 265 | | | | | 270 | | |
| Pro | Glu | Val | Lys | Phe | Asn | Trp | Tyr | Val | Asp | Gly | Val | Glu | Val | His | Asn |
| | | 275 | | | | | 280 | | | | | 285 | | | |
| Ala | Lys | Thr | Lys | Pro | Arg | Glu | Glu | Gln | Tyr | Asn | Ser | Thr | Tyr | Arg | Val |
| | 290 | | | | | 295 | | | | | 300 | | | | |
| Val | Ser | Val | Leu | Thr | Val | Leu | His | Gln | Asp | Trp | Leu | Asn | Gly | Lys | Glu |
| 305 | | | | | 310 | | | | | 315 | | | | | 320 |
| Tyr | Lys | Cys | Lys | Val | Ser | Asn | Lys | Ala | Leu | Pro | Ala | Pro | Ile | Glu | Lys |
| | | | | 325 | | | | | 330 | | | | | 335 | |
| Thr | Ile | Ser | Lys | Ala | Lys | Gly | Gln | Pro | Arg | Glu | Pro | Gln | Val | Tyr | Thr |
| | | | 340 | | | | | 345 | | | | | 350 | | |
| Leu | Pro | Pro | Ser | Arg | Glu | Glu | Met | Thr | Lys | Asn | Gln | Val | Ser | Leu | Thr |
| | | 355 | | | | | 360 | | | | | 365 | | | |
| Cys | Leu | Val | Lys | Gly | Phe | Tyr | Pro | Ser | Asp | Ile | Ala | Val | Glu | Trp | Glu |
| | 370 | | | | | 375 | | | | | 380 | | | | |
| Ser | Asn | Gly | Gln | Pro | Glu | Asn | Asn | Tyr | Lys | Thr | Thr | Pro | Pro | Val | Leu |
| 385 | | | | | 390 | | | | | 395 | | | | | 400 |
| Asp | Ser | Asp | Gly | Ser | Phe | Phe | Leu | Tyr | Ser | Lys | Leu | Thr | Val | Asp | Lys |

405                 410                 415
Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Ala Gly Gly Gly Ser Gly Gly Gly Ser Gly Gly Gly Ser
    450                 455                 460

Gly Gly Gly Ser Glu Glu Leu Gln Val Ile Gln Pro Asp Lys
465                 470                 475                 480

Ser Val Ser Val Ala Ala Gly Glu Ser Ala Ile Leu His Cys Thr Val
                485                 490                 495

Thr Ser Leu Ile Pro Val Gly Pro Ile Gln Trp Phe Arg Gly Ala Gly
            500                 505                 510

Pro Ala Arg Glu Leu Ile Tyr Asn Gln Thr Glu Gly His Phe Pro Arg
        515                 520                 525

Val Thr Thr Val Ser Glu Ser Thr Ala Arg Glu Asn Met Asp Phe Ser
    530                 535                 540

Ile Ser Ile Ser Asn Ile Thr Pro Ala Asp Ala Gly Thr Tyr Tyr Cys
545                 550                 555                 560

Val Lys Phe Arg Lys Gly Ser Pro Asp Thr Glu Phe Lys Ser Gly Ala
                565                 570                 575

Gly Thr Glu Leu Ser Val Arg
            580

<210> SEQ ID NO 189
<211> LENGTH: 583
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 189

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

```
Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Ala Gly Gly Gly Ser Gly Gly Gly Ser Gly Gly Gly Gly Ser
450                 455                 460

Gly Gly Gly Gly Ser Glu Glu Glu Leu Gln Val Ile Gln Pro Asp Lys
465                 470                 475                 480

Ser Val Ser Val Ala Ala Gly Glu Ser Ala Ile Leu His Cys Thr Val
                485                 490                 495

Thr Ser Leu Ile Pro Val Gly Pro Ile Gln Trp Phe Arg Gly Ala Gly
            500                 505                 510

Pro Ala Arg Glu Leu Ile Tyr Asn Gln Val Glu Gly His Phe Pro Arg
        515                 520                 525

Val Thr Thr Val Ser Glu Ser Thr His Arg Glu Asn Met Asp Phe Ser
    530                 535                 540

Ile Ser Ile Ser Asn Ile Thr Pro Ala Asp Ala Gly Thr Tyr Tyr Cys
545                 550                 555                 560

Val Lys Phe Arg Lys Gly Ser Pro Asp Thr Glu Phe Lys Ser Gly Ala
                565                 570                 575

Gly Thr Glu Leu Ser Val Arg
            580
```

-continued

```
<210> SEQ ID NO 190
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (3)..(3)
<223> OTHER INFORMATION: Glu or Gly
<220> FEATURE:
<221> NAME/KEY: MOD_RES
<222> LOCATION: (12)..(12)
<223> OTHER INFORMATION: Phe or Ser
<220> FEATURE:
<221> NAME/KEY: MOD_RES
<222> LOCATION: (14)..(14)
<223> OTHER INFORMATION: Leu or Ser
<220> FEATURE:
<221> NAME/KEY: MOD_RES
<222> LOCATION: (20)..(20)
<223> OTHER INFORMATION: Ser or Thr
<220> FEATURE:
<221> NAME/KEY: MOD_RES
<222> LOCATION: (22)..(22)
<223> OTHER INFORMATION: Ile or Thr
<220> FEATURE:
<221> NAME/KEY: MOD_RES
<222> LOCATION: (24)..(24)
<223> OTHER INFORMATION: His, Leu or Arg
<220> FEATURE:
<221> NAME/KEY: MOD_RES
<222> LOCATION: (27)..(27)
<223> OTHER INFORMATION: Ala or Val
<220> FEATURE:
<221> NAME/KEY: MOD_RES
<222> LOCATION: (45)..(45)
<223> OTHER INFORMATION: Ala or Gly
<220> FEATURE:
<221> NAME/KEY: MOD_RES
<222> LOCATION: (65)..(65)
<223> OTHER INFORMATION: Asp or Glu
<220> FEATURE:
<221> NAME/KEY: MOD_RES
<222> LOCATION: (66)..(66)
<223> OTHER INFORMATION: Leu or Ser
<220> FEATURE:
<221> NAME/KEY: MOD_RES
<222> LOCATION: (72)..(72)
<223> OTHER INFORMATION: Glu or Asn
<220> FEATURE:
<221> NAME/KEY: MOD_RES
<222> LOCATION: (77)..(77)
<223> OTHER INFORMATION: Pro or Ser
<220> FEATURE:
<221> NAME/KEY: MOD_RES
<222> LOCATION: (79)..(79)
<223> OTHER INFORMATION: Arg or Ser
<220> FEATURE:
<221> NAME/KEY: MOD_RES
<222> LOCATION: (81)..(81)
<223> OTHER INFORMATION: Gly or Ser
<220> FEATURE:
<221> NAME/KEY: misc_feature
<222> LOCATION: (103)..(103)
<223> OTHER INFORMATION: May or may not be present
<220> FEATURE:
<221> NAME/KEY: MOD_RES
<222> LOCATION: (104)..(104)
<223> OTHER INFORMATION: Thr or Val

<400> SEQUENCE: 190

Glu Glu Xaa Leu Gln Val Ile Gln Pro Asp Lys Xaa Val Xaa Val Ala
1               5                   10                  15

Ala Gly Glu Xaa Ala Xaa Leu Xaa Cys Thr Xaa Thr Ser Leu Ile Pro
            20                  25                  30
```

```
Val Gly Pro Ile Gln Trp Phe Arg Gly Ala Gly Pro Xaa Arg Glu Leu
        35                  40                  45

Ile Tyr Asn Gln Lys Glu Gly His Phe Pro Arg Val Thr Thr Val Ser
 50                  55                  60

Xaa Xaa Asp Leu Thr Lys Arg Xaa Asn Met Asp Phe Xaa Ile Xaa Ile
 65                  70                  75                  80

Xaa Asn Ile Thr Pro Ala Asp Ala Gly Thr Tyr Tyr Cys Val Lys Phe
                 85                  90                  95

Arg Lys Gly Ser Pro Asp Asp Xaa Glu Phe Lys Ser Gly Ala Gly Thr
            100                 105                 110

Glu Leu Ser Val Arg
        115

<210> SEQ ID NO 191
<211> LENGTH: 1782
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 191
gaaccgaagt cctccgacaa gactcacact tgtcccccat gcccggcccc tgagctgctg      60
ggaggcccat ccgtgttcct gttcccgccg aaacctaagg acaccctgat gatttcgaga     120
actccggaag tgacctgtgt ggtggtcgac gtgtcccacg aggatccgga ggtcaagttc     180
aattggtacg tcgacggagt ggaagtccac aacgccaaga ccaagccccg ggaggagcag     240
tacaactcca cttaccgggt ggtgtccgtg ctgaccgtgc tgcatcagga ttggctgaac     300
ggaaaggagt ataagtgcaa agtgtcaaac aaggcattgc ctgcgccaat cgaaaagacc     360
attagcaagg ccaagggcca gcccagggaa ccacaggtgt acactctgcc ccgtcccgc      420 gaagaaatga ccaagaacca agtgtcactg acatgcctcg tgaagggatt ttacccgtcc     480
gatatcgccg tggaatggga atcgaacggt caacctgaaa acaactacaa gacgacccct     540
ccggtcctgg acagcgatgg ctcattcttc ctgtactcca agcttacggt ggacaagtcc     600
cggtggcaac agggaaatgt gttttcgtgc tccgtgatgc atgaggctct gcacaaccac     660
tacacccaga agtcactctc cctgagcccc ggcgcggggg tggtggaag cggaggaggg      720 gggtctgggg gtggcggttc cggcggcggc ggatccgagg aggagctcca ggtcatccag     780
cctgacaagt ccgtgtcggt ggccgcggga gagtccgcca ttctgcactg caccgtgacc     840
tccctcatcc ccgtgggacc tatccagtgg ttcagaggag ccgggcccgc acgggaactg     900
atctataacc agaaggaggg ccatttcccc gcgtgacca ccgtgtccga gagcaccaag      960
agggaaaaca tggacttcag catttcgatc agcaacatca ctcccgctga cgccgggacc    1020
tactactgcg tgaagttccg gaaggaagc ccggacaccg agttcaaaag cggagccggc     1080
accgaactgt cggtccgcgc caagccttcc gccccggtgg tgtcaggacc ggccgcccga    1140
gcaactccgc aacacactgt gtcttttact tgcgaatccc acgggttcag ccctcgggac    1200
attaccctga gtggttcaa gaacgggaac gaactgagcg acttccagac caacgtggac     1260
ccagtgggcg aatcagtgtc ctactcgatc cattcgaccg ccaaggtcgt gttgacccgc    1320
gaggatgtgc actcccaagt catctgcgag gtggcccacg tgacactcca gggcgacccc    1380
ctgagaggca ccgcgaacct gtccgaaacc attcgcgtgc ccctacgct cgaagtgacc    1440 cagcagccag tccgcgccga aaaccaggtc aacgtgacct gtcaagtccg caagttctac    1500
```

-continued

```
ccgcaacggc tgcagcttac ctggctggag aacggcaacg tgtcccggac cgagactgcg      1560
agcaccgtca ccgagaacaa ggatggaacc tacaattgga tgtcctggct tctcgtgaat      1620
gtgtcggcgc atagggacga cgtgaagctg acttgccagg tcgaacacga cggacagccc      1680
gctgtgtcca agtcacacga tctcaaagtg tccgcccacc cgaaggagca gggaagcaac      1740
actgctgccg agaacaccgg ttccaacgaa agaaacatct ac                        1782
```

<210> SEQ ID NO 192
<211> LENGTH: 594
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 192

```
Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Ala Gly Gly Gly Ser Gly Gly Gly
225                 230                 235                 240

Gly Ser Gly Gly Gly Ser Gly Gly Gly Ser Glu Glu Glu Leu
                245                 250                 255

Gln Val Ile Gln Pro Asp Lys Ser Val Ser Val Ala Ala Gly Glu Ser
            260                 265                 270

Ala Ile Leu His Cys Thr Val Thr Ser Leu Ile Pro Val Gly Pro Ile
        275                 280                 285

Gln Trp Phe Arg Gly Ala Gly Pro Ala Arg Glu Leu Ile Tyr Asn Gln
    290                 295                 300
```

Lys Glu Gly His Phe Pro Arg Val Thr Thr Val Ser Glu Ser Thr Lys
305                 310                 315                 320

Arg Glu Asn Met Asp Phe Ser Ile Ser Ile Ser Asn Ile Thr Pro Ala
            325                 330                 335

Asp Ala Gly Thr Tyr Tyr Cys Val Lys Phe Arg Lys Gly Ser Pro Asp
            340                 345                 350

Thr Glu Phe Lys Ser Gly Ala Gly Thr Glu Leu Ser Val Arg Ala Lys
            355                 360                 365

Pro Ser Ala Pro Val Val Ser Gly Pro Ala Ala Arg Ala Thr Pro Gln
        370                 375                 380

His Thr Val Ser Phe Thr Cys Glu Ser His Gly Phe Ser Pro Arg Asp
385                 390                 395                 400

Ile Thr Leu Lys Trp Phe Lys Asn Gly Asn Glu Leu Ser Asp Phe Gln
                405                 410                 415

Thr Asn Val Asp Pro Val Gly Glu Ser Val Ser Tyr Ser Ile His Ser
            420                 425                 430

Thr Ala Lys Val Val Leu Thr Arg Glu Asp Val His Ser Gln Val Ile
        435                 440                 445

Cys Glu Val Ala His Val Thr Leu Gln Gly Asp Pro Leu Arg Gly Thr
    450                 455                 460

Ala Asn Leu Ser Glu Thr Ile Arg Val Pro Pro Thr Leu Glu Val Thr
465                 470                 475                 480

Gln Gln Pro Val Arg Ala Glu Asn Gln Val Asn Val Thr Cys Gln Val
                485                 490                 495

Arg Lys Phe Tyr Pro Gln Arg Leu Gln Leu Thr Trp Leu Glu Asn Gly
            500                 505                 510

Asn Val Ser Arg Thr Glu Thr Ala Ser Thr Val Thr Glu Asn Lys Asp
            515                 520                 525

Gly Thr Tyr Asn Trp Met Ser Trp Leu Leu Val Asn Val Ser Ala His
        530                 535                 540

Arg Asp Asp Val Lys Leu Thr Cys Gln Val Glu His Asp Gly Gln Pro
545                 550                 555                 560

Ala Val Ser Lys Ser His Asp Leu Lys Val Ser Ala His Pro Lys Glu
                565                 570                 575

Gln Gly Ser Asn Thr Ala Ala Glu Asn Thr Gly Ser Asn Glu Arg Asn
            580                 585                 590

Ile Tyr

<210> SEQ ID NO 193
<211> LENGTH: 114
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 193

Glu Glu Glu Leu Gln Val Ile Gln Pro Asp Lys Ser Val Ser Val Ala
1               5                   10                  15

Ala Gly Glu Ser Ala Ile Leu Leu Cys Thr Val Thr Ser Leu Ile Pro
            20                  25                  30

Val Gly Pro Ile Gln Trp Phe Arg Gly Ala Gly Pro Ala Arg Glu Leu
        35                  40                  45

Ile Tyr Asn Gln Lys Glu Gly His Phe Pro Arg Val Thr Thr Val Ser
    50                  55                  60

```
Glu Ser Thr Lys Arg Glu Asn Met Asp Phe Ser Ile Ser Ile Ser Asn
 65                  70                  75                  80

Ile Thr Pro Ala Asp Ala Gly Thr Tyr Tyr Cys Val Lys Phe Arg Lys
                 85                  90                  95

Gly Ser Pro Asp Thr Glu Phe Lys Ser Gly Ala Gly Thr Glu Leu Ser
                100                 105                 110

Val Arg

<210> SEQ ID NO 194
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 194

Glu Glu Gly Leu Gln Val Ile Gln Pro Asp Lys Ser Val Ser Val Ala
  1               5                  10                  15

Ala Gly Glu Ser Ala Ile Leu His Cys Thr Ala Thr Ser Leu Ile Pro
                 20                  25                  30

Val Gly Pro Ile Gln Trp Phe Arg Gly Ala Gly Pro Gly Arg Glu Leu
                 35                  40                  45

Ile Tyr Asn Gln Lys Glu Gly His Phe Pro Arg Val Thr Thr Val Ser
     50                  55                  60

Asp Leu Thr Lys Arg Asn Asn Met Asp Phe Ser Ile Arg Ile Gly Asn
 65                  70                  75                  80

Ile Thr Pro Ala Asp Ala Gly Thr Tyr Tyr Cys Val Lys Phe Arg Lys
                 85                  90                  95

Gly Ser Pro Asp Asp Val Glu Phe Lys Ser Gly Ala Gly Thr Glu Leu
                100                 105                 110

Ser Val Arg
        115

<210> SEQ ID NO 195
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 195

Glu Glu Glu Leu Gln Val Ile Gln Pro Asp Lys Phe Val Leu Val Ala
  1               5                  10                  15

Ala Gly Glu Thr Ala Thr Leu Arg Cys Thr Ala Thr Ser Leu Ile Pro
                 20                  25                  30

Val Gly Pro Ile Gln Trp Phe Arg Gly Ala Gly Pro Gly Arg Glu Leu
                 35                  40                  45

Ile Tyr Asn Gln Lys Glu Gly His Phe Pro Arg Val Thr Thr Val Ser
     50                  55                  60

Asp Leu Thr Lys Arg Asn Asn Met Asp Phe Ser Ile Arg Ile Gly Asn
 65                  70                  75                  80

Ile Thr Pro Ala Asp Ala Gly Thr Tyr Tyr Cys Val Lys Phe Arg Lys
                 85                  90                  95

Gly Ser Pro Asp Asp Val Glu Phe Lys Ser Gly Ala Gly Thr Glu Leu
                100                 105                 110

Ser Val Arg
```

115

<210> SEQ ID NO 196
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 196

Glu Glu Glu Leu Gln Val Ile Gln Pro Asp Lys Ser Val Leu Val Ala
1               5                   10                  15

Ala Gly Glu Thr Ala Thr Leu Arg Cys Thr Ala Thr Ser Leu Ile Pro
            20                  25                  30

Val Gly Pro Ile Gln Trp Phe Arg Gly Ala Gly Pro Gly Arg Glu Leu
        35                  40                  45

Ile Tyr Asn Gln Lys Glu Gly His Phe Pro Arg Val Thr Thr Val Ser
    50                  55                  60

Asp Leu Thr Lys Arg Asn Asn Met Asp Phe Pro Ile Arg Ile Gly Asn
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg
        115

<210> SEQ ID NO 197
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 197

Glu Glu Glu Leu Gln Val Ile Gln Pro Asp Lys Ser Val Ser Val Ala
1               5                   10                  15

Ala Gly Glu Ser Ala Ile Leu His Cys Thr Val Thr Ser Leu Ile Pro
            20                  25                  30

Val Gly Pro Ile Gln Trp Phe Arg Gly Ala Gly Pro Ala Arg Glu Leu
        35                  40                  45

Ile Tyr Asn Gln Lys Glu Gly His Phe Pro Arg Val Thr Thr Val Ser
    50                  55                  60

Glu Ser Thr Lys Arg Glu Asn Met Asp Phe Ser Ile Ser Ile Ser Asn
65                  70                  75                  80

Ile Thr Pro Ala Asp Ala Gly Thr Tyr Tyr Cys Val Lys Phe Arg Lys
                85                  90                  95

Gly Ser Pro Asp Thr Glu Phe Lys Ser Gly Ala Gly Thr Glu Leu Ser
            100                 105                 110

Val Arg

<210> SEQ ID NO 198
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 198

Glu Glu Glu Leu Gln Val Ile Gln Pro Asp Lys Ser Val Leu Val Ala
1               5                   10                  15

Ala Gly Glu Thr Ala Thr Leu Arg Cys Thr Ala Thr Ser Leu Ile Pro
            20                  25                  30

Val Gly Pro Ile Gln Trp Phe Arg Gly Ala Gly Pro Ala Arg Glu Leu
        35                  40                  45

Ile Tyr Asn Gln Lys Glu Gly His Phe Pro Arg Val Thr Thr Val Ser
    50                  55                  60

Glu Ser Thr Lys Arg Glu Asn Met Asp Phe Ser Ile Ser Ile Ser Asn
65                  70                  75                  80

Ile Thr Pro Ala Asp Ala Gly Thr Tyr Tyr Cys Val Lys Phe Arg Lys
                85                  90                  95

Gly Ser Pro Asp Thr Glu Phe Lys Ser Gly Ala Gly Thr Glu Leu Ser
            100                 105                 110

Val Arg

<210> SEQ ID NO 199
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 199

Glu Glu Glu Leu Gln Val Ile Gln Pro Asp Lys Ser Val Leu Val Ala
1               5                   10                  15

Ala Gly Glu Thr Ala Thr Leu Arg Cys Thr Ala Thr Ser Leu Ile Pro
            20                  25                  30

Val Gly Pro Ile Gln Trp Phe Arg Gly Ala Gly Pro Gly Arg Glu Leu
        35                  40                  45

Ile Tyr Asn Gln Lys Glu Gly His Phe Pro Arg Val Thr Thr Val Ser
    50                  55                  60

Asp Leu Thr Lys Arg Asn Asn Met Asp Phe Ser Ile Arg Ile Ser Asn
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg
        115

<210> SEQ ID NO 200
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 200

Glu Glu Glu Leu Gln Val Ile Gln Pro Asp Lys Ser Val Ser Val Ala
1               5                   10                  15

Ala Gly Glu Ser Ala Ile Leu His Cys Thr Val Thr Ser Leu Ile Pro
            20                  25                  30

Val Gly Pro Ile Gln Trp Phe Arg Gly Ala Gly Pro Ala Arg Glu Leu

```
                35                  40                  45
Ile Tyr Asn Gln Lys Glu Gly His Phe Pro Arg Val Thr Thr Val Ser
         50                  55                  60

Glu Ser Thr Lys Arg Glu Asn Met Asp Phe Ser Ile Ser Ile Ser Asn
 65                  70                  75                  80

Ile Thr Pro Ala Asp Ala Gly Thr Tyr Tyr Cys Val Lys Phe Arg Lys
                 85                  90                  95

Gly Ser Pro Asp Thr Glu Phe Lys Ser Gly Ala Gly Thr Glu Leu Ser
            100                 105                 110

Val Arg

<210> SEQ ID NO 201
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 201

Gly Gly Gly Gly Ser Gly Gly Gly Gly Ser Gly Gly Gly Gly Ser Gly
 1               5                  10                  15

Gly Gly Gly Ser
            20

<210> SEQ ID NO 202
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 202

Gly Gly Gly Gly Ser
 1               5

<210> SEQ ID NO 203
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 203

Gly Gly Gly Gly Ser Gly Gly Gly Gly Ser Gly Gly Gly Gly Ser
 1               5                  10                  15

<210> SEQ ID NO 204
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 204

Gly Gly Gly Gly Ser Gly Gly Gly Gly Ser Gly Gly Gly Gly Ser Gly
 1               5                  10                  15

Gly Gly Gly Ser Gly Gly Gly Gly Ser
            20                  25
```

```
<210> SEQ ID NO 205
<211> LENGTH: 72
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (1)..(8)
<223> OTHER INFORMATION: This region may encompass 0-8 Gly residues,
      wherein some positions may be absent
<220> FEATURE:
<221> NAME/KEY: misc_feature
<222> LOCATION: (10)..(17)
<223> OTHER INFORMATION: This region may encompass 0-8 Gly residues,
      wherein some positions may be absent
<220> FEATURE:
<221> NAME/KEY: misc_feature
<222> LOCATION: (19)..(26)
<223> OTHER INFORMATION: This region may encompass 0-8 Gly residues,
      wherein some positions may be absent
<220> FEATURE:
<221> NAME/KEY: misc_feature
<222> LOCATION: (28)..(35)
<223> OTHER INFORMATION: This region may encompass 0-8 Gly residues,
      wherein some positions may be absent
<220> FEATURE:
<221> NAME/KEY: misc_feature
<222> LOCATION: (37)..(44)
<223> OTHER INFORMATION: This region may encompass 0-8 Gly residues,
      wherein some positions may be absent
<220> FEATURE:
<221> NAME/KEY: misc_feature
<222> LOCATION: (46)..(53)
<223> OTHER INFORMATION: This region may encompass 0-8 Gly residues,
      wherein some positions may be absent
<220> FEATURE:
<221> NAME/KEY: misc_feature
<222> LOCATION: (55)..(62)
<223> OTHER INFORMATION: This region may encompass 0-8 Gly residues,
      wherein some positions may be absent
<220> FEATURE:
<221> NAME/KEY: misc_feature
<222> LOCATION: (64)..(71)
<223> OTHER INFORMATION: This region may encompass 0-8 Gly residues,
      wherein some positions may be absent
<220> FEATURE:
<221> NAME/KEY: misc_feature
<222> LOCATION: (1)..(72)
<223> OTHER INFORMATION: This sequence may encompass 0-8 'GlyxSer'
      repeating units, wherein X is 0-8
<220> FEATURE:
<223> OTHER INFORMATION: See specification as filed for detailed
      description of substitutions and preferred embodiments

<400> SEQUENCE: 205

Gly Gly Gly Gly Gly Gly Gly Ser Gly Gly Gly Gly Gly Gly Gly
1               5                   10                  15

Gly Ser Gly Gly Gly Gly Gly Gly Gly Ser Gly Gly Gly Gly Gly
            20                  25                  30

Gly Gly Gly Ser Gly Gly Gly Gly Gly Gly Gly Ser Gly Gly Gly
        35                  40                  45

Gly Gly Gly Gly Gly Ser Gly Gly Gly Gly Gly Gly Gly Ser Gly
    50                  55                  60

Gly Gly Gly Gly Gly Gly Ser
65                  70

<210> SEQ ID NO 206
<211> LENGTH: 10
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 206

Gly Gly Gly Gly Ser Gly Gly Gly Gly Ser
1               5                   10